(12) United States Patent
Sillers et al.

(10) Patent No.: US 11,162,125 B2
(45) Date of Patent: *Nov. 2, 2021

(54) PRODUCTION OF MALONYL-COA DERIVED PRODUCTS VIA ANAEROBIC PATHWAYS

(71) Applicant: LALLEMAND HUNGARY LIQUIDITY MANAGEMENT LLC, Budapest (HU)

(72) Inventors: William Ryan Sillers, Lebanon, NH (US); Shital A. Tripathi, Berkeley, CA (US); Arthur J. Shaw, IV, Grantham, NH (US); Aaron Argyros, White River Junction, VT (US); David A. Hogsett, Grantham, NH (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 0 days.

This patent is subject to a terminal disclaimer.

(21) Appl. No.: 16/166,274

(22) Filed: Oct. 22, 2018

(65) Prior Publication Data

US 2020/0270657 A1 Aug. 27, 2020

Related U.S. Application Data

(63) Continuation of application No. 13/814,616, filed as application No. PCT/US2011/046869 on Aug. 5, 2011, now Pat. No. 10,138,504.

(60) Provisional application No. 61/371,582, filed on Aug. 6, 2010.

(51) Int. Cl.
| | |
|---|---|
| C12P 17/18 | (2006.01) |
| C12N 1/22 | (2006.01) |
| C12N 9/10 | (2006.01) |
| C12N 9/88 | (2006.01) |
| C12P 7/64 | (2006.01) |

(52) U.S. Cl.
CPC ............... *C12P 17/182* (2013.01); *C12N 1/22* (2013.01); *C12N 9/1018* (2013.01); *C12N 9/88* (2013.01); *C12P 7/6409* (2013.01); *G01N 2333/91034* (2013.01)

(58) Field of Classification Search
CPC .......... C12N 9/1018; C12N 9/88; C12N 1/22; G01N 2333/91034; C12P 7/6409; C12P 17/182
See application file for complete search history.

(56) References Cited

U.S. PATENT DOCUMENTS

| | | | |
|---|---|---|---|
| 5,252,466 A | 10/1993 | Cronan, Jr. | |
| 5,487,987 A | 1/1996 | Frost et al. | |
| 5,616,496 A | 4/1997 | Frost et al. | |
| 6,852,517 B1 | 2/2005 | Suthers et al. | |
| 7,011,959 B1 | 3/2006 | Santi et al. | |
| 7,186,541 B2 | 3/2007 | Gokarn et al. | |
| 7,393,676 B2 | 7/2008 | Gokarn et al. | |
| 7,638,316 B2 | 12/2009 | Gokarn et al. | |
| 7,799,545 B2 | 9/2010 | Burgard et al. | |
| 7,846,712 B2 | 12/2010 | Zhang et al. | |
| 8,034,591 B2 | 10/2011 | Winkler et al. | |
| 8,048,654 B2 | 11/2011 | Berry et al. | |
| 8,048,976 B2 | 11/2011 | McPhee | |
| 8,062,871 B2 | 11/2011 | Burgard et al. | |
| 8,076,120 B2 | 12/2011 | Gokarn et al. | |
| 8,088,607 B2 | 1/2012 | Burgard et al. | |
| 8,097,439 B2 | 1/2012 | Alibhai et al. | |
| 8,217,128 B2 | 7/2012 | McPhee | |
| 8,247,201 B2 | 8/2012 | Tajima et al. | |
| 9,029,124 B2 | 5/2015 | Robertson et al. | |
| 9,410,131 B2 | 8/2016 | Milo et al. | |
| 10,138,504 B2 * | 11/2018 | Sillers .................. | C12P 17/182 |
| 2004/0076982 A1 | 4/2004 | Gokarn et al. | |
| 2007/0184524 A1 | 8/2007 | Gokarn et al. | |
| 2008/0076167 A1 | 3/2008 | Gokarn et al. | |

(Continued)

FOREIGN PATENT DOCUMENTS

| | | |
|---|---|---|
| WO | 95/07996 A1 | 3/1995 |
| WO | 01/16346 A1 | 3/2001 |

(Continued)

OTHER PUBLICATIONS

Bar-Even, et al., Design and analysis of synthetic carbon fixation pathways, PNAS, vol. 107 (19), pp. 8889-8894 (2010).
Broun, et al., Catalytic plasticity of fatty acid modification enzymes underlying chemical diversity of plant lipids; Science, vol. 282, pp. 1315-1317 (1998).
Davis, M., et al., Overproduction of Acetyl-CoA Carboxylase Activitiy Increases the Rate of Fatty Acid Biosynthesis in *Escherichia coli*, Journal of Biological Chemistry, vol. 275, pp. 28593-28598 (Sep. 8, 2000).

(Continued)

*Primary Examiner* — Ganapathirama Raghu
(74) *Attorney, Agent, or Firm* — Nutter McClennen & Fish LLP

(57) ABSTRACT

The present invention provides for novel metabolic pathways to convert biomass and other carbohydrate sources to malonyl-CoA derived products, such as hydrocarbons and other bioproducts, under anaerobic conditions and with the net production of ATP. More specifically, the invention provides for a recombinant microorganism comprising one or more native and/or heterologous enzymes that function in one or more engineered metabolic pathways to achieve conversion of a carbohydrate source to, e.g., long-chain hydrocarbons and hydrocarbon derivatives, wherein the one or more native and/or heterologous enzymes is activated, upregulated, downregulated, or deleted. The invention also provides for processes to convert biomass to malonyl-CoA derived products which comprise contacting a carbohydrate source with a recombinant microorganism of the invention.

20 Claims, 72 Drawing Sheets

Specification includes a Sequence Listing.

(56) References Cited

U.S. PATENT DOCUMENTS

| | | |
|---|---|---|
| 2008/0092829 A1 | 4/2008 | Renninger et al. |
| 2008/0261287 A1 | 10/2008 | Winkler et al. |
| 2008/0293060 A1 | 11/2008 | Schirmer et al. |
| 2009/0053783 A1 | 2/2009 | Gokarn et al. |
| 2009/0275097 A1 | 11/2009 | Sun et al. |
| 2009/0305364 A1 | 12/2009 | Burgard et al. |
| 2010/0056714 A1 | 3/2010 | McPhee |
| 2010/0056743 A1 | 3/2010 | McPhee |
| 2010/0068773 A1 | 3/2010 | Marx et al. |
| 2010/0071259 A1 | 3/2010 | Hu et al. |
| 2010/0105955 A1 | 4/2010 | Alibhai et al. |
| 2010/0105963 A1 | 4/2010 | Hu |
| 2010/0297716 A1 | 11/2010 | Tajima et al. |
| 2010/0317822 A1 | 12/2010 | Boussie et al. |
| 2010/0317823 A1 | 12/2010 | Boussie et al. |
| 2010/0317825 A1 | 12/2010 | Boussie et al. |
| 2010/0330626 A1 | 12/2010 | Burgard et al. |
| 2011/0059485 A1 | 3/2011 | Caiazza et al. |
| 2011/0125118 A1 | 5/2011 | Lynch |
| 2011/0144377 A1 | 6/2011 | Eliot et al. |
| 2011/0195466 A1 | 8/2011 | Burgard et al. |
| 2011/0218318 A1 | 9/2011 | Boussie et al. |
| 2011/0306790 A1 | 12/2011 | Murphy et al. |
| 2012/0135481 A1 | 5/2012 | Jessen et al. |

FOREIGN PATENT DOCUMENTS

| | | |
|---|---|---|
| WO | 02/42418 A2 | 5/2002 |
| WO | 2006/009434 A1 | 1/2006 |
| WO | 2009/035595 A1 | 3/2009 |
| WO | 2009/072562 A1 | 6/2009 |
| WO | 2009/151728 A2 | 12/2009 |
| WO | 2010/144862 A2 | 12/2010 |
| WO | 2011/003034 A2 | 1/2011 |
| WO | 2011/063055 A2 | 5/2011 |
| WO | 2011/094457 A1 | 8/2011 |
| WO | 2011/140386 A2 | 11/2011 |
| WO | 2012/019175 A2 | 2/2012 |

OTHER PUBLICATIONS

Deok, et al., Influence of gluconeogenic phosphoenolpyruvate carboxykinase (PCK) expression on succinic acid fermentation in *Escherichia coli* under high bicarbonate condition, J. Microbiol. Biotechnol., vol. 16(9), pp. 1448-1452 (2006).

Chica, et al., Semi-rational approaches to engineering enzyme activity: combining the benefits of directed evolution and rational design, Curr. Opi. Biotechnol, vol. 16, pp. 378-384 (2005).

Devos, et al., Practical limits of function prediction; Proteins: Structure, Function and Genetics, vol. 41, pp. 98-107 (2000).

Enzyme Entry 2.2.3.1.; one page downloaded from http://enzyme.expasy.org/ on Sep. 10, 2016.

Falentin, H., et al., The Complete Genome of Propionibacterium freudenreichii CIRM-BIAI, a Hard Actinobacterium with Food and Probiotic Applications, Plos One, vol. 5, No. 7, pp. 1-12 (Jan. 1, 2010).

Houwen, et al., Enzymatic evidence for involvement of methylmalonyl-CoA pathway in propionate oxidation by Syntrophobacter wolinil. Arch Microbiol., vol. 155, pp. 52-55 (1990).

Kimchi-Sarfaty, et al., A "Silent" polymorphism in the MDR1 gene changes substrate specificity, Science, vol. 315, pp. 525-528 (2007).

Kisselev, L., Polypeptide release factors in prokaryotes and eukaryotes: same function, different structure, Structure, vol. 10, pp. 8-9 (2002).

International Search Report and Written Opinion dated Dec. 5, 2011 Appl. No. PCT/US2011/046869.

Millard, et al., Enhanced production of succinic acid by overexpression of phosphoenolpyruvate carboxlase in *Escherichia coli*, Appl. Environ. Microbiol., vol. 62(5), pp. 18108-18110 (1996).

Murtif et al., Mutagenesis affecting carboxyl terminus of the biotinyl subunit of transcarboxylase, J. Biol. Chem., vol. 262(24), pp. 11813-11816 (1987).

Nackley, et al., Human Caechol-O-Methytransferase haplotypes modulate protein expression by altering mRNA secondary structure, Science, vol. 314, pp. 1930-1933 (2006).

Sauna, et al., Silent polymorhisms speak: Flow they affect pharmacogenomics and the treatment of cancer, Cancer Res., vol. 67(20), pp. 9609-9612 (2007).

Seffernick, et al., Melamine deaminase and Atrazine chlorohydrolase: 98 percent identical but functionally different. J. Bacteriol., vol. 183(8), pp. 2405-2410 (2001).

Sen, et al., Developments in directed evolution for improving enzyme functions, Appl. Biochem. Biotechnol., vol. 143, pp. 212-223 (2007).

Shenoy, et al., Effect of mutations at Met-88 and Met-90 on the biotination of apo 1.3S subunit of transcarboxylase. FASEB J., vol. 2, pp. 2505-2511 (1988).

Steen, E., et al., Microbial production of fatty-acid-derived fuels and chemicals from plant biomass, Nature, vol. 463, No. 7280, pp. 559-562 (Jan. 28, 2010).

Suwannakham, S., et al., Enhanced proprionic acid fermentation byPropionibacterium acidipropionici mutant obtained by adaptation in a firbrous-bed bioreactor, Biotechnology and BioEngineering, vol. 91, pp. 325-337 (Jun. 23, 2005).

Whisstock, et al., Prediction of protein function from protein sequence; Q. Rev. Biophysics, vol. 36 (3), pp. 307-340 (2003).

Wishart, et al., A single mutation converts a novel phosphotyrosine binding domain into a dual-specificity phosphatase, J. Viol. Chem., vol. 270 (45), pp. 26782-26785 (1995).

Witkowsi, et al., Conversion of b-ketoacyl synthase to a Malonyl Decarboxylase by replacement of the active cystein with glutamine; Biochemistry, vol. 38, pp. 11643-11650 (1999).

Zelle Rintz, M., et al., Phosphoenolpyruvate Carboxykinase as the Sole Anaplerotic Enzyme in *Saccharomyces cerevisiae*, Applied and Environmental Microbiology, vol. 76, No. 16, pp. 5383-5389 (Aug, 1, 2020).

Zhang, X., et al., Metabolic evolution of energy-conserving pathways for succinate production in *Escherichia coli*, Proceedings of the National Academy of Sciences, vol. 106, No. 48, pp. 20180-20185 (Dec. 1, 2009).

[No Author Listed] Accession No. AAS20429, NCBI Database, Bugler, M. and Fuchs, G., accessed at www.ncbi.nlm.nih.gov/protein/AAS20429, accessed on Jun. 11, 2013; 2 pages.

[No Author Listed] Accession No. YP_001636209.1, NCBI Database, Copeland, A., et al., accessed at www.ncbi.nlm.nih.gov/proteinNP _001636209.1, accessed on Jun. 11, 2013; 3 pages.

[No Author Listed] Accession No. YP 002570540, NCBI Database, Lucas, S., et al., accessed at www.ncbi.nlm.nih.gov/protein/YP 002570540, accessed on Jun. 11, 2013; 3 pages.

[No Author Listed] Accession No. YP_002462600, NCBI Database, Lucas, S., et al., accessed at www.ncbi.nlm.nih.gov/protein/YP_ 002462600, accessed on Jun. 11, 2013; 3 pages.

[No Author Listed] Accession No. ZP_076845961, NCBI Database, Kuznetsov, B. B. and Beletsky, A. V., accessed at www.ncbi.nlm.nih.gov/protein/ZP 07684596.1 ?report=genpept, accessed on Jun. 11, 2013; 2 pages.

[No Author Listed] Accession No. YP 001433009, NCBI Database, Copeland, A., et al.., accessed at www.ncbi.nlm.nih.gov/protein/YP _001433009, accessed on Jun. 11, 2013; 3 pages.

[No Author Listed] Accession No. YP 001277512, NCBI Database, Copeland, A., et al., accessed at www.ncbi.nlm.nih.gov/protein/YP _001277512, accessed on Jun. 11, 2013; 3 pages.

[No Author Listed] Accession No. ZP 01039179.1, NCBI Database, Falkowski, P., et al.., accessed at www.ncbi.nlm.nih/gov/protein/ZP 010391791 ?report=genpept, accessed on Jun. 11, 2013; 2 pages.

[No Author Listed] Accession No. ZP_04957196.1, NCBI Database, Amann, R., et al., accessed at www.ncbi.nlm.nih.gov/protein/ZP_04957196.1?report=genpept, accessed on Jun. 11, 2013; 2 pages.

[No Author Listed] Accession No. U00096.2, NCBI Database, Blattner, F. R., et al., accessed at www.ncbi.nlm.nih.gov/nuccore/U00096, accessed on Jun. 11, 2013; 119 pages.

Aklujkar, M., et al., "The Genome of Geobacter bemidjiensis, exemplar for the subsurface Glade of *Geobacter* species that

(56) References Cited

OTHER PUBLICATIONS predominate in FE(III)-reducing subsurface environments," BMC Genomics 11:490, BioMed Central, England (Sep. 2010); (18 pages).
Aldai, N., et al., "Gas-liquid chromatographic method for analysing complex mixtures of fatty acids including conjugated linoleic acids (cis9trans11 and trans10cis12 isomers) and long-chain (n-3 or n-6) polyunsaturated fatty acids: Application to the intramuscular fat of beef meat," Journal of Chromatography a 1110:133-39, Elsevier B.V., Netgherlands (2006).
An, J.H., et al., "A gene cluster encoding malonyl-CoA decarboxylase (MatA), malonyl-CoA synthetase (MatB) and a putative dicarboxylate carrier protein (MatC) in Rhizobium trifolii-cloning, sequencing, and expression of the enzymes in *Escherichia coli*," Eur J Biochem. Oct. 15, 1998;257(2)395-402.
Beller, H. R., et al., "Genes Involved in Long-Chain Alkene Biosynthesis in Micrococcus luteus," Appl Environ Microbiol. Feb. 2010; 76(4): 1212-1223; published ahead of print on Dec. 28, 2009.
Berrios-Rivera, S. J., et al., "Metabolic Engineering of *Escherichia coli* : Increase of NADH Availability by Overexpressing an NADP-Dependent Formate Dehydrogenase," Metabolic Engineering 4, 217-229 (2002).
Black, P. N., et al., "Transmembrane Movement of Exogenous Long-Chain Fatty Acids: Proteins, Enzymes, and Vectorial Esterification," Microbiol Mol Biol Rev. Sep. 2003; 67(3): 454-472.
Burgard, A. P., "OptKnock: A Bilevel Programming Framework for Identifying Gene Knockout Strategies for Microbial Strain Optimization," Biotech. Bioeng. 84(6): 647-57, Wiley Periodicals, Inc. US (2003).
Carey, P. R., et al., "Transcarboxylase: one of nature's early nanomachines," IUBMB Life. Oct. 2004;56(10):575-83.
Davis, M. S., et al., "Inhibition of *Escherichia coli* acetyl coenzyme A carboxylase by acyl-acyl carrier protein," J Bacteriol. Feb. 2001;183(4):1499-503.
Heath, R. J., et al., "Regulation of fatty acid elongation and initiation by acyl-acyl carrier protein in *Escherichia coli*," J Biol Chem. Jan. 26, 1996;271(4)1833-6.
Hopner, T., et al., "Determination with Formate Dehydrogenase," in Bergmeyer H.U. ed, Methods of Enzymatic Analysis, Ed 2, vol. 3, pp. 1551-1555, Academic Press, New York (1974).
Hügler, M., et al., "Malonyl-Coenzyme A Reductase from Chloroflexus aurantiacus, a Key Enzyme of the 3-Hydroxypropionate Cycle for Autotrophic CO2 Fixation," J Bacteriol. May 2002; 184(9): 2404-2410.
Inui, H., et al., "Wax ester fermentation in Euglena gracilis," FEBS Lett., 150(1): 89-93, Elsevier Biomedical Press, Netherlands (1982).
Inui, H., et al., "Fatty acid synthesis in mitochondria of Euglena gracilis," Eur. J. Biochem. 142:121-26, FEBS, England (1984).
Jenke-Kodama, H., et al., "Evolutionary implications of bacterial polyketide synthases," Mol Biol Evol. Oct. 2005;22 (10):2027-39. Oxford University Press, England.
Jeppson, M., et al., "Reduced oxidative pentose phosphate pathway flux in recombinant xylose-utilizing *Saccharomyces cerevisiae* strains improves the ethanol yield from xylose," Appl Environ Microbiol. Apr. 2002;68 (4):1604-9.
Kalscheuer, R., et al., "A novel bifunctional wax ester synthase/acyl-CoA:diacylglycerol acyltransferase mediates wax ester and triacylglycerol biosynthesis in Acinetobacter calcoaceticus ADP1," J Biol Chem. Mar. 7, 2003;278 (10):8075-82.
Kalscheuer, R., et al., "Microdiesel: *Escherichia coli* engineered for fuel production," Microbiology. Sep. 2006;152 (Pt 9):2529-36.
Karhumaa, K., et al., "Comparison of the xylose reductase-xylitol dehydrogenase and the xylose isomerase pathways for xylose fermentation by recombinant *Saccharomyces cerevisiae*," Microb Cell Fact. Feb. 5, 2007;6:5; 10 pages.
Kieboom, J., et al., "Identification and molecular characterization of an efflux pump involved in Pseudomonas putida S12 solvent tolerance," J Biol Chem. Jan. 2, 1998; 273(1):85-91.
Kim, Y., et al., "Construction of an *Escherichia coli* K-12 mutant for homoethanologenic fermentation of glucose or xylose without foreign genes," Appl Environ Microbiol. Mar. 2007;73(6):1766-71; published ahead of print Jan. 26, 2007.
Kosaka, T., et al., "The genome of Pelotomaculum thermopropionicum reveals niche-associated evolution in anaerobic microbiota," Genome Res. Mar. 2008;18(3):442-8.
Kuyper, M., et al., "Evolutionary engineering of mixed-sugar utilization by a xylose-fermenting *Saccharomyces cerevisiae* strain," FEMS Yeast Res. Jul. 2005;5(10):925-34.
Kuyper, M., et al., "Metabolic engineering of a xylose-isomerase-expressing *Saccharomyces cerevisiae* strain for rapid anaerobic xylose fermentation," FEMS Yeast Res. Feb. 2005;5(4-5):399-409.
Kuyper, M., et al., "Minimal metabolic engineering of *Saccharomyces cerevisiae* for efficient anaerobic xylose fermentation: a proof of principle," FEMS Yeast Res. Mar. 2004;4(6):655-64.
Leal, T.F. and De Sá-Nogueira, I., "Purification, characterization and functional analysis of an endo-arabinose (AbnA) from Bacillus subtilis," FEMS Microbiol. Let., 241:41-48, Elsevier, B.V., Netherlands (2004).
Li, S-J., et al, "Growth rate regulation of *Escherichia coli* acetyl coenzyme A carboxylase, which catalyzes the first committed step of lipid biosynthesis," J Bacteriol. Jan. 1993;175(2):332-40.
Li, N., et al., "Conversion of fatty aldehydes to alka(e)nes and formate by a cyanobacterial aldehyde decarbonylase: cryptic redox by an unusual dimetal oxygenase," J Am Chem Soc. Apr. 27, 2011;133(16):6158-61.
Liang, S.-T., et al., "Activities of constitutive promoters in *Escherichia coli*," J. Mol. Bio. vol. 292, Issue 1, Sep. 10, 1999, pp. 19-37.
Liu, X., et al., "Two novel metal-independent long-chain alkyl alcohol dehydrogenases from Geobacillus thermodenitrificans NG80-2," Microbiology. Jun. 2009;155:2078-85.
Magnuson, K. et al., "Regulation of fatty acid biosynthesis in *Escherichia coli*," Microbiol Rev. Sep. 1993; 57(3): 522-542.
Matte, A., et al., "Structure and mechanism of phosphoenolpyruvate carboxykinase," J Biol Chem. Mar. 28, 1997;272(13):8105-8.
Mota, L. J., et al., "Mode of action of AraR, the key regulator of L-arabinose metabolism in Bacillus subtilis," Mol. Microbial. 33(3):476-89, Blackwell Science Ltd., England (1999).
Mota, L. J., et al., "Control of the Arabinose Regulon in Bacillus subtilis by AraR in Vivo: Crucial Roles of Operators, Cooperativity, and DNA Looping," J. Bacteriol. 183(14):4190-201, American Society for Microbiology, United States (2001).
Nakamura, Y., et al. "Codon usage tabulated from international DNA sequence databases: status for the year 2000," Nucl. Acids Res. 28(1):292, Oxford University Press, England (2000).
National Microbial Pathogen Data Resource, Seed Subsystem: L-Arabinose_utilization, accessed at http://www .hmpdr.org/FIG/subsys.cgi?user=&ssa _name= L-Arabinose utilization&reQuest= show ssa, accessed on Jun. 11, 2013.
Neumann, G., et al.., "Prediction of the Adaptability of Pseudomonas putida DOT-T1E to a Second Phase of a Solvent for Economically Sound Two-Phase Biotransformations," Appl. Environ. Microbial 71(11):6606-12, American Society for Microbiol., United States (2005).
Pelletier E. et al., "Candidatus Cloacamonas Acidaminovorans": Genome Sequence Reconstruction Provides a First Glimpse of a New Bacterial Division, J Bacteriol. Apr. 2008; 190(7): 2572-2579.
Peralta-Yahya, P. P. and Keasling, J.D., "Advanced biofuel production in microbes," Biotechnol. J 5:147-62, Wiley-VCH Verlag GmbH & Co. KGaA, Germany (Feb. 2010).
Picataggio, S., et at., "Metabolic Engineering of Candida tropicalis for the Production of Long-Chain Dicarboxylic Acids," Biotechnology 10:894-98, Nature Pub. Co., United States (1992).
Rathnasingh, C., et al., "Development and Evaluation of Efficient Recombinant *Escherichia coli* Strains for the Production of 3-Hydroxypropionic Acid From Glycerol," Biotech. Bioeng 104(4):729-39, Wiley Periodicals, Inc., United States (2009).
Rathnasingh, C., et al., "Production of 3-hydroxypropionic acid via malonyl-CoA pathway using recombinant *Escherichia coli* strains," J Biotech. 157:633-40, Elsevier B.V. Netherlands (2012).
Reiser, S. and Somerville, C., "Isolation of Mutants of Acinetobacter calcoaceticus Deficient in Wax Ester Synthesis and Complementation of One Mutation with a Gene Encoding a Fatty Acyl Coenzyme A Reductase," J. Bacteriol. 179(9):2969-75 (1997).

(56) References Cited

OTHER PUBLICATIONS

Rodolfi, L., et al., "Microalgae for Oil: Strain Selection, Induction of Lipid Synthesis and Outdoor Mass Cultivation in a Low-Cost Photobioreactor," Biotech. Bioeng. 102(1):100-12, Wiley Periodicals, Inc., United States (2009).

Sá-Nogueira, I., et al, "The Bacillus subtilis L-arabinose (ara) operon: nucleotide sequence, genetic organization and expression," Microbiology, 143:957-969, Society for General Microbiology, Great Britain (1997).

Sauer, U., "Evolutionary Engineering of Industrially Important Microbial Phenotypes," Advances in Biochemical Engineering/Biotechnology 73:129-69, Springer-Verlag, Germany (2001).

Schleif, R., "Regulation of the L-arabinose operon of *Escherichia coli*," Trends Genet. 16(12):559-65, Elsevier Science Ltd., England (2000).

Shanks, R.M.Q. et al., "*Saccharomyces cerevisiae*-based Molecular Tool Kit for Manipulation of Genes from Gram-Negative Bacteria," Appl. Environ. Microbiol., 2006, 72(7): 5027-5036.

Shaw, A.J. et al., "Natural Competence in *Thermoanaerobacter* and *Thermoanaerobacterium* Species," Appl. Environ. Microbiol., 2010, 76(14):4713-4719.

Sukovich, D. J., et al., "Widespread Head-to-Head Hydrocarbon Biosynthesis in Bacteria and Role of OleA," Appl Environ Microbiol. Jun. 2010; 76(12): 3850-3862.

Tsuruta, H., et al., "High-level production of amorpha-4,11-diene, a precursor of the antimalarial agent artemisinin, in *Escherichia coli*," PLoS One 2009; 4(2): e4489.

Vanhanen, S., et al., "A consensus sequence for long-chain fatty-acid alcohol oxidases from Candida identifies a family of genes involved in lipid omega-oxidation in yeast with homologues in plants and bacteria," J Biol Chem. Feb. 11, 2000;275(6):4445-52.

Van Beilen, J.B., et al., "Analysis of Pseudomonas putida alkane-degradation gene clusters and flanking insertion sequences: evolution and regulation of the alk genes," Microbiology, Jun. 2001 147: 1621-1630.

Van Walsum, G.P., et al., "Allocation of ATP to synthesis of cells and hydrolytic enzymes in cellulolytic fermentative microorganisms: Bioenergetics, kinetics, and bioprocessing," Biotech. Bioeng., 58:316-320, (1998).

Wahlen, B. D., et al., "Purification, Characterization, and Potential Bacterial Wax Production Role of an NADPH-Dependent Fatty Aldehyde Reductase from Marinobacter aquaeolei VT8," Appl Environ Microbiol. May 2009; 75(9): 2758-2764.

Wang, L., et al., "Isolation and characterization of a novel thermophilic Bacillus strain degrading long-chain n-alkanes," Extremophiles 10:347-56, Springer-Verlag, Germany (2006).

Watanabe, S., et al., "Cloning, Expression, and Characterization of Bacterial L-Arabinose 1-Dehydrogenase Involved in an Alternative Pathway of L-Arabinose Metabolism," J. Biol. Chem., 281(5):2612-2623, American Society for Biochemistry and Molecular Biology, United States (2006).

Whited, G. M., et al., "Development of a gas-phase bioprocess for isoprene-monomer production using metabolic pathway engineering," Industrial Biotechnology 6(3):152-63, Mary Ann Liebert, Inc., United States (Jun. 2010).

Wood, H. G. and Stjernholm, R., "Transcarboxylase, II. Purification and Properties of Methylmalonyl-Oxaloacetic Transcarboxylase," PNAS. 47:289-303, National Academy of Sciences, United States (1961).

Yan, Y. and Liao, J. C., "Engineering metabolic systems for production of advanced fuels," J. Ind. Microbiol. Biotechnol. 36:471-79, Springer, England (2009).

\* cited by examiner

FIG. 2
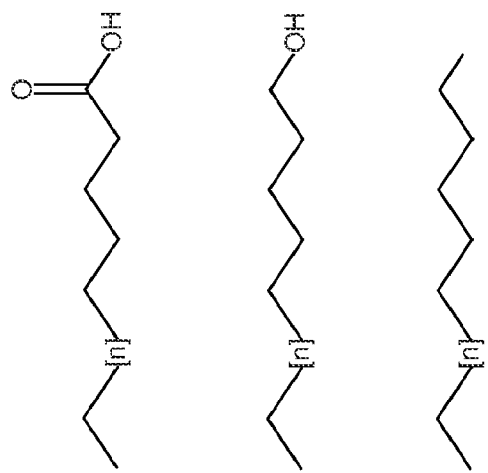
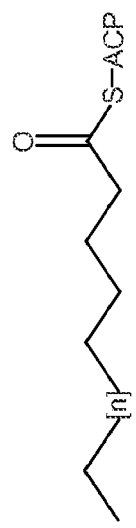
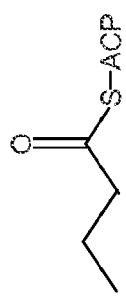

FIG. 7A

Transcarboxylase 5S subunit

```
                                          1                                                  50
SEQ. ID NO. 11:   Pfreud 5S      (1)   MSPREIEVSEPK VG L  LDAHQSI  ETRAME  VGACA  AK Y
SEQ. ID NO. 19:   Pacnes 5S      (1)   ----------MSERKTGV L  PDAHQSI  ETRAME  VDACA  A  E
SEQ. ID NO. 25:   Cthe_0701      (1)   ----------MAKVK  T  PDAHQSI  R E  LFIIDKI  EI Y
SEQ. ID NO. 33:   Tsacch orf888  (1)   ----------MSKIK  TV RDAHQSI  A  TEE LFI EKL  E
                                         51                                                 100
SEQ. ID NO. 11:   Pfreud 5S      (51)  M VI  TGGA  TS    EDEVERL  TERKLMPNS  QML GQNL GY
SEQ. ID NO. 19:   Pacnes 5S      (43)  M I  TGGA  T     EDEVERL  TERKLLPNS  QML GQNL GY
SEQ. ID NO. 25:   Cthe_0701      (41)  H  V  TGGA  V    EDEVERL  I KCHCK TP QML GQNL GY
SEQ. ID NO. 33:   Tsacch orf888  (41)  T  I  TGGA  T     EDEVERL  L KKAIK TP QML GQNL GY
                                        101                                                 150
SEQ. ID NO. 11:   Pfreud 5S      (101) R  NE  WDR  KS    GMDV  FDA  PE  MAHMAAV  AGK
SEQ. ID NO. 19:   Pacnes 5S      (93)  R  M  WDK  KA    BMDV  FDA L PE  BHANAAV  AGK
SEQ. ID NO. 25:   Cthe_0701      (91)  K  A   Y   KVA   D I  F I  P   ETAIBAC  KE G
SEQ. ID NO. 33:   Tsacch orf888  (91)  K  PE   L  VE    DI   F F  P   EVPLKS  KVGA
                                        151                                                 200
SEQ. ID NO. 11:   Pfreud 5S      (151) GTIC  ISE  TVEGY  LG  LI  GADSI   KDAAI  QE  V
SEQ. ID NO. 19:   Pacnes 5S      (143) GTIC  TS   PESEY Q  R TI  GADSI   KDAAI  QE  V
SEQ. ID NO. 25:   Cthe_0701      (141) GTVC  TSE  IELFV  KT   VE ADSI   KDAGL  V   G
SEQ. ID NO. 33:   Tsacch orf888  (141) A  IV  VS   DHYI VKS  D  L  ADSI   G  I  V     G
                                        201                                                 250
SEQ. ID NO. 11:   Pfreud 5S      (201) A   YGQK   Q    S  VT  VSL  KAIPAG   D  I  SMSL
SEQ. ID NO. 19:   Pacnes 5S      (193) G  ENH-P VQ  L   S  VTLVLQ  KAIPAG   A  I  SMSL
SEQ. ID NO. 25:   Cthe_0701      (191) A   EIV--KVP  IT     SMTYI KAIPAG  IVD  I  SMSTS
SEQ. ID NO. 33:   Tsacch orf888  (191) S   AL--Y F    V  L  SMTYI KAIPAG   VD  I  SLAI
                                        251                                                 300
SEQ. ID NO. 11:   Pfreud 5S      (251) NF   SVE  EM       YD  H  KDE  KAIRPKYKPESKIL DT
SEQ. ID NO. 19:   Pacnes 5S      (242) N   SLVE       MD  L  KDE  KKVREKYKPFSKILVN
SEQ. ID NO. 25:   Cthe_0701      (239) QF     VAT KG P    LDK S  ADY RPLKEKYI EGLLDVK M
SEQ. ID NO. 33:   Tsacch orf888  (239) QF A   IVAA K   D   LKLI A  E VVKQ HK D  MSLLMS
                                        301                                                 350
SEQ. ID NO. 11:   Pfreud 5S      (301) ----S-  KS I  GGMLS  ME   AQ   EDRMDF  A  VPRV  KA
SEQ. ID NO. 19:   Pacnes 5S      (292) ----N-I  S I  GGMLS  ME   AQ  GDRMDF  A  VPRV  KDA
SEQ. ID NO. 25:   Cthe_0701      (289) GVDVNTLKY V  GGMLS  LV  KQ   VDK E  I  VPRV  D
SEQ. ID NO. 33:   Tsacch orf888  (289) - VDVKA  S I  GGMLS  LV  KQON  L  KY V  LN VPRV  DL
                                        351                                                 400
SEQ. ID NO. 11:   Pfreud 5S      (347) LVTE  S   VGTQAV  M    RMTG  PADINL  A  PADN
SEQ. ID NO. 19:   Pacnes 5S      (338) LVTE  S   VGTQAV  L MNGS  NITA  PADLA    PIGEINPEI
SEQ. ID NO. 25:   Cthe_0701      (339) LVTE  ST  VGTQAV  N VT --ER MV  SKALTK  Y  PARVIPE V
SEQ. ID NO. 33:   Tsacch orf888  (338) LVTE  S   VGTQAV  LN T --ER  IV  KDYVK  Y  PPAI D
                                        401                                                 450
SEQ. ID NO. 11:   Pfreud 5S      (395) VKLAE  QSGK    TQ  PADI LP  EWEEQ   EAAA KGPNGI  DVT
SEQ. ID NO. 19:   Pacnes 5S      (388) V MAKK QTGKE   DQ PADI LP  EWD LV  QAK   GPDC  DVT PN
SEQ. ID NO. 25:   Cthe_0701      (383) QKKILK--  E  TV  AI   E LD  IRN---EMKEYLE  DV N
SEQ. ID NO. 33:   Tsacch orf888  (387) RKKIIG--  SV  N  A  I   LDECKN---EIKEFIE  DV S
                                        451                                                 500
SEQ. ID NO. 11:   Pfreud 5S      (445)   VA PV  E HHAEGPHSVALTDAQLKA   GDEKSLAVAGPVTNMWVG
SEQ. ID NO. 19:   Pacnes 5S      (438)   G AFK     AQGPKSVAMTEAQLKA  K G-TGAAGIAGPVN NYVG
SEQ. ID NO. 25:   Cthe_0701      (433)   CVAEK      KAQKY EPD  Y  NRVHEV-----------------
SEQ. ID NO. 33:   Tsacch orf888  (432)   V ARR  FE  QAKKYRIDSTLLNI  ERVHFI-----------------
                                        501      511
SEQ. ID NO. 11:   Pfreud 5S      (495) GTVREVTVQQA
SEQ. ID NO. 19:   Pacnes 5S      (487) GNSHQVTVEPR
SEQ. ID NO. 25:   Cthe_0701      (466) -----------
SEQ. ID NO. 33:   Tsacch orf888  (465) -----------
```

FIG. 7B

Transcarboxylase 1.3S subunit

```
                                      1                                                  50
SEQ. ID NO. 8:    Pfreud 1.3S    (1)  -M LKVT GTA D  DVDK HENPMGT LFGG  GGAPAPRAA GAG-
SEQ. ID NO. 19:   Pacnes 1.3S    (1)  -M LKVT  VA D  DVDKTANAPMAPILFGSGAS---  MKAS GG-
SEQ. ID NO. 23:   Cthe_0700      (1)  MK  LI  NGN    EEIR GASAPQVT STP AAPAPS APA P KT
SEQ. ID NO. 31:   Tsacch or0947  (1)  MK  IVT  GKK D   EEVK  VA EKKAKE TAAKNA  ASVKSK---
                                      51                                                 100
SEQ. ID NO. 8:    Pfreud 1.3S    (49) --------AGKAGEGE P  LA   VSKILV  D         AMK
SEQ. ID NO. 19:   Pacnes 1.3S    (46) --------AGKAGE EV P LA  VARILVA   KA  OVL T  AMK
SEQ. ID NO. 23:   Cthe_0700      (51) AAPKKDS VPAGATA K  MF   IRV  D KR OVL   AMK
SEQ. ID NO. 31:   Tsacch or0947  (48) QVEV N---EVK GF  INA MF  LLVKIS      RS VL   AMK
                                      101                        132
SEQ. ID NO. 8:    Pfreud 1.3S    (92)   NA T    VE  VL  RDA    QG   IG
SEQ. ID NO. 19:   Pacnes 1.3S    (89)   NA A    VK  IL  AVGE   QG  VALG
SEQ. ID NO. 23:   Cthe_0700      (101)  VA N   IVASI  SKGA  NV    VSLR
SEQ. ID NO. 31:   Tsacch or0947  (96)   S Y   II S  SKGAS NT     YLR
```

FIG. 7C

Transcarboxylase 12S subunit (N-terminus)

```
                                            1                                                  50
SEQ. ID NO. 14:   Pfreud 12S-N     (1)   MAENNNEKLASTMEGRVEQ AE RQVIEA GE RV K   CK
SEQ. ID NO. 17:   Pacnes 12S       (1)   MAEKKPIKLADTMAGRIEQ AL RH VEL GE EDRL K  DR CK
SEQ. ID NO. 21:   Cthe_0699        (1)   ----------MDKV KIGL REKLAQVEQ GG AEKTA K H DA V
SEQ. ID NO. 29:   Tsacch or0945    (1)   ----------MSID RIE L RREMVLE GG LDKVEKQ  K GI  R
                                            51                                                100
SEQ. ID NO. 14:   Pfreud 12S-N    (51)   LNN   PH  D VGAFRK  TTL       AVV  AL   Y  RGT  LG
SEQ. ID NO. 17:   Pacnes 12S      (51)   T  M   AY  D VGAFRK  TTL      AK   AL   V  CPAT  G  V
SEQ. ID NO. 21:   Cthe_0699       (41)   TQA    S  V    PV T  SID       KK   G   V  CG   L
SEQ. ID NO. 29:   Tsacch or0945   (41)   IY       S   AYV H CID    P QRT     VGG  GI   LL V
                                            101                                               150
SEQ. ID NO. 14:   Pfreud 12S-N   (101)   AS  D T VM GE SA E TQSI VV   QAIL    FL YY  DSGG AE   I
SEQ. ID NO. 17:   Pacnes 12S     (101)   AS  D T   GE SA E TQSI VV   QSLL     FL FF  SGGA    I
SEQ. ID NO. 21:   Cthe_0699      (91)    AA  D T I GG SI   M A II K  DMAMKM   FIS N DSGGA  DG I
SEQ. ID NO. 29:   Tsacch or0945  (91)    YA   D T I GG SI Y A II KI NDMALKM E IG N DSGGAP EG
                                            151                                               200
SEQ. ID NO. 14:   Pfreud 12S-N   (151)   SI SE YGKM  AN VKL SGV EQ A  AG  CA GG AS GP     DI  I  K
SEQ. ID NO. 17:   Pacnes 12S     (151)   SI SE YGKM  AN VKL SGV EQ A  AG  CA GG AS GPA    DI  I  K A
SEQ. ID NO. 21:   Cthe_0699      (141)   A   G  I YRN  LAS GV  EQI SV  G   AGGA V  PA    DI   V  T S
SEQ. ID NO. 29:   Tsacch or0945  (141)   A SG Y I PRN  LAS GV  EQI SV  G   AGGA V  PA    DI   V  K S
                                            201                                               250
SEQ. ID NO. 14:   Pfreud 12S-N   (200)   M    IG  GV  S  G   AD   GG AE   MA   N    VAEDDA  ELI A
SEQ. ID NO. 17:   Pacnes 12S     (200)   M    IG  GV  S  G   AD   GG AD   MST  N    VAEDDA  VLI A
SEQ. ID NO. 21:   Cthe_0699      (191)   C   IG  GV  S  G   FE   GG AET  NS   VA  RS    EGIEQI
SEQ. ID NO. 29:   Tsacch or0945  (191)   C   IG  GV  A VG  V SAP  GG SIT  STK  GVA  RAE  DEECLKM
                                            251                                               300
SEQ. ID NO. 14:   Pfreud 12S-N   (250)   K    GF  P  NTEEA   VM N   VSPNTE   RI   IDG    VRDV
SEQ. ID NO. 17:   Pacnes 12S     (250)   K L S    NTEDAQISN  N   VSPQ E   RI   LDG    VRDV
SEQ. ID NO. 21:   Cthe_0699      (241)   K  I SY    NL D PIVPTQ   I RITDN VG   DD   P  MMEI
SEQ. ID NO. 29:   Tsacch or0945  (241)   R  I SY    NLEDPPQLAT    I RFSGR II   DD  PK    MKDV
                                            301                                               350
SEQ. ID NO. 14:   Pfreud 12S-N   (299)   KI   WG DYL V  AGY T  LVTA   AN V  R  VG I A  Q    MS   AS
SEQ. ID NO. 17:   Pacnes 12S     (299)   KI  CW DYL V  AGW T  IV A   AV V R  VG I A  Q   MAA V I S
SEQ. ID NO. 21:   Cthe_0699      (291)   V  LN DF  I QK   T   II Q   V GT  I   V G I A NQ   AA V  S
SEQ. ID NO. 29:   Tsacch or0945  (291)   I   EE VI   SQAM      TT A   K R  VG I A NQ    VA  V  N
                                            351                                               400
SEQ. ID NO. 14:   Pfreud 12S-N   (349)   KAA      T  G SI    LVQLV DVR       GV Q Y G    RHGAK   YA  S
SEQ. ID NO. 17:   Pacnes 12S     (349)   KAA  IT  G ST    LVQLV DVR    G  VQ LY GG    RHCAK  TYA  S
SEQ. ID NO. 21:   Cthe_0699      (341)   KA  ARI   V   GI A NI   LIT  DV  G   GF H   GV  RHCAK   YA  S
SEQ. ID NO. 29:   Tsacch or0945  (341)   KA SR  I   V   GI A NII  LNIV DV  G  I     G V  RHCAK   YA  S
                                            401                                               450
SEQ. ID NO. 14:   Pfreud 12S-N   (399)   TVP  ITVV   KAYGG    LA  RI  GA   V  A     T AVMG   AAN
SEQ. ID NO. 17:   Pacnes 12S     (399)   TVP   VV    KAYGG    L   RI  GA   V  A     T AVMG   AAN V
SEQ. ID NO. 21:   Cthe_0699      (391)   TVP   VI    KAYGG AV  A NSK   GA    V  A    T AVMG  PGAN
SEQ. ID NO. 29:   Tsacch or0945  (391)   TVPR VTLIV  KAYGG AV  A CSK   GA  V V  A    T AVMG P GAAN
                                            451                                               500
SEQ. ID NO. 14:   Pfreud 12S-N   (449)   I RKE    KAAL D  DAM  AEK  I  SN  N   P VAA  QV DV    AD R
SEQ. ID NO. 17:   Pacnes 12S     (449)   I RE   KDSE    A AAK  EL RNA    P VA   DV  I DEAD R
SEQ. ID NO. 21:   Cthe_0699      (441)   I KK   AAAL D NET   KL    P K     P   VA   VDD I L AT    I
SEQ. ID NO. 29:   Tsacch or0945  (441)   V KK   KSSD  V     NEK     RN A     P   VA   VDD V LQ   P
                                            501              526
SEQ. ID NO. 14:   Pfreud 12S-N   (499)   KIAS  EMYAT  R T  EA  KNHG NF  C
SEQ. ID NO. 17:   Pacnes 12S     (499)   KITA  ETYAT  Q G  EA  KNHG V  C
SEQ. ID NO. 21:   Cthe_0699      (491)   RLIS  LEMLAS     N RA KNHGN  L
SEQ. ID NO. 29:   Tsacch or0945  (491)   RLIS  DMLMS N S R  KNHGNF V
```

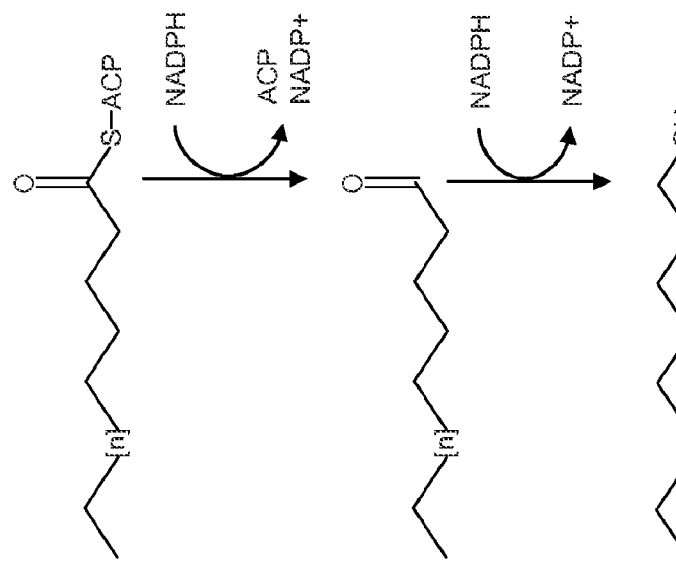
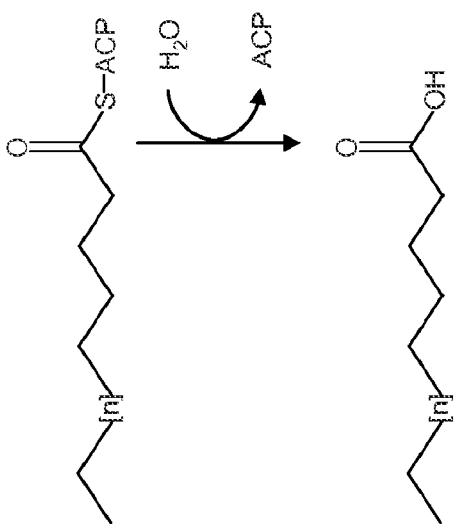
FIG. 13

FIG. 22A

|  | pMU690 | pMU3061 | pMU3062 | pMU3063 | pMU3064 |
|---|---|---|---|---|---|
| Sum | 45 | 154 | 201 | 39 | 54 |
| 12:0 | 0.00 | 49.53 | 2.82 | 0.25 | 0.25 |
| 14:0 | 1.94 | 1.88 | 70.37 | 3.57 | 1.76 |
| 14:1 | 0.00 | 15.92 | 2.56 | 0.16 | 0.14 |
| 15:0 | 0.00 | 0.00 | 0.43 | 0.14 | 0.00 |
| 15:1 | 0.00 | 0.00 | 0.00 | 0.00 | 0.00 |
| 16:0 | 21.87 | 5.39 | 19.30 | 12.41 | 20.21 |
| 16:1w5 | 0.00 | 0.00 | 0.00 | 0.00 | 0.00 |
| 16:1w7 | 5.74 | 4.01 | 75.74 | 6.28 | 5.57 |
| 17:0 | 0.49 | 0.38 | 0.52 | 0.37 | 0.34 |
| 17:1 | 5.76 | 1.85 | 3.21 | 4.93 | 5.72 |
| 18:0 | 1.76 | 1.94 | 1.72 | 1.37 | 2.19 |
| 18:1w9 | 0.37 | 0.54 | 0.16 | 0.14 | 0.17 |
| 18:1w7 | 5.73 | 10.16 | 7.53 | 5.36 | 12.13 |
| 18:2w6 | 0.00 | 0.36 | 7.65 | 0.34 | 0.35 |
| 20:0 | 0.00 | 0.00 | 0.00 | 0.00 | 0.00 |
| 20:1w9 | 0.00 | 0.00 | 0.49 | 0.00 | 0.27 |
| 20:2w6 | 0.00 | 0.00 | 3.64 | 0.00 | 0.00 |
| 20:3w6 | 0.00 | 0.00 | 1.33 | 0.00 | 0.00 |
| 20:5w3 | 0.00 | 0.00 | 1.05 | 0.00 | 0.00 |
| 22:0 | 0.00 | 0.00 | 0.00 | 0.00 | 0.00 |
| 22:1w9 | 0.30 | 0.13 | 0.29 | 0.23 | 0.22 |
| 24:0 | 0.00 | 0.00 | 0.00 | 0.00 | 0.00 |
| other | 0.57 | 61.53 | 2.05 | 3.72 | 4.42 |

|        | µmax  | SD   |
|--------|-------|------|
| M2767  | 0.005 | 0.00 |
| M2767-T3 | 0.24 | 0.00 |

|        | µmax | SD   |
|--------|------|------|
| M2772  | 0.01 | 0.00 |
| M2772-T3 | 0.18 | 0.00 |

FIG. 31

12S subunits

|  |  |  | 1 | 50 |
|---|---|---|---|---|
| SEQ. ID NO. 67: | D.propionicus_12S | (1) | ----------------TKEKE QKKAKALL QE RDN I QKKYA | |
| SEQ. ID NO. 51: | C.kroppenstedtii_12S | (1) | MSEQ----PHDP PER GG EEDNN RL QA D DRGKM | |
| SEQ. ID NO. 14: | P.feudenreichii_12S | (1) | MAENNNLKLAS EGR EG A G QV EA ER K QG C N | |
| SEQ. ID NO. 59: | G.bemidjiensis_12S | (1) | ----------- S EK KA DK SEE KL RS I Q AQ S I | |
| SEQ. ID NO. 37: | C.bescii_12S | (1) | ----------- TN RE K E LKL E K Q DSK L | |
| SEQ. ID NO. 45: | C.cellulolyticum_12S | (1) | ----------- QI K NM TT AK EEK A R AD I A | |
| SEQ. ID NO. 21: | C.thermocellum_12S | (1) | ----------- DKV K GL LAQ EQ A I A DA | |
| SEQ. ID NO. 29: | T.saccharolyticum_12S | (1) | ----------- DR ED L KEM LEK LK E Q K L A | |
| | Consensus | (1) | MSM EKI QLKEKR KI GGG DKIDKQHA GKLTARER | |

|  |  |  | 51 | 100 |
|---|---|---|---|---|
| SEQ. ID NO. 67: | D.propionicus_12S | (41) | QL PG KL YM I FF G AC PY | |
| SEQ. ID NO. 51: | C.kroppenstedtii_12S | (48) | TK DI Q TGM ARK TTH KADAPA G AY E | |
| SEQ. ID NO. 14: | P.feudenreichii_12S | (51) | NN PH DEV A PK TTL KAVV AI V RG TI P MA | |
| SEQ. ID NO. 59: | G.bemidjiensis_12S | (41) | EA KD Q GI AP TN AGKES A C A SV GG M H | |
| SEQ. ID NO. 37: | C.bescii_12S | (39) | EY PG N M V T Q KDTF K CG A K PY | |
| SEQ. ID NO. 45: | C.cellulolyticum_12S | (41) | HL NG VDA I YG F QKKV PG A YN DL P | |
| SEQ. ID NO. 21: | C.thermocellum_12S | (41) | QA E L I FY T SIL QKKV PG D YN EL F | |
| SEQ. ID NO. 29: | T.saccharolyticum_12S | (41) | YK DE V ID V I E KQR IP E VC ED L | |
| | Consensus | (51) | I LLDE SF EIDAFVEHRC DFGMDK KVPGDGVVTGYGTI GR VHV | |

|  |  |  | 101 | 150 |
|---|---|---|---|---|
| SEQ. ID NO. 67: | D.propionicus_12S | (91) | Y G SGTL CM G VT I | |
| SEQ. ID NO. 51: | C.kroppenstedtii_12S | (98) | TT GS A MOSM VAM KA ATT D FI DSGGA EG | |
| SEQ. ID NO. 14: | P.feudenreichii_12S | (101) | AD I G A K TOST VET QQ LT T LFFY GGAR CEG I | |
| SEQ. ID NO. 59: | G.bemidjiensis_12S | (91) | K AL AGG A D VQ LG R T V FN I GG N | |
| SEQ. ID NO. 37: | C.bescii_12S | (89) | Y A A Y M KA K CK C V GG A C GV | |
| SEQ. ID NO. 45: | C.cellulolyticum_12S | (91) | K N VM VDA I V DM LV A AI GGA EL C K | |
| SEQ. ID NO. 21: | C.thermocellum_12S | (91) | K V TY GG GEM HA TT MDM AL A GGA EL C K | |
| SEQ. ID NO. 29: | T.saccharolyticum_12S | (91) | Y V SS G Y AK T N MALM CA GGA C EG V | |
| | Consensus | (101) | AAQDFTVIGGSLGEMHA KI KVMDMALK G PFIGINDSGGARIQEGID | |

|  |  |  | 151 | 200 |
|---|---|---|---|---|
| SEQ. ID NO. 67: | D.propionicus_12S | (141) | T T VL G G AGGA YS A KIQ | |
| SEQ. ID NO. 51: | C.kroppenstedtii_12S | (148) | GR DL YM V VI AG AGGA YSPA D QTPE- | |
| SEQ. ID NO. 14: | P.feudenreichii_12S | (151) | SYG N RLS Q AI A AGG SYS A D TKK- | |
| SEQ. ID NO. 59: | G.bemidjiensis_12S | (141) | K V YR TM L DY V S A AGG A YS A D QTAK- | |
| SEQ. ID NO. 37: | C.bescii_12S | (139) | K D I TLA GV PGI AAIN G AGGA YS A D FNKK- | |
| SEQ. ID NO. 45: | C.cellulolyticum_12S | (141) | S GY DI FY NV L GV PQI SVI AGGA VYS A D FI VDK | |
| SEQ. ID NO. 21: | C.thermocellum_12S | (141) | S GY DI FY NV SG V PQI SVIM GP AGGA VYS A D FI VDK | |
| SEQ. ID NO. 29: | T.saccharolyticum_12S | (141) | LA GY D FY NVL A GV PC SAGGA VYS A D FI M D | |
| | Consensus | (151) | ALSGYGDIFYRNVLASGVIPQISVIMGPCAGGAVYSPALTDFIIMVDKTS | |

|  |  |  | 201 | 250 |
|---|---|---|---|---|
| SEQ. ID NO. 67: | D.propionicus_12S | (191) | Y V LK G AM TDYAA N QY | |
| SEQ. ID NO. 51: | C.kroppenstedtii_12S | (197) | T V ES KP AD GG A AM TA NI VA DD Q AI EA | |
| SEQ. ID NO. 14: | P.feudenreichii_12S | (200) | V V A DE GG AA AI NI ARD N A EL A | |
| SEQ. ID NO. 59: | G.bemidjiensis_12S | (190) | K EA G LSA G PL QMNH A HEV A DN LV R C | |
| SEQ. ID NO. 37: | C.bescii_12S | (189) | VT A V G GG Y S K VAHEV A D YHL DK | |
| SEQ. ID NO. 45: | C.cellulolyticum_12S | (191) | K V SY G DVS EN G Y YA T VAHP SSE C ED | |
| SEQ. ID NO. 21: | C.thermocellum_12S | (191) | K V KSYG DV A T NI VAHP SSE C EQ | |
| SEQ. ID NO. 29: | T.saccharolyticum_12S | (191) | K AV KA V I C VAH RA NDE C LKMV | |
| | Consensus | (201) | QMFITGPQVIKSVTGEDVSAEELGGADTHSS SGVAHFVAE DEEAI II | |

|  |  |  | 251 | 300 |
|---|---|---|---|---|
| SEQ. ID NO. 67: | D.propionicus_12S | (241) | K Q D AP D PT RSE N DN AA KK | |
| SEQ. ID NO. 51: | C.kroppenstedtii_12S | (247) | QD L Q T RPP IVDPDE-VVEPD S A BV GR V SD R | |
| SEQ. ID NO. 14: | P.feudenreichii_12S | (250) | K I Q T A SFV PNN-DVS PNTE P I GN A A | |
| SEQ. ID NO. 59: | G.bemidjiensis_12S | (240) | K V R QK NN-NI VPDKTN SSQ KN R Y | |
| SEQ. ID NO. 37: | C.bescii_12S | (239) | Y DE F MSS SEK FVPE EN SQPE I Y | |
| SEQ. ID NO. 45: | C.cellulolyticum_12S | (241) | K V S TMYYGVS AADR LAES NS E SN P DK A | |
| SEQ. ID NO. 21: | C.thermocellum_12S | (241) | K V SDV I P DNI T N V QS P ME | |
| SEQ. ID NO. 29: | T.saccharolyticum_12S | (241) | KL LEDP QLA DD N FSDP I DSPK V I | |
| | Consensus | (251) | KKLLSFLP NNLEDPP V SDD I R D L DIIP D NKAYDMKDVIT | |

|  |  |  | 301 | 350 |
|---|---|---|---|---|
| SEQ. ID NO. 67: | D.propionicus_12S | (291) | ET N I L K A V G Y AN SYY D D | |
| SEQ. ID NO. 51: | C.kroppenstedtii_12S | (296) | Y YED I G V VV W G GV A CE NA | |
| SEQ. ID NO. 14: | P.feudenreichii_12S | (299) | W DI PA T LY A Y K PY G N A | |
| SEQ. ID NO. 59: | G.bemidjiensis_12S | (289) | RL GD V PLT A Y R L N A L | |
| SEQ. ID NO. 37: | C.bescii_12S | (289) | NY G PY YG KV G YD S | |
| SEQ. ID NO. 45: | C.cellulolyticum_12S | (291) | K DE F GV SCV G V W A D A A | |
| SEQ. ID NO. 21: | C.thermocellum_12S | (291) | SY E KD D K K Y GA A A | |
| SEQ. ID NO. 29: | T.saccharolyticum_12S | (291) | E V A MAQ I G E A QN I C | |
| | Consensus | (301) | KIVD GDFLEVQA FAQNIVIGFARINGRSVGIVANQPKVMAGVLDINAS | |

FIG. 31 (cont.)

```
                                                        351                                           400
SEQ. ID NO. 67:    D.propionicus_12S    (341)  [alignment block]
SEQ. ID NO. 51:    C.kroppenstedtii_12S (346)
SEQ. ID NO. 14:    P.feudenreichii_12S  (349)
SEQ. ID NO. 59:    G.bemidjiensis_12S   (339)
SEQ. ID NO. 37:    C.bescii_12S         (339)
SEQ. ID NO. 45:    C.cellulolyticum_12S (341)
SEQ. ID NO. 21:    C.thermocellum_12S   (341)
SEQ. ID NO. 29:    T.saccharolyticum_12S (341)
                   Consensus            (351)  DKAARFVRFCDAFNIPLLTLVDVPGPLPGVNQEHGGI IRHGAKMLYAYSE 401                                           450
SEQ. ID NO. 67:    D.propionicus_12S    (391)
SEQ. ID NO. 51:    C.kroppenstedtii_12S (396)
SEQ. ID NO. 14:    P.feudenreichii_12S  (399)
SEQ. ID NO. 59:    G.bemidjiensis_12S   (389)
SEQ. ID NO. 37:    C.bescii_12S         (389)
SEQ. ID NO. 45:    C.cellulolyticum_12S (391)
SEQ. ID NO. 21:    C.thermocellum_12S   (391)
SEQ. ID NO. 29:    T.saccharolyticum_12S (391)
                   Consensus            (401)  ATVPKITVILRKAYGGAYLAMCSKDLGAD VPAWPSAEIAVMGPDGAANI 451                                           500
SEQ. ID NO. 67:    D.propionicus_12S    (441)
SEQ. ID NO. 51:    C.kroppenstedtii_12S (446)
SEQ. ID NO. 14:    P.feudenreichii_12S  (449)
SEQ. ID NO. 59:    G.bemidjiensis_12S   (439)
SEQ. ID NO. 37:    C.bescii_12S         (439)
SEQ. ID NO. 45:    C.cellulolyticum_12S (441)
SEQ. ID NO. 21:    C.thermocellum_12S   (441)
SEQ. ID NO. 29:    T.saccharolyticum_12S (441)
                   Consensus            (451)  IFRKEIKAADDP       R EKI EYRE FSNPYVAAARGYVDDVIE 501                        532
SEQ. ID NO. 67:    D.propionicus_12S    (485)
SEQ. ID NO. 51:    C.kroppenstedtii_12S (496)
SEQ. ID NO. 14:    P.feudenreichii_12S  (493)
SEQ. ID NO. 59:    G.bemidjiensis_12S   (483)
SEQ. ID NO. 37:    C.bescii_12S         (483)
SEQ. ID NO. 45:    C.cellulolyticum_12S (485)
SEQ. ID NO. 21:    C.thermocellum_12S   (485)
SEQ. ID NO. 29:    T.saccharolyticum_12S (485)
                   Consensus            (501)  PADTR KIISALEMLATKRENRPSKKHGNIPL
```

5S subunits

```
                                                        1                                             50
SEQ. ID NO. 25:    Cthermocellum_5S     (1)   ---------------------MAK
SEQ. ID NO. 49:    Ccellulolyticum_5S   (1)   ---------------------MPG
SEQ. ID NO. 63:    Gbemidjiensis_5S     (1)   --------------------MDPI
SEQ. ID NO. 55:    Ckroppenstedtii_5S   (1)   -------VQQPTNRLNVVAMTTRK
SEQ. ID NO. 11:    Pfreudenreichii_5S   (1)   --------MSPREIEVSEPREG
SEQ. ID NO. 71:    Dpropionicus_5S_1.3S (1)   MSDQVKMTAMNYATDRPAAENPV
SEQ. ID NO. 41:    Cbescii_5S           (1)   ----------------------MGV
SEQ. ID NO. 33:    Tsaccharolyticum_5S  (1)   ---------------------MSK
                   Consensus            (1)         VKITETVLRDAHQSLIATRM TEDMLPI 51                                            100
SEQ. ID NO. 25:    Cthermocellum_5S     (32)  IDK
SEQ. ID NO. 49:    Ccellulolyticum_5S   (32)  VEK
SEQ. ID NO. 63:    Gbemidjiensis_5S     (33)  CDD
SEQ. ID NO. 55:    Ckroppenstedtii_5S   (46)  CDD
SEQ. ID NO. 11:    Pfreudenreichii_5S   (42)  CAD
SEQ. ID NO. 71:    Dpropionicus_5S_1.3S (51)  ADM
SEQ. ID NO. 41:    Cbescii_5S           (31)  APV
SEQ. ID NO. 33:    Tsaccharolyticum_5S  (32)  ASK
                   Consensus            (51)  B LD IGYWSVECWGGATFDACIRPLNEDPWERLRTLKKIMKKTPLQML
SEQ. ID NO
```

```
                                              451                                            500
SEQ. ID NO. 25:  Cthermocellum_5S     (415)  -N░░░░░░░░░░░░░░░░░░░QY░K----------------AQ
SEQ. ID NO. 49:  Ccellulolyticum_5S   (415)  -EA░░░░░░░░░░░░░░░░░░KQ░I---------------░D
SEQ. ID NO. 63:  Gbemidjiensis_5S     (418)  ALP░░GCDGS░░░░░░░░░░PG░AT░S--------------░G
SEQ. ID NO. 55:  Ckroppenstedtii_5S   (430)  AD░░DGTDGS░░░░░░░░░░░APG░KT░P------------░G
SEQ. ID NO. 11:  Pfreudenreichii_5S   (426)  AAA░G░NGT░░░░░░░░░░░░AP░░EH░A------------░G
SEQ. ID NO. 71:  Dpropionicus_5S_1.3S (447)  -K░░G░LAKDI░░░░░░░░VT░K░░LEW░YGITPAPPEVKPLTLEDVK
                 Cbescii_5S           (414)  -E░░░░░░░░░░░░░CL░░░L░EN░░KI░F-----------AK
SEQ. ID NO. 33:  Tsaccharolyticum_5S  (414)  -N░░░░░░░░░░░░░░░░░VR░░EY░Q--------------AK
                 Consensus            (451)   EIKEYIEQDEDVLTYALFPQVA KFF  R             E
                                              501                                            550
SEQ. ID NO. 25:  Cthermocellum_5S     (448)  ░░░EPDM░DYE░RVHPV-----------------------------
SEQ. ID NO. 49:  Ccellulolyticum_5S   (448)  ░░ATAPAS░EI░PEVVAAISAVVNEMGERDGT QYRIGNISKLNQNQNRW
SEQ. ID NO. 63:  Gbemidjiensis_5S     (452)  PR░░GRDP░TGASETSIPEGHPGKITGPVT░T░TLS░QPHK░T░APYGQE
SEQ. ID NO. 55:  Ckroppenstedtii_5S   (464)  PKN░GFTKE░LE░EEAKASGDATAIREPIM░K░TTG░RSHT░S░EPA---
SEQ. ID NO. 11:  Pfreudenreichii_5S   (460)  P░S░ALTDA░LK-AEAEGDEKSLAVAGPVT░N░NVG░TVRE░T░QQA---
SEQ. ID NO. 71:  Dpropionicus_5S_1.3S (496)  ░R░DELVAKAKAG░LIEPKPAAPEKTANVRT░N░FVD░EYFN░E░DPTGDF
                 Cbescii_5S           (447)  ░░░DADL░GN░VYPV-------------------------------
SEQ. ID NO. 33:  Tsaccharolyticum_5S  (447)  ░░░DSTL░IE░RVHPI------------------------------
                 Consensus            (501)  KYKV   VQ K               Y V    G    V V
                                              551                                            600
SEQ. ID NO. 25:  Cthermocellum_5S     (466)  -----------------------------------------------
SEQ. ID NO. 49:  Ccellulolyticum_5S   (498)  SLYGMLDRFRTKI----------------------------------
SEQ. ID NO. 63:  Gbemidjiensis_5S     (502)  -----------------------------------------------
SEQ. ID NO. 55:  Ckroppenstedtii_5S   (511)  -----------------------------------------------
SEQ. ID NO. 11:  Pfreudenreichii_5S   (506)  -----------------------------------------------
SEQ. ID NO. 71:  Dpropionicus_5S_1.3S (546)  QPMVAAAPK PAAPAAAPKAAAPAAAAPAAAPKAAAPAAAAPAPAAVEGGT
                 Cbescii_5S           (464)  -----------------------------------------------
SEQ. ID NO. 33:  Tsaccharolyticum_5S  (465)  -----------------------------------------------
                 Consensus            (551)
                                              601                                            650
SEQ. ID NO. 25:  Cthermocellum_5S     (466)  -----------------------------------------------
SEQ. ID NO. 49:  Ccellulolyticum_5S   (511)  -----------------------------------------------
SEQ. ID NO. 63:  Gbemidjiensis_5S     (502)  -----------------------------------------------
SEQ. ID NO. 55:  Ckroppenstedtii_5S   (511)  -----------------------------------------------
SEQ. ID NO. 11:  Pfreudenreichii_5S   (506)  -----------------------------------------------
SEQ. ID NO. 71:  Dpropionicus_5S_1.3S (596)  PLLAPMPGMIVKNLVNVGDAVKAGDPILVLEAMKMENNLGSPCDGTVKAL
                 Cbescii_5S           (464)  -----------------------------------------------
SEQ. ID NO. 33:  Tsaccharolyticum_5S  (465)  -----------------------------------------------
                 Consensus            (601)
                                              651         668
SEQ. ID NO. 25:  Cthermocellum_5S     (466)  ------------------
SEQ. ID NO. 49:  Ccellulolyticum_5S   (511)  ------------------
SEQ. ID NO. 63:  Gbemidjiensis_5S     (502)  ------------------
SEQ. ID NO. 55:  Ckroppenstedtii_5S   (511)  ------------------
SEQ. ID NO. 11:  Pfreudenreichii_5S   (506)  ------------------
SEQ. ID NO. 71:  Dpropionicus_5S_1.3S (646)  NFGSGDSVAKDTVLAIIG
                 Cbescii_5S           (464)  ------------------
SEQ. ID NO. 33:  Tsaccharolyticum_5S  (465)  ------------------
                 Consensus            (651)
```

FIG. 31 (cont.)

1.3S subunits

```
                                           1                                                  50
SEQ. ID NO. 31:  Tsaccharolyticum_1.3S   (1) KKEIKVKGRKDEIEVIKKVQVASEKKAKEDTKAKNKSDASVKSK---
SEQ. ID NO.  8:  Pfreudenreichii_1.3S    (1) -MKLKVKVKTAELEVKAQVDKSHENPMGTILFGGGTGGNPAPRAKGGAG-
SEQ. ID NO. 53:  Ckroppenstedtii_1.3S    (1) -MKLTVKVKVEKSEVEVVVEHEKRPTLGTIITGGNSN-QPTPTAPTTKS-
SEQ. ID NO. 61:  Gbemidjiensis_1.3S      (1) -VQLTNKIDKFKKKEVVEEGKEVRTEGAFPPTKTMQKYPVYSKHFKAT
SEQ. ID NO. 39:  Cbescii_1.3S            (1) KRKEKNKSQEFVKLKEKLGVKNATSVVPRPKIGHFEPKQEKHEDKKK-
SEQ. ID NO. 47:  Ccellulolyticum_1.3S    (1) KSKIKKVKTPKYMVKSEKGGGRPISAAPKLRATKPGHTSAAPKAQF--
SEQ. ID NO. 23:  Cthermocellum_1.3S      (1) KKKLKKKNQKLEVKIKIRDKASAPQVTLSTPSAAPKPSPAPKQEKKT
                               Consensus  (1) M KF VTVNG  YDVEVEEI  E              A      A  T
                                           51                                                100
SEQ. ID NO. 31:  Tsaccharolyticum_1.3S  (48) --QVEVKNEVKDKFKNAMPKTILDKKSQKQTVRRDKKLIKAMKMK
SEQ. ID NO.  8:  Pfreudenreichii_1.3S   (49) ---------AGNKGEGKPAPLAKTSFKYKEKTVAGTVLKKAMKMK
SEQ. ID NO. 53:  Ckroppenstedtii_1.3S   (48) --------VQGVSKNTAPLAKSVSKVDVEEKQATTAKVVKKAMKMK
SEQ. ID NO. 61:  Gbemidjiensis_1.3S     (50) PPLAAPTPASKSEKICRSKIAKVVPKIVAQVKQHKEMNKKLAMKMK
SEQ. ID NO. 39:  Cbescii_1.3S           (50) -----QSFVLSKDKNKKVAQLFKDTVLKKSEKGVVDANEPVIKAMKMK
SEQ. ID NO. 47:  Ccellulolyticum_1.3S   (49) --------QAGNKGDVAKKEKVYLKVKVAIKEVNKQVLKKAMKMK
SEQ. ID NO. 23:  Cthermocellum_1.3S     (51) AAPKKDSTVPKGATEKKKKEDPKNQKTYNKKQVLKKAMKMK
                               Consensus (51)           A  A SI APLPGTVLKILV  GD VK GDVLLILEAMKME
                                           101       133
SEQ. ID NO. 31:  Tsaccharolyticum_1.3S  (96) SKKAYDTKITKKNSSKRASKNTKKKVYK-
SEQ. ID NO.  8:  Pfreudenreichii_1.3S   (92) TKKNAKTDKKEKGLVKERDAKGKSGLIKKS-
SEQ. ID NO. 53:  Ckroppenstedtii_1.3S   (91) TKRKAKNKGTKTLHVQPKDAKVKGSLKEKGD
SEQ. ID NO. 61:  Gbemidjiensis_1.3S    (100) KEKAHMSKGVEKKLKSVKEAKVPKQALAEFK
SEQ. ID NO. 39:  Cbescii_1.3S           (96) NEKVFKEKKRTHVKEQKVAKSKLLFEKE-
SEQ. ID NO. 47:  Ccellulolyticum_1.3S   (91) NEKVAPAKKNTKANKEAGKKTAKSKLNK
SEQ. ID NO. 23:  Cthermocellum_1.3S    (101) KVAENKGTVAKIMKSKKASKNVEKVILSKK-
                               Consensus (101) NEITAP DGKV AI V  G AVQ GDLLL IA
```

12S C-term subunit

```
                                                  1                                              50
SEQ. ID NO. 57:  Ckroppenstedtii_12Scterm  (1) MNTDNASSAELSQLLARLSNQVEKLSRNVTKLENEVAAKKQRSDEEKPK
SEQ. ID NO. 16:  Pfreudenreichii_12Scterm  (1) --------------MADEEEKDLMIATLNKRVASLESELGSKQS-DTQGKTK
SEQ. ID NO. 27:  Cthermocellum_12Scterm    (1) ----------------------------------------MKEQKNK
SEQ. ID NO. 35:  Tsaccharolyticum_12Scterm (1) -----------------------------------------MEEKNK
SEQ. ID NO. 43:  Cbescii_12Scterm          (1) ---------------------------------MYAQVSTISTKTKK
SEQ. ID NO. 69:  Dpropionicus_12Scterm     (1) --------------------------------MAKKNKKMAAAKAAV
SEQ. ID NO. 65:  Gbemidjiensis_12Scterm    (1) --------------------------VDEEKEQEHDPEKTPK
                               Consensus   (1)                                         L      I EE
                                                 51                                              100
SEQ. ID NO. 57:  Ckroppenstedtii_12Scterm (51) KIAKSAAYKAKRGTVRAKHFLK-----HRSKSQQKKQAKQHKKKWQ
SEQ. ID NO. 16:  Pfreudenreichii_12Scterm (39) KLTAKSAAYKKLGKDGSAEVKHPAP------SPNKVREKKRAKQNHKIR-
SEQ. ID NO. 27:  Cthermocellum_12Scterm    (9) KILAKIASIAALETEKPKYKLVKRSFKRIPQTSPVKSATKKIERKRRKM--
SEQ. ID NO. 35:  Tsaccharolyticum_12Scterm (9) KVAVKEAKAYKAPKYEKNFRKVIKRVDSNMPEKRKAKLYNQKR-----
SEQ. ID NO. 43:  Cbescii_12Scterm         (15) EKACKAKKHIVKSE-KQYKIKKNITKQ-----QNEKVKGAKEMMKNQSQMF
SEQ. ID NO. 69:  Dpropionicus_12Scterm    (16) NAYLKQEEEAKYKAQLLAAKNSKAPAG------PSIKAIAKRQDKKNFRRLI
SEQ. ID NO. 65:  Gbemidjiensis_12Scterm   (17) KEMVKKAKAKAKSKTVRIKRARFVKPN--LINAKGQSSKVVKQASHNLR
                               Consensus  (51) IL   ISAAIAAYLGN G  K  V   K          W   GR  LM  S
                                                 101
SEQ. ID NO. 57:  Ckroppenstedtii_12Scterm (96) -----
SEQ. ID NO. 16:  Pfreudenreichii_12Scterm (83) -----
SEQ. ID NO. 27:  Cthermocellum_12Scterm   (57) -----
SEQ. ID NO. 35:  Tsaccharolyticum_12Scterm(53) -----
SEQ. ID NO. 43:  Cbescii_12Scterm         (60) YRWR-
SEQ. ID NO. 69:  Dpropionicus_12Scterm    (61) QMKAF
SEQ. ID NO. 65:  Gbemidjiensis_12Scterm   (65) R----
                               Consensus (101)
```

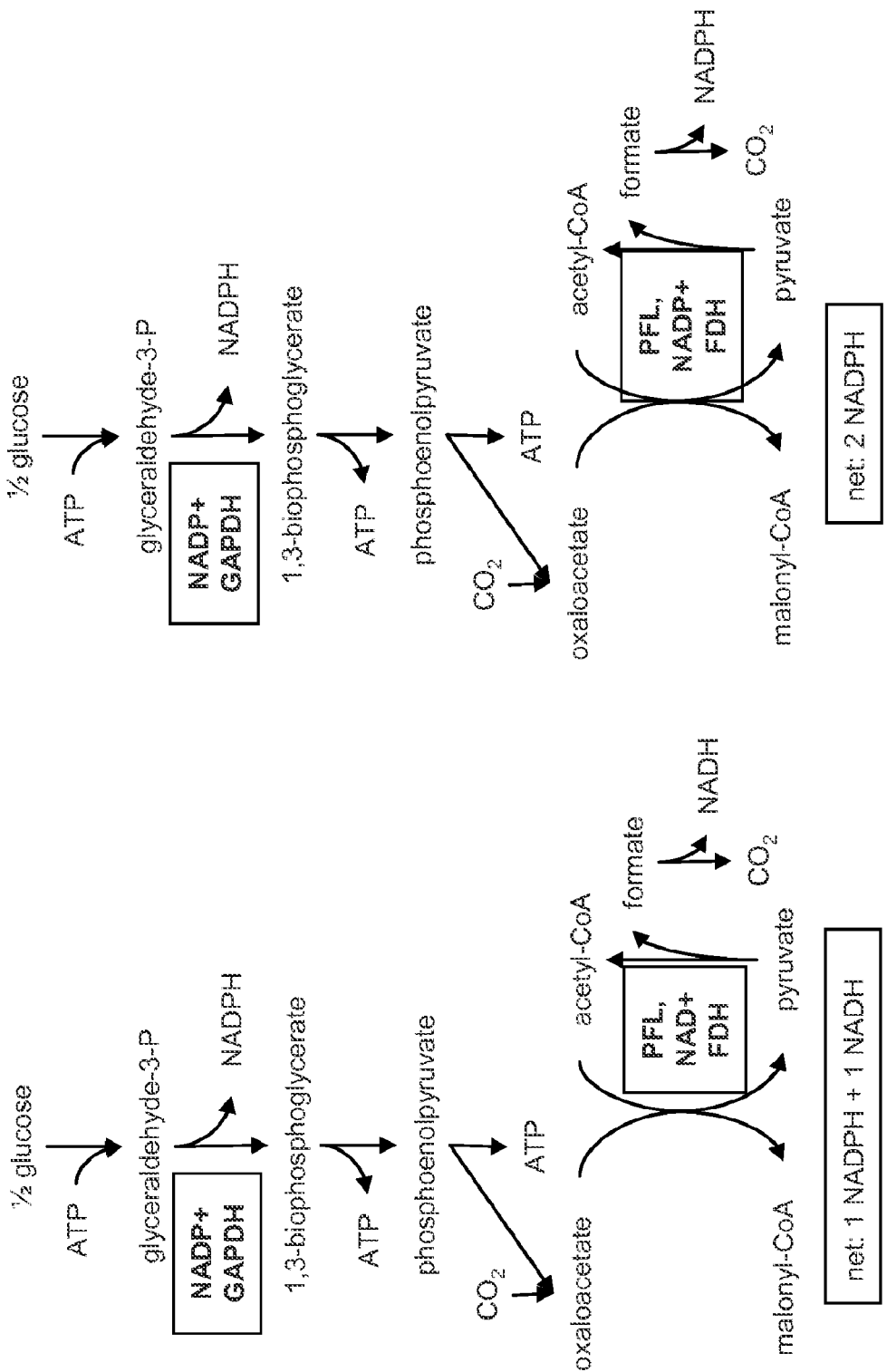

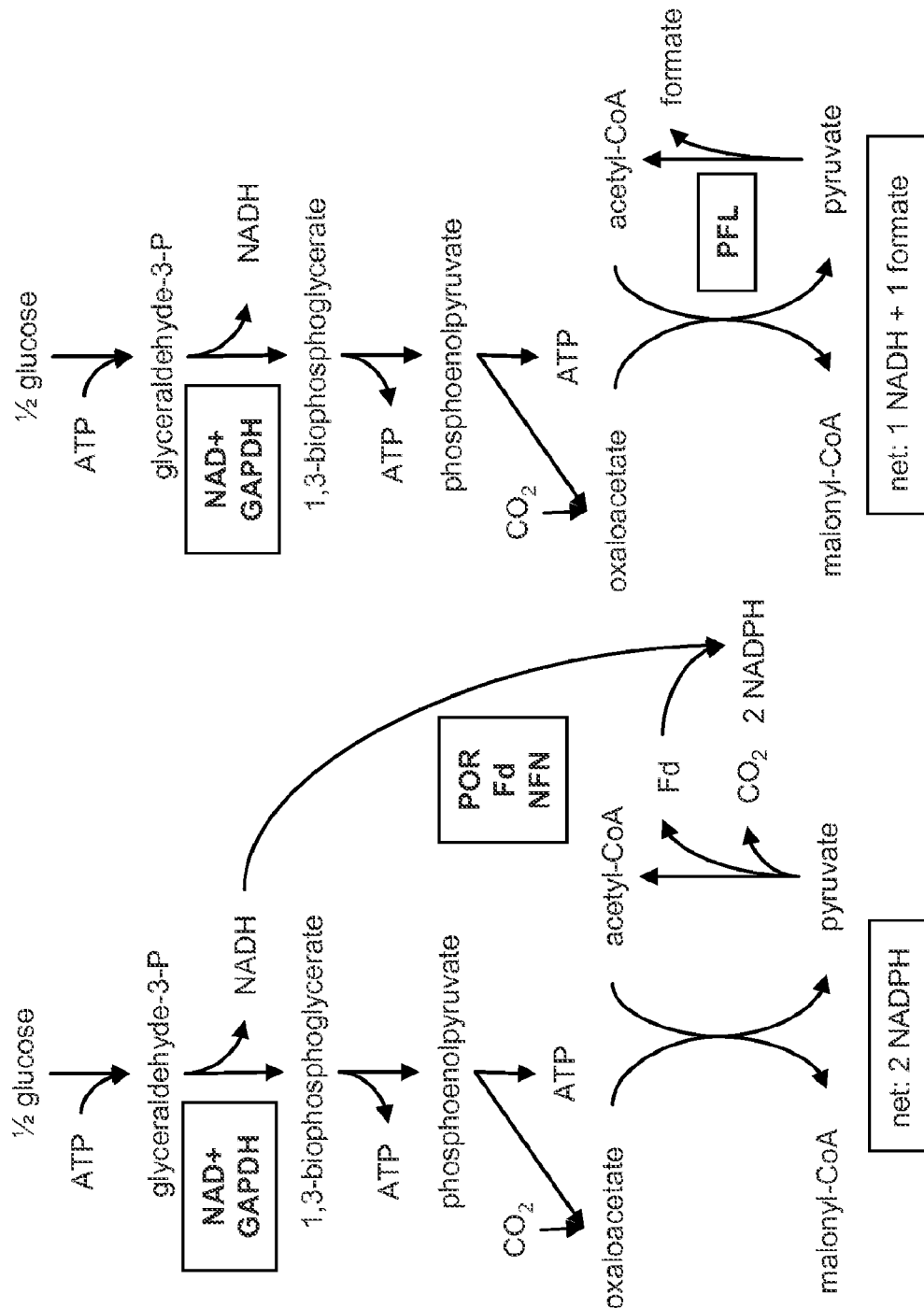

gpd2:adoles ADH-fba term pfk-adh pMU2770 - pMU2606-AA46
25247 bp

GPD1:adoles-ADH-YCL183-pMU2606 with primers
24329 bp

FIG. 46

| SEQ. ID NO. | Accession | Start | Sequence region (1-50) |
|---|---|---|---|
| SEQ. ID NO. 1: | AAS20429 | (1) | |
| SEQ. ID NO. 296: | YP_001277512 | (1) | |
| SEQ. ID NO. 295: | YP_001433009 | (1) | |
| SEQ. ID NO. 297: | ZP_01039179 | (1) | |
| SEQ. ID NO. 298: | ZP_04957196 | (1) | |
| SEQ. ID NO. 294: | ZP_07684596 | (1) | |
| SEQ. ID NO. 293: | YP_002462600 | (1) | |
| SEQ. ID NO. 291: | YP_001636209 | (1) | |
| SEQ. ID NO. 292: | YP_002570540 | (1) | |
| Consensus | | (1) | MS  GRL GKIALITGGAGNIGSEITRRFLAEGATVVISGRN |

Positions 51–100:

| SEQ. ID NO. 1: | AAS20429 | (45) |
| SEQ. ID NO. 296: | YP_001277512 | (48) |
| SEQ. ID NO. 295: | YP_001433009 | (45) |
| SEQ. ID NO. 297: | ZP_01039179 | (50) |
| SEQ. ID NO. 298: | ZP_04957196 | (51) |
| SEQ. ID NO. 294: | ZP_07684596 | (44) |
| SEQ. ID NO. 293: | YP_002462600 | (45) |
| SEQ. ID NO. 291: | YP_001636209 | (45) |
| SEQ. ID NO. 292: | YP_002570540 | (45) |
| Consensus | | (51) | KL A  ERLIAEAGV  ERIDL VMDGSDP AVRAGIAAIVA |

Positions 101–150:

| SEQ. ID NO. 1: | AAS20429 | (88) |
| SEQ. ID NO. 296: | YP_001277512 | (98) |
| SEQ. ID NO. 295: | YP_001433009 | (95) |
| SEQ. ID NO. 297: | ZP_01039179 | (95) |
| SEQ. ID NO. 298: | ZP_04957196 | (95) |
| SEQ. ID NO. 294: | ZP_07684596 | (87) |
| SEQ. ID NO. 293: | YP_002462600 | (88) |
| SEQ. ID NO. 291: | YP_001636209 | (88) |
| SEQ. ID NO. 292: | YP_002570540 | (88) |
| Consensus | | (101) | G IDILVNNAGSAGARRRL EIPLTES ELGPGDEETL  SIANLLGMA |

Positions 151–200:

| SEQ. ID NO. 1: | AAS20429 | (137) |
| SEQ. ID NO. 296: | YP_001277512 | (147) |
| SEQ. ID NO. 295: | YP_001433009 | (144) |
| SEQ. ID NO. 297: | ZP_01039179 | (143) |
| SEQ. ID NO. 298: | ZP_04957196 | (143) |
| SEQ. ID NO. 294: | ZP_07684596 | (136) |
| SEQ. ID NO. 293: | YP_002462600 | (137) |
| SEQ. ID NO. 291: | YP_001636209 | (137) |
| SEQ. ID NO. 292: | YP_002570540 | (137) |
| Consensus | | (151) | WNLMRIAAPHMP GSAVINVSTIFSRTEYYGRIPYVVPKAALNALSQ AA |

Positions 201–250:

| SEQ. ID NO. 1: | AAS20429 | (187) |
| SEQ. ID NO. 296: | YP_001277512 | (197) |
| SEQ. ID NO. 295: | YP_001433009 | (194) |
| SEQ. ID NO. 297: | ZP_01039179 | (193) |
| SEQ. ID NO. 298: | ZP_04957196 | (193) |
| SEQ. ID NO. 294: | ZP_07684596 | (186) |
| SEQ. ID NO. 293: | YP_002462600 | (187) |
| SEQ. ID NO. 291: | YP_001636209 | (187) |

```
                               1101                                                1150
SEQ. ID NO. 1:    AAS20429     (1065)
SEQ. ID NO. 296:  YP_001277512 (1078)
SEQ. ID NO. 295:  YP_001433009 (1075)
SEQ. ID NO. 297:  ZP_01039179  (1068)
SEQ. ID NO. 298:  ZP_04957196  (1055)
SEQ. ID NO. 294:  ZP_07684596  (1066)
SEQ. ID NO. 243:  YP_002462600 (1064)
SEQ. ID NO. 291:  YP_001636209 (1064)
SEQ. ID NO. 292:  YP_002570540 (1064)
                  Consensus    (1101) FRPLPS PLVGRKDSDWSTVLS AEFAELCE QLTHHFRVARKIAL DGA
                               1151                                                1200
SEQ. ID NO. 1:    AAS20429     (1115)
SEQ. ID NO. 296:  YP_001277512 (1127)
SEQ. ID NO. 295:  YP_001433009 (1124)
SEQ. ID NO. 297:  ZP_01039179  (1112)
SEQ. ID NO. 298:  ZP_04957196  (1105)
SEQ. ID NO. 294:  ZP_07684596  (1116)
SEQ. ID NO. 243:  YP_002462600 (1114)
SEQ. ID NO. 291:  YP_001636209 (1114)
SEQ. ID NO. 292:  YP_002570540 (1114)
                  Consensus    (1151) SL LVTPETTA STTEQFALANFVKTTLHAFTATIGVESERTA RILVNQ
                               1201                                                1250
SEQ. ID NO. 1:    AAS20429     (1165)
SEQ. ID NO. 296:  YP_001277512 (1177)
SEQ. ID NO. 295:  YP_001433009 (1174)
SEQ. ID NO. 297:  ZP_01039179  (1162)
SEQ. ID NO. 298:  ZP_04957196  (1155)
SEQ. ID NO. 294:  ZP_07684596  (1166)
SEQ. ID NO. 243:  YP_002462600 (1164)
SEQ. ID NO. 291:  YP_001636209 (1164)
SEQ. ID NO. 292:  YP_002570540 (1164)
                  Consensus    (1201) VDLTRRARAEEPRDP E QQELERFIEAVLLVTAPLP EADSRY GRIHR
                               1251
SEQ. ID NO. 1:    AAS20429     (1215)
SEQ. ID NO. 296:  YP_001277512 (1227)
SEQ. ID NO. 295:  YP_001433009 (1224)
SEQ. ID NO. 297:  ZP_01039179  (1212)
SEQ. ID NO. 298:  ZP_04957196  (1205)
SEQ. ID NO. 294:  ZP_07684596  (1216)
SEQ. ID NO. 243:  YP_002462600 (1214)
SEQ. ID NO. 291:  YP_001636209 (1214)
SEQ. ID NO. 292:  YP_002570540 (1214)
                  Consensus    (1251) GRAITV
```

PRODUCTION OF MALONYL-COA DERIVED PRODUCTS VIA ANAEROBIC PATHWAYS

CROSS-REFERENCE TO RELATED APPLICATIONS

The present application is a continuation of U.S. application Ser. No. 13/814,616 filed Aug. 23, 2013 (now U.S. Pat. No. 10,138,504), which is a '371 U.S. national phase application of PCT/US2011/046869, filed Aug. 5, 2011, entitled "Production of Malonyl-COA Derived Products Via Anaerobic Pathways," which claims priority to U.S. Provisional Application No. 61/371,582 filed Aug. 6, 2010, each application of which is hereby incorporated by reference in its entirety.

REFERENCE TO SEQUENCE LISTING SUBMITTED ELECTRONICALLY VIA EFS-WEB

The content of the electronically submitted sequence listing (Name: 115235-260SeqList.txt Size: 448,711 bytes; and Date of Creation: Oct. 19, 2018) filed with the application is incorporated herein by reference in its entirety.

BACKGROUND OF THE INVENTION

Depleting petroleum reserves, recurrent energy crises, increasing demand, and climate change have provided significant impetus in the search for sustainable technologies to replace petroleum as a source of fuels and chemical feedstocks. Long chain fatty acids and other derivatives are commercially attractive as fuel and chemical feedstocks because they can directly replace crude petroleum (as "bio-crude"), which is composed primarily of alkanes, alkenes, and aromatic hydrocarbons. In particular, cellulosic biomass is a preferred source of generating long chain fatty acids and other derivatives for use as fuel and chemical feedstocks, which are compatible with existing petroleum refining and distribution and can substitute for diesel, gasoline, jet fuel, and other derivatives of crude oil.

Currently, commercial and academic efforts are focused on bio-based petroleum replacement fuels made from microorganisms such as microalgae and that require aerobic microbial production. Algae bio-petroleum can appear as a very attractive option because fuel production occurs directly from sunlight and CO2. However, algal volumetric productivities are 100-fold lower than fermentative processes, requiring significantly higher biorefinery capital expenditures. See Liliana et al., Biotechnology and Bioengineering 102:100-12 (2009). In addition, lower capital algal options, such as open pond culturing, have many technical hurdles to clear before commercial deployment despite decades of research into the issue.

Other efforts are underway to produce fatty acid compounds from sugars and plant biomass, but all current methods require oxygen to be supplied during fermentation, and are not full consolidated bioprocessing (CBP) processes. Unlike traditional ethanol fermentations, aerobic biofuel synthesis routes feature product formation which is uncoupled from ATP generation and cell growth. Uncoupling of product formation from cell growth simplifies metabolic engineering and has allowed for rapid development of first generation biocatalysts. However, there is a price to be paid for aerobic production when the technology is scaled up to meet industrial needs. First, there are significant costs associated with scaling-up aerobic fermentations, such as, those due to the need for aeration and heat removal. In practice, these constraints limit the size of aerobic fermentors, with those used in anaerobic fuel ethanol production being an order of magnitude larger. Second, although maximum theoretical product yields from an aerobic process are only slightly lower than an anaerobic process, in practice it is extraordinarily difficult to approach this maximum since there is no biological incentive for microbes to reach high product yields.

To reach the best aerobic process hydrocarbon yields to date, researchers have resorted to high cell density fermentation, which resulted in product yields between 30-40% of the theoretical maximum. See Tsuruta et al., *PLoS ONE* 4:e4489 (2009); Whited et al., *Industrial Biotechnology* 6:152-163 (2010). While these yields may be quite acceptable for pharmaceutical or specialty chemical production, fuel biorefinery process models have shown that fermentation yields lower than 85% of theoretical result in unattractive process economics. However, an anaerobic, oxygen-free fermentation not only creates higher product yields, but also removes many significant scale-up problems associated with aerobic fermentation. Hydrocarbon fuel production also has process benefits compared to ethanol fuel production, such as a lower product recovery cost and a lower product toxicity to fermenting organisms. The latter could result in smaller fermentation volumes needed to reach equivalent productivities.

An anaerobic biocatalyst requires a higher degree of metabolic pathway integration to couple product formation with ATP generation, NAD(P)H regeneration, and cell growth. However, once these requirements are met, natural evolutionary forces can be harnessed to increase product yields and productivities, driving them towards theoretical maxima. See Burgard et al., *Biotechnology and Bioengineering* 84:647-57 (2003); Sauer, *Advances in Biochemical Engineering/Biotechnology* 73:129-69 (2001). Higher yields, combined with a lower-cost path for scale-up, make an anaerobic process a preferred option for developing microbes to produce fungible biofuels. The invention describes a method to produce long chain fatty acids and their derivatives in an organism or consortia of organisms in a CBP process that is anaerobic.

Integral to the process of producing any end product, including those that can be produced using the methods of the invention, is an adequate supply of metabolic substrates. Malonyl-CoA is such a key metabolic precursor for the biological synthesis of various bioproducts, including, but not limited to, fatty acid derived long chain hydrocarbon compounds such as fatty alcohols, fatty aldehydes, fatty acids, wax esters, and alkanes. However, the biosynthesis of malonyl-CoA is known to occur through only a few mechanisms in vivo-namely from acetyl-CoA, carbon dioxide, and ATP by acetyl-CoA carboxylase (acc, EC 6.4.1.2) or from malonate, CoA, and ATP by malonyl-CoA synthetase (matB) (An and Kim, *Eur. J. Biochem.* 257:395-402 (1998)). Yet, both of these mechanisms require the consumption of ATP to drive the reaction towards malonyl-CoA. In contrast, to produce fatty acid derived hydrocarbons, or any other bioproducts that use malonyl-CoA as a precursor, anaerobically at high yield, the route to malonyl-CoA should result in a net production of ATP. The invention describes recombinant microorganisms, pathways, and methods for producing desired end-products from malonyl-CoA precursors with a net production of ATP.

BRIEF SUMMARY OF THE INVENTION

The recombinant microorganisms and methods of the invention use metabolic pathways that allow for the production of malonyl-CoA derived products, such as hydrocarbons and hydrocarbon derivatives and other bioproducts, under anaerobic conditions. The metabolic pathways allow for the production of long chain compounds, including, e.g., chain lengths from four carbon atoms up to 40 or more carbon atoms per molecule, and cellular growth in the absence of oxygen or other mechanisms to generate cellular energy (ATP) besides fermentative metabolism.

An aspect of the invention is the ability to produce long chain compounds at high yield with an anaerobic process rather than with an aerobic process. Anaerobic production results in a higher product yield, easier scalability, and better process thermodynamics. For lignocellulosic biomass conversion, an anaerobic process is even more desirable, as the requirement for oxygen transfer in a medium with suspended solids is highly unattractive from an engineering perspective. Additional advantages include, but are not limited to:

1) Production of a direct (fungible) replacement for petroleum;

2) Lower separation costs from a dilute aqueous fermentation as a result of the immiscible nature of long chain hydrocarbons compared to fully miscible shorter chain compounds;

3) Greater downstream product diversity and flexibility; and

4) Potentially lower product toxicity for fermenting organism which will allow for reduced fermentor volume and lower capital costs in a cellulosic biomass process.

One aspect of the invention relates to a recombinant microorganism comprising one or more native and/or heterologous enzymes that function in one or more engineered metabolic pathways to convert a carbohydrate source to a hydrocarbon, wherein the one or more native and/or heterologous enzymes is activated, upregulated, downregulated, or deleted. In certain embodiments, the conversion of a carbohydrate source to a hydrocarbon is under anaerobic conditions. In certain embodiments, the conversion of a carbohydrate source to a hydrocarbon is under microaerophilic conditions.

In certain embodiments, the one or more engineered metabolic pathways produce net ATP. In some embodiments, the one or more engineered metabolic pathway produces at least about 0.5 net ATP; at least about 1.0 net ATP; at least about 1.5 net ATP; or at least about 2.0 net ATP. In other embodiments the net ATP production is at least about at least about 0.1 net ATP; at least about 0.2 net ATP; at least about 0.3 net ATP; at least about 0.4 net ATP; at least about 0.5 net ATP; at least about 0.6 net ATP; at least about 0.7 net ATP; at least about 0.8 net ATP; at least about 0.9 net ATP; at least about 1.0 net ATP; 1.1 net ATP; at least about 1.2 net ATP; at least about 1.3 net ATP; at least about 1.4 net ATP; at least about 1.5 net ATP; at least about 1.6 net ATP; at least about 1.7 net ATP; at least about 1.8 net ATP; at least about 1.9 net ATP; or at least about 2.0 net ATP.

In particular aspects of the invention, the hydrocarbon produced by the recombinant microorganism is an alkane, an alkene, a hydrocarbon derivative, or a combination of any of these hydrocarbons. In some embodiments, the hydrocarbon produced is selected from the group consisting of an alkane; an alkene; an alkyne; a hydrocarbon derivative; and combinations of these hydrocarbons. In certain aspects, the hydrocarbon derivative is an aldehyde; an alcohol; an ester; a fatty acid; an unsaturated fatty acid; a branched-chain fatty acid; a branched methoxy fatty acid; a multi-methyl branched acid; a divinyl-ether fatty acid; a w-phenylalkanoic acid; or a dicarboxylic acid. In some the hydrocarbon derivative is selected from the group consisting of an aldehyde; an alcohol; an ester; a fatty acid; an unsaturated fatty acid; a branched-chain fatty acid; a branched methoxy fatty acid; a multi-methyl branched acid; a divinyl-ether fatty acid; a w-phenylalkanoic acid; a dicarboxylic acid; and combinations of these hydrocarbon derivatives.

In certain aspects of the invention, the hydrocarbon or hydrocarbon derivative produced by the recombinant microorganism comprises a carbon backbone of $C_4$-$C_{40}$. In some embodiments, the hydrocarbon or hydrocarbon derivative comprises a carbon backbone selected from the group consisting of $C_6$-$C_{36}$; $C_8$-$C_{32}$; $C_{10}$-$C_{28}$; $C_{12}$-$C_{24}$; $C_{14}$-$C_{22}$; $C_{16}$-$C_{20}$; and combinations thereof. In other embodiments, the hydrocarbon or hydrocarbon derivative comprises a carbon backbone selected from the group consisting of $C_{12}$; $C_{14}$; $C_{16}$; $C_{18}$; $C_{20}$; $C_{22}$; $C_{24}$; and combinations of thereof. In one embodiment, the hydrocarbon or hydrocarbon derivative comprises a carbon backbone of $C_{16}$.

In some aspects of the invention, the carbohydrate source converted to a hydrocarbon is from biomass or from carbohydrates, such as a sugar or a sugar alcohol. In one embodiment, the carbohydrate source converted to a hydrocarbon is a lignocellulosic material. In some embodiments, the carbohydrate is a monosaccharides (e.g., glucose, fructose, galactose, xylose, arabinose, rhamnose, galacturonic acid, xylitol, sorbitol, or ribose), a disaccharide (e.g., sucrose, cellobiose, maltose, or lactose), an oligosaccharide (e.g., xylooligomers, cellodextrins, or maltodextrins), or a polysaccharide (e.g., xylan, cellulose, starch, mannan, or pectin).

In a particular aspect of the invention, one of the engineered metabolic pathways in the recombinant microorganism comprises the conversion of oxaloacetate and acetyl-CoA to malonyl-CoA and pyruvate. In one embodiment, the oxaloacetate and acetyl-CoA is converted to malonyl-CoA and pyruvate by a transcarboxylase. In some embodiments, the transcarboxylase is encoded by a heterologous transcarboxylase polynucleotide. In certain embodiments, the transcarboxylase is encoded by a polynucleotide from a *Thermoanaerobacter* species, *P. freudenreichii*, *P. acnes*, or *C. thermocellum*. In one embodiment, the transcarboxylase is genetically modified In another aspect of the invention, one of the engineered metabolic pathways comprises the conversion of phosphoenolpyruvate to oxaloacetate. In one embodiment, the phosphoenolpyruvate is converted to oxaloacetate by a phosphoenolpyruvate carboxykinase. In some embodiments, the phosphoenolpyruvate carboxykinase is encoded by a heterologous phosphoenolpyruvate carboxykinase polynucleotide. In certain embodiments, the phosphoenolpyruvate carboxykinase is encoded by a polynucleotide from a *Thermoanaerobacter* species, *E. coli*, *S. cerevisiae*, or *C. thermocellum*.

In other aspects of the invention, one of the engineered metabolic pathways further comprises at least one of the following steps: conversion of malonyl-CoA to malonyl-ACP; conversion of malonyl-ACP to an $acyl_n$-ACP; conversion of an $acyl_n$-ACP to a β-keto $ester_{n+2}$-ACP; conversion of a β-keto $ester_{n+2}$-ACP to a β-D-$hydroxyacyl_{n+2}$-ACP; conversion of a β-D-$hydroxyacyl_{n+2}$-ACP to a trans-2-unsaturated $acyl_{n+2}$-ACP; or conversion of a trans-2-unsaturated $acyl_{n+2}$-ACP to an $acyl_{n+2}$-ACP.

In some aspects of the invention, one of the engineered metabolic pathways further comprises the conversion of pyruvate and CoA-SH into acetyl-CoA and $CO_2$ and NAD (P)H.

In some aspects of the invention, one or more of the native enzymes in the engineered metabolic pathways are downregulated or deleted. In certain embodiments, the downregulated or deleted native enzyme is an enzyme involved in central metabolism. In some embodiments, the downregulated or deleted native enzyme is selected from the group consisting of a pyruvate kinase; a hydrogenase; a lactate dehydrogenase; a phosphotransacetylase; an acetate kinase; an acetaldehyde dehydrogenase; an alcohol dehydrogenase; a pyruvate formate lyase; a pyruvate decarboxylase; an enzyme involved in degradation of fatty acids and their derivatives; and combinations of thereof.

In some aspects of the invention, the microorganism is a thermophilic or a mesophilic bacterium. In certain embodiments, the thermophilic or mesophilic bacterium is a species of the genera *Escherichia, Propionibacterium, Thermoanaerobacterium, Thermoanaerobacter, Clostridium, Geobacillus, Saccharococcus, Paenibacillus, Bacillus, Caldicellulosiruptor, Anaerocellum, Anoxybacillus, Klebsiella, Lactobacillus, Lactococcus,* or *Corynebacterium*. In other embodiments, the microorganism is a bacterium selected from the group consisting of: *E. coli* strain B, strain C, strain K, strain W, *Shewanella, Propionibacterium acnes, Propionibacterium freudenreichii, Propionibacterium shermanii, Propionibacterium pentosaceum, Propionibacterium arabinosum, Clostridium acetobutylicum, Clostridium beijerinckii, Thermoanaerobacterium thermosufurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thermocellum, Clostridium clariflavum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, Caldicellulosiruptor acetigenus, Caldicellulosiruptor saccharolyticus, Caldicellulosiruptor kristjanssonii, Caldicellulosiruptor owensensis, Caldicellulosiruptor lactoacelicus, Lactobacillus thermophilus, Lactobacillus bulgaricus, Lactococcus lactis,* and *Anaerocellum thermophilum*. In one embodiment, recombinant microorganism is selected from the group consisting of *Clostridium thermocellum*, and *Thermoanaerobacterium saccharolyticum*.

Another aspect of the invention relates to a process for converting a carbohydrate source to a hydrocarbon comprising contacting the carbohydrate source with a recombinant microorganism of the invention. In some embodiments, the carbohydrate source comprises lignocellulosic biomass. In certain embodiments, the lignocellulosic biomass is selected from the group consisting of grass, switch grass, cord grass, rye grass, reed canary grass, mixed prairie grass, miscanthus, sugar-processing residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, agave, and combinations thereof. In other embodiments, the carbohydrate source comprises a carbohydrate. In certain embodiments, the carbohydrate is a sugar, a sugar alcohol, or a mixture thereof.

In some aspects of the invention, the hydrocarbon produced by the recombinant microorganism is secreted.

Another aspect of the invention relates to an engineered metabolic pathway for producing a hydrocarbon from consolidated bioprocessing media.

One aspect of the invention relates to a recombinant microorganism comprising a native and/or heterologous enzyme that converts oxaloacetate and acetyl-CoA to malonyl-CoA and pyruvate, wherein said one or more native and/or heterologous enzymes is activated, upregulated, downregulated, or deleted. In some embodiments, the microorganism produces a hydrocarbon. In some embodiments, the enzyme is a transcarboxylase. In one embodiment, the transcarboxylase is encoded by a polynucleotide from a *Thermoanaerobacter* species, *P. freudenreichii P. acnes,* or *C. thermocellum*. In another embodiment, the transcarboxylase is genetically modified.

In some embodiments, the genetic modification produces an altered catalytic activity and/or an altered substrate specificity to improve the conversion of a substrate to a product as compared to the native enzyme. In some embodiments, the genetic modification alters catalytic activity and/or substrate specificity to provide a genetically modified polypeptide that converts a substrate to a product that is not catalyzed by the native enzyme in vivo, or is catalyzed at only minimal turnover.

BRIEF DESCRIPTION OF THE DRAWINGS/FIGURES

FIG. 2 depicts three steps in the synthesis of hydrocarbons and hydrocarbon derivatives.

FIG. 7A is an alignment of the transcarboxylase 5S subunits from *P. freudenreichii, P. acnes, C. thermocellum,* and *T. saccharolyticum*.

FIG. 7B is an alignment of the transcarboxylase 1.3S subunits from *P. freudenreichii, P. acnes, C. thermocellum,* and *T. saccharolyticum*.

FIG. 7C is an alignment of the transcarboxylase 12S subunit (N-terminus) from *P. freudenreichii, P. acnes, C. thermocellum,* and *T. saccharolyticum*.

FIG. 13 depicts the final step of the anaerobic fatty acid pathway.

Figure 20B:
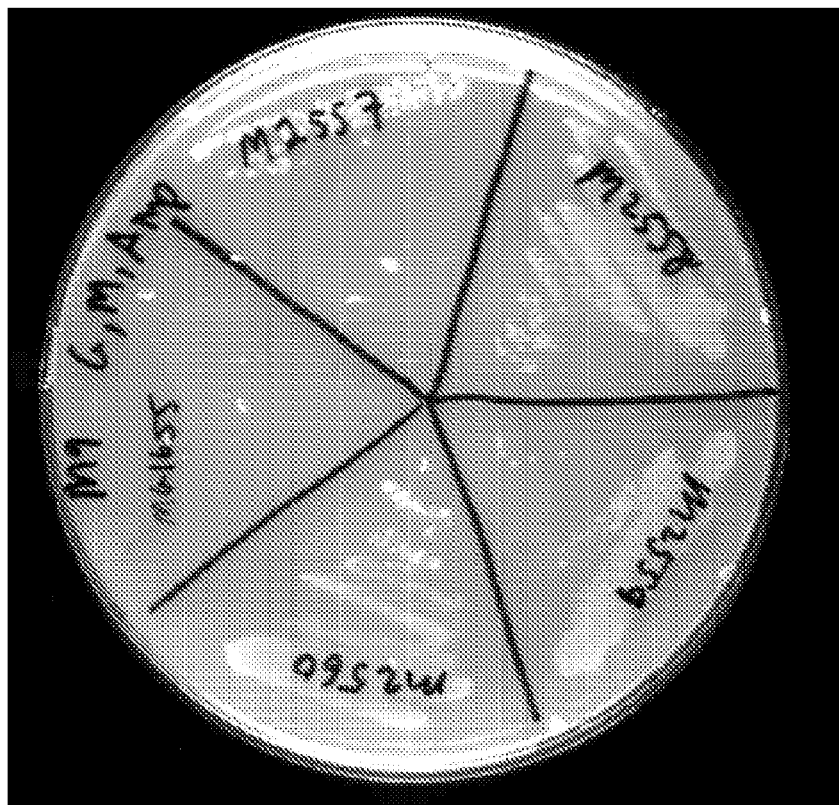
Figure 20A:
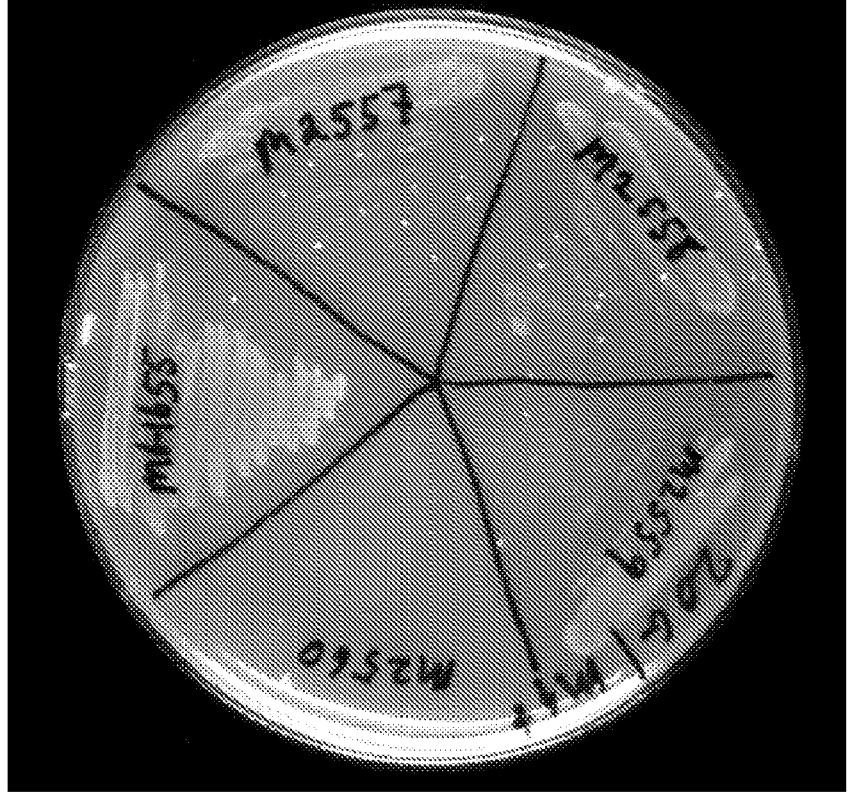

FIG. 20A and FIG. 20B demonstrates growth of transformants containing putative transcarboxylases on selective media.

Figure 21A:
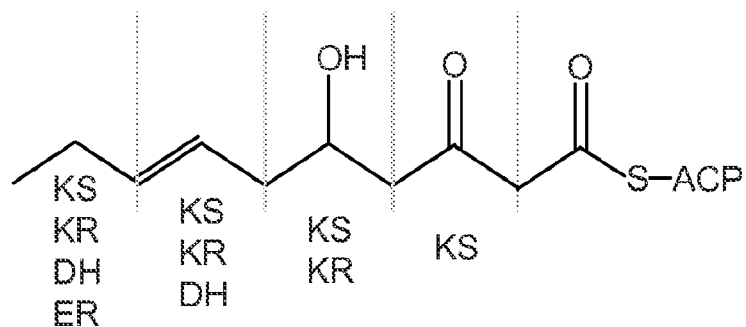

FIG. 21A depicts polyketide chain synthesis, which proceeds by the addition or condensation of different functional groups to an acyl-ACP chain using a combination of enzymatic activities per two-carbon chain extension.

Figure 21B:
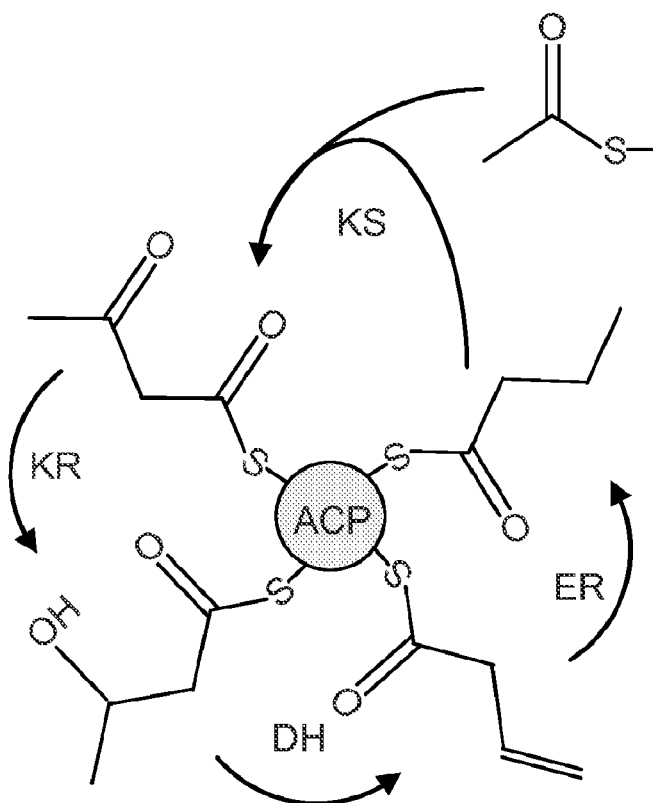

FIG. 21B depicts fatty acid chain synthesis, which proceeds by four enzymatic steps per two-carbon chain extension.

FIG. 22A depicts the total fatty acid content (shown in μg/mL) for *E. coli* strain M2933 carrying different acyl-ACP chain termination enzymes.

Figure 22B:
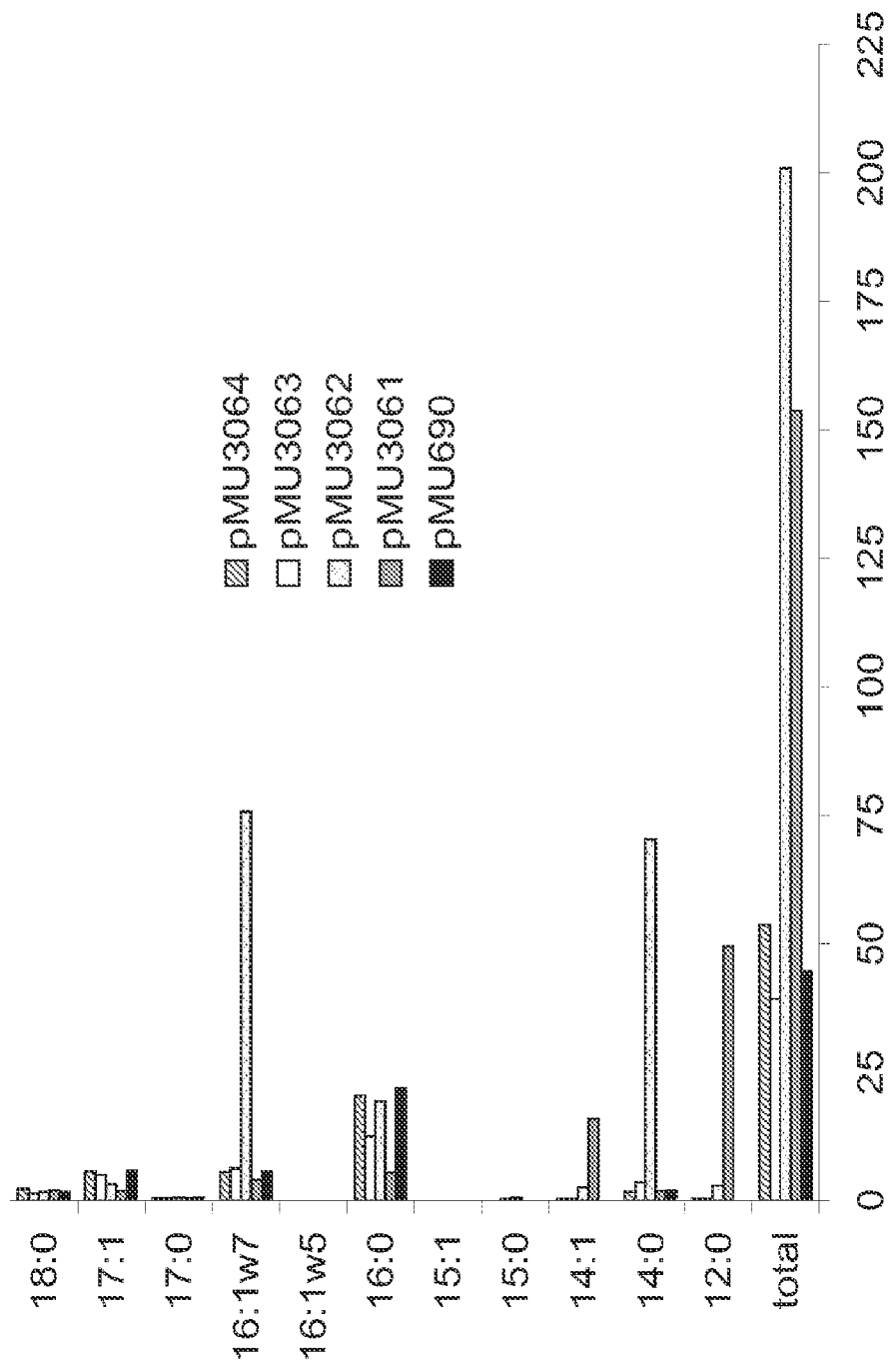

FIG. 22B is a graphical representation of the data from FIG. 22A.

Figure 23:
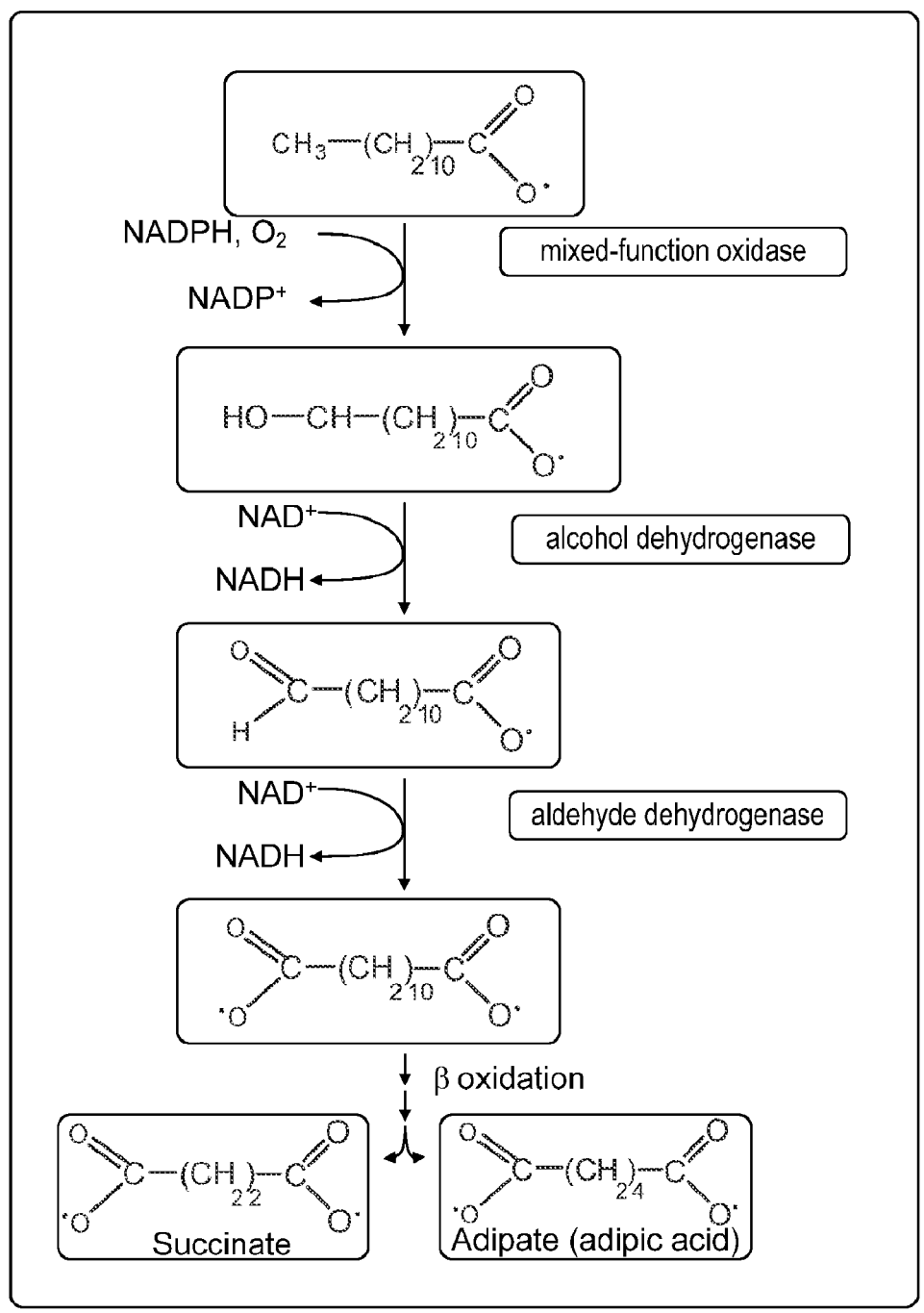

FIG. 23 depicts the synthesis of succinate and adipate using omega oxidation.

Figure 24:
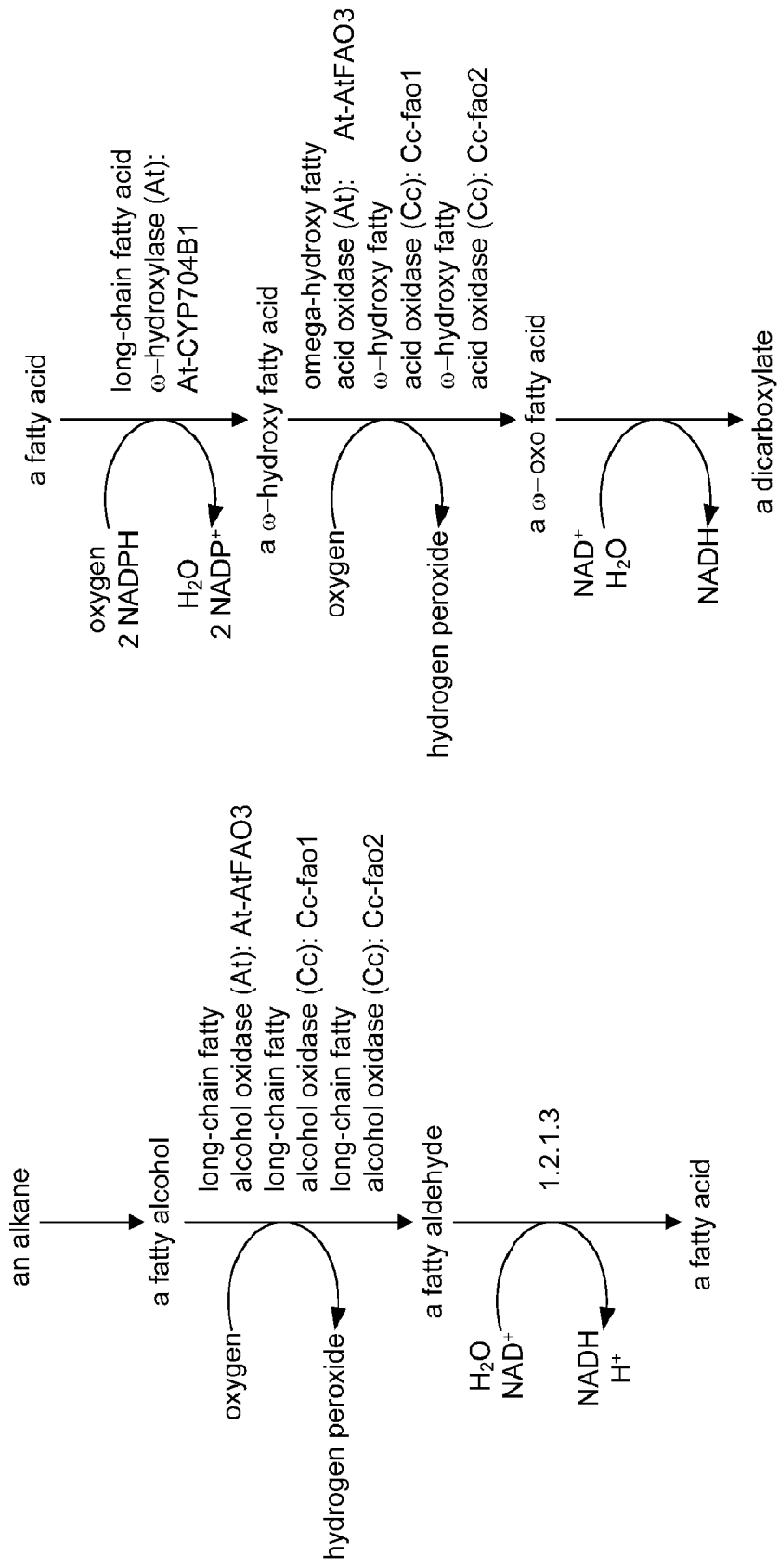

FIG. 24 depicts the synthesis of a dicarboxylate using omega oxidation.

Figure 25:
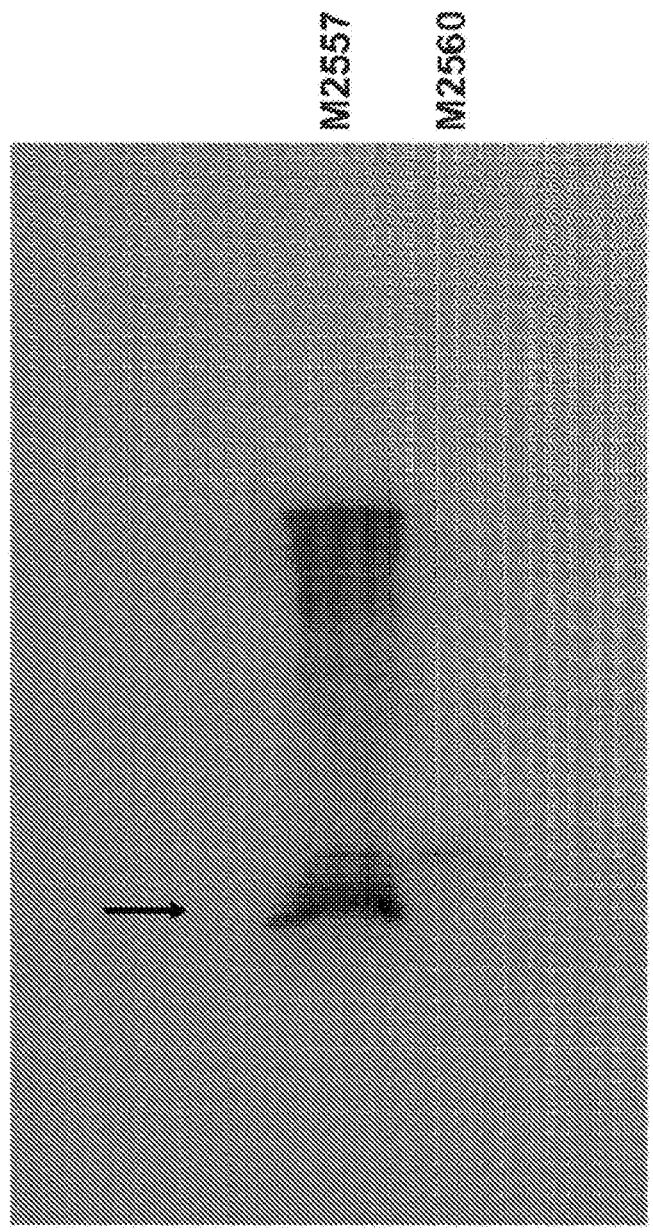

FIG. 25 is a western blot demonstrating the presence of biotinylated enzyme in construct M2557 but not in M2560.

Figure 26A:
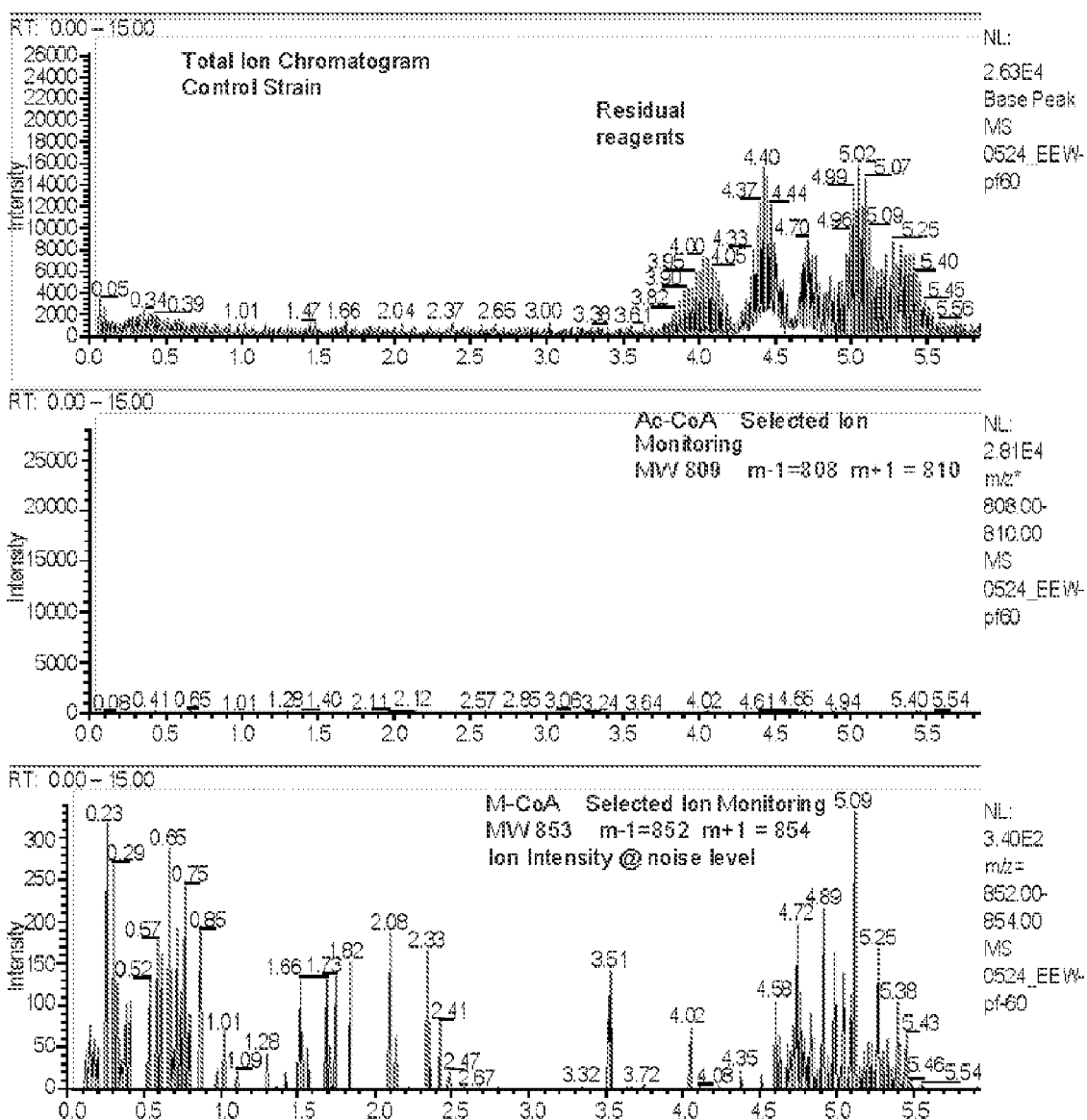
Figure 26A:
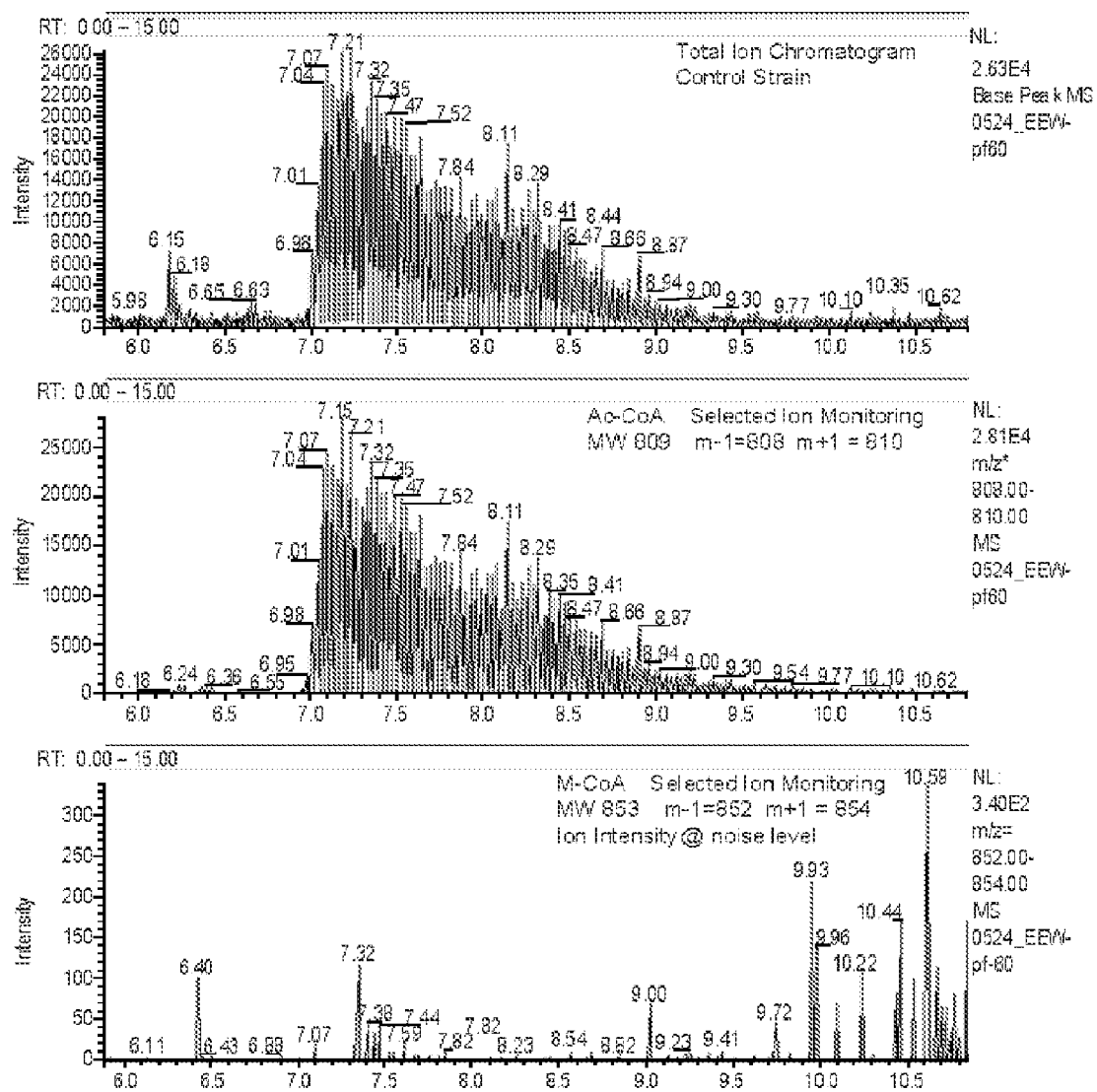
Figure 26A:
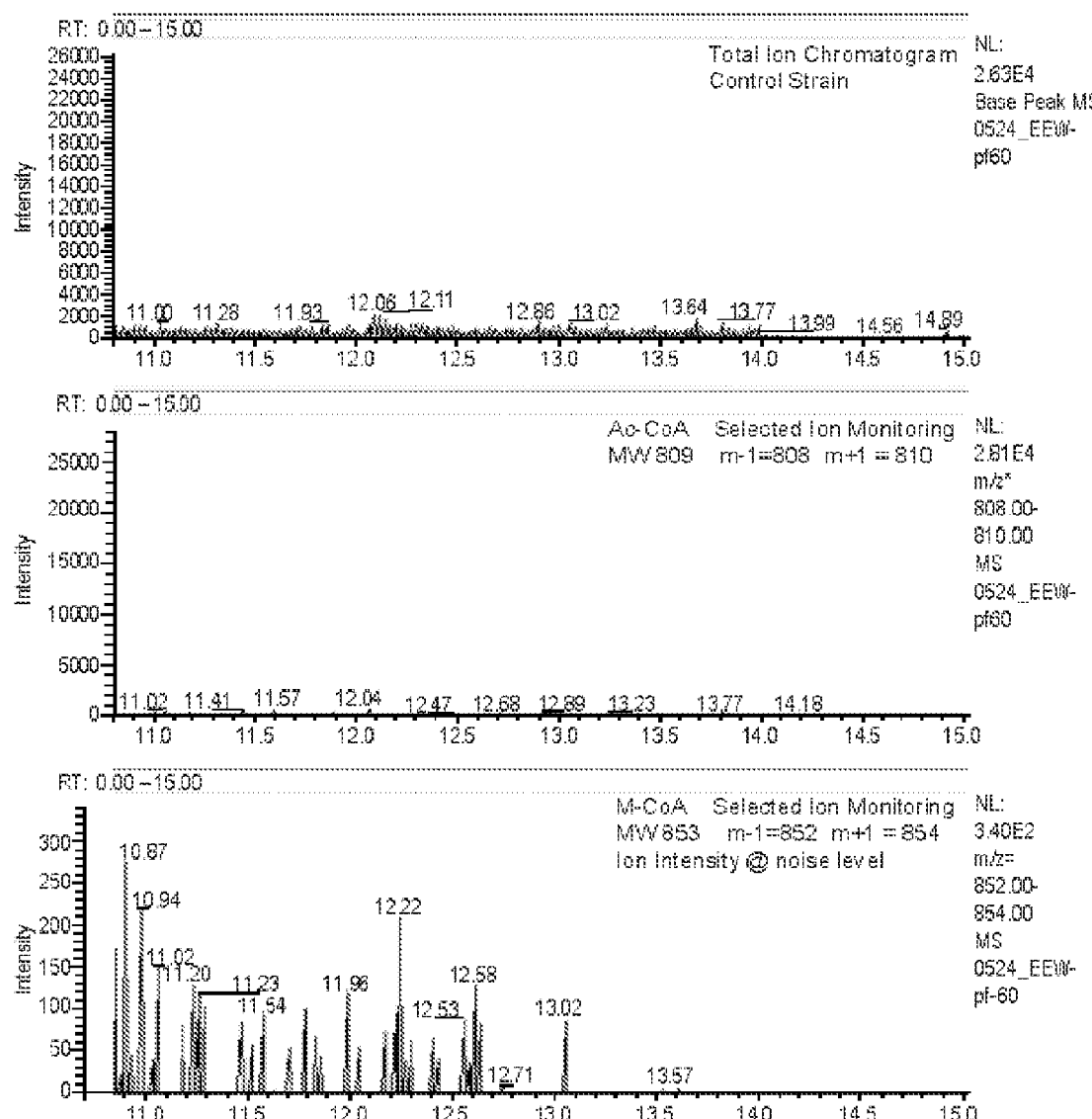

FIG. 26A depicts a mass spectrum of the transcarboxylase assay products for the negative control sample.

Figure 26B:
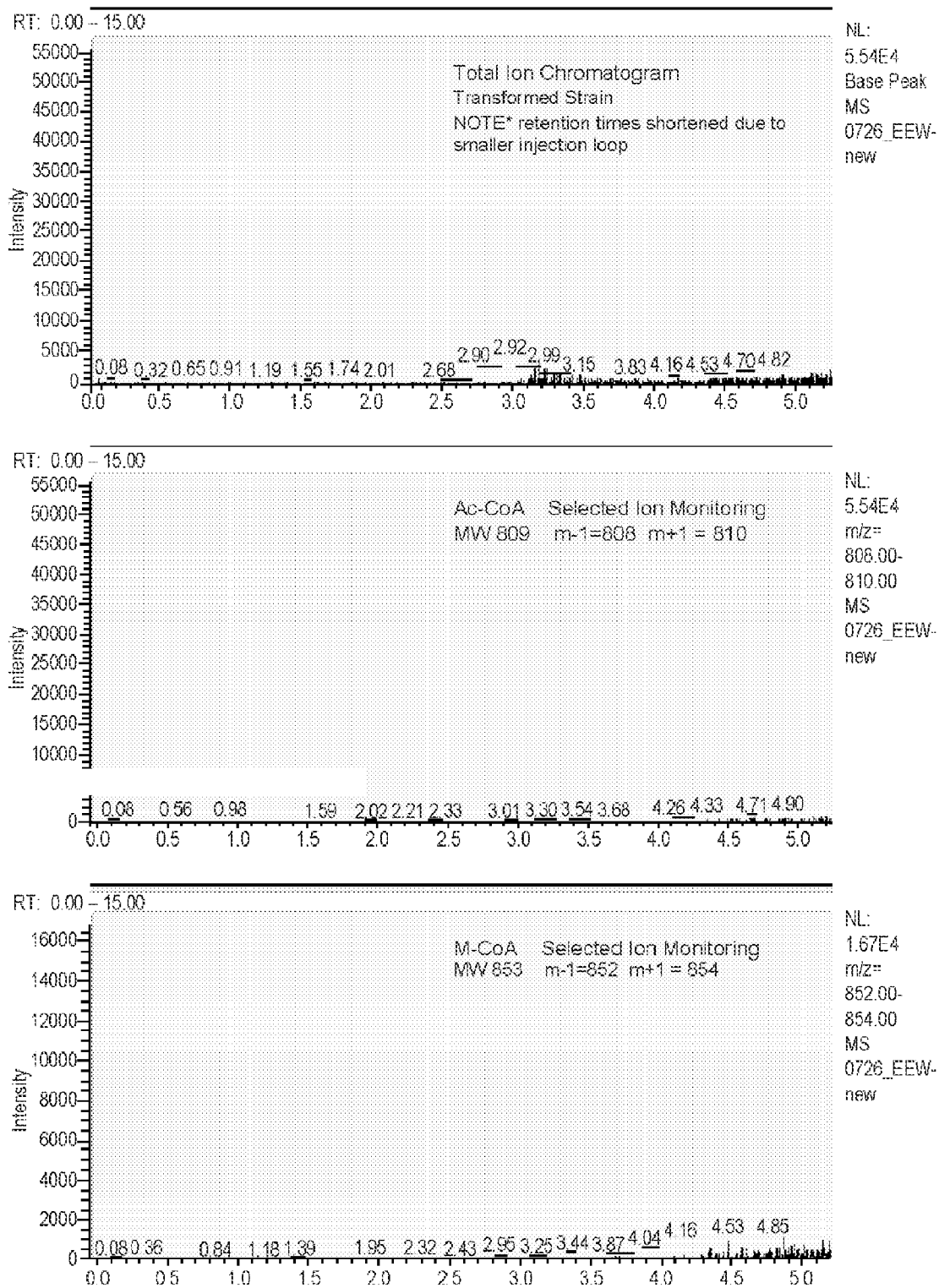
Figure 26B:
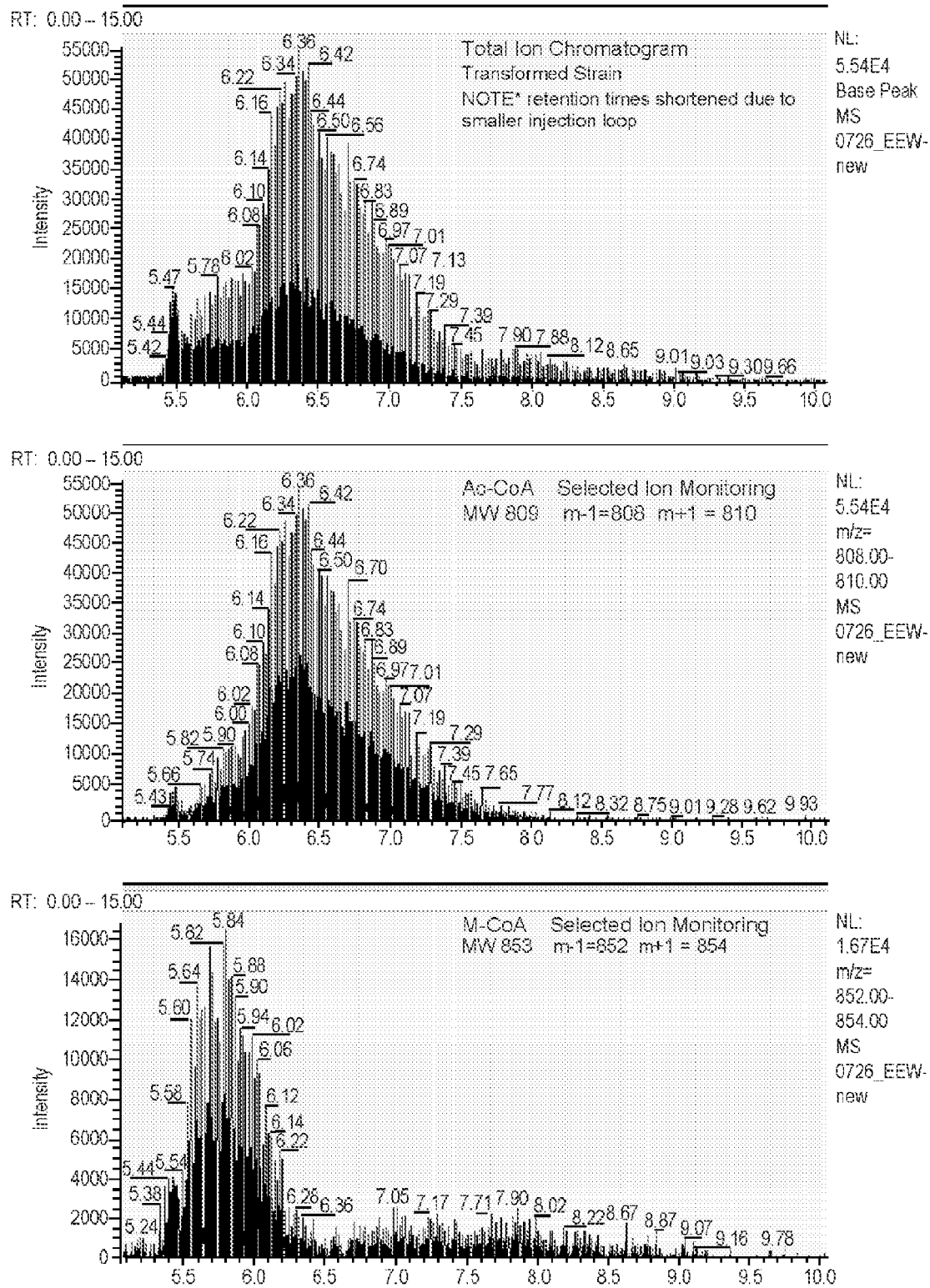
Figure 26B:
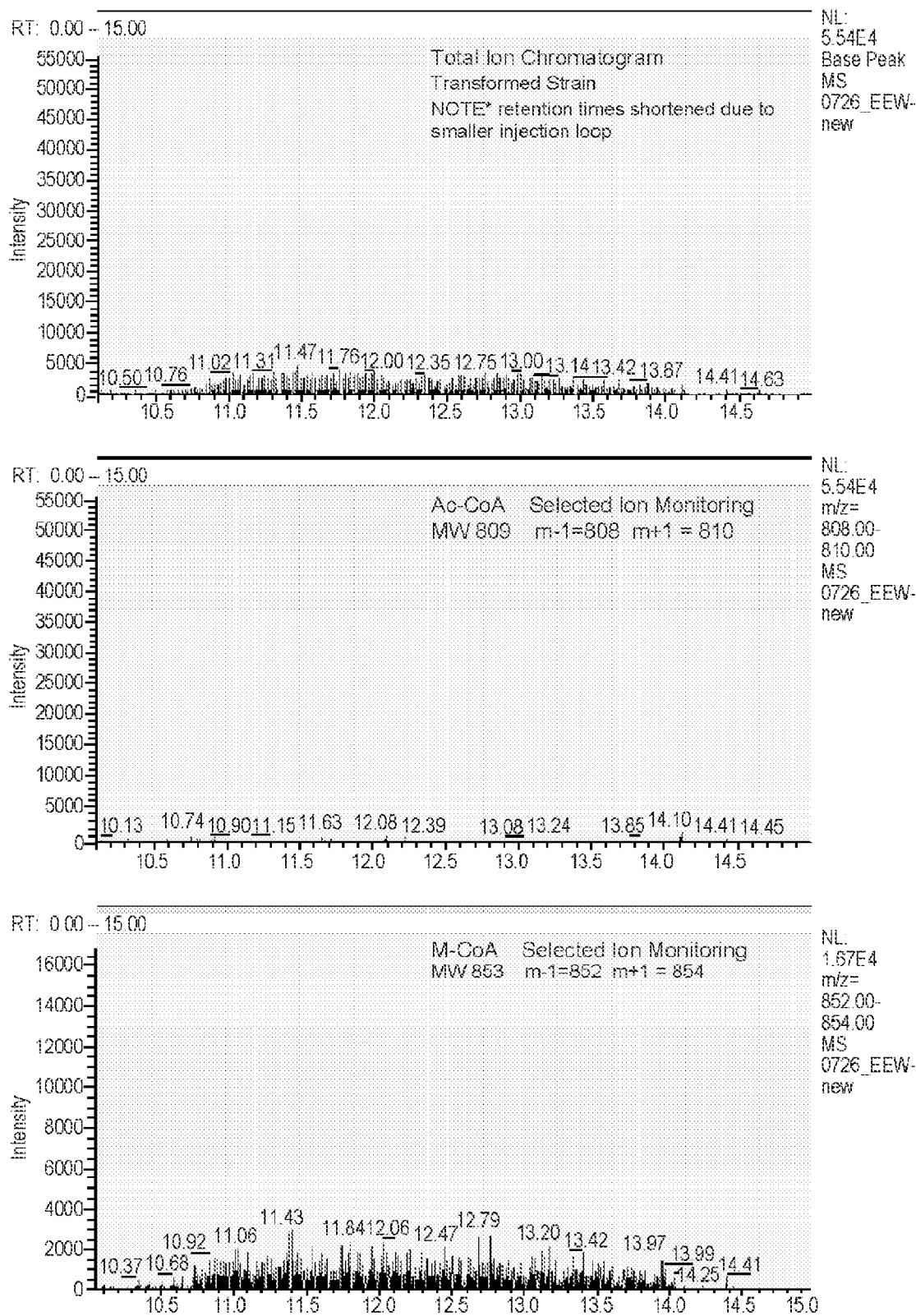

FIG. 26B depicts a mass spectrum of the transcarboxylase assay products for the transcarboxylase sample.

Figure 27A:
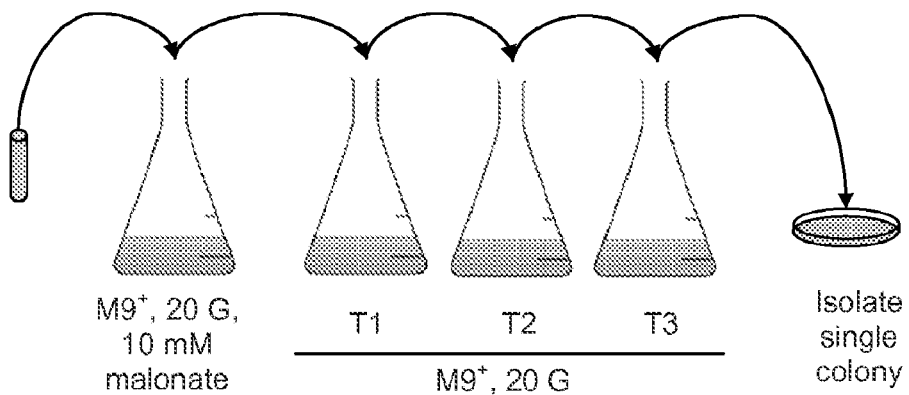

FIG. 27A depicts a schematic for the use of the accC:: matBC *E. coli* strain M2470 to select for more efficient malonyl-CoA production by transcarboxylases.

Figure 27B:
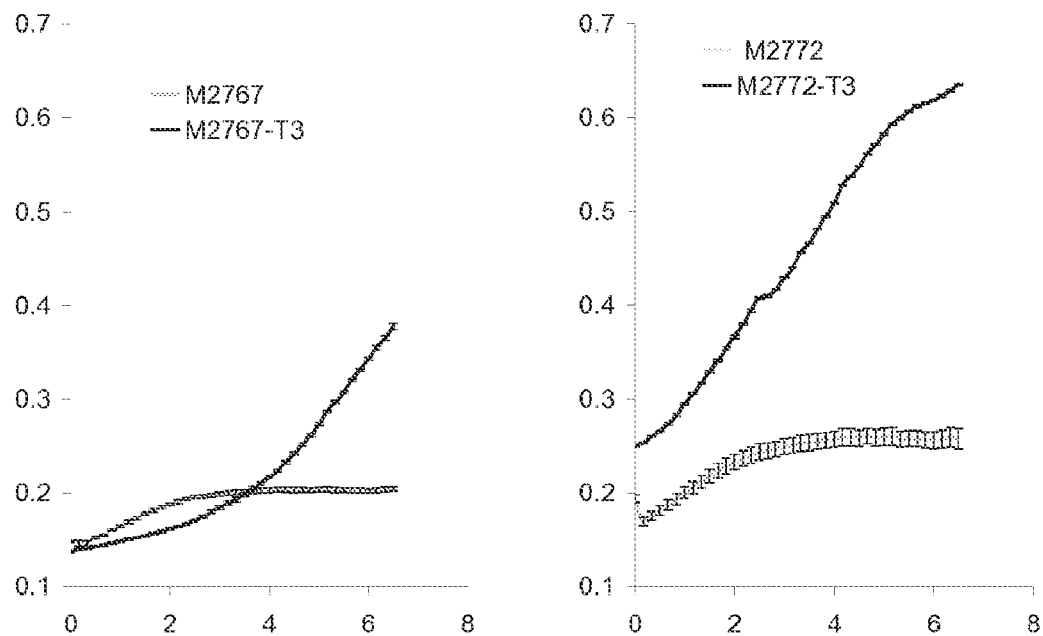

FIG. 27B shows the growth rates for the original strain and T3 strain.

Figure 28:
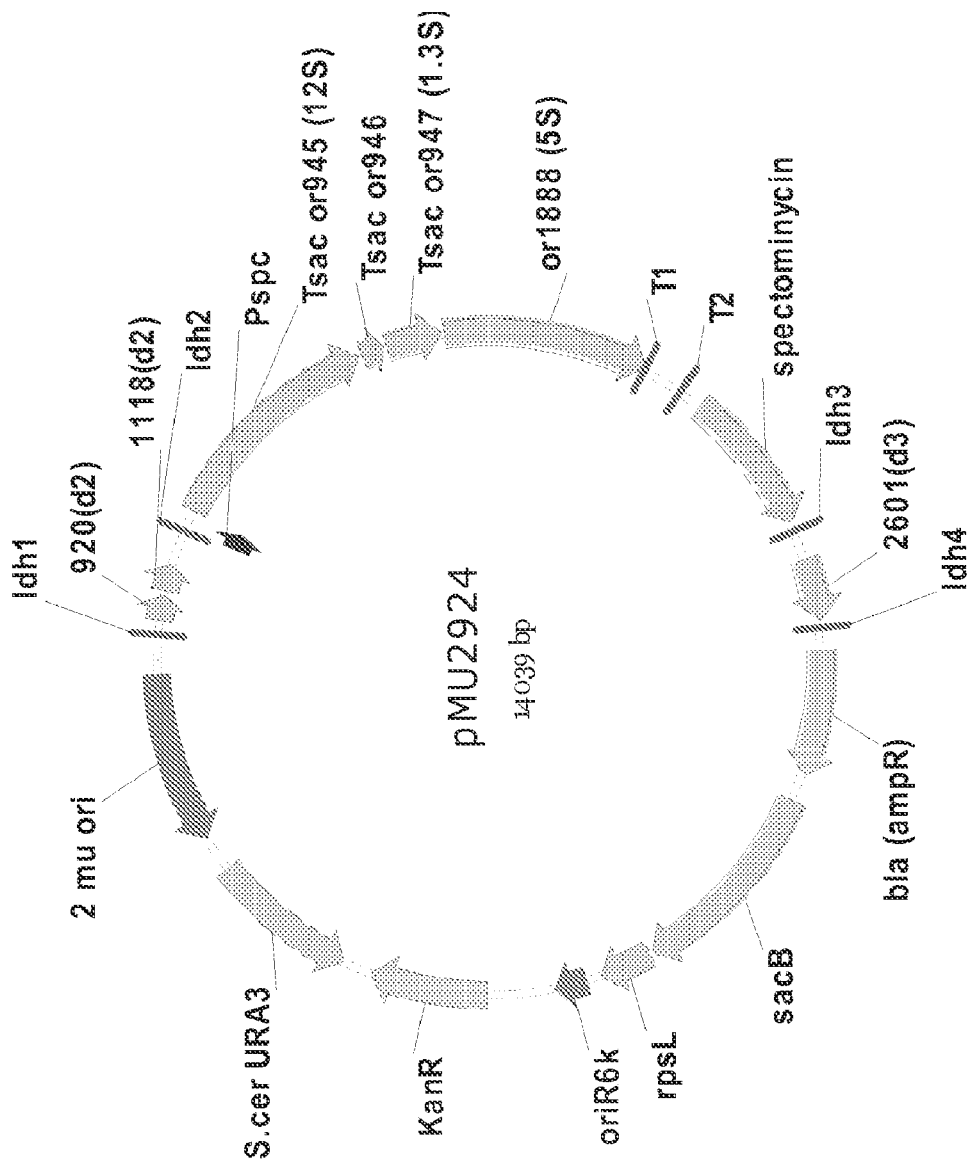

FIG. 28 depicts the vector pMU2924.

Figure 29:
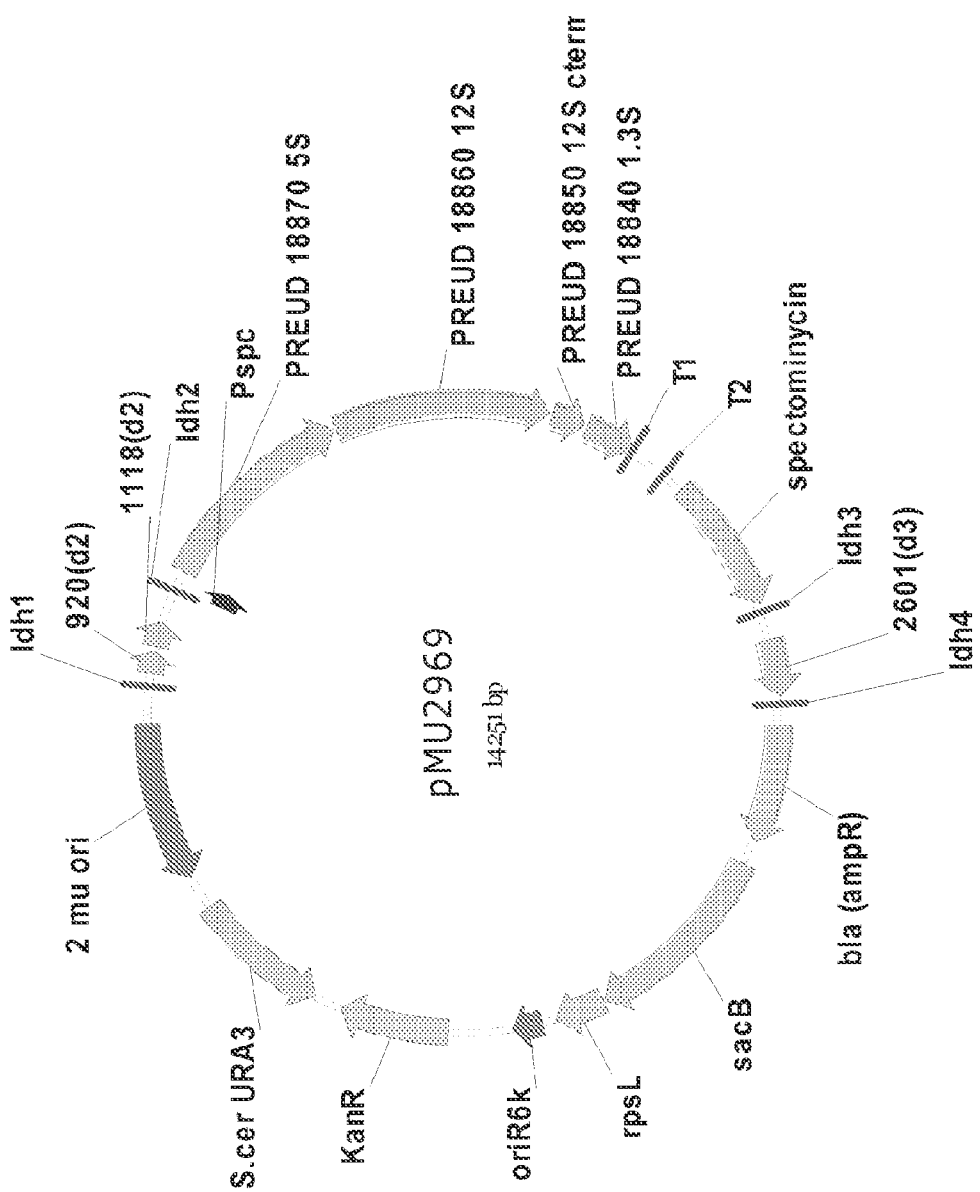

FIG. 29 depicts the vector pMU2969.

Figure 30:
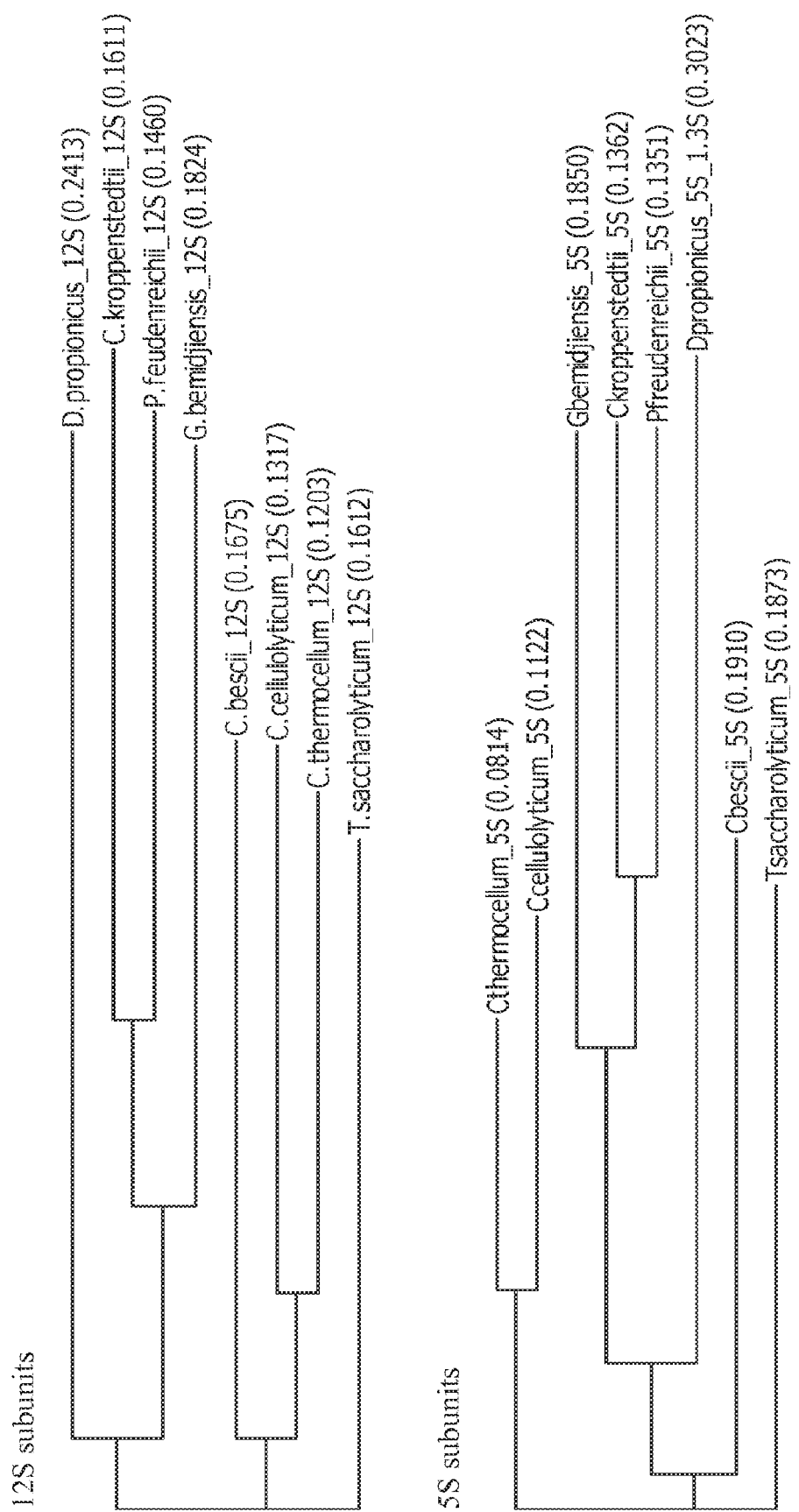
Figure 30:
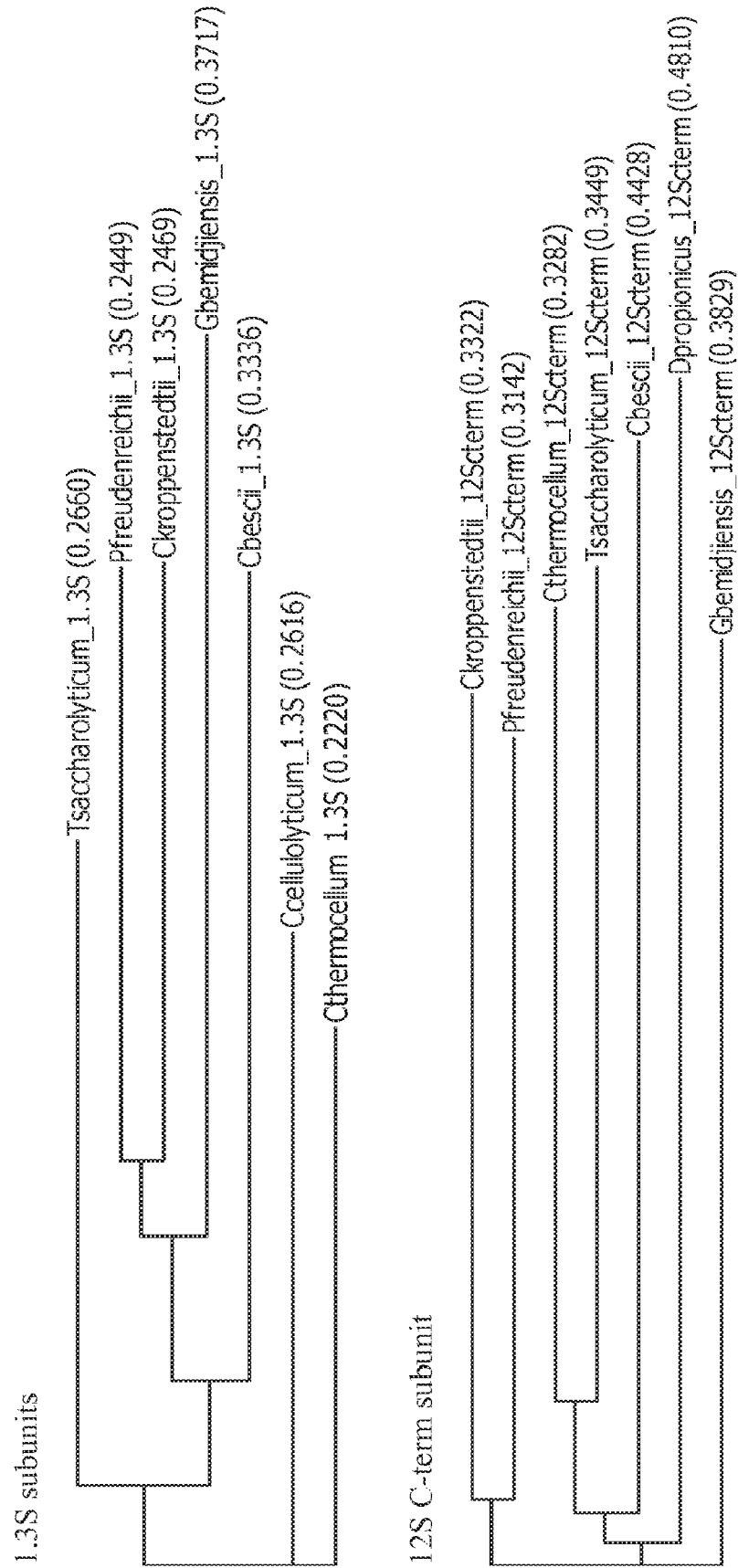
Figure 32A:
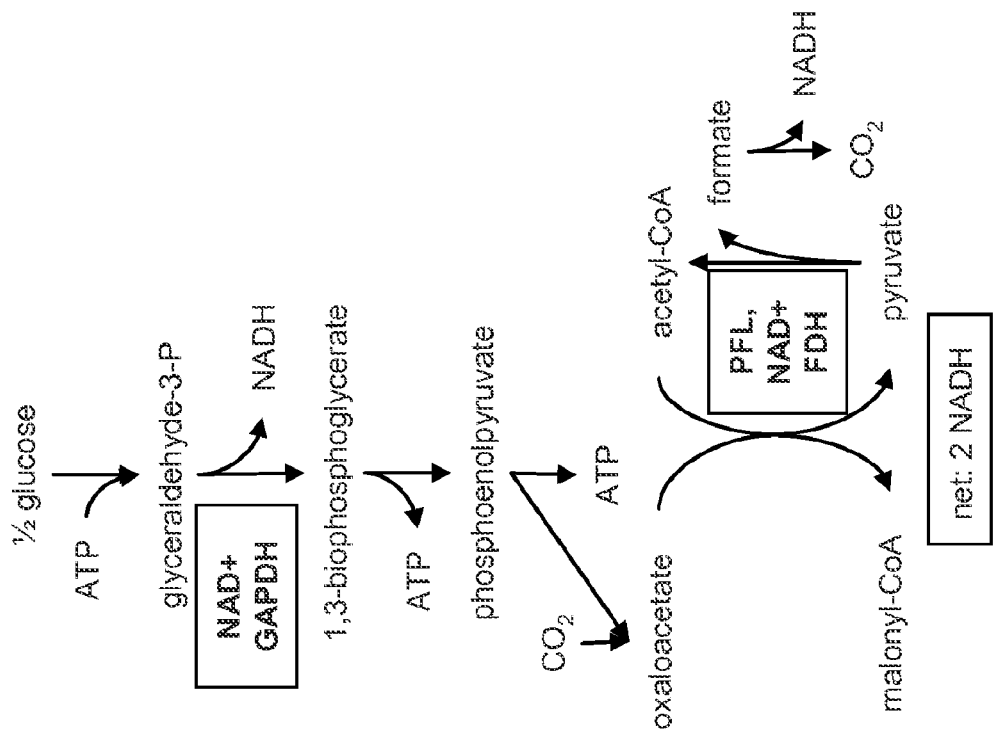
Figure 32B:
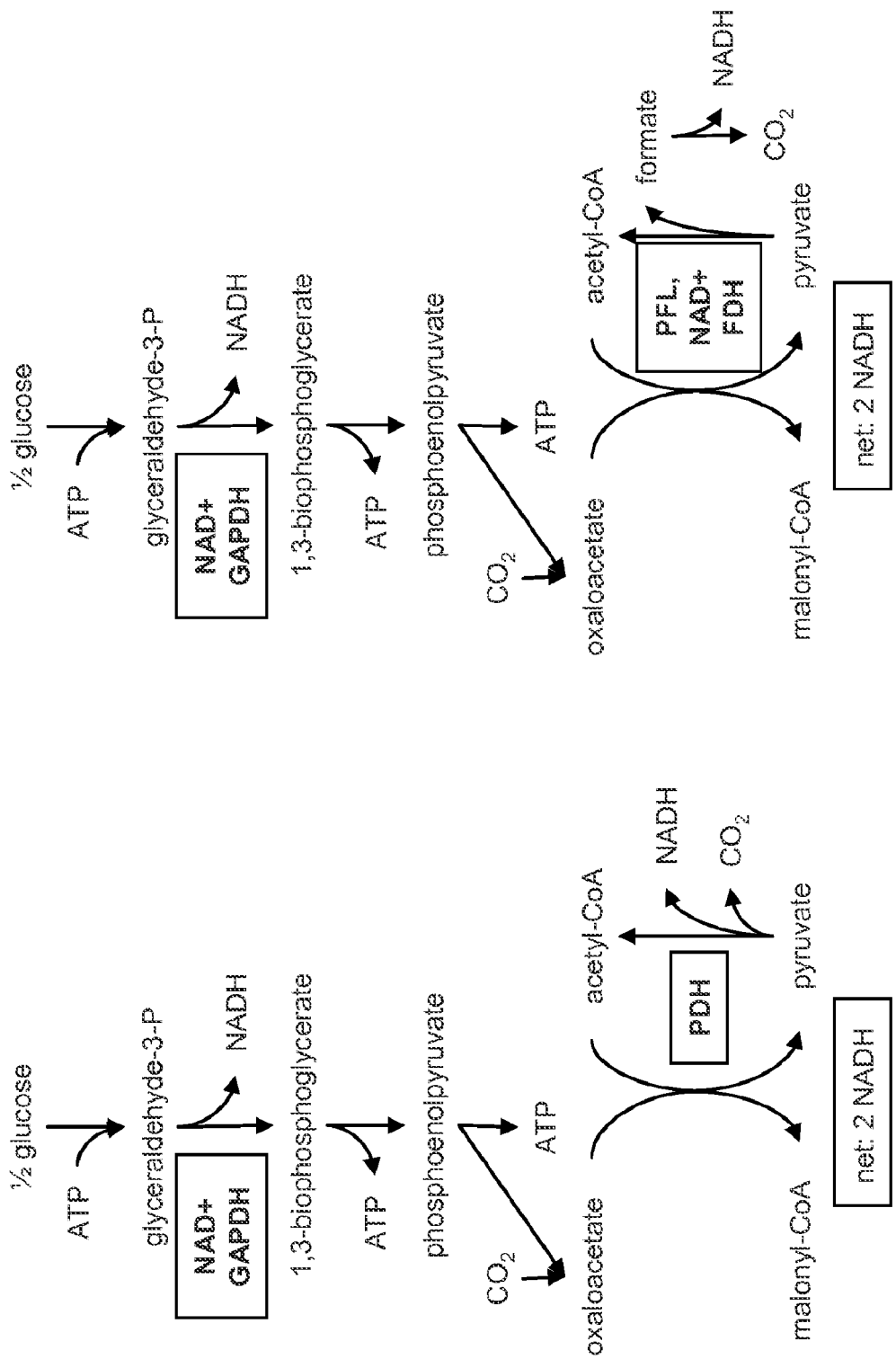
Figure 32D:
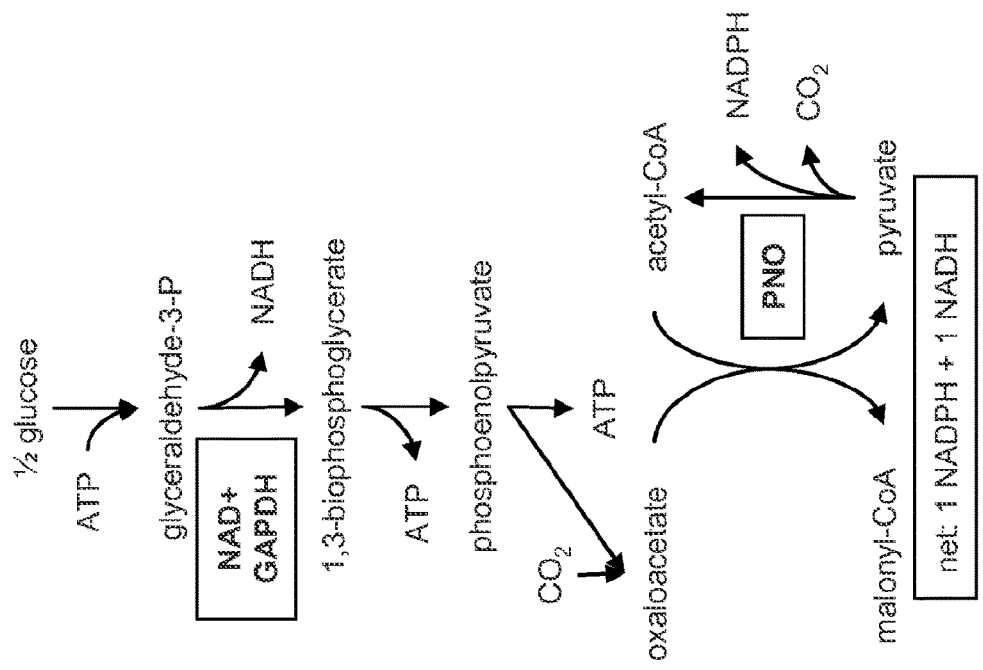
Figure 32C:
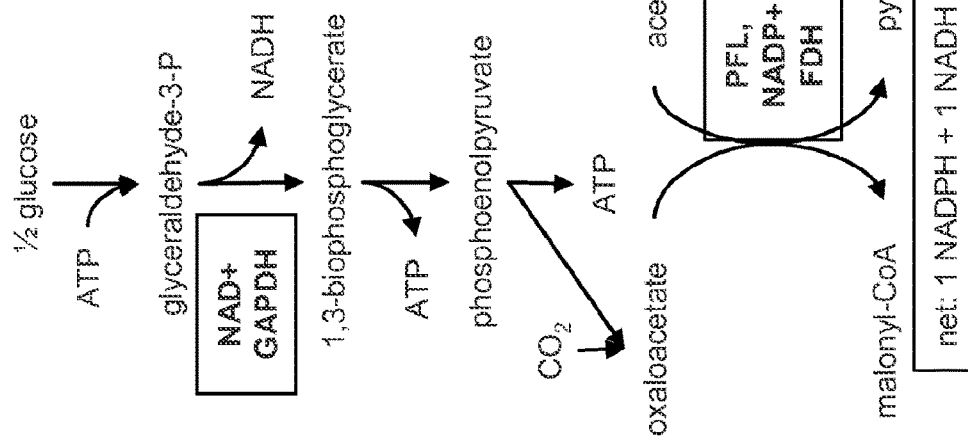
Figure 32J:
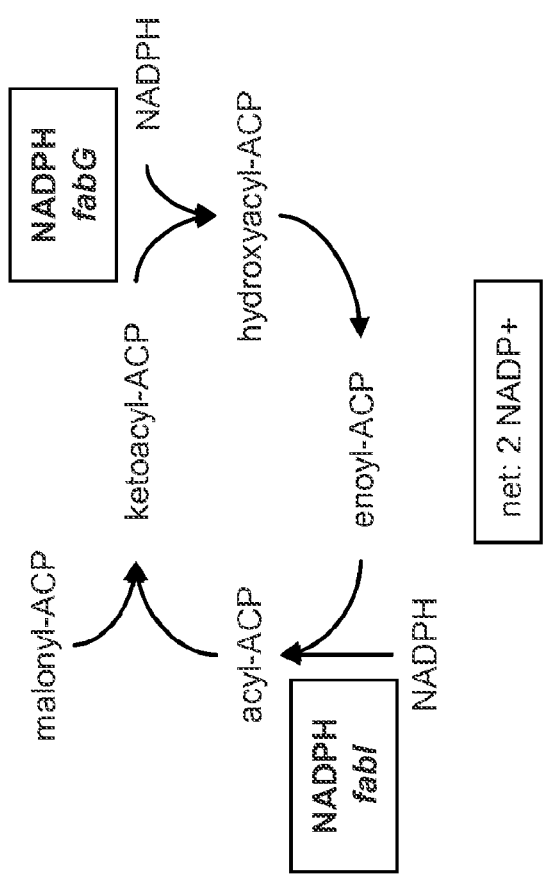
Figure 32I:
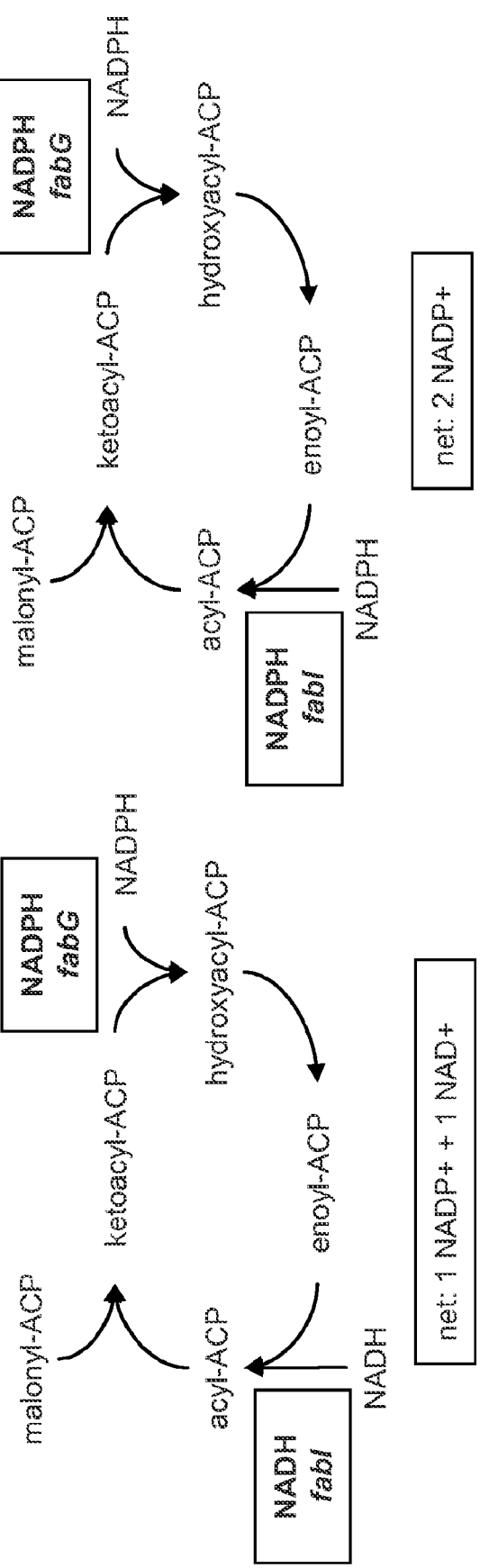

FIG. 30 is a phylogenetic tree depicting relatedness between 12S, 5S, 1.3S, and 12S C-term subunits of transcarboxylases from *D. propionicus, C. kroppenstedtii, P. fuedenreichii, G. bemidjiensis, C. bescii, C. Cellulolyticum, C. thermocellum*, and *T. sacchamlyticum*.

Figure 31:
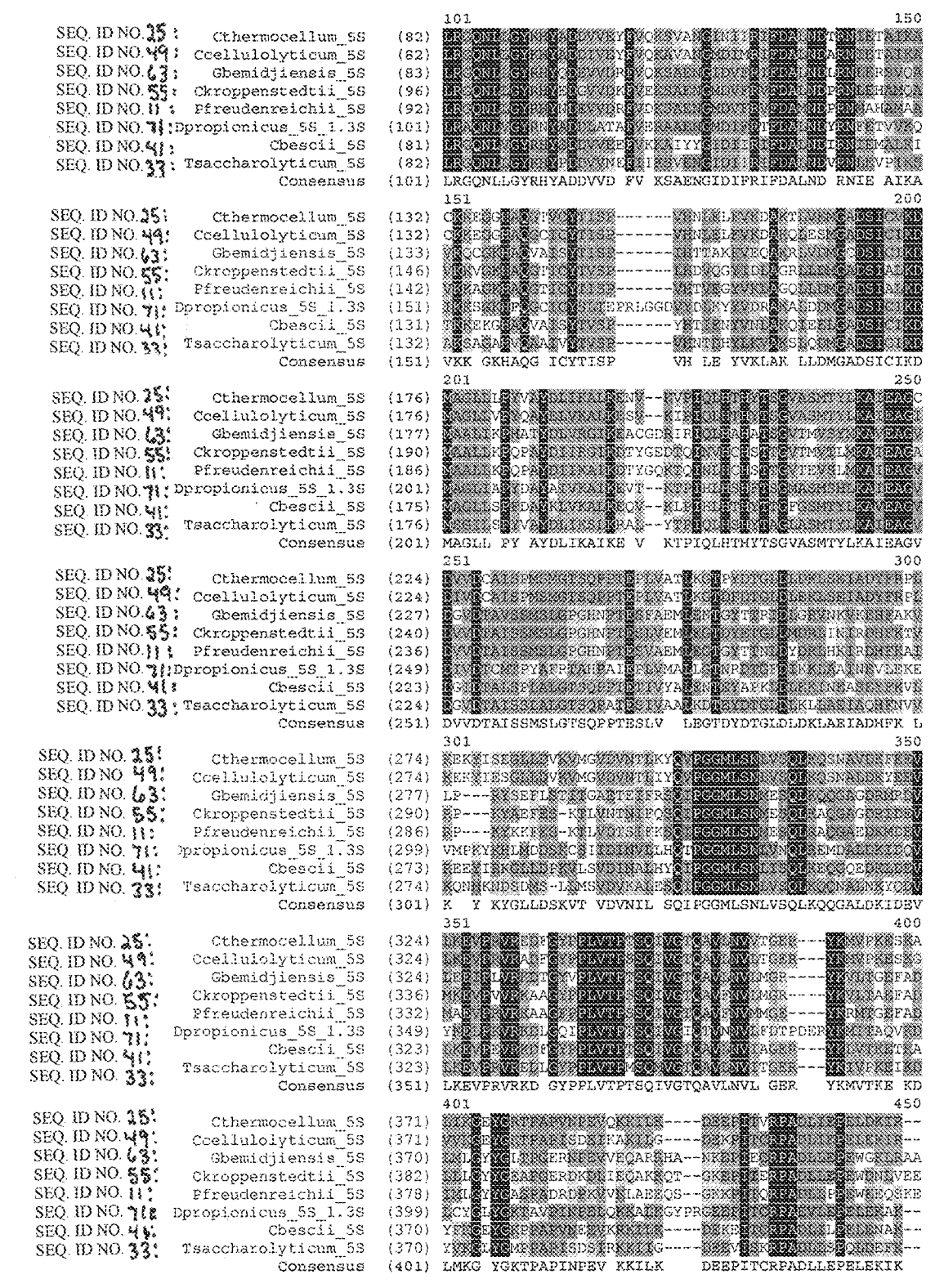

FIG. 31 is an alignment of the transcarboxylase subunits from *D. propionicus, C. kroppenstedtii, P. fuedenreichii, G. bemidjiensis, C. bescii, C. Cellulolyticum, C. thermocellum*, and *T. sacchamlyticum*.

FIG. 32A to FIG. 32L depicts different schematic routes that correspond to co-factor pathway selection presented in Table 10.

Figure 33:
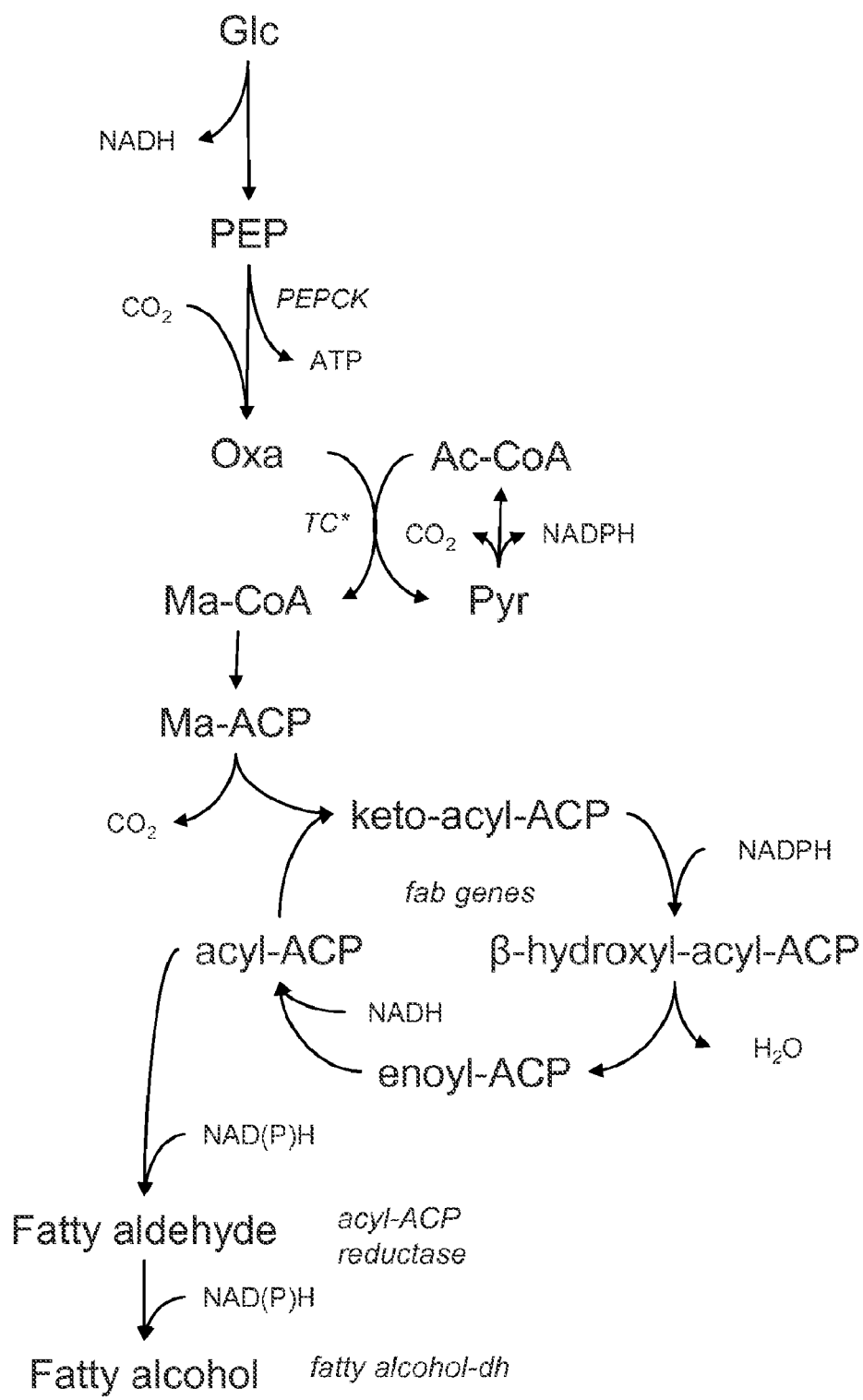

FIG. 33 depicts a pathway for the conversion of glucose to fatty aldehyde or fatty alcohol.

Figures 34A, 34B:
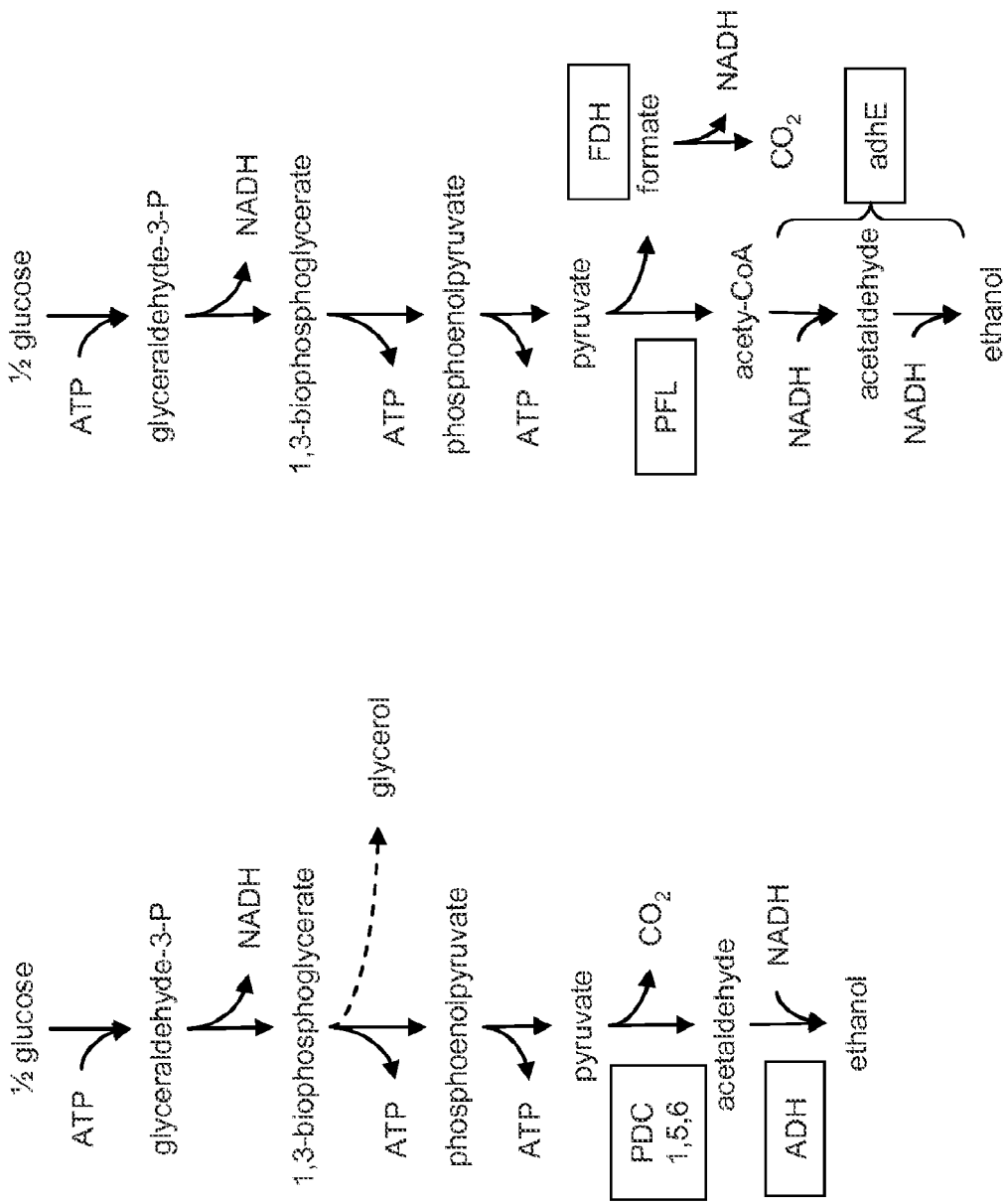

FIG. 34A depicts the pathways of the fermentative metabolism of *S. cerevisiae* involving the native pyruvate decarboxylase (pdc) based ethanol pathway.

FIG. 34B depicts the pathways for the conversion of the fermentative metabolism of *S. cerevisiae*, as shown in FIG. 34A, into the one involving an intermediary pyruvate formate lyase and alcohol/aldehyde dehydrogenase (pfl adhE) based ethanol pathway.

Figure 34C:
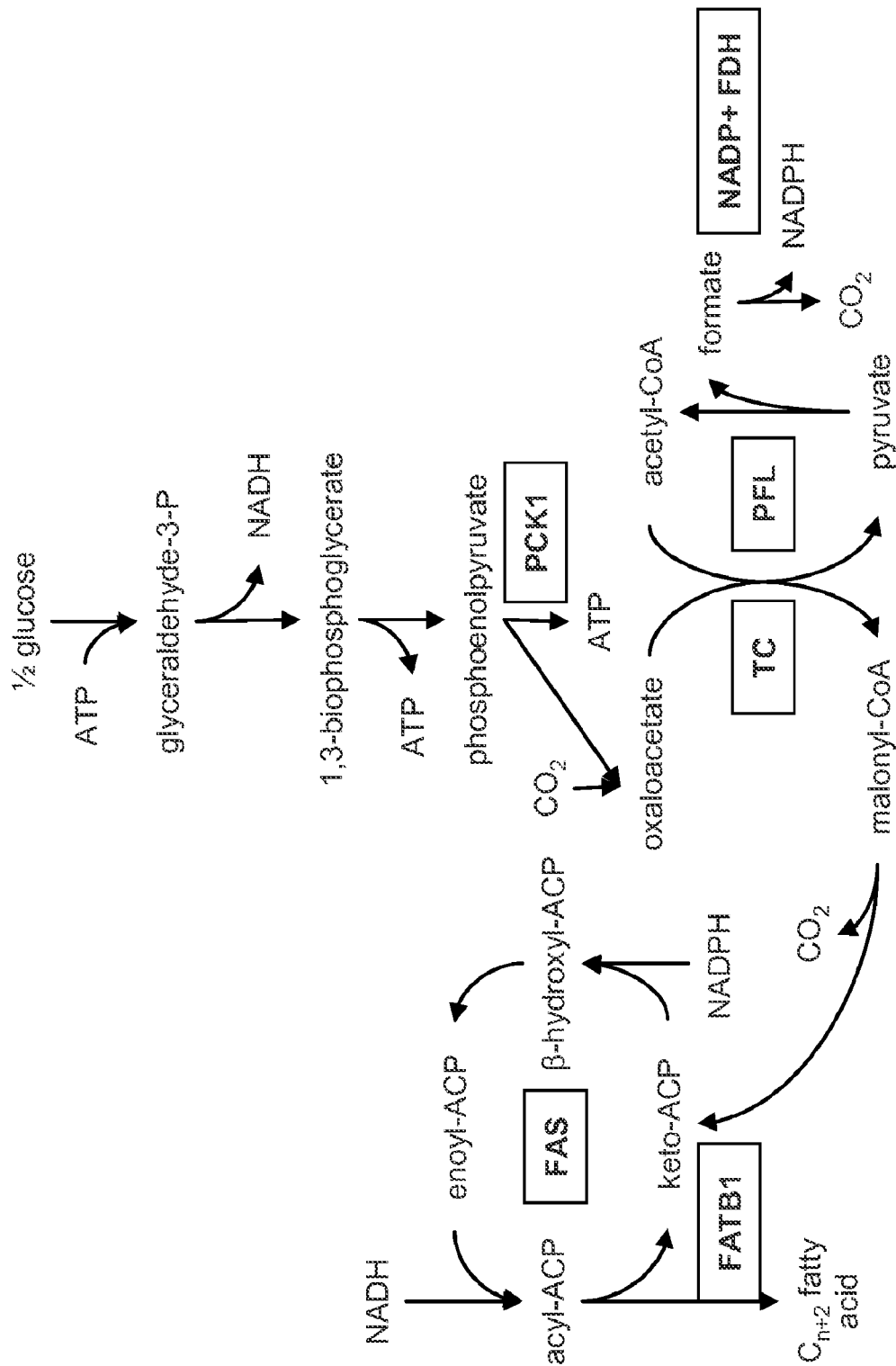

FIG. 34C depicts the pathways for the conversion of the fermentative metabolism of *S. cerevisiae*, as in shown in FIG. 34B, into the one involving an the transcarboxylase based palmitic acid pathway.

Figure 35:
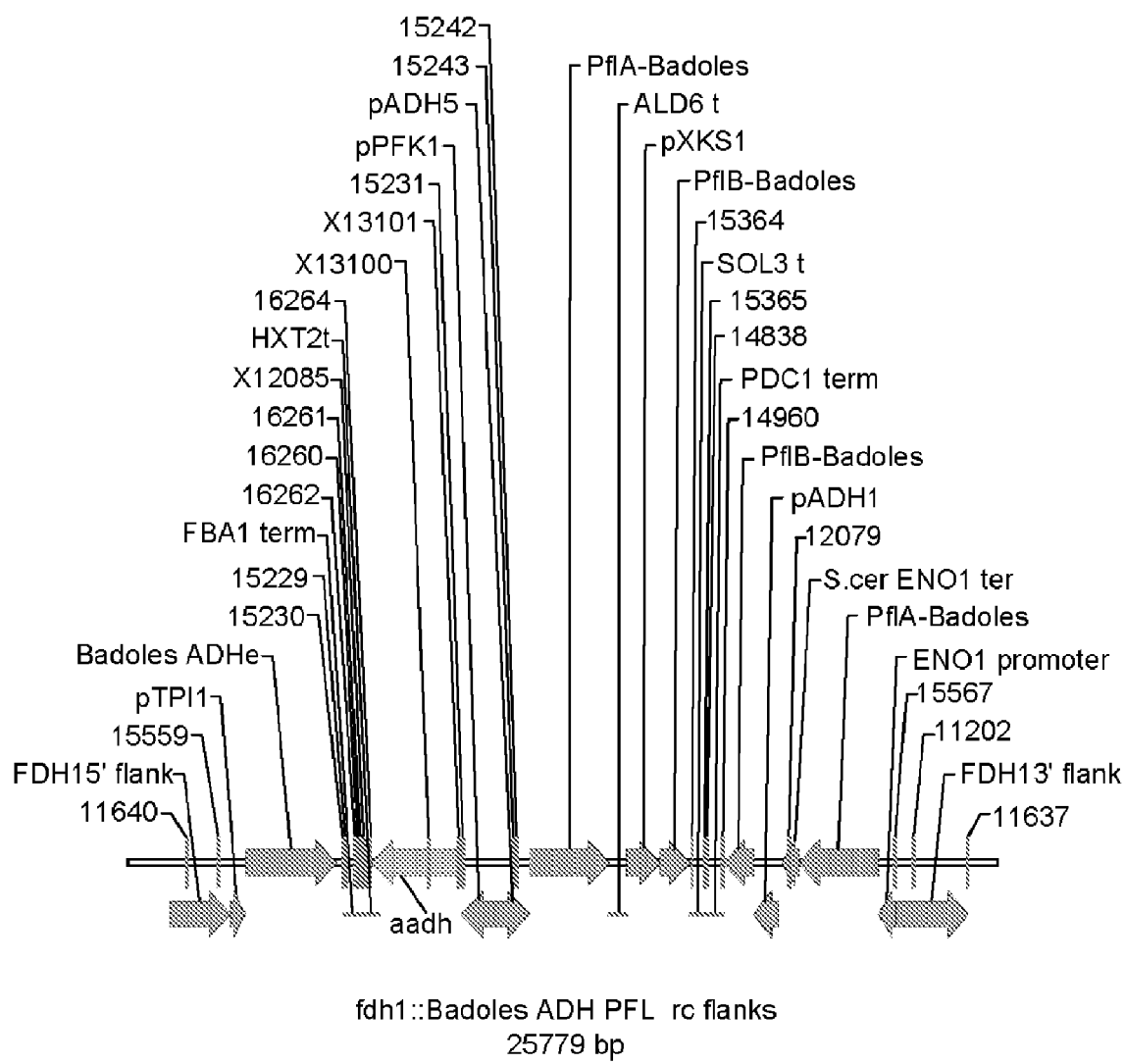

FIG. 35 depicts an integration design which deletes FDH1 and replaces the gene with two copies of ADH and two copies of PFL.

Figure 36:
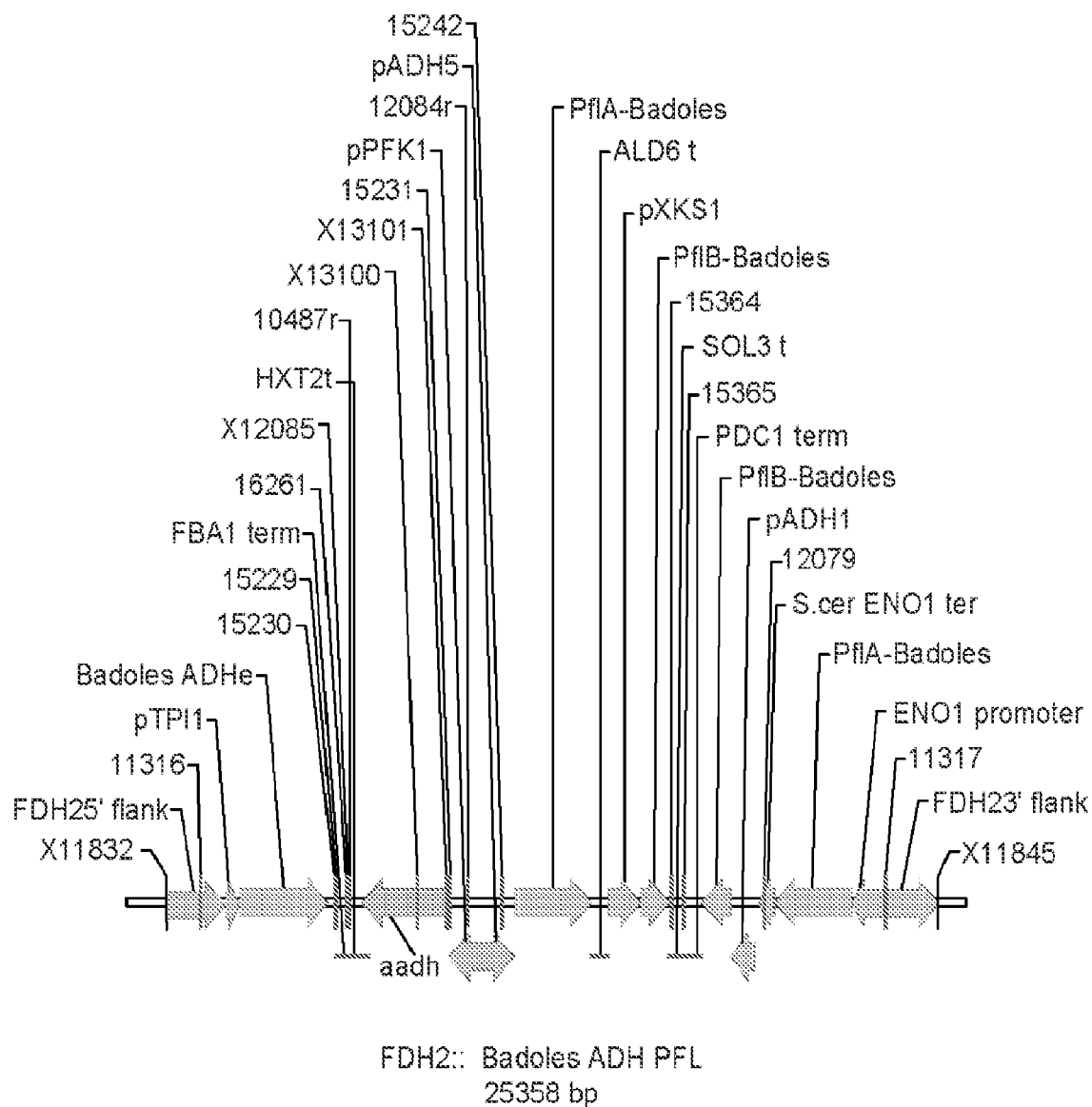

FIG. 36 depicts an integration design which deletes FDH2 and replaces the gene with two copies of ADH and two copies of PFL.

Figure 37:
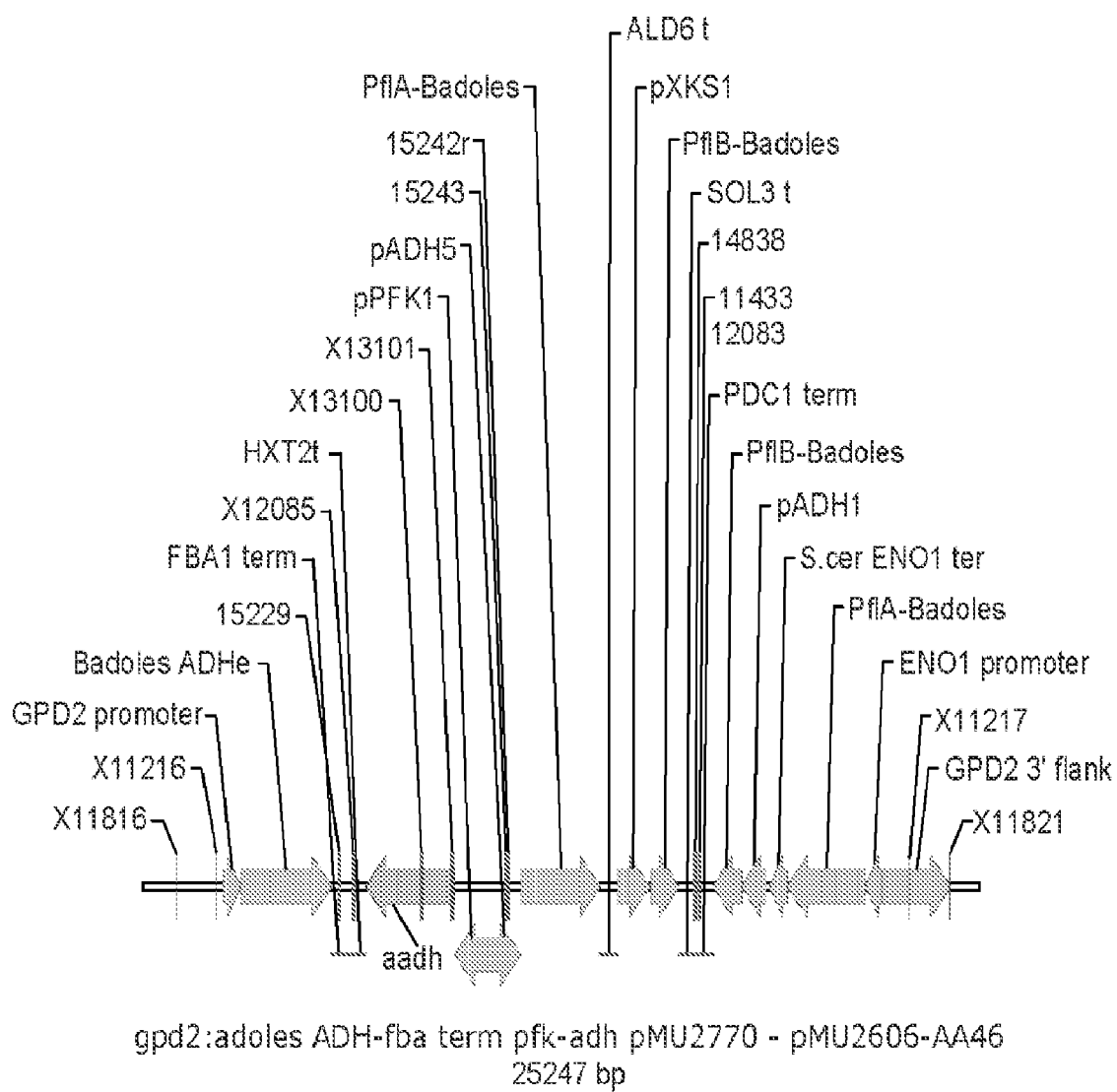

FIG. 37 depicts an integration design which deletes GPD2 and replaces the gene with two copies of ADH and two copies of PFL.

Figure 38:
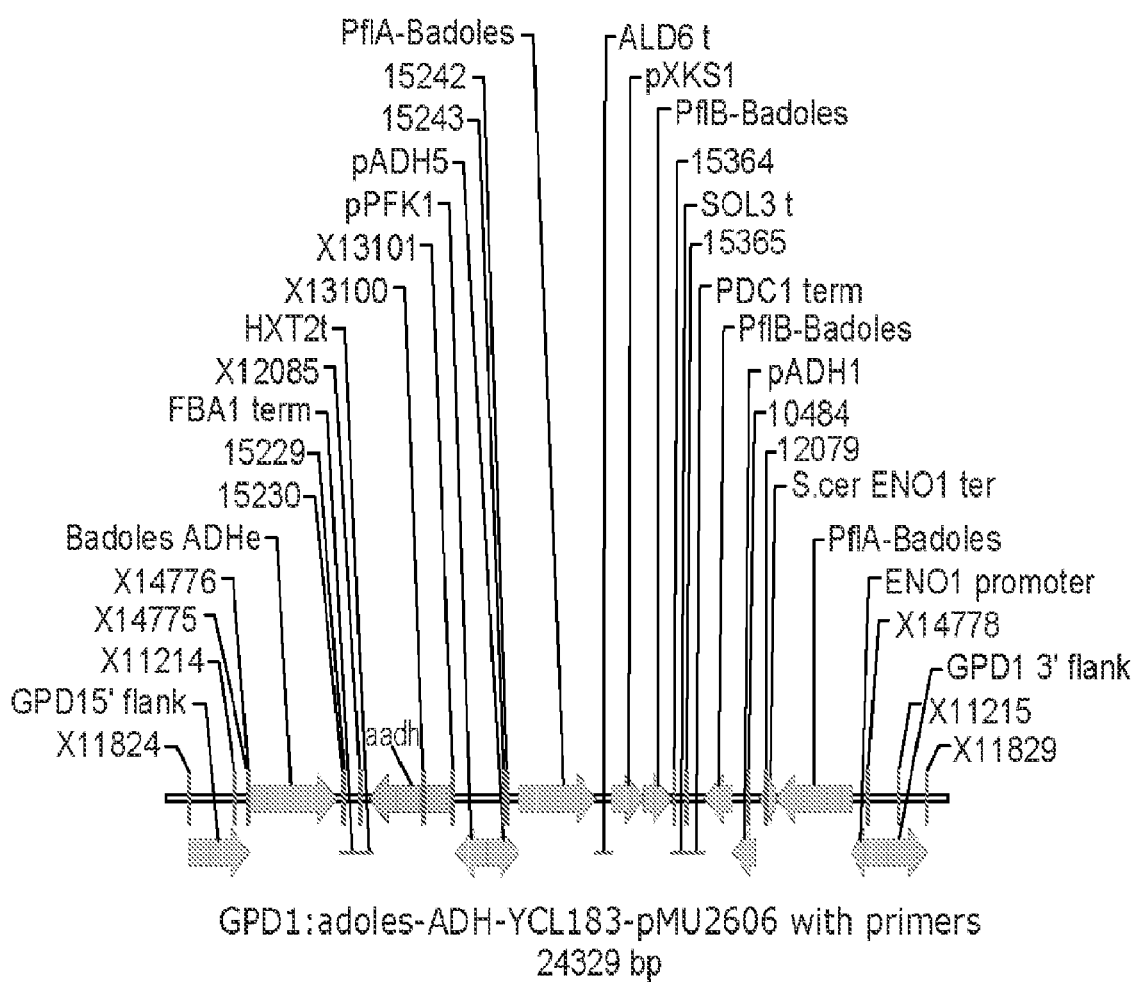

FIG. 38 depicts an integration design which deletes GPD1 and replaces the gene with two copies of ADH and two copies of PFL.

Figure 39:
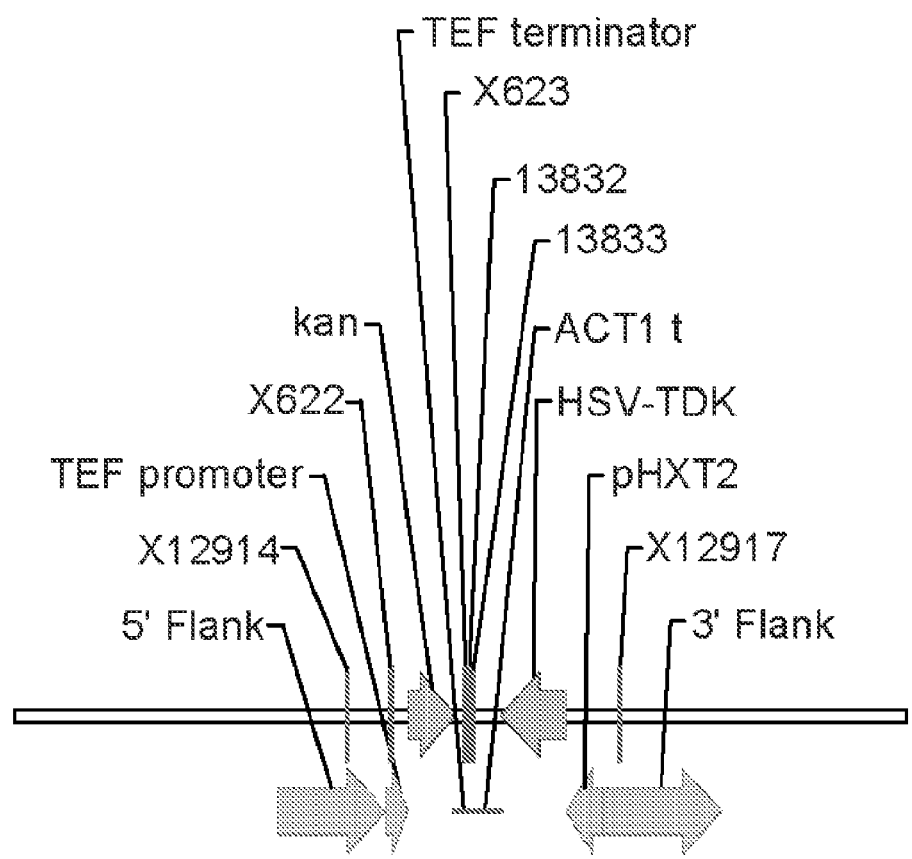

FIG. 39 depicts an integration design which deletes PDC5 and replaces a counter selective gene HSV-TDK and an antibiotic marker (Kan).

Figure 40:
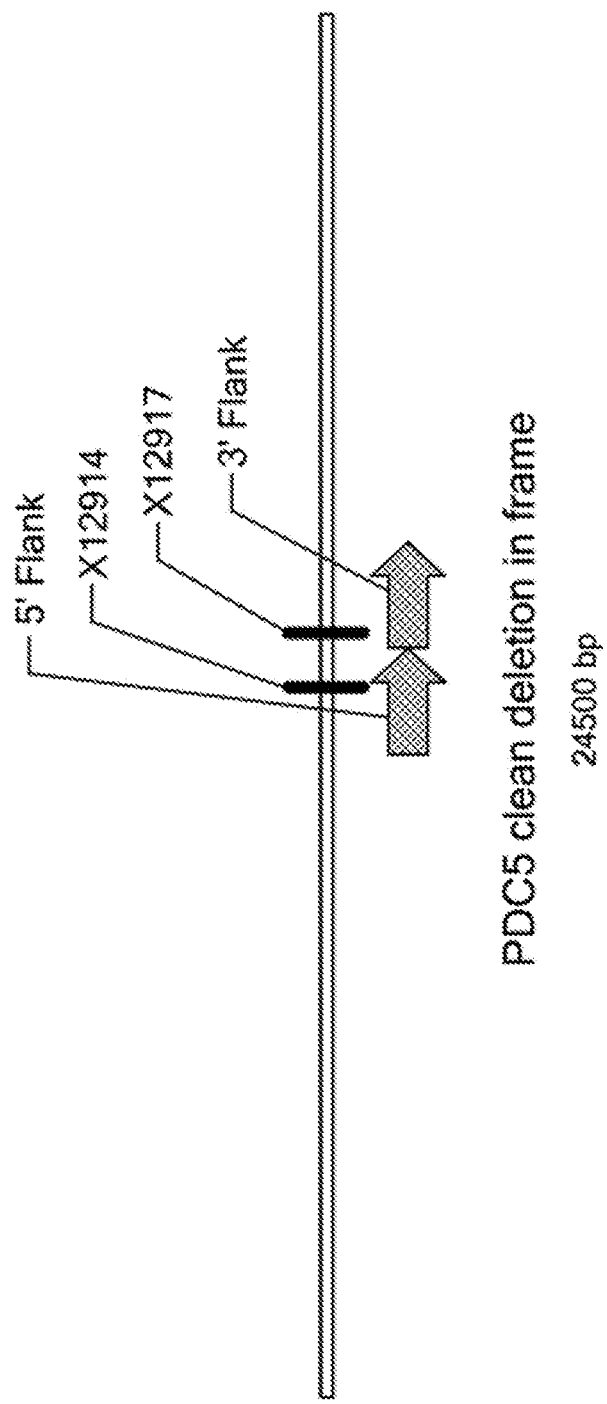

FIG. 40 depicts an integration design which removes the marker shown in FIG. 39 resulting in a clean deletion of PDC5.

Figure 41:
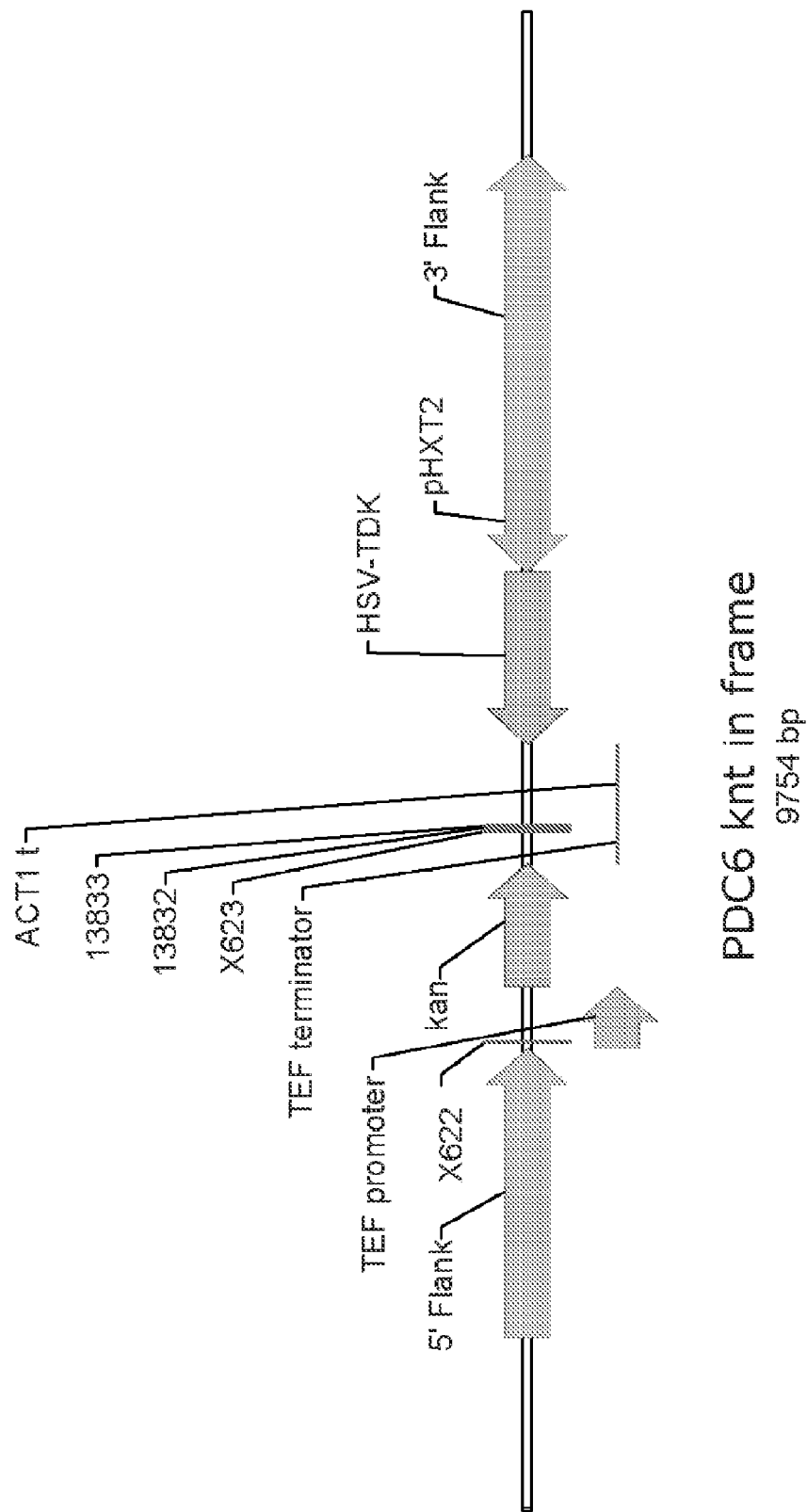

FIG. 41 depicts an integration design which deletes PDC6 and replaces a counter selective gene HSV-TDK and an antibiotic marker (Kan).

Figure 42:
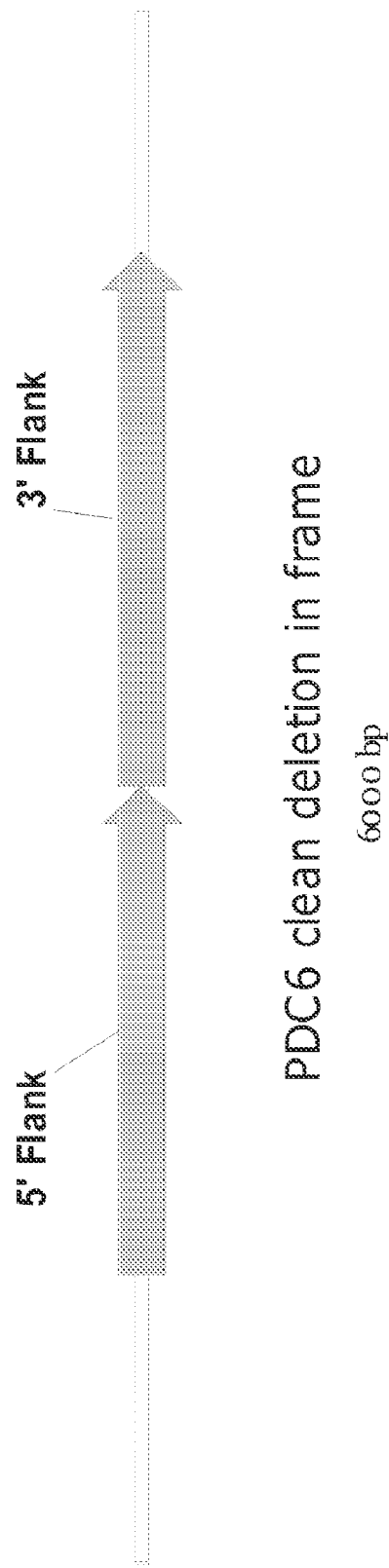

FIG. 42 depicts an integration design which removes the marker shown in FIG. 41 resulting in a clean deletion of PDC6.

Figure 43:
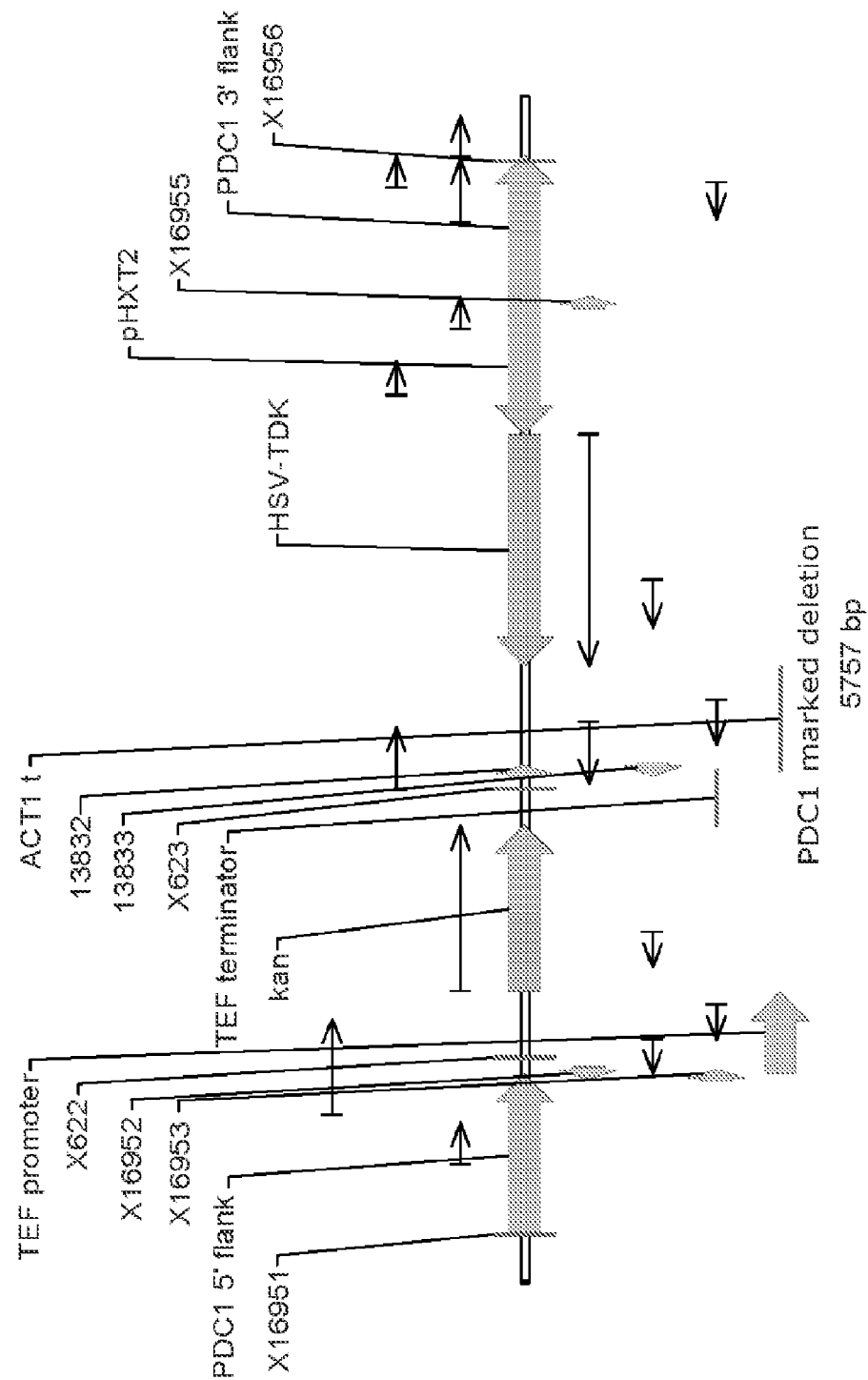

FIG. 43 depicts an integration design which deletes PDC1 and replaces it with a counter selective gene HSV-TDK and an antibiotic marker (Kan).

Figure 44:
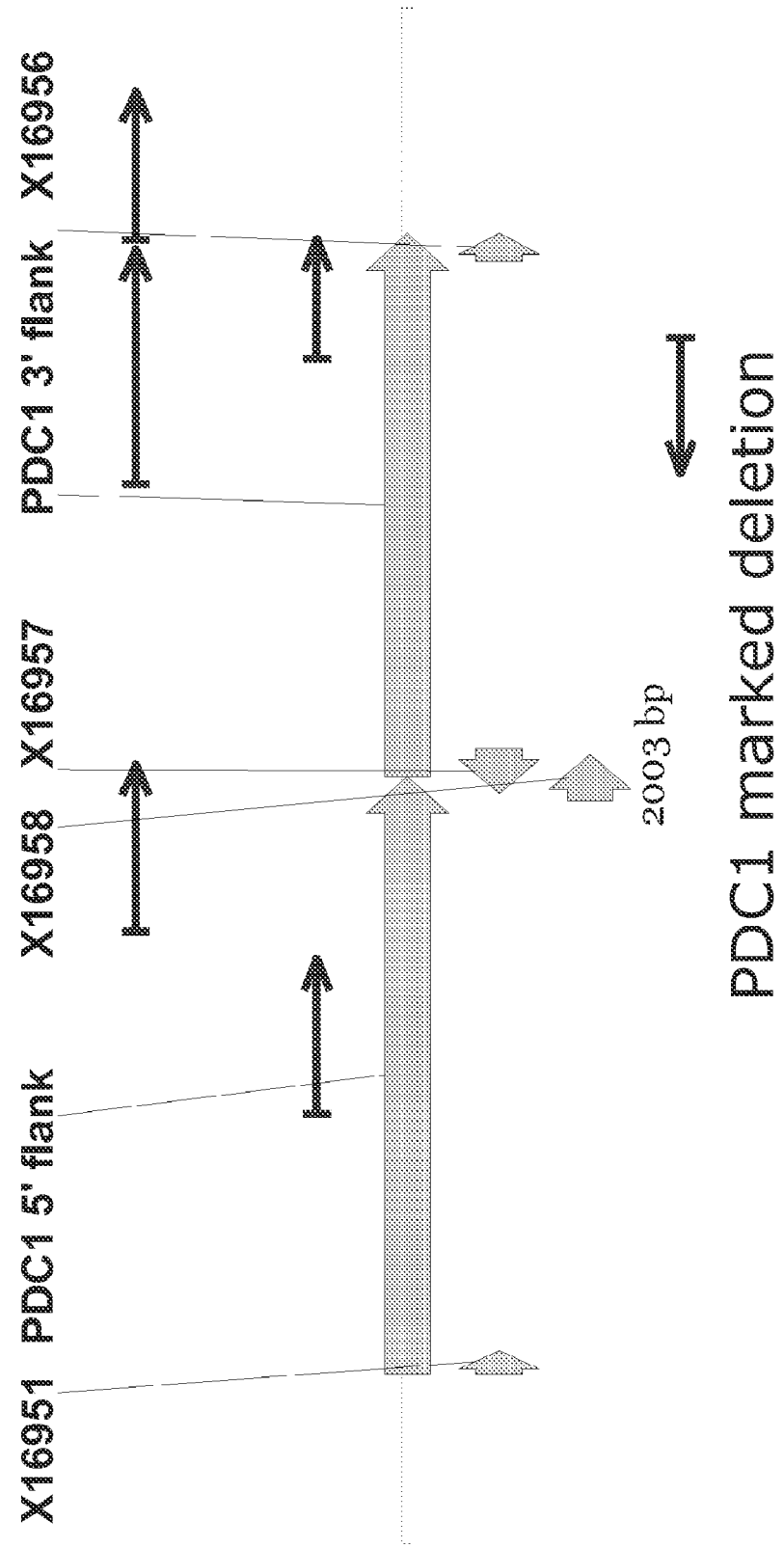

FIG. 44 depicts an integration design which removes the marker shown in FIG. 41 resulting in a clean deletion of PDC1.

Figure 45:
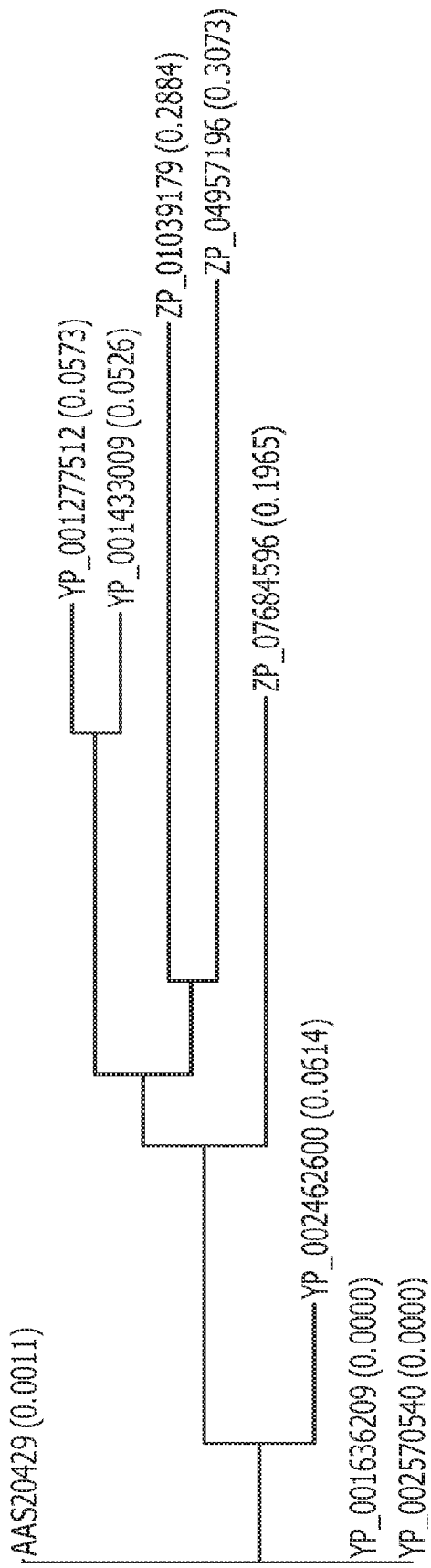

FIG. 45 is a phylogenetic tree depicting relatedness between bifunctional malonyl-CoA reductases from *C. aurantiacus, C. aurantiacus* J-10-fl, *Chlomfiexus* sp. Y-400-fl, *C. aggregans* DSM 9485, *O. trichoides* DG6, *R. castenholzii* DSM 13941, *R. osefexus* sp. RS-1, *Erythrobacter* sp. NAP1, and gamma proteobacterium NOR51-B.

Figure 46:
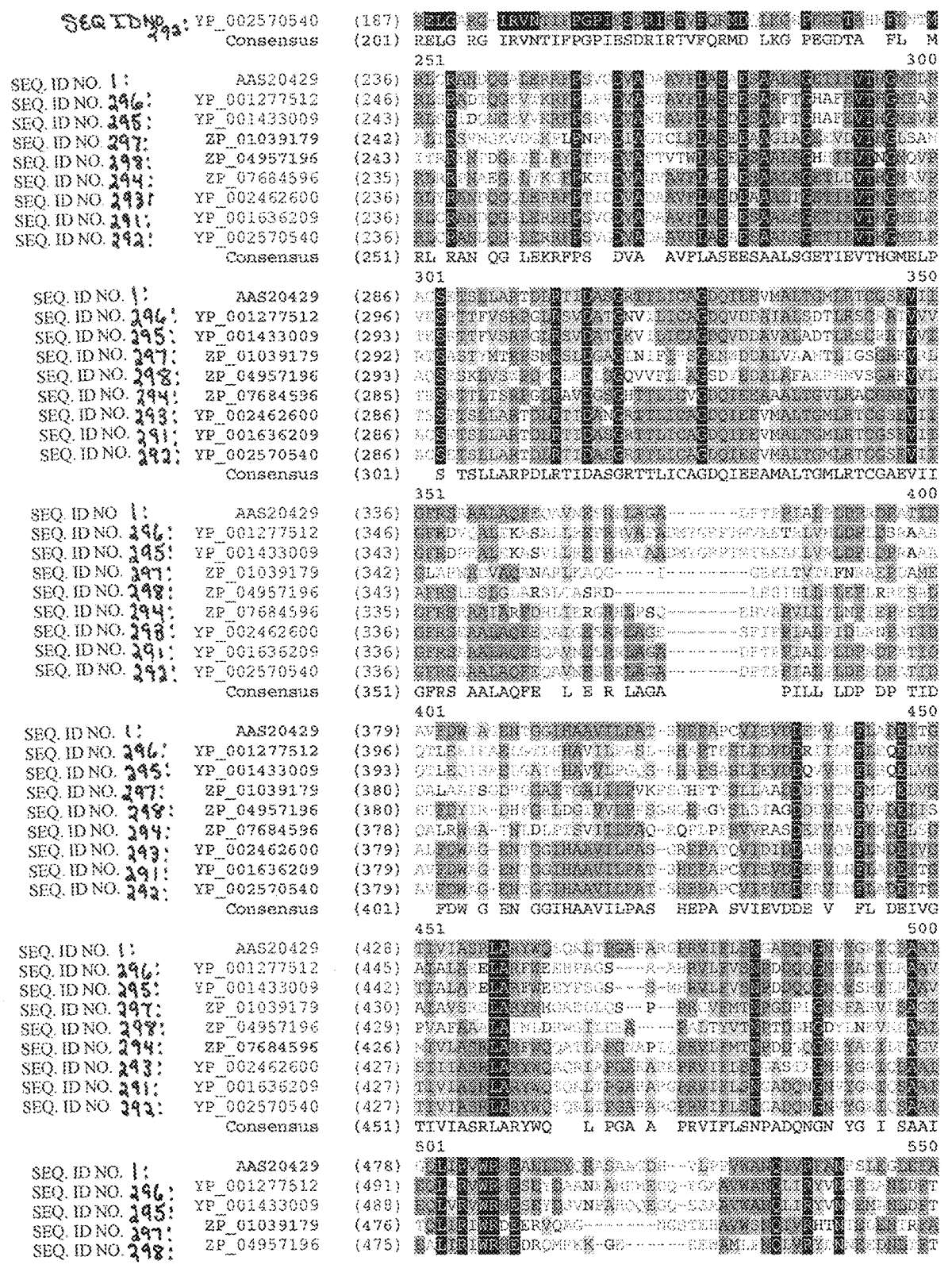
Figure 46:
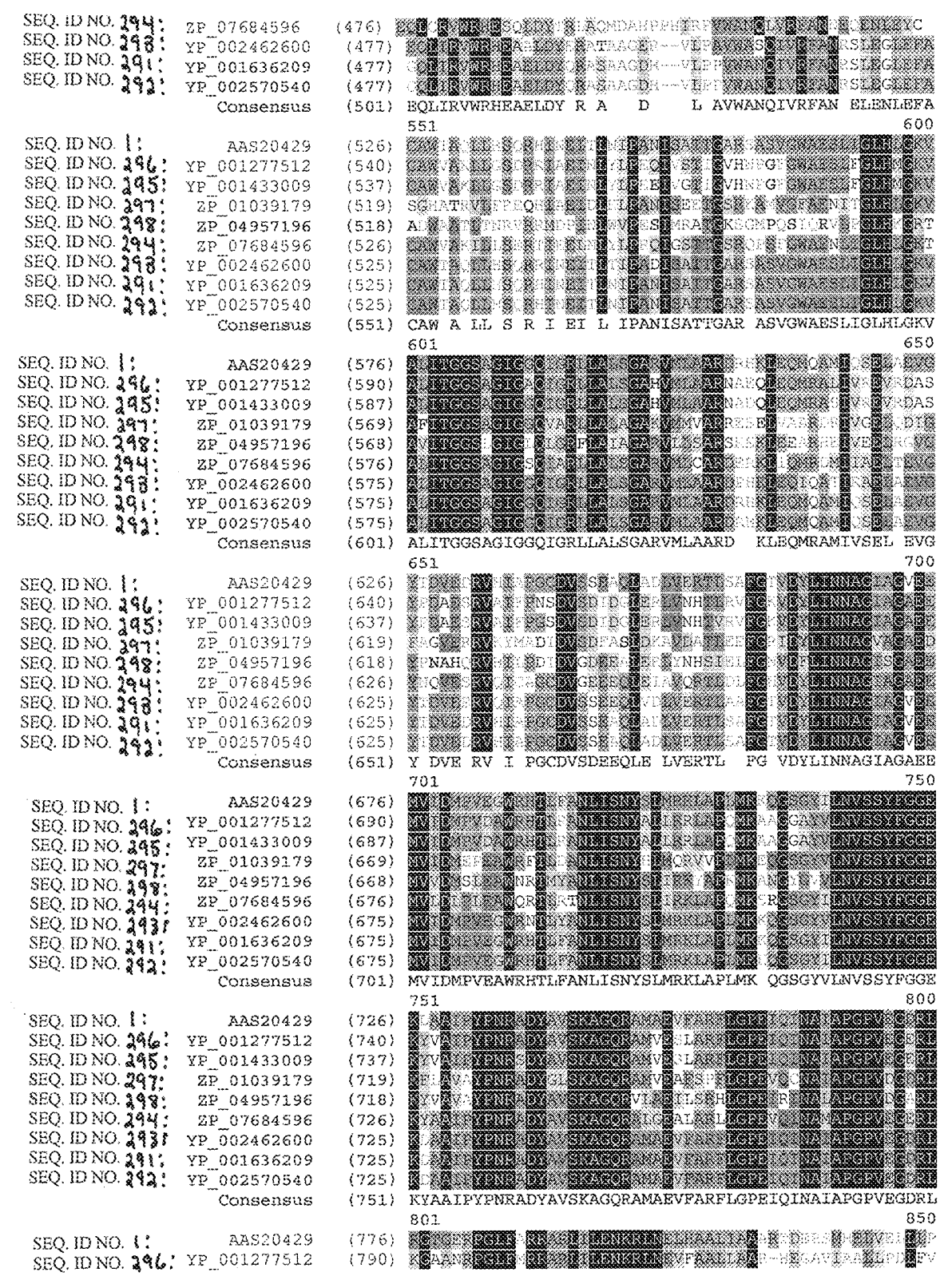
Figure 46:
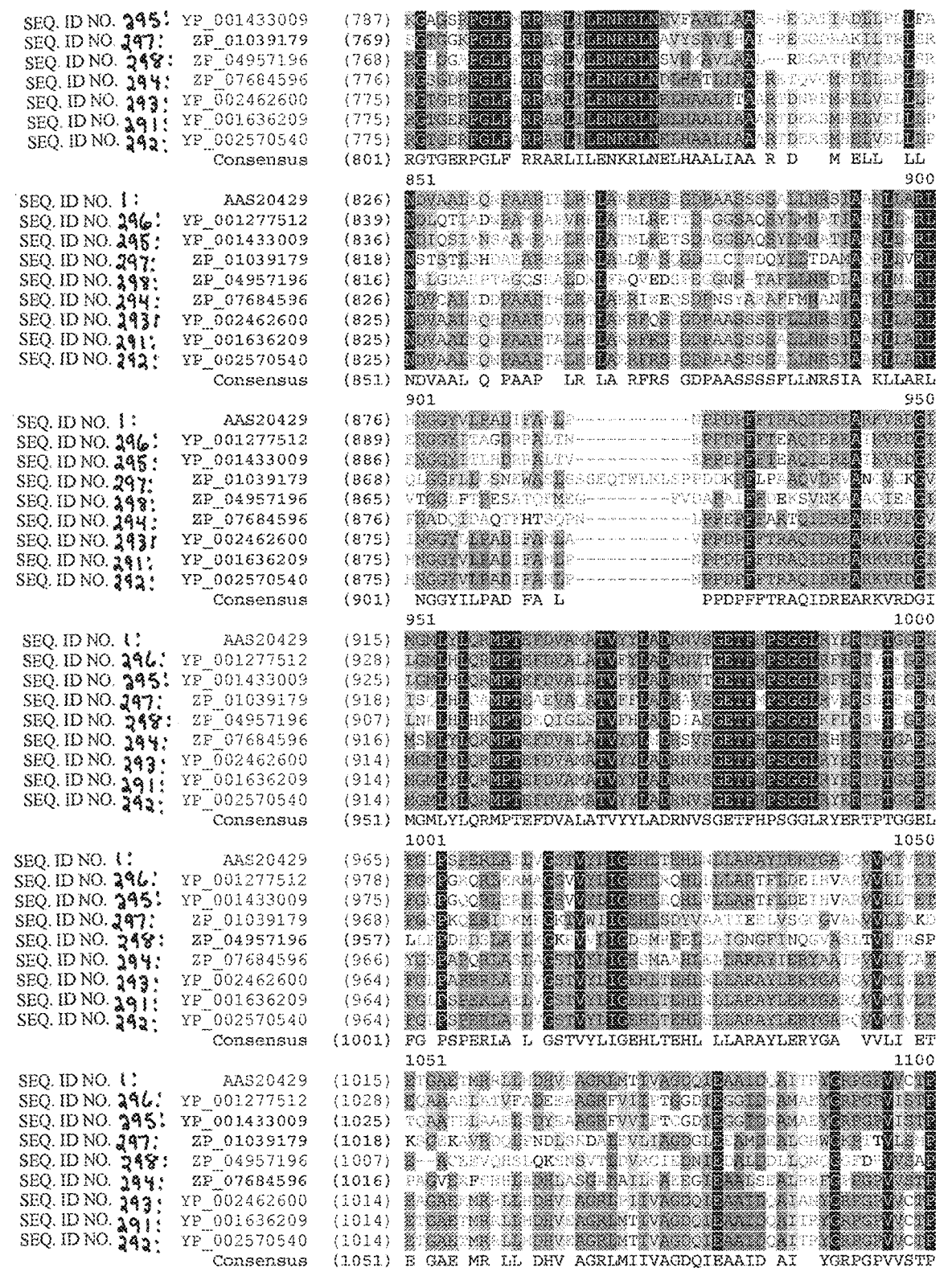

FIG. 46 is an alignment of bifunctional malonyl-CoA reductases from *C. aurantiacus, C. aurantiacus* J-10-fl, *Chloroflexus* sp. Y-400-fl, *C. aggregans* DSM 9485, *O. trichoides* DG6, *R. castenholzii* DSM 13941, *R. oselexus* sp. RS-1, *Erythrobacter* sp. NAP1, and gamma proteobacterium NOR51-B.

DETAILED DESCRIPTION OF THE INVENTION

Definitions

The indefinite articles "a" and "an" preceding an element or component of the invention are intended to include plurals of the element or component, e.g., one or at least one of the element or component, unless the context is such that only the singular form is intended.

The term "heterologous" when used in reference to a polynucleotide, a gene, a polypeptide, or an enzyme refers to a polynucleotide, gene, polypeptide, or an enzyme not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene may be introduced into the host organism by, e.g., gene transfer. A heterologous gene may include a native coding region that is a portion of a chimeric gene including non-native regulatory regions that is reintroduced into the native host. Foreign genes can comprise native genes inserted into a non-native organism, or chimeric genes.

The term "heterologous polynucleotide" is intended to include a polynucleotide that encodes one or more polypeptides or portions or fragments of polypeptides. A heterologous polynucleotide may be derived from any source, e.g., eukaryotes, prokaryotes, viruses, or synthetic polynucleotide fragments.

The terms "promoter" or "surrogate promoter" is intended to include a polynucleotide that can transcriptionally control a gene-of-interest that it does not transcriptionally control in nature. In certain embodiments, the transcriptional control of a surrogate promoter results in an increase in expression of the gene-of-interest. In certain embodiments, a surrogate promoter is placed 5' to the gene-of-interest. A surrogate promoter may be used to replace the natural promoter, or may be used in addition to the natural promoter. A surrogate promoter may be endogenous with regard to the host cell in which it is used, or it may be a heterologous polynucleotide sequence introduced into the host cell, e.g., exogenous with regard to the host cell in which it is used.

The terms "gene(s)" or "polynucleotide" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA. The term gene is also intended to cover all copies of a particular gene, e.g., all of the DNA sequences in a cell encoding a particular gene product.

The term "transcriptional control" is intended to include the ability to modulate gene expression at the level of transcription. In certain embodiments, transcription, and thus gene expression, is modulated by replacing or adding a surrogate promoter near the 5' end of the coding region of a gene-of-interest, thereby resulting in altered gene expression. In certain embodiments, the transcriptional control of one or more genes is engineered to result in the optimal expression of such genes, e.g., in a desired ratio. The term also includes inducible transcriptional control as recognized in the art.

The term "expression" is intended to include the expression of a gene at least at the level of mRNA production.

The term "expression product" is intended to include the resultant product, e.g., a polypeptide, of an expressed gene.

The term "polypeptide" is intended to encompass a singular "polypeptide," as well as plural "polypeptides," and refers to a molecule composed of monomers (amino acids) linearly linked by amide bonds (also known as peptide bonds). The term "polypeptide" refers to any chain or chains of two or more amino acids and does not refer to a specific length of the amino acids. Thus, peptides, dipeptides, tripeptides, oligopeptides, "protein," "amino acid chain," "enzyme," or any other term used to refer to a chain or chains of two or more amino acids, are included within the definition of "polypeptide," and the term "polypeptide" may be used instead of, or interchangeably with, any of these terms. A polypeptide may be derived from a natural biological source or produced by recombinant technology. It may be generated in any manner, including by chemical synthesis.

The term "increased expression" is intended to include an alteration in gene expression at least at the level of increased mRNA production and, preferably, at the level of polypeptide expression. The term "increased production" is intended to include an increase in the amount of a polypeptide expressed, in the level of the enzymatic activity of the polypeptide, or a combination thereof, as compared to the native production of, or the enzymatic activity of, the polypeptide.

The terms "activity," "activities," "enzymatic activity," and "enzymatic activities" are used interchangeably and are intended to include any functional activity normally attributed to a selected polypeptide when produced under favorable conditions. Typically, the activity of a selected polypeptide encompasses the total enzymatic activity associated with the produced polypeptide. The polypeptide produced by a host cell and having enzymatic activity may be located in the intracellular space of the cell, cell-associated, secreted into the extracellular milieu, or a combination thereof. Techniques for determining total activity as compared to secreted activity are described herein and are known in the art.

The term "secreted" is intended to include the movement of polypeptides to the periplasmic space or extracellular milieu. The term "increased secretion" is intended to include situations in which a given polypeptide is secreted at an increased level (i.e., in excess of the naturally-occurring amount of secretion). In certain embodiments, the term "increased secretion" refers to an increase in secretion of a given polypeptide that is at least about 10% or at least about 100%, 200%, 300%, 400%, 500%, 600%, 700%, 800%, 900%, 1000%, or more, as compared to the naturally-occurring level of secretion.

The term "secretory polypeptide" is intended to include any polypeptide(s), alone or in combination with other polypeptides, that facilitate the transport of another polypeptide from the intracellular space of a cell to the extracellular milieu. In certain embodiments, the secretory polypeptide(s) encompass all the necessary secretory polypeptides sufficient to impart secretory activity to a Gram-negative or Gram-positive host cell or to a yeast host cell. Typically, secretory proteins are encoded in a single region or locus that may be isolated from one host cell and transferred to another host cell using genetic engineering. In certain embodiments, the secretory polypeptide(s) are derived from any bacterial cell having secretory activity or any yeast cell having secretory activity. In certain embodiments, the secretory polypeptide(s) are derived from a host cell having Type H secretory activity. In certain embodiments, the host cell is a thermophilic bacterial cell. In certain embodiments, the host cell is a yeast cell.

The term "derived from" is intended to include the isolation (in whole or in part) of a polynucleotide segment from an indicated source or the purification of a polypeptide from an indicated source. The term is intended to include, for example, direct cloning, PCR amplification, or artificial synthesis from or based on a sequence associated with the indicated polynucleotide source.

By "thermophilic" is meant an organism that thrives at a temperature of about 45° C. or higher.

By "mesophilic" is meant an organism that thrives at a temperature of about 20-45° C.

Certain embodiments of the present invention provide for the "insertion," (e.g., the addition, integration, incorporation, or introduction) of certain genes or particular polynucleotide sequences within thermophilic or mesophilic microorganisms, which insertion of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

In certain embodiments, the polynucleotide sequences of the invention are genetically modified such that the encoded enzyme is engineered to alter catalytic activity and/or alter substrate specificity to improve the conversion of a substrate to a product as compared to the native enzyme. In certain aspects, the genetic modification alters catalytic activity and/or substrate specificity to provide an encoded enzyme that converts a substrate to a product that is not catalyzed by the native enzyme in vivo, or is catalyzed at only minimal turnover. Techniques to genetically modify polynucleotides are known in the art and include, but are not limited to, alteration, insertion, and/or deletion of one or more nucleic acids in the polynucleotide. Such techniques to alter, insert, and/or delete nucleic acids include, but are not limited to, random, site-directed, or saturating mutagenesis.

Certain embodiments of the present invention provide for the "inactivation" or "deletion" of certain genes or particular polynucleotide sequences within thermophilic or mesophilic microorganisms, which "inactivation" or "deletion" of genes or particular polynucleotide sequences may be understood to encompass "genetic modification(s)" or "transformation(s)" such that the resulting strains of said thermophilic or mesophilic microorganisms may be understood to be "genetically modified" or "transformed." In certain embodiments, strains may be of bacterial, fungal, or yeast origin.

The term "consolidated bioprocessing" or "CBP" is intended to include a processing strategy for cellulosic biomass that involves consolidating into a single process step, four biologically-mediated events: enzyme production, hydrolysis, hexose fermentation, and pentose fermentation. Implementing this strategy requires development of microorganisms that both utilize cellulose, hemicellulosics, and other biomass components while also producing a product of interest at sufficiently high yield and concentrations. The feasibility of CBP is supported by kinetic and bioenergetic analysis. See van Walsum and Lynd (1998) *Biotech. Bioeng.* 58:316.

The term "CBP organism" is intended to include microorganisms of the invention, e.g., microorganisms that have properties suitable for CBP.

In one aspect of the invention, the genes or particular polynucleotide sequences are inserted to activate the activity for which they encode, such as the expression of an enzyme. In certain embodiments, genes encoding enzymes in the metabolic production of fatty acids may be added to a mesophilic or a thermophilic organism.

In one aspect of the invention, the genes or particular polynucleotide sequences are partially, substantially, or completely deleted, silenced, inactivated, or down-regulated in order to inactivate the activity for which they encode, such as the expression of an enzyme. Deletions provide maximum stability because there is no opportunity for a reverse mutation to restore function. Alternatively, genes can be partially, substantially, or completely deleted, silenced, inactivated, or down-regulated by insertion of nucleic acid sequences that disrupt the function and/or expression of the gene (e.g., P1 transduction or other methods known in the art). The terms "eliminate," "elimination," and "knockout" are used interchangeably with the terms "deletion," "partial deletion," "substantial deletion," or "complete deletion." In certain embodiments, strains of thermophilic or mesophilic microorganisms of interest may be engineered by site directed homologous recombination to knockout the production of organic acids. In still other embodiments, RNAi or antisense DNA (asDNA) may be used to partially, substantially, or completely silence, inactivate, or down-regulate a particular gene of interest.

In certain embodiments, the genes targeted for deletion or inactivation as described herein may be endogenous to the native strain of the microorganism, and may thus be understood to be referred to as "native gene(s)" or "endogenous gene(s)." An organism is in "a native state" if it has not been genetically engineered or otherwise manipulated by the hand of man in a manner that intentionally alters the genetic and/or phenotypic constitution of the organism. For example, wild-type organisms may be considered to be in a native state. In other embodiments, the gene(s) targeted for deletion or inactivation may be non-native to the organism.

Similarly, the enzymes of the invention as described herein can be endogenous to the native strain of the microorganism, and can thus be understood to be referred to as "native" or "endogenous."

The term "upregulated" means increased in activity, e.g., increase in enzymatic activity of the enzyme as compared to activity in a native host organism.

The term "downregulated" means decreased in activity, e.g., decrease in enzymatic activity of the enzyme as compared to activity in a native host organism.

The term "activated" means expressed or metabolically functional.

As used herein, the term "hydrocarbon" is intended to include compounds containing only carbon and hydrogen, such as aliphatic hydrocarbons and aromatic hydrocarbons. Examples of hydrocarbons include, but are not limited to, alkanes, alkenes, or alkynes.

As used herein, the term "hydrocarbon derivative" is intended to include compounds formed by the addition of at least one functional group to a hydrocarbon. Examples of hydrocarbon derivatives include, but are not limited to, aldehydes, alcohols, esters, fatty acids, unsaturated fatty acids, branched-chain fatty acids, branched methoxy fatty acids, multi-methyl branched acids, divinyl-ether fatty acids, w-phenylalkanoic acids, dicarboxylic acids.

The term "carbohydrate source" is intended to include any source of carbohydrate including, but not limited to, biomass or carbohydrates, such as a sugar or a sugar alcohol. "Carbohydrates" include, but are not limited to, monosaccharides (e.g., glucose, fructose, galactose, xylose, arabinose, or ribose), sugar derivatives (e.g., sorbitol, glycerol, galacturonic acid, rhamnose, xylitol), disaccharides (e.g., sucrose, cellobiose, maltose, or lactose), oligosaccharides (e.g., xylooligomers, cellodextrins, or maltodextrins), and polysaccharides (e.g., xylan, cellulose, starch, mannan, alginate, or pectin).

As used herein, the term "microaerophilic" is intended to include conditions in which oxygen is present at lower concentrations than atmospheric oxygen content. A microaerophilic organism is one that requires a lower concentration of oxygen for growth than is present in the atmosphere. Microaerophilic conditions include those in which oxygen is present at less than about 5%, less than about 10%, less than about 15%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90%, less than about 95%, or less than about 99% of atmospheric oxygen concentration.

As used herein, the term "malonyl-CoA derived product" or "malonyl-CoA derived bioproduct" is intended to include those products that are synthesized from, derived from, or are used as an intermediate in their synthesis from, malonyl-CoA. The term includes products such as hydrocarbons, hydrocarbon derivatives, polyketides, organic acids, including but not limited to adipic acid and 3-hydroxypropionate, and any other products from which malonyl-CoA can serve as a precursor.

Metabolic Pathway Engineering

Many bacteria have the ability to ferment simple hexose sugars into a mixture of acidic and pH-neutral products via the process of glycolysis. The glycolytic pathway is abundant and comprises a series of enzymatic steps whereby a six carbon glucose molecule is broken down, via multiple intermediates, into two molecules of the three carbon compound pyruvate. This process results in the net generation of ATP (biological energy supply) and the reduced cofactor NADH.

Pyruvate is an important intermediary compound of metabolism. For example, under aerobic conditions pyruvate may be oxidized to acetyl coenzyme A (acetyl CoA), which then enters the tricarboxylic acid cycle (TCA), which in turn generates synthetic precursors, $CO_2$ and reduced cofactors. The cofactors are then oxidized by donating hydrogen equivalents, via a series of enzymatic steps, to oxygen resulting in the formation of water and ATP. This process of energy formation is known as oxidative phosphorylation.

Under anaerobic conditions (no available oxygen), fermentation occurs in which the degradation products of organic compounds serve as hydrogen donors and acceptors. Excess NADH from glycolysis is oxidized in reactions involving the reduction of organic substrates to products, such as lactate and ethanol. In addition, ATP is regenerated from the production of organic acids, such as acetate, in a process known as substrate level phosphorylation. Therefore, the fermentation products of glycolysis and pyruvate metabolism include a variety of organic acids, alcohols and $CO_2$.

Biomass

Biomass can include any type of biomass known in the art or described herein. The terms "lignocellulosic material," "lignocellulosic substrate," and "cellulosic biomass" mean any type of biomass comprising cellulose, hemicellulose, lignin, or combinations thereof, such as but not limited to woody biomass, forage grasses, herbaceous energy crops, non-woody-plant biomass, agricultural wastes and/or agricultural residues, forestry residues and/or forestry wastes, paper-production sludge and/or waste paper sludge, wastewater-treatment sludge, municipal solid waste, corn fiber from wet and dry mill corn ethanol plants, and sugar-processing residues. The terms "hemicellulosics," "hemicellulosic portions," and "hemicellulosic fractions" mean the non-lignin, non-cellulose elements of lignocellulosic material, such as but not limited to hemicellulose (i.e., comprising xyloglucan, xylan, glucuronoxylan, arabinoxylan, mannan, glucomannan, and galactoglucomannan), pectins (e.g., homogalacturonans, rhamnogalacturonan I and II, and xylogalacturonan), and proteoglycans (e.g., arabinogalactan-protein, extensin, and proline-rich proteins).

In a non-limiting example, the lignocellulosic material can include, but is not limited to, woody biomass, such as recycled wood pulp fiber, sawdust, hardwood, softwood, and combinations thereof; grasses, such as switch grass, cord grass, rye grass, reed canary grass, miscanthus, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; succulents, such as but not limited to, Agave; and forestry wastes, such as but not limited to, recycled wood pulp fiber, sawdust, hardwood (e.g., poplar, oak, maple, birch, willow), softwood, or any combination thereof. Lignocellulosic material may comprise one species of fiber; alternatively, lignocellulosic material may comprise a mixture of fibers that originate from different lignocellulosic materials. Other lignocellulosic materials are agricultural wastes, such as cereal straws, including wheat straw, barley straw, canola straw and oat straw; corn fiber; stovers, such as corn stover and soybean stover; grasses, such as switch grass, reed canary grass, cord grass, and miscanthus; or combinations thereof.

Paper sludge is also a viable feedstock for lactate or acetate production. Paper sludge is solid residue arising from pulping and paper-making, and is typically removed from process wastewater in a primary clarifier. At a disposal cost of $30/wet ton, the cost of sludge disposal equates to $5/ton of paper that is produced for sale. The cost of disposing of wet sludge is a significant incentive to convert the material for other uses, such as conversion to ethanol. Processes provided by the present invention are widely applicable. Moreover, the saccharification and/or fermentation products may be used to produce ethanol or higher value added chemicals, such as organic acids, aromatics, esters, acetone and polymer intermediates.

Xylose Metabolism

Xylose is a five-carbon monosaccharide that can be metabolized into useful products by a variety of organisms. There are two main pathways of xylose metabolism, each unique in the characteristic enzymes they utilize. One pathway is called the "Xylose Reductase-Xylitol Dehydrogenase" or XR-XDH pathway. Xylose reductase (XR) and xylitol dehydrogenase (XDH) are the two main enzymes used in this method of xylose degradation. XR, encoded by the XYL1 gene, is responsible for the reduction of xylose to xylitol and is aided by cofactors NADH or NADPH. Xylitol is then oxidized to xylulose by XDH, which is expressed through the XYL2 gene, and accomplished exclusively with the cofactor NAD+. Because of the varying cofactors needed in this pathway and the degree to which they are available for usage, an imbalance can result in an overproduction of xylitol byproduct and an inefficient production of desirable ethanol. Varying expression of the XR and XDH enzyme levels have been tested in the laboratory in the attempt to optimize the efficiency of the xylose metabolism pathway.

The other pathway for xylose metabolism is called the "Xylose Isomerase" (XI) pathway. Enzyme XI is responsible for direct conversion of xylose into xylulose, and does not proceed via a xylitol intermediate. Both pathways create xylulose, although the enzymes utilized are different. After production of xylulose both the XR-XDH and XI pathways proceed through enzyme xylulokinase (XK), encoded on gene XKS1, to further modify xylulose into xylulose-5-P where it then enters the pentose phosphate pathway for further catabolism.

Studies on flux through the pentose phosphate pathway during xylose metabolism have revealed that limiting the speed of this step may be beneficial to the efficiency of fermentation to ethanol. Modifications to this flux that may improve ethanol production include a) lowering phosphoglucose isomerase activity, b) deleting the GND1 gene, and c) deleting the ZWF1 gene. See Jeppsson et al., *Appl. Environ. Microbiol.* 68:1604-09 (2002). Since the pentose phosphate pathway produces additional NADPH during metabolism, limiting this step will help to correct the already evident imbalance between NAD(P)H and NAD+ cofactors and reduce xylitol byproduct. Another experiment comparing the two xylose metabolizing pathways revealed that the XI pathway was best able to metabolize xylose to produce the greatest ethanol yield, while the XR-XDH pathway reached a much faster rate of ethanol production. See Karhumaa et al., *Microb Cell Fact.* 6:5 (Feb. 5, 2007); see also International Publication No. WO2006/009434, incorporated herein by reference in its entirety.

Arabinose Metabolism

Arabinose is a five-carbon monosaccharide that can be metabolized into useful products by a variety of organisms. L-Arabinose residues are found widely distributed among many heteropolysaccharides of different plant tissues, such as arabinans, arabinogalactans, xylans and arabinoxylans. *Bacillus* species in the soil participate in the early stages of plant material decomposition, and *B. subtilis* secretes three enzymes, an endo-arabanase and two arabinosidases, capable of releasing arabinosyl oligomers and L-arabinose from plant cell.

Three pathways for L-arabinose metabolism in microorganisms have been described. Many bacteria, including *Escherichia coli*, use arabinose isomerase (AraA; E.C. 5.3.1.4), ribulokinase (AraB; E.C. 2.7.1.16), and ribulose phosphate epimerase (AraD; E.C. 5.1.3.4) to sequentially convert L-arabinose to D-xylulose-5-phosphate through L-ribulose and L-ribulose 5-phosphate. See, e.g., Sa-Nogueira I., et al., *Microbiology* 143:957-69 (1997). The D-xylulose-5-phosphate then enters the pentose phosphate pathway for further catabolism. In the second pathway, L-arabinose is converted to L-2-keto-3-deoxyarabonate (L-KDA) by the consecutive action of enzymes arabinose dehydrogenase (ADH), arabinolactone (AL), and arabinonate dehydratase (AraC). See, e.g., Watanabe, S., et al., *J. Biol. Chem.* 281: 2612-2623 (2006). L-KDA can be further metabolized in two alternative pathways: 1) L-KDA conversion to 2-ketoglutarate via 2-ketoglutaric semialdehyde (KGSA) by L-KDA dehydratase and KGSA dehydrogenase or 2) L-KDA conversion to pyruvate and glycolaldehyde by L-KDA aldolase. In the third, fungal pathway, L-arabinose is converted to D-xylulose-5-phosphate through L-arabinitol, L-xylulose, and xylitol, by enzymes such as NAD(P)H-dependent aldose reductase (AR), L-arabinitol 4-dehydrogenase (ALDH), L-xylulose reductase (LXR), xylitol dehydrogenase (XylD), and xylulokinase (XylB). These, and additional proteins involved in arabinose metabolism and regulation may be found at the website of National Microbial Pathogen Data Resource (NMPDR) nmpdr.org/FIG/wiki/rest.cgi/NmpdrPlugin/SeedViewer?page=Subsystems;subsystem=L-Arabinose utilization, visited Jul. 29, 2011, which is incorporated by reference herein in its entirety.

AraC protein regulates expression of its own synthesis and the other genes of the Ara system. See Schleif, R., *Trends Genet.* 16(12):559-65 (2000). In *E. coli*, the AraC protein positively and negatively regulates expression of the proteins required for the uptake and catabolism of the sugar L-arabinose. Homologs of AraC, such as regulatory proteins RhaR and RhaS of the rhamnose operon, have been identified that contain regions homologous to the DNA-binding domain of AraC (Leal, T. F. and de Sa-Nogueira, I., *FEMS Microbiol Lett.* 241(1):41-48 (2004)). Such arabinose regulatory proteins are referred to as the AraC/XylS family. See also, Mota, L. J., et al., *Mol. Microbiol.* 33(3):476-89 (1999); Mota, L. J., et al., *J. Bacteriol.* 183(14):4190-201 (2001).

In *E. coli*, the transport of L-arabinose across the *E. coli* cytoplasmic membrane requires the expression of either the high-affinity transport operon, araFGH, a binding protein-dependent system on the low-affinity transport operon, araE, or a proton symporter. Additional arabinose transporters include those identified from *K marxianus* and *P. guilliermondii*, disclosed in U.S. Pat. No. 7,846,712, which is incorporated by reference herein.

In some embodiments, the recombinant microorganisms of the invention have the ability to metabolize arabinose using one or more of the above enzymes.

Vectors and Host Cells

The present invention also relates to vectors which include genes encoding for enzymes of the present invention, as described above, as well as host cells which are genetically engineered with vectors of the invention and the production of polypeptides of the invention by recombinant techniques.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The DNA sequence in the expression vector is operatively associated with an appropriate expression control sequence(s) (promoter) to direct mRNA synthesis. Any suitable promoter to drive gene expression in the host cells of the invention can be used. Additionally, promoters known to control expression of genes in prokaryotic or lower eukaryotic cells can be used. The expression vector also contains a ribosome binding site for translation initiation and a transcription terminator. The vector can also include appropriate sequences for amplifying expression, or can include additional regulatory regions.

The vector containing the appropriate selectable marker sequence as used herein, as well as an appropriate promoter or control sequence, can be employed to transform an appropriate thermophilic host to permit the host to express the protein.

Host cells useful in the present invention include any prokaryotic or eukaryotic cells; for example, microorganisms selected from bacterial, algal, and yeast cells. Among host cells thus suitable for the present invention are microorganisms, for example, of the genera *Aeromonas, Asper-*

*gillus, Bacillus, Escherichia, Kluyveromyces, Pichia, Rhodococcus, Saccharomyces* and *Streptomyces*.

In some embodiments, the host cells are microorganisms. In one embodiment the microorganism is a yeast. According to the present invention the yeast host cell can be, for example, from the genera *Saccharomyces, Kluyveromyces, Candida, Pichia, Schizosaccharomyces, Hansenula, Kloeckera, Schwanniomyces*, and *Yarrowia*. Yeast species as host cells may include, for example, *S. cerevisiae, S. bulderi, S. barnetti, S. exiguus, S. uvarum, S. diastaticus, K. lactis, K. marxianus*, or *K. fragilis*. In some embodiments, the yeast is selected from the group consisting of *Saccharomyces cerevisiae, Schizosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In another embodiment, the yeast is a thermotolerant *Saccharomyces cerevisiae*. The selection of an appropriate host is deemed to be within the scope of those skilled in the art from the teachings herein.

In some embodiments, the host cell is an oleaginous cell. The oleaginous host cell can be an oleaginous yeast cell. For example, the oleaginous yeast host cell can be from the genera *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. According to the present invention, the oleaginous host cell can be an oleaginous microalgae host cell. For example, the oleaginous microalgea host cell can be from the genera Thraustochytrium or Schizochytrium. Biodiesel could then be produced from the triglyceride produced by the oleaginous organisms using conventional lipid transesterification processes. In some particular embodiments, the oleaginous host cells can be induced to secrete synthesized lipids. Embodiments using oleaginous host cells are advantageous because they can produce biodiesel from lignocellulosic feedstocks which, relative to oilseed substrates, are cheaper, can be grown more densely, show lower life cycle carbon dioxide emissions, and can be cultivated on marginal lands.

In some embodiments, the host cell is a thermotolerant host cell. Thermotolerant host cells can be particularly useful in simultaneous saccharification and fermentation processes by allowing externally produced cellulases and ethanol-producing host cells to perform optimally in similar temperature ranges.

Thermotolerant host cells can include, for example, *Issatchenkia orientalis, Pichia mississippiensis, Pichia mexicana, Pichia farinosa, Clavispora opuntiae, Clavispora lusitaniae, Candida mexicana, Hansenula polymorpha* and *Kluyveromyces* host cells. In some embodiments, the thermotolerant cell is an *S. cerevisiae* strain, or other yeast strain, that has been adapted to grow in high temperatures, for example, by selection for growth at high temperatures in a cytostat.

In some particular embodiments, the host cell is a *Kluyveromyces* host cell. For example, the *Kluyveromyces* host cell can be a *K. lactis, K. marxianus, K. blattae, K. phafii, K. yarrowii, K. aestuarii, K. dobzhanskii, K. wickerhamii K. thermotolerans*, or *K. waltii* host cell. In one embodiment, the host cell is a *K. lactis*, or *K. marxianus* host cell. In another embodiment, the host cell is a *K. marxianus* host cell.

In some embodiments, the thermotolerant host cell can grow at temperatures above about 30° C., about 31° C., about 32° C., about 33° C., about 34° C., about 35° C., about 36° C., about 37° C., about 38° C., about 39° C., about 40° C., about 41° C. or about 42° C. In some embodiments of the present invention the thermotolerant host cell can produce ethanol from cellulose at temperatures above about 30° C., about 31° C., about 32° C., about 33° C., about 34° C., about 35° C., about 36° C., about 37° C., about 38° C., about 39° C., about 40° C., about 41° C., about 42° C., or about 43° C., or about 44° C., or about 45° C., or about 50° C.

In some embodiments of the present invention, the thermotolerant host cell can grow at temperatures from about 30° C. to 60° C., about 30° C. to 55° C., about 30° C. to 50° C., about 40° C. to 60° C., about 40° C. to 55° C. or about 40° C. to 50° C. In some embodiments of the present invention, the thermotolerant host cell can produce ethanol from cellulose at temperatures from about 30° C. to 60° C., about 30° C. to 55° C., about 30° C. to 50° C., about 40° C. to 60° C., about 40° C. to 55° C. or about 40° C. to 50° C.

In some embodiments, the host cell has the ability to metabolize xylose. Detailed information regarding the development of the xylose-utilizing technology can be found in the following publications: Kuyper M., et al., *FEMS Yeast Res.* 4: 655-64 (2004); Kuyper M., et al., *FEMS Yeast Res.* 5:399-409 (2005); and Kuyper M., et al., *FEMS Yeast Res.* 5:925-34 (2005), which are herein incorporated by reference in their entirety. For example, xylose-utilization can be accomplished in *S. cerevisiae* by heterologously expressing the xylose isomerase gene, XylA, e.g., from the anaerobic fungus *Piromyces* sp. E2, overexpressing five *S. cerevisiae* enzymes involved in the conversion of xylulose to glycolytic intermediates (xylulokinase, ribulose 5-phosphate isomerase, ribulose 5-phosphate epimerase, transketolase and transaldolase) and deleting the GRE3 gene encoding aldose reductase to minimize xylitol production.

The host cells can contain antibiotic markers or can contain no antibiotic markers.

Aspects of the present invention relate to the use of thermophilic and thermotolerant microorganisms as hosts. Their potential in process applications in biotechnology stems from their ability to grow at relatively high temperatures with attendant high metabolic rates, production of physically and chemically stable enzymes, elevated yields of end products, and lower susceptibility to microbial contamination. Major groups of thermophilic bacteria include eubacteria and archaebacteria. Thermophilic eubacteria include: phototropic bacteria, such as cyanobacteria, purple bacteria, and green bacteria; Gram-positive bacteria, such as *Bacillus, Clostridium*, Lactic acid bacteria, and *Actinomyces*; and other eubacteria, such as *Thiobacillus, Spirochete, Desulfotomaculum*, Gram-negative aerobes, Gram-negative anaerobes, and *Thermotoga*. Within archaebacteria are considered Methanogens, extreme thermophiles (an art-recognized term), and *Thermoplasma*. In certain embodiments, the present invention relates to Gram-negative organotrophic thermophiles of the genera *Thermus*, Gram-positive eubacteria, such as genera *Clostridium*, and also which comprise both rods and cocci, genera in group of eubacteria, such as *Thermosipho* and *Thermotoga*, genera of Archaebacteria, such as *Thermococcus, Thermoproteus* (rod-shaped), *Thermofilum* (rod-shaped), *Pyrodictium, Acidianus, Sulfolobus, Pyrobaculum, Pyrococcus, Thermodiscus, Staphylothermus, Desulfurococcus, Archaeoglobus*, and *Methanopyrus*.

Some examples of thermophilic or mesophilic (including bacteria, procaryotic microorganism, and fungi), which may be suitable for the present invention include, but are not limited to: *Clostridium thermosulfurogenes, Clostridium* cellulolyticum, Clostridium thermocellum, Clostridium thermohydrosulfuricum, Clostridium thermoaceticum, Clostridium thermosaccharolyticum, Clostridium tartarivorum, Clostridium thermocellulaseum, Clostridium phytofermentans, Clostridium straminosolvens, Thermoanaerobacterium thermosaccarolyticum, Thermoanaerobacterium saccharolyticum, Thermobacteroides acetoethylicus, Thermoanaerobium brockii, Methanobacterium thermoautotrophicum, Anaerocellum thermophilium, Pyrodictium occultum, Thermoproteus neutrophilus, Thermofilum librum, Thermothrix thioparus, Desulfovibrio thermophilus, Thermoplasma acidophilum, Hydrogenomonas thermophilus, Thermomicrobium roseum, Thermus flavas, Thermus ruber, Pyrococcus furiosus, Thermus aquaticus, Thermus thermophilus, Chloroflexus aurantdacus, Thermococcus litoralls, Pyrodictium abyssi, Bacillus stearothermophilus, Cyanidium caldarium, Mastigocladus laminosus, Chlamydothrix calldissima, Chlamydothrix penicillata, Thiothrix carnea, Phormidium tenuissimum, Phormidium geysericola, Phormidium subterraneum, Phormidium bjahensi, Oscillatoria fiiformis, Synechococcus lividus, Chloroflexus aurantiacus, Pyrodictium brockii, Thiobacillus thiooxidans, Sulfolobus acidocaldarius, Thiobacillus thermophilica, Bacillus stearothermophilus, Cercosulcifer hamathensis, Vahlkampfia reichi, Cyclidium citrullus, Dactylaria gallopava, Synechococcus lividus, Synechococcus elongatus, Synechococcus minervae, Synechocystis aquatilus, Aphanocapsa thermalis, Oscillatoria terebriformis, Oscillatoria amphibia, Oscillatoria germinata, Oscillatoria okenii, Phormidium laminosum, Phormidium parparasiens, Symploca thermalis, Bacillus acidocaldarias, Bacillus coagulans, Bacillus thermocatenalatus, Bacillus lichenmformis, Bacillus pamilas, Bacillus macerans, Bacillus circulans, Bacillus laterosporus, Bacillus brevis, Bacillus subtills, Bacillus sphaericus, Desulfotomaculum nigrificans, Streptococcus thermophilus, Lactobacillus thermophilus, Lactobacillus bulgaricus, Bifidobacterium thermophilum, Streptomyces fragmentosporus, Streptomyces thermonitrificans, Streptomyces thermovulgaris, Pseudonocardia thermophila, Thermoactinomyces vulgaris, Thermoactinomyces sacchari, Thermoactinomyces candidas, Thermomonospora curvata, Thermomonospora viridis, Thermomonospora citrina, Microbispora thermodiastatica, Microbispora aerata, Microbispora bispora, Actinobifda dichotomica, Actinobifida chromogena, Micropolyspora caesia, Micropolyspora faeni, Micropolyspora cectivugida, Micropolyspora cabrobrunea, Micropolyspora thermovirida, Micropolyspora viridinigra, Methanobacterium thermoautothropicum, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus, Clostridium clartfavum, E. coli strain B, strain C, strain K, strain W, Shewanella, Propionibacterium acnes, Propionibacterium freudenreichii, Propionibacterium shermanii, Propionibacterium pentosaceum, Propionibacterium arabinosum, Clostridium acetobutylicum, Clostridium beijerinckii, Lactobacillus thermophilus, Lactobacillus bulgaricus, Lactococcus lactis, variants thereof, and/or progeny thereof.

In particular embodiments, the present invention relates to thermophilic bacteria selected from the group consisting of Clostridium cellulolyticum, Clostridium thermocellum, and Thermoanaerobacterium saccharolyticum.

In certain embodiments, the present invention relates to thermophilic bacteria selected from the group consisting of Fervidobacterium gondwanense, Clostridium thermolacticum, Moorella sp., and Rhodothermus marinus.

In certain embodiments, the present invention relates to thermophilic bacteria of the genera Thermoanaerobacterium or Thermoanaerobacter, including, but not limited to, species selected from the group consisting of: Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brockii, variants thereof, and progeny thereof.

In certain embodiments, the present invention relates to microorganisms of the genera Geobacillus, Saccharococcus, Paenibacillus, Bacillus, and Anoxybacillus, including, but not limited to, species selected from the group consisting of: Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis, variants thereof, and progeny thereof.

In certain embodiments, the present invention relates to mesophilic bacteria selected from the group consisting of Saccharophagus degradans; Flavobacterium johnsoniae; Fibrobacter succinogenes; Clostridium hungatei; Clostridium phytofermentans; Clostridium cellulolyticum; Clostridium aldrichii; Clostridium termitididis; Acetivibrio cellulolyticus; Acetivibrio ethanolgignens; Acetivibrio multivorans; Bacteroides cellulosolvens; Alkalibacter saccharofomentans, variants thereof, and progeny thereof. In certain embodiments, the present invention relates to mesophilic bacteria selected from the group consisting of Escherichia coli, E. coli strain B, strain C, strain K, strain W, Shewanella, Propionibacterium acnes, Propionibacterium freudenreichii, Propionibacterium shermanii, Propionibacterium pentosaceum, Propionibacterium arabinosum, Clostridium acetobutylicum, Clostridium beijerinckii, variants thereof, and progeny thereof.

Codon-Optimized Polynucleotides

The polynucleotides encoding heterologous polypeptides can be codon-optimized. As used herein the term "codon-optimized coding region" means a nucleic acid coding region that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism.

The CAI of codon optimized sequences of the present invention corresponds to between about 0.8 and 1.0, between about 0.8 and 0.9, or about 1.0. A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can be removed from the sequences if these are known to effect transcription negatively. Furthermore, specific restriction enzyme sites may be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC Tyr (Y) | TGC |
|   | TTA Leu (L) | TCA Ser (S) | TAA Ter | TGA Ter |
|   | TTG Leu (L) | TCG Ser (S) | TAG Ter | TGG Trp (W) |
| C | CCT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | AAT Ile (I) | ACT Thr (T) | AAT Asn (N) | AGT Ser (S) |
|   | ATC Ile (I) | ACC Thr (T) | AAC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the website of Codon Usage Database kazusa.or.jp/codon/(visited Jul. 30, 2010), and these tables can be adapted in a number of ways. See Nakamura, Y., et al. "Codon usage tabulated from the international DNA sequence databases: status for the year 2000, "*Nucl. Acids Res.* 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | GAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence can vary significantly using this method; however, the sequence always encodes the same polypeptide.

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the Vector NTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function at the website of Eurofins Genomics entelechon.com/bioinformatics/backtranslation.php?lang=eng (visited Jul. 30, 2010) and the "backtranseq" function available at the website of EMBOSS explorer emboss.bioinformatics.nl/cgi-bin/emboss/backtranseq (visited Jul. 30, 2010). Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence is synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they are ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The disadvantage of this approach is that synthesizing codon-optimized nucleic acid fragments encoding each fragment, variant, and derivative of a given polypeptide, although routine, would be time consuming and would result in significant expense.

Transposons

To select for foreign DNA that has entered a host it is preferable that the DNA be stably maintained in the organism of interest. With regard to plasmids, there are two processes by which this can occur. One is through the use of replicative plasmids. These plasmids have origins of replication that are recognized by the host and allow the plasmids to replicate as stable, autonomous, extrachromosomal elements that are partitioned during cell division into daughter cells. The second process occurs through the integration of a plasmid onto the chromosome. This predominately happens by homologous recombination and results in the insertion of the entire plasmid, or parts of the plasmid, into the host chromosome. Thus, the plasmid and selectable marker(s) are replicated as an integral piece of the chromosome and segregated into daughter cells. Therefore, to ascertain if plasmid DNA is entering a cell during a transformation event through the use of selectable markers requires the use of a replicative plasmid or the ability to recombine the plasmid onto the chromosome. These qualifiers cannot always be met, especially when handling organisms that do not have a suite of genetic tools.

One way to avoid issues regarding plasmid-associated markers is through the use of transposons. A transposon is a mobile DNA element, defined by mosaic DNA sequences that are recognized by enzymatic machinery referred to as a transposase. The function of the transposase is to randomly insert the transposon DNA into host or target DNA. A selectable marker can be cloned onto a transposon by standard genetic engineering. The resulting DNA fragment can be coupled to the transposase machinery in an in vitro reaction and the complex can be introduced into target cells by electroporation. Stable insertion of the marker onto the chromosome requires only the function of the transposase machinery and alleviates the need for homologous recombination or replicative plasmids.

The random nature associated with the integration of transposons has the added advantage of acting as a form of mutagenesis. Libraries can be created that comprise amalgamations of transposon mutants. These libraries can be used in screens or selections to produce mutants with desired phenotypes. For instance, a transposon library of a CBP organism could be screened for the ability to produce more ethanol, or less lactic acid and/or more acetate.

Hydrocarbon Synthesis

Hydrocarbons consist of carbon and hydrogen and include aliphatic hydrocarbons and aromatic hydrocarbons. Non-limiting examples of hydrocarbons include, alkanes, alkenes, alkynes, and hydrocarbon derivatives. The latter of which includes those compounds formed by the addition of at least one functional group to a hydrocarbon. Examples of hydrocarbon derivatives include, but are not limited to, aldehydes, alcohols, esters, fatty acids, unsaturated fatty acids, branched-chain fatty acids, branched methoxy fatty acids, multi-methyl branched acids, divinyl-ether fatty acids, w-phenylalkanoic acids, dicarboxylic acids.

Hydrocarbons produced by the recombinant microorganisms and methods of the invention include carbon backbones of at least 4 carbons and up to 40 or more carbons. Such chain lengths are referred to as long-chain hydrocarbons. In certain aspects, the chain lengths include $C_6$-$C_{36}$; $C_8$-$C_{32}$; $C_{10}$-$C_{28}$; $C_{12}$-$C_{24}$; $C_{14}$-$C_{22}$; or $C_{16}$-$C_{20}$. In some embodiments, the chain length comprises a carbon backbone of $C_{12}$, $C_{14}$, $C_{16}$, $C_{18}$, $C_{20}$, and/or $C_{22}$. In further embodiments, the chain length comprises a carbon backbone of $C_{16}$.

To produce hydrocarbons and hydrocarbon derivatives according to the invention, the following stoichiometric equations provide examples of an electron-balanced process.

Fatty Acid: $2C_6H_{12}O_6 \rightarrow C_8H_{16}O_2 + 4CO_2 + 2H_2O + 2H_2$

Fatty Alcohol: $2C_6H_{12}O_6 \rightarrow C_8H_{18}O + 4CO_2 + 3H_2O$

N-alkane: $2C_6H_{12}O_6 + O_2 \rightarrow C_7H_{16} + 5CO_2 + 4H_2O$

Wax ester: $4C_6H_{12}O_6 \rightarrow C_{16}H_{32}O_2 + 8CO_2 + 6H_2O + 2H_2$

Figure 6:
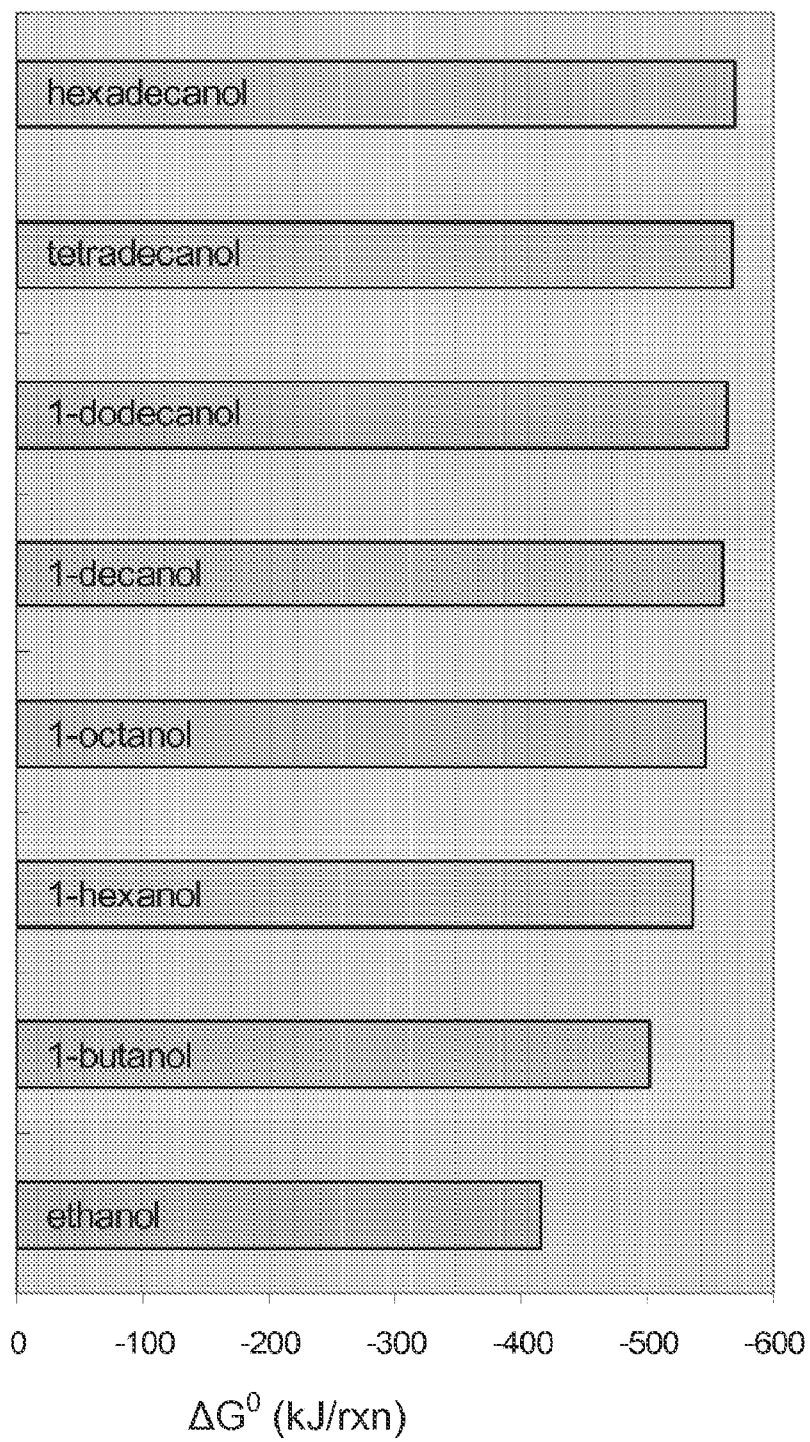
FIG. 6 depicts the Gibbs free energy change for the conversion of glucose into the specified alcohols.

The synthesis of hydrocarbons becomes more thermodynamically favorable as the chain length increases (see FIG. 6 (values derived from Stull et al., The Chemical Thermodynamics of Organic Compounds, Wiley, New York, N.Y. (1969))). For example, the stoichiometry for the production of a fatty alcohol proceeds according to the following equation, where n is the number of glucose molecules and x is the number of carbon atoms in the saturated fatty alcohol.

$n$ Glucose+$(4n/x)C_x$alcohol+$2n$ $CO_2$+$n[2-(4/x)]H_2O$

As can be seen, the number of $H_2O$ molecules generated increases as chain length increases. This helps contribute to a more overall thermodynamically favorable reaction. Gibbs free energy changes per 2 glucose molecules (n=2) for specific alcohols are shown in FIG. 6.

The Gibbs free energy change for the production of heptan, accounting for the requirement of elemental oxygen for the conversion of a fatty aldehyde to alkane by aldehyde decarbonylase (Li et al., *JACS*, 133:6158-6161 (2011)) is:

2 Glucose+$O_2$+1 heptane+$5CO_2$+$4H_2O$ $\Delta G° = -1044.0$ kJ/reaction

The Gibbs free energy change for the production of octanal is:

2 Glucose$\rightarrow$1 octanal+$4CO_2$+$3H_2O$+$H_2$ $\Delta G° = -512.2$ kJ/reaction Other sugars, including, but not limited to, xylose or arabinose, have a similar Gibbs free energy change as glucose. While some steps in the production of hydrocarbons or hydrocarbon derivatives can be slightly unfavorable, e.g., aldolase or triosephosphate isomerase in glycolysis, the overall reaction will be thermodynamically favorable when the final steps include chain termination steps, e.g., acid, aldehyde, alcohol, and/or ester formation. The very low aqueous concentrations of the final hydrocarbons or hydrocarbon derivatives will further drive the thermodynamic equilibrium towards product formation.

Polyketide Synthesis

Polyketides are a structurally and functionally diverse family of natural products that possess a wide range of biological and pharmacological properties. Such properties include, but are not limited to, antibiotic, antitumor, antifungal, and immunosuppressive activities. Jenke-Kodama, H., et al., *Mol. Biol. Evol.* 22(10):2027-39 (2005). Polyketides are synthesized as secondary metabolites in bacteria, fungi, plants, and animals by different classes of polyketide synthases (PKS), which resemble the classes of fatty acid synthases. Id Polyketide synthesis proceeds by the addition or condensation of different functional groups to an acyl-ACP chain. See FIG. 21. And while fatty acid elongation includes four enzymatic steps per two carbon chain extension (KS (ketosynthase), KR (ketoreductase), DH (dehydratase), ER (enoyl reductase)) (FIG. 21B), PKS elongation can include a combination of enzymatic activities, e.g., (KS), (KS, KR), (KS, KR, DH), or (KS, KR, DH, ER), at each step (FIG. 21A). Malonyl-CoA produced by the recombinant microorganisms and pathways of the invention can be used as a metabolic precursor for polyketides.

Organic Acid Synthesis

Malonyl-CoA produced by the recombinant microorganisms and pathways of the invention can be used as a metabolic precursor for number of bioproducts. For example, the organic acid 3-hydroxypropionic acid ("3-

HP"), also known as 3-hydroxypropanoate, is used in the production of various industrial chemicals such as renewable polyesters, acrylic acid, malonic acid, and co-polymers with lactic acid. Although 3-HP can be produced by organic chemical synthesis, it is desirable to use bio-alternative methods that allow for more cost effective, efficient, and renewable production. While some microorganisms are known to produce 3-HP (see, e.g., WO 01/16346; WO 02/42418; US 2011/0144377; US 2011/0125118, each of which is incorporated by reference herein), few biological systems have been developed that would result in its efficient production. Production of malonyl-CoA at high yield via transcarboxylase in an anaerobic process would allow for efficient high yield 3-hydroxypropionic acid production using a suitable enzymatic pathway from malonyl-CoA to 3-hydroxypropionic acid and a suitable redox system to generate NADPH during carbohydrate deconstruction. See, e.g., redox systems are "F" and "G" in Table 10.

Enzymes employed for the production of 3-HP by the recombinant microorganisms and methods of the invention include 1) malonyl-CoA reductase (EC 1.2.7.5), 2) 3-hydroxypropionate dehydrogenase (EC 1.1.1.59 and EC 1.1.1.298), and 3) a bifunctional enzyme which harbors aldehyde dehydrogenase and alcohol dehydrogenase domains (Hogler et al., *J. Bacteriol.* 184:2402-2410 (2002)).

The following example pathways demonstrate the production of 3-HP from a malonyl-CoA metabolic precursor using the above-referenced enzymes:

1) Malonyl CoA Reductase (EC 1.2.1.75)
   Malonate semialdehyde+coenzyme A+NADP(+)<=>malonyl-CoA+NADPH 2a) 3-Hydroxypropionate Dehydrogenase (EC 1.1.1.59
    3-hydroxypropanoate+NAD(+)<=>Malonate semialdehyde+NADH 2b) 3-Hydroxypropionate Dehydrogenase (EC 1.1.1.298)
    3-hydroxypropanoate+NADP(+)<=>Malonate semialdehyde+NADPH 3) bifunctional dehydrogenase (aldehyde-alcohol)
   malonyl-CoA+NADPH+H$^+$-malonate semialdehyde+NADP$^+$+CoA
   malonate semialdehyde (3-oxopropanoate)+NADPH+H$^+$-3-hydroxypropionate+NADP$^+$ The sequence of a malonyl-CoA reductase from *Chloroflexus aurantiacus* is provided below:

```
C. aurantiacus Malonyl-CoA Reductase (amino acid
sequence; >gi|42561982|gb|AAS20429.1)
                                        (SEQ ID NO: 1)
MSGTGRLAGKIALITGGAGNIGSELTRRFLAEGATVIISGRNRAKLTALAE

RMQAEAGVPAKRIDLEVMDGSDPVAVRAGIEAIVARHGQIDILVNNAGSAG

AQRRLAEIPLTEAELGPGAEETLHASIANLLGMGWHLMRIAAPHMPVGSAV

INVSTIFSRAEYYGRIPYVTPKAALNALSQLAARELGARGIRVNTIFPGPI

ESDRIRTVFQRMDQLKGRPEGDTAHHFLNTMRLCRANDQGALERRFPSVGD

VADAAVFLASAESAALSGETIEVTHGMELPACSETSLLARTDLRTIDASGR

TTLICAGDQIEEVMALTGMLRTCGSEVIIGERSAAALAQFEQAVNESRRLA

GADFTPPIALPLDPRDPATIDAVFDWGAGENTGGIHAAVILPATSHEPAPC

VIEVDDERVLNFLADEITGTIVIASRLARYWQSQRLTPGARARGPRVIFLS

NGADQNGNVYGRIQSAAIGQLIRVWRHEAELDYQRASAAGDHVLPPVWANQ

IVRFANRSLEGLEFACAWTAQLLHSQRHINEITLNIPANISATTGARSASV

GWAESLIGLHLGKVALITGGSAGIGGQIGRLLALSGARVMLAARDRHKLEQ

MQAMIQSELAEVGYTDVEDRVHIAPGCDVSSEAQLADLVELTLSAFGTVDY

LINNAGIAGVEEMVIDMPVEGWRHTLFANLISNYSLMRKLAPLMKKQGSGY

ILNVSSYFGGEKDAAIPYPNRADYAVSKAGQRAMAEVFARFLGPEIQINAI

APGPVEGDRLRGTGERPGLFARRARLILENKRLNELHAALIAAARTDERSM

HELVELLLPNDVAALEQNPAAPTALRELARRFRSEGDPAASSSSALLNRSI

AAKLLARLHNGGYVLPADIFANLPNPPDPFFTRAQIDREARKVRDGIMGML

YLQRMPTEFDVAMATVYYLADRNVSGETFHPSGGLRYERTPTGGELFGLPS

PERLAELVGSTVYLIGEHLTEHLNLLARAYLERYGARQVVMIVETETGAET

MRRLLHDHVEAGRLMTIVAGDQIEAAIDQAITRYGRPGPVVCTPFRPLPTV

PLVGRKDSDWSTVLSEAEFAELCEHQLTHHFRVARKIALSDGASLALVTPE

TTATSTTEQFALANFIKTTLHAFTATIGVESERTAQRILINQVDLTRRARA

EEPRDPHERQQELERFIEAVLLVTAPLPPEADTRYAGRIHRGRAITV
```

Additional malonyl-CoA reductase enzyme examples include, but are not limited to, those from *Chloroflexus* sp., *Oscillochloris* sp., *Roseiflexus* sp., and marine gamma protcobacterium. See, e.g., Hügler et al., *J. Bacteriol.* 184:2402-2410 (2002); Rathnasingh, C., et al., *Biotech Bioeng.* 104(4) (2009); Rathnasingh, C., et al., "Production of 3-hydroxypropionic acid via malonyl-CoA pathway using recombinant *Escherichia coli* strains," *J. Biotech* (Epub Jun. 23, 2011). A phylogenetic tree and an alignment of several malonyl-CoA reductase enzymes is shown in FIGS. 45 and 46. These alignments were made using malonyl-CoA reductase enzymes from *Chloroflexus aurantiacus* (GenBank Accession No. AAS20429; SEQ ID NO:1); *Chloroflexus aurantiacus* J-10-fl (GenBank Accession No. YP_001636209; SEQ ID NO:291); *Chloroflexus* sp. Y-400-fl (GenBank Accession No. YP_002570540; SEQ ID NO:292); *Chloroflexus aggregans* DSM 9485 (GenBank Accession No. YP_002462600; SEQ ID NO:293); *Oscillochloris trichoides* DG6 (GenBank Accession No. ZP_07684596; SEQ ID NO:294); *Roseiflexus castenholzii* DSM 13941 (GenBank Accession No. YP_001433009; SEQ ID NO:295); *Roseiflexus* sp. RS-1 (GenBank Accession No. YP_001277512; SEQ ID NO:296); *Erythrobacter* sp. NAP1 (GenBank Accession No. ZP_01039179; SEQ ID NO:297); gamma proteobacterium NOR51-B (GenBank Accession No. ZP_04957196 SEQ II) NO:298).

Another product that can be produced from a malonyl-CoA metabolic precursor, and/or as an end-product of the fatty acid syntheses described herein, is adipic acid. Adipic acid is a six-carbon dicarboxylic acid, which is used as a chemical intermediate in the synthesis of polymers, such as polyamides (nylons), polyurethanes, and plasticizers, as well as a food acidulant. Chemical synthesis of adipic acid uses various noxious chemicals for oxidation and/or hydration of ketoalcohols or cyclohexanes, which present environmental safety and energy input concerns. Engineering a biological system to produce adipic acid from a carbohydrate source can avoid these concerns and provide a renewable means for producing adipic acid-derived products.

Attempts at the bioproduction of adipic acid have used alternative synthetic pathways, catalysts, substrates, intermediates, and/or recombinant microorganisms. See, e.g., WO2011/003034, WO1995/007996, WO2009/151728, and WO2010/144862, each of which is incorporated by reference herein. In particular, WO2011/003034 discloses the synthesis of adipic acid from, inter alia, fatty acids, fatty alcohols, alkanes, and oils, but does not, however, disclose the synthesis of adipic acid from a malonyl-CoA metabolic precursor. The pathways of the invention for producing malonyl-CoA can be used to produce a $C_{12}$ fatty acid or fatty alcohol, which can be further engineered to produce adipic acid via omega oxidation using. See, e.g., FIGS. 23 and 24 ("At" is *Arabidopsis thaliana*; "Cc" is *Candida cloacae*); WO2011/003034; Vanhanen S., et al., *J Biol. Chem.* 275(6): 4445-52 (2000); Picataggio, S., et al., *Bio/Technology* 10(8): 894-98 (1992). To accommodate the oxidation of the fatty acid or fatty alcohol, either a facultative anaerobe (e.g., *E. coli* or *S. cerevisiae*) can be engineered to include an adipic acid pathway that can be switched to aerobic conditions after a pool of malonyl-CoA or fatty acids/alcohols is synthesized, or a facultative anaerobe or aerobe comprising an adipic acid pathway can be engineered to use in tandem or in series with a recombinant microorganism of the invention that produces fatty acids or fatty alcohols.

To generate adipic acid from a fatty acid or fatty alcohol using omega oxidation pathway, enzymes such as, e.g., a mixed function oxidase to hydroxylate the omega carbon and alcohol and aldehyde dehydrogenases to oxidate the introduced hydroxyl group, can be used.

Phosphoenolpyruvate Carboxykinase

Figure 1A:
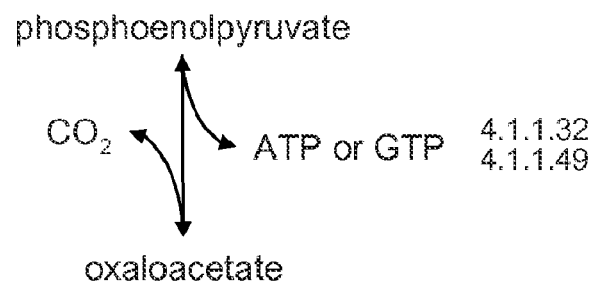
FIG. 1A depicts the conversion of phosphoenolpyruvate to oxaloacetate catalyzed by an enzyme from EC 4.1.1.32 or 4.1.1.49.

Phosphoenolpyruvate carboxykinase (PEPCK) includes those enzymes that catalyze the conversion of phosphoenolpyruvate (PEP) to oxaloacetate (see FIG. 1A) and that correspond to Enzyme Commission Number 4.1.1.49 or 4.1.1.32. See, e.g., Matte, A., et al., *J. Biol. Chem.* 272: 8105-08 (1997). The reaction is reversible and is used in succinic acid producing bacteria to convert PEP to oxaloacetate. *E. coli* can mutate to use PEPCK when flux is directed primarily to succinic acid. PEPCK requires $Mg^{2+}$ as a co-factor. A number of ATP and GTP using enzymes have been described, including, e.g., a GTP-utilizing PEPCK in *C. thermocellum* and ATP-utilizing PEPCK in *T. saccharolyticum, T. tengcongensis, E. coli* and *S. cerevisiae*.

PEPCKs have been classified according to nucleotide specificity, i.e., those that are ATP-dependent and those that are GTP- or ITP-dependent. Within each group, the species show significant amino acid sequence identity, in the range of 40-80%, and share similar nucleotide and oxaloacetate binding "consensus motifs" between the groups, including key conserved residues at or near the active sites. See Matte, A., et al., *J. Biol. Chem.* 272:8105-08 (1997). Additional structural characterizations have been described in, e.g., Matte, A., et al., *J. Biol. Chem.* 272:8105-08 (1997). Examples of PEPCK sequences include:

*C. thermocellum* PEPCK (GTP)

```
>Cthe_2874
                                         (SEQ ID NO: 2)
atgacatcaacaaacatgacaaaaaacaaaaaactgctggattgggttaag gaaatggctgaaatgtgtcagcctgatgaaatttattggtgcgatggttcg gaggaagaaaatgagcgcttgataaagttgatggtggattcaggtttggct acgcctttgaatcctgaaaagcgacctggatgttatacttccgcagcgatc cgtccgacgagcccgtgttgaggacagaactttttattgcatccaaaccaa agaagatgcaggacctacaaacaactggatagatccggttgagctcaaggc aactatgaaagagttgtacaagggttgtatgaagggaagaacaatgtatgt tattcctttctccatgggacctatcggttcacccatttcaaaaatcggcgt
```

-continued
```
tgaattgaccgacagcccttatgttgttgttaacatgcgcattatgactcg cataggcaaggctgtgttggatcagctcggagaagacggagattttgtacc ttgtctccactcagtcggtgctccgctcaaagagggagaaaaggataaagg ttggccatgcgcaccaatcgaaaagaaatacataagccacttcccggaaga aaggactatatggtcatatggttccggatacggtggaaatgcgcttttagg aaagaaatgctttgcacttcgtattgcatctgttatggcacgtgacgaagg ttggcttgctgaacacatgcttatccttcgcataacagaccctgaaggaaa caagacatatgttacaggtgctttcccaagcgcatgcggaaagacgaacct ggctatgcttattcctacaattcccggatggaaagttgaaacaatcggtga cgatattgcatggatgagatttggaaaagacggccgatgtatgctatcaac cagaagcaggattctaggtgttgctccgggtacatccatggattcaaatcc gaacgcaatgcatacaattaagaaaaatactatatttacaaacgttgcatt gactgatgacggcgatgtttggtgggaaggcatcggaactgaaccgccggc tcatctcatagactggcagggtaaagactggactcctgattccggaactt ggcagcacatcccaacggacgtatacagcacctgcaagtcagtgccagtaa ttgacctgaatgggaggatccggaaggtgtgccgatttcagcaatccttat cggtggacgccgtccgaacaccattccgcttgttcatgaaagctttgactg gaaccatggtgtattcatgggttcaatcatgggttctgaaattacggctgc cgcaatttcaaacaaaatcggacaggtacgccgtgacccgtttgctatgct gcctttcataggctacaacgtaaatgactatttgcagcactggttgaacat gggtaccaagactgacccaagcaagcttcccaagatattctatgtaaactg gttccgcaaggacagcaacggtaaatggttgtggcctggatacggtgaaaa cagccgtgttctcaagtggattgttgaaagagtcacggaaaaggtaaagca gtaaagacacctataggatatatgcctacagttgacgctatcgacacaacc ggccttgatgtaagcaaagaggatatggaagaactcttgagcgttaacaaa gaacagtggctccaggaagttgagtcaataaaagaacattataagtcatac ggagaaaaactgccgaaagaattgtgggcacaattggaggctcttgaacaa cgtttgaaagagtataacggttaa
```

*T. saccharolyticum* PEPCK

```
>or2173
                                         (SEQ ID NO: 3)
ATGATTATGAAAAAATCAAAGAAATGTTTCAATCTGAATATTGACGACAA

AGAAACCTTGAATACTTTTGGAAGTTCGAGAGGAGAATTGTTTATGATAG

ATTTAGATGATGTATTTAAAAATTGTGGCAGTATTCTTTACAATTTACCT

GTTTCAGATTTGATAGAGGAAGCCATAAGAAATAATGAAGGGAAATTGTT

AGAAAATGGTGCATTAGATGTTTTTACAGGTAAATATACGGGAAGAATAC

CAAAAGATAAATACATTGTAAATGAAGAATCTATTCATAATGATATTTGG

TGGGAAAATAATAATTCAATGGAAAAAGAAAATTTTATTAGAGTTTTAAA

CAGAGTAATTGATTATTTAAAAAAGAGCAGAAAATTGTATGTTTTTAAAG

GTTTTGTTGGCGCAGACCCGCGATATAGATATCAAGTAACCGTTATTAAT
```

-continued
GAATATGCGTATCAAAACGCTTTTGTACATCAATTATTTATTAATCCTAA
AAATGAAGAAGAACTTAAAAAGGAATCCGATTTTACAGTTATTTGTGTGC
CGAATTTTTAGCTGATCCAATTTATGATGGAACTAATTCTGAGGCATTTA
TTATTATAAGTTTTGAAGAAAAATTAATTTTAATTGGTGGAACAAGATAT
TCAGGAGAAATAAAAAAATCTGTCTTCACAATGATGAATTATTTGATGTT
AAAAAGGAATGTACTGCCTATGCATTGTGCAGCTAATATAGGTTCCAATA
ATGATACAGCGCTTTTTTTGGGTTGTCGGGAACCGGCAAGACAACTTTA
TCAACGGATCCAGAAAGATTTTTAATTGGCGACGATGAACATGGATGGTC
TTCACATGGAATTTTTAATTTTGAGGGTGGATGCTATGCAAAGTGTATAA
ATTTATCCCCATATAATGAACCTGAAATATGGAATGCAATTAGATTTGGA
ACAATTTTAGAAAATGTTATTTATGATGTAAATAATATGCCAGTCTATAC
AAGTAGTAAAATAACTGAAAATACAAGAGCTTCTATATCCACTTGAGTACA
TCCCTAGGAAAGCGTCAAATGGCATTGGCGGTAATCCTAAAATTATATTT
TTCTTGGCAGCCGATGGTTTTGGAGTATTGCGTCCAATTTCTAAGCTGAC
AAATGAACAGGCTGTTGACTATTTCTTATTAGGATATACGAGCAAAATAC
CAGGAAGAGAAAAGGGAATTTGCGAACCACAAGCAACGTTTTCATCATGT
TTTGGAGCACCATTTTTGCCATCATATCCAATGAGGTATGCTGAATTGTT
AAAGAAAAAATCGCAGAAATGATTCAGTTGTTTATTTAATAAATACTG
GATGGATAGGTGGACATTATGGAATTGGCAAAAGGATAGATTTAAAATAC
ACAAGAGAAATCATAAAAAATGTTTTAAATGGTGAATTGGAAAAAGCAAA
ATTTAAAAAAGATACAGTATTTGATTTGATGATACCAGAAAGTGCAATA
ACATTCCAGATGAATTATTAGATCCTATAAAAACATGGGAAGACAAAAAT
GATTACTTCCAAACTGCTAATAATTTATTATCTGCATTTAAAGCGAGATT
AGATTATATAAAAAATGGGATTCATCA E. coli K12 PEPCK (ATP)
(SEQ ID NO: 4)
ATGCGCGTTAACAATGGTTTGACCCCGCAAGAACTCGAGGCTTATGGTAT
CAGTGACGTACATGATATCGTTTACAACCCAAGCTACGACCTGCTGTATC
AGGAAGAGCTCGATCCGAGCCTGACAGGTTATGAGCGCGGGGTGTTAACT
AATCTGGGTGCCGTTGCCGTCGATACCGGGATCTTCACCGGTCGTTCACC
AAAAGATAAGTATATCGTCCGTGACGATACCACTCGCGATACTTTCTGGT
GGGCAGACAAAGGCAAAGGTAAGAACGACAACAAACCTCTCTCTCCGGAA
ACCTGGCAGCATCTGAAAGGCCTGGTGACCAGGCAGCTTTCCGGCAAACG
TCTGTTCGTTGTCGACGCTTTCTGTGGTGCGAACCCGGATACTCGTCTTT
CCGTCCGTTTCATCACCGAAGTGGCCTGGCAGGCGCATTTTGTCAAAAAC
ATGTTTATTCGCCCGAGCGATGAAGAACTGGCAGGTTTCAAACCAGACTT
TATCGTTATGAACGGCGCGAAGTGCACTAACCCGCAGTGGAAAGAACAGG
GTCTCAACTCCGAAAACTTCGTGGCGTTTAACCTGACCGAGCGCATGCAG
CTGATTGGCGGCACCTGGTACGGCGGCGAAATGAAGAAAGGGATGTTCTC
GATGATGAACTACCTGCTGCCGCTGAAAGGTATCGCTTCTATGCACTGCT
CCGCCAACGTTGGTGAGAAAGGCGATGTTGCGGTGTTCTTCGGCCTTTCC
GGCACCGGTAAAACCACCCTTTCCACCGACCCGAAACGTCGCCTGATTGG
CGATGACGAACACGGCTGGGACGATGACGGCGTGTTTAACTTCGAAGGCG
GCTGCTACGCAAAAACTATCAAGCTGTCGAAAGAAGCGGAACCTGAAATC
TACAACGCTATCCGTCGTGATGCGTTGCTGGAAAACGTCACCGTGCGTGA
AGATGGCACTATCGACTTTGATGATGGTTCAAAAACCGAGAACACCCGCG
TTTCTTATCCGATCTATCACATCGATAACATTGTTAAGCCGGTTTCCAAA
GCGGGCCACGCGACTAAGGTTATCTTCCTGACTGCTGATGCTTTCGGCGT
GTTGCCGCCGGTTTCTCGCCTGACTGCCGATCAAACCCAGTATCACTTCC
TCTCTGGCTTCACCGCCAAACTGGCCGGTACTGAGCGTGGCATCACCGAA
CCGACGCCAACCTTCTCCGCTTGCTTCGGCGCGGCATTCCTGTCGCTGCA
CCCGACTCAGTACGCAGAAGTGCTGGTGAAACGTATGCAGGCGGCGGGCG
CGCAGGCTTATCTGGTTAACACTGGCTGGAACGGCACTGGCAAACGTATC
TCGATTAAAGATACCCGCGCCATTATCGACGCCATCCTCAACGGTTCGCT
GGATAATGCAGAAACCTTCACTCTGCCGATGTTTAACCTGGCGATCCCAA
CCGAACTGCCGGGCGTAGACACGAAGATTCTCGATCCGCGTAACACCTAC
GCTTCTCCGGAACAGTGGCAGGAAAAAGCCGAAACCCTGGCGAAACTGTT
TATCGACAACTTCGATAAATACACCGACACCCCTGCGGGTGCCGCGCTGG
TAGCGGCTGGTCCGAAACTGTAA S. cerevisiae PEPCK (ATP)
(SEQ ID NO: 5)
ATGTCCCCTTCTAAAATGAATGCTACAGTAGGATCTACTTCCGAAGTTGA
ACAAAAAATCAGACAAGAATTGGCTCTTAGTGACGAAGTCACCACCATCA
GACGCAATGCTCCAGCTGCCGTTTTGTATGAAGATGGTCTAAAAGAAAAT
AAAACTGTCATTTCATCAAGCGGTGCATTGATCGCTTATTCCGGTGTTAA
AACCGGAAGATCTCCAAAGGACAAACGTATTGTTGAAGAACCTACCTCGA
AAGACGAAATTTGGTGGGGTCCGGTCAATAAACCATGTTCTGAAAGAACA
TGGTCTATCAACCGTGAAAGAGCTGCAGATTACTTGAGAACAAGAGACCA
CATTTATATTGTCGATGCATTTGCAGGATGGGATCCAAAATACAGAATCA
AAGTCCGCGTTGTTTGTGCCAGGGCTTACCACGCTTTATTCATGACAAAT
ATGCTTATTAGACCTACAGAAGAAGAATTAGCCCATTTTGGAGAACCTGA
TTTTACTGTCTGGAACGCTGGTCAGTTCCCAGCCAATTTACACACCCAGG
ATATGTCTTCAAAGAGTACTATAGAAATTAACTTCAAAGCAATGGAAATG
ATCATTTTAGGTACCGAATACGCCGGTGAAATGAAAAAAGGTATTTTCAC
AGTTATGTTTTACTTGATGCCTGTGCACCATAACGTTTTAACTTTGCACT
CTTCCGCCAACCAGGGTATTCAAAACGGTGACGTTACTTTATTCTTTGGC
CTAAGTGGTACCGGGAAAACCACTTTATCCGCAGACCCACATAGATTGTT
GATCGGCGATGATGAACATTGTTGGTCCGACCATGGTGTCTTCAATATCG
AAGGTGGTTGTTACGCCAAGTGTATTAATTTATCTGCCGAAAAGGAGCCT
GAAATTTTCGACGCTATCAAGTTTGGTTCTGTATTAGAAAACGTTATCTA
TGACGAGAAGTCGCATGTAGTCGACTATGACGACTCTTCTATTACTGAAA
ATACTAGATGTGCCTACCCAATTGACTACATTCCAAGTGCCAAGATTCCA
TGTTTGGCGGACTCTCATCCAAAGAACATTATCCTGCTAACTTGTGATGC -continued
```
TTCGGGTGTTTTACCACCAGTATCTAAATTGACTCCTGAACAAGTCATGT

ACCATTTCATCTCTGGTACACTTCTAAAATGGCTGGTACTGAGCAAGGTG

TCACTGAACCTGAACCAACATTTTCATCTTGTTTCGGACAACCCTTCCTA

GCCTTGCACCCTATTAGATACGCAACCATGTTAGCTACAAAGATGTCTCA

ACATAAAGCTAATGCGTACTTAATCAACACCGGCTGGACTGGTTCTTCCT

ACGTATCTGGTGGTAAACGTTGCCCATTGAAGTACACAAGGGCCATTCTG

GATTCTATTCATGATGGTTCGTTAGCCAATGAAACGTACGAAACTTTACC

GATTTTCAATCTTCAAGTACCTACCAAGGTTAACGGTGTTCCAGCTGAGC

TTTTGAATCCTGCTAAAAACTGGTCTCAAGGTGAATCCAAATACAGAGGT

GCAGTTACCAACTTGGCCAACTTGTTTGTTCAAAATTTCAAGATTTATCA

AGACAGAGCCACACCAGATGTATTAGCCGCTGGTCCTCAATTCGAGTAA
```

Transcarboxylase

The conversion of oxaloacetate and acetyl-CoA to pyruvate and malonyl-CoA allows for the anaerobic high yield production of fatty acid derived hydrocarbons. This reaction has not been reported to occur in vivo. However, an in vitro substrate specificity study for fraction-purified (S)-methylmalonyl-CoA:pyruvate carboxytransferase (a transcarboxylase, "Me-TC," E. C. 2.1.3.1) showed the ability of this enzyme to utilize oxaloacetate and acetyl-CoA as substrates. See Wood and Stjernholm, *PNAS* 47:289-303 (1961). The in vitro reaction occurred at one half the velocity of the enzyme's natural substrates, oxaloacetate and propionyl-CoA, however, and the ability of the enzyme to produce malonyl-CoA in its native organism (*Propionibacterium shermanii*) was not determined. Me-TC enzymes are known to be present in other Propionibacteria (e.g., *Propionibacterium freudenreichii* and *Propionibacterium acnes*), which ferment carbohydrates and lactate to propionate and acetate, and in obligately syntrophic bacteria such as *Pelotomaculum thermopropionicum*, *Candidatus Cloacamonas acidaminovorans*, and *Geobacter bemidjiensis*, which convert propionate and other medium chain organic acids and alcohols to acetate and hydrogen or reduced metals. Falentin et al., *PLOS one* 5(7): e11748 (2010); Kosaka et al., *Genome Res.* 18:442-448 (2008); Pelletier et al., *J. Bact.* 190:2572-2579 (2008); Aklujkar et al., *BMC Genomics* 11:490 (2010).

Figure 1B:
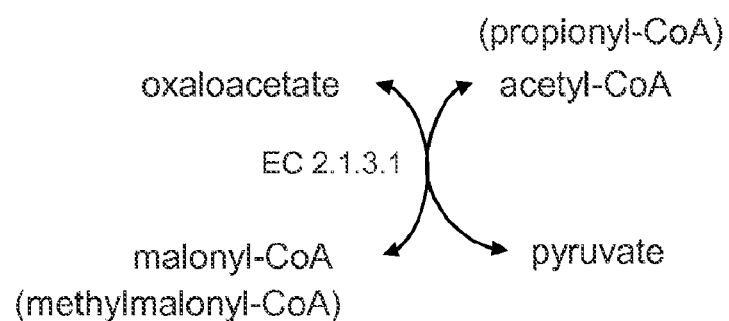
FIG. 1B depicts the conversion of oxaloacetate and acetyl-CoA to malonyl-CoA and pyruvate catalyzed by an enzyme from EC 2.1.3.1.

As used herein, transcarboxylase (TC) includes enzymes that catalyze the conversion of oxaloacetate and acetyl-CoA to malonyl-CoA and pyruvate (see FIG. 1B) and that correspond to Enzyme Commission Number 2.1.3.1 (methylmalonyl-CoA carboxyltransferase). In vivo, TC also catalyzes the conversion of methylmalonyl-CoA and pyruvate to oxaloacetate and propionyl-CoA. The reaction is reversible and requires co-factors such as Biotin, Co, or $Zn^{2+}$. TC consists of 3-4 subunits encoding domains for: a 5S subunit, a 12S subunit, and a 1.3S subunit; a 12S C-terminal subunit may also be present. See Carey et al., *IUBMB Life* 56:575-83 (2004). TC enzymatic activity has been observed in *Propionibacterium* species such as *Propionibacterium freudenreichii* and *Propionibacterium acnes*, *Bacteroides fragilis*, *Veillonella parvula*, *Veillonella gazogenes*, *Pelotomaculum thermopropionicum*, *Candidatus Cloacamonas acidaminovorans*, and *Geobacter bemidjiensis*. See Falentin et al., *PLoS One* 5:e11748 (2010); Kosaka et al., *Genome Res.* 18:442-4482008 (2008); Pelletier et al., *J. Bact.* 190:2572-2579 (2008); and Aklujkar et al., *BMC Genomics* 11:490 (2010). Based on similarity to TC enzymes, high similarity TC genes have been identified in *Thermoanaerobacter* strains (*T. saccharolyticum* or0945, or0947, and or1888), *C. thermocellum* (Cthe_0699, Cthe_0700, and Cthe_0701), *Caldicellulosiruptor bescii*, *Clostridium cellulolyticum*, and *Corynebacterium kroppenstedtii*. Protein engineering, either across all subunits or on a specific subunit, using techniques known to those in the art, can be employed to increase enzymatic activity towards malonyl-CoA generation.

An alignment of *C. thermocellum* and *T. saccharolyticum* homologs of TC from *Propionibacterium freudenreichii* CIRM-BIA1 and *Propionibacterium acnes* is shown in FIGS. 7A-7C. Additional sequences of TC include:

*Propionibacterium freudenreichii* subsp. *shermanii* CIRM-BIA1 Transcarboxylase

```
>PFREUD_18840 (1.3S subunit nucleotide sequence)
Antisense strand:
                                                                    (SEQ ID NO: 6)
tcagccgatc ttgatgagac cctgaccgcc ctgcacggcg tcacgctcct tgacaaggac cttctcgacc ttgccgtcgg tgggagcgtt gatctcggtc tccatcttca tggcctcgag aacgagcacg gtctgaccag ccttgaccgt gtcaccctcc ttcacgagga tcttggagac ggtgccggcc agcggagcgg gaatctcgcc ctctccggcc ttaccggcgc ctgcgccacc tgctgcgcgc ggtgccggcg cgccgccggt gccgccgccg aacaggatgg tgcccatcgg gttttcgtgt gacttgtcga cgtcaacgtc aacgtcatac gcagtgccgt tgactgttac cttcagtttc at Sense strand:
                                                                    (SEQ ID NO: 7)
atgaaactgaaggtaacagtcaacggcactgcgtatgacgttgacgttgacgtcgacaagtcacacgaaaacccgatgggcaccat cctgttcggcggcggcaccggcggcgcgccggcaccgcgcgcagcaggtggcgcaggcgccggtaaggccggagagggcgagattc ccgctccgctggccggcaccgtctccaagatcctcgtgaaggagggtgacacggtcaaggctggtcagaccgtgctcgttctcgag gccatgaagatggagaccgagatcaacgctcccaccgacggcaaggtcgagaaggtccttgtcaaggagcgtgacgccgtgcaggg cggtcagggtctcatcaagatcggc >PFREUD_18840 (1.3S subunit amino acid sequence)
                                                                    (SEQ ID NO: 8)
MKLKVTVNGTAYDVDVDVDKSHENPMGTILFGGGTGGAPAPRAAGGAGAGKAGEGEIPAPLAGTVSKILVKEGDTVKAGQTVLVLE

AMKMETEINAPTDGKVEKVLVKERDAVQGGQGLIKIG
```

\>PFREUD_18870 (5S subunit nucletotide sequence)
Antisense strand:

(SEQ ID NO: 9)

tcacgcctgc tgaacggtga cttcgcggac ggttccgccc acgttcacgt tgtaggtgac gggaccggcc acggcgagcg acttctcgtc gccctcggcc tcggcattca gctgggcatc ggtgagagcc acgctgtgcg ggccctcggc gcgatgctcg aagaagaccg gagcgacctg cgggaacagt gcataggtga gcacgtcctc gtcggtgccg ttgaagccct tgagggccgc ggcctccttg gactgctcct cccactcggg gggcagcaga tcggccgggc gctgggtgat cggcttcttg ccggactgct cctcggccaa cttgaccacc ttcggatcgc gatcggccgg gctggcgccg tagtagccga gcatgatgtc ggcgaactcg ccggtcatcc tcttgtactc gcccatcatc acgttgaaca cggcctgcgt gccgacgatc tggctggacg gggtgaccag gggcgggaag ccggcggcct gcggacgcg cggcacctct gccatgacct cgtccatctt gtcctcggcg ccctgggcgc gcagctgcga ctccatgttg gagagcatgc cgccggggat ctgcgacttg aagatcgagg tgtcgacaag cgtcttcgac tcgaacttct tgtacttcgg gcggatggcc ttgaagtgat cgcggatctt gtgcaggcga tcgtagtcaa ggttggtggt gtacccggtg ccctcgagca tctcggcaac cgactcggtg gggttgtggc ccgggccgag cgacatggac gagatggcgg tgtcgacgac gtcgacgccg gcctcgatgg ccttcatgag ggagacctcg gtgacacccg tggtggagtg gcagtgcagg ttgatctgcg tcttctggcc gtaggtgtcc ttgatggcct tgatgatgtc gtaggccggc tgcggcttga gcagggcggc catgtccttc agggcgatgg aatcagcacc catgtcgagc agctgaccag caagcttgac atagccctca acggtgtgga ccgggctgat cgtgtagcaa atggtgccct gcgcgtgctt gccggccttc ttgacggcag ccatggcgtg cgccatgttg cggggatcat tcatggcgtc gaagacacgg aacacgtcca tgccgttctc agcggacttg tcgacgaagc gatcgacgac ctcgtcgttg tagtggcggt aacccagcag gttctggcca cgcagcagca tctggagacg gctgttgggc atcagcttgc ggaacgtgcg cagacgctcc caaggatcct cgttgaggaa gcggatacac gagtcatacg tggcaccacc ccaacactcc actgaccagt acccggcagc atcaatgtct gcacaggcgc cgaccatgtc ttccattgcc attcgtgtgg ccatcaggct ctgatgggca tcgcgcagca cgagctcggt gataccaacc tcgcgcggct cggaaacctc aatttctcgc ggactcat Sense strand:

(SEQ ID NO: 10)

atgagtccgcgagaaattgaggtttccgagccgcgcgaggttggtatcaccgagtcgtgctgcgcgatgcccatcagagcctgat ggccacacgaatggcaatggaagacatggtcggcgcctgtgcagacattgatgctgccgggtactggtcagtggagtgttggggtg gtgccacgtatgactcgtgtatccgcttcctcaacgaggatccttgggagcgtctgcgcacgttccgcaagctgatgcccaacagc cgtctccagatgctgctgcgtggccagaacctgctgggttaccgccactacaacgacgaggtcgtcgatcgatcgtcgacaagtcc gctgagaacggcatggacgtgttccgtgtcttcgacgccatgaatgatccccgcaacatggcgcacgccatggctgccgtcaagaa ggccggcaagcacgcgcagggcaccatttgctacacgatcagcccggtccacaccgttgagggctatgtcaagcttgctggtcagc tgctcgacatgggtgctgattccatcgccctgaaggacatggccgccctgctcaagccgcagccggcctacgacatcatcaaggcc atcaaggacacctacggccagaagacgcagatcaacctgcactgccactccaccacgggtgtcaccgaggtctccctcatgaaggc catcgaggccgcgtcgacgtcgtcgacaccgccatctcgtccatgtcgctcggccgggccacaacccaccgagtcggttgccg agatgctcgagggcaccgggtacaccaccaaccttgactacgatcgcctgcacaagatccgcgatcacttcaaggccatccgcccg aagtacaagaagttcgagtcgaagacgcttgtcgacacctcgatcttcaagtcgcagatccccggcggcatgctctccaacatgga gtcgcagctgcgcgcccagggcgccgaggacaagatggacgaggtcatggcagaggtgccgcgcgtccgcaaggccgccggcttcc cgcccctggtcacccccgtccagccagatcgtcggcacgcaggccgtgttcaacgtgatgatgggcgagtacaagaggatgaccggc gagttcgccgacatcatgctcggctactacgcgccagcccggccgatcgcgatccgaaggtggtcaagttggccgaggagcagtc cggcaagaagccgatcacccagcgcccggccgatctgctgcccccgagtgggaggagcagtccaaggaggccgcggccctcaagg gcttcaacggcaccgacgaggacgtgctcacctatgcactgttcccgcaggtcgctccggtcttcttcgagcatcgcgccgagggc ccgcacagcgtggctctcaccgatgcccagctgaaggccgaggccgagggcgacgagaagtcgctcgccgtggccggtcccgtcac ctacaacgtgaacgtgggcggaaccgtccgcgaagtcaccgttcagcaggcgtga \>PFREUD_18870 (5S subunit amino acid sequence)

-continued

>(SEQ ID NO: 11)
MSPREIEVSEPREVGITELVLRDAHQSLMATRMAMEDMVGACADIDAAGYWSVECWGGATYDSCIRFLNEDPWERLRTFRKLMPNS

RLQMLLRGQNLLGYRHYNDEVVDRFVDKSAENGMDVFRVFDAMNDPRNMAHAMAAVKKAGKHAQGTICYTISPVHTVEGYVKLAGQ

LLDMGADSIALKDMAALLKPQPAYDIIKAIKDTYGQKTQINLHCHSTTGVTEVSLMKAIEAGVDVVDTAISSMSLGPGHNPTESVA

EMLEGTGYTTNLDYDRLHKIRDHFKAIRPKYKKFESKTLVDTSIFKSQIPGGMLSNMESQLRAQGAEDKMDEVMAEVPRVRKAAGF

PPLVTPSSQIVGTQAVFNVMMGEYKRMTGEFADIMLGYYGASPADRDPKVVKLAEEQSGKKPITQRPADLLPPEWELQSKEAAALK

GFNGTDEDVLTYALFPQVAPVFFEHRAEGPHSVALTDAQLKAEAEGDEKSLAVAGPVTYNVNVGGTVREVTVQQA

>PFREUD_18860 (12S subunit nucleotide sequence)
Antisense strand:

(SEQ ID NO: 12)
tcagcagggg aagtttccat gcttcttcgc cgggcgggtc tgacgcttgg tggcgtacat ctccagggcg gaagcaatct ttcgacgggt atcagccggg tcaatcacgt cgtcgacctg accgcgggcg gcggccacgt acggcgtgtt gaacgcgttc tggtactcct cgatcttctc ggcgcgcatg gcgtcgggat cgtcggcagc cttgatctcc ttgcggaaga tcacatttgc cgcaccctcg gcgcccatca ccgcaatctc ggcgctgggc caggcgtaca cggcgtcggc accaaggtca cggttgcaca tggccaggta ggagccgccg taggccttgc ggagcaccac ggtgatcttc ggcacggtgg cctcggagta ggcgtacagc atattcgcgc catggcgaat gatgccgccg tactcctgct gcacgccggg caggaagccc ggcacgtcga ccagctgcac cagcgggatg ttgaacgaat cgcagaaatt cacgaattcg cgcggccttgt cagaggcgtt gatgtcgagg caacccgaca tcaccgacgg ctgattggcc acgatgccca ccgaacgacc attgacccgg gcgaaggcgg tcacgaggtt ggtggcatag ccggccttga cctcgaggta gtcacccag tcgacgatct tggcaatgac atcgcgcacg tcatagccct tcttgccgtc aatcggaacg atgtcgcgca gctcggtatt ggggctgacg tcattgttcg ggttgacgaa ggatgcttcc tcagtgttgt tctgcggaag gaagctcagc agcttcttgg caatgagctc cgcggcgtcg tgtcctcgg ccacgaagtg gatattgccc gagatggcca tatgggcctc agcgccaccg agttcgtcag cggtgacatc ctcgccggtg accgacttga tgacctgggg gcccgtgatg aacatatggg ccttcttggt catgatgatg aagtcagtca gtgccggcga atacgaggcg ccaccggcac aggggccggc aatgatggcg atctgcggca cgacgcccga cagcttcacg ttggcgaaga acatcttgcc gtaaccgctc agcgagtcga tgccctcctg gatccggcg ccgcccgaat cgtagaagaa caggaagggc gtgccggtga gcagcgcctg ttccatcgtc tcgacgacct tcgtggactg cgtctcgcca gccgaaccac ccatgaccgt gaagtcctgg gacgcggcgt gcacgggacg accaaggatg gtgccacggc cggtgaccac gccatctgcc gggacgacgg ccttgtccat gccgaacaac gtggtgcggt gcttgcggaa agcgccgacc tcgtcgaacg aatggggatc gagcaggttg ttcaggcgct cacgagcggt ctgcttaccc tgggaatgtt gcttctcgac gcgacgttcg ccgccaccgg cttcgatcac ctggcgctgc tctgcgagct gctccacgcg accttccatg gtgctggcga gcttcaaatt gttgttttca gccat Sense Strand:

(SEQ ID NO: 13)
atggctgaaaacaacaatttgaagctcgccagcaccatggaaggtcgcgtggagcagctcgcagagcagcgccaggtgatcgaagc cggtggcggcgaacgtcgcgtcgagaagcaacattcccagggtaagcagaccgctcgtgagcgcctgaacaacctgctcgatcccc attcgttcgacgaggtcggcgattccgcaagcaccgcaccacgttgttcggcatggacaaggccgtcgtcccggcagatggcgtgg tcaccggccgtggcaccatccttggtcgtcccgtgcacgccgcgtcccaggacttcacggtcatgggtggttcggctggcgagacg cagtccacgaaggtcgtcgagacgatggaacaggcgctgctcaccggcacgcccttcctgttatctacgattcgggcggcgcccgg atccaggagggcatcgactcgctgagcggttacggcaagatgttcttcgccaacgtgaagctgtcgggcgtcgtgccgcagatcgc catcattgccggcccctgtgccggtggcgcctcgtattcgccggcactgactgacttcatcatcatgaccaagaaggcccatatgt tcatcacgggccccaggtcatcaagtcggtcaccggcgaggatgtcaccgctgacgaactcggtggcgctgaggcccatatggcc atctcgggcaatatccacttcgtggccgaggacgacgacgccgcggagctcattgccaagaagctgctgagcttccttccgcagaa caacactgaggaagcatccttcgtcaacccgaacaatgacgtcagccccaataccgagctgcgcgacatcgttccgattgacggca agaagggctatgacgtgcgcgatgtcattgccaagatcgtcgactggggtgactacctcgaggtcaaggccggctatgccaccaac ctcgtgaccgccttcgcccgggtcaatggtcgttcggtgggcatcgtggccaatcagccgtcggtgatgtcgggttgcctcgacat -continued caacgcctctgacaaggccgccgaattcgtgaatttctgcgattcgttcaacatcccgctggtgcagctggtcgacgtgccgggct tcctgcccggcgtgcagcaggagtacggcggcatcattcgccatggcgcgaagatgctgtacgcctactccgaggccaccgtgccg aagatcaccgtggtgctccgcaaggcctacggcggctcctacctggccatgtgcaaccgtgaccttggtgccgacgccgtgtacgc aggcccagcgccgagattgcggtgatgggcgccgagggtgcggcaaatgtgatcttccgcaaggagatcaaggctgccgacgatcc cgacgccatgcgcgccgagaagatcgaggagtaccagaacgcgttcaacacgccgtacgtggccgccgcccgcggtcaggtcgacg acgtgattgacccggctgatacccgtcgaaagattgatccgccctggagatgtacgccaccaagcgtcagacccgcccggcgaaga agcatggaaacttcccctgc >PFREUD_18860 (12S subunit amino acid sequence)
(SEQ ID NO: 14)
MAENNNLKLASTMEGRVEQLAEQRQVIEAGGGERRVEKQHSQGKQTARERLNNLLDPHSFDEVGAFRKHRTTLFGMDKAVVPADGV VTGRGTILGRPVHAASQDFTVMGGSAGETQSTKVVETMEQALLTGTPFLFFYDSGGARIQEGIDSLSGYGKMFFANVKLSGVVPQI AIIAGPCAGGASYSPALTDFIIMTKKAHMFITGPQVIKSVTGEDVTADELGGAEAHMAISGNIHFVAEDDDAAELIAKKLLSFLPQ NNTEEASFVNPNNDVSPNTELRDIVPIDGKKGYDVRDVIAKIVDWGDYLEVKAGYATNLVTAFARVNGRSVGIVANQPSVMSGCLD INASDKAAEFVNFCDSFNIPLVQLVDVPGFLPGVQQEYGGIIRHGAKMLYAYSEATVPKITVVLRKAYGGSYLAMCNRDLGADAVY AWPSAEIAVMGAEGAANVIFRKEIKAADDPDAMRAEKIEEYQNAFNTPYVAAARGQVDDVIDPADTRRKIASALEMYATKRQTRPA

KKHGNFPC

>P. freudenreichii_(12S_C-term nucleotide sequence)
(SEQ ID NO: 15)
atggctgatgaggaagagaaggacctgatgatcgccacgctcaacaagcgcgtcgcgtcattggagtctgagttgggttcactcca gagcgatacccaggtgtcaccgaggacgtactgacggccatttcggccgccgttgcggcctatctcggcaacgatggatcggctg aggtcgtccatttcgccccgagcccgaactgggtccgcgagggtcgtcgggctctgcagaaccattccattcgt >P. freudenreichii_(12S_C-term amino acid sequence)
(SEQ ID NO: 16)
MADEEEKDLMIATLNKRVASLESELGSLQSDTQGVTEDVLTAISAAVAAYLGNDGSAEVVHFAPSPNWVREGRRALQNHSIR

*Propionibacterium acnes* SK137 Transcarboxylase

P. acnes (12S subunit)
(SEQ ID NO: 17)
atggctgagaagaaaccaatcaagaggccgataccatggccggccgat cgagcagctcgccgacgagcgccacgctgtggagcttggcggggggcgag gatcgcctgcaaaagcagcgtgacaggggcaagcagacagcccgtgaac ggatcgacaacctcgttgatgcttattccttcgatgaggtgggtgcgtt ccgtaagcacgccaccacccttttcggcatggacaaggccgaagttccc gccgacggcgtagtcaccggtcgtgcgaccatccatggtcgcccggtcc acatcgcgtctcaggacttcaccgtcatgggtgggtcggctggcgagac ccagtcgacgaaggtcgtcgagacgatggaacagtccctgctgaccggc actccgtttctgttatctatgactcgggcggcgcccgaattcaagaagg catcgactcgctgtccgggtacggcaagatgttctacgcgaacgtcaag ctgtcgggcgtcgtgccgcagatcgccatcattgctggcccctgcgccg gcggcgcctcctattcccggccagaccgacttcatcatcatgacgaag aaggcccacatgttcattacgggccccggagtcatcaagtcggttaccg gtgaggaggtgactgctgacgacctgggtggtgcggatgcgcacatgtc cacctcgggcaatatccacttcgtggccgaagatgacgacgccgcagtg ctcatcgcgcagaagttgctgagcttcctgccgcaaaacaacactgagg acgcccagatctccaaccccaatgacgatgtctccccgcagcctgagct gcgcgacatcgttccgctggatggtaagaagggctacgacgtccgcgac gtcatctccaagatcgtcgactggggcgactacctagaggtcaaggccg gttgggcgaccaacatcgtcaccgcctttgcccgggtcaatggtcgtac cgtcggcatcgtggccaaccagccgaaggtgatgtcgggttgccttgac atcaatgcttcggacaaggctgccgagttcattaccttctgcgactcgt tcaatattccgttggtgcagttggttgacgttcctggatcctgcctggt gtccagcaggagtacggcggcatcatccgccacggcgcgaagatgctgt atgcctactccgaggccaccgtcccgaagatcaccgtggtgctgcgtaa ggcttacggcggctcctaccttgccatgtgcaaccgtgacctgggtgct gacgccgtctatgcctggccgagcgcggagattgcggtgatgggtgccg atggcgctgccaacgtcattttccgtcgccagatcaaggactctgagga tcccgcagccaccgtgccgcgaagatcgaggagtaccgcaacgccttc aacacgccttacgtggctgccgcccgtggacaggttgacgacgtgatcg atcccgcggacacccgtcgcaagatcaccgccgctctggagacctacgc cactaagcgtcagtcccgtccggccaagaagcacggcgtcatgccttgc tga

P. acnes (5S subunit)

(SEQ ID NO: 18)

atgagtccacgaaagattggcgttaccgagacgtgctccgcgacgcgca
tcagagcctgcttgccactcgcatggccatggaggacatggttgatgcc
tgtgccgacattgatgcggcaggcttctggtccgttaatgctggggcg
gagctaccttcgattcttgcatccgattcctcaacgaagacccatggga
gcgtctgcgtacttccgcaagctgctgccgaactcccggttgcagatg
ctgctgcgtggccaaaaccttctgggctaccgccactacaacgacgagg
tcgtcgacaagtttgtcgagaagtcggccgagaacggcatggacgtgtt
ccgggtgttcgacgctctgaacgatcctcgcaaccttgagcacgcgatg
gcagccgtcangaagaccggcaagcacgcccagggcaccatctgctaca
ccacttccccgattcacaccccagagagcttcgtcaagcaggccgatcg
tctcatcgacatgggtgccgactcgatcgccttcaaggacatggctgct
ttgctcaagccgcagcctgcctacgacatcatcaagggcattaaggaga
accatccggacgtgcagatcaacctgcactgccactccaccacgggcgt
caccctggtcaccctgcagaaggccatcgaggctggtgtcgacgtcgtc
gacaccgctatctcgtcgatgtcgctcggccggggcacaacccaaccg
agtctttggtcgagatgctcgagggcaccgagtacaccaccggcctcga
catggatcgcctgctcaagatccgcgaccacttcaagaaggtgcgtccg
aagtacaagaagttcgagtcgaagacgctggtcaacaccaacatcttcc
agtcccagatcccgggcggaatgactccaacatggagtcccagctcgag
gcccagggtgctggagaccgcatggatgaggtcatgaaggaggtgccgc
gcgttcgtaaggatgccggctacccgccgctggtcacccgtcctccca
gatcgtgggaacccaggcggtgttcaacgtcctgatgggcaatggttcg
tacaagaacctcactgccgagtagccgacctcatgcttggctactacgg
caagcccattggcgagctcaatcccgagatcgttgagatggccaagaag
cagaccggcaaggagccgatcgactgccgtcccgccgacctgctcgagc
ctgagtgggaccagaggtcgagcaggccaagagtcttgagggcttcgac
ggctccgacgaggacgttcttaccaacgccctgttcccgggagttgccc
cgaagttcctcaaggaacgcgcacagggcccgaagagcgtcgcgatgac
cgaggcacagagaaggccgagaaggaaggcaccggcgctgccggcatcg
ccggaccggtcaactacaacgtgacggtcggtggcaacagccaccaggt
gaccgtcgagcctgcgtga

P. acnes (1.3S subunit)

(SEQ ID NO: 19)

atgaagctcaaggtgaccgtcaatgacgtcgcatacgacgttgacgttg
acgttgataagaccgccaatgcgccgatggcgccgatcctctttggtgg
cggcgccggcggcccgatgaaggcatccggtggcggcgccggtaaggcc
ggtgagggcgaggttcccgcaccgctagagggactgttgccaagatcct
ggtggccgaaggagatgccgtcaaggccggtcaggtgctcctgaccctc
gaggccatgaagatggagaccgagatcaatgccccggcggacggaaccg
tcaagggggatcctggtggagtcggtgacgccgtccagggtggtcaggc
ctggtggctctgggctga

C. thermocellum Transcarboxylase

>Cthe_0699 (12S subunit nucleotide sequence)

(SEQ ID NO: 20)

atggacaaagtagacaagatcggcatctccgtgaaaaactggcccaggtt
gaacagggcggaggagagaaaaaatcgcaaaacagcatgatgccggaaaa
atgacagcaagagaaagaatccaggattatttgatgaaaacagattgttg
agatcgacacatttgttgagacaagaagcattgacttcgatatgcaaaaa
aagaaagtcccgggagacggtgttgtaacagggtatggttccatagacgg
acgtctggtattgttgcggcgcaggactttactgtaatcggtgggtctag
ggtgaaatgcatgccgcaaaaatcaccaaagtaatggacatggcaatgaa
aatgggcgcaccgtttataagcattaatgattccggcggtgcaagaattg
aagaaggaattgacgcactcaagggatttggagatatcttctacagaaat
actttggcttcaggtgtaattccccagatttcagttatcatgggaccatg
cgcaggcggagcggtatattctcctgcaataaccgacttatatttatgg
ttgacaaaaccagtcagatgtttataacgggaccccaggtaattaagtcc
gtaaccggagaagacgtgacattgaaaaacttggcggtgcggaaacccac
aactccataagcggtgttgctcacttcagaagttcaagtgaaaaagaatg
tatagagcaaatcaaaaagatatagttatcttcctgataacaatattcc
gatgttccgattgttccaactcaggatgacataaacagaattactgacaa
cctggtcgatatcattccgcaggactccaacaagcatatgacatgatgga
ataatcacttccgtagttgacaacggtgactttttgaaattcaaaaag
actttgcaaaaaacattataatggtttcggcagaatgaacggcggaacc
gtcggtatagtggcaaatcagccaaaagttgccgcaggggttttggatgt
gaactcactgacaaagccgcaaggtttgttcgtttctgtgatgcgttcaa
cattccaattataacctttaccgatgtaccggggtatctgcccggagtag
gccaggagcacagcggagtaataagacacggtgcaaagatcatatgatta
ctgaagccaccgttccaaaaatcaatgttattgtcagaaaagcttacggc
ggtgcatatattgccatgaacagcaagcaccttggagcggacatggtatt
tgcgtggcatcggcggaaattgcagttatgggaccggaaggtgcggcaaa
catcatttcaagaaagatatagctgctgccgatgacccaatggaaacaa
gaaagaggctcattgaagaatatcgtgaaaaattctccaatccgtatgtt
gcagcttcaaggggttatgttgatgatgtaattgatccggcaacaacaag
gataagactgattagtgcccttgaaatgcttgcaagtaagagagaaaaca
gacctgccaaaaagcatggaaatattccattataa >C. thermocellum_(12S subunit amino acid sequence)

(SEQ ID NO: 21)

MDKVDKIGLLREKLAQVEQGGGAEKIAKQHDAGKMTARERIQALFDENSF
VEIDTFVETRSIDFDMQKKKVPGDGVVTGYGSIDGRLVFVAAQDFTVIGG
SLGEMHAAKITKVMDMAMKMGAPFISINDSGGARIEEGIDALKGFGDIFY
RNTLASGVIPQISVIMGPCAGGAVYSPAITDFIFMVDKTSQMFITGPQVI
KSVTGEDVTEEKLGGAETHNSISGVAHFRSSSEKECIEQIKKLISYLPDN
NLSDVPIVPTQDDINRITDNLVDIIPQDSNKPYDMMEHTSVVDNGDFFEI

QKDFAKNIIIGFGRMNGGTVGIVANQPKVAAGVLDVNSSDKAARFVRFCD

AFNIPIITFTDVPGYLPGVGQEHSGVIRHGAKLLYAFSEATVPKINVIVR

KAYGGAYIAMNSKHLGADMVFAWPSAEIAVMGPEGAANIIFKKDIAAADD

PMETRKRLIEEYREKFSNPYVAASRGYVDDVIDPATTRIRLISALEMLAS

KRENRPAKKHGNIPL

>Cthe_0700 (1.3S subunit nucleotide sequence)
(SEQ ID NO: 22)
atgaaaaagttttttgataaaggtaaacggaaatcaatatgaggttgaagt tgaagaaatcagagacggtgcttcagcaccacaggttactctcagcacac cttcggctgcacctgcgccttcaccggcaccggctcaggaaacgaaaaca gctgcaccaaagaaagacagcacagtaccggcaggtgctacggcaattaa agctccgatgccgggtaccatactcgacattcgtgtaaatcaaggggata cggtaaagaaaggccaagttatttaattcttgaagcaatgaagatggaaa atgaaatagttgctccaaatgacggtacagttgcatcaattaatgtttca aagggtgcatctgtaaacgtcggagaggttcttgtctcattaaaatag >C. thermocellum_(1.3S subunit amino acid 
sequence)
(SEQ ID NO: 23)
MKKFLIKVNGNQYEVEVEEIRDGASAPQVTLSTPSAAPAPSPAPAQETKT

AAPKKDSTVPAGATAIKAPMPGTILDIRVNQGDTVKKGQVLLILEAMKME

NEIVAPNDGTVASINVSKGASVNVGEVLVSLK

>Cthe_0701 (5S subunit nucleotide sequence)
(SEQ ID NO: 24)
atggctaaggtaaaaattaccgaaacggcgctgagggatgcccatcaatc tacattgcaacaagaatgagaatagaagagatgcttcctatcatagataa actggacgagatcggttatcattctaggaggtatggggcggtgcaacatt gatgcctgcctgagattttgaatgaagacccgtgggaaggcttagaat tataaaaagccactgcaagaaaactcccctttcaaatgctataagaggca gaatctttgggttacaagcattatgccgatgacgttgtgagtactttgt acaaaagagcgttgcaaacggtataaacataatgaagaattttcgacgcct tgaatgacaccagaaatatagaaactgcaatcaaagcctgcaaaaagaa ggcggtcatgctcagggaacggtatgttatacaataagtcccgttcacaa tcttgaacttttttgtcaaagatgcaaagactcttgtggaaatgggagaga ctccatatgcgtaaaggatatggcaggacttctgatccatatgttgcata tgaccttatcaaagcattaaaagaaacgtaaaagtgccgattcaacttc atcccactatacgagcggtgttgcttcaatgacatatctgaaggcaatt gaggcagggtgcgatgttgtggactgcgctatctcaccaatgtcaatggg aacatcccagcctccgacagaacctcttgtggcaaccttaaaaggcacgc cgtacgataccggacttgacctggataaattaagtgaaatcgcagactac ttcagacctctcaaagaaagtatatttcagaaggacttcttgatgtaaa ggttatgggagttgacgtaaacactctcaaataccaggtacccggtgaa tgctttcaaacctggtgtctcagttaaagcagtccaatgcggttgataaa ttcgaagaggttctgaaagaagtgccaagagtaagagaagacttcggata tcctccgttggttacacctacaagccagattgtaggtactcaggcagttt taaatgtggtaacgggtgaaagatacaaaatggttccaaaagaatccaag gcactgatcaagggtgaatacggcagaacaccggctccggtcaaccctga agttcagaagaagattttaaaagatgaagagccgattacagttagacctg ctgatttgatagagcccgagcttgacaagatcagaaatgaaatgaaagaa tacctggaacaagacgaggacgttttgtcctatgcactgttcccgcaggt ggcagagaagttcttccaatacaggaaagctcaaaaatataagatagaac cggacatggtcgattacgaaaacagggttcatccggtttaa >C.thermocellum_(5S subunit amino acid sequence)
(SEQ ID NO: 25)
MAKVKITETALRDAHQSLIATRMRIEEMLPIIDKLDEIGYHSLEVWGGAT

FDACLRFLNEDPWERLRIIKSHCKKTPLQMLLRGQNLLGYKHYADDVVEY

FVQKSVANGINIIRIFDALNDTRNIETAIKACKKEGGHAQGTVCYTISPV

HNLELFVKDAKTLVEMGADSICVKDMAGLLLPYVAYDLIKALKENVKVPI

QLHTHYTSGVASMTYLKAIEAGCDVVDCAISPMSMGTSQPPTEPLVATLK

GTPYDTGLDLDKLSEIADYFRPLKEKYISEGLLDVKVMGVDVNTLKYQVP

GGMLSNLVSQLKQSNAVDKFEEVLKEVPRVREDFGYPPLVTPTSQIVGTQ

AVINVVTGERYKMVPKESKALIKGEYGRTPAPVNPEVQKKILKDEEPITV

RPADLIEPELDKIRNEMKEYLEQDEDVLSYALFPQVAEKFFQYRKAQKYK

IEPDMVDYENRVHPV

>C.thermocellum_(12S C-term nucleotide sequence)
(SEQ ID NO: 26)
atgaaagagcaaataaatgaagaaattattctggcaatatcagcggccat tgctgattggaaacaagacccggatacaagcttgtagtaagatcatttaa aagaatacccccaaacttctcctgtatggtccgctacaggaaaaatcgaga gaatcagaagaagtatg >C.thermocellum_12S_C-term amino acid seqence
(SEQ ID NO: 27)
MKEQINEEIILAISAAIAALETRPGYKLVVRSFKRIPQTSPVWSATGKIE

RIRRSM

*T. saccharolyticum* Transcarboxylase

>or0945 (12S subunit nucleotide sequence)
(SEQ ID NO: 28)
atgtcaatagatgataggattgaagacctttatagaagaagagagatggt tttagaaggcggtggtttagataaagtagagaaacaacaccaaaaggga aagcttaccgcaagagagaggatatacaagcttttagatgaagatagct ttgtggaaatagatgcgtatgttgagcacaggtgtattgactttggcat ggaaaagcaaaggatacctggcgaaggcgtagtgacagggtatgggacg atagatggaaggcttgtctacgtttatgcacaggattttacggttttag gaggatcattaggcgagtatcatgcaaagaaaatcacaaaaatcatgga tatggctttaaagatgggagcaccgctcattggattaaatgattccgga ggtgccagaatacaggaaggcgtcgatgctttatcgggatatggcaaca tattttcagaaacacgctggcatcaggcgtaataccgcaaatatcggt gataatggggcccagcgctggaggtgcagtttattcgcctgctatactg actttatattcatggtagacaagacaagtcagatgtttataactggacc

```
gcaggtcataaaagccgtcacaggtgaagatgtttcggcagaggagatg gtggatcgattactcacagcacgaaaagcggtgtggcgcattttagggc tgaaaacgacgaagagtgtttgaagatggtgaggaagctattaagttac cttccatcaaacaatttggaagatccgccacagttggcgacagatgacg acataaacagattttccgataggcttattgagataatcccagatagtcc taataagccatacgatatgaaagaagtaatttcggaaatagtggatgaa ggcgtgtattttgaatcacaggcaatgtatgcgcaaaacataataacgg catttgcaaggcttaatggaaggacggtagggataatagcaaatcagcc taaagttttggctggatgtctcgacatcaatgcgtctgataaggcatcg aggtttataaggattgcgatgcatttaacatcccgcttacaatatagta gatgttccaggattatgcctggaacgaatcaagagtacggtgaataat acgccatggggcaaagatgttgtacgatactctgaggctacagtgccaa aagtgactctcattgtgaggaaagcttatggcggtgataccttgccatg tgcagcaaagacttaggagctgattagttttggcatggcctactgctga aatagcggtcatgggacctgatggggcagcaaacatcgtgttaaaaat gaaataaaatcgtagatgatcagtggctgcaagaaatgaaaagataaat gagtacagggagaatttcgcaaatccatacagggcagcagcgagaggat atgtagatgatgtagttctgccgcaagagacgagacctcgcctcatctc ggcgttcgatatgcttatgagcaaaagggagtcaaggcccagcaaaaag catggcaattttcctgtttaa >T. saccharolyticum_(12S subunit amino acid
sequence)
                                         (SEQ ID NO: 29)
MSIDDRIEDLLRRREMVLEGGGLDKVEKQHQKGKLTARERIYKLLDEDSF

VEIDAYVEHRCIDFGMEKQRIPGEGVVTGYGTIDGRLVYVYAQDFTVLGG

SLGEYHAKKITKIMDMALKMGAPLIGLNDSGGARIQEGVDALSGYGNIFF

RNTLASGVIPQISVIMGPSAGGAVYSPALTDFIFMVDKTSQMFITGPQVI

KAVTGEDVSAEELGGSITHSTKSGVAHFRAENDEECLKMVRKLLSYLPSN

NLEDPPQLATDDDINRFSDRLIEIIPDSPNKPYDMKEVISEIVDEGVYFE

SQAMYAQNIITAFARLNGRTVGIIANQPKVLAGCLDINASDKASRFIRFC

DAFNIPLLNIVDVPGFLPGTNQEYGGIIRHGAKMLYAYSEATVPKVTLIV

RKAYGGAYLAMCSKDLGADFVLAWPTAEIAVMGPDGAANIVFKNEIKSSD

DPVAARNEKINEYRENFANPYRAAARGYVDDVVLPQETRPRLISAFDMLM

SKRESRPSKKHGNFPV

>or0947 (1.3S subunit nucleotide sequence)
                                         (SEQ ID NO: 30)
atgaaaaatttatagtaactgtcaatggaaaaaaatacgatgtggaagt agaagaagtaaaagtcgacgtggcaagtgagaaaaaagcaaaagaagata ctgctgctaaaaatgcgtcagatgcaagtgtaaaaagcaaacaggttgaa gtaaaaaacgaagtcaaagacggtttctcaatcaatgcaccgatgccggg aactatattggatgtcaaaataagccaaggccagactgtcagacgaggcg atgtgcttttaatactggaagccatgaagatggaaaatgaaatcacgtca cctacgatggcacaataatatccataaatgtttcaaaaggtgcctctgt aaatacaggcgatgtgcttttgtacttaaaatga >T. saccharolyticum_(1.3S subunit amino acid
sequence)
                                         (SEQ ID NO: 31)
MKKFIVTVNGKKYDVEVEEVKVDVASEKKAKEDTAAKNASDASVKSKQVE

VKNEVKDGFSINAPMPGTILDVKISQGQTVRRGDVLLILEAMKMENEITS

PYDGTIISINVSKGASVNTGDVLLYLK

>or1888 (5S subunit nucleotide sequence)
                                         (SEQ ID NO: 32)
atgtctaagataaaaataacggagactgttttaagagatgcacatcaatc gttgctggcaaccagaatgacaaccgatgaaatgcttcctatagcagaaa aattagatgaagttggttttactcgctggaagcatggggcggtgctacat ttgatgcatgtatgagattttgaatgaagacccatgggaaagattaaga ctataaagaaggcgattaagaagacacctatcaaatgcttttaagaggtc aaaatttactcggatataaacactatcccgatgatgtcgtaaatgaattt ataataaaatctgttgaaaatggtatagatataataagaattttttgatgc gttaaatgatgtgagaaatttagaagtgccaataaaatctgcaaaaagtg caggtgctcatgtacaggcagctattgtatatacagttagtcctgtacat aatacagatcattatttgaaagtggcaaagtctcttcaagatatgggtgc ggattccatatgcattaaggatatgtctggaatatatcaccctatgttg catacgatttgattaaatctctgaaaagagcactttacacgccaattcaa ctgcatagccattatacagcaggactggatcaatgacttatttaaaagcc atagaagctggtgtagacggggttgatacagctatttcttcgcttgcctt aggaacatcacaaccagctacagaatcaatcgtggctgcattgaaagata cagaatatgatacagggctagatttaaaattgatgctgagatagctcagc attttaatgtagtcaaacagaatcacaaaaatgacagcgatatgtattga tatgtctgttgatgttaaagcattagaaagtcaaataccaggggaatgt tatcaaatttggtttcacagctaaagcagcagaatgcattaaacaaatat caagacgtcttgaaagaagttccaagggtacgcgaagatttgggatatcc tcctcttgttactccaatgagccagatggttggaacccaggctgttttaa atgttattacaggggagagatataaaatcgttcctaaagaaattaaagat tatgtcaaaggtttatatgggatgccaccagctccaatttcagattctat acgaaagaaataatcggcgatgaagaagtaatttcaaagaggccagcag atttactaagtcctcaattggatgaatttaaaaatgagataaaggaattt atagagcaagatgaagatgttttatcatatgcattatttcctcaagtagc aagaagattttcgagtataggcaagccaaaaaatacagaattgattcaa cattattaaatatcgaagaaagggttcatccgatataa >T. saccharolyticum_(5S subunit amino acid
sequence)
                                         (SEQ ID NO: 33)
MSKIKITETVLRDAHQSLLATRMTTDEMLPIAEKLDEVGFFSLEAWGGAT

FDACMRFLNEDPWERLRLLKKAIKKTPLQMLLRGQNLLGYKHYPDDVVNE

FIIKSVENGIDIIRIFDALNDVRNLEVPIKSAKSAGAHVQAAIVYTVSPV

HNTDHYLKVAKSLQDMGADSICIKDMSGILSPYVAYDLIKSLKRALYTPI
```

```
QLHSYTAGLASMTYLKAIEAGVDGVDTAISSLALGTSQPATESIVAALK

DTEYDTGLDLKLLAEIAQHFNVVKQNHKNDSDMSLLMSVDVKALESQIPG

GMLSNLVSQLKQQNALNKYQDVLKEVPRVREDLGYPPLVTPMSQMVGTQA

VLNVITGERYKIVPKEIKDWKGLYGMPPAPISDSIRKKIIGDEEVISKRP

ADLLSPQLDEFKNEIKEFIEQDEDVLSYALFPQVARRFFEYRQAKKYRID

STLLNIEERVHPI

>T. saccharolyticum_(12S_C-term nucleotide
sequence)
                                  (SEQ ID NO: 34)
atggaagagataaatgaagaaatagttgctgtcattgaagctgcgattta cgcggcatttggtcagtacgaaaagaatttccgcatcaaggtaataaaga gagtggactcaaatatgccggaatggagaaaagctggcctttacaatcag atgagatag >T. saccharolyticum_(12S_C-term amino acid
sequence)
                                  (SEQ ID NO: 35)
MEEINEEIVAVIEAAIYAAFGQYEKNFRIKVIKRVDSNMPEWRKAGLYNQ

MR
```

*Caldicellulosiruptor bescii* DSM 6725 Transcarboxylase

```
>C. bescii_(12S subunit nucleotide sequence)
                                  (SEQ ID NO: 36)
atgacaaacaagctcagagagctcaagcaaaagagagaaagaatactaa agcttggtggagaagataaaataaaaaaacagcatgatagcaaaaaact tacttgtagagagagaatagaatatttacttgaccctggaagcttcaat gaaatagatatgtttgttgaacacagatgtcaagaatttgatatgaaag atacattttgtccctgtgatggtgttgtaacggggttatggaacaatcaa tggcagaaaagttttttgtttatgacaagattttacttcgataggcggtt ctatggcgagatgcatgcaaaaaagatttgtaaagtatggacttagcat taaaatatggttgtccagtgataggtataaatgattctggtggtgcaag aattcaagaaggtgttgatgcattagcaggatatggtgaaatcttctat agaaataccatggcatcaggtgtaattccacaaattgcagctataatgg gaccttgtgcaggtggagctgtatactctcctgctattatggatatata ttatggtggacaaaaccagccaaatgtttgttacaggacctcaggttat aaaagctgtgactgagaggagatatcctttgaagagcttggtggcgct tacactcacagacaaagagtggagttgctcattttattgcagaggatga gtatcacctacttgatatgataaagtatttattgtcgtttatacettca aataacatggaagacccacctttataatgtcatagattcagaaaaaag atttgttcccgagacgaaaatataattccgcaagagccaaacaaagctt atgatgtaaaagaataatttataaagtagtagacaaccaagaattttt agaagtacaaccttattttgctcaaaatgctgttgtaggatttggtaga ataggggattagcgtaggaattgtagcaaatcagcccaaagtaacgc tggagtgcttgattatgattcgtctgacaagatagcacgattgtaaga ttttgtgatgcttttaatattcccataataacatttacgacgtgcctg gattttttgccaggtgttaaccaagagcacaatggaataattcgtcatgg
```

```
ggctaaggttttgtatgcatactcagaggcaacagttccaaagataaat gtaattttgagaaaagcatatggtggggatacattgcaatgagcagcaa acacattggtgcagactttgtgtttgcatggccaactgccgagatagag ttatgggaccagatggcgcagcaaatattatatttagaaaagagataca aagcgctcaaaatcccgaagaggaaagaaaaagaaggatagaagagtat actcaaaagtttgcaaatccatacattgcagctgcccgtgggtatgttg acgatgtgattgagccacagcttacccgtaacaaaatcattgaggcgct caaaatttccattacaaaaagagagcaaaggccccaaaaaagcatggc aatattccatta >C. bescii_(12S subunit amino acid sequence)
                                  (SEQ ID NO: 37)
MTNKLRELKQKRERILKLGGEDKIKKQHDSKKLTCRERIEYLLDPGSFN

EIDMFVEHRCQEFDMKDTFVPCDGVVTGYGTINGRKVFVYAQDFTSIGG

SLGEMHAKKICKVLDLALKYGCPVIGINDSGGARIQEGVDALAGYGEIF

YRNTMASGVIPQIAAIMGPCAGGAVYSPAIMDFIFMVDKTSQMFVTGPQ

VIKAVTGEEISFEELGGAYTHSSKSGVAHFIAEDEYHLLDMIKYLLSHP

SNNMEDPPFIMSSDSEKRFVPELENIIPQEPNKAYDVKEIIYKVVDNQE

FLEVQPYFAQNAVVGFGRIGGFSVGIVANQPKVNAGVLDYDSSDKIARF

VRFCDAFNIPIITFTDVPGFLPGVNQEHNGIIRHGAKVLYAYSEATVPK

INVILRKAYGGAYIAMSSKHIGADFVFAWPTAEIAVMGPDGAANIIFRK

EIQSAQNPEEERKRRIEEYTQKFANPYIAAARGYVDDVIEPQLTRNKII

EALKISITKREQRPPKKHGNIPL

>C. bescii_(1.3S subunit nucleotide sequence)
                                  (SEQ ID NO: 38)
atgagaaagttcaaggtgaagatcaatagccaagaatttgttgtagaag tggaagaaatagg agttgaaatgctacttctgtcgtgccaaggccta agattggccattttgagccaaaacaggaaaaacatgaggataaaacaaa acaaagccctgtactttatctgataaaaaattcggttgttgcccagatcc gggtactattgtaaggctgctaaaaagtgaaggtgatgtgttgatgca aatgaacctgttttaattcttgaagccatgaaaatggaaatgaataa ctgcacctgtcaaaggaaaaattaaaagaatacatgtaaaggaagggca gaaggtagcaaaggagatttgctatttgaaatagag >C. bescii_(1.3S subunit amino acid sequence)
                                  (SEQ ID NO: 39)
MRKFKVKINSQEFVVEVEEIGVENATSVVPRPKIGHFEPKQEKHEDKTK

QSPVLSSDKNSVVAQLPGTIVRLLKSEGDVVDANEPVLILEAMKMENEI

TAPVKGKIKRIHVKEGQKVAKGDLLFEIE

>C. bescii_(5S subunit nucleotide sequence)
                                  (SEQ ID NO: 40)
atgggggtaaaaataacagaaacaatactcagagatgctcatcagtcac tcattgcaacccgcatgacaactgaaagatgcttgagattgctcctgt gcttgaccaagttggttattattcggttgagtgctggggcggtgctaca tttgatgcgtgtctgaggtttttcaatgaagagccatgggaaagattaa aaagactgagaactgcttttaaaaagacaaagctccagatgcttcttcg
```

-continued aggacaaaatcttgttgggtatagacattattctgatgatgttgttgaa
gagtttgtaaaaaaggccatatactatggcattgatattataagaatat
ttgatgcacttaatgacatccggaatattgaaatggctctaaaaataac
aaaaaaagaaaaaggacatgcccaggttgccatatcatacactgtctca
ccttatcatactattgaaaactatgtaaatttggcaaaacaaatagaag
aacttggggcagactcaatttgtataaaagacatggctgggcttctctc
tccatttgatgcttataaacttgtaaaagcgttaaaagagcaggtaaaa
cttcctattcatcttcatacacactacaccacaggatttggatcaatga
catatttgaaagctgtcgaagcaggtgtggatggtattgacacggcttt
atctccgcttgcactgggcacatcccagcctccaaccgaaacaattgta
tatgcacttgaaaatacagaatatgctccaaaacttgatttagaaaaga
tcaacgaggcaagcgaatattttaaagtactcagagaagaatatataag
aaaagggcttcttgacccgaaagtattaagtgttgatataaacgctctt
cattatcaaatacctggtggaatgctatcaaatcttatttctcagctaa
aagaacaagggcaggaagacaagttagatgaggttttaaaagaggtacc
tgaggttcgaaaagattttggatatccgccacttgtaactcctacgagt
caaattgtgggaacacaagctgttttgaatgttatagcaggtgagagat
acaaacttgtcacaaaagaaacaaaagcatattttaaaggtgagtatgg
gaaacctccagctcctgtgaatgaagaggtaaaaagaaaaatcttgaaa
gacgaaaagagataacctgcagacctgcagatttgattttgccagagc
ttgaaaatgcaaaagaaaagattaaggagtatattgaaaatgatactga
tgtggtaacttactgtttattccctcaacttgcagaaaattttttcaaa
ttaaggttcgcaaaaaatacaaggttgacgctgatcttgttcagggta
acaaagtgtatcctgtg >C. bescii_(5S subunit amino acid sequence)
(SEQ ID NO: 41)
MGVKITETILRDAHQSLIATRMTTEQMLEIAPVLDQVGYYSVECWGGAT

FDACLRFFNEDPWERLKRLRTAFKKTKLQMLLRGQNLVGYRHYSDDVVE

EFVKKAIYYGIDIIRIFDALNDIRNIEMALKITKKEKGHAQVATSYTVS

PYHTIENYVNLAKQIEELGADSICIKDMAGLLSPFDAYKLVKALKEQVK

LPIHLHTHYTTGFGSMTYLKAVEAGVDGIDTALSPLALGTSQPPTETIV

YALENTEYAPKLDLEKINEASEYFKVLREEYIRKGLLDPKVLSVDINAL

HYQIPGGMLSNLISQLKEQGQEDKLDEVLKEVPEVRKDFGYPPLVTPTS

QIVGTQAVLNVIAGERYKLVTKETKAYFKGEYGKPPAPVNEEVKRKILK

DEKEITCRPADLILPELENAKEKIKEYIENDTDVVTYCLFPQLAENFFK

LRFAKKYKVDADLVQGNKVYPV

>C. bescii_(12S_C-term nucleotide sequence)
(SEQ ID NO: 42)
atgtatgctcaggtcagtactattcaaccattacaaagaagaacttg
cttgtatttgtgcatgtctgcacattgtgatgggtgaaggtcaatataa
aattaccaacataactaaacagcaaaacaagtgggtcaaaggtgcaaga
gaaatgatgctcaatcagtcacagatgttttatagatggagg >C. bescii_(12S_C-term amino acid sequence)
(SEQ ID NO: 43)
MYAQVSTISTITKEELACICACLHIVMGEGQYKITNITKQQNKWVKGAR

EMMLNQSQMFYRWR

*Clostridium cellulolyticum* H10 ATCC 35319 Transcarboxylase

>C. cellulolyticum_(12S subunit nucleotide sequence)
(SEQ ID NO: 44)
atgtcacaaattgaaaagatacaaaatttaaaaaaacatgaaaaaaactat
agctaaaggcggcggagaagagaaaatagcaaaaagacacgcagatggaa
agattctgccagagaaagaatccatttgttgtttgatgaaaacagttttg
ttgaggtagatgcattcatagaatccagatgattgactttggtatgcaga
agaagaaacttccaggtgacggggttgttaccggttacggaacagttaat
ggcagaaaggtctttgtttcatcacaggactttactgttataggcggttc
attgggagagatgcacgcaaagaaaattacaaaggttatggatatggctc
tgaaaatgggagcaccgttcatagccattaatgattccggcggagctcgt
attgaggaaggtctggatgctctttcaggttacggagatattttttacag
gaatactcttgcatcaggcgttattccgcagatatcagtaataatgggc
catgtgcaggtggtgcggtatattccccggccataactgattttatattc
atggtggaaaaaacaagtcagatgtttattacaggcccacaggtaataaa
gtctgttacgggtgaagatgtatcagttgaaaatctgggaggtgcagatg
ttcatactgctacaagcggtgtagcacatttcaaatcttcaagcgaagaa
gagtgtatagaagataaagaggatttaagttttattcccgataataat
gtatcagatactatgtactacggagtgtctgatgctgccgacagattagc
cgaaagcctcaacagcattattccagaagagtcaaacaagccatatgaca
tgtttgacgtaatagcagaagtagtagatgatggagatttangaagttca
gagttatttactcagaatataataatcggatttgcaagaatgaatggcag
aagtgttggtattgttgcaaaccagcctaagataatggcagggtcactag
atatgaacgcggctgataaggcggcacgtttcgttcgtttctgtgatgca
tttaatattcctgtcgtttcattaaccgatgtacctgcattcctgcccgg
ggtagcccaggagcataacggcataatacgtcacggtgcaaaactcctat
atgattctctgaagcaacagtaccaaagataaatgttattatagaaaggc
atatggaggagcatatattgctatgaacagtaaaacaataggtgccgata
tggttttggcatggccatcagctgaaattgcagttatgggacctgacgga
gcagcaaatattatatttaaaaaggatattgctgcgtcggaagatccagc
agaaaccagaaaggaaaagattgcggaatatagagataaattctcaaatc
cttatgtagcagcatcaagagggtatattgatgatgttatcgagccttct
gaaaccagagtaaaaattataactgctctggaaatgctggatacaaagag
ggaaaacaggccttcaaaaaaacatgaaacattccgcta >C. cellulolyticum_(12S subunit amino acid sequence)
(SEQ ID NO: 45)
MSQIEKTQNLKNMKKTIAKGGGEEKIAKRHADGKLSARERIHLLFDENSF

VEVDAFIESRCFDFGMQKKKLPGDGVVTGYGTVNGRKVFVSSQDFTVIGG

-continued

SLGEMHAKKITKVMDMALKMGAPFIAINDSGGARIEEGLDALSGYGDIFY

RNTLASGVIPQISVIMGPCAGGAVYSPAITDFIFMVEKTSQMFITGPQVI

KSVTGEDVSVENLGGADVHTATSGVAHFKSSSEEECIEDIKRLLSFIPDN

NVSDTMYYGVSDAADRLAESLNSIIPEESNKPYDMFDVIAEVVDDGDFFE
VQSYFSQNIIGFARMNGRSVGIVANQPKIMAGSLDMNAADKAARFVRFC
DAFNIPVVSLTDVPAFLPGVAQEHNGIIRHGAKLLYAFSEATVPKINVIL

RKAYGGAYIAMNSKTIGADMVLAWPSAEIAVMGPDGAANIIFKKDIAASE

DPAETRKEKIAEYRDKFSNPYVAASRGYIDDVIEPSETRVKIITALEMLD

TKRENRPSKKHGNIPL

>*C. cellulolyticum*_(1.3S subunit nucleotide sequence)
(SEQ ID NO: 46)

atgagtaaatatataataaaggtaaacggaactccttatgaagtagaggt
tgaagaagtgggcgggggaaggcccatttcagctgctccaaagctaagag
ctaccaagccgggacatacctctgctgcaaaagcagcacagccgcaggca
ggtaaagcaggtgatgttgctgctccaatgccgggaactgttttaaaggt
aaaggttgctatcggtgatgaagtaaagaaggggcaggtacttttaatac
ttgaagctatgaaaatggagaatgaaatagttgctccggctgacggtaaa
gttacggcgttaaacgtcgaggccggaaagtctgttactgctggagaact
aatggtgtctatagcc >*C. cellulolyticum*_(1.3S subunit amino acid sequence)
(SEQ ID NO: 47)
MSKYIIKVNGTPYEVEVEEVGGGRPISAAPKLRATKPGHTSAAKAAQPQA

GKAGDVAAPMPGTVLKVKVAIGDEVKKGQVLLILEAMKMENEIVAPADGK

VTALNVEAGKSVTAGELMVSIA

>*C. cellulolyticum*_(5S subunit nucleotide sequence)
(SEQ ID NO: 48)

atgccaggcgtaagaattacggaaacagttttaagagatgctcaccagtc
ccttatagcaaccagaatgaagaccgaagaaatgcttccaattgttgaga
agcttgacaatattggttaccattcactggaagcttggggcggagctact
tttgactcatgtatgagatttttgaatgaagatccatggatgagacttag
aaaaataaaagatgttgcaaagaaaacacctctgcaaatgatataggggc
cagaaccttttaggatacaaacactatgccgatgatatagttgagtactt
tgttcagaaggctgttgcaaacggcatggacattatgagaatattcgatg
cactaaatgatgccaggaatatcgagacggcaattaaggcatgtaaaaag
gaaggcggccatgctcagggctgtatttgctatactataagtcctgttca
caatcttgagctttttgtaaaagatgcaaagcagttggagagcatgggag
cagattctatctgtataaaagacatggccggacttctggtgccgtatcag
gcttatgaactggtaaaggattgaaagaaagtgtaaagataccgatacaa
ttgcacactcactatactagcggtgtagcatctatgacgtatttgaaggc
tatagaagcaggtatagatattgttgactgtgcaatttcacctatgtcaa
tgggaacgtcacagccgcctacagagcctttggtggcaactttaaaggga
actgatttcgatactggactggatttggaaaaactcagtgaaattgcaga -continued ctatttcagaccccttaaagaaaaatatattgagagcggactattagacg
ttaaggtaatgggtgttgacgttaacactcttatttatcaggtacctggt
ggaatgctttcaaatcttgtttcacaattgaagcagtcaaatgctttgga
taaatatgaagaggttctcaaggaagttcccagagtaagagccgatttcg
gctatcctccgcttgtaacaccatcaagtcagatagttggtacccaagcg
gtacttaatgtattgactggtgagagatacaagatggtaccaaaggaatc
aaaaggcgttgtaaaggggggaatacggtaaaacccctgcacctattagtg
atgaaataaaagctaagattctgggcgatgaaaagcctataacatgcaga
cctgctgaccttattgaacctgagcttgaaaagattagagaagctgttaa
ggattatatagagcaggatgaagatgtactttcatacgcaatgcttcctc
aggttgccgagaagttattaaacagcgtattgaggatagaaataaggcta
ctgcacccgcatcagacgaaataaaacccgaagttgtagcggcaatatca
gccgtagtaaacgaaatgggcgaaagagacggcacacagtacagaatcgg
aaatatctctaagttgaaccagaatcagaacagatggagtctgtatggta
tgcttgatagattcagaacaaaaatt >*C. cellulolyticum*_(5S subunit amino acid sequence)
(SEQ ID NO: 49)
MPGVRITETVLRDAHQSLIATRMKTEEMLPIVEKLDNIGYHSLEAWGGAT

FDSCMRFLNEDPWMRLRKIKDVAKKTPLQMLLRGQNLLGYKHYADDIVEY

FVQKAVANGMDIMRIFDALNDARNIETAIKACKKEGGHAQGCICYTISPV

HNLELFVKDAKQLESMGADSICIKDMAGLLVPYQAYELVKALKESVKIPI

QLHTHYTSGVASMTYLKAIEAGIDIVDCAISPMSMGTSQPPTEPLVATLK

GTDFDTGLDLEKLSEIADYFRPLKEKYIESGLLDVKVMGVDVNTLIYQVP

GGMLSNLVSQLKQSNALDKYEEVLKEVPRVRADFGYPPLVTPSSQIVGTQ

AVLNVLTGERYKMVPKESKGVVKGEYGKTPAPISDEIKAKILGDEKPITC

RPADLIEPELEKIREAVKDYIEQDEDVLSYAMLPQVAEKFFKQRIEDRNK

ATAPASDEIKPEVVAAISAVVNEMGERDGTQYRIGNISKLNQNQNRWSLY

GMLDRFRTKI

*Corynebacterium kroppenstedtii* DSM 44385Transcarboxylase

>*C. kroppenstedtii*_(12S subunit nucleotide sequence)
(SEQ ID NO: 50)

atgagtgagcaacctcacgatcccagcatgcctgagcgcctcggacagct
ggaagaagaaagaaaccgcatccgactcggcggcgggcaggcacgcctgg
acaagcagcacgaccgcggcaagatgaccgcccgcgagcgcatcaccaag
cttgtcgacgaagacacgttccaggaaaccggaatgttcgccaagcaccg
gacaacgcacttcggcatggacaaggccgacgcccccgccgacggcgtcg
tcaccggatccggcgcggtctacggacggccagtgcacatcgcgtcccag
gacttcagcgtcatgggcggatctgctggcgaaatgcagtccaacaaagt
ggtcgccatgatgaaggcgtccgcgaccaccggcacccccttcgtattat
caacgactccggcggagctcgtgtccaagagggcatcgactccactccgg -continued

```
atacggccgcgtgttctacaacaacgtgctgctaccggactcgtaccgca
ggtaccatcatcgccggcccgtgcgctggtggtgcggcctactcgcggc
actgacggacttcatcatccagacccgcaaggccaacatgttcatcaccg
gccccaaggtcatcgagtccgtgaccggcgaaaaagtcacggccgacgaa
ctcggtggtgccgatgcccacatgagcacagaggcaacattcacttcgtc
gccgacgatgacgagcaagccatcctgatcgcgcagaagctcctgagctt
cctgccgcaaaacaacaccgaagagccgcccatcgtcgatccggacgagg
ttgtcgagcccgacgattccaccgcgacatcgtcccgtcgatggccgca
agggctacgacgtccgcgatatcatccgcaagatcgtcgactacggcgac
ttcctcgaggtccaggccggatacgcccaaaacctcgtggtcggatttgc
ccgcgtcgttggccggacagtcggtatcgtcgctaaccagtcgcaagtga
tgtccgcgttctggacatcaactcgtcggacaaaggcgcaagcttcgtt
cgcttctgcgactccttcaatattccgctcctcaccctcgtcgacgtccc
cggcttcatgccaggtgtcgcacaagagcatggcggaatcattcgccacg
gcgcaagatgctgttcgcctactcggcggccaccgtgccgaagctgacc
gtggtcctccgcaaatcctatggcggatcgtacctggccatgtgctccaa
ggaccttggcgcggaccgcgtctgggcgtggcccaccgctgaaattgcgg
tcatgggtgccgacggagccgtgaacgtcgtcttccgtaaggaaatcaag
aaagcccaggaagagggtggcgacgaagccgctgcagcaaagaagagcga
actcgtccagactacaaagacaccttctcgacgccatacatggcggcgtc
ccgaggcctcgtcgatgacatcatcgaccccgcggacacacgtcgcgaaa
ttgctaggccctggagttgctgaccaacaagcgtgagaaccggccgtcca
agaagcacggcctggcacccaac
```

\>C. kroppenstedtii_(12S subunit amino acid sequence)
(SEQ ID NO: 51)
MSEQPHDPSMPERLGQLEEERNRIRLGGGQARLDKQHDRGKMTARERITK
LVDEDTFQETGMFAKHRTTHFGMDKADAPADGVVTGSGAVYGRPVHIASQ
DFSVMGGSAGEMQSNKVVAMMKASATTGTPFVFINDSGGARVQEGIDSLS
GYGRVFYNNVLLSGLVPQVSIIAGPCAGGAAYSPALTDFIIQTRKANMFI
TGPKVIESVTGEKVTADELG -continued >C. kroppenstedtii_(5S subunit amino acid sequence)

(SEQ ID NO: 55)
MTTRKIGVTELALRDAHQSLMATRMALEDMVDACEDIDKAGYWSVECWGG
ATFDACIRELNEDPWERLRTFRKLMPNSRLQMLLRGQNLLGYRHYEDGVV
DKFVEKSAENGMDVFRVEDALNDPRNLEHAMQAVKKVGKHAQGTICYTVS
PLHDVQGYIDLAGRLLDMGADSIALKDMAALLKPQPAYDIIRGIKDTYGE
DTQINVHCHSTTGVTMVTLMKAIEAGADVVDTAISSMSLGPGHNPTESLV
EMLEGTDYETGLDMDRLINIRDHFKTVRPKYAEFESKTLVNTNIFQSQIP
GGMLSNMESQLKAQGAGDRIDEVMKEVPVVRKAAGYPPLVTPSSQIVGTQ
AVFNVLMGRYKVLTAEFADLLLGYYGEAPGERDKDLIEQAKKQTGKEPIT
ERPADLLEPEWDNLVEEADELDGTDGSDEDVLTNALFPQVAPGFEKTRPD
GPKNVGKTKEQLEREEAKASGDATAIREPIMYKVTTGGRSHTVSVEPA

>C. kroppenstedtii_(12S_C-term subunit nucleotide sequence)

(SEQ ID NO: 56)

atgaatacagacaatgcatcctctgctgaactcagtcagttgttggcccg
cctgtccaaccaggtagaaaagctctcccgcaacgtcaccaagctcgaaa
atgaagttgcggcactgaagcagcgctctgacgaggaaattcctgaagat
gtatgattgcgatcagtgcggccgtatccgcctacatgggtaaccgcgga
accgtgcgcgcagttcacttcttgcgccatcgcagaggtcacagcaaggt
cggcaggcagttcagcacaaggcgaaatggcaa >C. kroppenstedtii_(12S_C-term subunit amino acid sequence)

(SEQ ID NO: 57)

MNTDNASSAELSQLLARLSNQVEKLSRNVTKLENEVAALKQRSDEEIPED
VLIAISAAVSAYMGNRGTVRAVHFLRHRSWSQQGRQAVQHKAKWQ

*Geobacter bemidjiensis* BEM($^T$) Transcarboxylase

>G. bemidjiensis_(12S subunit nucleotide sequence)

(SEQ ID NO: 58)

atgtccatagaagagaagataaaagcgctgaacgacaagaagagcaagct
gaagagggcggcgggcgctcgaagatcgaccagcagcacgcccagggaag
cctgaccgcccgggagcggatagaggcgctggtggacaaggacagcttcc
aggaaatcggcatatcgccaggcaccgctgcaccaatttcggcatggccg
ggaaggaactgccggccgaaggggtggtcaccggcgcagggagcgtgggc
gggaggatggtgcacctggcgagccaggatttcaccgtcgccggggatc
ggcgggcgaggtgcacagcgacaagatcgtgcaggcgatgctggggtcgc
tgaagaccggaaccccatcgtatcatgaacgattccggcggcgccaggat
ccaggaagggatcgactcgttagccggctacggcaaggtcttctaccaca
acgtgatgctcagcggggtggtgccgcagatctcgctcatctgcggcccc
tgtgccgggggcgcggcctacagcccggcgctcaccgatttcatcatcca
gaccgccaaggcgcgcatgttcatcaccggccatccgtgatcaaggaggc
gaccggcgaagagatcagcgccgaggagctgggagggccactgtcgcaga
tgaaccatagcggcgtagcccatttcgtggcggagaacgacctggtggcg
cttcgcatctgcaagaagctcctttcctacctcccctccaacaacatcga
ggacccgccgcagttggaaagcgacgacgtcatcgtcccggacaagacgt
tgaacagcatcgtgccgtcggagcagaagaaggcctacgacgtgaggaac
gtgatcacgcgcctgatcgacggcggcgacttcctggaggtgcagcctct
gttcgctgccaacatcgtggtcgggttcggcaggatactcgggcggagcg
tcggcatcgtcgccaatcagccgtcggtcttggcgggggcgctggacatc
aacgcttcggacaagggagccaggttcgtccggttctgcaacgccttcaa
catcccgctggtgaccaggtggacgttccgggttactccccggggtacag
caggagaagggggggatcatccgccacggcgccaagatgctcttcgccta
cgccgcggccaccgtcccgaagataaccgtcatcatgcgcaaggcgtacg
gcggcgccttcctcgccatgtgcggcaaggagttggagaccgatcgggat
tcgcctggcccagcgccgagatcgcggtcatgggaccgcagggagcggtc
aacgtcatcttccggaacgagatcgcccaggcggaagatcccaagaaaaa
gcgcgacgagctgatcgcttcttaccagggaaccttcgccactccctatg
cggccgcggcacgccgcgatgtggacgacatcatcgagcccgccgatacg
aggcgccacctcgccatgacgctggacatcctgagcaccaagcgcgaatt
caggcccatgaagaagcatggcctcattccgctg >G. bemidjiensis_(12S subunit amino acid sequence)

(SEQ ID NO: 59)

MSIEEKIKALNDKKSKLKLGGGRSKIDQQHAQGSLTARERIEALVDKDSF
QEIGIFARHRCTNFGMAGKELPAEGVVTGAGSVGGRMVHLASQDFTVAGG
SAGEVHSDKIVQAMLGSLKTGTPFVFMNDSGGARIQEGIDSLAGYGKVFY
HNVMLSGVVPQISLICGPCAGGAAYSPALTDFIIQTAKARMFITGPSVIK
EATGEEISAELLGGPLSQMNHSGVAHFVAENDLVALRICKKLLSYLPSNN
IEDPPQLESDDVIVPDKTLNSIVPSEQKKAYDVRNVITRLIDGGDFLEVQ
PLFAANIVVGFGRILGRSVGIVANQPSVLAGALDINASDKGARFVRFCNA
FNIPLVTLVDVPGFLPGVQQEKGGIIRHGAKMLFAYAAATVPKITVIMRK
AYGGAFLAMCGKELETDRVFAWPSAEIAVMGPQGAVNVIFRNETAQAEDP
KKKRDELIASYQGTFATPYAAAARRDVDDIIEPADTRRHLAMTLDILSTK
REFRPMKKHGLIPL

>G. bemidjiensis _(1.3S subunit nucleotide sequence)

(SEQ ID NO: 60)

gtgcaactgaccatgaccattgacggagagaaataccgggtggacgtaga
agtcgaggaaggggaagaggtgcgtacggaaggggccttccctcccaccg
cgactatgcaggcgtacccggtgtattcggcgcatccaaccgcgaccccg
ccgctggccgcgccgaccccggcctccagttcggaaaagatctgccgcag
tcccatcgcgggggtggttttcaagatcgtggcgcaggtgggtcaacacc
tggagatgaacgacctgctggtcgtcctcgaggcgatgaagatggagacc
aacatcaccgcgcacatgtccgggaaggtggaaaagattctggtttccgt
gggcgaagcggtgcagcctggacaggcaattgccgaatttgcc >G. bemidjiensis_(1.3S subunit amin acid sequence)

(SEQ ID NO: 61)

VQLTMTIDGKKYRVDVEVEEGEEVRTEGAFPPTATMQAYPVYSAHPTATP
PLAAPTPASSSEKICRSPIAGVVFKIVAQVGQHLEMNDLLVVLEAMKMET

NITAHMSGKVEKILVSVGEAVQPGQAIAEFA

>G. bemidjiensis_(5S subunit nucleotide sequence)
(SEQ ID NO: 62)
atggaccgcattatcg acataaccgaactggctctgcgcgacgcgcacc agagccttatcgctacgaggctcgggatagacgacatggttccggtgtgc gaggacctggaccaggcgggctactggtccatcgagtgctggggcggggc cacctatgacgcctgcatccgctttctcaacgaagatccgtgggtgaggc ttaggaccttcaaggagctgatgccgaaaaccccgctgcagatgcttttg cgggggcagaaccattgggataccggcattaccaggacgaggtggtggac cggttcgtccagaagagcgccgagaacggcatcgacgtgttccggatctt cgatgcgctgaacgatctgaggaacctggagcggtcggtccaggcggtga agcagtgcggaaagcacgcgcaggtcgccatctcctataccatcagcccc attcacaccacggcgaaattcgtggagcaggcgaagcgcctggtcgacat ggggtgcgactccatctgcatcaaggacatggcggcgctgatcaagccgc acgcgacatacgacctggtgagagggatcaaagaggcctgcggcgaccgg atccggatacagctgcatgcgcacgccaccagcggcgtgaccatggtgag ttacatgaaggcggtggaggcgggcgtggacggcgtggacacggcggtga gttccatgagcctcgggcccggacacaacccgacggagagctttgcggag atgctggaaaatacgggctacaccacgcgcatcgacctcggccgggtgaa caaggtgaaggagcatttcgccaaggtgctccccaggtactcagaattcc tctccaccatcaccggcgcggagacggagatcttcaggagccagattcca ggcgggatgctttccaacatggagagccagttgaagcagcaggggggctgg ggaccggatgcgcgacgtgctggaagagataccgctggtgagaaaggaca cgggatacgtcccgaggtaaccccgaccagccagatcgtcgggacccagg cggtgctgaacgtattgatggggcgctacaaggtgctgaccggcgagttc gccgacctgatgctcggctactacggcctcacgccgggagaacggaaccc ggaggtggtggagcaggcgcgccgccacgcgaataaggagccgatagagt gccgccccgcagatctattggagccggaatggggcaagctgcgggcggcg gcgctcccttggagggttgcgacggcagcgacgaggacgtgctcaccta cgccactttccgcaggtggcgccgaagttcttcgccacgaggagtgaagg accccgaaacctggggcgcgatcccgtcaccggagcttcggaaaccagca ttccccgaagggcacccgggaagatcaccggccccgtcacctacacggtc accttgagcgggcagccgcacaaggtgacggttgcaccctacggccagga at >G. bemidjiensis_(5S subunit amino acid sequence)
(SEQ ID NO: 63)
MDRIIDITELALRDAHQSLIATRLGIDDMVPVCEDLDQAGYWSIECWGGA
TYDACIRFLNEDPWVRLRTFKELMPKTPLQMLLRGQNLLGYRHYQDEVVD
RFVQKSAENGTDVFRIFDALNDLRNLERSVQAVKQCGKHAQVAISYTISP
IHTTAKFVEQAKRLVDMGCDSICIKDMAALIKPHATYDLVRGIKEACGDR
IRIQLHAHATSGVTMVSYMKAVEAGVDGVDTAVSSMSLGPGHNPTESFAE
MLENTGYTTRIDLGRVNKVKEHFAKVLPRYSEFLSTITGAETEIFRSQIP
GGMLSNMESQLKQQGAGDRMRDVLEEIPLVRKDTGYVPLVTPTSQIVGTQ
AVLNVLMGRYKVLTGEFADLMLGYYGLTPGERNPEVVEQARRHANKEPIE
CRPADLLEPEWGKLRAAALPLEGCDGSDEDVLTYALFPQVAPKFFATRSE
GPRNLGRDPVTGASETSIPEGHPGKITGPVTYTVTLSGQPHKVTVAPYGQ
E >G. bemidjiensis_(12S_C-term subunit nucleotide sequence)
(SEQ ID NO: 64)
gtggacgaagagatggagcaggaacacgatccggaaatcacgcccgaact gctgatggtgatgtccgccgcgatagccgcgtatctgggcaagaccgtga ggataaggcgggccaggttcgtcgacccgaatctgatcaacgcctgggga cagtcgagccgcgtggtgctgcaggcgtcgcacaacttgaggaga >G. bemidjiensis_(12S_C-term subunit amino acid sequence)
(SEQ ID NO: 65)
VDEEMEQEHDPEITPELLMVMSAAIAAYLGKTVRIRRARFVDPNLINAWG
QSSRVVLQASHNLRR

*Desulfobulbus propionicus* DSM 2032 Transcarboxylase

>D. propionicus DSM 2032_(12S subunit nucleotide sequence)
(SEQ ID NO: 66)
atgagcacaaaggaaaaattagagcagctaaagcaaaaaagggccaaag ccttgctgggcggcggtcaggataaaatcgacaagatccactcccaggg caaatataccgcccgtgagcgtattcaactcctcctcgacccaggcacc ttcgaggaatacgatgctttcaagctccatcgctgctacaacttcggca tggaaaaaatcaagtttacggcgacggtatcgtcaccggatatggcaag aggccggccggccggtttatatttacgcgcaggacttttcggtcctcgc cggttctattccggaaccttggctgaaaaaatatgcaaaatcatggata gggcatgaaaaacggcattccggtcatcggattgaacgactccggtggc gcccgtatccaggaaggtatcgaggccctggcaggatataccgaaatat cacccgtaatgttacgatcgggtgttgttccccagatttccggtgttttt cggaccagcgccggtggcgccgtttactacctgccctgaccgacttcat catccaggtcaagatccagtcctacatgttcctgacaggtcccaaggtc gttaagactgtgttaaacgaggacgtcaccaccgagcagttgggtggtg cggccatgcataccaccaagtccggcgtcaccgactatgctgccgagaa cgaggacgacgccattcagtacatcaaggatctgatgagctatttgccg cagaacaatctggagaatcctccggatgcccctgcgacgatccgatca cccgccgctccgaactgacaacgacatcattccggacaacccgaatgcc gcctacgacatgaaaaaggtcatcaccgagacggcagacaacggtatct tcttttgaaatcaagaagaatttcgctccgaacatcgtcatcggttttgc ccgttatggtggcaaggctattggcatcgttgccaaccagccgtcctac tacgccggtgttctcgacatcgattcctcgatcaaaggtgcccgcttca tccgcttctgcgactgcttcaacattccgatccttaccttcgtcgacgt ccctggcttcctgcccggcactgcacaggaattcggcggcgttatccgc aacggcgccaagatgctgtatgcctacgccgaatcgacagtgccaaagg -continued taacgattattacccgtaaatcctatggcggcgcctactgcgctatgtc gtccaagcacctgcgaaccgatatcaactactcctggccgaccggtgaa atcgccgttatgggctccaaaggcgcggtcgaagtcctgcacgccaagg gcgctaaagcagcagaagatcccagagcgttcctggccgaaaaagaaaa cgagtacaacgagcagttctccaatccatattgtgcggccgagcgtggc tatatcgacgatgtcattgaaccgccgaaaccaggtaccgtatcatca acgcgtttgagtcgatctctggaaagcgtgacacgatcccgatgaagaa acacggcaatatcccgctg >D. propionicus DSM 2032_(12S subunit amino acid
sequence)
(SEQ ID NO: 67)
MSTKEKLEQLKQKRAKALLGGGQDKIDKIHSQGKYTARERIQLLLDPGT

FEEYDAFKLHRCYNFGMEKIKFFGDGIVTGYGKLAGRPVYIYAQDFSVL

AGSLSGTLAEKICKIMDLGMKNGIPVIGLNDSGGARIQEGIEALAGYTE

IFTRNVLASGVVPQISGVFGPCAGGAVYSPALTDFIIQVKIQSYMFLTG

PKVVKTVLNEDVTTEQLGGAAMHTTKSGVTDYAAENEDDAIQYIKDLMS

YLPQNNLENPPDAPCDDPITRRSELLNDIIPDNPNAAYDMKKVITETAD

NGIFFEIKKNFAPNIVIGFARYGGKAIGIVANQPSYYAGVLDIDSSIKG

ARFIRFCDCFNIPILTFVDVPGFLPGTAQEFGGVIRNGAKMLYAYAEST

VPKVTIITRKSYGGAYCAMSSKHLRTDINYSWPTGEIAVMGSKGAVEVL

HAKGAKAAEDPRAFLAEKENEYNEQFSNPYCAAERGYIDDVIEPAETRY

RIINAFESISGKRDTIPMKKHGNIPL

>D. propionicus DSM 2032_(12S_c-terminal
nucleotide sequence)
(SEQ ID NO: 68)
atggcaaaaatgaacaaaaaaatggctgcggcccttgcagccgttaatg cctacctgatgcaggaagaggaggcggcataccaggcccagttgctggc tgccaaatctgttgcaccagccgggccaagcttatgggcaattgccggc cgtcaggatatcatgaatttccgcaggctgattcaaatgaaagccttc >D. propionicus DSM 2032_(12S_c-terminal amino
acid sequence)
(SEQ ID NO: 69)
MAKMNKKMAAALAAVNAYLMQEEEAAYQAQLLAAKSVAPAGPSLWAIAG

RQDIMNFRRLIQMKAF

>D. propionicus DSM 2032_(5S_1.3S_fusion
nucleotide sequence)
(SEQ ID NO: 70)
atgagcgaccaagtgaaaatgaccgccatgaattatgcaactgaccggc ctgctgcagaaaatccggtcaaagttatggacttgagccttcgtgacgg ccaccagtctctgttcgccacccgcggcgcaccgaggacatgattccg atcgcggaaatgatggacgagatcggcttctgggcagttgagacctggg gtggcgccaccttgacaccatgcaccgcttcctcaacgaggacccgtg ggagcgtctccgcaccctgaaacgttacatcaagaagaccccttctcc atgttgctgcgcgcgcagaacctggttggataccgtaactatgccgatg acttggccaccgcattgttgagcgcgctgccgagaacggtatggatatc ttccggacctttgacgccacaacgattaccgtaacttcgagaccgttgt taaacagatcaagaagagcggcaagcacttccagggttgtatttgctat tcgctgaccgaaccgcgtctgggcggggatgtttatgacctgaagtact atgtcgaccgcgccaaagcgcttgacgacatgggcgctgactccatctg catcaaggacatggccggtctgatcgccccatacgacgcctacgccatc gtcaaggctatcaaggaagtcaccaagacccccgatccacctgcacagcc acttcacctctggtatggcgtccatgagtcatctgaaggccattgaggc tggcgtagatatcgttgacacctgcatgaccccgtacgctttccgtacc gcccatccggccatcgagccgttggtcatggccctgctcggcaccaacc gcgacaccggtttcgacatcaagaaactggccgccatcaacgaggtgct agagaaagaggttatgccgaaatacaagcacctcatggatgactccaag gctcaatcatcgatatcaacgttcttctccatcagacccgggcggcat gctaccaacctggtcaaccagttgcgtgagatggatgctctggacaaga tcgatcaggtctacaaagagctgccgaaagttcggaaagacctcggcca gattccgctggttaccccgaccagccagatcgttggcatccagaccgtg aacaacgtgctgtttgacactcctgatgagcgctacaagatgatcaccg cccaggtcaaagacctgtgctacggtactatggtaaaaccgctgtgccg atcaaccagaactgcagaagaaggctctgaaaggctatccgcgcggtga agagccgatcacctgccgtccggcagaggtgcttgagcccgagttggaa aaggccaagaaagagattggcgatctcgccaaggatatcgatgacttgg tactctacgccatctacccggtcaccgggaagaagttccttgagtggaa gtatggcattaccccggcaccgcccgaagtcaagccgctcaccatgagg atgtcaagaagcgtgatgaactggtggccaaggccaaggctggcaagct catcgagcccaagcccgctgctccggagaagaccgctaacgttcggacc ttcaacgtatcgtcgacggtgagtatttcaacgttgaggtcgacccgac cggtgacttccagccgatggtcgccgctgctccgcggcctgccgcacct gccgctgcaccgaaagctgctgcacctgccgctgctgcacctgagccgc gccgaaggctgctgcacctgccgccgccgaccggctccagccgctgttg agggaggaaccccgctgttggccccatgcccggcatgatcgtcaagaa tctggtcaatgttggtgatgcggtcaaagaggcgacccccatcctcgtta tgaggccatgaagatggagaacaatctcggttaccgtgcgatggtactg tgaaggcgataattttggcagcggtgactcggttgccaaggataccgtc ctggcaatcatcgga >D. propionicus DSM 2032_(5S_1.3S_fusion amino
acid sequence)
(SEQ ID NO: 71)
MSDQVKMTAMNYATDRPAAENPVKVMDLSLRDGHQSLFATRGRTEDMIP

IAEMMDEIGFWAVETWGGATFDTMHRFLNEDPWERLRTLKRYIKKTPFS

MLLRAQNLVGYRNYADDLATAFVERAAENGMDIFRTFDALNDYRNFETV

VKQIKKSGKHFQGCICYSLTEPRLGGDVYDLKYYVDRAKALDDMGADSI

CIKDMAGLIAPYDAYAIVKAIKEVTKTPIHLHSHFTSGMASMSHLKAIE

AGVDIVDTCMTPYAFRTAHPAIEPLVMALLGTNRDTGFDIKKLAAINEV

LEKEVMPKYKHLMDDSKCSIIDINVLLHQTPGGMLSNLVNQLREMDALD

```
KIDQVYKELPKVRKDLGQIPLVTPTSQIVGIQTVNNVLFDTPDERYKMI

TAQVKDLCYGLYGKTAVPINPELQKKALKGYPRGEEPLFCRPAEVLEPE

LEKAKKEIGDLAKDIDDLVLYAIYPVTGKKFLEWKYGITPAPPEVKPLT

LEDVKKRDELVAKAKAGKLIEPKPAAPEKTANVRTENVEVDGEYFNVEV

DPTGDFQPMVAAAPRPAAPAAAPKAAAPAAAAPAAAPKAAAPAAAAPAP

AAVEGGTPLLAPMPGMIVKNLVNVGDAVKAGDPILVLEAMKMENNLGSP

CDGTVKALNFGSGDSVAKDTVLAIIG
```

Engineered Pathways to Produce Hydrocarbons and Other Malonyl-CoA Derived Products Production of a bio-product at high yield requires a balanced chemical equation describing the conversion of substrate to product and a thermodynamically feasible reaction with a negative change in Gibbs free energy. Long chain hydrocarbons, e.g., those that have carbon backbones of at least four carbons and up, derived from fatty acids satisfy both of these requirements. For example, production of a $C_{16}$ fatty alcohol can be described by the following equation:

$$4C_6H_{12}O_6 \rightarrow C_{16}H_{34}O + 8CO_2 + 7H_2O$$

Production of a $C_{16}$ fatty alcohol results in a Gibbs free energy change of −285 kJ/mol glucose. For comparison, production of ethanol results in a Gibbs free energy change of −208 kJ/mol glucose.

The present invention describes the engineering of a recombinant microorganism to convert a native fatty acid biosynthetic pathway into a fermentative pathway, i.e., one that generates net positive ATP and is redox neutral. As shown below, a native fatty acid pathway generates zero net ATP, which stems from the mechanism of producing malonyl-CoA, the acyl-ACP chain precursor used to increase chain length. Malonyl-CoA is formed from the conversion of one glucose into two acetyl-CoA, which produces two ATP and four NAD(P)H. However, ATP is required to produce malonyl-CoA from acetyl-CoA, which results in a net zero ATP balance. In the synthetic route shown below, malonyl-CoA formation is accomplished without the concomitant use of ATP.

Native Pathway: Glucose+CoA+2 Malonyl-CoA+
2NADH+2NAD(P)H

Synthetic Pathway: Glucose+CoA+2 Malonyl-CoA+
2ATP+2NADH+2NAD(P)H

In either case, the NAD(P)H produced during malonyl-CoA synthesis is balanced via reduction of the growing acyl-ACP chain.

Figure 3A:
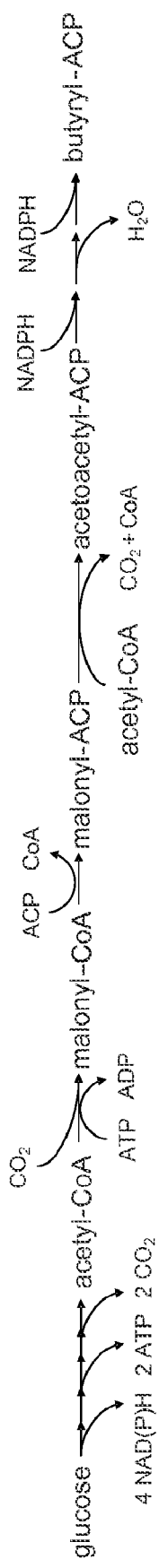
FIG. 3A depicts the net reaction and a native pathway for the conversion of glucose to butyryl-ACP.
Figure 3B:
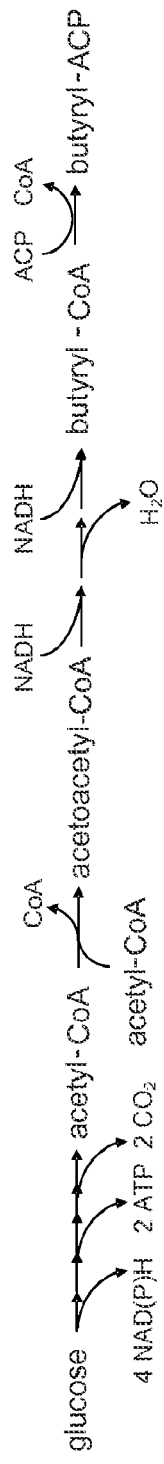
FIG. 3B depicts the net reaction and a Clostridial pathway for the conversion of glucose to butyryl-ACP.
Figure 3C:
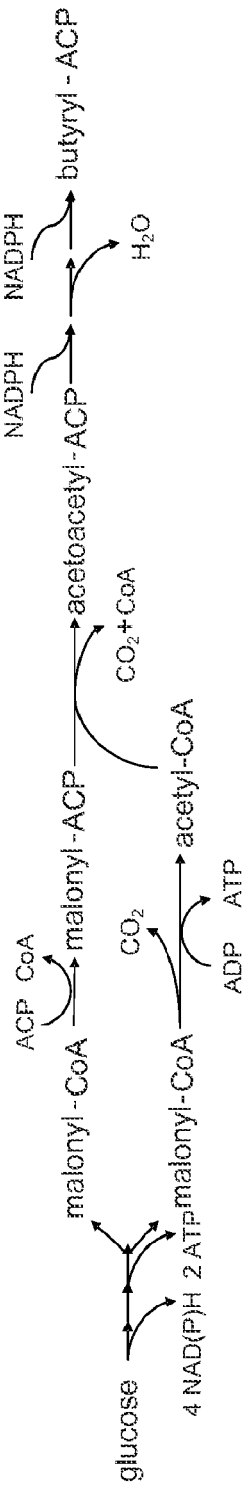
FIG. 3C depicts the net reaction and a pathway for the conversion of glucose to butyryl-ACP using a transcarboxylase catalyst.

The synthetic pathways described herein proceed according to three steps: chain initiation, chain extension, and chain termination (see FIG. 2) and can be carried out in aerobic or anaerobic conditions. In some embodiments, the synthetic pathways produce a hydrocarbon and/or a hydrocarbon derivative under anaerobic conditions. In some embodiments, the synthetic pathways produce a polyketide or an organic acid under aerobic or anaerobic conditions. Chain initiation can proceed by one of several options that are ATP positive and in which NAD(P)H is balanced by chain termination and $H_2$ generation (see FIG. 3A-3C).

Figure 4:
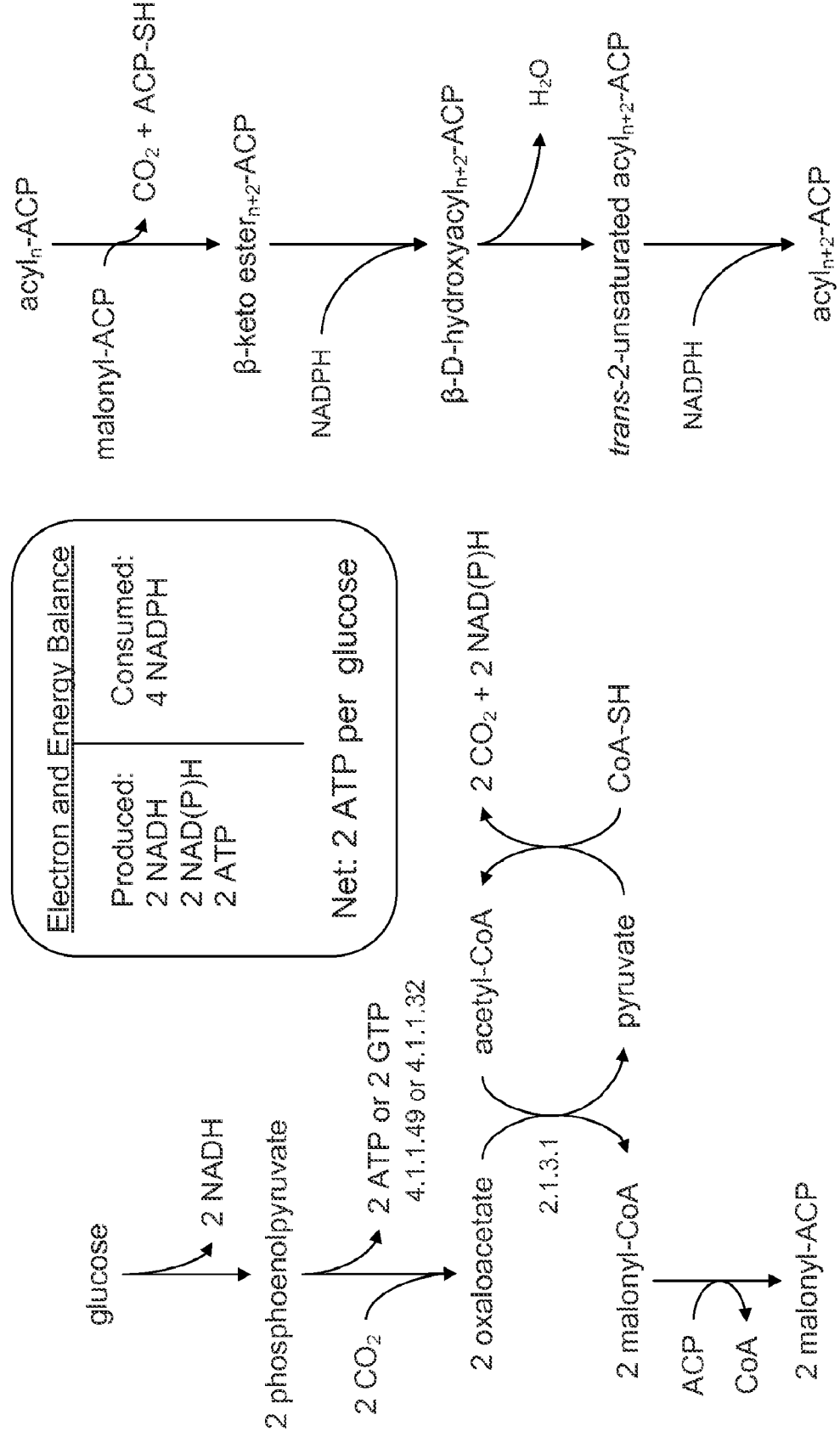
FIG. 4 depicts a pathway for the conversion of glucose to $acyl_{n+2}$-ACP.

5J In native cells, e.g., E. coli, chain extension proceeds from pyruvate to acetyl-CoA to malonyl-CoA. See Steen et al., Nature 463:559-562 (2010). To conserve ATP during the generation of malonyl-CoA, two enzymes are introduced into the central metabolic network for chain extension: a phosphoenolpyruvate carboxykinase (PEPCK) to convert phosphoenolpyruvate to oxaloacetate and a transcarboxylase (TC) to convert oxaloacetate and acetyl-CoA to malonyl-CoA and pyruvate (see FIG. 4 or FIG. 33). The introduction of these enzymes results in the production of 2 NADH, 2 NAD(P)H, and 2 ATP, resulting in a net production of ATP per carbohydrate, such as but not limited to, glucose. For example, for glucose, the net production of ATP per 6 carbons is about 2. For xylose, the net production of ATP per 5 carbons is about 1.67 ATP. When considering the net production of ATP per hydrocarbon produced rather than sugar consumed, for every 4 carbons of hydrocarbon, the net is about 2 ATP. Thus, for a $C_{16}$ fatty acid, the net ATP is about 8. The conversion of phosphoenolpyruvate to oxaloacetate using PEPCK results in the net production of ATP. See FIG. 4. For example, the net production of ATP in the recombinant microorganisms of the invention includes at least about 0.5 net ATP; at least about 1.0 net ATP; at least about 1.5 net ATP; or at least about 2.0 net ATP during anaerobic growth. The conversion of oxaloacetate and acetyl-CoA to malonyl-CoA and pyruvate by TC then requires the regeneration of acetyl-CoA from the TC-generated pyruvate. The recycling of pyruvate by conversion of pyruvate and CoA-SH into acetyl-CoA and $CO_2$ and NAD(P)H not only facilitates flux in the direction of producing malonyl-CoA, but also generates the reduced NAD(P)H needed to balance redox. Enzymes that can be used to catalyze this pyruvate recycling pathway include, but are not limited to, a pyruvate dehydrogenase, a pyruvate:ferredoxin oxidoreductase and ferredoxin:NAD(P)H oxidoreductase, or a pyruvate formate lyase and formate dehydrogenase.

In addition, competing metabolic pathways can be removed or attenuated. These include, but are not limited to, pyruvate kinase, hydrogenase, lactate dehydrogenase, phosphotransacetylase, acetate kinase, acetaldehyde dehydrogenase, alcohol (ethanol) dehydrogenase, pyruvate formate lyase, pyruvate decarboxylase, and native enzymes involved in the degradation of fatty acids and their derivatives.

PEPCK and TC can be derived from C. thermocellum and T. saccharolyticum or other organisms. Engineering of these enzymes into the recombinant microorganism of the invention may require alteration of substrate specificity to minimize undesirable side reactions. In addition, cofactor specificity in the overall metabolic pathway can be modified, which has been done with other, similar proteins. To increase flux to malonyl-CoA production, native pathways for organic acid and ethanol production can be modified. Each of these engineering steps is within the abilities of those skilled in the art.

The acyl-ACP chain can be extended though the fatty acid biosynthesis (Fab) enzymes present in all organisms that produce fatty acids. These include FabB, FabF, FabG, FabZ, and FabI. Overexpression of these enzymes can benefit hydrocarbon formation; however, the native biosynthetic pathway is largely regulated by the availability of the malonyl-CoA precursor and the accumulation of long-chain fatty acyl-ACP compounds. See Li et al., Journal of Bacteriology 175:332-340 (1993); Davis et al., Journal of Biological Chemistry 275:28593-28598 (2000); Davis and Cronan, Journal of Bacteriology 183; Heath and Rock, Journal of Biological Chemistry 271:1833-1836 (1996)). Supply of sufficient precursor and removal of fatty acyl-ACP via chain termination steps allows for sufficient flux through this chain extension pathway.

Figure 5A:
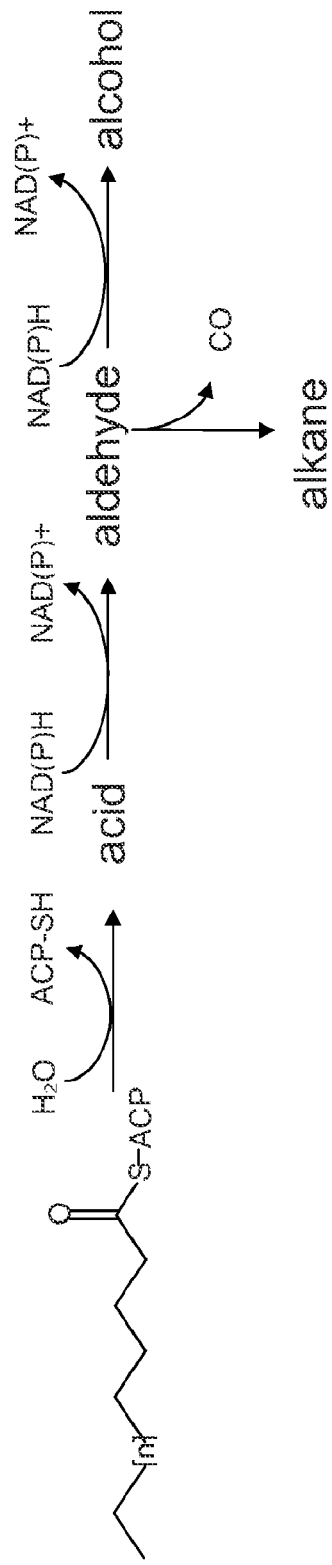
FIG. 5A depicts a pathway for the conversion of a fatty acyl-ACP to a fatty alcohol.
Figure 5B:
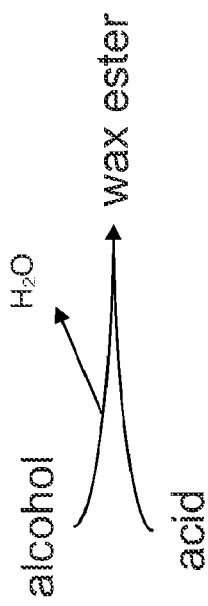
FIG. 5B depicts a pathway for the conversion of an alcohol and an acid to a wax ester.

Once an acyl-ACP chain has reached its desired length, the reaction is terminated and the hydrocarbon product is excreted from the cell. Many chain termination options are available in the art to produce hydrocarbon products or hydrocarbon derivative products, including, but not limited to, fatty acids, alcohols, aldehydes, wax esters, or alkanes (see FIG. 5A and 5B). See Steen et al., *Nature* 463:559-562 (2010); Sukovich, et al., *Applied and Environmental Microbiology* 76:3850-62 (2010); Kalscheuer and Steinbüchel, *Journal Biological Chemistry* 278:8075-82 (2003); Reiser and Somerville, *Journal of Bacteriology* 179:2969-2975 (1997); Kalscheuer et al., *Microbiology* 152:2529-36 (2006); Beller et al., *Applied and Environmental Microbiology* 76:1212-23 (2010). The termination steps, in concert with chain extension, impart properties on the final compound to mimic petroleum based diesel, gasoline, or jet fuel. For example, production of $C_{14-18}$ fatty alcohols and esters as first generation products can be directly blended to create cellulosic diesel, or serve as a bio-crude that could be converted into other fuels with conventional catalysis technology. Production of fatty alcohols requires expression of a fatty acyl reductase and a fatty aldehyde reductase. See Reiser and Somerville, *Journal of Bacteriology* 179:2969-75 (1997); Steen et al., *Nature* 463:559-562 (2010). Some organisms, such as *E. coli*, have native fatty aldehyde reductase activity, while enzymes such as the jojoba acyl reductase is a bifunctional acyl-ACP/aldehyde reductase. See Reiser and Somerville, *Journal of Bacteriology* 179: 2969-75 (1997). Wax esters can be produced via an acyltransferase in the presence of ethanol or a long-chain alcohol. See Kalscheuer and Steinbüchel, *Journal Biological Chemistry* 278:8075-82 (2003); Reiser and Somerville, *Journal of Bacteriology* 179:2969-2975 (1997); Kalscheuer et al., *Microbiology* 152:2529-36 (2006).

The chain length of the hydrocarbon product or hydrocarbon derivative product is controlled based on, e.g., the specificity of the native organism. See. Wang et al., *Extremophiles* 10:347-56 (2006); van Beilen el al., *Microbiology* 147:1621-30 (2001). Based on techniques known in the art, termination enzymes can be screened and engineered to develop hydrocarbon products or hydrocarbon derivative products with the desired chain length. See Steen et al., *Nature* 463:559-562 (2010); Sukovich, et al., *Applied and Environmental Microbiology* 76:3850-62 (2010); Kalscheuer and Steinbüchel, *Journal Biological Chemistry* 278: 8075-82 (2003); Reiser and Somerville, *Journal of Bacteriology* 179:2969-2975 (1997); Kalscheuer et al., *Microbiology* 152:2529-36 (2006); Beller et al., *Applied and Environmental Microbiology* 76:1212-23 (2010).

Hydrocarbon products or hydrocarbon derivative products can exit the cell through a membrane "flip" mechanism. In such a mechanism, the polar hydrophilic-hydrophobic compound enters the lipid bi-layer on the intracellular side with the hydrophilic head pointing towards the inside of the cell, flips over so that the hydrophilic head points outside of the cell, and then exits the bi-layer into the extracellular environment. See Black and DiRusso, *Microbiology and Molecular Biology Reviews* 67:454-472 (2003). Alternatively, to ensure efflux from the recombinant microorganism, high efficiency hydrophobic compound efflux transporters can be engineered, although at a cost of one ATP per molecule extruded. See Kieboom et al., *Journal of Biological Chemistry* 273:85-91 (1998). Such mechanisms allow for collection of the hydrocarbon products or hydrocarbon derivative products in the fermentation medium, in addition to other products naturally secreted or expelled by the host cell.

As hydrocarbon products or hydrocarbon derivative products accumulate in the fermentation media, the products can form a 2-phase organic layer after saturating the aqueous fermentation volume. See Neumann et al., *Applied and Environmental Microbiology* 71:6606-612 (2005). At saturating concentrations, toxicity correlates to the "minimum membrane concentration" of a compound, which is a function of the octanol/water partition coefficient and the aqueous solubility. Generally, as chain length increases, compounds become less toxic.

Product recovery and product toxicity are independent of substrate concentration. This provides the advantages that either a minimal pretreatment can be run at low fermentor solids or, when using refined material, the refined material can be run at very high solids without product toxicity to the fermenting organisms. In addition, because the hydrocarbon products are insoluble, product recovery can be at low cost. This means that the hydrocarbon products can be readily purified for use in fuels and chemical feedstocks.

EXEMPLIFICATION

The invention now being generally described, it will be more readily understood by reference to the following examples, which are included merely for purposes of illustration of certain aspects and embodiments of the present invention, and are not intended to limit the invention.

Example 1

The present prophetic example describes the engineering of a recombinant microorganism to convert a native fatty acid biosynthetic pathway into a fermentative pathway, i.e., one that generates net positive ATP and is redox neutral during anaerobic growth.

1.1 Production of Hexadecanol in *T. saccharolyticum*

Gene overexpression and gene deletion followed by evolutionary engineering will be performed to create a strain producing 1-hexadecanol.

The strain *T. saccharolyticum* JW/SL-YS485 has an established transformation system based on a natural competence protocol. See Shaw et al., *Applied and Environmental Microbiology* 76:4713-4719 (2010). Recombinant DNA, either linear or plasmid based, can be introduced with the following protocol.

1.1.1 *T. saccharolyticum* Transformation Protocol

Prior to use, petri dishes, 50 mL and 15 mL conical falcon tubes, and pipet tips are all placed in the anaerobic chamber at least overnight. Transformations are performed in an anaerobic chamber by inoculation of 10 mL liquid medium M122 (pH 6.1 or 6.7—there is less precipitation at pH 6.1 and it facilitates OD measurement, but kanamycin selection is better at pH 6.7) with 1-3 µL of a frozen working stock culture of *T. saccharolyticum*, which has been frozen-down when in exponential growth. After mixing, 1 mL aliquots of the 10 mL medium are transferred to tubes containing between 0.25 µg-1 µg DNA. The tubes are then incubated at 55° C. for 16-18 hours (overnight) to an OD of 0.6-1. Maintaining cells past 18 hours in stationary phase can dramatically reduce transformation efficiencies.

Next, 100 µL and 500 µL aliquots of the transformant culture are mixed with 25 mL liquid medium M122 pH 6.7 at 55° C. containing 1.2% agar and kanamycin at 200 g/mL. The mixture is poured into petri dishes and allowed to solidify at room temperature for 30 minutes, or until completely solid, and the petri dishes are incubated at 55° C. in a moisture retaining container until colony formation (24-48 hours).

1.1.2 Gene Deletion

Figure 8:
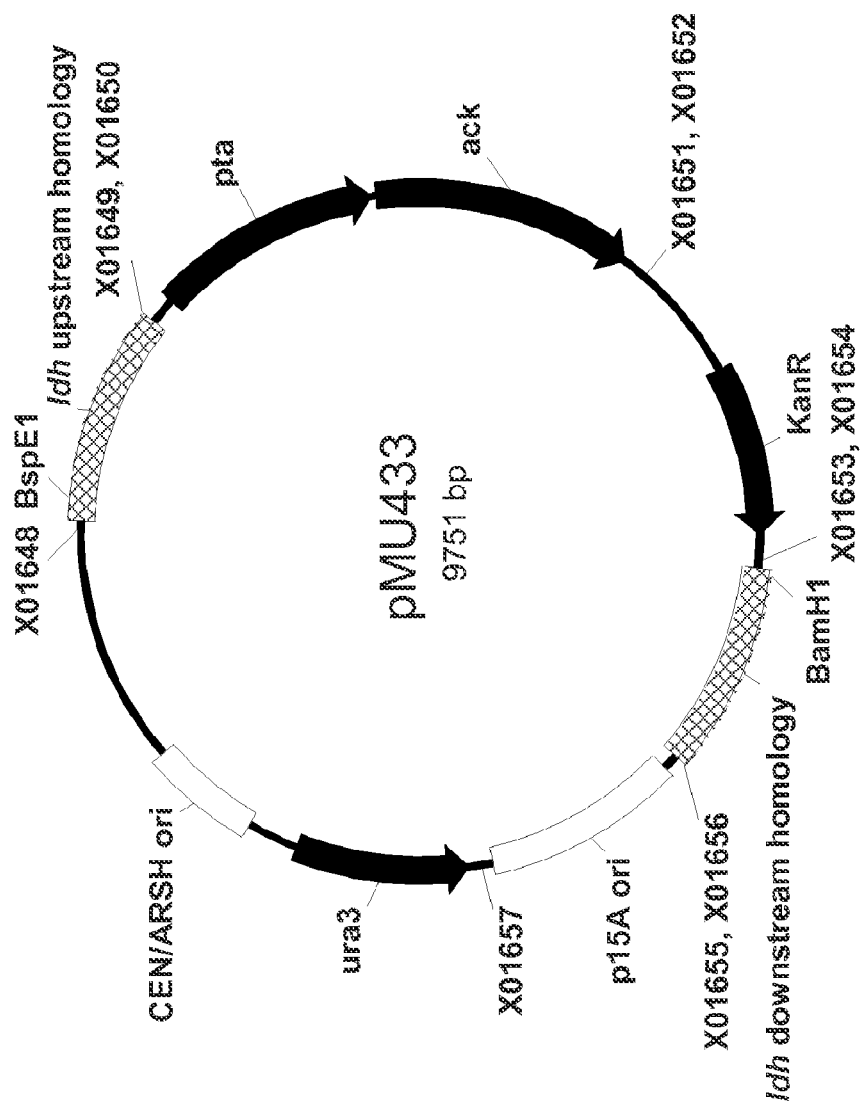
FIG. 8 depicts the vector pMU433.

Gene deletions will be performed with a marker removal system, which allows for clean genomic deletions and marker recycling. The plasmid pMU433 (see FIG. 8) contains the marker removal cassette, namely the pta and ack genes linked to a kanamycin resistance gene. Genes targeted for deletion include L-lactate dehydrogenase, bifunctional alcohol dehydrogenase adhE, pyruvate kinase, pyruvate formate lyase, and phosphotransacetylase and acetate kinase. To construct deletion vectors, homology regions are generated from the target gene sequences from *T. saccharolyticum* and cloned into pMU433.

```
L-lactate dehydrogenase
                                          (SEQ ID NO: 72)
atgagcaaggtagcaataataggatctggttttgtaggtgcaacatcggc
atttacgctggcattaagtgggactgtgacagatatcgtgaggtggattt
aaacaaggacaaggctataggcgatgcactggacataagccatggcatac
cgctaatacagcctgtaaatgtgtatgcaggtgactacaaagatgtgaaa
ggcgcagatgtaatagttgtgacagcaggtgctgctcaaaagccgggaga
gacacggcttgaccttgtaaagaaaaatacagccatatttaagtccatga
tacctgagcttttaaagtacaatgacaaggccatatatttgattgtgaca
aatcccgtagatatactgacgtacgttacatacaagatttctggacttcc
atggggcagagttttggttctggcaccgttcttgacagctcaaggttta
gatacctttaagcaagcactgcaatatagatccgagaaatgtccacgga
aggataatcggcgagcatggtgacacagagtttgcagcatggagcataac
aaacatatcgggtatatcatttaatgagtactgcagcatatgcggacgcg
tctgcaacacaaatttcagaaaggaagtagaagaagaagtcgtaaatgct
gcttacaagataatagacaaaaaaggtgctacatactatgctgtggcagt
tgcagtaagaaggattgtggagtgcatcttaagagatgaaaattccatcc
tcacagtatcatctccattaaatggacagtacggcgtgaaagatgatcat
taagcttgccatctatcgtaggcaggaatggcgttgccaggattttggac
ttgcctttatctgacgaagaagtggagaagtttaggcattcagcaagtgt
catggcagatgtcataaaacaattagatata
Bifunctional alcohol dehydrogenase adhE
                                          (SEQ ID NO: 73)
atggcaacgacaaaaacggaattagacgttcagaagcagatagatctact
tgtgtcaagagcacaagaggctcagaaaaaattcatgtcttacacgcaag
agcaaatcgacgcaatagttaaggcaatggctttagcaggcgttgacaaa
cacgtagagctggcaaagatggcgtacgaagagacaaaaatgggtgtata
cgaagataagataacaaaaaatctcttcgcaacagagtacgtgtaccacg
acataaaaaatgaaaagactgtaggaatcataaacgagaacatagaagaa
aactacatggaagtggcagaaccgataggcgtaattgccggtgtcacacc
tgtcacaaacccaacatctaccacgatgtttaaatgcttaatatccataa
agacgcgaaatcctataatattcagcttccatccaaaggcaataaagtgc
agcatcgcagcagccaaagtgatgtatgaagctgcactaaaggcaggcgc
acctgaaggatgcataggatggatagaaacgccatcaattgaggccacac
agatctcatgacacatccaggcgtatcgctgatccttgcaacgggcggtg
caggaatggtaaaagcggcatacagctcaggaaaaccggcattaggcgta
ggtcctggcaatgtgccatgctacatcgaaaaatcagcaaacataaagag
ggctgtatcggatacatactaagcaagacatttgacaatggagtaatatg
cgcatcagagcaggccgtaataatagacgaggaaatagcagatgaagtca
aaaagcttatgaaagaatacggctgctacttcttaaacaaagatgaaata
aagaagcttgagaaatttgcaattgatgagcaaagctgcgccatgagcca
gcagtggtaggtcagccagcggcgaagattgctgaaatggcaggatcaaa
gtccccgaaggcacaaagatattagtggcagagtacgaaggagtaggtcc
aaaatatcctctatcaagggagaaactaagcccgattcttgcttgctaca
ccgtcaaagactacaatgaaggaatcaaaaagtgcgaggaaatgactgaa
ttcggaggtttaggccactctgctgtaatacactctgaaaatcaaaacgt
cataaatgaatttgcaaggcgagtccgcacaggaagacttatcgtaaatt
caccatcatcacagggagcaataggagatatatacaatacaaacacgcca
tcacttacattaggctgtggttctatgggaagaaactcaacgacagacaa
tgtaagcgtcaagaaccttttgaatattaagcgtgtcgtgataaggaatg
atagaatgaaatggttcaagattccaccgaagatttactttgaaagcggg
tcactccagtacctgtgcaaagtcaaaagaaaaaaagcgtttatcgtcac
agatccattcatggttaagcttggatcgtagacaaagtgacatatcaatt
agacaaagcaaacatcgaatacgaaatattctcagaagtagagccagatc
catagttgacacagtcatgaacggcgtaaaaataatgaattcgtacaatc
ctgacttaataatcgctgtaggcggtggctctgcaatagacgcagcaaag
ggaatgtggcttttctacgaatatcctgatacagagtttgaaacattgag
gcttaaatttgcagacatcagaaaaagggcatttaagttcccagaacttg
gcaaaaaagcgctattcatcgcaataccgacaacaagcggcacaggctca
gaagtgacagcatttgccgtaataaccgacaaaaagagaaacatcaagta
tccactggcagactacgaacttacacctgacatagccataatagatcctg
accttacaaagactgtaccgccatctgtaacagcagacacaggcatggat
gtgctgacacacgccatagaagcatacgtatcagtaatggcatcagacta
cacagatgcactggcgaaaaggctataaagatcgtatttgaatacctgc
caagggcttataaaaacggcaatgatgaagaagcccgcgaaaagatgcac
aatgcttcctgcatggaggtatggcattcacaaatgcattcttaggaata
aaccacagcatggcacacatactgggcggaaagttccacataccacacgg
aagagcaaatgcaatacttctgccgtatgtaataaggtacaatgcagaaa
aacctacaaagtagtggcattcccacaatacgaatatccaaaagcagcag
aaagatatgcggaaatcgccaaattataggactgcctgcttcaactgttg
aagaaggcgtagaaagcttaatagaagctataaagaacctcatgaaagag
cttaacattccgcttacacttaaagacgccggcatcaacaaagaacagtt
tgaaaagaaatagaggaaatgtcagacatcgccttcaacgatcagtgca
cagggacaaacccgagaatgcctctcacaaaagaaattgcagagatctac
agaaaagcatacggtgca
```

Pyruvate kinase (SEQ ID NO: 74)
atgcgtagaactaagataatatgcacgattggtcctgccagtgaaaaata
tgagatattgaaagagcttatagaaagcggtataatatttgcaggttgaa
ttttcacatggggatcatgaagagcatggaagcagaatagacaatatta
taaagattagagaagaacttaagctgcctattgcaattatgcttgataca
aaaggggcctgaaataaggactggcagatttaaaggcggtgttgcagagct
taagaaggccagacatttacgataacatcaagggaaattgaaggagata
acactatttgttctgatcatacaaggggcttcctcaagatgtggagagag
gttctcgcatattgattgatgacggattagtatcattgaaagtcaatgac
gtaaaaggtgaagatatagtatgcactgtggagaattctggtacaatagg
tgatcacaaaggtgtaaatgtacctggtacaaagcttaatttgcctgcca
taacgcaaaaagacgtggatgatatagagtttggaataaaaaaaggaatc
gacatgattgcagcgtcttttgtcagaaaagcagcagatgtaaattgccat
aaggagattgttagaagacaatgacgctggccatatacttatcatatcaa
aaaattgaaaatcgcgaaggcgtagaaaatattgacgaaataatcaaagtc
tctgatggcataatggtagcccgcggcgatttgggtgtcgaaattcctat
agaggaaataccctatcgttcagaaaaggataattgaaaaatgcaacaaag
caggtaaaccagtagttactgctacacagatgcttgactctatgataaga
aatccaaggccaacaagggcagaagtaacagatgtagccaatgctatatt
ggatggcactgatgcgataatgttgtctggtgaaacagcgcaaggcaaat
atcctgtagaggatttaagacgatgtcaaagatagctgaaaagattgaga
cgtatataaattacaaagaaaatttagataaaaatgtggattacaatatt
tctatgacaaatgccataagccatgctacgtgcactaccgcgagagatat
aggcgcaactgccattattacatctacaatatcaggttatactgcgagaa
tggtgtctaagtatagaccgtcagcacctataatagcagtgacgccaaac
aaagatgttgcaagaaggcttagcatcgtgtggggtgtacatccattgat
atcacaggaagtcaattctacagatgaaatgatagaagtatcagtaaata
cggctttaaatgaaggattaattcgaaatggcgatattgtagtaatatcg
gcaggaataccctgtcgcgactacaggcacaacaaatatgttgaaggttca
tattgtgggagatgtaatagtaaaaggcacaggcataggcactaaatcca
taagtggtgttgtttccatcataagagatccatacaaggacaaagataag
ttcagagaaggagatatcatcgttgctcaaaaaactgaaagggattatat
gcctataattgagaaggcttcagctatcatacagaagaaggtggactaa
cgtcccatgctgcaatagttggattgaactatggattacctgtcattgta
ggctgtgaaggagtaacttcaaagcttaaagatggaatgacggtaactct
cgatactgccagaggattggtctacaaaggtatagtgaatataaaatag Pyruvate formate lyase (SEQ ID NO: 75)
atgatcaatgaatggcgcgggtacaggagggcaaatggcaaaagactatt
gacgttcaagatttttatccagaaaaattacacattatacgaaggcgatga
tagttattagaagggcctacagaaaagactattaagattggaacaaagtt
cttgagctaatgaaggaagaactgaaaaaaggtgtgttagatattgatac aaaaaagtatcgtctataacatcccatgatgcggggtatatagacaaaga
tcttgaggaaatagttggattgcagacagacaaacctcttaaaagagcta
taatgccttacggtggcataagaatggtcaaqaaagcttgcgaagcttat
ggatataaagtggacccaaaagtagaagagtatttacgaagtacagaaa
gacccacaatgatggtgtatttgatgcatatactccagaaataagagcag
caagacatgccggcataataacaggtcttccagatgcatatggcagagga
agaatcataggtgattacagaagagttgctcttttatggaattgatagact
catcgaagaaaaggaaaaagaaaaacttgagcttgattacgatgaatttg
atgaagcaactattcgcttgagagaagaattgacagaacagataaaagca
ttaaacgaaatgaaagagatggctttaaagtacggttatgacatatcaaa
gcctgcaaaaaatgcaaaagaagctgtgcagtggacttactttgccttcc
ttgctgctataaaggaacaaaatggtgccgctatgtcgctgggcagagta
tctacttttttagatatatacattgaaagagatcttaaagaaggaacatt
gacagagaaacaagcacaagagttaatggatcactttgtcatgaagatag
aatggtgaggttcttaaggactcctgattacaatgaactatttagtggcg
atcctgtttgggtgactgaatcaattggcggtgtaggcgtagacggaaga
cctcttgtcactaaaaattcattcaggatattaaatactttatataactt
aggtcctgcacctgagccaaacttgacggttttatggtccaaaaaccttc
ctgaaaactttaaaagattctgtgccaaggtatcaatagatacaagttct
attcaatatgaaaatgacgacttaatgaggccaatatacaatgacgacta
tagcatcgcctgctgtgtgtcagctatgaagacgggagaacagatgcaat
tttttggagcaagggcaaatctcgcgaaggcgctactgtatgctataaac
ggcggtatcgatgaaaggtataaaacgcaagtggcaccaaaatttaatcc
tataacgtctgagtatttagactacgatgaggtaatggcagcatatgaca
atatgttagagtggcttgcaaaagtgtatgttaaagctatgaatataata
cactacatgcacgatataacgcttatgaaagatccttatggctttgca
tgatagagacatcgtaaggacgatggcttttggaatcgcaggtattctgt
tgcggcagattcgttaagcgccataaagtatgctaaagtaaaagccataa
agatgaaaatggcatagcaatagattatgaagtggaaggagatttccct
aagtttggcaatgatgatgacagggttgactcaatagcagttgacattgt
agaaagattcatgaataagcttaaaaagcacaagacttacagaaactcta
taccaacactgtctgttttgacaataacgtcaaatgtggtgtacggcaaa
aagacgggtgctacacctgacggaagaaaagcgggagaaccttttgcgcc
aggcgcaaatccgatgcacggcagagatacaaaaggtgccatagcatcaa
tgaattcagtatcaaaaataccttatgacagttcattggatggtatatca
tacacatttacgattgtaccaaatgcgcttggcaaggatgacgaagataa
aattaataatcttgtaggactattagatggatatgcatttaatgcggggc
accacataaacatcaatgtttaaacagagatatgttgcttgatgctatg
gagcatcctgaaaaatatccgcagcttactataagggtttcagggtatgc
tgtcaatttcaataaaattaacgagagagcaacagttggaggttatatccc

```
gcacttttcacgaatctatg

Phosphotransacetylase and acetate kinase
                                       (SEQ ID NO: 76)
gtgtatacaatatatttatcttagtaagaggaatgtataaaaataaatat tttaaaggaagggacgatcttatgagcattattcaaaacatcattgaaaa agctaaaagcgataaaaagaaaattgttctgccagaaggtgcagaaccca ggacattaaaagctgctgaaatagttttaaaagaagggattgcagattta gtgcttcttggaaatgaagatgagataagaaatgctgcaaaagacttgga catatccaaagctgaaatcattgaccctgtaaagtctgaaatgtagatag gtatgctaatgatttctatgagttaaggaagaacaaaggaatcacgttgg aaaaagccagagaaacaatcaaggataatatctattttggatgtatgatg gttaaagaaggttatgctgatggattggtatctggcgctattcatgctac tgcagatttattaagacctgcatttcagataattaaaacggctccaggag caaagatagtatcaagctttttttataatggaagtgcctaattgtgaatat ggtgaaaatggtgtattatgtttgctgattgtgcggtcaacccatcgcct aatgcagaagaacttgcttctattgccgtacaatctgctaatactgcaaa gaatttgttgggctttgaaccaaaagttgccatgctatcattttctacaa aaggtagtgcatcacatgaattagtagataaagtaagaaaagcgacagag atagcaaaagaattgatgccagatgttgctatcgacggtgaattgcaatt ggatgctgctcttgttaaagaagttgcagagctaaaagcgccgggaagca aagttgcgggatgtgcaaatgtgatatattccctgatttacaagctggta atataggatataagcttgtacagaggttagctaaggcaaatgcaattgga cctataacacaaggaatgggtgcaccggttaatgatttatcaagaggatg cagctatagagatattgttgacgtaatagcaacaacagctgtgcaggctc aataaaatgtaaagtatggaggatgaaaattatgaaaatactggttatta attgcggaagttatcgctaaaatatcaactgattgaatcaactgatggaa atgtgttggcaaaaggccttgctgaaagaatcggcataaatgattccatg ttgacacataatgctaacggagaaaaaatcaagataaaaaaagacatgaa agatcacaaagacgcaataaaattggttttagatgctttggtaaacagtg actacggcgttataaaagatatgtctgagatagatgctgtaggacataga gttgttcacggaggagaatcttttacatcatcagttctcataaatgatga agtgttaaaagcgataacagattgcatagaattagctccactgcacaatc ctgctaatatagaaggaattaaagcttgccagcaaatcatgccaaacgtt ccaatggtggcggtatttgatacagcctttcatcagacaatgcctgatta tgcatatctttatccaataccttatgaatactacacaaagtacaggatta gaagatatggatttcatggcacatcgcataaatatgtttcaaatagggct gcagagattttgaataaacctattgaagatttgaaaatcataacttgtca tcttggaaatggaccagcattgctgctgtcaaatatggtaaatcaattga cacaagcatgggatttacaccattagaaggtttggctatgggtacacgat ctggaagcatagacccatccatcatttcgtatcttatggaaaaagaaaat ataagcgctgaagaagtagtaaatatattaaataaaaaatctggtgttta cggtatttcaggaataagcagcgattttagagacttagaagatgccgcct ttaaaaatggagatgaaagagctcagttggctttaaatgtgtttgcatat cgagtaaagaagacgattggcgcttatgcagcagctatgggaggcgtcga tgtcattgtatttacagcaggtgttggtgaaaatggtcctgagatacgag aatttatacttgatggattagagttttttagggttcagcaggataaagaaa aaaataaagtcagaggaaaagaaactattatatctacgccgaattcaaaa gttagcgtgatggttgtgcctactaatgaagaatacatgattgctaaaga tactgaaaagattgtaaagagtataaaa
```

For knockout vector construction, the 0.8-1.2 kb flanking regions (with primers) on both sides of target are first identified. Once identified, the new flanking regions are used to replace the L-ldh flanking regions in pMU433 using in silico analysis. Yeast-mediated ligation primers (4 total) for the two new flanking regions are made by adding to the targeting primers 5' regions homologous to DNA segments labeled "X01648,", "X01649," "X01654," and "X01655" on pMU433 shown in Table 3. Total primer length should be about 55-65 bp.

Next, the flanking regions from *T. saccharolyticum* YS485 genomic DNA are PCR amplified. PCR cleanup is not necessary if correct product was highly amplified.

TABLE 3

Primers for Knockout Vector Construction

| | | | |
|---|---|---|---|
| X01648 | (SEQ ID NO: 77) | GTCTTTCGACTGAGCCTTTCGTTTTATTTGATGCCTGG | pMU433 construction |
| X10649 | (SEQ ID NO: 78) | AATTGTAGAATACAATCCACTTCACAATGGGCACG | pMU433 construction |
| X01654 | (SEQ ID NO: 79) | AGGGGTCCCGAGCGCCTACGAGGAATTTGTATCG | pMU433 construction |
| X01655 | (SEQ ID NO: 80) | CCGTCAGTAGCTGAACAGGAGGGACAGCTGATAGA | pMU433 construction |

About 100-200 ng pMU433 per yeast transformation is then digested with BamH1/BspE1. Allowing digestion to proceed to completion helps reduce background during yeast transformation.

The digested DNA is transformed into ura3-*S. cerevisiae* (Invitrogen INVScl cat #C81000 or equivalent) following the "Lazy bones" yeast transformation protocol. See Shanks et al., *Applied and Environmental Microbiology* 72:5027-5036 (2006). Briefly, about 100 ng digested plasmid and 10-50 μL of each PCR amplified flanking region are mixed. Prior purification is not necessary for either plasmid or PCR unless there are BamH1/BspE1 sites in the flanking regions. Other yeast transformation protocols can suitably be used. To control for background, a plasmid only control can be used.

The transformed yeast are plated on SD-URA plates (SD Medium-URA MP Biomedicals #4812-075 or equivalent) and incubated at 30° C. The plates are incubated for 3-5 days and then yeast total DNA is harvested from plates containing colonies. If cell mass is low, the colonies can be streaked on a new plate to increase the number of colonies. Yeast DNA is isolated using the "Smash and Grab" protocol (see Shanks et al., *Applied and Environmental Microbiology* 72:5027-5036 (2006)), or an equivalent protocol.

Next, competent *E. coli* are transformed with 1-5 μL of yeast total DNA and selected on 50 or 100 Kan LB plates. Colonies are screened to verify the constructs. 2-5 g total plasmid DNA is then used for *T. saccharolyticum* transformations.

A second vector for gene deletion/marker removal is constructed using in silico analysis to place the two flanking regions adjacent to each other. Overlapping regions are added to the two adjacent primers on the flanking regions to obtain about 40 kb of homology between the regions when amplified.

Using two rounds of PCR amplification, the flanking regions can be connected. The first PCR amplification is a traditional amplification, and the second amplification is a dilution of the first round products to approximately 1 ng/μL. This dilution is used as a template; and the upstream flanking region 5' primer and downstream flanking region 3' primer are used for amplification. If necessary, optimization of annealing temperature or MgCl₂ can be performed. Alternatively, TOPO cloning (Invitrogen) or other known techniques can be used to make the second construct.

Following a PCR clean-up, 2-3 μg of the vector product is then used to transform *T. saccharolyticum*.

1.1.3 Gene Insertion

To create a metabolic route to 1-hexadecanol, native and/or recombinant genes are overexpressed. The native PEPCK and TC genes are overexpressed via insertion of high level promoters in front of the coding sequence for these genes. This is accomplished through the pMU433-based marker cycling system, except that the recombinant promoter region will remain behind after the marker is removed. High expression level promoter regions can be chosen, without limitation, from any of the following promoters:

adhE promoter
(SEQ ID NO: 81)
tcatataagtgtaaggtgattgttaaatgaataacaaaaattatttacat cacacagtccaaaattcaattcattcaagcgaatttcctgttgaaatgct tgaaaaactgatacaatcacctgaaatgtagagatttattgttaataaat taacacggaggtgtttatt cbp promoter
(SEQ ID NO: 82)
gagtcgtgactaagaacgtcaaagtaattaacaatacagctattatctca tgcttttaccccctttcataaaatttaattttatcgttatcataaaaaatt atagacgttatattgcttgccgggatatagtgctgggcattcgttggtgc aaaatgttcggagtaaggtggatattgatttgcatgttgatctattgcat tgaaatgattagttatccgtaaatattaattaatcatatcataaattaat tatatcataattgttttgacgaatgaaggttttggataaattatcaagt aaaggaacgctaaaaattttggcgtaaaatatcaaaatgaccacttgaat taatatggtaaagtagatataatattttggtaaacatgccttcagcaagg ttagattagctgtttccgtataaattaaccgtatggtaaaacggcagtca gaaaaataagtcataagattccgttatgaaaatatacttcggtagttaat aataagagatatgaggtaagagatacaagataagagatataaggtacgaa tgtataagatggtgcttttaggcacactaaataaaaaacaaataaacgaa aattttaaggaggacgaaag pta promoter
(SEQ ID NO: 83)
gtattctacaattaaacctaatacgctcataatatgcgcctactaaaaaa ttattaattgtacttattatatataaaaaatatgttaaaatgtaaaatgt gtatacaatatatttatcttagtaagaggaatgtataaaaataaatattt taaaggaagggacgatat hyd promoter
(SEQ ID NO: 84)
ataagcgaaagggtaaattgattgatttagatgatttgaatatggtagtc gactggatgtgcaagtaaagaaaacatatcaaattagtcgggattatcag aaaataaaaaattttttattttaactgttaaaaaaataattaacatatg gtataataattatgtcctattagcaatttttaaagattaatttttttaaaa ggagggtattag hfs promoter
(SEQ ID NO: 85)
gctgtaattgtccttgatgacgataggaagataaacattccaacaaaata tcttcccagcaatattgctgaagaagatgccatagatatttcattggatg tcaatgaaagaggacgaaaattaaaaaagttgattgaagaatcaagggag gaagactaattattaatttattaacgttaattgttaataaattaactatt gtttacacacatcttttatgtaataaaataattgtatacagtatacgg ech promoter
(SEQ ID NO: 86)
tactgaatggagaaactgcacaaaaagcttgttgacggcagcagaggaga ttattcctctgctattatgtgggaaaaactgcaaaattcattgaaatatt gttaaataataaacaaaattaattaatattaaatacaattgacttatcat ttaattagatttataatcaaaatgggtatttaaaaatgtatacaatatat aatattcattaaatgaaataaagaaggagtgaaaaa Next, recombinant genes encoding a fatty acyl-ACP reductase and hexadecanal dehydrogenase from organisms such as *Acinetobacter calcoaceticus* and *Geobacillus thermodenitrificans* (see Reiser and Somerville, *Journal of Bac-* teriology 179:2969-2975 (1997); Liu et al., *Microbiology* 155:2078-2085 (2009)) are identified (see below). These recombinant genes can be integrated into the genome, driven by a high level expression promoter, or expressed via a replicating plasmid such as pMU131 (see WO 2009/035595).

Nucleotide sequence of *Acinetobacter* acr1 fatty acyl-ACP (-CoA) reductase (GenBank# U77680)
(SEQ ID NO: 87)

```
cagaagatat ggttcggtta tcggttggga ttgaacatat
tgatgatttg attgcagatc tggaacaagc attggccaca
gtttgagcgt aaatttata aaaaacctct gcaatttcag
aggttttttt atatttgctt tattatcgta tgatgttcat
aattgatcta gcaaataata aaaattagag caattactct
aaaaacattt gtaatttcag atacttaaca cragattttt
taaccaaatc actttagatt aactttagtt ctggaaattt
tatttccctt taaccgtctt caatccaaat acaataatga
cagcctttac agtttgatat caatcaggga aaaacgcgtg
aacaaaaaac ttgaagctct cttccgagag aatgtaaaag
gtaaagtggc tttgatcact ggtgcatcta gtggaatcgg
tttgacgatt gcaaaagaa ttgctgcggc aggtgctcat
gtattattgg ttgcccgaac caagaaaca ctggaagaag
tgaaagctgc aattgaacag caaggggac aggcctctat
ttttccttgt gacctgactg acatgaatgc gattgaccag
ttatcacaac aaattatggc cagtgtcgat catgtcgatt
tcctgatcaa taatgcaggg cgttcgattc gccgtgccgt
acacgagtcg tttgatcgct tccatgattt tgaacgcacc
atgcagctga attacttttgg tgcggtacgt ttagtgttaa
atttactgcc acatatgatt aagcgtaaaa atggccagat
catcaatatc agctctattg gtgtattggc
caatgcgaccc gttttttctg cttatgtcgc gtctaaagct
gcgctggatg cctcagtcg ctgtctttca gccgaggtac
tcaagcataa aatctcaatt acctcgattt atatgccatt
ggtgcgtacc ccaatgatcg cacccaccaa aatttataaa
tacgtgccca cgctttcccc agaagaagcc gcagatctca
ttgtctacgc cattgtgaaa cgtccaacac gtattgcgac
gcacttgggt cgtctggcgt caattaccta tgccatcgca
ccagacatca ataatattct gatgtcgatt ggatttaacc
tattcccaag ctcaacggct gcactgggtg aacaggaaaa
attgaatctg ctacaacgtg cctatgcccg cttgttccca
ggcgaacact ggtaaaattt ataaagaag cctctcatac
cgagaggctt tttatggtt acgaccatca gccagattta
gaggaaattg acttttcctg tttttacatc ataaatcgca
ccaacaatat caatttcttt gcgatccagc atatctttaa
gtacagaact atgctgaata atgtattgaa tattatagtg
aacattcata gcagtcacct gatcaataaa tgctttgctt
aattcacgcg gttgcataat atcaaataca ctgccaaccg
aatgcatgag tggcccaagc acgtattgga tgtgtggcat
ttcctgaata tcggaaatct gcttatgttg caatcttaac
tggcatgcgc tggtgaccgc accacagtcg gtatgtccca
aaaccagaat cactttggaa cttttggctt gacaggcaaa
```

Nucleotide sequence of *Geobacillus thermodenitrificans* NG80-2 adh1 (Genbank Nucleotide CP000557, Protein ABO67118)
(SEQ ID NO: 88)

```
ttacgccttg tgcggctcta cgatcgtccc ggcaaacgcg
gcttcgtaaa tcgcacggat gtcggcttcc aacagcggca
acggactgcg ggcaagcaaa cgttctgtt ggacagcatc
tttcgtcaag cttttctagcg cgctttcggg aatgccaaat
cccccccaatg ttttcggaat gccgacatcg gcgacgaacc
gttctagttc ctcgacgcac cgataagacg cttccacttc
ggacaaaaaa cttgagttgc cgccaagcgc gttgaaaata
tcggccattc tcttcgtaca gctttgacgg atgtagccca
tcacatacgg caacagcaca gcattcgatt caccatgagc
gatatgaaac tgaccaccga gcggataagc
gagcgcatgc acaccggcta ccccggcgtt gaaaaatgcc
aagccggcca aataactgcc gttcgccata
tcaatgcgcg cctgttttgtc cgaaccgttg gccaccgctt
tgcgcagtga gcgtgaaatc agccgaatag cggcaacggc
caatccatcc gatgttgggc tcgcattgac cgacacatac
gcctcaactg catgggtgag tgcatcaatt cccgttgcgg
ccgttacccg cggtggaacg gaaacggtca gctgcggatc
aacgatcgcg acgtcggcca ataagtaatc
gtgcgtcacg acatctttcg tcgtttccaa agacaagaca
gagatgtttg tcacttccga cccggtgccc gatgtcgtgg
gaatcaaaat tttcggcaac cctttttttct caagtgttcg
cgttcctgtc aaatttaaat agtcagcgac cgagccatca
tgcaccgcca aaacagccgc cagtttcgcc aaatccagcg
cgctgccacc accaacaccg atgacaaggt
caaactttcc gtcgcgggca aacgccactg cttttttcccc
tgtctcaagc ggcggctctg gcacaacatc cgtatacaca
tgcacgctat acccttcttg acggagcggg gacgtcactt
gatcgactag gccgatcttc acaagcatcg ggtcggtaat
caccaaaata tgttttgctc ccaaccgctt cacttcagga
actaactggt caagcgctcc ccagccgaca tggctgagcg
gcggaaagac aatgcgggct acactcat
```

-continued

Nucleotide sequence of *Geobacillus thermodenitrificans* NG80-2 adh1 (Genbank Nucleotide CP000557, Protein ABO68223)

(SEQ ID NO: 89)

```
ttataaagac gcacgcaaaa tggcgagcac atcatcacga tttaacgttt tgaaacggcc aaactcacca aacgccatcg ctttatccgc catcagctcg agattttcct cgccgatgcc ataatcagcc aatcgagacg gcgccccgag gctcgaccaa aacgcgcgca accgctcgat gccctcaagc gccacgtcgc gctccgtttt gcccgtcgga tcgacgtcaa agacgcgcac cgccagttgg gcgaaacggc tgacattttc atcaagcaca tgtttcatcc aattcgggaa caaaatggcc aatccccgg cgtgcgggat atcgtataca gcagagaccg catgctcgat atcatgcgtc gcccaatcac cgcgcacgcc catttgcaaa aagccgttta aggcgatcgt gcccgagtac atgatcgtct cgcgcagctc gtagttctct aagtcgtcaa ccaattttgg cgccgcctca atgaccgttt ttaacactgc ctcgcacatc cggtcttgca gcggcgtgtt cggcgtatga tggaaatatt gctcaaacac atgggacatc atatcgacga tgccgtaaac ggtatggtct ttcggcaccg tcatcgtgta cgtcggatcc aaaatcgaaa attgcgggaa tgtcaccggg ctgccccagc cgtattttc tttcgtctcc caattggtga tcaccgatcc ggcgttcatt tccgagccgg tcgctgccag cgtcaggacc gtcccaaacg gcaacgcctc agtgacagtc gcttttttcg taatgaactc ccacggatcg ccatcaaact tcgcgccggc tgcaatcgct ttcgtacagt cgatcacact gccgccgcca acggcaagca aaaattcaat tccttcccgt ctgcaaatgt ctaccccttt tttgacggtc gaaaggcgcg ggttcggttc gacgcctggc agttcaacga cttcggcgcc aatgtccgtc aataggctca tgacttcatc atatagtccg tttcgtttaa tgctgccgcc cccatagaca agcagcactt ttttgccata tttcggcact ttttttttga gctgctcaat ttgtcctctc ccaaaaatga gtttggtcgg attgcgaaac gtaaaatttt gcat
```

1.1.4 Selection and Optimization of Engineered Strains

The engineered strain is cultured continuously via any of several methods, including chemostat, pH-auxostat, or serial batch transfer, to select for naturally occurring mutations that impart a benefit upon cellular growth and 1-hexadecanol formation. Because ATP generation and NAD(P)H regeneration are both coupled to 1-hexadecanol formation in the engineered strain, evolutionary forces will select for cells that are better able to carry out this conversion.

1.1.5 Detection of 1-Hexadecanol 1-hexadecanol formation in cultured engineered strains is detected via gas chromatography-mass spectrometry (GC/MS) with or without an extraction step prior to analysis. See Steen et al., *Nature* 463:559-562 (2010); Aldai et al., *Journal of Chromotography* 1110:133-139 (2006).

Example 2

2.1 Diverting Central Metabolic Flux Through Oxaloacetate in *E. coli*

Figure 9:
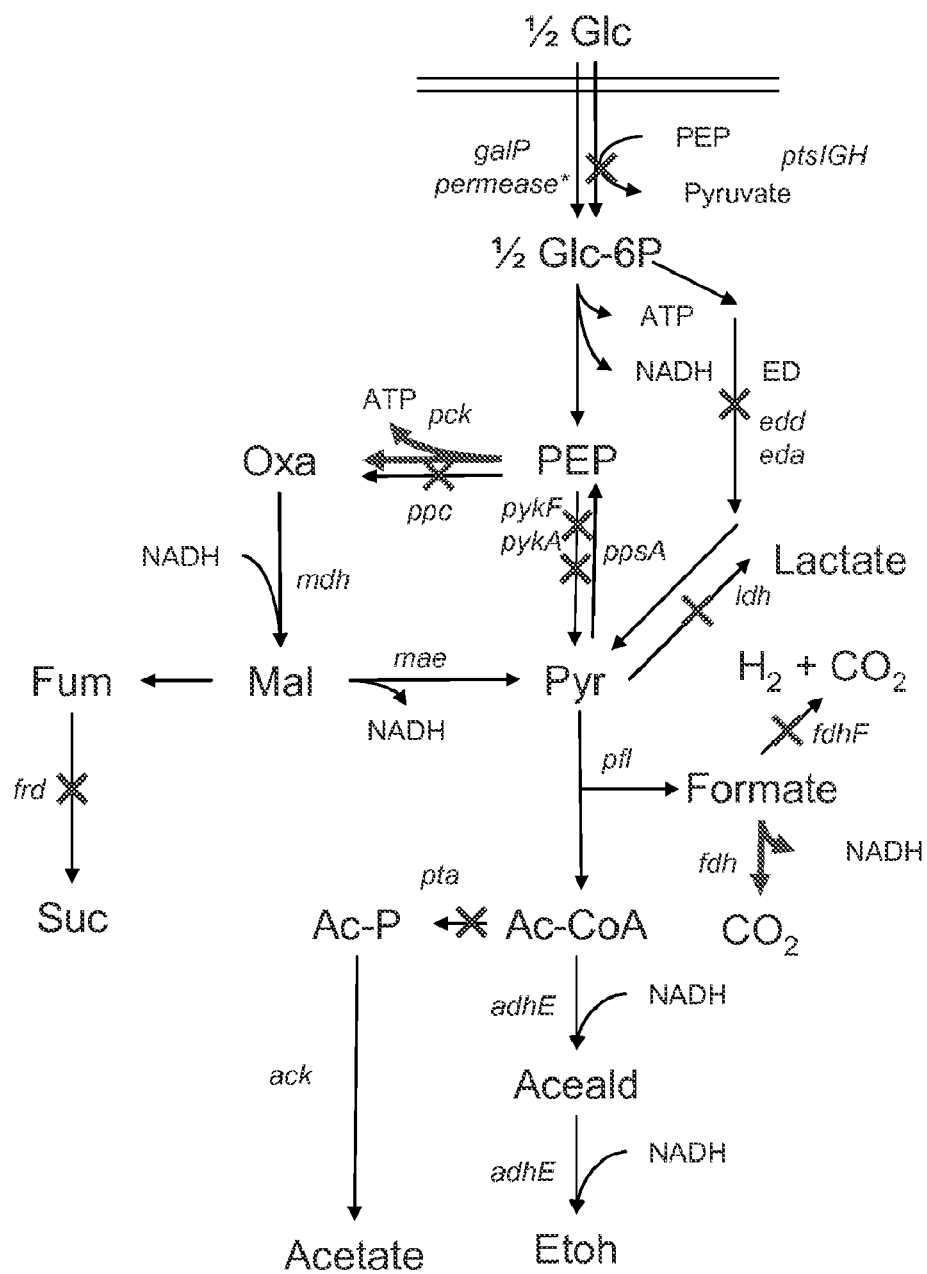
FIG. 9 depicts gene knockout and overexpression strategy to route anaerobic central metabolic flux through oxaloacetate as a key intermediate. Abbreviations: Glc—glucose, Glc-6P—glucose-6-phosphate, PEP—phosphoenolpyruvate, Oxa—oxaloacetate, Fum—fumarate, Mal—malate, Pyr—pyruvate, Ac-CoA—acetyl-CoA, Ac-P—acetylphosphate, Aceald—acetaldehyde, Etoh—ethanol.

This example describes engineering the central metabolic flux in *Escherichia coli* so that the majority of glycolytic flux passes from phosphoenolpyruvate to oxaloacetate rather than from phosphoenolpyruvate to pyruvate. See FIG. 9. This is accomplished via a series of gene deletions that inactivate competing pathways and gene overexpressions that activate desired pathways. Target genes are shown in Table 4. A set of minimal target gene deletions is shown in Table 5.

TABLE 4

Targets for Gene Inactivation

| *E. coli* gene name | description | locus tag [a] |
|---|---|---|
| edd | 6-phosphogluconate dehydratase | b1851 |
| ldhA | lactate dehydrogenase | b1380 |
| pta | phosphate acetyltransferase | b2297 |
| adhE | acetaldehyde dehydrogenase/alcohol dehydrogenase | b1241 |
| frdABCD | fumarate reductase (anaerobic) | b4151-b4154 |
| fdhF | formate dehydrogenase-H | b4079 |
| ppc | phosphoenolpyruvate carboxylase | b3956 |
| pykA | pyruvate kinase | b1854 |
| pykF | pyruvate kinase | b1676 |
| mdh | malate dehydrogenase | b3236 |
| maeA | malic enzyme NADH | b1479 |
| maeB | malic enzyme NADPH | b2463 |
| fadE | acyl coenzyme A dehydrogenase | b0221 |
| ptsI | PEP-protein phosphotransferase of PTS system | b2416 |
| PflB | pyruvate formate lyase | b0903 |
| aceEF | pyruvate dehydrogenase | b0114 |
| poxB | pyruvate oxidase | b0871 |
| mgsA | methylglyoxal synthase | b0963 |
| ppsA | phosphoenolpyruvate synthase | b1702 |

[a] locus tag numbers are given for the genome sequence of *E. coli* MG1655, which can be accessed via Genbank (Accession No. U00096) or the Kyoto Encyclopedia of Genes and Genomes (KEGG).

TABLE 5

Minimal Targets for Gene Inactivation

| gene name | description | locus tag |
|---|---|---|
| ldhA | lactate dehydrogenase | b1380 |
| pta | phosphate acetyltransferase | b2297 |
| adhE | acetaldehyde dehydrogenase/alcohol dehydrogenase | b1241 |
| pykA | pyruvate kinase | b1854 |
| pykF | pyruvate kinase | b1676 |
| mdh | malate dehydrogenase | b3236 |
| ptsI | PEP-protein phosphotransferase of PTS system | b2416 |

2.1.1 Deletion and Overexpression of Target Genes

Figure 11:
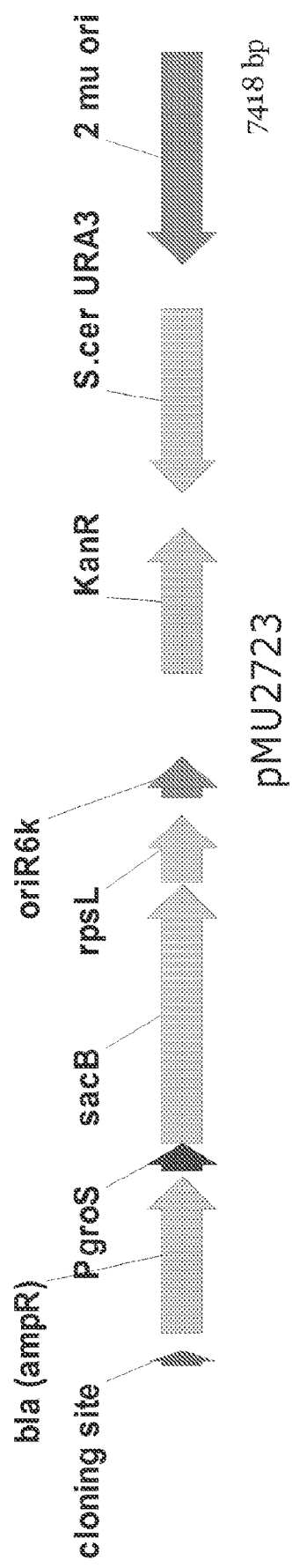
FIG. 11 depicts the vetor pMU2723 used to construct gene knockouts and chromosomal integrations in *E. coli*.

In order to perform gene modifications (either deletion or overexpression) in *E. coli* to redirect metabolic flux through oxaloacetate, 500 bp to 2000 bp flanking regions upstream and downstream of a target gene were amplified via PCR using primers (Table 6) and ligated into pMU2723 (FIG. 11) using standard molecular biology methods. See Shanks et al., AEM 72: 5027-5036 (2006). The pta::fdh and Pspc pckA promoter exchange modifications were performed by placement of the heterologous DNA (fdh or Pspc) between the two homologous flanking regions of the target gene, with appropriate design to allow either expression of fdh from the native pta promoter, or heterologous expression of the native pckA gene. The protocol used is described briefly below.

The starting strain, M2162 or subsequent progeny, was grown overnight in 8 mL of LB medium at 37° C. Two 500 mL baffled flasks, each containing 150 mL of LB, were pre-incubated at 37° C. and then inoculated with 2 mL of the overnight culture. These cultures were incubated at 37° C. with shaking until the OD reached 0.5 to 0.8 (checked OD every 20 min. after 2 hrs). The flasks were then placed in an ice bath for about 15 minutes after which the cultures were transferred to six 50 mL conical tubes. The tubes were spun at 4000 rpm for 8 minutes in a clinical swinging bucket centrifuge at 4° C. Following centrifugation, the supernatant was removed, about 10 mL of ice cold water was added to each tube, and the pellets were resuspended and transferred to two 50 mL tubes which were balanced to 50 mL with ice cold water. The tubes were centrifuged for 8 minutes in the conditions described above. The supernatants were removed and the pellets were resuspended with about 200 µL of cold water, after which 80 µL of the resuspended cells were transferred to a cold 1 mm gap cuvette which contained 2-4 µL of pre-added plasmid DNA targeting the gene of interest. The cuvette was electropulsed using an exponential decay pulse, 1.8 kV voltage, 25 µF capatance, 2000 resistance, and a 1 mm gap cuvette method. 1 mL of SOC medium was added to the cuvette and the entire volume was then transferred to a 14 mL falcon tube and incubated at 37° C. for 1 hour. 250 µL of cells were removed, plated on LB plates containing 50 µg/mL kanamycin, and incubated at 37° C. for 24-48 hours. Colony PCR was performed on kanamycin resistant colonies using one internal and one external primer to the site of integration with primers listed in Table 8. Two positive colonies we re-streaked on 50 µg/mL kanamycin plates and incubated overnight at 37° C. Two colonies were selected and grown in 5 mL of LB medium, either for 8 hours or overnight at 37° C. Serial dilutions of 1:10, 1:100, and 1:1000 of each LB culture were prepared, and 20 L of each dilution was plated on 10% w/v sucrose+500 µg/mL streptomycin plates. The plates were incubated overnight at either 37° C. or 42° C. Colony PCR was performed on 7 colonies from each initial LB culture with two primers, as listed in Table 8, external to the site of integration. Two positive colonies were re-streaked on 500 µg/mL streptomycin plates and incubated at 37° C. overnight. One colony from each plate was selected and re-patched on a kanamycin 50 µg/mL plate and a streptomycin 500 µg/mL plate. The patches that grew on the streptomycin but not the kanamycin plates were then used to make culture collection stocks.

TABLE 6

Primers Used to Create Gene Deletion and Gene Overexpression Plasmids for Routing Metabolic Flux Through Oxaloacetate

| Primer # | SEQ ID NO: | Primer sequence | Description |
| --- | --- | --- | --- |
| X12312 | 90 | TTTTGTCTGTCTTAATTTTTGGTATCATTATAGGATCTATGTAACCCAGGAAGCGGCAA | pta 1 |
| X12313 | 91 | ACGAGATTACTGCTGCTGTGCAGACTTTGCGTTCCATTGCACGGATCA | pta 2 |
| X12314 | 92 | TGATCCGTGCAATGGAACGCAAAGTCTGCACAGCAGCAGTAATCTCGT | pta 3 |
| X12315 | 93 | GATAACAATTTCACACAGGAAACAGCTATGACCATACGGCCTCTTCTCCCATACCAAAT | pta 4 |
| X12316 | 94 | TTTTGTCTGTCTTAATTTTTGGTATCATTATAGGAACGCAGTTGCTGGATATCAGAGGT | ldh 1 |
| X12317 | 95 | TACTGGTCAGAGCTTCTGCTGTCAACTCGTTCACCTGTTGCAGGTACT | ldh 2 |
| X12318 | 96 | AGTACCTGCAACAGGTGAACGAGTTGACAGCAGAAGCTCTGACCAGTA | ldh 3 |
| X12319 | 97 | GATAACAATTTCACACAGGAAACAGCTATGACCATTTGGGATGTGTGCATTACCCAACG | ldh 4 |
| X12320 | 98 | TTTTGTCTGTCTTAATTTTTGGTATCATTATAGGATACTGGTAAACGTCTGCCGACCAA | edd 1 |
| X12321 | 99 | ACAGCTTAGCGCCTTCTACAGCTTCGCGCGAACGTTCAATGATTCGAT | edd 2 |
| X12322 | 100 | ATCGAATCATTGAACGTTCGCGCGAAGCTGTAGAAGGCGCTAAGCTGT | edd 3 |
| X12323 | 101 | GAAACAATTTCACACAGGAAACAGCTATGACCATGCTGACATTGGCTATCCCTGCATT | edd 4 |
| X12324 | 102 | TTTTGTCTGTCTTAATTTTTGGTATCATTATAGGAGCGGGTCAATTTCCAGATAACGCA | frd 1 |
| X12325 | 103 | TCAGGAACAGGAATACGCGACCAAGATCGGCTTGAAAGGTTTGCACGA | frd 2 |
| X12326 | 104 | TCGTGCAAACCTTTCAAGCCGATCTTGGTCGCGTATTCCTGTTCCTGA | frd 3 |
| X12327 | 105 | GATAACAATTTCACACAGGAAACAGCTATGACCATGCGAAACATGCAACTGCCTTACCTT | frd 4 |

TABLE 6-continued

Primers Used to Create Gene Deletion and Gene Overexpression Plasmids for Routing Metabolic Flux Through Oxaloacetate

| Primer # | SEQ ID NO: | Primer sequence | Description |
|---|---|---|---|
| X12328 | 106 | TTTTGTCTGTCTTAATTTTTGGTATCATTATAGGATGGACCGAATGGACGATGGAGTTT | pfl 1 |
| X12329 | 107 | AGAATGCCTTTCACGCGTTCCATGTCGTTGCTTTATAGACACCCGCCT | pfl 2 |
| X12330 | 108 | AGGCGGGTGTCTATAAAGCAACGACATGGAACGCGTGAAAGGCATTCT | pfl 3 |
| X12331 | 109 | GATAACAATTTCACACAGGAAACAGCTATGACCATTTCCGTTAACGATACGCTTCGGGT | pfl 4 |
| X12332 | 110 | TTTTGTCTGTCTTAATTTTTGGTATCATTATAGOAATTCAAACGTTATGCCCGACGCTG | ppc 1 |
| X12333 | 111 | AGCGGGTCGGTGTAAATATTCCGTTCCTTGATGGTTTCTCCCAGCACT | ppc 2 |
| X12334 | 112 | AGTGCTGGGAGAAACCATCAAGGAACGGAATATTTACACCGACCCGCT | ppc 3 |
| X12335 | 113 | GATAACAATTTCACACAGGAAACAGCTATGACCATTTGAAATTAGCCAGTGGCGGCAAG | ppc 4 |
| X12336 | 114 | TTTTGTCTGTCTTAATTTTTGGTATCATTATAGGACAGCCGCTACATTAAAGGCACCAA | ptsI 1 |
| X12337 | 115 | CCAGCAGCGGCAGATCAAATTCAATGGCGGTTCGACTTTAGCCTGTAT | ptsI 2 |
| X12338 | 116 | ATACAGGCTAAAGTCGAACCGCCATTGAATTTGATCTGCCGCTGCTGG | ptsI 3 |
| X12339 | 117 | GATAACAATTTCACACAGGAAACAGCTATGACCATATGGTTTAGCGGCTATTTGCGTGC | ptsI 4 |
| X12340 | 118 | TTTTGTCTGTCTTAATTTTTGGTATCATTATAGGATGGCGAATGGCACTCCCTATGTTA | pykA 1 |
| X12341 | 119 | TGACAATCACCAGGTCACCAGACATCCGAATGAAATAACGCCGCGATG | pykA 2 |
| X12342 | 120 | CATCGCGGCGTTATTTCATTCGGATGTCTGGTGACCTGGTGATTGTCA | pykA 3 |
| X12343 | 121 | GATAACAATTTCACACAGGAAACAGCTATGACCATTGTTGATGAGATGTTTGCCACCGC | pykA 4 |
| X12344 | 122 | TTTTGTCTGTCTTAATTTTTGGTATCATTATAGGAATGCTGTACGTAATACGCCTGCGA | pykF 1 |
| X12345 | 123 | TCTTTAACAAGCTGCGGCACAACGATGGGAGAAACTTGCTTTCTGGGC | pykF 2 |
| X12346 | 124 | GCCCAGAAAGCAAGTTTCTCCCATCGTTGTGCCGCAGCTTGTTAAAGA | pykF 3 |
| X12347 | 125 | GATAACAATTTCACACAGGAAACAGCTATGACCATATCTTTAGCAGCCTGAACGTCGGA | pykF 4 |
| X13802 | 126 | TTATAGGTTAATGTCATGATAATAATGGTTTCTTCCGTCAAAGGGCAAATCACCGAAA | fdhF 1 |
| X13803 | 127 | GGGTTCCGCGCACATTTCCCCGAAAAGTGCCACCACTCGGAATAACCGGTTCGGGAAA | fdhF 2 |
| X13804 | 128 | CGCCTTCTATCGCCTTCTTGACGAGTTCTTCTGATACGACAAAGCGTTCGTCGCTTCA | fdhF 3 |
| X13805 | 129 | ACTGTTGGGAAGGGCGATCGGTGCGGGCCTCTTCGAATGAAGCCCAGTTCGCCCATTT | fdhF 4 |
| X14576 | 130 | TTATAGGTTAATGTCATGATAATAATGGTTTCTTGCGGATGCGAAGGCTTTGTTGTAT | Pspc pckA 1 |
| X14577 | 131 | TGGGTAGAAAAAATAAACGGCTCAGATTCCTGTCACGAAACGGTTGCT | Pspc pckA 2 |
| X14578 | 132 | AGCAACCGTTTCGTGACAGGAATCTGAGCCGTTTATTTTTTCTACCCA | Pspc pckA 3 |
| X14579 | 133 | GGTCAAACCATTGTTAACGCGCATTTTAGTGCTCCGCTAATGTCAACT | Pspc pckA 4 |

TABLE 6-continued

Primers Used to Create Gene Deletion and Gene Overexpression Plasmids for Routing Metabolic Flux Through Oxaloacetate

| Primer # | SEQ ID NO: | Primer sequence | Description |
|---|---|---|---|
| X14580 | 134 | AGTTGACATTAGCGGAGCACTAAAATGCGCGTTAACAATGGTTTGACC | Pspc pckA 5 |
| X14581 | 135 | GGGTTCCGCGCACATTTCCCCGAAAAGTGCCACCTAGAAGCGATACCTTTCAGCGGCA | Pspc pckA 6 |
| X14588 | 136 | TTATAGGTTAATGTCATGATAATAATGGTTTCTTTCTATGTAACCCAGGAAGCGGCAA | pta::fdh3 1 |
| X14589 | 137 | TGGGTAGAAAAAATAAACGGCTCACTTTGCGTTCCATTGCACGGATCA | pta::fdh3 2 |
| X14590 | 138 | TGATCCGTGCAATGGAACGCAAAGTGAGCCGTTTATTTTTCTACCCA | pta::fdh3 3 |
| X14591 | 139 | ATAAAGAACTAAGACAATCTTCATTTTAGTGCTCCGCTAATGTCAACT | pta::fdh3 4 |
| X14592 | 140 | AGTTGACATTAGCGGAGCACTAAAATGAAGATTGTCTTAGTTCTTTAT | pta::fdh3 5 |
| X14593 | 141 | ACGAGATTACTGCTGCTGTGCAGACTATTTCTTATCGTGTTTACCGTA | pta::fdh3 6 |
| X14594 | 142 | TACGGTAAACACGATAAGAAATAGTCTGCACAGCAGCAGTAATCTCGT | pta::fdh3 7 |
| X14595 | 143 | GGGTTCCGCGCACATTTCCCCGAAAAGTGCCACCACGGCCTCTTCTCCCATACCAAT | pta::fdh3 8 |
| X15570 | 144 | TTATAGGTTAATGTCATGATAATAATGGTTTCTTTGCGATCCGTAGCAGACACCATAA | maeA 1 |
| X15571 | 145 | GAATACTGCGCCAGCGTTTCACTTCGTTCCGCTTGTTCTTCGATGGTT | maeA 2 |
| X15572 | 146 | AACCATCGAAGAACAAGCGGAACGAAGTGAAACGCTGGCGCAGTATTC | maeA 3 |
| X15573 | 147 | GGGTTCCGCGCACATTTCCCCGAAAAGTGCCACCCATCAATGGCGATCACTTTGGCGT | maeA 4 |
| X15574 | 148 | TTATAGGTTAATGTCATGATAATAATGGTTTGAATTGACCGCCAGTTTGTCACACG | maeB 1 |
| X15575 | 149 | TCGCCGTGCATTTCACCATCAATCGAGCGCGGCGACAACTTCAATAAA | maeB 2 |
| X15576 | 150 | TTTATTGAAGTTGTCGCCGCGCTCCTATTGATGGTGAAATGCACGGCGA | maeB 3 |
| X15577 | 151 | GGGTTCCGCGCACATTTCCCCGAAAAGTGCCACCGCCATAAATCACCAATGCACCGCT | maeB 4 |
| X15578 | 152 | TTATAGGTTAATGTCATCTATAATAATGGTTTCTTCAGCTTGGCAGGCAGTAAACCATTT | mdh 1 |
| X15579 | 153 | TCAAATGCGCTCAGGGTACCGATATTCTGAACCTGAAGGCAGTTGGGT | mdh 2 |
| X15580 | 154 | ACCCAACTGCCTTCAGGTTCAGAATATCGGTACCCTGAGCGCATTTGA | mdh 3 |
| X15581 | 155 | GGGTTCCGCGCACATTTCCCCGAAAAGTGCCACCACTGGCGGTTTACCTACCATTCCA | mdh 4 |
| X15586 | 156 | TTATAGGTTAATGTCATGATAATAATGGTTTCTTTCGACATCGCTATTGTCACCACCA | adhE 1 |
| X15587 | 157 | TTTCGGAAGTTTGTGCCACAACATAATGCTCTCCTGATAATGTTAAAC | adhE 2 |
| X15588 | 158 | GTTTAACATTATCAGGAGAGCATTATGTTGTGGCACAAACTTCCGAAA | adhE 3 |
| X15589 | 159 | GGGTTCCGCGCACATTTCCCCGAAAAGTGCCACCCCAAGTGGTCGGCAATTTCAGCAT | adhE 4 |

Figure 10:
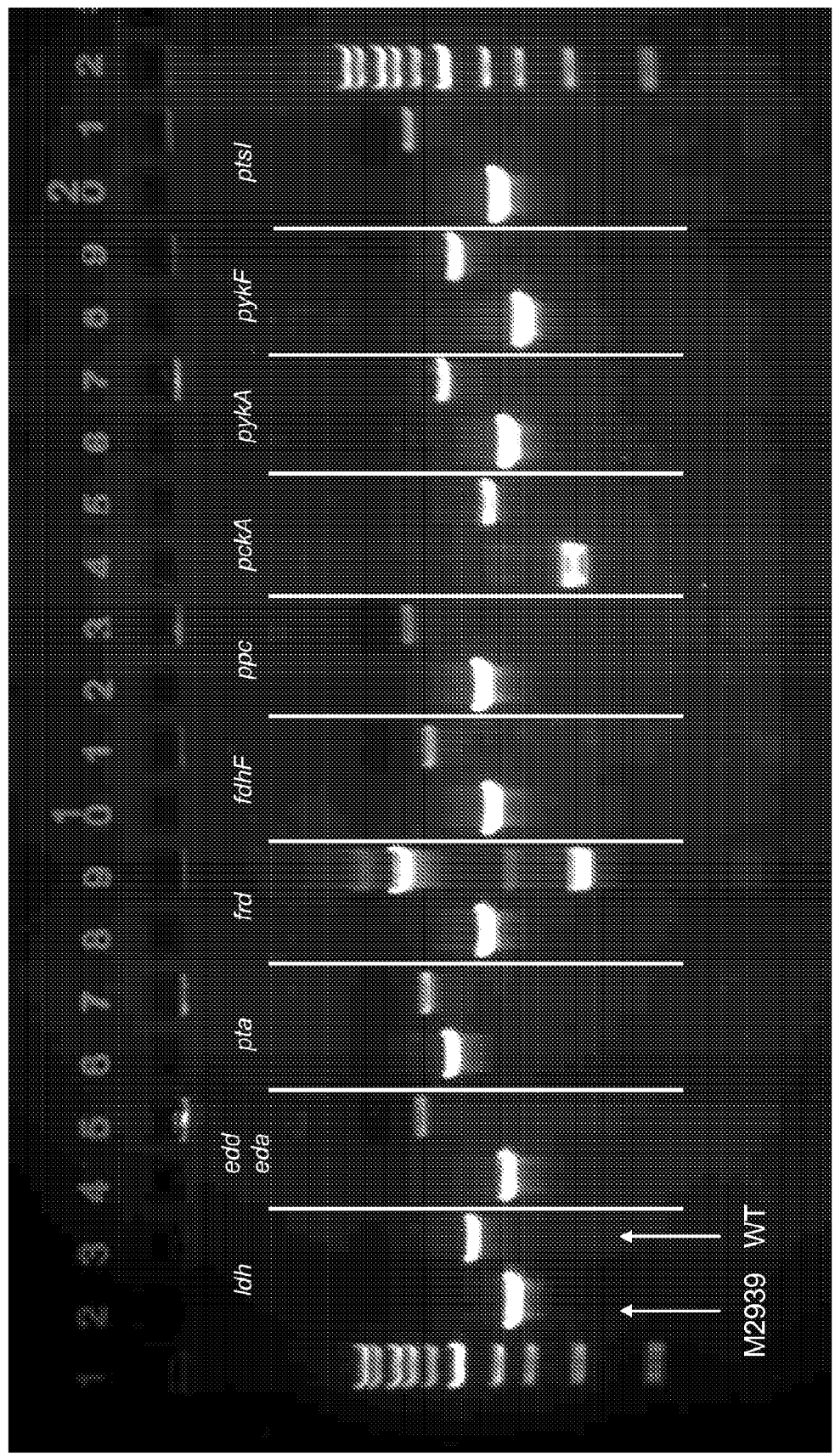
FIG. 10 is an agarose gel image showing deletions and overexpressions of target genes in the *E. coli* chromosome to redirect metabolic flux through oxaloacetate.

Gene modifications were confirmed on an agarose gel. See FIG. 10 and Table 7. Primers external to each region of interest were used to amplify DNA (Table 8), which was subsequently run on an agarose gel and stained with ethidium bromide to visualize DNA length. The ladder shown in lanes 1 and 22 of FIG. 10 is New England Biolabs 1 kb. DNA was amplified from strains M2939 (deletion and overexpression strain) and M2162 (wildtype). See Table 9 for a description of the bacterial strains.

TABLE 7

Predicted Size of Wildtype and Modified Target Genes

| Target | WT length (bp) | KO length (bp) |
|---|---|---|
| ldhA | 2686 | 1855 |
| edd | 4343 | 1931 |
| pta::fdh | 3992 | 3186 |
| frd | 5358 | 2241 |
| fdhF | 3927 | 2141 |
| ppc | 4739 | 2321 |
| pckA (promoter exchange) | 2003 | 1053/958 * |
| pykA | 3204 | 1803 |
| pykF | 2863 | 1594 |
| ptsI | 4418 | 1938 |

* after psiI restriction digest of PCR product to distinguish the wildtype (2003 bp) and promoter exchange (2011 bp) alleles.

TABLE 8

Primers Used to Verify Genome Alterations

| Primer # | SEQ ID NO: | Primer sequence | Description |
|---|---|---|---|
| X12354 | 160 | TTGCTGTATTTGACACCGCGTTCC | pta ext 1 |
| X12355 | 161 | TTTCACGAAAGAAGCGGTCGGACT | pta ext 2 |
| X12356 | 162 | GGCAAGTTTAACGTCGCAGTAGCA | ldh ext 1 |
| X12357 | 163 | TTTATGGCGGTGTCGTTTGGCTTG | ldh ext 2 |
| X12358 | 164 | ATATCTGGAAGAAGAGGGCGCGAA | edd ext 1 |
| X12359 | 165 | GATGCATTACGCCGTGTGGTTGAA | edd ext 2 |
| X12360 | 166 | AACAGCAATTGTAGCAGCGTGTCG | frd ext 1 |
| X12361 | 167 | TTGTTTGCCAGCATCACGATACCC | frd ext 2 |
| X12362 | 168 | CTGGGCGTTTATGCTTGCCGTATT | pfl ext 1 |
| X12363 | 169 | AGTCGTCAGTTGTGAGCTCGACTT | pfl ext 2 |
| X12364 | 170 | TATTCACGGTGGCGACGCTTCTAA | ppc ext 1 |
| X12365 | 171 | CGCCTGTTGCAGGATTTCAATGGT | ppc ext 2 |
| X12366 | 172 | AAAGCGTTAGGTGCAAACCTGGTG | pts ext 1 |
| X12367 | 173 | ATTGCCGTGCCTGCTATCAAACAG | pts ext 2 |
| X12368 | 174 | GCTATGGCACTGGAAGCCAATGTT | pykA ext 1 |
| X12369 | 175 | AGAACGTAGTGAAGCTGAACGCGA | pykA ext 2 |
| X12370 | 176 | TGAAGCTTACCGCCTCATCCTGAA | pykF ext 1 |
| X12371 | 177 | AGAATGGTGAACCAGAGCAAGGGA | pykF ext 2 |
| X12801 | 178 | GATTGATTACGCGGTGAAAGCGCA | fdh ext 1 |
| X12802 | 179 | ACACCCGGTATCAAACCCTTCCAT | fdh ext 2 |
| X14574 | 180 | CCGTGGCGATTAACGTGAACAACT | pckA ext 1 |
| X14575 | 181 | AGTCGATAGTGCCATCTTCACGCA | pckA ext 2 |
| X15500 | 182 | ACTGTTCCCTTCCCGCGTTTGATA | maeA ext 1 |
| X15591 | 183 | GCATCAACTGCCGAGTTAAACGCA | maeA ext 2 |
| X15592 | 184 | AGGTCGAAGCCAGCTTGATCAGAA | maeB ext 1 |
| X15593 | 185 | CGCTGACGGTTTGTGATAACGCTT | maeB ext 2 |
| X15594 | 186 | TACCTTCTGCTTTGCCCAGTGAGT | mdh ext 1 |
| X15595 | 187 | TGAAGCATTGCTGGTGGGATCTGA | mdh ext 2 |
| X15596 | 188 | AGTGGCACCACACCAATGCTTTCA | adhE ext 1 |
| X15597 | 189 | TGAACGCCAGCTTCACGGATAGAT | adhE ext 2 |
| X13673 | 300 | ATACGGGATAATACCGCGCCACAT | internal 1 |
| X13674 | 301 | CCATTCGACCACCAAGCGAAACAT | internal 2 |

TABLE 9

Lineage of Strains From M2162 to M2939

| M number | Genotype | Parent |
|---|---|---|
| M2162 | strepR | MG1655 |
| M2264 | strepR, Δedd Δeda | M2162 |
| M2273 | strepR, Δedd Δeda Δldh | M2264 |
| M2348 | strepR, Δedd Δeda Δldh Δppc | M2273 |
| M2371 | strepR, Δedd Δeda Δldh Δppc ΔfdhF | M2348 |
| M2379 | strepR, Δedd Δeda Δldh Δppc ΔfdhF Δfrd | M2371 |
| M2492 | strepR, Δedd Δeda Δldh Δppc ΔfdhF Δfrd ΔPpckA::Pspc pckA | M2379 |
| M2590 | strepR, Δedd Δeda Δldh Δppc ΔfdhF Δfrd ΔPpckA::Pspc pckA Δpta::fdh3 | M2492 |
| M2645 | strepR, Δedd Δeda Δldh Δppc ΔfdhF Δfrd ΔPpckA::Pspc pckA Δpta::fdh3 ΔpykF | M2590 |
| M2698 | strepR, Δedd Δeda Δldh Δppc ΔfdhF Δfrd ΔPpckA::Pspc pckA Δpta::fdh3 ΔpykF ΔpykA | M2645 |
| M2939 | Δpta::fdh3 ΔpykF ΔpykA ΔptsI | M2909 |

2.2 Creating a Balanced Reduction/Oxidation Pathway During Anaerobic Fatty Acid Production Reduction and oxidation (redox) reactions play a key role in catabolic metabolism, allowing the transfer of electrons from one compound to another, and in the process, creating free energy for use elsewhere in cellular metabolism. To facilitate transfer of electrons from one compound to another, cells use redox co-factors to shuttle electrons. Several compounds and proteins can function as redox co-factors—the most relevant for anaerobic growth on carbohydrates are the nicotinamide adenine dinucleotides NADH and NADPH, and the iron-sulfur protein Ferredoxin (Fd).

Since NADH, NADPH, and Fd function as electron shuttles, they must discharge as many electrons as they accept, i.e., their net electron accumulation is zero. Catabolic metabolism can be thought of in two parts: carbohydrate deconstruction, where electrons are placed onto redox co-factors, and end-product construction, where electrons are removed from redox co-factors. In order for a metabolic pathway to function efficiently and at high yield, the type of co-factors used in carbohydrate deconstruction must balance those used in end product construction.

During carbohydrate deconstruction, which in the anaerobic fatty acid pathway ultimately results in acetyl-CoA, electrons are removed at two steps: the conversion of glyceraldehyde-3-phosphate to 1,3-biphosphoglycerate+2e$^-$ and the conversion of pyruvate to acetyl-CoA+$CO_2$+2e$^-$. In *E. coli*, NAD+ is used as electron acceptor for the first conversion. For the second conversion, E. coli employs a NAD+ linked pyruvate dehydrogenase during aerobic growth, and pyruvate formate lyase (pfl) and a formate dehydrogenase directly linked to hydrogen production (fdhF) to produce formate or $H_2$ from the 2e removed from pyruvate.

E. coli strains have been engineered to produce ethanol from acetyl-CoA at high yield via anaerobic expression of pyruvate dehydrogenase (PDH) (Kim et al., AEM 73: 1766-1771 (2007)) or via heterologous expression of NAD+ formate dehydrogenase (Berrios-Rivera et al., Met Eng 4:217-229 (2002)). In both wildtype and these engineered E. coli strains, NADH is the primary redox co-factor.

In contrast, the electron accepting reactions of fatty acid elongation require either exclusively NADPH or 1:1 stoichiometric levels of NADPH and NADH, depending on the co-factor specificity (NADPH or NADH) of enoyl-ACP reductase.

In order to balance the NADPH necessary for fatty acid elongation, the redox enzymes involved in carbohydrate deconstruction should be engineered to produce NADPH. In Table 10 below, different redox enzyme systems are described that can produce, per 2 glucose molecule, 2 NADH, 1 NADH and 1 NADPH, or 2 NADPH. Use of one of these systems in a host microorganism, or a combination thereof, will allow for an overall balanced co-factor pathway for anaerobic fatty acid production. In addition to, or instead of, using these systems, the enzymes can be modified to have different cofactor specifities.

TABLE 10

Enzymes for an overall balanced co-factor pathway for anaerobic fatty acid production

| FIG. 32 | Carbohydrate deconstruction reactions | Redox enzymes | NADH | NADPH |
|---|---|---|---|---|
| A | ½ glucose -> acetyl-CoA + $CO_2$ + 4e$^-$ | NAD+ GAPDH, PDH | 2 | 0 |
| B | ½ glucose -> acetyl-CoA + $CO_2$ + 4e$^-$ | NAD+ GAPDH, PFL, NAD+ FDH | 2 | 0 |
| C | ½ glucose -> acetyl-CoA + $CO_2$ + 4e$^-$ | NAD+ GAPDH, PFL, NADP+ FDH | 1 | 1 |
| D | ½ glucose -> acetyl-CoA + $CO_2$ + 4e$^-$ | NAD+ GAPDH, PNO | 1 | 1 |
| E | ½ glucose -> acetyl-CoA + $CO_2$ + 4e$^-$ | NADP+ GAPDH, PFL, NAD+ FDH | 1 | 1 |
| F | ½ glucose -> acetyl-CoA + $CO_2$ + 4e$^-$ | NADP+ GAPDH, PFL, NADP+ FDH | 0 | 2 |
| G | ½ glucose -> acetyl-CoA + $CO_2$ + 4e$^-$ | NAD+ GAPDH, POR, Fd, NFN | 0 | 2 |
| H | ½ glucose -> acetyl-CoA + $CH_2O_2$ + 2e$^-$ | NAD+ GAPDH, PFL | 1 | 0 |
| | End product construction reactions | Redox enzymes | NAD+ | NADP+ |
| I | acetyl-CoA + 4e- + acyl$_{(n)}$-ACP -> acyl$_{(n+2)}$-ACP | FabG (NADPH), FabI (NADH) | 1 | 1 |
| J | acetyl-CoA + 4e- + acyl$_{(n)}$-ACP -> acyl$_{(n+2)}$-ACP | FabG (NADPH), FabI (NADPH) | 0 | 2 |
| K | acyl$_{(n+2)}$-ACP + 4e- -> acyl alcohol (fatty alcohol) | AcDH, ADH | 0-2 | 0-2 |
| L | acyl$_{(n+2)}$-ACP + $H_2O$ -> acyl acid (fatty acid) + 2 $CH_2O_2$ | BTE | 0 | 0 |

Abbreviations: GAPDH—glycerol-3-phospliosate dehydrogenase, PFL—pyruvate formate lyase, PDH—pyruvate dehydrogenase, PNO—pyruvate:NADP+ oxidoreductase, POR—pyruvate:ferredoxin oxidoreductase, Fd—ferredoxin, NFN—NADH ferredoxin:NADP+ oxidoreductase, FabG—β-ketoacyl-ACP reductase, FabI enoylacyl-ACP reductase, AAR—acyl-ACP reductase, ADH—alcohol dehydrogenase, BTE—acyl-ACP thioesterase, AdhE—bifunctional acetaldehyde/alcohol dehydrogenase.

Figure 12:
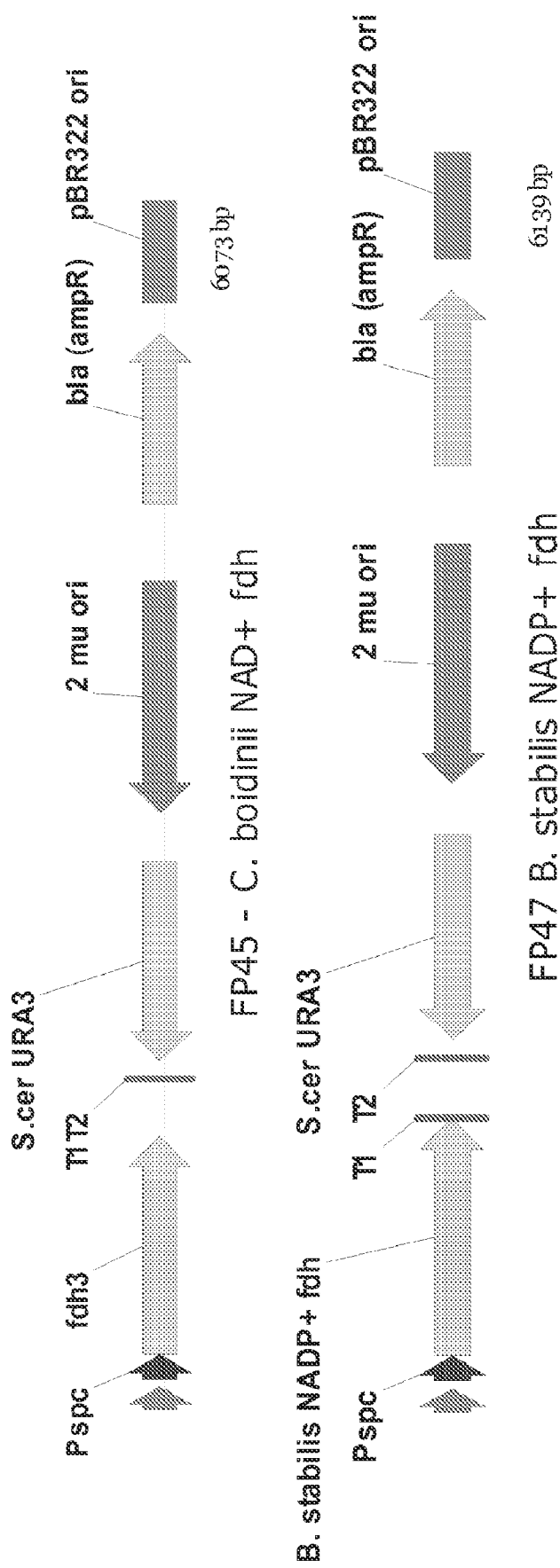
FIG. 12 depicts vectors FP45, FP47, FP66, FP67, FP68, and FP75, which are examples of heterologous redox enzymes designed for expression in *E. coli* to modify the native carbohydrate deconstruction pathway.
Figure 12:
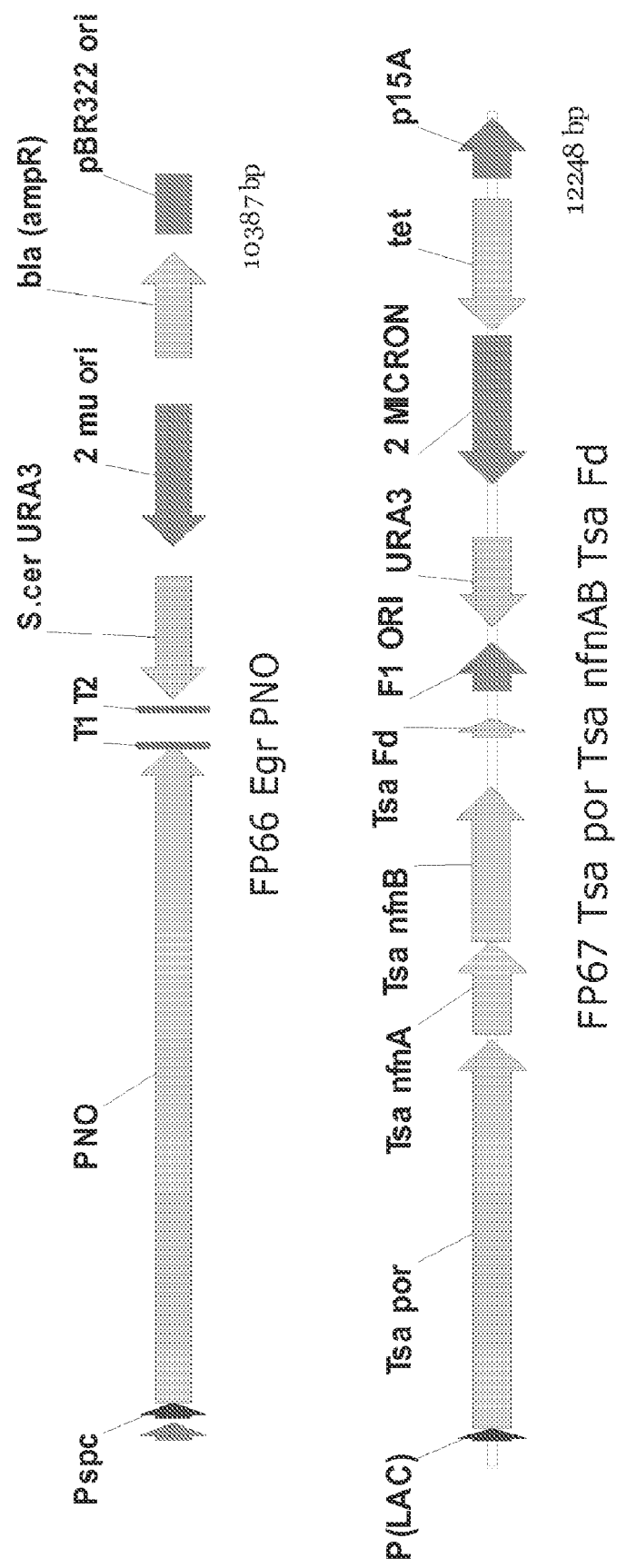
Figure 12:
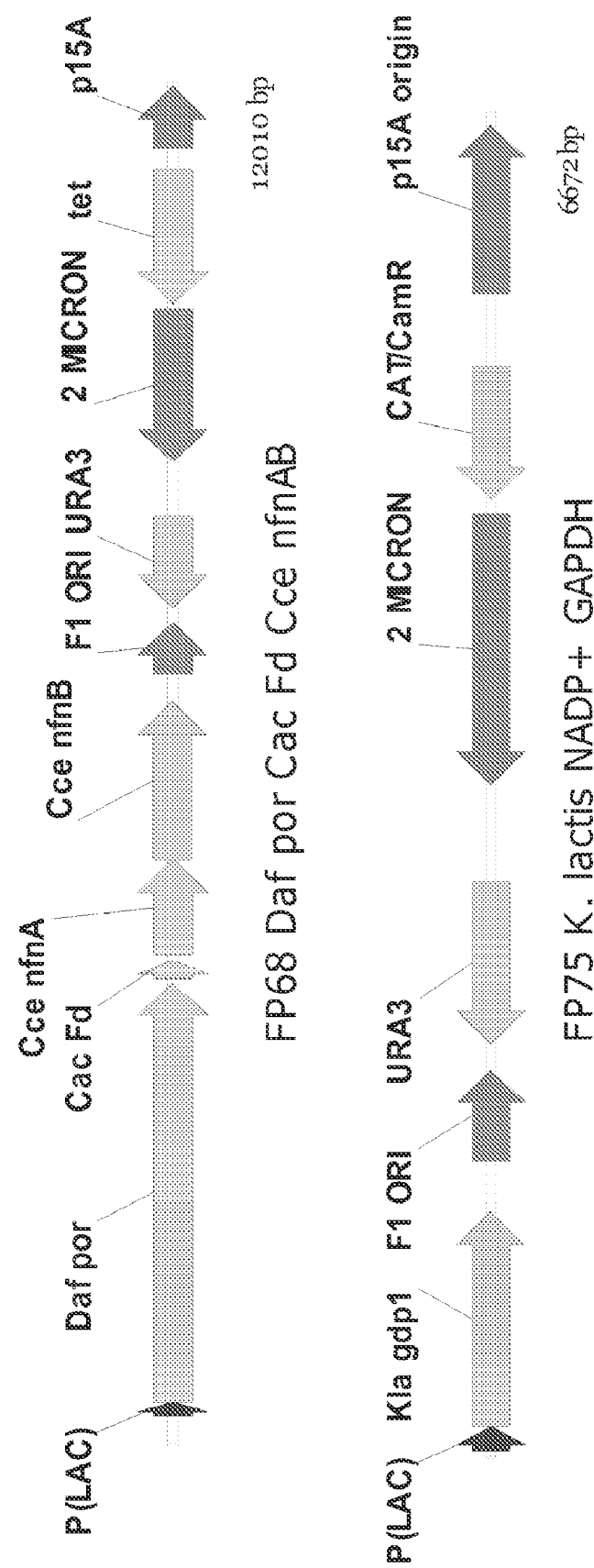

Enzymes used in the carbohydrate deconstruction reactions can be cloned into plasmids for expression in a host strain. For example, plasmids FP45, FP47, FP66, FP67, FP68, and FP75 are examples of heterologous redox enzymes designed for expression in E. coli to modify the native carbohydrate deconstruction pathway. See FIG. 12. Genes or gene operons are cloned under expression of either the constitutively active Pspc ribosomal promoter or the inducible Plac promoter. Cloning was performed via PCR amplification, using the primers listed in Table 11, or direct DNA synthesis of the desired gene products, followed by yeast gap-repair cloning with 30-60 bp homologous flanking regions. See Shanks et al., AEM 72:5027-5036 (2006). Transformed yeasts were selected via growth on SD-ura minimal medium for the presence of the ura3 gene. Plasmids were recovered from ura3+ yeast strains by standard miniprep (Qiagen) or phenol extract and ethanol precipitation. Crude yeast plasmid preps were then used to transform E. coli TOP10 cells (Invitrogen) using selection with the plasmid appropriate antibiotic, either carbenicillin (100 μg/mL), tetracycline (15 μg/mL), or chloramphenicol (25 μg/mL). E. coli mini-prepped plasmids were confirmed by restriction digest and agarose gel analysis.

TABLE 11

Primers for the Construction of Redox Balancing Plasmids FP45, FP47, FP67, FP68, and FP75 (FP66 was created from direct DNA synthesis (SEQ ID NO: 206), so no primers were used during its construction)

| Primer # | SEQ ID NO: | Primer sequence | Description | |
|---|---|---|---|---|
| X16072 | 190 | TCTCAGTAGTAGTTGACATTAGCGGAGCACTAAAATGAAGATTGTCTTAGTTCTTTAT | FP45 | 1 |
| X16073 | 191 | CAGTCTTTCGACTGAGCCTTTCGTTTTACGGCCGCTATTTCTTATCGTGTTTACCGTA | FP45 | 2 |
| X16082 | 192 | TCTCAGTAGTAGTTGACATTAGCGGAGCACTAAAATGGCAACCGTTCTGTGTGTTCTG | FP47 | 1 |
| X16083 | 193 | CAGTCTTTCGACTGAGCCTTTCGTTTTACGGCCGTTAGGTCAGACGATAGCTCTGTGC | FP47 | 2 |
| X16829 | 194 | TGTGAGCGGATAACAATTTCACACAGGAAACAGCTATGTCGAAGGTTATGAAAACCATG | FP67 | 1 |
| X16064 | 195 | GCTTTCACACCTCCAAGATTTCGTCTAATTTTGTTCAGCAAGCTTCTT | FP67 | 2 |
| X16065 | 196 | AAGAAGCTTGCTGAACAAAATTAGACGAAATCTTGGAGGTGTGAAAGC | FP67 | 3 |
| X16830 | 197 | CCTCGAGGTCGACGGTATCGATAAGCTTGATATCTTATTCAGCCTTAATAGCTCCTGTT | FP67 | 4 |
| X16831 | 198 | TGTGAGCGGATAACAATTTCACACAGGAAACAGCTATGGGAAAGAAAATGATGACGACT | FP68 | 1 |
| X16075 | 199 | TACACCTCCTTATCTTAATAGGCGTTCTACTTCTTCGTCCGCTTGCTGAG | FP68 | 2 |
| X16076 | 200 | CTCAGCAAGCGGACGAAGAAGTAGAACGCCTATTAAGATAAGGAGGTGTA | FP68 | 3 |
| X16077 | 201 | CCCGTCTGATATTTATGGTTCTACGACTTACTCTTGAACTGGAGCTCCTAC | FP68 | 4 |
| X16078 | 202 | GTAGGAGCTCCAGTTCAAGAGTAAGTCGTAGAACCATAAATATCAGACGGG | FP68 | 5 |
| X16832 | 203 | CCCTCGAGGTCGACGGTATCGATAAGCTTGATATCCTATTGGTTCTGCCGGATATAT | FP68 | 6 |
| X16981 | 204 | TGTGAGCGGATAACAATTTCACACAGGAAACAGCTATGCCCGAtATGACAAACGAATCT | FP75 | 1 |
| X16982 | 205 | CCCTCGAGGTCGACGGTATCGATAAGCTTGATATCTTAAACACCAGCTTCGAAGTCCTT | FP75 | 2 |

Sequence of the PNO gene and flanking regions used to create FP66 (SEQ ID NO: 206):
tgagccgtttattttttctacccatatccttgaagcggtgttataatgccgcgccctcgatatgggattttaacgacctgattttcggg
tctcagtagtagttgacattagcggagcactaaaatgaaacagagcgttcgtccgattattagcaatgttctgcgtaaagaagttgc
cctgtatagcaccattattggtcaggataaaggtaaagaaccgacaggtcgtacctataccagcggtccgaaaccggcaagcca
tattgaagttccgcatcatgttaccgttccggcaaccgatcgtaccccgaatccggatgcacagttttttcagagcgttgatgtagc
caggcaaccagccatgttgcatatgccctgagcgataccgcatttatctatccgattaccccgagcagcgttatgggtgaactggc
agatgtttggatggcacagggtcgtaaaaatgcctttggtcaggttgttgatgttcgtgaaatgcagagcgaagccggtgcagcg
ggtgcactgcatggtgcactggcagccggtgcgattgcaaccaccttaccgcaagccagggtctgctgctgatgattccgaata
tgtataaaatcgcaggcgaactgatgccgagcgttattcatgttgcagcacgtgagctggcaggtcatgcactgagcattttggtg
gtcatgcagatgttatggcagttcgtcagaccggttgggcaatgctgtagccataccagttcagcagagccatgatatggccactg
attagccatgtggcaaccctgaaaagcagcattccgtttgttcattttttttgatggttttcgcaccagccacgaagtgaacaaaatca
aaatgctgccgtatgccgaactgaaaaaactggttccgcctggccaccatggaacagcattgggcacgtagcctgaatccgatgc
atccgaccattcgtggcaccaatcagagcgcagatatctattttcagaatatggaaagcgccaaccagtattataccgatctggca
gaagttgttcaagaaaccatggatgaagttgcaccgtatattggtcgtcattacaaaatctttgagtatgttggtgcaccggatgcag
aagaggtgaccgttctgatgggtagcggtgccaccaccgttaatgaagcagttgatctgctggttaaacgcggtaaaaaagttgg
tgcagttctggttcatctgtatcgtccgtggtcaaccaaaagcatttgaaaaagttctgccgaaaaccgtgaaacgtattgcagcact
ggatcgttgcaaagaagttaccgcactgggcgaaccgctgtatctggatgttagcgccaccctgaacctgtttccggaacgtcag
aatgttaaagttattggtggtcgttatggtctgggtagcaaagatttcattccggaacatgcactggccatttatgcaaatctggcaa
gcgaaaatccgattcagcgttttaccgttggtattaccgatgatgttaccgccaccagcgtgccgtttgttaatgaacgtgttgatac
cctgccggaaggcacccgtcagtgtgttttttggggtattggtagtgatggcaccgttggtgcaaatcgtagcgcagttcgtattatt
ggtgataatagcgatctgatggtgcaggcgtattttcagtttgatgcattaaaagcggtggtgttaccagcagccatctgcgttttg
gtcctaaaccgattaccgcacagtatctggttaccaatgcagattatattgcctgccacttttcaagagtatgtgaaacgttttgatatg
ctggatgcaattcgtgaaggtggcacctttgttctgaatagccgttggaccaccgaagatatggaaaaagaaaatttccggcagatttt
cgtcgtaatgtggcacagaaaaaagtgcgcttttataacgttgatgcccgtaaaatttgcgatagctttggtctgggcaaacgcatt
aacatgctgatgcaggcatgttttttcaaactgagcggtgttctgccgctggccgaagcacagcgtctgctgaatgaaagcattgtt
catgagtatggcaaaaaaggtggtaaagtggtggaaatgaatcaggcagttgttaatgcagtgtttgccggtaccaccggatgcag
agttcaggttccggcagcatgggcaaatgcagttgataccagcaccgtcaccccgaccggtattgaatttgttgataaaatcatgc
gtccgtttgatggatttcaaaggtgatcagctgccggttagcgttatgacaccgggtggtacatttccggttggcaccaccccagtat
gcaaaacgtgcaattgcggcatttattttcgcagtggattccggcaaattgtacccagtgtaattattgcagctatgtttgtccgcatg
caaccattcgtccgtttgtgctgaccgatcaagaagtgcagctggccaccgaaaagcttttaccccgtaaagcaaaaggtgattat
cagggtatgaactttcgtattcaggttgcaccggaagattgtaccggttgtaccggtttgtgttgaaacctgtccggatgatgcactgg
aaatgaccgatgcgtttaccgccacaccggttcagcgtaccaattgggaatttgcaattaaaagttccgaatcgtggtacgatacc
gatcgctatagcctgaaaggtagccagtttcagcaacgctgctggaatttagcggtgcatgtgaaggttgtggtgaaaccccgt
atgttaaactgctgacccagctgtttggtaacgtaccgttattgcaaatgccaccggttgtagcagcatttgggtggtacggcag
gtctggctccgtataccaccaatgcaaaaggtcagggtcggcatggggtaatagccgtttgaagataatgccgaatttggttttg TABLE 11-continued Primers for the Construction of Redox Balancing Plasmids FP45, FP47, FP67, FP68, and FP75 (FP66 was created from direct DNA synthesis (SEQ ID NO: 206), so no primers were used during its construction)

| Primer # | SEQ ID NO: | Primer sequence | Description |
|---|---|---|---|

```
gtattgcagttgccaatgcacagaaacgtagccgtgttcgtgattgtattctgcaggccgttgaaaaaaagtggccgatgaaggt
ctgaccaccctgctggcacgtggctgcaggattggaataccggtgataaaacactgaaatatcaggaccagattattgccggtc
tggcacagcagcgtagtaaagatcactgctggaacaaatttatggcatgaaagatatgctgccgaatatcagccagtggattatt
ggcggtgatggttgggccaatgatattggattggtggcctggatcatgttctggcgagcggtcagaatctgaatgttctggtgctg
gataccgaaatgtatagcaatacaggtggtcaggcaagcaaaagcacccatatggcaagcgttgcaaaatttgccctgggtggt
aaacgtaccaacaaaaaaaacctgaccgaaatggccatgagctatggtaatgtttatgttgcaaccgttagccatggtaatatggc
ccagtgtgttaaagcctagttgaagcagaaagctatgatggtccgagcctgattgttggttatgcaccgtgcattgaacatggtctg
cgtgcaggtatggcacgtatggttcaagaatcagaagcagcaattgcaaccggttattggccactgtatcgttttgatccgcgtctg
gcaaccgaaggtaaaaaccgtttcagctggatagcaaacgtattaaaggtaacctgcaagaatatctggatcgccagaatcgtt
atgtgaacctgaaaaaaaacaatccgaaaggtgccgatctgctgaaaagccagatggcagataacattacagcacgctttaatcg
ttatcgtcgtatgctggaaggtccgaataccaaagcagcagcaccgagcggtaatcatgtgaccattctgtatggtagtgaaacc
ggtaatagcgaaggtctggcaaaagaactggccaccgattttgaacgtcgtgaatatagcgttgcagttcaggccctggatgatat
tgatgttgcggatctggaaaatatgggctagttgttattgccgtttcaacctgtggtcagggccagtttccgcgtaatagtcagctgtt
ttggcgtgaactgcagcgtgataaaccggaaggttggctgaaaaatctgaaaataccgttttttggcctgggtgatgacccattt
acttttattgtcataccgccaaacaaatcgatgcacgtctggcagcgctgggtgcacagcgtgttgttccgattggtttcggtgatga
tggtgatgaagatatgtttcataccggcttcaataattggattccgagcgtttggaatgagctgaaaaccaaaactccggaagaag
cactgtttacccgtcaattgccgttcagctgaccccgaatgcaacaccgcaggatatcattttgccaaaagcacaccggtgctga
gcattaccggtgcagaacgtattacaccggcagatcataccgcaattttgttaccattcgttggaaaaccgatctgagctatcagg
ttggtgatagcctgggtgtttttccagaaaataccgtagcgttgttgaagaattcctgcagtattatggcctgaacccgaaagatgt
tattaccattgaaaataaaggctcacgcgaactgccgcattgtatggccgttggtgacctgtttaccaaagttctggatattctgggt
aaaccgaataaccgcttctataaaaccctgagctatttcgccgttgataaagcagaaaaagaacgcctgctgaaaattgcagaaat
gggtccggaatatagcaacattctgtcagagatgtatcattatgccgacatctttcatatgtttccgagcgcacgtccgacactgca
gtatctgattgaaatgatcccgaacattaaaccgcgttattatagcattagtagcgcaccgattcatactccgggtgaagtgcatag
cctggttctgattgatacctggattaccctgagcggtaaacatcgtacgggtctgacctgtaccatgctggaacatctgcaggcag
gtcaggtggtggatggttgtattcatccgaccgcaatggaatttccggatcatgaaaaaccggttgttatgtgtgcaatgggttcag
gtctggcaccttttgttgcatttctgcgtgaacgtagcaccctgcgtaaacagggtaaaaaaacgggcaatatggcgctgtatttttg
gcaatcgttacgaaaaaaccgaattctgatgaaagaggaactgaaaggccatatcaatgatggtcgctgacactgcgttgtgca
tttagccgtgatgatccgaaaaaaaagtctatgtgcaggatctgatcaaaatggatgaaaaaatgatgtatgattacctggtggttc
agaaaggcagcatgtattgttgtggtagccgtagattatcaaaccggtgcaagaaagcctgaaacattgttttatgaaagcgggtg
gtctgaccgcagaacaggcagaaaatgaagttattgatatgataccacgggtcgctataacattgaagcgtggcggccgtaaaa
cgaaaggctcagtcgaaagactg
```

NAD+ linked fdh from *Candida boidinii* and NADP+ linked fdh from *Burkholderia stabilis* were expressed in *E. coli* TOP10. Biochemical activity measurements were made on cell free extracts, which resulted in the data presented in Table 12 below. The assay was conducted with 50 mM sodium formate and 1.1 mM NAD+ or NADP+ at pH 7.0 in sodium phosphate buffer, as adapted from Hopner, T. and Knappe, J., Methods of Enzymatic Analysis, 3:1551-1555 (1974). In a final volume of 1 mL, 0.55 mL of water, 0.375 mL of 200 mM sodium phosphate, pH 7.0, 0.375 mL of 200 mM sodium formate, 0.15 mL of 10.5 mM β-NAD+ or 10.5 mM D-NADP+, and 0.05 mL of crude enzyme prep were added to a 1.5 mL plastic cuvette in the order indicated. Absorbance at 340 nm was recorded for 1 minute with a Shimadzu spectrophotometer, and the rate was used to determine specific activity. Protein concentrations were determined by the Bradford method with BSA as the standard. As expected, fdh from *C. boidinii* preferred NAD+ as a co-factor, while fdh from *B. stabilis* preferred NADP+.

TABLE 12

Biochemical activity of Cell-free Extracts

| plasmid | description | NAD+ ($\mu mol\ min^{-1}\ mg^{-1}$) | NADP± ($\mu mol\ min^{-1}\ mg^{-1}$) |
|---|---|---|---|
| pMU2726 | empty vector | 0.00 ± 0.00 | 0.00 ± 0.01 |
| FP45 | *C. boidinii* fdh | 0.39 ± 0.04 | 0.01 ± 0.01 |
| FP47 | *B. stabilis* fdh | 0.06 ± 0.00 | 0.31 ± 0.02 |

2.3 Acyl-ACP Chain Termination Enzymes

The final step of the anaerobic fatty acid pathway involves cleavage of the acyl carrier protein (ACP) from the acyl chain, and addition of a functional group to the final carbon of the growing chain (FIG. 13). The chain termination enzyme(s) determine both the terminal functional group and the overall acyl chain length.

Figure 14:
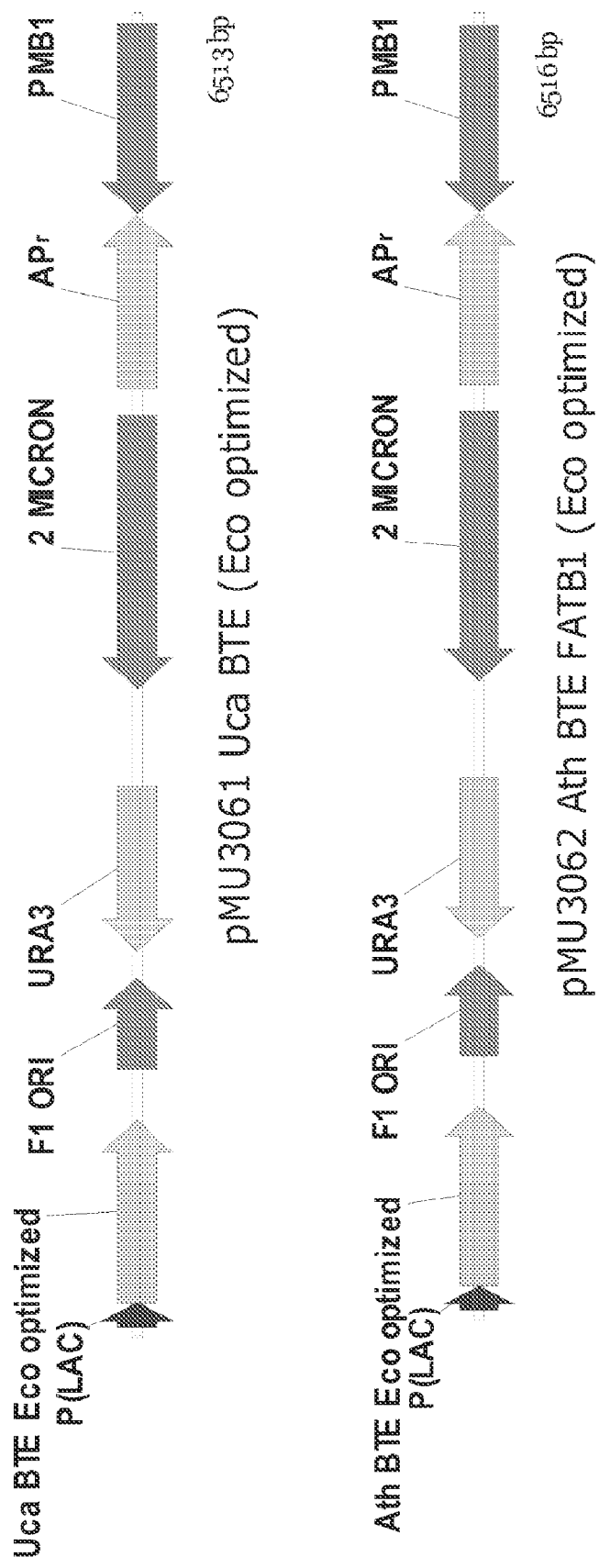
FIG. 14 depicts vectors pMU3061, pMU3062, pMU3063, and pMU3064.
Figure 14:
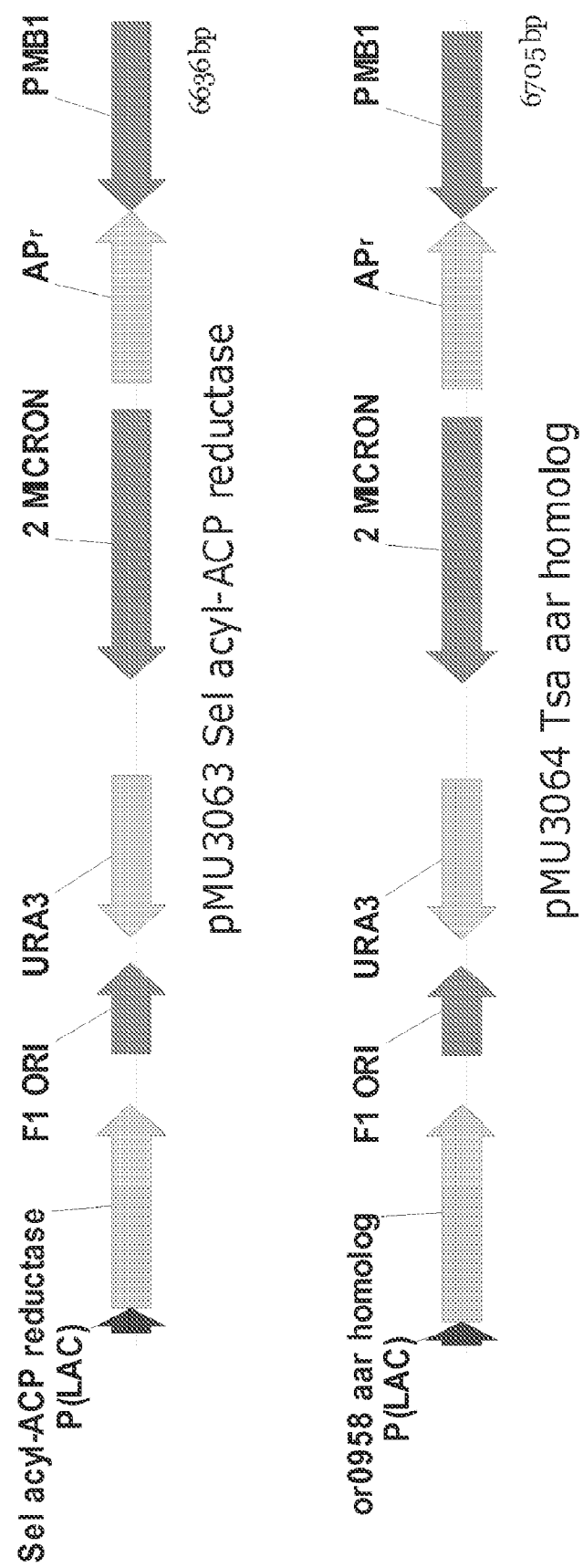

Plasmids encoding an *E. coli* codon optimized C12 acyl-ACP thioesterase (pMU3061), an *E. coli* codon optimized C16 acyl-ACP thioesterase (pMU3062), an acyl-ACP reductase (pMU3063), and an acyl-ACP reductase homolog (pMU3064) have been expressed in *E. coli* strain M2933 harboring a deletion in the acyl-CoA dehydrogenase fadE, an enzyme involved in fatty acid degradation. The expression plasmids used for these enzymes are shown in FIG. 14.

*E. coli* strains were grown to saturation over 48 hours in 5 mL LB medium at 30° C. in aerobic culture tubes containing 100 μg/mL Carbenicillin and 1 mM IPTG. Total fatty acid quantification was performed by lipid extraction followed by methyl ester derivatization and analysis by gas chromatograph with flame ionization detection. Extraction and derivatization was performed by adding 0.5 mL sample to a 13×100 mm glass tube with Teflon coated cap, addition of 4 mL 4% sulfuric acid in methanol followed by vortexing. The samples were then incubated at 70° C. in a water bath for 30 minutes, cooled to room temperature, followed by addition of 2 mL water and 2 mL hexane with vortexing at each step. The hexane layer was transferred to a new tube and dried under nitrogen. 50 μL hexane was then used to re-constitute the fatty acids for gas chromatograph analysis. Total fatty acids for M2933 strains carrying either plasmid pMU960 (empty vector), pMU3061, pMU3062, pMU3063, or pMU3064 are shown in FIGS. 22A and 22B. Individual fatty acids are also shown using a standard naming convention of X:Y, where X is the carbon number and Y is the number of unsaturated bonds.

Example 3

3.1 Methodology to Screen for Transcarboxylase Activity

To confirm that putative transcarboxylase genes have in vivo oxaloacetate:acetyl-CoA carboxytransferase activity, an E. coli strain was constructed that requires recombinant production of malonyl-CoA for growth. Wildtype E. coli produces malonyl-CoA, a metabolite essential for growth, exclusively via the enzyme acetyl-CoA carboxylase (ACC). ACC is composed of the four subunit genes accA, accB, accC, and accD, which are located at three different loci on the E. coli genome.

Because malonyl-CoA is essential, ACC cannot be disrupted directly in wildtype E. coli without resulting in a lethal phenotype. To overcome this, a conditional pathway for malonyl-CoA biosynthesis was first introduced into wildtype E. coli. This pathway, encoded by matBC from Rhizobacterium trifolii, transports exogenous malonate across the cell membrane, and then uses malonate, ATP, and CoA to produce malonyl-CoA, AMP, and $PP_i$. See An and Kim, Eur. J Biochem., 257:395-402 (1998).

3.1.1 Construction of Strain M2470

Figure 15:
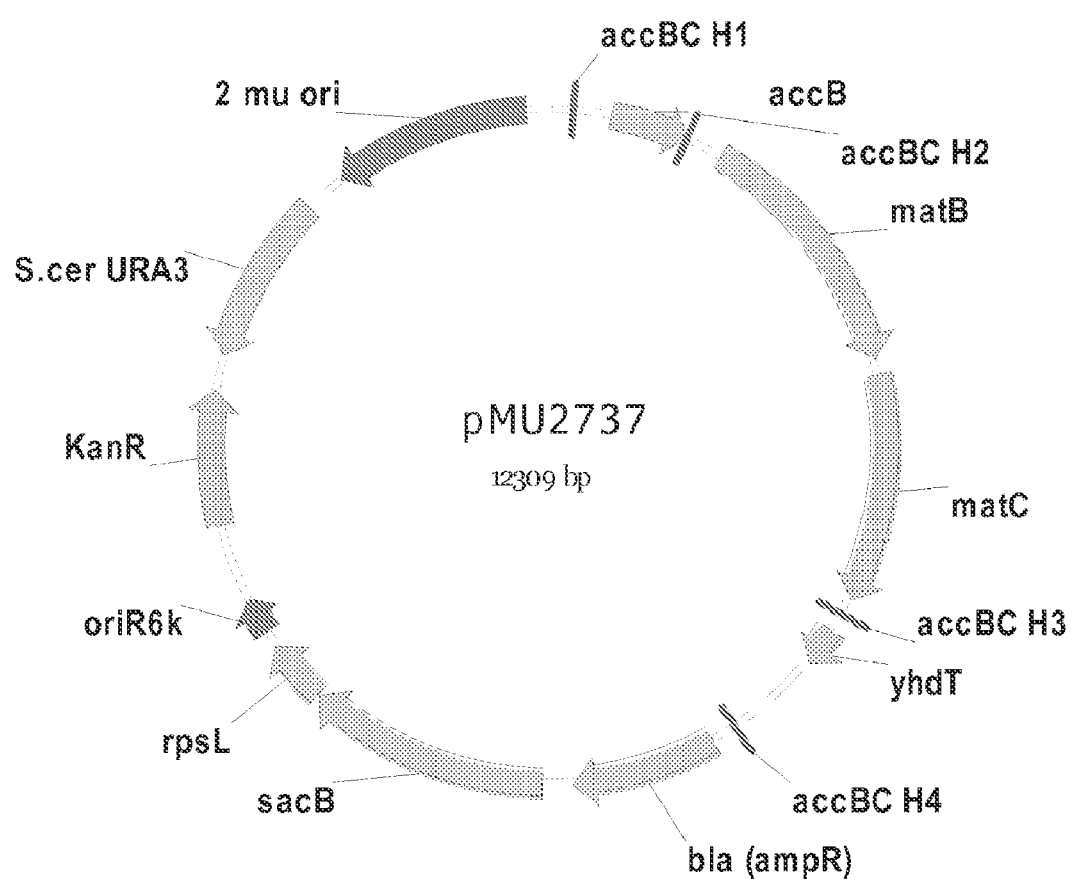
FIG. 15 depicts the vector pMU2737.
Figure 16:
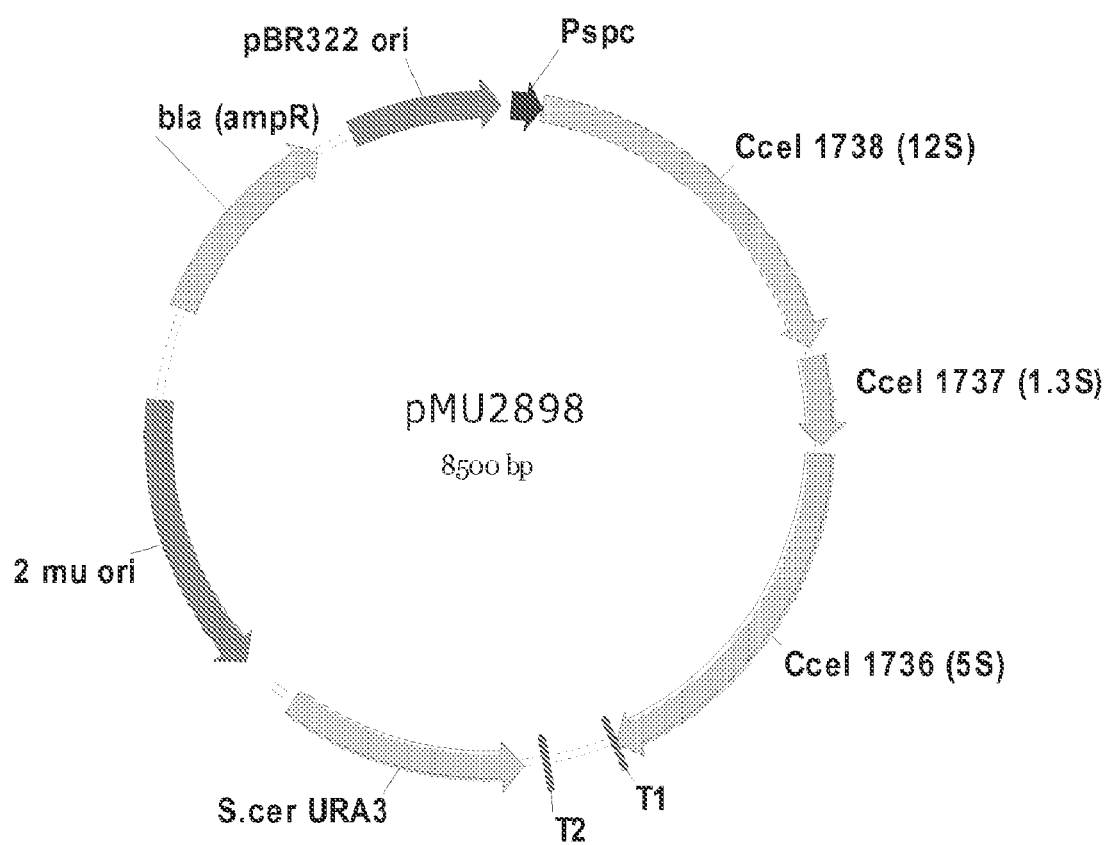
FIG. 16 depicts the vector pMU2898.
Figure 17:
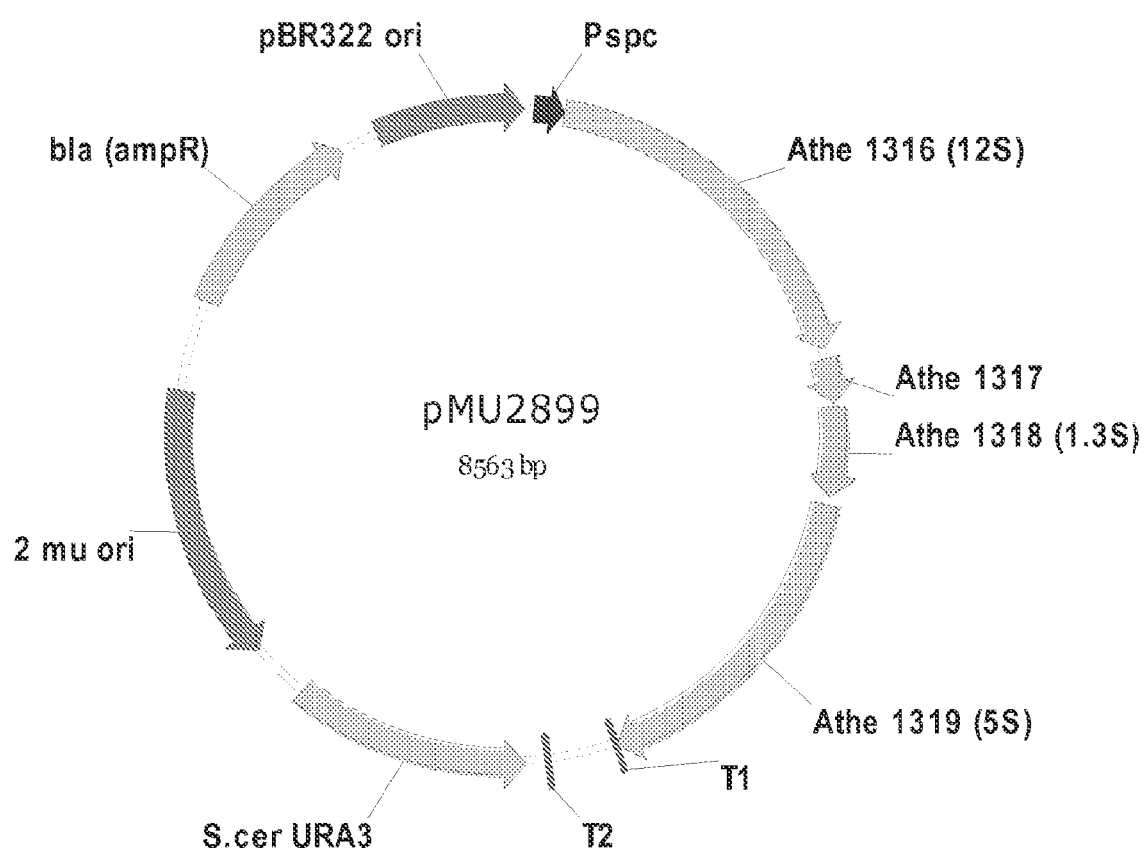
FIG. 17 depicts the vector pMU2899.
Figure 18:
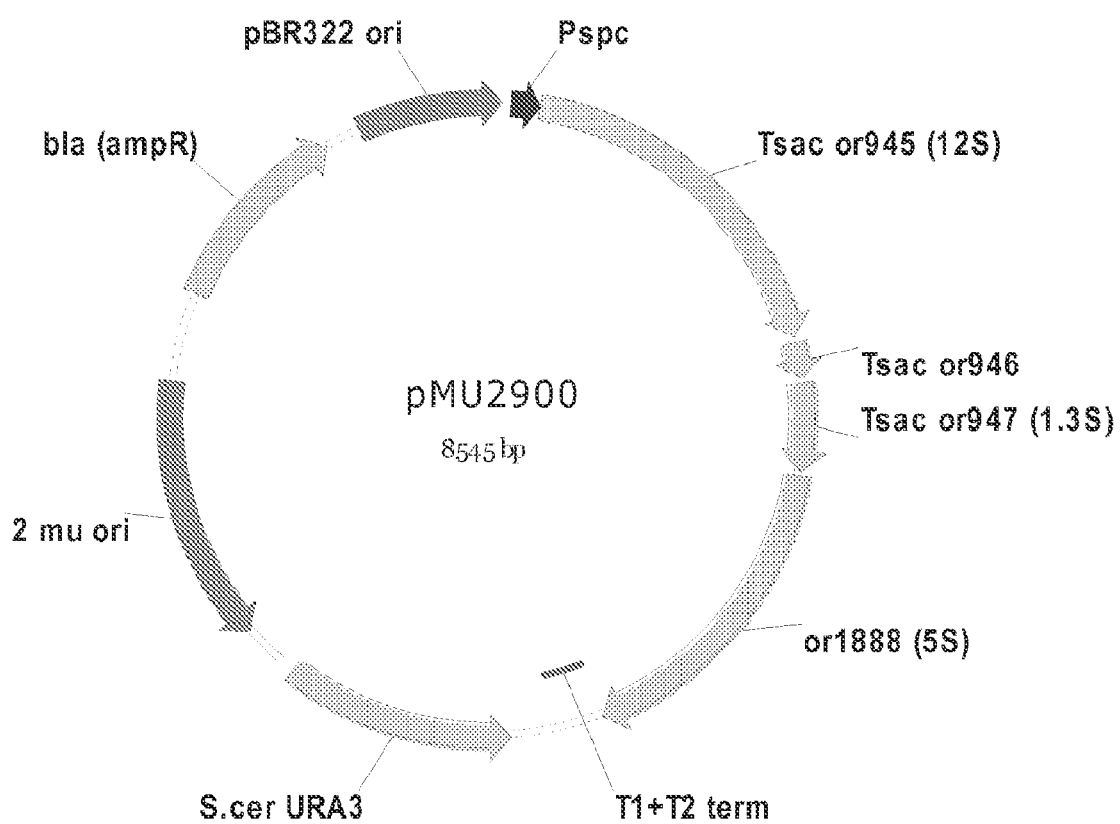
FIG. 18 depicts the vector pMU2900.
Figure 19:
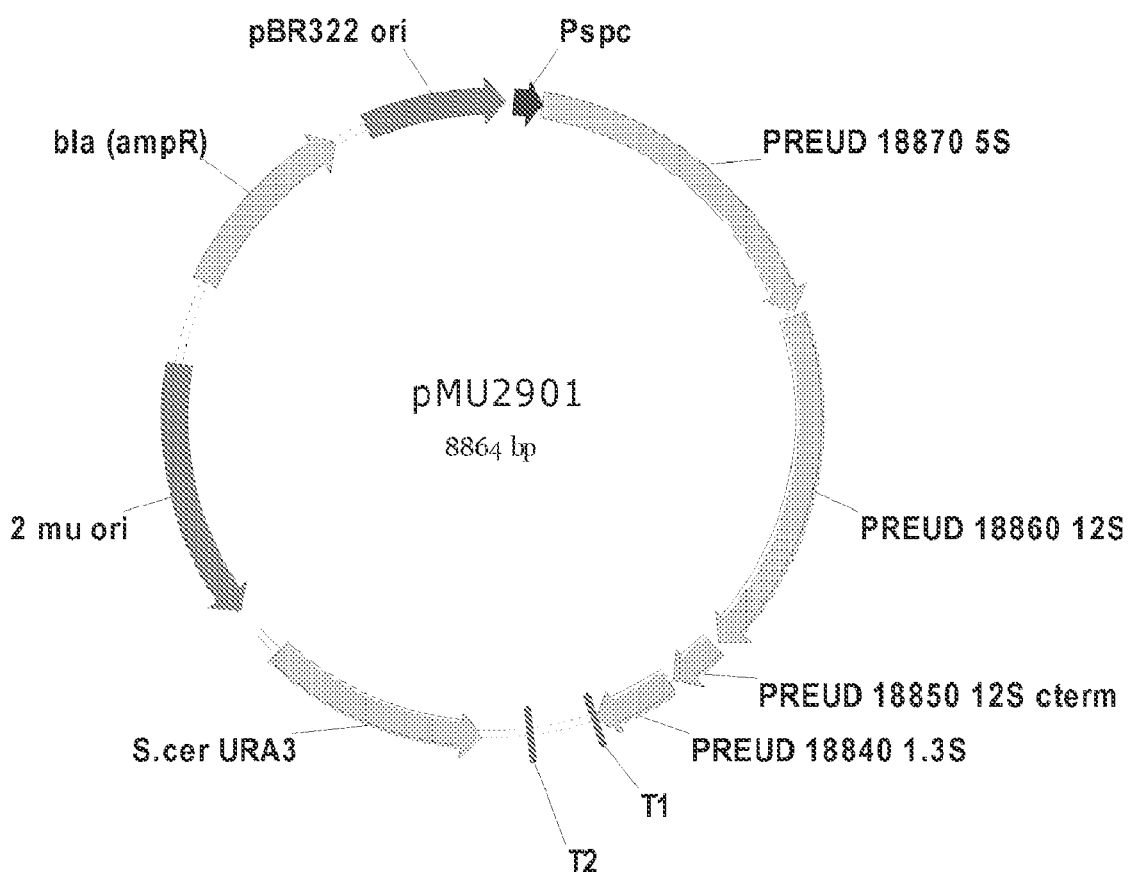
FIG. 19 depicts the vector pMU2901.

Strain M2470 is a ΔaccC::matBC strain built from E. coli K12 strain MG1655 (ATCC Accession No. 700926). To construct M2470, plasmid pMU2737 (FIG. 15; SEQ ID NO: 285) was transformed into strain MG1655 with selection on 100 μg/mL ampicillin and 50 μg/mL kanamycin. pMU2737 is a non-replicating plasmid, and confirmation of a single cross over integration was detected via colony PCR. The single cross-over meridiploid contains both a functional and a non-functional copy of accC, as well as the matBC genes, and positive ($amp^R$, $kan^R$) and negative selective (sacB, rpsL) markers. Upon plating on the negative selective condition, 10% w/v sucrose supplemented with 10 mM sodium malonate, the meridiploid resolved exclusively to the wildtype, functional accC gene copy. This suggested that matBC was not able to catalyze the conversion of exogenous malonate to malonyl-CoA at a rate sufficient to allow for observable colony formation. To overcome this, the meridiploid strain was grown aerobically in M9 minimal medium supplemented with 1.4 mM glucose and 10 mM malonate. After two transfers, each lasting ~48 hours in 50 mL of this medium, the culture was re-plated on 10% w/v sucrose supplemented with 10 mM sodium malonate. Upon screening, most (>90%) of the colony isolates now had the non-functional accC copy and matBC genes. An isolate was further purified and designated M2470. It is able to grow only when exogenous malonate is present in the medium.

3.1.2 Construction and Screening of Putative Transcarboxylase Genes

Plasmids pMU2898 (SEQ ID NO:286), pMU2899 (SEQ ID NO:287), pMU2900 (SEQ ID NO:288), and pMU2901 (SEQ ID NO:289) (FIGS. 16-19) were constructed via yeast homologous cloning to express putative transcarboxylases from Clostridium cellulolyticum H10 ATCC 35319, Caldicellulosiruptor bescii DSM 6725, Thermoanaerobacterium saccharolyticum JW/SL-YS485, and Propionibacterium freudenreichii CIRM-BIA1, respectively. Percent consensus and identity positions across the four subunits of these putative transcarboxylases, as well as from Corynebacterium kroppenstedtii DSM 44385, Geobacter bemidjiensis Bem($^T$), and Clostridium thermocellum ATCC 27405, is depicted in Table 13. A phylogenetic tree and alignment of these transcarboxylases, including from D. propionincus DSM 2032, is shown in FIGS. 30-31.

TABLE 13

Percent Consensus and Identity Positions Across Putative Transcarboxylases

| | Consensus positions | Identity positions |
| --- | --- | --- |
| 5S subunit | 75.5% | 29.8% |
| 1.3S subunit | 58.6% | 12.0% |
| 12S subunit | 85.0% | 35.0% |
| 12S C-terminal subunit* | 36.5% | 1.9% |

*C. cellulolyticum does not have a 12S C-terminal subunit

The four putative transcarboxylases were cloned into pMU2727, a replicating vector with the pBR322 origin, $amp^R$, Pspc promoter, and T1T2 terminator. Pspc is a moderately high level constitutive ribosomal promoter. See Liang et al., J. Mol Bio 292:19-37 (1999).

These plasmids were then transformed into M2470 and transformants were selected on medium containing, per liter, 10 g glucose, 1.48 g disodium malonate, 100 mg ampicillin, 15 g agar, and the modified M9 base medium: 12.8 g $Na_2HPO_4.7H_2O$, 3 g $KH_2PO_4$, 0.5 g NaCl, 1 g $NH_4Cl$, 0.5 g $MgSO_4$, 0.015 g $CaCl_2$, 0.02 g thiamine, 0.02 g $CoSO_4$, 0.02 g $ZnSO_4$, 0.02 g $MnSO_4$, 0.015 g biotin. Transformants were confirmed by plasmid mini-prep, and re-patched onto modified M9 medium plates containing 20 g glucose and 15 g agar per liter ("M9+20 glucose"). If growth was observed on M9+20 glucose plates, colonies were re-grown in either liquid or solid medium of the same composition, and scored for growth and growth rate (Table 14 and FIG. 20A). As a control, transformants were also plated on solid medium comprising M9 base medium, 10 g/L glucose, 10 mM malonate, and 100 μg/mL ampicillin (Table 14 and FIG. 20B). The following transformants were isolated and tested for growth: MG1655-wildtype, M2560-ΔaccC::matBC+ pMU2727 empty vector ($amp^R$), and M2557, M2558, M2559-ΔaccC::matBC+pMU2900 T. saccharolyticum TC ($amp^R$).

TABLE 14

Growth of Transformants Containing Putative Transcarboxylases

| Strain | M9 + 20 glu | M9 + malonate + amp |
| --- | --- | --- |
| MG1655 WT | ++++ | − |
| M2470 | − | +++ |
| M2560 (aka. M2470 + pMU2727) | − | +++ |
| M2557 (aka. M2470 + pMU2900) #1 | +++ | +++ |
| M2558 (aka. M2470 + pMU2900) #2 | +++ | +++ |
| M2559 (aka. M2470 + pMU2900) #3 | +++ | +++ |
| M2470 + pMU2898 | + | +++ |
| M2470 + pMU2899 | ++ | +++ |
| M2470 + pMU2901 | + | +++ |

++++ = visible growth within 24 hours
+++ = visible growth within 48 hours
++ = visible growth within 96 hours
+ = visible growth within 168 hours
− = no visible growth after 200+ hours 3.2 Assays for Recombinant Transcarboxylase and In Vitro Transcarboxylase Activity To determine the presence and activity of the T. saccharolyticum transcarboxylase enzyme that was engineered into the E. coli ΔaccC::matBC strain and screened using the assay above, several biochemical assays were conducted.

Initial evaluation of activity in cell lysate was inconclusive. The *T. saccharolyticum* transcarboxylase enzyme was then purified using the biotin binding domain located in the 1.3S protein. Without wishing to be bound by theory, Streptavidin binding of the 1.3S subunit could co-purify both the 5S and 12S proteins which associate with the 1.3S subunit in the native host. *E. coli* ΔaccC::matBC cells were grown in M9+ medium at 37° C. in aerobic shake flasks to an OD of 6 in 1.8 L total volume and lysed with Y-PER (Pierce) according to product instructions, in the presence of 100 mM potassium phosphate, pH 6.8, 1 mg/mL reduced glutathione, 1:10,000 dilution of Sigma bacterial protease inhibitors, and 0.5 U/mL DNase I. After 2-3 freeze/thaw cycles, the cells were lysed as determined by microscopic evaluation. The lysate was centrifuged to remove debris and the supernatant was retained for further evaluation of activity. Two constructs were evaluated using this affinity assay, M2557 and M2560, which were either the strain engineered to produce the 12S, 5S, 1.3S, and 12S C-terminal components of the *T. saccharolyticum* transcarboxylase system or the empty vector control strain, respectively (see above).

To determine the presence of the biotin-containing enzyme, the lysates were then purified using monomeric avidin resin with a batch binding protocol (Pierce) according to product instructions. After the sample was incubated with the resin, the protein was eluted from the column with 4 mM biotin. The eluted fractions were analyzed on via Western blot with avidin-HRP as the detection. Samples were run on a 4-20% tris glycine gel then transferred to a PVDF membrane. After overnight blocking in TBS/1 % BSA, streptavidin HRP was added. The HRP was detected with ECL chemilunescent and imaged on a chemiluminescent gel doc system. FIG. 25 depicts the results of this affinity assay comparing M2557 and M2560.

The monomeric avidin-purified lysate was purified again with Streptavidin Dynabeads with a batch binding system carried out with 1 mL of lysate mixed with 100 μL of washed streptavidin Dynabeads. After incubation at room temperature for 30 min, the sample was washed with 100 mM potassium phosphate, 1 mg/mL reduced glutathione, pH 6.8 and eluted from the beads by boiling in SDS-PAGE sample buffer. The re-purified lysate was then analyzed via Western Blot as above. The band on the Western Blot that ran at the same location as the one indicated with an arrow in FIG. 25 was sequenced on a Procise N-terminal sequencer. The sequencing data indicated that the N-terminus of the protein was MKKFIVTVNG (SEQ ID NO:299), consistent with the N-terminus of the 1.3S protein.

The enzymatic activity of the monomeric avidin-purified transcarboxylase complex was then assessed using an LC/MS detection assay. The monomeric avidin purified lysate was mixed with oxaloacetate, acetyl CoA and reduced glutathione and incubated at 40° C. for 1.5 hours. The sample was then analyzed by LC/MS using a BioRad 87H column and a Thermo LCQ (HPLC $C_1j$ column-formate/methanol eluent) ion trap mass spectrometer. The results are shown in FIGS. 26A and 26B. In FIG. 26A, the negative control sample was analyzed. Using selected ion monitoring, acetyl CoA was detected but no malonyl CoA was detected (FIG. 26A, lower two panels). When the transcarboxylase sample was analyzed with selected ion monitoring both acetyl and malonyl CoA (FIG. 26B, lower two panels) were detected thereby indicating that the transcarboxylase enzyme complex was functional.

3.3 Use of *E. coli* ΔaccC::matBC Strain to Select for Faster-Growing Transcarboxylase-Expressing Strains The *E. coli* accC::matBC strain M2470 can also be used to select for more efficient malonyl-CoA production by transcarboxylases. This selection is based on the principle that malonyl-CoA generation is the rate-limiting factor for growth of this strain. Thus, more efficient generation of malonyl-CoA will result in a faster growing strain which is able to out-compete the remaining culture and dominate the cell population during serial transfer or other continuous or semi-continuous selection systems. See, e.g., FIG. 27A.

First, strain M2470 was transformed with an integrating plasmid (e.g., pMU2924, pMU2969) carrying a transcarboxylase and spectinomycin antibiotic resistance marker flanked by DNA regions homologous to the ldh gene (lactate dehydrogenase). Using kanR, ampR, sacB, and rpsL based selections, the transcarboxylase and specR marker were securely integrated into the genome via two homologous recombination events. During this period, the strain was grown on M9+ base medium with the addition of 2-20 g/L glucose and 1.48 g/L disodium malonate. The medium was prepared at room temperature, adjusted to pH 7.5 with 10 M NaOH or 10 M HCl, and filter sterilized into a pre-sterilized bottle with a 0.22 μm filter. Subsequently, the strain was grown aerobically at 37° C. in 350 mL of M9+ medium with only glucose in a 1 L shake flask. If substantial growth (OD>1) occurred, a 0.1 mL transfer was made to a fresh 350 mL flask, which is repeated 3 times, at which point a small culture volume is plated to isolate a single colony on solid M9+ glucose medium (prepared via addition of 15 g/L melted agar as a 2× stock to 2× liquid media, pre-incubated at 50° C.). See FIG. 27A. This strain is referred to as the $3^{rd}$ transfer (T3) isolate. Growth rates for the original strain and T3 isolate were then compared in M9+ medium with 20 g/L glucose as the sole carbon and energy source. An increased growth rate indicates an improved ability to generate malonyl-CoA. Plasmids used for this example were pMU2924 (*T. saccharolyticum* TC; FIG. 28; SEQ ID NO:207) and pMU2969 (*P. freudenreichii* TC; FIG. 29; SEQ ID NO:208), which generated strains M2767 and M2772, respectively. Growth rates for the original strain and T3 strain of each are shown in FIG. 27B.

Example 4

4.1 High Yield Palmitic Acid Production in *S. cerevisiae*

The present prophetic example describes the engineering of a recombinant yeast microorganism to convert a native pyruvate decarboxylase (pdc) based ethanol pathway (FIG. 34A) to an intermediary pyruvate formate lyase and alcohol/aldehyde dehydrogenase (pfl adhE) based ethanol pathway (FIG. 34B), and finally to a transcarboxylase based palmitic acid pathway (FIG. 34C).

The genetic modifications described below are used to create a strain capable of anaerobic growth in the absence of functional pyruvate decarboxylase and glycerol-3-phosphate dehydrogenase. To accomplish this, constructs were designed to replace GPD1, GPD2, FDH1, and FDH2 with two copies of a bifunctional alcohol/aldehyde dehydrogenase and two copies of a pyruvate formate lyase, both of which were cloned from *B. adolescentis* (Table 15). See, e.g., PCT/US2011/035416, which is incorporated by reference herein in its entirety, for additional details on the construction of such strain. Additionally, constructs were designed to make deletions of PDC5, PDC6, and PDC1.

Either a NAD+ or NADP+ linked formate dehydrogenase is then re-introduced into the strain to create the metabolic pathway shown in (FIG. 34B).

TABLE 15

Coding sequences of pfl and adhE

| GenBank Accession # | Host strain | Gene donor | gene | protein |
|---|---|---|---|---|
| YP_909854 | S. cerevisiae | Bifidobacterioum adolescentis | pflA | pyruvate formate lyase activating enzyme |
| YP_909855 | S. cerevisiae | Bifidobacterioum adolescentis | pflB | pyruvate formate lyase |
| YP_909182 | S. cerevisiae | Bifidobacterioum adolescentis | adhE | alcohol/aldehyde dehydrogenase |

B. adolescentis adhE (amino acid sequence)
(SEQ ID NO: 209)
MADAKKKEEPTKPTPEEKLAAAEAEVDALVKKGLKALDEFEKLDQKQVDI
TIVAKASVAALNKFILVLAKMAVEETHRGLVEDKATKNIFACEHVTNYLA
GQKTVGIIREDDVLGIDEIAEPVGVVAGVTPVTNPTSTAIFKSLIALKTR
CPIIFGFHPGAQNCSVAAAKIVRDAAIAAGAPENCIQWIEHPSIEATGAL
MKIIDGVATILATGGPGMVKAAYSSGKPALGVGAGNAPAYYDKNVDVVRA
ANDLILSKHFDYGMICATEQAIIADKDIYAPLVKELKRRKAYFVNADEKA
KLEQYMFGCTAYSGQTPKLNSVVPGKSPQYIAKAAGFEIPEDATILAAEC
KEVGENEPLTMEKLAPVQAVLKSDNKEQAFEMCEAMLKHGAGHTAAIHTN
DRDLVREYGQRMHACRIIWNSPSSLGGVGDIYNAIAPSLTLGCGSYGGNS
VSGNVQAVNLINIKRIARRNNNMQWFKIPAKTYFEPNAIKYLRDMYGIEK
AVIVCDKVMEQLGIVDKIIDQLRARSNRVTFRIIDYVEPEPSVETVERGA
AMMREEFEPDTIIAVGGGSPMDASKIMWLLYEHPEISFSDVREKFFDIRK
RAFKIPPLGKKAKLVCIPTSSGTGSEVTPFAVITDHKTGYKYPITDYALT
PSVAIVDPVLARTQPRKLASDAGFDALTHAFEAYVSVYANDFTDGMALHA
AKLVWDNLAESVNGEPGEEKTRAQEKMHNAATMAGMAFGSAFLGMCHGMA
HTIGALCHVAHGRTNSILLPYVIRYNGSVPEEPTSWPKYNKYIAPERYQE
IAKNLGVNPGKTPEEGVENLAKAVEDYRDNKLGMNKSFQECGVDEDYYWS -continued
IIDQIGMRAYEDQCAPANPRIPQIEDMKDIAIAAYYGVSQAEGHKLRVQR
QGEAATEEASERA B. adolescentis pflA (amino acid sequence)
(SEQ ID NO: 210)
MSEHIFRSTTRHMLRDSKDYVNQTLMGGESGFESPIGLDRLDRIKALKSG DIGFVHSWDINTSVDGPGTRMTVFMSGCPLRCQYCQNPDTWKMRDGKPVY
YEAMVKKIERYADLFKATGGGITFSGGESMMQPAFVSRVEHAAKQMGVHT
CLDTSGELGASYTDDMVDDIDLCLLDVKSGDEETYHKVIGGILQPTIDEG
QRLAKAGKKIWVRFVLVPGLTSSEENVENVAKICETEGDALEHMVLPFHQ
LGRPKWHMLNIPYPLEDQKGPSAAMKQRVVEQFQSHGFTVY B. adolescentis pflB (amino acid sequence)
(SEQ ID NO: 211)
MAAVDATAVSQEELEAKAWEGFTEGNWQKDIDVRDFIQKNYTPYEGDESF
LADATDKTKHLWKYLDDNYLSVERKQRVYDVDTHTPAGIDAFPAGYIDSP
EVDNVIVGLQTDVPCKRAMMPNGGWRMVEQAIKEAGKEPDPEIKKIFTKY
RKTHNDGVFGVYTKQIKVARHNKILTGLPDAYGRGRIIGDYRRVALYGVN
ALIKFKQRDKDSIPYRNDFTEPEIEHWIRFREEHDEQIKALKQLINLGNE
YGLDLSRPAQTAQEAVQWTYMGYLASVKSQDGAAMSFGRVSTFFDVYFER
DLKAGKITETDAQEIIDNLVMKLRIVRFLRTKDYDAIFSGDPYWATWSDA
GFGDDGRTMVTKTSFRLLNTLTLEHLGPGPEPNITIFWDPKLPEAYKRFC
ARISIDTSAIQYESDKEIRSHWGDDAAIACCVSPMRVGKQMQFFAARVNS
AKALLYAINGGRDEMTGMQVIDKGVIDPIKPEADGTLDYEKVKANYEKAL
EWLSETYVMALNIIHYMHDKYAYESIEMALHDKEVYRTLGCGMSGLSIAA
DSLSACKYAKVYPIYNKDAKTTPGHENEYVEGADDDLIVGYRTEGDFPLY
GNDDDRADDIAKWVVSTVMGQVKRLPVYRDAVPTQSILTITSNVEYGKAT
GAFPSGHKKGTPYAPGANPENGMDSHGMLPSMFSVGKIDYNDALDGISLT
NTITPDGLGRDEEERIGNLVGILDAGNGHGLYHANINVLRKEQLEDAVEH
PEKYPHLTVRVSGYAVNFVKLTKEQQLDVISRTFHQGAVVD To generate a recombinant yeast microorganism as described in this example, individual molecular components are integratively assembled.

1) The deletion of the FDH1 gene and replacement with two copies of ADH and two copies of PFL is illustrated in FIG. 35. The primers used to generate the molecular components of this integrative assembly are shown in FIG. 35, Table 16, and Table 26 (below).

TABLE 16

Primers used to generate the integrative assembly of FIG. 35.
Each column indicates a PCR fragment that needs to be generated.

| Name | FDH15' Flank rc | pTPI-ADH-FBAt | ADHpPFKrc | PFL-pADH5 | PFL-pENORC | FDH13' Flank rc |
|---|---|---|---|---|---|---|
| Primers | X15559/X15565 | X15564/X14843 | X14844/X14835 | X14836/X14837 | X14838/X15567 | X15566/X15553 |
| Template | S.ce gDNA | pMU2746 | pMU2745 | pMU2770 | pMU2606 | S.ce gDNA |

2) The deletion of the FDH2 gene and replacement with two copies of ADH and two copies of PFL is illustrated in FIG. 36. The primers used to generate the molecular components of this integrative assembly are shown in FIG. 36, Table 17, and Table 26 (below).

TABLE 17

Primers used to generate the integrative assembly of FIG. 36.
Each column indicates a PCR fragment that needs to be generated.

| Name | FDH2 5' Flank | FBA(t)-ADH1 | PFK-ADH2 | PFL-F | PFL-R | FDH2 3' Flank |
|---|---|---|---|---|---|---|
| Primers | X16096/X16097 | X16098/X14843 | X14844/X14835 | X14836/X14837 | X14838/X16099 | X16100/X11845 |
| Template | S.ce gDNA | pMU2746 | pMU2745 | pMU2770 | pMU2606 | S.ce gDNA |

3) The deletion of the GPD2 gene and replacement with two copies of ADH and two copies of PFL is illustrated in FIG. 37. The primers used to generate the molecular components of this integrative assembly are shown in FIG. 37, Table 18, and Table 26 (below).

TABLE 18

Primers used to generate the integrative assembly of FIG. 37.
Each column indicates a PCR fragment that needs to be generated.

| Name | GPD2 5' flank | FBA(t)-ADH1 | PFK-ADH2 | PFL-F | PFL-R | GPD2 3' flank |
|---|---|---|---|---|---|---|
| Primers | X11816/X14847 | X14845/X14843 | X14844/X14835 | X14836/X14837 | X14838/X14849 | X14850/X11821 |
| Template | S.ce gDNA | YCL150 | YCL149 | pMU2770 | pMU2760 | S.ce gDNA |

4) The deletion of the GPD1 gene and replacement with two copies of ADH and two copies of PFL is illustrated in FIG. 38. The primers used to generate the molecular components of this integrative assembly are shown in FIG. 38, Table 19, and Table 26 (below).

TABLE 19

Primers used to generate the integrative assembly of FIG. 38.
Each column indicates a PCR fragment that needs to be generated.

| Name | GPD1 5' flank | FBA(t)-ADH1 | PFK-ADH2 | PFL-F | PFL-R | GPD1 3' flank |
|---|---|---|---|---|---|---|
| Primers | X11824/X14776 | X14775/X14843 | X14844/X14835 | X14836/X14837 | X14838/X14829 | X14778/X11829 |
| Template | S.ce gDNA | pMU2746 | pMU2745 | pMU2770 | pMU2606 | S.ce gDNA |

5) The deletion of the PDC5 gene and replacement with a counter selective gene HSV-TDK and an antibiotic marker (Kan) is illustrated in FIG. 39. The primers used to generate the molecular components of this integrative assembly are shown in FIG. 39, Table 20, and Table 26 (below).

TABLE 20

Primers used to generate the integrative assembly of FIG. 39. Each
column indicates a PCR fragment that needs to be generated.

| Name | PDC5 5' Flank | KNT | PDC5 3' Flank |
|---|---|---|---|
| Primers | X16463/X16464 | X16467/X16468 | X16465/X16466 |
| Template | S. ce gDNA | M2543/TB396 | S. ce gDNA |

6) The removal of the marker shown in FIG. 39 resulting in a clean deletion of the PDC5 gene is illustrated in FIG. 40. The primers used to generate the molecular components of this integrative assembly are shown in FIG. 40, Table 21, and Table 26 (below).

TABLE 21

Primers used to generate the integrative assembly of FIG. 40. Each
column indicates a PCR fragment that needs to be generated.

| Name | PDC5 5' Flank | PDC5 3' Flank |
|---|---|---|
| Primers | X16463/X16495 | X16494/X16466 |
| Template | S. ce gDNA | S. ce gDNA |

7) The deletion of the PDC6 gene and replacement with a counter selective gene HSV-TDK and an antibiotic marker (Kan) is illustrated in FIG. 41. The primers used to generate the molecular components of this integrative assembly are shown in FIG. 41, Table 22, and Table 26 (below).

TABLE 22

Primers used to generate the integrative assembly of FIG. 41. Each
column indicates a PCR fragment that needs to be generated.

| Name | PDC6 5' Flank | KNT | PDC6 3' Flank |
|---|---|---|---|
| Primers | X16471/X16472 | X16475/X16476 | X16473/X16474 |
| Template | S. ce gDNA | M2543/TB396 | S. ce gDNA |

8) The removal of the marker shown in FIG. 41 resulting in a clean deletion of the PDC6 gene is illustrated in FIG. 42. The primers used to generate the molecular components of this integrative assembly are shown in FIG. 42, Table 23, and Table 26 (below).

TABLE 23

Primers used to generate the integrative assembly of FIG. 42. Each column indicates a PCR fragment that needs to be generated.

| Name | PDC6 5' Flank | PDC6 3' Flank |
|---|---|---|
| Primers | X16471/X16497 | X16496/X16474 |
| Template | S. ce gDNA | S. ce gDNA |

9) The deletion of the PDC1 gene and replacement with a counter selective gene HSV-TDK and an antibiotic marker (Kan) is illustrated in FIG. 43. The primers used to generate the molecular components of this integrative assembly are shown in FIG. 43, Table 24, and Table 26 (below).

TABLE 24

Primers used to generate the integrative assembly of FIG. 43. Each column indicates a PCR fragment that needs to be generated.

| Name | PDC1 5' Flank | KNT | PDC1 3' Flank |
|---|---|---|---|
| Primers | X16951/X16952 | X16953/X 16954 | X16955/X16956 |
| Template | S. ce gDNA | M2543/TB396 | S. ce gDNA |

10) The removal of the marker shown in FIG. 43 resulting in a clean deletion of the PDC1 gene is illustrated in FIG. 44. The primers used to generate the molecular components of this integrative assembly are shown in FIG. 44, Table 25, and Table 26 (below).

TABLE 25

Primers used to generate the integrative assembly of FIG. 44. Each column indicates a PCR fragment that needs to be generated.

| Name | PDC1 5' Flank | PDC1 3' Flank |
|---|---|---|
| Primers | X16952/X16953 | X16954/X16955 |
| Template | S. ce gDNA | S. ce gDNA |

TABLE 26

Primer sequences used to create the integrative assemblies illustrated in FIGS. 35-44.

| Primer # | SEQ ID NO. | Primer sequence |
|---|---|---|
| X11316 | 212 | GTAATACATCACCTCGATGAAAGAGA |
| X11816 | 213 | GCAGTCATCAGGATCGTAGGAGATAAGCA |
| X11821 | 214 | TCACAAGAGTGTGCAGAAATAGGAGGTGGA |
| X11822 | 215 | GTTGGGGGAAAAAGAGGCAACAGGAAAGATCAGAGACAGCAAGCATTGATAAGGAAGGG |
| X11823 | 216 | CCCTTCCTTATCAATGCTTGCTGTCTCTGATCTTTCCTGTTGCCTCTTTTTCCCCCAAC |
| X11824 | 217 | AAGCCTACAGGCGCAAGATAACACATCAC |
| X11829 | 218 | CTCAGCATTGATCTTAGCAGATTCAGGATCTAGGT |
| X11830 | 219 | TATGTTATCTTTCTCCAATAAATCTAATCTTCATGTAGACTATCAGCAGCAGCAGACAT |
| X11831 | 220 | GATAATATAAAGATGTCTGCTGCTGCTGATAGTCTACATGAAGATTAGATTTATTGGAG |
| X11845 | 221 | TTACTTGTGAAACTGTCTCCGCTATGTCAG |
| X14775 | 222 | CCCCCTCCACAAACACAAATATTGATAATATAAAGATGGCAGACGCAAAGAAGAAGGAA |
| X14778 | 223 | ATTTATTGGAGAAAGATAACATATCATACTTTCC |
| X14829 | 224 | GAAAGTATGATATGTTATCTTTCTCCAATAAATCTAGTCTTCTAGGCGGGTTATCTACT |
| X14835 | 225 | CAAATTCTAACCAACTTCAAAATGACATAGTACCTCATCTATAATTTTTACCCTGATCT |
| X14836 | 226 | AGTTAGATCAGGGTAAAAATTATAGATGAGGTACTATGTCATTTTGAAGTTGGTTAGAA |

TABLE 26-continued

Primer sequences used to create the integrative assemblies illustrated in FIGS. 35-44.

| Primer # | SEQ ID NO. | Primer sequence |
| --- | --- | --- |
| X14837 | 227 | GGTCCATGTAAAATGATTGCTCCAATGATTGAAATTGATTCAGG TCAAAATGGATTCAG |
| X14838 | 228 | ACGTCCCTGAATCCATTTTGACCTGAATCAATTTCAATCATTGGA GCAATCATTTTACA |
| X14843 | 229 | GGTGGAACCATTTACTGTATTTTCAATGTAACGCTAGAGAATAA ATTCAAGTTAAAAGA |
| X14844 | 230 | CATCATCTTTTAACTTGAATTTATTCTCTAGCGTTACATTGAAAA TACAGTAAATGGTT |
| X15380 | 231 | TAGGTCTAGAGATCTGTTTAGCTTGC |
| X15382 | 232 | GAGACTACATGATAGTCCAAAGA |
| X15546 | 233 | GGACGAGGCAAGCTAAACAGATCTCTAGACCTACTTTATATTAT CAATATTTGTGTTTG |
| X15547 | 234 | CCGTTTCTTTTCTTTGGACTATCATGTAGTCTCATTTATTGGAGA AAGATAACATATCA |
| X15548 | 235 | GGACGAGGCAAGCTAAACAGATCTCTAGACCTATGATAAGGAA GGGGAGCGAAGGAAAA |
| X15549 | 236 | CCGTTTCTTTTCTTTGGACTATCATGTAGTCTCCTCTGATCTTTCC TGTTGCCTCTTTT |
| X15552 | 237 | CCGTTTCTTTTCTTTGGACTATCATGTAGTCTCGAGTGATTATGA GTATTTGTGAGCAG |
| X15553 | 238 | ACCAGCGTCTGGTGGACAAACGGCCTTCAAC |
| X15554 | 239 | GGACGAGGCAAGCTAAACAGATCTCTAGACCTAATTAATTTTCA GCTGTTATTTCGATT |
| X15555 | 240 | CCGTTTCTTTTCTTTGGACTATCATGTAGTCTCGAGTGATTATGA GTATTTGTGAGCAG |
| X15559 | 241 | GGAAGGCACCGATACTAGAACTCCG |
| X15564 | 242 | CTAATCAAATCAAAATAACAGCTGAAAATTAATCTACTTATTCC CTTCGAGATTATATC |
| X15565 | 243 | GTTCCTAGATATAATCTCGAAGGGAATAAGTAGATTAATTTTCA GCTGTTATTTTGATT |
| X15566 | 244 | TCGGATCAGTAGATAACCCGCCTAGAAGACTAGGAGTGATTATG AGTATTTGTGAGCAG |
| X15567 | 245 | AAAACTTCTGCTCACAAATACTCATAATCACTCCTAGTCTTCTAG GCGGGTTATCTACT |
| X15870 | 246 | CTAATCAAATCAAAATAACAGCTGAAAATTAATGAGTGATTATG AGTATTTGTGAGCAG |
| X15871 | 247 | AAAACTTCTGCTCACAAATACTCATAATCACTCATTAATTTTCAG CTGTTATTTGATT |
| X16096 | 248 | CATGGTGCTTAGCAGCAGATGAAAGTGTCA |
| X16097 | 249 | GTTCCTAGATATAATCTCGAAGGGAATAAGTAGATTAATTTTCA GCTGTTATTTCGATT |
| X16098 | 250 | CTAATCAAATCGAAATAACAGCTGAAAATTAATCTACTTATTCC CTTCGAGATTATATC |
| X16099 | 251 | AAAACTTCTGCTCACAAATACTCATAATCACTCCTAGTCTTCTAG GCGGGTTATCTACT |
| X16100 | 252 | TCGGATCAGTAGATAACCCGCCTAGAAGACTAGGAGTGATTATG AGTATTTGTGAGCAG |

TABLE 26-continued

Primer sequences used to create the integrative assemblies illustrated in FIGS. 35-44.

| Primer # | SEQ ID NO. | Primer sequence |
|---|---|---|
| X16463 | 253 | CAGAGTTTGAAGATATCCAAATGGT |
| X16464 | 254 | TTTGTTCTTCTTGTTATTGTATTGTGTTG |
| X16465 | 255 | GCTAATTAACATAAAACTCATGATTCAACG |
| X16466 | 256 | ACATAGGTTTGCAAGCTTTATAATCTG |
| X16467 | 257 | AGAACAACACAATACAATAACAAGAAGAACAAATAGGTCTAGAGATCTGTTTAGCTTGC |
| X16468 | 258 | AAACGTTGAATCATGAGTTTTATGTTAATTAGCGAGACTACATGATAGTCCAAAGAAAA |
| X16469 | 259 | AGAACAACACAATACAATAACAAGAAGAACAAACTACTTATTCCCTTCGAGATTATATC |
| X16470 | 260 | AAACGTTGAATCATGAGTTTTATGTTAATTAGCCTAGTCTTCTAGGCGGGTTATCTACT |
| X16471 | 261 | AAGAATCTGTTAGTTCGAACTCCAG |
| X16472 | 262 | TTTGTTGGCAATATGTTTTTGCTATATTAC |
| X16473 | 263 | GCCATTAGTAGTGTACTCAAACGAA |
| X16474 | 264 | ACGACTCAACATATGTATGTTGCT |
| X16475 | 265 | CACGTAATATAGCAAAAACATATTGCCAACAAATAGGTCTAGAGATCTGTTTAGCTTGC |
| X16476 | 266 | AACAATAATTCGTTTGAGTACACTACTAATGGCGAGACTACATGATAGTCCAAAGAAAA |
| X16477 | 267 | CACGTAATATAGCAAAAACATATTGCCAACAAACTACTTATTCCCTTCGAGATTATATC |
| X16478 | 268 | AACAATAATTCGTTTGAGTACACTACTAATGGCCTAGTCTTCTAGGCGGGTTATCTACT |
| X16951 | 269 | ATGTTCCGCTGATGTGATGTGCAAGATAAAC |
| X16952 | 270 | GAGGCAAGCTAAACAGATCTCTAGACCTATTTGATTGATTTGACTGTGTTATTTTGCGT |
| X16953 | 271 | ATAACCTCACGCAAAATAACACAGTCAAATCAATCAAATAGGTCTAGAGATCTGTTTAG |
| X16954 | 272 | AAAACTTTAACTAATAATTAGAGATTAAATCGCTTAGAGACTACATGATAGTCCAAAGA |
| X16955 | 273 | GTCCCCCCGTTTCTTTTCTTTGGACTATCATGTAGTCTCTAAGCGATTTAATCTCTAAT |
| X16956 | 274 | TCGGTCATTGGGTGAGTTTAAGCATTAGCAGCAATG |
| X16957 | 275 | TAAAACTTTAACTAATAATTAGAGATTAAATCGCTTATTTGATTGATTTGACTGTGTTA |
| X16958 | 276 | CACGCAAAATAACACAGTCAAATCAATCAAATAAGCGATTTAATCTCTAATTATTAGTT |

Heterologous genes for the production of a transcarboxylase based palmitic acid pathway (FIG. 34C) can then be introduced in a yeast microorganism engineered using the above integrative assemblies to replace GPD1, GPD2, FDH1, and FDH2 with two copies of a bifunctional alcohol/aldehyde dehydrogenase and two copies of a pyruvate formate lyase and to delete PDC5, PDC6, and PDC1. Such heterologous genes include, but are not limited to, S. cerevisiae NAD+ FDH1 to create the metabolic pathway in (FIG. 34B) and B. stabilis NADP+ FDH, S. cerevisiae PCK1, P. freudenreichii Transcarboxylase (see SEQ ID NOs:6-16), A. thaliana FATB1 to create the metabolic pathway in (FIG. 34C). Additional enzymes are identified in PCT/US2011/035416, which is incorporated by reference herein in its entirety. The pathways described herein can be engineered for production of a malonyl-CoA derived product in the yeast cytosol.

>SceNAD+_FDH1
(SEQ ID NO: 277)
atgtcgaagggaaaggttttgctggttctttacgaaggtggtaagcatgc tgaagagcaggaaaagttattggggtgtattgaaaatgaacttggtatca gaaatttcattgaagaacagggatacgagttggttactaccattgacaag gaccctgagccaacctcaacggtagacagggagttgaaagacgctgaaat tgtcattactacgccctttttccccgcctacatctcgagaaacaggattg cagaagctcctaacctgaagctctgtgtaaccgctggcgtcggttcagac catgtcgatttagaagctgcaaatgaacggaaaatcacggtcaccgaagt tactggttctaacgtcgtttctgtcgcagagcacgttatggccacaattt tggttttgataagaaactataatggtggtcatcaacaagcaattaatggt gagtgggatattgccggcgtggctaaaaatgagtatgatctggaagacaa ataaatttcaacgtaggtgccggtagaattggatatagggttctggaaa gattggtcgcatttaatccgaagaagttactgtactacgactaccaggaa ctacctgcggaagcaatcaatagattgaacgaggccagcaagcttttcaa tggcagaggtgatattgttcagagagtagagaaattggaggatatggttg ctcagtcagatgttgttaccatcaactgtccattgcacaaggactcaagg ggtttattcaataaaaagcttatttcccacatgaaagatggtgcatactt ggtgaataccgctagaggtgctatttgtgtcgcagaagatgttgccgagg cagtcaagtctggtaaattggctggctatggtggtgatgtctgggataag caaccagcaccaaaagaccatccctggaggactatggacaataaggacca cgtgggaaacgcaatgactgttcatatcagtggcacatctctggatgctc aaaagaggtacgctcagggagtaaagaacatcctaaatagttactttcc aaaaagtttgattaccgtccacaggatatattgtgcagaatggttcttat gccaccagagcttatggacagaagaaa >SceNAD+_FDH1
(SEQ ID NO: 278)
MSKGKVLLVLYEGGKHAEEQEKLLGCIENELGIRNFIEEQGYELVTTIDK

DPEPTSTVDRELKDAEIVITTPFFPAYISRNRIAEAPNLKLCVTAGVGSD

HVDLEAANERKITVTEVTGSNVVSVAEHVMATILVLIRNYNGGHQQAING

EWDIAGVAKNEYDLEDKIISTVGAGRIGYRVLERLVAFNPKKLLYYDYQE

LPAEAINRLNEASKLFNGRGDIVQRVEKLEDMVAQSDVVTINCPLHKDSR

GLFNKKLISHMKDGAYLVNTARGAICVAEDVAEAVKSGKLAGYGGDVWDK

QPAPKDHPWRTMDNKDHVGNAMTVHISGTSLDAQKRYAQGVKNILNSYFS

ICKFDYRPQDIIVQNGSYATRAYGQKK

>BstabilisNADP+_FDH
(SEQ ID NO: 279)
atggctaccgttttgtgtgtcttgtatccagatccagttgatggttatcc accacattatgttagagataccattccagttattaccagatacgctgatg gtcaaactgctccaactccagctggtccaccaggttttagaccaggtgaa ttggttggttctgtttctggtgctttgggtttgagaggttatttggaagc tcatggtcatactttgatcgttacctctgataaggatggtccagattctg aattcgaaagaagattgccagacgccgatgttgtatttctcaaccatttt ggccagcttacttgaccgctgaaagaattgctagagcaccaaaattgag attggctttgactgctggtattggttctgatcatgttgatttggatgctg ctgctagagcccatattactgttgctgaagttactggttccaactctatt tcagttgccgaacacgttgttatgactactaggctttggtcagaaactac ttgccatctcatgctattgctcaacaaggtggttggaatattgctgattg tgtactagatcctacgatgttgaaggtatgcattaggtactgaggtgctg gtagaattggtaggctgttagagaagattgaagccatttggtttacactt gcactacacccaaagacatagattggatgcagctatcgaacaagaattgg gtttaacttatcatgctgatccagctcattggctgctgctgttgatata gttaacttgcaaatcccattatacccatccaccgaacatttgtttgatgc tgctatgattgctagaatgaagagaggtgcatacttgattaacaccgcta gagctaaattggttgatagagatgagttgttagagctgttaatctggtca tttggctggttatggtggtgatgtaggtttccacaaccagctccagagat catccttggagagctatgcctttaatggtatgactccacatatctccgg tacatctttgtctgctcaagctagatatgctgctggtactttggaaatat tgcaatgttggtttgacggtagaccaatcagaaacgaatatttgattgtc gacggtggtactttagctggtactggtgctcaatcttacagattaact >BstabilisNADP+_FDH
(SEQ ID NO: 280)
MATVLCVLYPDPVDGYPPHYVRDTIPVITRYADGQTAPTPAGPPGFRPGE

LVGSVSGALGLRGYLEAHGHTLIVTSDKDGPDSEFERRLPDADVVISQPF

WPAYLTAERIARAPKLRLALTAGIGSDHVDLDAAARAHITVAEVTGSNSI

SVAEHVVMTTLALVRNYLPSHAIAQQGGWNIADCVSRSYDVEGMFIFGTV

GAGRIGIAVLRRLKPFGLHLHYTQRHRLDAAIEQELGLTYHADPASLAAA

VDIVNLQIPLYPSTEHLFDAAMIARMKRGAYLINTARAKLVDRDAVVRAV

TSGHLAGYGGDVWFPQPAPADHPWRAMPFNGMTPHISGTSLSAQARYAAG

TLEILQCWFDGRPIRNEYLIVDGGTLAGTGAQSYRLT

>ScePCK1
(SEQ ID NO: 281)
atgtccccttctaaaatgaatgctacagtaggatctacttccgaagttga acaaaaaatcagacaagaattggctatagtgacgaagtcaccaccatcag acgcaatgctccagctgccgttttgtatgaagatggtctaaaagaaaata aaactgtcatttcatcaagcggtgcattgatcgcttattccggtgttaaa accggaagatctccaaaggacaaacgtattgttgaagaacctacctcgaa agacgaaatttggtggggtccggtcaataaaccatgttctgaaagaacat ggtctatcaaccgtgaaagagctgcagattacttgagaacaagagaccac atttatattgtcgatgcatttgcaggatgggatccaaaatacagaatcaa agtccgcgttgtttgtgccagggcttaccacgctttattcatgacaaata tgcttattagacctacagaagaagaattagcccattttggagaacctgat tttactgtctggaacgctggtcagttcccagccaatttacacacccagga tatgtcttcaaagagtactatagaaattaacttcaaagcaatggaaatga tcatttaggtaccgaatacgccggtgaaatgaaaaaggtatatcacag ttatgttttacttgatgcctgtgcaccataacgttttaactttgcactct

```
tccgccaaccagggtattcaaaacggtgacgttactttattctttggcct aagtggtaccgggaaaaccactttatccgcagacccacatagattgttga tcggcgatgatgaacattgttggtccgaccatggtgtcttcaatatcgaa ggtggttgttacgccaagtgtattaatttatctgccgaaaaggagcctga aattttcgacgctatcaagtttggttctgtattagaaaacgttatctatg acgagaagtcgcatgtagtcgactatgacgactatctattactgaaaata ctagatgtgcctacccaattgactacattccaagtgccaagattccatgt ttggcggactctcatccaaagaacattatcctgctaacttgtgatgatcg ggtgtataccaccagtatctaaattgactcctgaacaagtcatgtaccat ttcatctctggttacacttctaaaatggctggtactgagcaaggtgtcac tgaacctgaaccaacattttcatcttgtttcggacaacccttcctagcct tgcacccctattagatacgcaaccatgttagctacaaagatgtctcaacat aaagctaatgcgtacttaatcaacaccggctggactggttcttcctacgt atctggtggtaaacgttgcccattgaagtacacaagggccattctggatt ctattcatgatggttcgttagccaatgaaacgtacgaaactttaccgatt ttcaatcttcaagtacctaccaaggttaacggtgttccagctgagctttt gaatcctgctaaaaactggtctcaaggtgaatccaaatacagaggtgcag ttaccaacttggccaacttgtttgttcaaaatttcaagatttatcaagac agagccacaccagatgtattagccgctggtcctcaattcgag
```

>ScePCK1

(SEQ ID NO: 282)

MSPSKMNATVGSTSEVEQKIRQELALSDEVTTIRRNAPAAVLYEDGLKEN

KTVISSSGALIAYSGVKTGRSPKDKRIVEEPTSKDEIWWGPVNKPCSERT

WSINRERAADYLRTRDHIYIVDAFAGWDPKYRIKVRVVCARAYHALFMTN

MLIRPTEEELAILFGEPDFTVWNAGQFPANLHTQDMSSKSTIEINFKAME

MIILGTEYAGEMKKGIFTVMFYLMPVHHNVLTLHSSANQGIQNGDVTLFF

GLSGTGKTTLSADPHRLLIGDDEHCWSDHGVFNIEGGCYAKCINLSAEKE

PEIFDAIKFGSVLENVIYDEKSHVVDYDDSSITENTRCAYPIDYIPSAKI

PCLADSHPKNIILLTCDASGVLPPVSKLTPEQVMYHFISGYTSKMAGTEQ

GVTEPEPTFSSCFGQPFLALHPIRYATMLATKMSQHKANAYLINTGWTGS

SYVSGGKRCPLKYTRAILDSIHDGSLANETYETLPIFNLQVPTKVNGVPA

ELLNPAKNWSQGESKYRGAVTNLANLFVQNFKIYQDRATPDVLAAGPQFE

>Ath_FATB1_mature_peptide (SEQ ID NO: 283)

```
atgcttgattggaaacctaggcgttctgacatgctggtggatccttttgg tataggagaattgttcaggatggccttgtgttccgtcagaattttttcta ttaggtcatatgaaataggtgctgatcgctctgcatctatagaaaccgtc atgaatcatctgcaggaaacggcgcttaatcatgttaagactgctggatt gcttggagatgggtttggctctacacctgagatgtttaagaagaacttga tatgggttgtcactcgtatgcaggttgtggttgataaatatcctacttgg ggagatgttgttgaagtagacacctgggtcagtcaatctggaaagaatgg tatgcgtcgtgattggctagttcgggattgtaatactggagaaaccttaa cacgagcatcaagtgtgtgggtgatgatgaataaactgacaaggagattg tcaaagattcctgaagaggttcgaggggaaatagagccttattttgtgaa ttctgatcctgtccttgccgaggacagcagaaagttaacaaaaattgatg acaagactgctgactatgttcgatctggtctcactcctcgatggagtgac ctagatgttaaccagcatgtgaataatgtaaagtacattgggtggatcct ggagagtgctccagtgggaataatggagaggcagaagctgaaaagcatga ctctggagtatcggagggaatgcgggagagacagtgtgcttcagtccctc actgcagttacgggttgcgatatcggtaacctggcaacagcgggggatgt ggaatgtcagcatttgctccgactccaggatggagcggaagtggtgagag gaagaacagagtggagtagtaaaacaccaacaacaacttggggaactgca ccg
```

>Ath_FATB1_mature_peptide (SEQ ID NO: 284)

MLDWKPRRSDMLVDPFGIGRIVQDGLVFRQNFSIRSYEIGADRSASIETV

MNHLQETALNHVKTAGLLGDGFGSTPEMFKKNLIWVVTRMQVVVDKYPTW

GDVVEVDTWVSQSGKNGMRRDWLVRDCNTGETLTRASSVWVMMNKLTRRL

SKIPEEVRGEIEPYFVNSDPVLAEDSRKLTKIDDKTADYVRSGLTPRWSD

LDVNQHVNNVKYIGWILESAPVGIMERQKLKSMTLEYRRECGRDSVLQSL

TAVTGCDIGNLATAGDVECQHLLRLQDGAEVVRGRTEWSSKTPTTTWGTA

P

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant yeast microorganism comprising one or more engineered metabolic pathways to convert a carbohydrate source to a hydrocarbon, wherein the one or more engineered metabolic pathways comprises
   (a) the conversion of phosphoenolpyruvate to oxaloacetate by a phosphoenolpyruvate carboxykinase and
   (b) the conversion of oxaloacetate and acetyl-CoA to malonyl-CoA and pyruvate by a heterologous transcarboxylase Enzyme Commission Number 2.1.3.1;
   wherein the one or more engineered metabolic pathways further comprises downregulation or deletion of native pyruvate decarboxylase, and
   wherein the one or more engineered metabolic pathway further comprises a heterologous pyruvate formate lyase, pyruvate dehydrogenase, pyruvate:ferredoxin oxidoreductase or pyruvate:NADP+oxidoreductase.

2. The recombinant microorganism of claim 1, wherein the conversion of a carbohydrate source to a hydrocarbon is under anaerobic or microaerophilic conditions.

3. The recombinant microorganism of claim 1, wherein said hydrocarbon is selected from the group consisting of:
   (a) an alkane;
   (b) an alkene;
   (c) an alkyne;
   (d) a hydrocarbon derivative; and
   (e) combinations of (a)-(d).

4. The recombinant microorganism of claim 3, wherein said hydrocarbon derivative is selected from the group consisting of:
   (a) an aldehyde;
   (b) an alcohol;
   (c) an ester;
   (d) a fatty acid;
   (e) an unsaturated fatty acid;
   (f) a branched-chain fatty acid;
   (g) a branched methoxy fatty acid;
   (h) a multi-methyl branched acid;
   (i) a divinyl-ether fatty acid;
   (j) a w-phenylalkanoic acid;
   (k) a dicarboxylic acid; and
   (l) combinations of (a)-(k).

5. The recombinant microorganism of claim 4, wherein said hydrocarbon or hydrocarbon derivative comprises a carbon backbone of C4-C40.

6. The recombinant microorganism of claim 5, wherein said hydrocarbon or hydrocarbon derivative comprises a carbon backbone selected from the group consisting of:
   (a) C6-C36;
   (b) C8-C32;
   (C) C10-C28;
   (d) C12-C24;
   (e) C14-C22;
   (f) C16-C20; and
   (g) combinations of (a)-(f).

7. The recombinant microorganism of claim 5, wherein said hydrocarbon or hydrocarbon derivative comprises a carbon backbone selected from the group consisting of: (a) C12; (b) C14; (c) C16; (d) C18; (e) C20; (f) C22; (g) C24; and (h) combinations of (a)-(g).

8. The recombinant microorganism of claim 7, wherein one of said engineered metabolic pathways further comprises the conversion of pyruvate and CoA-SH into acetyl-CoA and CO2 and NAD(P)H.

9. The recombinant microorganism of claim 1, wherein one of said engineered metabolic pathways further comprises at least one of the following steps:
   (a) conversion of malonyl-CoA to malonyl-ACP;
   (b) conversion of malonyl-ACP to an acyl-ACP;
   (c) conversion of an acyln-ACP to a β-keto ester.n+2-ACP;
   (d) conversion of a β-keto estern+2-ACP to a β-D-hydroxyacyln+2-ACP;
   (e) conversion of a β-D-hydroxyacyln+2-ACP to a trans-2-unsaturated acyl.n+2-ACP; or
   (f) conversion of a trans-2-unsaturated acyln+2-ACP to an acyln+2-ACP.

10. The recombinant microorganism of claim 1, wherein said phosphoenolpyruvate carboxykinase is encoded by a polynucleotide from a *Thermoanaerobacter* species, *E. coli*, *S. cerevisiae* or *C. thermocellum*.

11. The recombinant microorganism of claim 1, wherein said transcarboxylase is encoded by a polynucleotide from a *Thermoanaerobacter* species, *P. freudenreichii*, *P. acnes*, *C. thermocellum*, *C. bescii*, *C. cellulolyticum*, *C. kroppenstedtii*, *B. fragilis*, *V. parvula V. gazogenes*, *P. thermopropionicum*, *Candidatus*, *Cloacamonas acidaminovorans*, *G. bemidjiensis* or *D. propionicus*.

12. The recombinant microorganism of claim 1, wherein said downregulated or deleted native enzyme is selected from the group consisting of:
   (a) a pyruvate kinase;
   (b) a hydrogenase;
   (c) a lactate dehydrogenase;
   (d) a phosphotransacetylase;
   (e) an acetate kinase;
   (f) an acetaldehyde dehydrogenase;
   (g) an alcohol dehydrogenase;
   (h) a pyruvate formate lyase;
   (i) a pyruvate decarboxylase;
   (j) an enzyme involved in degradation of fatty acids and their derivatives;
   and (k) combinations of (a)-(j).

13. The recombinant microorganism of claim 1, wherein said downregulated or deleted native enzyme is selected from the group consisting of:

(a) a lactate dehydrogenase;
(b) a phosphate acetyltransferase;
(c) an acetaldehyde dehydrogenase/alcohol dehydrogenase;
(d) a pyruvate kinase;
(e) a malate dehydrogenase;
(f) a PEP-protein phosphotransferase of PTS system; and
(g) combinations of (a)-(f).

14. A process for converting a carbohydrate source to a hydrocarbon comprising contacting the carbohydrate source with a recombinant microorganism B according to claim 1.

15. An engineered metabolic pathway for producing a 1 hydrocarbon in a consolidated bioprocessing (CBP) organism according to claim 1.

16. The recombinant microorganism of claim 1, wherein the conversion of a carbohydrate source to a hydrocarbon is redox neutral.

17. The recombinant microorganism of claim 1, wherein one of said engineered metabolic pathways further comprises the conversion of acyln+2-ACP to a fatty acid.

18. The recombinant microorganism of claim 17, wherein said acyln+2-ACP is converted to a fatty acid by a chain termination enzyme.

19. The recombinant microorganism of claim 18, wherein said chain termination enzyme is selected from an *E. coli* codon optimized C12 acyl-ACP thioesterase, an *E. coli* codon optimized C16 acyl-ACP thioesterase, an acyl-ACP reductase and an acyl-ACP reductase homolog.

20. The recombinant yeast microorganism of claim 1, wherein said yeast microorganism is selected from the group consisting of *Saccharomyces cerevisiae, Kluyveromyces lactis, Kluyveromyces marxianus, Pichia pastoris, Yarrowia lipolytica, Hansenula polymorpha, Phaffia rhodozyma, Candida utilis, Arxula adeninivorans, Pichia stipitis, Debaryomyces hansenii, Debaryomyces polymorphus, Schizosaccharomyces pombe, Candida albicans,* and *Schwanniomyces occidentalis.*

* * * * *

SEQUENCE LISTING

```
<160> NUMBER OF SEQ ID NOS: 301

<210> SEQ ID NO 1
<211> LENGTH: 1220
<212> TYPE: PRT
<213> ORGANISM: C. aurantiacus

<400> SEQUENCE: 1
```

```
Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
                20                  25                  30

Gly Ala Thr Val Ile Ile Ser Gly Arg Asn Arg Ala Lys Leu Thr Ala
            35                  40                  45

Leu Ala Glu Arg Met Gln Ala Glu Ala Gly Val Pro Ala Lys Arg Ile
        50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
                100                 105                 110

Thr Glu Ala Glu Leu Gly Pro Gly Ala Glu Glu Thr Leu His Ala Ser
                115                 120                 125

Ile Ala Asn Leu Leu Gly Met Gly Trp His Leu Met Arg Ile Ala Ala
        130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
                180                 185                 190

Gly Ile Arg Val Asn Thr Ile Phe Pro Gly Pro Ile Glu Ser Asp Arg
            195                 200                 205

Ile Arg Thr Val Phe Gln Arg Met Asp Gln Leu Lys Gly Arg Pro Glu
        210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
                260                 265                 270

Gly Glu Thr Ile Glu Val Thr His Gly Met Glu Leu Pro Ala Cys Ser
            275                 280                 285

Glu Thr Ser Leu Leu Ala Arg Thr Asp Leu Arg Thr Ile Asp Ala Ser
        290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Leu Ala Gln Phe Glu Gln Ala Val Asn Glu
                340                 345                 350

Ser Arg Arg Leu Ala Gly Ala Asp Phe Thr Pro Ile Ala Leu Pro
                355                 360                 365

Leu Asp Pro Arg Asp Pro Ala Thr Ile Asp Ala Val Phe Asp Trp Gly
        370                 375                 380

Ala Gly Glu Asn Thr Gly Gly Ile His Ala Ala Val Ile Leu Pro Ala
385                 390                 395                 400

Thr Ser His Glu Pro Ala Pro Cys Val Ile Glu Val Asp Asp Glu Arg
                405                 410                 415

Val Leu Asn Phe Leu Ala Asp Glu Ile Thr Gly Thr Ile Val Ile Ala
```

```
                420             425             430
Ser Arg Leu Ala Arg Tyr Trp Gln Ser Gln Arg Leu Thr Pro Gly Ala
            435             440             445
Arg Ala Arg Gly Pro Arg Val Ile Phe Leu Ser Asn Gly Ala Asp Gln
450             455             460
Asn Gly Asn Val Tyr Gly Arg Ile Gln Ser Ala Ala Ile Gly Gln Leu
465             470             475             480
Ile Arg Val Trp Arg His Glu Ala Glu Leu Asp Tyr Gln Arg Ala Ser
            485             490             495
Ala Ala Gly Asp His Val Leu Pro Pro Val Trp Ala Asn Gln Ile Val
            500             505             510
Arg Phe Ala Asn Arg Ser Leu Glu Gly Leu Glu Phe Ala Cys Ala Trp
            515             520             525
Thr Ala Gln Leu Leu His Ser Gln Arg His Ile Asn Glu Ile Thr Leu
            530             535             540
Asn Ile Pro Ala Asn Ile Ser Ala Thr Thr Gly Ala Arg Ser Ala Ser
545             550             555             560
Val Gly Trp Ala Glu Ser Leu Ile Gly Leu His Leu Gly Lys Val Ala
            565             570             575
Leu Ile Thr Gly Gly Ser Ala Gly Ile Gly Gly Gln Ile Gly Arg Leu
            580             585             590
Leu Ala Leu Ser Gly Ala Arg Val Met Leu Ala Ala Arg Asp Arg His
            595             600             605
Lys Leu Glu Gln Met Gln Ala Met Ile Gln Ser Glu Leu Ala Glu Val
            610             615             620
Gly Tyr Thr Asp Val Glu Asp Arg Val His Ile Ala Pro Gly Cys Asp
625             630             635             640
Val Ser Ser Glu Ala Gln Leu Ala Asp Leu Val Glu Arg Thr Leu Ser
            645             650             655
Ala Phe Gly Thr Val Asp Tyr Leu Ile Asn Asn Ala Gly Ile Ala Gly
            660             665             670
Val Glu Glu Met Val Ile Asp Met Pro Val Glu Gly Trp Arg His Thr
            675             680             685
Leu Phe Ala Asn Leu Ile Ser Asn Tyr Ser Leu Met Arg Lys Leu Ala
            690             695             700
Pro Leu Met Lys Lys Gln Gly Ser Gly Tyr Ile Leu Asn Val Ser Ser
705             710             715             720
Tyr Phe Gly Gly Glu Lys Asp Ala Ala Ile Pro Tyr Pro Asn Arg Ala
            725             730             735
Asp Tyr Ala Val Ser Lys Ala Gly Gln Arg Ala Met Ala Glu Val Phe
            740             745             750
Ala Arg Phe Leu Gly Pro Glu Ile Gln Ile Asn Ala Ile Ala Pro Gly
            755             760             765
Pro Val Glu Gly Asp Arg Leu Arg Gly Thr Gly Glu Arg Pro Gly Leu
            770             775             780
Phe Ala Arg Arg Ala Arg Leu Ile Leu Glu Asn Lys Arg Leu Asn Glu
785             790             795             800
Leu His Ala Ala Leu Ile Ala Ala Arg Thr Asp Glu Arg Ser Met
            805             810             815
His Glu Leu Val Glu Leu Leu Pro Asn Asp Val Ala Ala Leu Glu
            820             825             830
Gln Asn Pro Ala Ala Pro Thr Ala Leu Arg Glu Leu Ala Arg Arg Phe
            835             840             845
```

```
Arg Ser Glu Gly Asp Pro Ala Ala Ser Ser Ser Ala Leu Leu Asn
    850                 855                 860

Arg Ser Ile Ala Ala Lys Leu Leu Ala Arg Leu His Asn Gly Gly Tyr
865                 870                 875                 880

Val Leu Pro Ala Asp Ile Phe Ala Asn Leu Pro Asn Pro Pro Asp Pro
                885                 890                 895

Phe Phe Thr Arg Ala Gln Ile Asp Arg Glu Ala Arg Lys Val Arg Asp
            900                 905                 910

Gly Ile Met Gly Met Leu Tyr Leu Gln Arg Met Pro Thr Glu Phe Asp
        915                 920                 925

Val Ala Met Ala Thr Val Tyr Tyr Leu Ala Asp Arg Asn Val Ser Gly
    930                 935                 940

Glu Thr Phe His Pro Ser Gly Gly Leu Arg Tyr Glu Arg Thr Pro Thr
945                 950                 955                 960

Gly Gly Glu Leu Phe Gly Leu Pro Ser Pro Glu Arg Leu Ala Glu Leu
                965                 970                 975

Val Gly Ser Thr Val Tyr Leu Ile Gly Glu His Leu Thr Glu His Leu
            980                 985                 990

Asn Leu Leu Ala Arg Ala Tyr Leu Glu Arg Tyr Gly Ala Arg Gln Val
        995                 1000                1005

Val Met Ile Val Glu Thr Glu Thr Gly Ala Glu Thr Met Arg Arg
    1010                1015                1020

Leu Leu His Asp His Val Glu Ala Gly Arg Leu Met Thr Ile Val
    1025                1030                1035

Ala Gly Asp Gln Ile Glu Ala Ala Ile Asp Gln Ala Ile Thr Arg
    1040                1045                1050

Tyr Gly Arg Pro Gly Pro Val Val Cys Thr Pro Phe Arg Pro Leu
    1055                1060                1065

Pro Thr Val Pro Leu Val Gly Arg Lys Asp Ser Asp Trp Ser Thr
    1070                1075                1080

Val Leu Ser Glu Ala Glu Phe Ala Glu Leu Cys Glu His Gln Leu
    1085                1090                1095

Thr His His Phe Arg Val Ala Arg Lys Ile Ala Leu Ser Asp Gly
    1100                1105                1110

Ala Ser Leu Ala Leu Val Thr Pro Glu Thr Thr Ala Thr Ser Thr
    1115                1120                1125

Thr Glu Gln Phe Ala Leu Ala Asn Phe Ile Lys Thr Thr Leu His
    1130                1135                1140

Ala Phe Thr Ala Thr Ile Gly Val Glu Ser Glu Arg Thr Ala Gln
    1145                1150                1155

Arg Ile Leu Ile Asn Gln Val Asp Leu Thr Arg Arg Ala Arg Ala
    1160                1165                1170

Glu Glu Pro Arg Asp Pro His Glu Arg Gln Gln Glu Leu Glu Arg
    1175                1180                1185

Phe Ile Glu Ala Val Leu Leu Val Thr Ala Pro Leu Pro Pro Glu
    1190                1195                1200

Ala Asp Thr Arg Tyr Ala Gly Arg Ile His Arg Gly Arg Ala Ile
    1205                1210                1215

Thr Val
    1220

<210> SEQ ID NO 2
<211> LENGTH: 1818
```

<212> TYPE: DNA
<213> ORGANISM: C. thermocellum

<400> SEQUENCE: 2

```
atgacatcaa caaacatgac aaaaaacaaa aaactgctgg attgggttaa ggaaatggct      60
gaaatgtgtc agcctgatga aatttattgg tgcgatggtt cggaggaaga aaatgagcgc     120
ttgataaagt tgatggtgga ttcaggtttg gctacgcctt tgaatcctga aaagcgacct     180
ggatgttatc tcttccgcag cgatccgtcc gacgttgccc gtgttgagga cagaactttt     240
attgcatcca aaccaaaga agatgcagga cctacaaaca actggataga tccggttgag     300
ctcaaggcaa ctatgaaaga gttgtacaag ggttgtatga agggaagaac aatgtatgtt     360
attcctttct ccatgggacc tatcggttca cccatttcaa aaatcggcgt tgaattgacc     420
gacagccctt atgttgttgt taacatgcgc attatgactc gcataggcaa ggctgtgttg     480
gatcagctcg gagaagacgg agattttgta ccttgtctcc actcagtcgg tgctccgctc     540
aaagagggag aaaaggataa aggttggcca tgcgcaccaa tcgaaaagaa atacataagc     600
cacttcccgg aagaaggac tatatggtca tatggttccg gatacggtgg aaatgcgctt     660
ttaggaaaga aatgctttgc acttcgtatt gcatctgtta tggcacgtga cgaaggttgg     720
cttgctgaac acatgcttat ccttcgcata acagaccctg aaggaaacaa gacatatgtt     780
acaggtgctt ccccaagcgc atgcggaaag acgaacctgg ctatgcttat tcctacaatt     840
cccggatgga agttgaaac aatcggtgac gatattgcat ggatgagatt tggaaaagac     900
ggccgtttgt atgctatcaa ccctgaagca ggattctttg tgttgctcc gggtacatcc     960
atggattcaa atccgaacgc aatgcataca attaagaaaa atactatatt tacaaacgtt    1020
gcattgactg atgacggcga tgtttggtgg gaaggcatcg aactgaacc gccggctcat    1080
ctcatagact ggcagggtaa agactggact cctgattccg gaactttggc agcacatccc    1140
aacggacgtt ttacagcacc tgcaagtcag tgccctgtaa ttgctcctga atgggaggat    1200
ccggaaggtg tgccgatttc agcaatcctt atcggtggac gccgtccgaa caccattccg    1260
cttgttcatg aaagctttga ctggaaccat ggtgtattca tgggttcaat catgggttct    1320
gaaattacgg ctgccgcaat ttcaaacaaa atcggacagg tacgccgtga cccgtttgct    1380
atgctgcctt tcataggcta caacgtaaat gactatttgc agcactggtt gaacatgggt    1440
accaagactg acccaagcaa gcttcccaag atattctatg taaactggtt ccgcaaggac    1500
agcaacggta atggttgtg gcctggatac ggtgaaaaca gccgtgttct caagtggatt    1560
gttgaaagag tcaacggaaa aggtaaagca gtaaagacac ctataggata tatgcctaca    1620
gttgacgcta tcgacacaac cggccttgat gtaagcaaag aggatatgga agaactcttg    1680
agcgttaaca agaacagtg gctccaggaa gttgagtcaa taaaagaaca ttataagtca    1740
tacggagaaa aactgccgaa agaattgtgg gcacaattgg aggctcttga caacgtttg    1800
aaagagtata acggttaa                                                  1818
```

<210> SEQ ID NO 3
<211> LENGTH: 1632
<212> TYPE: DNA
<213> ORGANISM: T. saccharolyticum

<400> SEQUENCE: 3

```
atgattatga aaaatcaaa gaatgtttc aatctgaata ttgacgacaa agaaaccttg      60
aatactttg gaagttcgag aggagaattg tttatgatag atttagatga tgtatttaaa     120
```

```
aattctggca gtattcttta caatttacct gtttcagatt tgatagagga agccataaga      180
aataatgaag ggaaattgtt agaaaatggt gcattagatg ttttttacagg taaatatacg     240 ggaagaatac caaaagataa atacattgta aatgaagaat ctattcataa tgatatttgg     300
tgggaaaata ataattcaat ggaaaaagaa aattttatta gagttttaaa cagagtaatt     360
gattatttaa aaagagcag aaaattgtat gttttttaaag gttttgttgg cgcagacccg      420
cgatatagat atcaagtaac cgttattaat gaatatgcct atcaaaacgc ttttgtacat     480
caattattta ttaatcctaa aaatgaagaa gaacttaaaa aggaatccga ttttacagtt     540
atttgtgtgc cgaatttttt agctgatcca atttatgatg gaactaattc tgaggcattt     600
attattataa gttttgaaga aaaattaatt ttaattggtg gaacaagata ttcaggagaa     660
ataaaaaaat ctgtcttcac aatgatgaat tatttgatgt taaaaggaa tgtactgcct      720 atgcattgtg cagctaatat aggttccaat aatgatacag cgcttttttt tgggttgtcg     780
ggaaccggca agacaacttt atcaacggat ccagaaagat ttttaattgg cgacgatgaa     840 catgatggt cttcacatgg aatttttaat tttgagggtg gatgctatgc aaagtgtata      900 aattatccc catataatga acctgaaata tggaatgcaa ttagatttgg aacaattta       960 gaaaatgtta tttatgatgt aaataaatg ccagtctata caagtagtaa aataactgaa     1020
aatacaagag cttcatatcc acttgagtac atccctagga aagcgtcaaa tggcattggc    1080
ggtaatccta aaattatatt tttcttggca gccgatgctt ttggagtatt gcctccaatt    1140
tctaagctga caaatgaaca ggctgttgac tatttcttat taggatatac gagcaaaata    1200
ccaggaacag aaaagggaat ttgcgaacca caagcaacgt tttcatcatg ttttggagca    1260 ccattttgc catcatatcc aatgaggtat gctgaattgt taaagaaaaa aatcgcagaa     1320
aatgattcag ttgtttattt aataaatact ggatggatag gtggacatta tggaattggc    1380
aaaaggatag atttaaaata cacaagagaa atcataaaaa atgtttaaa tggtgaattg     1440 gaaaaagcaa aatttaaaaa agatacagta tttgatttga tgataccaga aaagtgcaat    1500
aacattccag atgaattatt agatcctata aaaacatggg aagacaaaaa tgattacttc    1560
caaactgcta ataatttatt atctgcattt aaagcgagat tagattatat aaaaaatggg    1620
attcatcaat aa                                                         1632
```

<210> SEQ ID NO 4
<211> LENGTH: 1623
<212> TYPE: DNA
<213> ORGANISM: E. coli

<400> SEQUENCE: 4

```
atgcgcgtta caatggtttt gaccccgcaa gaactcgagg cttatggtat cagtgacgta       60
catgatatcg tttacaaccc aagctacgac ctgctgtatc aggaagagct cgatccgagc      120
ctgacaggtt atgagcgcgg ggtgttaact aatctgggtg ccgttgccgt cgataccggg      180
atcttcaccg gtcgttcacc aaaagataag tatatcgtcc gtgacgatac cactcgcgat      240
actttctggt gggcagacaa aggcaaaggt aagaacgaca caaacctct ctctccggaa       300 acctggcagc atctgaaagg cctggtgacc aggcagcttt ccggcaaacg tctgttcgtt     360
gtcgacgctt tctgtggtgc gaacccggat actcgtcttt ccgtccgttt catcaccgaa     420
gtggcctggc aggcgcattt tgtcaaaaac atgtttattc gcccgagcga tgaagaactg     480
gcaggtttca aaccagactt tatcgttatg aacggcgcga gtgcactaa cccgcagtgg      540 aaagaacagg gtctcaactc cgaaaacttc gtggcgttta cctgaccga gcgcatgcag      600
```

```
ctgattggcg gcacctggta cggcggcgaa atgaagaaag ggatgttctc gatgatgaac    660
tacctgctgc cgctgaaagg tatcgcttct atgcactgct ccgccaacgt tggtgagaaa    720
ggcgatgttg cggtgttctt cggcctttcc ggcaccggta aaaccaccct ttccaccgac    780
ccgaaacgtc gcctgattgg cgatgacgaa cacggctggg acgatgacgg cgtgtttaac    840
ttcgaaggcg gctgctacgc aaaaactatc aagctgtcga agaagcgga acctgaaatc    900 tacaacgcta tccgtcgtga tgcgttgctg aaaaacgtca ccgtgcgtga agatggcact    960
atcgactttg atgatggttc aaaaaccgag aacacccgcg tttcttatcc gatctatcac   1020
atcgataaca ttgttaagcc ggtttccaaa gcgggccacg cgactaaggt tatcttcctg   1080
actgctgatg ctttcggcgt gttgccgccg gtttctcgcc tgactgccga tcaaacccag   1140
tatcacttcc tctctggctt caccgccaaa ctggccggta ctgagcgtgg catcaccgaa   1200
ccgacgccaa ccttctccgc ttgcttcggc gcggcattcc tgtcgctgca cccgactcag   1260
tacgcagaag tgctggtgaa acgtatgcag gcggcgggcg cgcaggctta tctggttaac   1320
actggctgga acggcactgg caaacgtatc tcgattaaag ataccgcgc cattatcgac    1380 gccatcctca acggttcgct ggataatgca gaaaaccttca ctctgccgat gtttaacctg   1440
gcgatcccaa ccgaactgcc gggcgtagac acgaagattc tcgatccgcg taacacctac   1500
gcttctccgg aacagtggca ggaaaaagcc gaaaccctgg cgaaactgtt tatcgacaac   1560
ttcgataaat acaccgacac ccctgcgggt gccgcgctgg tagcggctgg tccgaaactg   1620
taa                                                                  1623

<210> SEQ ID NO 5
<211> LENGTH: 1650
<212> TYPE: DNA
<213> ORGANISM: S. cerevisiae

<400> SEQUENCE: 5 atgtccccttt ctaaaatgaa tgctacagta ggatctactt ccgaagttga acaaaaaatc     60
agacaagaat tggctcttag tgacgaagtc accaccatca gacgcaatgc tccagctgcc    120
gttttgtatg aagatggtct aaaagaaaat aaaactgtca tttcatcaag cggtgcattg    180
atcgcttatt ccggtgttaa aaccggaaga tctccaaagg acaaacgtat tgttgaagaa    240
cctacctcga aagacgaaat ttggtggggt ccggtcaata accatgttc tgaaagaaca    300 tggtctatca accgtgaaag agctgcagat tacttgagaa caagagacca catttatatt    360
gtcgatgcat ttgcaggatg ggatccaaaa tacagaatca aagtccgcgt tgtttgtgcc    420
agggcttacc acgctttatt catgacaaat atgcttatta gacctacaga agaagaatta    480
gcccattttg gagaacctga ttttactgtc tggaacgctg gtcagttccc agccaattta    540
cacacccagg atatgtcttc aaagagtact atagaaatta acttcaaagc aatggaaatg    600
atcattttag gtaccgaata cgccggtgaa atgaaaaag gtatttttcac agttatgttt    660 tacttgatgc ctgtgcacca taacgtttta actttgcact cttccgccaa ccagggtatt    720
caaaacggtg acgttacttt attctttggc ctaagtggta ccggaaaaac cactttatcc    780
gcagacccac atagattgtt gatcggcgat gatgaacatt gttggccga ccatggtgtc    840 ttcaatatcg aaggtggttg ttacgccaag tgtattaatt tatctgccga aaaggagcct    900
gaaattttcg acgctatcaa gtttggttct gtattagaaa acgttatcta tgacgagaag   960
tcgcatgtag tcgactatga cgactcttct attactgaaa atactagatg tgcctaccca   1020
```

```
attgactaca ttccaagtgc caagattcca tgtttggcgg actctcatcc aaagaacatt    1080
atcctgctaa cttgtgatgc ttcgggtgtt ttaccaccag tatctaaatt gactcctgaa    1140
caagtcatgt accatttcat ctctggttac acttctaaaa tggctggtac tgagcaaggt    1200
gtcactgaac ctgaaccaac attttcatct tgtttcggac aacccttcct agccttgcac    1260
cctattagat acgcaaccat gttagctaca aagatgtctc aacataaagc taatgcgtac    1320
ttaatcaaca ccggctggac tggttcttcc tacgtatctg gtggtaaacg ttgcccattg    1380
aagtacacaa gggccattct ggattctatt catgatggtt cgttagccaa tgaaacgtac    1440
gaaactttac cgattttcaa tcttcaagta cctaccaagg ttaacggtgt tccagctgag    1500
cttttgaatc ctgctaaaaa ctggtctcaa ggtgaatcca atacagagg tgcagttacc     1560 aacttggcca acttgtttgt tcaaaatttc aagatttatc aagacagagc cacaccagat    1620
gtattagccg ctggtcctca attcgagtaa                                     1650

<210> SEQ ID NO 6
<211> LENGTH: 372
<212> TYPE: DNA
<213> ORGANISM: Propionibacterium freudenreichii

<400> SEQUENCE: 6
tcagccgatc ttgatgagac cctgaccgcc ctgcacggcg tcacgctcct tgacaaggac      60
cttctcgacc ttgccgtcgg tgggagcgtt gatctcggtc tccatcttca tggcctcgag     120
aacgagcacg gtctgaccag ccttgaccgt gtcaccctcc ttcacgagga tcttggagac     180
ggtgccggcc agcggagcgg gaatctcgcc ctctccggcc ttaccggcgc ctgcgccacc     240
tgctgcgcgc ggtgccggcg cgccgccggt gccgccgccg aacaggatgg tgcccatcgg     300
gttttcgtgt gacttgtcga cgtcaacgtc aacgtcatac gcagtgccgt tgactgttac     360
cttcagtttc at                                                        372

<210> SEQ ID NO 7
<211> LENGTH: 369
<212> TYPE: DNA
<213> ORGANISM: Propionibacterium freudenreichii

<400> SEQUENCE: 7
atgaaactga aggtaacagt caacggcact gcgtatgacg ttgacgttga cgtcgacaag      60
tcacacgaaa acccgatggg caccatcctg ttcggcggcg gcaccggcgg cgcgccggca     120
ccgcgcgcag caggtggcgc aggcgccggt aaggccggag agggcgagat tcccgctccg     180
ctggccggca ccgtctccaa gatcctcgtg aaggagggtg acacggtcaa ggctggtcag     240
accgtgctcg ttctcgaggc catgaagatg gagaccgaga tcaacgctcc caccgacggc     300
aaggtcgaga aggtccttgt caaggagcgt gacgccgtgc agggcggtca gggtctcatc     360
aagatcggc                                                            369

<210> SEQ ID NO 8
<211> LENGTH: 123
<212> TYPE: PRT
<213> ORGANISM: Propionibacterium freudenreichii

<400> SEQUENCE: 8

Met Lys Leu Lys Val Thr Val Asn Gly Thr Ala Tyr Asp Val Asp Val
1               5                   10                  15

Asp Val Asp Lys Ser His Glu Asn Pro Met Gly Thr Ile Leu Phe Gly
            20                  25                  30
```

```
Gly Gly Thr Gly Gly Ala Pro Ala Pro Arg Ala Ala Gly Gly Ala Gly
         35                  40                  45
Ala Gly Lys Ala Gly Glu Gly Glu Ile Pro Ala Pro Leu Ala Gly Thr
 50                  55                  60
Val Ser Lys Ile Leu Val Lys Glu Gly Asp Thr Val Lys Ala Gly Gln
 65                  70                  75                  80
Thr Val Leu Val Leu Glu Ala Met Lys Met Glu Thr Glu Ile Asn Ala
                 85                  90                  95
Pro Thr Asp Gly Lys Val Glu Lys Val Leu Val Lys Glu Arg Asp Ala
                100                 105                 110
Val Gln Gly Gly Gln Gly Leu Ile Lys Ile Gly
                115                 120

<210> SEQ ID NO 9
<211> LENGTH: 1518
<212> TYPE: DNA
<213> ORGANISM: Propionibacterium freudenreichii

<400> SEQUENCE: 9
tcacgcctgc tgaacggtga cttcgcggac ggttccgccc acgttcacgt tgtaggtgac    60
gggaccggcc acggcgagcg acttctcgtc gccctcggcc tcggccttca gctgggcatc   120
ggtgagagcc acgctgtgcg ggccctcggc gcgatgctcg aagaagaccg gagcgacctg   180
cgggaacagt gcataggtga gcacgtcctc gtcggtgccg ttgaagccct tgaggccgc    240 ggcctccttg gactgctcct cccactcggg gggcagcaga tcggccgggc gctgggtgat   300
cggcttcttg ccggactgct cctcggccaa cttgaccacc ttcggatcgc gatcggccgg   360
gctggcgccg tagtagccga gcatgatgtc ggcgaactcg ccggtcatcc tcttgtactc   420
gcccatcatc acgttgaaca cggcctgcgt gccgacgatc tggctggacg gggtgaccag   480
gggcgggaag ccggcggcct gcggacgcg cggcacctct gccatgacct cgtccatctt    540
gtcctcggcg ccctgggcgc gcagctgcga ctccatgttg gagagcatgc cgccggggat   600
ctgcgacttg aagatcgagg tgtcgacaag cgtcttcgac tcgaacttct tgtacttcgg   660
gcggatggcc ttgaagtgat cgcggatctt gtgcaggcga tcgtagtcaa ggttggtggt   720
gtacccggtg ccctcgagca tctcggcaac cgactcggtg gggttgtggc ccgggccgag   780
cgacatggac gagatggcgg tgtcgacgac gtcgacgccg gcctcgatgg ccttcatgag   840
ggagacctcg gtgacacccg tggtggagtg gcagtgcagg ttgatctgcg tcttctggcc   900
gtaggtgtcc ttgatggcct tgatgatgtc gtaggccggc tgcggcttga gcagggcggc   960
catgtccttc agggcgatgg aatcagcacc catgtcgagc agctgaccag caagcttgac  1020
atagccctca acgtgtggga ccgggctgat cgtgtagcaa atggtgccct gcgcgtgctt  1080
gccggccttc ttgacggcag ccatggcgtg cgccatgttg cggggatcat tcatggcgtc  1140
gaagacacgg aacacgtcca tgccgttctc agcggacttg tcgacgaagc gatcgacgac  1200
ctcgtcgttg tagtggcggt aacccagcag gttctggcca cgcagcagca tctggagacg  1260
gctgttgggc atcagcttgc ggaacgtgcg cagacgctcc caaggatcct cgttgaggaa  1320
gcggatacac gagtcatacg tggcaccacc ccaacactcc actgaccagt acccggcagc  1380
atcaatgtct gcacaggcgc cgaccatgtc ttccattgcc attcgtgtgg ccatcaggct  1440
ctgatgggca tcgcgcagca cgagctcggt gataccaacc tcgcgcggct cggaaacctc  1500
aatttctcgc ggactcat                                                1518
```

<210> SEQ ID NO 10
<211> LENGTH: 1518
<212> TYPE: DNA
<213> ORGANISM: Propionibacterium freudenreichii

<400> SEQUENCE: 10

```
atgagtccgc gagaaattga ggtttccgag ccgcgcgagg ttggtatcac cgagctcgtg    60
ctgcgcgatg cccatcagag cctgatggcc acacgaatgg caatggaaga catggtcggc   120
gcctgtgcag acattgatgc tgccgggtac tggtcagtgg agtgttgggg tggtgccacg   180
tatgactcgt gtatccgctt cctcaacgag gatccttggg agcgtctgcg cacgttccgc   240
aagctgatgc caacagccg tctccagatg ctgctgcgtg gccagaacct gctgggttac   300
cgccactaca cgacgaggt cgtcgatcgc ttcgtcgaca gtccgctga gaacggcatg   360
gacgtgttcc gtgtcttcga cgccatgaat gatccccgca acatggcgca cgccatggct   420
gccgtcaaga aggccggcaa gcacgcgcag ggcaccattt gctacacgat cagcccggtc   480
cacaccgttg agggctatgt caagcttgct ggtcagctgc tcgacatggg tgctgattcc   540
atcgccctga aggacatggc cgccctgctc aagccgcagc cggcctacga catcatcaag   600
gccatcaagg acacctacgg ccagaagacg cagatcaacc tgcactgcca ctccaccacg   660
ggtgtcaccg aggtctccct catgaaggcc atcgaggccg cgtcgacgt cgtcgacacc   720
gccatctcgt ccatgtcgct cggcccgggc acaaccccca ccgagtcggt tgccgagatg   780
ctcgagggca ccgggtacac caccaacctt gactacgatc gcctgcacaa gatccgcgat   840
cacttcaagg ccatccgccc gaagtacaag aagttcgagt cgaagacgct tgtcgacacc   900
tcgatcttca gtcgcagat ccccggcggc atgctctcca catggagtc gcagctgcgc   960
gcccagggcg ccgaggacaa gatggacgag gtcatggcag aggtgccgcg cgtccgcaag  1020
gccgccggct tcccgcccct ggtcaccccg tccagccaga tcgtcggcac gcaggccgtg  1080
ttcaacgtga tgatgggcga gtacaagagg atgaccggcg agttcgccga catcatgctc  1140
ggctactacg gcgccagccc ggccgatcgc gatccgaagg tggtcaagtt ggccgaggag  1200
cagtccggca agaagccgat cacccagcgc ccggccgatc tgctgccccc gagtgggag  1260
gagcagtcca aggaggccgc ggccctcaag ggcttcaacg gcaccgacga ggacgtgctc  1320
acctatgcac tgttcccgca ggtcgctccg gtcttcttcg agcatcgcgc cgagggcccg  1380
cacagcgtgg ctctcaccga tgcccagctg aaggccgagg ccgagggcga cgagaagtcg  1440
ctcgccgtgg ccgggtcccgt cacctacaac gtgaacgtgg cggaaccgt ccgcgaagtc  1500
accgttcagc aggcgtga                                                 1518
```

<210> SEQ ID NO 11
<211> LENGTH: 505
<212> TYPE: PRT
<213> ORGANISM: Propionibacterium freudenreichii

<400> SEQUENCE: 11

```
Met Ser Pro Arg Glu Ile Glu Val Ser Glu Pro Arg Glu Val Gly Ile
1               5                   10                  15

Thr Glu Leu Val Leu Arg Asp Ala His Gln Ser Leu Met Ala Thr Arg
            20                  25                  30

Met Ala Met Glu Asp Met Val Gly Ala Cys Ala Asp Ile Asp Ala Ala
        35                  40                  45

Gly Tyr Trp Ser Val Glu Cys Trp Gly Gly Ala Thr Tyr Asp Ser Cys
    50                  55                  60
```

```
Ile Arg Phe Leu Asn Glu Asp Pro Trp Glu Arg Leu Arg Thr Phe Arg
65                  70                  75                  80

Lys Leu Met Pro Asn Ser Arg Leu Gln Met Leu Leu Arg Gly Gln Asn
                85                  90                  95

Leu Leu Gly Tyr Arg His Tyr Asn Asp Glu Val Val Asp Arg Phe Val
            100                 105                 110

Asp Lys Ser Ala Glu Asn Gly Met Asp Val Phe Arg Val Phe Asp Ala
        115                 120                 125

Met Asn Asp Pro Arg Asn Met Ala His Ala Met Ala Ala Val Lys Lys
130                 135                 140

Ala Gly Lys His Ala Gln Gly Thr Ile Cys Tyr Thr Ile Ser Pro Val
145                 150                 155                 160

His Thr Val Glu Gly Tyr Val Lys Leu Ala Gly Gln Leu Leu Asp Met
            165                 170                 175

Gly Ala Asp Ser Ile Ala Leu Lys Asp Met Ala Ala Leu Leu Lys Pro
        180                 185                 190

Gln Pro Ala Tyr Asp Ile Ile Lys Ala Ile Lys Asp Thr Tyr Gly Gln
            195                 200                 205

Lys Thr Gln Ile Asn Leu His Cys His Ser Thr Thr Gly Val Thr Glu
210                 215                 220

Val Ser Leu Met Lys Ala Ile Glu Ala Gly Val Asp Val Val Asp Thr
225                 230                 235                 240

Ala Ile Ser Ser Met Ser Leu Gly Pro Gly His Asn Pro Thr Glu Ser
            245                 250                 255

Val Ala Glu Met Leu Glu Gly Thr Gly Tyr Thr Thr Asn Leu Asp Tyr
        260                 265                 270

Asp Arg Leu His Lys Ile Arg Asp His Phe Lys Ala Ile Arg Pro Lys
        275                 280                 285

Tyr Lys Lys Phe Glu Ser Lys Thr Leu Val Asp Thr Ser Ile Phe Lys
290                 295                 300

Ser Gln Ile Pro Gly Gly Met Leu Ser Asn Met Glu Ser Gln Leu Arg
305                 310                 315                 320

Ala Gln Gly Ala Glu Asp Lys Met Asp Glu Val Met Ala Glu Val Pro
            325                 330                 335

Arg Val Arg Lys Ala Ala Gly Phe Pro Pro Leu Val Thr Pro Ser Ser
        340                 345                 350

Gln Ile Val Gly Thr Gln Ala Val Phe Asn Val Met Met Gly Glu Tyr
            355                 360                 365

Lys Arg Met Thr Gly Glu Phe Ala Asp Ile Met Leu Gly Tyr Tyr Gly
        370                 375                 380

Ala Ser Pro Ala Asp Arg Asp Pro Lys Val Val Lys Leu Ala Glu Glu
385                 390                 395                 400

Gln Ser Gly Lys Lys Pro Ile Thr Gln Arg Pro Ala Asp Leu Leu Pro
            405                 410                 415

Pro Glu Trp Glu Gln Ser Lys Glu Ala Ala Leu Lys Gly Phe
        420                 425                 430

Asn Gly Thr Asp Glu Asp Val Leu Thr Tyr Ala Leu Phe Pro Gln Val
            435                 440                 445

Ala Pro Val Phe Phe Glu His Arg Ala Glu Gly Pro His Ser Val Ala
        450                 455                 460

Leu Thr Asp Ala Gln Leu Lys Ala Glu Ala Glu Gly Asp Glu Lys Ser
465                 470                 475                 480
```

Leu Ala Val Ala Gly Pro Val Thr Tyr Asn Val Asn Val Gly Gly Thr
            485                 490                 495

Val Arg Glu Val Thr Val Gln Gln Ala
            500                 505

<210> SEQ ID NO 12
<211> LENGTH: 1575
<212> TYPE: DNA
<213> ORGANISM: Propionibacterium freudenreichii

<400> SEQUENCE: 12

```
tcagcagggg aagtttccat gcttcttcgc cgggcgggtc tgacgcttgg tggcgtacat      60
ctccagggcg gaagcaatct ttcgacgggt atcagccggg tcaatcacgt cgtcgacctg     120
accgcgggcg gcggccacgt acggcgtgtt gaacgcgttc tggtactcct cgatcttctc     180
ggcgcgcatg gcgtcgggat cgtcggcagc cttgatctcc ttgcggaaga tcacatttgc     240
cgcaccctcg gcgcccatca ccgcaatctc ggcgctgggc caggcgtaca cggcgtcggc     300
accaaggtca cggttgcaca tggccaggta ggagccgccg taggccttgc ggagcaccac     360
ggtgatcttc ggcacggtgg cctcggagta ggcgtacagc atcttcgcgc catggcgaat     420
gatgccgccg tactcctgct gcacgccggg caggaagccc ggcacgtcga ccagctgcac     480
cagcgggatg ttgaacgaat cgcagaaatt cacgaattcg gcggccttgt cagaggcgtt     540
gatgtcgagg caacccgaca tcaccgacgg ctgattggcc acgatgccca ccgaacgacc     600
attgacccgg gcgaaggcgg tcacgaggtt ggtggcatag ccggccttga cctcgaggta     660
gtcaccccag tcgacgatct tggcaatgac atcgcgcacg tcatagccct tcttgccgtc     720
aatcggaacg atgtcgcgca gctcggtatt ggggctgacg tcattgttcg ggttgacgaa     780
ggatgcttcc tcagtgttgt tctgcggaag gaagctcagc agcttcttgg caatgagctc     840
cgcggcgtcg tcgtcctcgg ccacgaagtg gatattgccc gagatggcca tatgggcctc     900
agcgccaccg agttcgtcag cggtgacatc ctcgccggtg accgacttga tgacctgggg     960
gcccgtgatg aacatatggg ccttcttggt catgatgatg aagtcagtca gtgccggcga    1020
atacgaggcg ccaccggcac aggggccggc aatgatggcg atctgcggca cgacgcccga    1080
cagcttcacg ttggcgaaga acatcttgcc gtaaccgctc agcgagtcga tgccctcctg    1140
gatccgggcg ccgcccgaat cgtagaagaa caggaagggc gtgccggtga gcagcgcctg    1200
ttccatcgtc tcgacgacct tcgtggactg cgtctcgcca gccgaaccac ccatgaccgt    1260
gaagtcctgg gacgcggcgt gcacgggacg accaaggatg tgccacggcc ggtgaccac     1320 gccatctgcc gggacgacgg ccttgtccat gccgaacaac gtggtgcggt gcttgcggaa    1380
agcgccgacc tcgtcgaacg aatggggatc gagcaggttg ttcaggcgct cacgagcggt    1440
ctgcttaccc tgggaatgtt gcttctcgac gcgacgttcg ccgccaccgg cttcgatcac    1500
ctggcgctgc tctgcgagct gctccacgcg accttccatg gtgctggcga gcttcaaatt    1560
gttgttttca gccat                                                    1575
```

<210> SEQ ID NO 13
<211> LENGTH: 1572
<212> TYPE: DNA
<213> ORGANISM: Propionibacterium freudenreichii

<400> SEQUENCE: 13

```
atggctgaaa acaacaattt gaagctcgcc agcaccatgg aaggtcgcgt ggagcagctc      60
gcagagcagc gccaggtgat cgaagccggt ggcggcgaac gtcgcgtcga gaagcaacat     120
```

```
tcccagggta agcagaccgc tcgtgagcgc ctgaacaacc tgctcgatcc ccattcgttc      180
gacgaggtcg gcgctttccg caagcaccgc accacgttgt tcggcatgga caaggccgtc      240
gtcccggcag atggcgtggt caccggccgt ggcaccatcc ttggtcgtcc cgtgcacgcc      300
gcgtcccagg acttcacggt catgggtggt tcggctggcg agacgcagtc cacgaaggtc      360
gtcgagacga tggaacaggc gctgctcacc ggcacgccct tcctgttctt ctacgattcg      420
ggcggcgccc ggatccagga gggcatcgac tcgctgagcg gttacggcaa gatgttcttc      480
gccaacgtga agctgtcggg cgtcgtgccg cagatcgcca tcattgccgg ccctgtgcc       540
ggtggcgcct cgtattcgcc ggcactgact gacttcatca tcatgaccaa gaaggcccat      600
atgttcatca cgggcccca ggtcatcaag tcggtcaccg gcgaggatgt caccgctgac       660
gaactcggtg gcgctgaggc ccatatggcc atctcgggca atatccactt cgtggccgag      720
gacgacgacg ccgcggagct cattgccaag aagctgctga gcttccttcc gcagaacaac      780
actgaggaag catccttcgt caacccgaac aatgacgtca gccccaatac cgagctgcgc      840
gacatcgttc cgattgacgg caagaagggc tatgacgtgc gcgatgtcat tgccaagatc      900
gtcgactggg gtgactacct cgaggtcaag gccggctatg ccaccaacct cgtgaccgcc      960
ttcgcccggg tcaatggtcg ttcggtgggc atcgtggcca atcagccgtc ggtgatgtcg     1020
ggttgcctcg acatcaacgc ctctgacaag gccgccgaat cgtgaatttt ctgcgattcg     1080
ttcaacatcc cgctggtgca gctggtcgac gtgccgggct cctgcccgg cgtgcagcag      1140
gagtacggcg gcatcattcg ccatggcgcg aagatgctgt acgcctactc cgaggccacc     1200
gtgccgaaga tcaccgtggt gctccgcaag gcctacggcg gctcctacct ggccatgtgc     1260
aaccgtgacc ttggtgccga cgccgtgtac gcctggccca cgccgagat tgcggtgatg      1320
ggcgccgagg gtgcggcaaa tgtgatcttc cgcaaggaga tcaaggctgc cgacgatccc     1380
gacgccatgc gcgccgagaa gatcgaggag taccagaacg cgttcaacac gccgtacgtg     1440
gccgccgccc gcggtcaggt cgacgacgtg attgacccgg ctgatacccg tcgaaagatt     1500
gcttccgccc tggagatgta cgccaccaag cgtcagaccc gcccggcgaa gaagcatgga     1560
aacttccccct gc                                                         1572
```

<210> SEQ ID NO 14
<211> LENGTH: 524
<212> TYPE: PRT
<213> ORGANISM: Propionibacterium freudenreichii

<400> SEQUENCE: 14

Met Ala Glu Asn Asn Leu Lys Leu Ala Ser Thr Met Glu Gly Arg
1               5                   10                  15

Val Glu Gln Leu Ala Glu Gln Arg Gln Val Ile Glu Ala Gly Gly Gly
            20                  25                  30

Glu Arg Arg Val Glu Lys Gln His Ser Gln Gly Lys Gln Thr Ala Arg
        35                  40                  45

Glu Arg Leu Asn Asn Leu Leu Asp Pro His Ser Phe Asp Glu Val Gly
    50                  55                  60

Ala Phe Arg Lys His Arg Thr Thr Leu Phe Gly Met Asp Lys Ala Val
65                  70                  75                  80

Val Pro Ala Asp Gly Val Val Thr Gly Arg Gly Thr Ile Leu Gly Arg
                85                  90                  95

Pro Val His Ala Ala Ser Gln Asp Phe Thr Val Met Gly Gly Ser Ala
            100                 105                 110

-continued

```
Gly Glu Thr Gln Ser Thr Lys Val Val Glu Thr Met Glu Gln Ala Leu
            115                 120                 125
Leu Thr Gly Thr Pro Phe Leu Phe Phe Tyr Asp Ser Gly Gly Ala Arg
    130                 135                 140
Ile Gln Glu Gly Ile Asp Ser Leu Ser Gly Tyr Gly Lys Met Phe Phe
145                 150                 155                 160
Ala Asn Val Lys Leu Ser Gly Val Val Pro Gln Ile Ala Ile Ile Ala
                165                 170                 175
Gly Pro Cys Ala Gly Gly Ala Ser Tyr Ser Pro Ala Leu Thr Asp Phe
            180                 185                 190
Ile Ile Met Thr Lys Lys Ala His Met Phe Ile Thr Gly Pro Gln Val
            195                 200                 205
Ile Lys Ser Val Thr Gly Glu Asp Val Thr Ala Asp Glu Leu Gly Gly
            210                 215                 220
Ala Glu Ala His Met Ala Ile Ser Gly Asn Ile His Phe Val Ala Glu
225                 230                 235                 240
Asp Asp Asp Ala Ala Glu Leu Ile Ala Lys Lys Leu Leu Ser Phe Leu
                245                 250                 255
Pro Gln Asn Asn Thr Glu Glu Ala Ser Phe Val Asn Pro Asn Asn Asp
            260                 265                 270
Val Ser Pro Asn Thr Glu Leu Arg Asp Ile Val Pro Ile Asp Gly Lys
            275                 280                 285
Lys Gly Tyr Asp Val Arg Asp Val Ile Ala Lys Ile Val Asp Trp Gly
            290                 295                 300
Asp Tyr Leu Glu Val Lys Ala Gly Tyr Ala Thr Asn Leu Val Thr Ala
305                 310                 315                 320
Phe Ala Arg Val Asn Gly Arg Ser Val Gly Ile Val Ala Asn Gln Pro
                325                 330                 335
Ser Val Met Ser Gly Cys Leu Asp Ile Asn Ala Ser Asp Lys Ala Ala
            340                 345                 350
Glu Phe Val Asn Phe Cys Asp Ser Phe Asn Ile Pro Leu Val Gln Leu
            355                 360                 365
Val Asp Val Pro Gly Phe Leu Pro Gly Val Gln Gln Glu Tyr Gly Gly
            370                 375                 380
Ile Ile Arg His Gly Ala Lys Met Leu Tyr Ala Tyr Ser Glu Ala Thr
385                 390                 395                 400
Val Pro Lys Ile Thr Val Val Leu Arg Lys Ala Tyr Gly Gly Ser Tyr
                405                 410                 415
Leu Ala Met Cys Asn Arg Asp Leu Gly Ala Asp Ala Val Tyr Ala Trp
            420                 425                 430
Pro Ser Ala Glu Ile Ala Val Met Gly Ala Glu Gly Ala Ala Asn Val
            435                 440                 445
Ile Phe Arg Lys Glu Ile Lys Ala Ala Asp Pro Asp Ala Met Arg
            450                 455                 460
Ala Glu Lys Ile Glu Glu Tyr Gln Asn Ala Phe Asn Thr Pro Tyr Val
465                 470                 475                 480
Ala Ala Ala Arg Gly Gln Val Asp Asp Val Ile Asp Pro Ala Asp Thr
                485                 490                 495
Arg Arg Lys Ile Ala Ser Ala Leu Glu Met Tyr Ala Thr Lys Arg Gln
            500                 505                 510
Thr Arg Pro Ala Lys Lys His Gly Asn Phe Pro Cys
            515                 520
```

<210> SEQ ID NO 15
<211> LENGTH: 246
<212> TYPE: DNA
<213> ORGANISM: P.freudenreichii

<400> SEQUENCE: 15

| | |
|---|---:|
| atggctgatg aggaagagaa ggacctgatg atcgccacgc tcaacaagcg cgtcgcgtca | 60 |
| ttggagtctg agttgggttc actccagagc gataccagg gtgtcaccga ggacgtactg | 120 |
| acggccattt cggccgccgt tgcggcctat ctcggcaacg atggatcggc tgaggtcgtc | 180 |
| catttcgccc cgagcccgaa ctgggtccgc gagggtcgtc gggctctgca gaaccattcc | 240 |
| attcgt | 246 |

<210> SEQ ID NO 16
<211> LENGTH: 82
<212> TYPE: PRT
<213> ORGANISM: P.freudenreichii

<400> SEQUENCE: 16

Met Ala Asp Glu Glu Lys Asp Leu Met Ile Ala Thr Leu Asn Lys
1               5                   10                  15

Arg Val Ala Ser Leu Glu Ser Glu Leu Gly Ser Leu Gln Ser Asp Thr
            20                  25                  30

Gln Gly Val Thr Glu Asp Val Leu Thr Ala Ile Ser Ala Ala Val Ala
        35                  40                  45

Ala Tyr Leu Gly Asn Asp Gly Ser Ala Glu Val Val His Phe Ala Pro
    50                  55                  60

Ser Pro Asn Trp Val Arg Glu Gly Arg Arg Ala Leu Gln Asn His Ser
65                  70                  75                  80

Ile Arg

<210> SEQ ID NO 17
<211> LENGTH: 1575
<212> TYPE: DNA
<213> ORGANISM: P. acnes

<400> SEQUENCE: 17

| | |
|---|---:|
| atggctgaga agaaaccaat caagctggcc gataccatgg ccggccggat cgagcagctc | 60 |
| gccgacgagc gccacgctgt ggagcttggc ggggcgagg atcgcctgca aaagcagcgt | 120 |
| gacaggggca agcagacagc ccgtgaacgg atcgacaacc tcgttgatgc ttattccttc | 180 |
| gatgaggtgg gtgcgttccg taagcaccgc accacccttt cggcatgga caaggccgaa | 240 |
| gttcccgccg acggcgtagt caccggtcgt gcgaccatcc atggtcgccc ggtccacatc | 300 |
| gcgtctcagg acttcaccgt catggtggg tcggctggcg agacccagtc gacgaaggtc | 360 |
| gtcgagacga tggaacagtc cctgctgacc ggcactccgt ttctgttctt ctatgactcg | 420 |
| ggcggcgccc gaattcaaga aggcatcgac tcgctgtccg ggtacggcaa gatgttctac | 480 |
| gcgaacgtca agctgtcggg cgtcgtgccg cagatcgcca tcattgctgg ccctgcgcc | 540 |
| ggcggcgcct cctattcccc ggccctgacc gacttcatca tcatgacgaa gaaggcccac | 600 |
| atgttcatta cgggccccgg agtcatcaag tcggttaccg tgaggaggt gactgctgac | 660 |
| gacctgggtg gtgcggatgc gcacatgtcc acctcgggca atatccactt cgtggccgaa | 720 |
| gatgacgacg ccgcagtgct catcgcgcag aagttgctga gcttcctgcc gcaaaacaac | 780 |
| actgaggacg cccagatctc caaccccaat gacgatgtct cccgcagcc tgagctgcgc | 840 |

```
gacatcgttc cgctggatgg taagaagggc tacgacgtcc gcgacgtcat ctccaagatc    900
gtcgactggg gcgactacct agaggtcaag gccggttggg cgaccaacat cgtcaccgcc    960
tttgcccggg tcaatggtcg taccgtcggc atcgtggcca accagccgaa ggtgatgtcg   1020
ggttgccttg acatcaatgc ttcggacaag gctgccgagt tcattacctt ctgcgactcg   1080
ttcaatattc cgttggtgca gttggttgac gttcctggct cctgcctgg tgtccagcag    1140 gagtacggcg gcatcatccg ccacggcgcg aagatgctgt atgcctactc cgaggccacc   1200
gtcccgaaga tcaccgtggt gctgcgtaag gcttacggcg gctcctacct tgccatgtgc   1260
aaccgtgacc tgggtgctga cgccgtctat gcctggccga gcgcggagat tgcggtgatg   1320
ggtgccgatg gcgctgccaa cgtcattttc cgtcgccaga tcaaggactc tgaggatccc   1380
gcagccaccc gtgccgcgaa gatcgaggag taccgcaacg ccttcaacac gccttacgtg   1440
gctgccgccc gtggacaggt tgacgacgtg atcgatcccg cggacacccg tcgcaagatc   1500
accgccgctc tggagaccta cgccactaag cgtcagtccc gtccggccaa gaagcacggc   1560
gtcatgcctt gctga                                                   1575

<210> SEQ ID NO 18
<211> LENGTH: 1494
<212> TYPE: DNA
<213> ORGANISM: P. acnes

<400> SEQUENCE: 18
atgagtccac gaaagattgg cgttaccgag ctcgtgctcc gcgacgcgca tcagagcctg     60
cttgccactc gcatggccat ggaggacatg gttgatgcct gtgccgacat tgatgcggca    120
ggcttctggt ccgttgaatg ctggggcgga gctaccttcg attcttgcat ccgattcctc    180
aacgaagacc catgggagcg tctgcgtact ttccgcaagc tgctgccgaa ctcccggttg    240
cagatgctgc tgcgtggcca aaaccttctg ggctaccgcc actacaacga cgaggtcgtc    300
gacaagtttg tcgagaagtc ggccgagaac ggcatggacg tgttccgggt gttcgacgct    360
ctgaacgatc ctcgcaacct tgagcacgcg atggcagccg tcaagaagac cggcaagcac    420
gcccagggca ccatctgcta caccacttcc ccgattcaca ccccagagag cttcgtcaag    480
caggccgatc gtctcatcga catgggtgcc gactcgatcg ccttcaagga catggctgct    540
ttgctcaagc cgcagcctgc ctacgacatc atcaagggca ttaaggagaa ccatccggac    600
gtgcagatca acctgcactg ccactccacc acgggcgtca ccctggtcac cctgcagaag    660
gccatcgagc tggtgtcgac cgtcgtcgac ccgctatct cgtcgatgtc gctcggcccg    720
gggcacaacc caaccgagtc tttggtcgag atgctcgagg gcaccgagta caccaccggc    780
ctcgacatgg atcgcctgct caagatccgc gaccacttca gaaggtgcg tccgaagtac    840 aagaagttcg agtcgaagac gctggtcaac accaacatct ccagtccca gatcccgggc    900 ggaatgctct ccaacatgga gtcccagctc gaggcccagg gtgctggaga ccgcatggat    960
gaggtcatga aggaggtgcc gcgcgttcgt aaggatgccg gctaccccgc ctggtcacc   1020 ccgtcctccc agatcgtggg aaccccaggcg gtgttcaacg tcctgatggg caatggttcg   1080
tacaagaacc tcactgccga gtttgccgac ctcatgcttg gctactacgg caagcccatt   1140
ggcgagctca atcccgagat cgttgagatg gccaagaagc agaccggcaa ggagccgatc   1200
gactgccgtc ccgccgacct gctcgagcct gagtgggacc agctggtcga gcaggccaag   1260
agtcttgagg gcttcgacgg ctccgacgag gacgttctta ccaacgccct gttcccggga   1320
gttgccccga agttcctcaa ggaacgcgca cagggcccga agagcgtcgc gatgaccgag   1380
```

```
gcacagctga aggccgagaa ggaaggcacc ggcgctgccg gcatcgccgg accggtcaac    1440
tacaacgtga cggtcggtgg caacagccac caggtgaccg tcgagcctgc gtga          1494

<210> SEQ ID NO 19
<211> LENGTH: 363
<212> TYPE: DNA
<213> ORGANISM: P. acnes

<400> SEQUENCE: 19
atgaagctca aggtgaccgt caatgacgtc gcatacgacg ttgacgttga cgttgataag     60
accgccaatg cgccgatggc gccgatcctc tttggtggcg cgccggcgg cccgatgaag    120 gcatccggtg cggcgccgg taaggccggt gagggcgagg ttcccgcacc gctagctggg    180
actgttgcca agatcctggt ggccgaagga gatgccgtca aggccggtca ggtgctcctg    240
accctcgagg ccatgaagat ggagaccgag atcaatgccc cggcggacgg aaccgtcaag    300
gggatcctgg tggctgtcgg tgacgccgtc cagggtggtc agggcctggt ggctctgggc    360
tga                                                                  363

<210> SEQ ID NO 20
<211> LENGTH: 1551
<212> TYPE: DNA
<213> ORGANISM: C. thermocellum

<400> SEQUENCE: 20
atggacaaag tagacaagat cggccttctc cgtgaaaaac tggcccaggt tgaacagggc     60
ggaggagctg aaaaaatcgc aaaacagcat gatgccggaa aaatgacagc aagagaaaga    120
atccaggctt tatttgatga aaacagcttt gttgagatcg acacatttgt tgagacaaga    180
agcattgact tcgatatgca aaaaagaaa gtcccgggag acggtgttgt aacagggtat    240
ggttccatag acggacgtct ggtctttgtt cggcgcagg actttactgt aatcggtggg    300
tctttgggtg aaatgcatgc cgcaaaaatc accaaagtaa tggacatggc aatgaaaatg    360
ggcgcaccgt ttataagcat taatgattcc ggcggtgcaa gaattgaaga aggaattgac    420
gcactcaagg gatttggaga tatcttctac agaaatactt tggcttcagg tgtaattccc    480
cagatttcag ttatcatggg accatgcgca ggcggagcgg tatattctcc tgcaataacc    540
gactttatat ttatggttga caaaaccagt cagatgttta acgggacc ccaggtaatt    600 aagtccgtaa ccggagaaga cgtgactttt gaaaaacttg gcggtgcgga aacccacaac    660
tccataagcg gtgttgctca cttcagaagt tcaagtgaaa agaatgtat agagcaaatc    720 aaaaagctta ttagttatct tcctgataac aatctttccg atgttccgat tgttccaact    780
caggatgaca taaacagaat tactgacaac ctggtcgata tcattccgca ggactccaac    840
aagccttatg acatgatgga ataatcact tccgtagttg acaacggtga ctttttgaa    900 attcaaaaag actttgcaaa aacattata ataggtttcg gcagaatgaa cggcggaacc    960
gtcggtatag tggcaaatca gccaaaagtt gccgcagggg ttttggatgt gaactcctct   1020
gacaaagccg caaggtttgt tcgtttctgt gatgcgttca acattccaat tataaccttt   1080
accgatgtac cggggtatct gccccggagta ggccaggagc acagcggagt aataagcac   1140 ggtgcaaagc ttctttatgc tttctctgaa gccaccgttc caaaaatcaa tgttattgtc   1200
agaaaagctt acgcggtgc atatattgcc atgaacagca agcaccttgg agcggacatg   1260
gtatttgcgt ggccttcggc ggaaattgca gttatgggac cggaaggtgc ggcaaacatc   1320
```

-continued

```
attttcaaga aagatatagc tgctgccgat gacccaatgg aaacaagaaa gaggctcatt      1380
gaagaatatc gtgaaaaatt ctccaatccg tatgttgcag cttcaagggg ttatgttgat      1440
gatgtaattg atccggcaac aacaaggata agactgatta gtgcccttga aatgcttgca      1500
agtaagagag aaaacagacc tgccaaaaag catggaaata ttccattata a              1551
```

<210> SEQ ID NO 21
<211> LENGTH: 516
<212> TYPE: PRT
<213> ORGANISM: C. thermocellum

<400> SEQUENCE: 21

```
Met Asp Lys Val Asp Lys Ile Gly Leu Leu Arg Glu Lys Leu Ala Gln
1               5                   10                  15

Val Glu Gln Gly Gly Gly Ala Glu Lys Ile Ala Lys Gln His Asp Ala
            20                  25                  30

Gly Lys Met Thr Ala Arg Glu Arg Ile Gln Ala Leu Phe Asp Glu Asn
        35                  40                  45

Ser Phe Val Glu Ile Asp Thr Phe Val Glu Thr Arg Ser Ile Asp Phe
    50                  55                  60

Asp Met Gln Lys Lys Val Pro Gly Asp Gly Val Val Thr Gly Tyr
65                  70                  75                  80

Gly Ser Ile Asp Gly Arg Leu Val Phe Val Ala Ala Gln Asp Phe Thr
                85                  90                  95

Val Ile Gly Gly Ser Leu Gly Glu Met His Ala Ala Lys Ile Thr Lys
            100                 105                 110

Val Met Asp Met Ala Met Lys Met Gly Ala Pro Phe Ile Ser Ile Asn
        115                 120                 125

Asp Ser Gly Gly Ala Arg Ile Glu Glu Gly Ile Asp Ala Leu Lys Gly
    130                 135                 140

Phe Gly Asp Ile Phe Tyr Arg Asn Thr Leu Ala Ser Gly Val Ile Pro
145                 150                 155                 160

Gln Ile Ser Val Ile Met Gly Pro Cys Ala Gly Gly Ala Val Tyr Ser
                165                 170                 175

Pro Ala Ile Thr Asp Phe Ile Phe Met Val Asp Lys Thr Ser Gln Met
            180                 185                 190

Phe Ile Thr Gly Pro Gln Val Ile Lys Ser Val Thr Gly Glu Asp Val
        195                 200                 205

Thr Phe Glu Lys Leu Gly Gly Ala Glu Thr His Asn Ser Ile Ser Gly
    210                 215                 220

Val Ala His Phe Arg Ser Ser Glu Lys Glu Cys Ile Glu Gln Ile
225                 230                 235                 240

Lys Lys Leu Ile Ser Tyr Leu Pro Asp Asn Asn Leu Ser Asp Val Pro
                245                 250                 255

Ile Val Pro Thr Gln Asp Asp Ile Asn Arg Ile Thr Asp Asn Leu Val
            260                 265                 270

Asp Ile Ile Pro Gln Asp Ser Asn Lys Pro Tyr Asp Met Met Glu Ile
        275                 280                 285

Ile Thr Ser Val Val Asp Asn Gly Asp Phe Phe Glu Ile Gln Lys Asp
    290                 295                 300

Phe Ala Lys Asn Ile Ile Ile Gly Phe Gly Arg Met Asn Gly Gly Thr
305                 310                 315                 320

Val Gly Ile Val Ala Asn Gln Pro Lys Val Ala Ala Gly Val Leu Asp
                325                 330                 335
```

Val Asn Ser Ser Asp Lys Ala Ala Arg Phe Val Arg Phe Cys Asp Ala
            340                 345                 350

Phe Asn Ile Pro Ile Ile Thr Phe Thr Asp Val Pro Gly Tyr Leu Pro
        355                 360                 365

Gly Val Gly Gln Glu His Ser Gly Val Ile Arg His Gly Ala Lys Leu
    370                 375                 380

Leu Tyr Ala Phe Ser Glu Ala Thr Val Pro Lys Ile Asn Val Ile Val
385                 390                 395                 400

Arg Lys Ala Tyr Gly Gly Ala Tyr Ile Ala Met Asn Ser Lys His Leu
                405                 410                 415

Gly Ala Asp Met Val Phe Ala Trp Pro Ser Ala Glu Ile Ala Val Met
            420                 425                 430

Gly Pro Glu Gly Ala Ala Asn Ile Ile Phe Lys Lys Asp Ile Ala Ala
        435                 440                 445

Ala Asp Asp Pro Met Glu Thr Arg Lys Arg Leu Ile Glu Glu Tyr Arg
    450                 455                 460

Glu Lys Phe Ser Asn Pro Tyr Val Ala Ala Ser Arg Gly Tyr Val Asp
465                 470                 475                 480

Asp Val Ile Asp Pro Ala Thr Thr Arg Ile Arg Leu Ile Ser Ala Leu
                485                 490                 495

Glu Met Leu Ala Ser Lys Arg Glu Asn Arg Pro Ala Lys Lys His Gly
            500                 505                 510

Asn Ile Pro Leu
        515

<210> SEQ ID NO 22
<211> LENGTH: 399
<212> TYPE: DNA
<213> ORGANISM: C. thermocellum

<400> SEQUENCE: 22
atgaaaaagt ttttgataaa ggtaaacgga atcaatatg aggttgaagt tgaagaaatc     60
agagacggtg cttcagcacc acaggttact ctcagcacac cttcggctgc acctgcgcct    120
tcaccggcac cggctcagga aacgaaaaca gctgcaccaa agaaagacag cacagtaccg    180
gcaggtgcta cggcaattaa agctccgatg ccgggtacca tactcgacat tcgtgtaaat    240
caaggggata cggtaaagaa aggccaagtt cttttaattc ttgaagcaat gaagatggaa    300
aatgaaatag ttgctccaaa tgacggtaca gttgcatcaa ttaatgtttc aaagggtgca    360
tctgtaaacg tcggagaggt tcttgtctca ttaaaatag                           399

<210> SEQ ID NO 23
<211> LENGTH: 132
<212> TYPE: PRT
<213> ORGANISM: C. thermocellum

<400> SEQUENCE: 23

Met Lys Lys Phe Leu Ile Lys Val Asn Gly Asn Gln Tyr Glu Val Glu
1               5                   10                  15

Val Glu Glu Ile Arg Asp Gly Ala Ser Ala Pro Gln Val Thr Leu Ser
            20                  25                  30

Thr Pro Ser Ala Ala Pro Ala Pro Ser Pro Ala Pro Gln Glu Thr
        35                  40                  45

Lys Thr Ala Ala Pro Lys Lys Asp Ser Thr Val Pro Ala Gly Ala Thr
    50                  55                  60

Ala Ile Lys Ala Pro Met Pro Gly Thr Ile Leu Asp Ile Arg Val Asn

```
              65                  70                  75                  80
Gln Gly Asp Thr Val Lys Lys Gly Gln Val Leu Leu Ile Leu Glu Ala
                    85                  90                  95
Met Lys Met Glu Asn Glu Ile Val Ala Pro Asn Asp Gly Thr Val Ala
                100                 105                 110
Ser Ile Asn Val Ser Lys Gly Ala Ser Val Asn Val Gly Glu Val Leu
            115                 120                 125
Val Ser Leu Lys
        130

<210> SEQ ID NO 24
<211> LENGTH: 1398
<212> TYPE: DNA
<213> ORGANISM: C. thermocellum

<400> SEQUENCE: 24
atggctaagg taaaaattac cgaaacggcg ctgagggatg cccatcaatc tctcattgca        60
acaagaatga gaatagaaga gatgcttcct atcatagata aactggacga gatcggttat       120
cattctttgg aggtatgggg cggtgcaacc tttgatgcct gcctgagatt tttgaatgaa       180
gacccgtggg aaaggcttag aattataaaa agccactgca agaaaactcc ccttcaaatg       240
cttttaagag gccagaatct tttgggttac aagcattatg ccgatgacgt tgtggagtac       300
tttgtacaaa agagcgttgc aaacggtata acataataa gaattttcga cgccttgaat       360
gacaccagaa atatagaaac tgcaatcaaa gcctgcaaaa agaaggcgg tcatgctcag       420 ggaacggtat gttatacaat aagtcccgtt cacaatcttg aacttttgt caaagatgca       480 aagactcttg tggaaatggg agctgactcc atatgcgtaa aggatatggc aggacttctg       540
cttccatatg ttgcatatga ccttatcaaa gcattaaaag aaaacgtaaa agtgccgatt       600
caacttcata cccactatac gagcggtgtt gcttcaatga catatctgaa ggcaattgag       660
gcagggtgcg atgttgtgga ctgcgctatc tcaccaatgt caatgggaac atcccagcct       720
ccgacagaac ctcttgtggc aaccttaaaa ggcacgccgt acgataccgg acttgacctg       780
gataaattaa gtgaaatcgc agactacttc agacctctca agaaaagta tatttcagaa       840 ggacttcttg atgtaaaggt tatgggagtt gacgtaaaca ctctcaaata ccaggtaccc       900
ggtggaatgc tttcaaacct ggtgtctcag ttaaagcagt ccaatgcggt tgataaattc       960
gaagaggttc tgaaagaagt gccaagagta agagaagact tcggatatcc tccgttggtt      1020
acacctacaa gccagattgt aggtactcag gcagttttaa atgtggtaac gggtgaaaga      1080
tacaaaatgg ttccaaaaga atccaaggca ctgatcaagg gtgaatacgg cagaacaccg      1140
gctccggtca accctgaagt tcagaagaag atttttaaaag atgaagagcc gattacagtt      1200
agacctgctg atttgataga gcccgagctt gacaagatca gaaatgaaat gaagaatac      1260 ctggaacaag acgaggacgt tttgtcctat gcactgttcc cgcaggtggc agagaagttc      1320
ttccaataca ggaaagctca aaatataag atagaaccgg acatggtcga ttacgaaaac      1380
agggttcatc cggtttaa                                                   1398

<210> SEQ ID NO 25
<211> LENGTH: 465
<212> TYPE: PRT
<213> ORGANISM: C.thermocellum

<400> SEQUENCE: 25

Met Ala Lys Val Lys Ile Thr Glu Thr Ala Leu Arg Asp Ala His Gln
```

-continued

```
1               5                   10                  15
Ser Leu Ile Ala Thr Arg Met Arg Ile Glu Glu Met Leu Pro Ile Ile
            20                  25                  30

Asp Lys Leu Asp Glu Ile Gly Tyr His Ser Leu Glu Val Trp Gly Gly
            35                  40                  45

Ala Thr Phe Asp Ala Cys Leu Arg Phe Leu Asn Glu Asp Pro Trp Glu
            50                  55                  60

Arg Leu Arg Ile Ile Lys Ser His Cys Lys Lys Thr Pro Leu Gln Met
65                  70                  75                  80

Leu Leu Arg Gly Gln Asn Leu Leu Gly Tyr Lys His Tyr Ala Asp Asp
                85                  90                  95

Val Val Glu Tyr Phe Val Gln Lys Ser Val Ala Asn Gly Ile Asn Ile
            100                 105                 110

Ile Arg Ile Phe Asp Ala Leu Asn Asp Thr Arg Asn Ile Glu Thr Ala
            115                 120                 125

Ile Lys Ala Cys Lys Lys Glu Gly Gly His Ala Gln Gly Thr Val Cys
            130                 135                 140

Tyr Thr Ile Ser Pro Val His Asn Leu Glu Leu Phe Val Lys Asp Ala
145                 150                 155                 160

Lys Thr Leu Val Glu Met Gly Ala Asp Ser Ile Cys Val Lys Asp Met
                165                 170                 175

Ala Gly Leu Leu Leu Pro Tyr Val Ala Tyr Asp Leu Ile Lys Ala Leu
            180                 185                 190

Lys Glu Asn Val Lys Val Pro Ile Gln Leu His Thr His Tyr Thr Ser
            195                 200                 205

Gly Val Ala Ser Met Thr Tyr Leu Lys Ala Ile Glu Ala Gly Cys Asp
            210                 215                 220

Val Val Asp Cys Ala Ile Ser Pro Met Ser Met Gly Thr Ser Gln Pro
225                 230                 235                 240

Pro Thr Glu Pro Leu Val Ala Thr Leu Lys Gly Thr Pro Tyr Asp Thr
                245                 250                 255

Gly Leu Asp Leu Asp Lys Leu Ser Glu Ile Ala Asp Tyr Phe Arg Pro
            260                 265                 270

Leu Lys Glu Lys Tyr Ile Ser Glu Gly Leu Leu Asp Val Lys Val Met
            275                 280                 285

Gly Val Asp Val Asn Thr Leu Lys Tyr Gln Val Pro Gly Gly Met Leu
            290                 295                 300

Ser Asn Leu Val Ser Gln Leu Lys Gln Ser Asn Ala Val Asp Lys Phe
305                 310                 315                 320

Glu Glu Val Leu Lys Glu Val Pro Arg Val Arg Glu Asp Phe Gly Tyr
                325                 330                 335

Pro Pro Leu Val Thr Pro Thr Ser Gln Ile Val Gly Thr Gln Ala Val
            340                 345                 350

Leu Asn Val Val Thr Gly Glu Arg Tyr Lys Met Val Pro Lys Glu Ser
            355                 360                 365

Lys Ala Leu Ile Lys Gly Glu Tyr Gly Arg Thr Pro Ala Pro Val Asn
            370                 375                 380

Pro Glu Val Gln Lys Lys Ile Leu Lys Asp Glu Pro Ile Thr Val
385                 390                 395                 400

Arg Pro Ala Asp Leu Ile Glu Pro Leu Asp Lys Ile Arg Asn Glu
                405                 410                 415

Met Lys Glu Tyr Leu Glu Gln Asp Glu Asp Val Leu Ser Tyr Ala Leu
            420                 425                 430
```

```
Phe Pro Gln Val Ala Glu Lys Phe Phe Gln Tyr Arg Lys Ala Gln Lys
        435                 440                 445

Tyr Lys Ile Glu Pro Asp Met Val Asp Tyr Glu Asn Arg Val His Pro
    450                 455                 460

Val
465

<210> SEQ ID NO 26
<211> LENGTH: 168
<212> TYPE: DNA
<213> ORGANISM: C.thermocellum

<400> SEQUENCE: 26
atgaaagagc aaataaatga agaaattatt ctggcaatat cagcggccat tgctgctttg    60
gaaacaagac ccggatacaa gcttgtagta agatcattta aagaatacc ccaaacttct   120 cctgtatggt ccgctacagg aaaaatcgag agaatcagaa gaagtatg              168

<210> SEQ ID NO 27
<211> LENGTH: 56
<212> TYPE: PRT
<213> ORGANISM: C.thermocellum

<400> SEQUENCE: 27

Met Lys Glu Gln Ile Asn Glu Glu Ile Ile Leu Ala Ile Ser Ala Ala
  1               5                  10                  15

Ile Ala Ala Leu Glu Thr Arg Pro Gly Tyr Lys Leu Val Val Arg Ser
             20                  25                  30

Phe Lys Arg Ile Pro Gln Thr Ser Pro Val Trp Ser Ala Thr Gly Lys
         35                  40                  45

Ile Glu Arg Ile Arg Arg Ser Met
     50                  55

<210> SEQ ID NO 28
<211> LENGTH: 1551
<212> TYPE: DNA
<213> ORGANISM: T. saccharolyticum

<400> SEQUENCE: 28
atgtcaatag atgataggat tgaagaccct cttagaagaa gagagatggt tttagaaggc    60
ggtggtttag ataaagtaga gaaacaacac caaaagggaa agcttaccgc aagagagagg   120
atatacaagc ttttagatga agatagcttt gtggaaatag atgcgtatgt tgagcacagg   180
tgtattgact ttggcatgga aaagcaaagg atacctggcg aaggcgtagt gacagggtat   240
gggacgatag atggaaggct tgtctacgtt tatgcacagg attttacggt tttaggagga   300
tcattaggcg agtatcatgc aaagaaaatc acaaaaatca tggatatggc tttaaagatg   360
ggagcaccgc tcattggatt aaatgattcc ggaggtgcca gaatacagga aggcgtcgat   420
gctttatcgg gatatggcaa catattttc agaaacacgc tggcatcagg cgtaataccg   480
caaatatcgg tgataatggg gcccagcgct ggaggtgcag tttattcgcc tgctcttact   540
gactttatat tcatggtaga caagacaagt cagatgttta aactggacc gcaggtcata   600 aaagccgtca caggtgaaga tgtttcggca gaggagcttg gtggatcgat tactcacagc   660
acgaaaagcg gtgtggcgca ttttagggct gaaaacgacg aagagtgttt gaagatggtg   720
aggaagctat taagttacct tccatcaaac aatttggaag atccgccaca gttggcgaca   780
gatgacgaca taaacagatt ttccgatagg cttattgaga taatcccaga tagtcctaat   840
```

```
aagccatacg atatgaaaga agtaatttcg gaaatagtgg atgaaggcgt gtattttgaa       900
tcacaggcaa tgtatgcgca aaacataata acggcatttg caaggcttaa tggaaggacg       960
gtagggataa tagcaaatca gcctaaagtt ttggctggat gtctcgacat caatgcgtct      1020
gataaggcat cgaggtttat aaggttttgc gatgcattta acatcccgct tctcaatata      1080
gtagatgttc caggattttt gcctggaacg aatcaagagt acggtggaat aatacgccat      1140
ggggcaaaga tgttgtacgc ttactctgag gctacagtgc aaaagtgac tctcattgtg       1200 aggaaagctt atggcggtgc ttaccttgcc atgtgcagca aagacttagg agctgatttt      1260
gttttggcat ggcctactgc tgaaatagcg gtcatgggac ctgatgggc agcaaacatc       1320 gtgtttaaaa atgaaataaa atcgtctgat gatcctgtgg ctgcaagaaa tgaaaagata      1380
aatgagtaca gggagaattt cgcaaatcca tacagggcag cagcgagagg atatgtagat      1440
gatgtagttc tgccgcaaga gacgagacct cgcctcatct cggcgttcga tatgcttatg      1500
agcaaaaggg agtcaaggcc cagcaaaaag catggcaatt ttcctgttta a              1551

<210> SEQ ID NO 29
<211> LENGTH: 516
<212> TYPE: PRT
<213> ORGANISM: T. saccharolyticum

<400> SEQUENCE: 29

Met Ser Ile Asp Asp Arg Ile Glu Asp Leu Arg Arg Arg Glu Met
1               5                   10                  15

Val Leu Glu Gly Gly Gly Leu Asp Lys Val Glu Lys Gln His Gln Lys
            20                  25                  30

Gly Lys Leu Thr Ala Arg Glu Arg Ile Tyr Lys Leu Leu Asp Glu Asp
        35                  40                  45

Ser Phe Val Glu Ile Asp Ala Tyr Val Glu His Arg Cys Ile Asp Phe
    50                  55                  60

Gly Met Glu Lys Gln Arg Ile Pro Gly Glu Gly Val Val Thr Gly Tyr
65                  70                  75                  80

Gly Thr Ile Asp Gly Arg Leu Val Tyr Val Ala Gln Asp Phe Thr
            85                  90                  95

Val Leu Gly Gly Ser Leu Gly Glu Tyr His Ala Lys Lys Ile Thr Lys
            100                 105                 110

Ile Met Asp Met Ala Leu Lys Met Gly Ala Pro Leu Ile Gly Leu Asn
        115                 120                 125

Asp Ser Gly Gly Ala Arg Ile Gln Glu Gly Val Asp Ala Leu Ser Gly
    130                 135                 140

Tyr Gly Asn Ile Phe Phe Arg Asn Thr Leu Ala Ser Gly Val Ile Pro
145                 150                 155                 160

Gln Ile Ser Val Ile Met Gly Pro Ser Ala Gly Ala Val Tyr Ser
            165                 170                 175

Pro Ala Leu Thr Asp Phe Ile Phe Met Val Asp Lys Thr Ser Gln Met
        180                 185                 190

Phe Ile Thr Gly Pro Gln Val Ile Lys Ala Val Thr Gly Glu Asp Val
    195                 200                 205

Ser Ala Glu Glu Leu Gly Gly Ser Ile Thr His Ser Thr Lys Ser Gly
    210                 215                 220

Val Ala His Phe Arg Ala Glu Asn Asp Glu Glu Cys Leu Lys Met Val
225                 230                 235                 240

Arg Lys Leu Leu Ser Tyr Leu Pro Ser Asn Asn Leu Glu Asp Pro Pro
```

```
                245                 250                 255
Gln Leu Ala Thr Asp Asp Ile Asn Arg Phe Ser Asp Arg Leu Ile
            260                 265                 270

Glu Ile Ile Pro Asp Ser Pro Asn Lys Pro Tyr Asp Met Lys Glu Val
                275                 280                 285

Ile Ser Glu Ile Val Asp Gly Val Tyr Phe Glu Ser Gln Ala Met
        290                 295                 300

Tyr Ala Gln Asn Ile Ile Thr Ala Phe Ala Arg Leu Asn Gly Arg Thr
305                 310                 315                 320

Val Gly Ile Ile Ala Asn Gln Pro Lys Val Leu Ala Gly Cys Leu Asp
                325                 330                 335

Ile Asn Ala Ser Asp Lys Ala Ser Arg Phe Ile Arg Phe Cys Asp Ala
                340                 345                 350

Phe Asn Ile Pro Leu Leu Asn Ile Val Asp Val Pro Gly Phe Leu Pro
                355                 360                 365

Gly Thr Asn Gln Glu Tyr Gly Gly Ile Ile Arg His Gly Ala Lys Met
        370                 375                 380

Leu Tyr Ala Tyr Ser Glu Ala Thr Val Pro Lys Val Thr Leu Ile Val
385                 390                 395                 400

Arg Lys Ala Tyr Gly Gly Ala Tyr Leu Ala Met Cys Ser Lys Asp Leu
                405                 410                 415

Gly Ala Asp Phe Val Leu Ala Trp Pro Thr Ala Glu Ile Ala Val Met
            420                 425                 430

Gly Pro Asp Gly Ala Ala Asn Ile Val Phe Lys Asn Glu Ile Lys Ser
            435                 440                 445

Ser Asp Asp Pro Val Ala Ala Arg Asn Glu Lys Ile Asn Glu Tyr Arg
        450                 455                 460

Glu Asn Phe Ala Asn Pro Tyr Arg Ala Ala Arg Gly Tyr Val Asp
465                 470                 475                 480

Asp Val Val Leu Pro Gln Glu Thr Arg Pro Arg Leu Ile Ser Ala Phe
                485                 490                 495

Asp Met Leu Met Ser Lys Arg Glu Ser Arg Pro Ser Lys Lys His Gly
            500                 505                 510

Asn Phe Pro Val
        515

<210> SEQ ID NO 30
<211> LENGTH: 384
<212> TYPE: DNA
<213> ORGANISM: T. saccharolyticum

<400> SEQUENCE: 30
atgaaaaaat ttatagtaac tgtcaatgga aaaaaatacg atgtggaagt agaagaagta      60
aaagtcgacg tggcaagtga gaaaaaagca aagaagata ctgctgctaa aaatgcgtca     120
gatgcaagtg taaaaagcaa acaggttgaa gtaaaaaacg aagtcaaaga cggtttctca     180
atcaatgcac cgatgccggg aactatattg gatgtcaaaa taagccaagg ccagactgtc     240
agacgaggcg atgtgctttt aatactggaa gccatgaaga tggaaaatga aatcacgtca     300
ccttacgatg cacaataat atccataaat gtttcaaaag gtgcctctgt aaatacaggc     360
gatgtgcttt tgtacttaaa atga                                            384

<210> SEQ ID NO 31
<211> LENGTH: 127
<212> TYPE: PRT
```

<213> ORGANISM: T. saccharolyticum

<400> SEQUENCE: 31

Met Lys Lys Phe Ile Val Thr Val Asn Gly Lys Lys Tyr Asp Val Glu
1               5                   10                  15

Val Glu Glu Val Lys Val Asp Val Ala Ser Glu Lys Lys Ala Lys Glu
            20                  25                  30

Asp Thr Ala Ala Lys Asn Ala Ser Asp Ala Ser Val Lys Ser Lys Gln
        35                  40                  45

Val Glu Val Lys Asn Glu Val Lys Asp Gly Phe Ser Ile Asn Ala Pro
    50                  55                  60

Met Pro Gly Thr Ile Leu Asp Val Lys Ile Ser Gln Gly Gln Thr Val
65                  70                  75                  80

Arg Arg Gly Asp Val Leu Leu Ile Leu Glu Ala Met Lys Met Glu Asn
                85                  90                  95

Glu Ile Thr Ser Pro Tyr Asp Gly Thr Ile Ile Ser Ile Asn Val Ser
            100                 105                 110

Lys Gly Ala Ser Val Asn Thr Gly Asp Val Leu Leu Tyr Leu Lys
        115                 120                 125

<210> SEQ ID NO 32
<211> LENGTH: 1395
<212> TYPE: DNA
<213> ORGANISM: T. saccharolyticum

<400> SEQUENCE: 32

| | | | | | |
|---|---|---|---|---|---|
| atgtctaaga | taaaaataac | ggagactgtt | ttaagagatg | cacatcaatc | gttgctggca | 60 |
| accagaatga | caaccgatga | aatgcttcct | atagcagaaa | aattagatga | agttggtttt | 120 |
| ttctcgctgg | aagcatgggg | cggtgctaca | tttgatgcat | gtatgagatt | tttgaatgaa | 180 |
| gacccatggg | aaagattaag | acttttaaag | aaggcgatta | agaagacacc | tcttcaaatg | 240 |
| cttttaagag | gtcaaaattt | actcggatat | aaacactatc | ccgatgatgt | cgtaaatgaa | 300 |
| tttataataa | aatctgttga | aaatggtata | gatataataa | gaattttttga | tgcgttaaat | 360 |
| gatgtgagaa | atttagaagt | gccaataaaa | tctgcaaaaa | gtgcaggtgc | tcatgtacag | 420 |
| gcagctattg | tatatacagt | tagtcctgta | cataatacag | atcattattt | gaaagtggca | 480 |
| aagtctcttc | aagatatggg | tgcggattcc | atatgcatta | aggatatgtc | tggaatatta | 540 |
| tcaccctatg | ttgcatacga | tttgattaaa | tctctgaaaa | gagcacttta | cacgccaatt | 600 |
| caactgcata | gccattatac | agcaggactg | gcttcaatga | cttatttaaa | agccatagaa | 660 |
| gctggtgtag | acggggttga | tacagctatt | tcttcgcttg | ccttaggaac | atcacaacca | 720 |
| gctacagaat | caatcgtggc | tgcattgaaa | gatacagaat | atgatacagg | gctagattta | 780 |
| aaattgcttg | ctgagatagc | tcagcatttt | aatgtagtca | aacagaatca | caaaaatgac | 840 |
| agcgatatgt | ctttgcttat | gtctgttgat | gttaaagcat | tagaaagtca | aataccaggg | 900 |
| ggaatgttat | caaatttggt | ttcacagcta | agcagcaga | atgcattaaa | caaatatcaa | 960 |
| gacgtcttga | agaagttcc | aagggtacgc | gaagatttgg | gatatcctcc | tcttgttact | 1020 |
| ccaatgagcc | agatggttgg | aacccaggct | gttttaaatg | ttattacagg | ggagagatat | 1080 |
| aaaatcgttc | ctaaagaaat | taagattat | gtcaaaggtt | tatatgggat | gccaccagct | 1140 |
| ccaatttcag | attctatacg | aaagaaaata | atcggcgatg | aagaagtaat | ttcaaagagg | 1200 |
| ccagcagatt | tactaagtcc | tcaattggat | gaatttaaaa | atgagataaa | ggaatttata | 1260 |
| gagcaagatg | aagatgttttt | atcatatgca | ttatttcctc | aagtagcaag | aagatttttc | 1320 |

```
gagtataggc aagccaaaaa atacagaatt gattcaacat tattaaatat cgaagaaagg    1380
gttcatccga tataa                                                    1395
```

<210> SEQ ID NO 33
<211> LENGTH: 464
<212> TYPE: PRT
<213> ORGANISM: T. saccharolyticum

<400> SEQUENCE: 33

```
Met Ser Lys Ile Lys Ile Thr Glu Thr Val Leu Arg Asp Ala His Gln
1               5                   10                  15

Ser Leu Leu Ala Thr Arg Met Thr Thr Asp Glu Met Leu Pro Ile Ala
            20                  25                  30

Glu Lys Leu Asp Glu Val Gly Phe Phe Ser Leu Glu Ala Trp Gly Gly
        35                  40                  45

Ala Thr Phe Asp Ala Cys Met Arg Phe Leu Asn Glu Asp Pro Trp Glu
    50                  55                  60

Arg Leu Arg Leu Leu Lys Ala Ile Lys Lys Thr Pro Leu Gln Met
65                  70                  75                  80

Leu Leu Arg Gly Gln Asn Leu Leu Gly Tyr Lys His Tyr Pro Asp Asp
                85                  90                  95

Val Val Asn Glu Phe Ile Ile Lys Ser Val Glu Asn Gly Ile Asp Ile
            100                 105                 110

Ile Arg Ile Phe Asp Ala Leu Asn Asp Val Arg Asn Leu Glu Val Pro
        115                 120                 125

Ile Lys Ser Ala Lys Ser Ala Gly Ala His Val Gln Ala Ala Ile Val
    130                 135                 140

Tyr Thr Val Ser Pro Val His Asn Thr Asp His Tyr Leu Lys Val Ala
145                 150                 155                 160

Lys Ser Leu Gln Asp Met Gly Ala Asp Ser Ile Cys Ile Lys Asp Met
                165                 170                 175

Ser Gly Ile Leu Ser Pro Tyr Val Ala Tyr Asp Leu Ile Lys Ser Leu
            180                 185                 190

Lys Arg Ala Leu Tyr Thr Pro Ile Gln Leu His Ser His Tyr Thr Ala
        195                 200                 205

Gly Leu Ala Ser Met Thr Tyr Leu Lys Ala Ile Glu Ala Gly Val Asp
    210                 215                 220

Gly Val Asp Thr Ala Ile Ser Ser Leu Ala Leu Gly Thr Ser Gln Pro
225                 230                 235                 240

Ala Thr Glu Ser Ile Val Ala Ala Leu Lys Asp Thr Glu Tyr Asp Thr
                245                 250                 255

Gly Leu Asp Leu Lys Leu Leu Ala Glu Ile Ala Gln His Phe Asn Val
            260                 265                 270

Val Lys Gln Asn His Lys Asn Asp Ser Asp Met Ser Leu Leu Met Ser
        275                 280                 285

Val Asp Val Lys Ala Leu Glu Ser Gln Ile Pro Gly Gly Met Leu Ser
    290                 295                 300

Asn Leu Val Ser Gln Leu Lys Gln Gln Asn Ala Leu Asn Lys Tyr Gln
305                 310                 315                 320

Asp Val Leu Lys Glu Val Pro Arg Val Arg Glu Asp Leu Gly Tyr Pro
                325                 330                 335

Pro Leu Val Thr Pro Met Ser Gln Met Val Gly Thr Gln Ala Val Leu
            340                 345                 350
```

```
Asn Val Ile Thr Gly Glu Arg Tyr Lys Ile Val Pro Lys Glu Ile Lys
            355                 360                 365

Asp Tyr Val Lys Gly Leu Tyr Gly Met Pro Pro Ala Pro Ile Ser Asp
        370                 375                 380

Ser Ile Arg Lys Lys Ile Ile Gly Asp Glu Val Ile Ser Lys Arg
385                 390                 395                 400

Pro Ala Asp Leu Leu Ser Pro Gln Leu Asp Glu Phe Lys Asn Glu Ile
                405                 410                 415

Lys Glu Phe Ile Glu Gln Asp Glu Asp Val Leu Ser Tyr Ala Leu Phe
            420                 425                 430

Pro Gln Val Ala Arg Arg Phe Phe Glu Tyr Arg Gln Ala Lys Lys Tyr
        435                 440                 445

Arg Ile Asp Ser Thr Leu Leu Asn Ile Glu Glu Arg Val His Pro Ile
    450                 455                 460

<210> SEQ ID NO 34
<211> LENGTH: 159
<212> TYPE: DNA
<213> ORGANISM: T. saccharolyticum

<400> SEQUENCE: 34
atggaagaga taaatgaaga aatagttgct gtcattgaag ctgcgattta cgcggcattt      60
ggtcagtacg aaaagaattt ccgcatcaag gtaataaaga gagtggactc aaatatgccg     120
gaatggagaa aagctggcct ttacaatcag atgagatag                            159

<210> SEQ ID NO 35
<211> LENGTH: 52
<212> TYPE: PRT
<213> ORGANISM: T. saccharolyticum

<400> SEQUENCE: 35

Met Glu Glu Ile Asn Glu Glu Ile Val Ala Val Ile Glu Ala Ala Ile
1               5                   10                  15

Tyr Ala Ala Phe Gly Gln Tyr Glu Lys Asn Phe Arg Ile Lys Val Ile
            20                  25                  30

Lys Arg Val Asp Ser Asn Met Pro Glu Trp Arg Lys Ala Gly Leu Tyr
        35                  40                  45

Asn Gln Met Arg
    50

<210> SEQ ID NO 36
<211> LENGTH: 1542
<212> TYPE: DNA
<213> ORGANISM: C. bescii

<400> SEQUENCE: 36
atgacaaaca agctcagaga gctcaagcaa aagagagaaa gaatactaaa gcttggtgga      60
gaagataaaa taaaaaaaca gcatgatagc aaaaaactta cttgtagaga gagaatagaa     120
tatttacttg accctggaag cttcaatgaa atagatatgt tgttgaaaca cagatgtcaa     180
gaatttgata tgaaagatac atttgtcccc tgtgatggtg ttgtaacggg ttatggaaca     240
atcaatggca gaaagttttt tgtttatgct caagatttta cttcgatagg cggttctctt     300
ggcgagatgc atgcaaaaaa gatttgtaaa gttttggact agcattaaaa atatggttgt     360
ccagtgatag gtataaatga ttctggtggt gcaagaattc aagaaggtgt tgatgcatta     420
gcaggatatg gtgaaatctt ctatagaaat accatggcat caggtgtaat tccacaaatt     480
```

```
gcagctataa tgggaccttg tgcaggtgga gctgtatact ctcctgctat tatggatttt      540 attttatgg tggacaaaac cagccaaatg tttgttacag gacctcaggt tataaaagct      600
gtgactggag aggagatatc ctttgaagag cttggtggcg cttacactca cagctcaaag      660
agtggagttg ctcattttat tgcagaggat gagtatcacc tacttgatat gataaagtat      720
ttattgtcgt ttataccttc aaataacatg gaagacccac cttttataat gtcatctgat      780
tcagaaaaaa gatttgttcc cgagctcgaa aatataattc cgcaagagcc aaacaaagct      840
tatgatgtaa aagaaataat ttataaagta gtagacaacc aagaattttt agaagtacaa      900 ccttatttg ctcaaaatgc tgttgtagga tttggtagaa taggggcttt agcgtagga      960 attgtagcaa atcagcccaa agtgaacgct ggagtgcttg attatgattc gtctgacaag     1020
atagcacgat ttgtaagatt ttgtgatgct tttaatattc ccataataac atttacagac     1080
gtgcctggat ttttgccagg tgttaaccaa gagcacaatg gaataattcg tcatggggct     1140
aaggttttgt atgcatactc agaggcaaca gttccaaaga taaatgtaat tttgagaaaa     1200
gcatatggtg gggcttacat tgcaatgagc agcaaacaca ttggtgcaga ctttgtgttt     1260
gcatggccaa ctgccgagat agctgttatg ggaccagatg gcgcagcaaa tattatattt     1320
agaaaagaga tacaaagcgc tcaaaatccc gaagaggaaa gaaaaagaag gatagaagag     1380
tatactcaaa agtttgcaaa tccatacatt gcagctgccc gtgggtatgt tgacgatgtg     1440
attgagccac agcttacccg taacaaaatc attgaggcgc tcaaaatttc cattacaaaa     1500
agagagcaaa ggcccccaaa aaagcatggc aatattccat ta                       1542

<210> SEQ ID NO 37
<211> LENGTH: 514
<212> TYPE: PRT
<213> ORGANISM: C. bescii

<400> SEQUENCE: 37

Met Thr Asn Lys Leu Arg Glu Leu Lys Gln Lys Arg Glu Arg Ile Leu
1               5                   10                  15

Lys Leu Gly Gly Glu Asp Lys Ile Lys Lys Gln His Asp Ser Lys Lys
            20                  25                  30

Leu Thr Cys Arg Glu Arg Ile Glu Tyr Leu Leu Asp Pro Gly Ser Phe
        35                  40                  45

Asn Glu Ile Asp Met Phe Val Glu His Arg Cys Gln Glu Phe Asp Met
    50                  55                  60

Lys Asp Thr Phe Val Pro Cys Asp Gly Val Val Thr Gly Tyr Gly Thr
65                  70                  75                  80

Ile Asn Gly Arg Lys Val Phe Val Tyr Ala Gln Asp Phe Thr Ser Ile
                85                  90                  95

Gly Gly Ser Leu Gly Glu Met His Ala Lys Lys Ile Cys Lys Val Leu
            100                 105                 110

Asp Leu Ala Leu Lys Tyr Gly Cys Pro Val Ile Gly Ile Asn Asp Ser
        115                 120                 125

Gly Gly Ala Arg Ile Gln Glu Gly Val Asp Ala Leu Ala Gly Tyr Gly
    130                 135                 140

Glu Ile Phe Tyr Arg Asn Thr Met Ala Ser Gly Val Ile Pro Gln Ile
145                 150                 155                 160

Ala Ala Ile Met Gly Pro Cys Ala Gly Gly Ala Val Tyr Ser Pro Ala
                165                 170                 175

Ile Met Asp Phe Ile Phe Met Val Asp Lys Thr Ser Gln Met Phe Val
            180                 185                 190
```

```
Thr Gly Pro Gln Val Ile Lys Ala Val Thr Gly Glu Ile Ser Phe
        195                 200                 205
Glu Glu Leu Gly Gly Ala Tyr Thr His Ser Ser Lys Ser Gly Val Ala
210                 215                 220
His Phe Ile Ala Glu Asp Glu Tyr His Leu Leu Asp Met Ile Lys Tyr
225                 230                 235                 240
Leu Leu Ser Phe Ile Pro Ser Asn Asn Met Glu Asp Pro Pro Phe Ile
                245                 250                 255
Met Ser Ser Asp Ser Glu Lys Arg Phe Val Pro Glu Leu Glu Asn Ile
                260                 265                 270
Ile Pro Gln Glu Pro Asn Lys Ala Tyr Asp Val Lys Ile Ile Tyr
                275                 280                 285
Lys Val Val Asp Asn Gln Glu Phe Leu Glu Val Gln Pro Tyr Phe Ala
290                 295                 300
Gln Asn Ala Val Val Gly Phe Gly Arg Ile Gly Gly Phe Ser Val Gly
305                 310                 315                 320
Ile Val Ala Asn Gln Pro Lys Val Asn Ala Gly Val Leu Asp Tyr Asp
                325                 330                 335
Ser Ser Asp Lys Ile Ala Arg Phe Val Arg Phe Cys Asp Ala Phe Asn
                340                 345                 350
Ile Pro Ile Ile Thr Phe Thr Asp Val Pro Gly Phe Leu Pro Gly Val
                355                 360                 365
Asn Gln Glu His Asn Gly Ile Ile Arg His Gly Ala Lys Val Leu Tyr
370                 375                 380
Ala Tyr Ser Glu Ala Thr Val Pro Lys Ile Asn Val Ile Leu Arg Lys
385                 390                 395                 400
Ala Tyr Gly Gly Ala Tyr Ile Ala Met Ser Ser Lys His Ile Gly Ala
                405                 410                 415
Asp Phe Val Phe Ala Trp Pro Thr Ala Glu Ile Ala Val Met Gly Pro
                420                 425                 430
Asp Gly Ala Ala Asn Ile Ile Phe Arg Lys Glu Ile Gln Ser Ala Gln
                435                 440                 445
Asn Pro Glu Glu Glu Arg Lys Arg Ile Glu Glu Tyr Thr Gln Lys
450                 455                 460
Phe Ala Asn Pro Tyr Ile Ala Ala Ala Arg Gly Tyr Val Asp Asp Val
465                 470                 475                 480
Ile Glu Pro Gln Leu Thr Arg Asn Lys Ile Ile Glu Ala Leu Lys Ile
                485                 490                 495
Ser Ile Thr Lys Arg Glu Gln Arg Pro Pro Lys Lys His Gly Asn Ile
                500                 505                 510
Pro Leu

<210> SEQ ID NO 38
<211> LENGTH: 381
<212> TYPE: DNA
<213> ORGANISM: C. bescii

<400> SEQUENCE: 38
atgagaaagt tcaaggtgaa gatcaatagc caagaatttg ttgtagaagt ggaagaaata    60
ggagttgaaa atgctacttc tgtcgtgcca aggcctaaga ttggccattt tgagccaaaa   120
caggaaaaac atgaggataa acaaaacaa agccctgtac tttcttctga taaaaattcg   180
gttgttgccc agcttccggg tactattgta aggctgctaa aaagtgaagg tgatgttgtt   240
```

```
gatgcaaatg aacctgtttt aattcttgaa gccatgaaaa tggaaaatga ataactgca      300 cctgtcaaag gaaaaattaa agaatacatg gtaaggaag ggcagaaggt agcaaaagga      360
gatttgctat ttgaaataga g                                                381
```

<210> SEQ ID NO 39
<211> LENGTH: 127
<212> TYPE: PRT
<213> ORGANISM: C. bescii

<400> SEQUENCE: 39

```
Met Arg Lys Phe Lys Val Lys Ile Asn Ser Gln Glu Phe Val Val Glu
1               5                   10                  15

Val Glu Glu Ile Gly Val Glu Asn Ala Thr Ser Val Val Pro Arg Pro
            20                  25                  30

Lys Ile Gly His Phe Glu Pro Lys Gln Glu Lys His Glu Asp Lys Thr
        35                  40                  45

Lys Gln Ser Pro Val Leu Ser Ser Asp Lys Asn Ser Val Val Ala Gln
50                  55                  60

Leu Pro Gly Thr Ile Val Arg Leu Leu Lys Ser Glu Gly Asp Val Val
65                  70                  75                  80

Asp Ala Asn Glu Pro Val Leu Ile Leu Glu Ala Met Lys Met Glu Asn
                85                  90                  95

Glu Ile Thr Ala Pro Val Lys Gly Lys Ile Lys Arg Ile His Val Lys
            100                 105                 110

Glu Gly Gln Lys Val Ala Lys Gly Asp Leu Leu Phe Glu Ile Glu
        115                 120                 125
```

<210> SEQ ID NO 40
<211> LENGTH: 1389
<212> TYPE: DNA
<213> ORGANISM: C. bescii

<400> SEQUENCE: 40

```
atgggggtaa aaataacaga acaatactc agagatgctc atcagtcact cattgcaacc      60
cgcatgacaa ctgaacagat gcttgagatt gctcctgtgc ttgaccaagt tggttattat     120
tcggttgagt gctggggcgg tgctacattt gatgcgtgtc tgaggttttt caatgaagac    180
ccatgggaaa gattaaaaag actgagaact gctttttaaaa agacaaagct ccagatgctt   240
cttcgaggac aaaatcttgt tgggtataga cattattctg atgatgttgt tgaagagttt    300
gtaaaaaagg ccatatacta tggcattgat attataagaa tatttgatgc acttaatgac    360
atccggaata ttgaaatggc tctaaaaata acaaaaaaag aaaaaggaca tgcccaggtt    420
gccatatcat acactgtctc accttatcat actattgaaa actatgtaaa tttggcaaaa    480
caaatagaag aacttggggc agactcaatt tgtataaaag acatggctgg gcttctctct    540
ccatttgatg cttataaact tgtaaaagcg ttaaaagagc aggtaaaact tcctattcat    600
cttcatacac actacaccac aggatttgga tcaatgacat atttgaaagc tgtcgaagca    660
ggtgtggatg gtattgacac ggctttatct ccgcttgcac tgggcacatc ccagcctcca    720
accgaaacaa ttgtatatgc acttgaaaat acagaatatg ctccaaaact tgatttagaa    780
aagatcaacg aggcaagcga atattttaaa gtactcagag aagaatatat aagaaaaggg    840
cttcttgacc cgaaagtatt aagtgttgat ataaacgctc ttcattatca aatacctggt    900
ggaatgctat caaatcttat ttctcagcta aagaacaag gcaggaaga caagttagat    960 gaggttttaa agaggtacc tgaggttcga aaagattttg gatatccgcc acttgtaact    1020
```

```
cctacgagtc aaattgtggg aacacaagct gttttgaatg ttatagcagg tgagagatac    1080
aaacttgtca caaagaaac aaaagcatat tttaaaggtg agtatgggaa acctccagct    1140
cctgtgaatg aagaggtaaa aagaaaaatc ttgaaagacg aaaagagat aacctgcaga    1200 cctgcagatt tgattttgcc agagcttgaa aatgcaaaag aaaagattaa ggagtatatt    1260
gaaaatgata ctgatgtggt aacttactgt ttattccctc aacttgcaga aaattttttc    1320
aaattaaggt tcgcaaaaaa atacaaggtt gacgctgatc ttgttcaggg taacaaagtg    1380
tatcctgtg                                                              1389
```

<210> SEQ ID NO 41
<211> LENGTH: 463
<212> TYPE: PRT
<213> ORGANISM: C. bescii

<400> SEQUENCE: 41

| Met | Gly | Val | Lys | Ile | Thr | Glu | Thr | Ile | Leu | Arg | Asp | Ala | His | Gln | Ser |
|---|---|---|---|---|---|---|---|---|---|---|---|---|---|---|---|
| 1 | | | | 5 | | | | | 10 | | | | | 15 | |

| Leu | Ile | Ala | Thr | Arg | Met | Thr | Thr | Glu | Gln | Met | Leu | Glu | Ile | Ala | Pro |
| | | | 20 | | | | | 25 | | | | | 30 | | |

| Val | Leu | Asp | Gln | Val | Gly | Tyr | Tyr | Ser | Val | Glu | Cys | Trp | Gly | Gly | Ala |
| | | 35 | | | | | 40 | | | | | 45 | | | |

| Thr | Phe | Asp | Ala | Cys | Leu | Arg | Phe | Phe | Asn | Glu | Asp | Pro | Trp | Glu | Arg |
| | 50 | | | | | 55 | | | | | 60 | | | | |

| Leu | Lys | Arg | Leu | Arg | Thr | Ala | Phe | Lys | Lys | Thr | Lys | Leu | Gln | Met | Leu |
| 65 | | | | | 70 | | | | | 75 | | | | | 80 |

| Leu | Arg | Gly | Gln | Asn | Leu | Val | Gly | Tyr | Arg | His | Tyr | Ser | Asp | Asp | Val |
| | | | | 85 | | | | | 90 | | | | | 95 | |

| Val | Glu | Glu | Phe | Val | Lys | Lys | Ala | Ile | Tyr | Tyr | Gly | Ile | Asp | Ile | Ile |
| | | | 100 | | | | | 105 | | | | | 110 | | |

| Arg | Ile | Phe | Asp | Ala | Leu | Asn | Asp | Ile | Arg | Asn | Ile | Glu | Met | Ala | Leu |
| | | 115 | | | | | 120 | | | | | 125 | | | |

| Lys | Ile | Thr | Lys | Lys | Glu | Lys | Gly | His | Ala | Gln | Val | Ala | Ile | Ser | Tyr |
| | 130 | | | | | 135 | | | | | 140 | | | | |

| Thr | Val | Ser | Pro | Tyr | His | Thr | Ile | Glu | Asn | Tyr | Val | Asn | Leu | Ala | Lys |
| 145 | | | | | 150 | | | | | 155 | | | | | 160 |

| Gln | Ile | Glu | Glu | Leu | Gly | Ala | Asp | Ser | Ile | Cys | Ile | Lys | Asp | Met | Ala |
| | | | | 165 | | | | | 170 | | | | | 175 | |

| Gly | Leu | Leu | Ser | Pro | Phe | Asp | Ala | Tyr | Lys | Leu | Val | Lys | Ala | Leu | Lys |
| | | | 180 | | | | | 185 | | | | | 190 | | |

| Glu | Gln | Val | Lys | Leu | Pro | Ile | His | Leu | His | Thr | His | Tyr | Thr | Thr | Gly |
| | | 195 | | | | | 200 | | | | | 205 | | | |

| Phe | Gly | Ser | Met | Thr | Tyr | Leu | Lys | Ala | Val | Glu | Ala | Gly | Val | Asp | Gly |
| | 210 | | | | | 215 | | | | | 220 | | | | |

| Ile | Asp | Thr | Ala | Leu | Ser | Pro | Leu | Ala | Leu | Gly | Thr | Ser | Gln | Pro | Pro |
| 225 | | | | | 230 | | | | | 235 | | | | | 240 |

| Thr | Glu | Thr | Ile | Val | Tyr | Ala | Leu | Glu | Asn | Thr | Glu | Tyr | Ala | Pro | Lys |
| | | | | 245 | | | | | 250 | | | | | 255 | |

| Leu | Asp | Leu | Glu | Lys | Ile | Asn | Glu | Ala | Ser | Glu | Tyr | Phe | Lys | Val | Leu |
| | | | 260 | | | | | 265 | | | | | 270 | | |

| Arg | Glu | Glu | Tyr | Ile | Arg | Lys | Gly | Leu | Leu | Asp | Pro | Lys | Val | Leu | Ser |
| | | 275 | | | | | 280 | | | | | 285 | | | |

| Val | Asp | Ile | Asn | Ala | Leu | His | Tyr | Gln | Ile | Pro | Gly | Gly | Met | Leu | Ser |
| | 290 | | | | | 295 | | | | | 300 | | | | |

```
Asn Leu Ile Ser Gln Leu Lys Glu Gln Gly Gln Glu Asp Lys Leu Asp
305                 310                 315                 320

Glu Val Leu Lys Glu Val Pro Glu Val Arg Lys Asp Phe Gly Tyr Pro
            325                 330                 335

Pro Leu Val Thr Pro Thr Ser Gln Ile Val Gly Thr Gln Ala Val Leu
        340                 345                 350

Asn Val Ile Ala Gly Glu Arg Tyr Lys Leu Val Thr Lys Glu Thr Lys
    355                 360                 365

Ala Tyr Phe Lys Gly Glu Tyr Gly Lys Pro Ala Pro Val Asn Glu
370                 375                 380

Glu Val Lys Arg Lys Ile Leu Lys Asp Glu Lys Glu Ile Thr Cys Arg
385                 390                 395                 400

Pro Ala Asp Leu Ile Leu Pro Glu Leu Glu Asn Ala Lys Glu Lys Ile
            405                 410                 415

Lys Glu Tyr Ile Glu Asn Asp Thr Asp Val Val Thr Tyr Cys Leu Phe
        420                 425                 430

Pro Gln Leu Ala Glu Asn Phe Phe Lys Leu Arg Phe Ala Lys Lys Tyr
    435                 440                 445

Lys Val Asp Ala Asp Leu Val Gln Gly Asn Lys Val Tyr Pro Val
450                 455                 460

<210> SEQ ID NO 42
<211> LENGTH: 189
<212> TYPE: DNA
<213> ORGANISM: C. bescii

<400> SEQUENCE: 42
atgtatgctc aggtcagtac tatttcaacc attacaaaag aagaacttgc ttgtatttgt      60
gcatgtctgc acattgtgat gggtgaaggt caatataaaa ttaccaacat aactaaacag     120
caaaacaagt gggtcaaagg tgcaagagaa atgatgctca atcagtcaca gatgttttat     180
agatggagg                                                             189

<210> SEQ ID NO 43
<211> LENGTH: 63
<212> TYPE: PRT
<213> ORGANISM: C. bescii

<400> SEQUENCE: 43

Met Tyr Ala Gln Val Ser Thr Ile Ser Thr Ile Thr Lys Glu Glu Leu
1               5                   10                  15

Ala Cys Ile Cys Ala Cys Leu His Ile Val Met Gly Glu Gly Gln Tyr
            20                  25                  30

Lys Ile Thr Asn Ile Thr Lys Gln Gln Asn Lys Trp Val Lys Gly Ala
        35                  40                  45

Arg Glu Met Met Leu Asn Gln Ser Gln Met Phe Tyr Arg Trp Arg
    50                  55                  60

<210> SEQ ID NO 44
<211> LENGTH: 1548
<212> TYPE: DNA
<213> ORGANISM: C. cellulolyticum

<400> SEQUENCE: 44
atgtcacaaa ttgaaaagat acaaaattta aaaaacatga aaaaaactat agctaaaggc      60
ggcggagaag agaaaatagc aaaaagacac gcagatggaa agctttctgc cagagaaaga     120
```

```
atccatttgt tgtttgatga aaacagtttt gttgaggtag atgcattcat agaatccaga    180
tgctttgact ttggtatgca gaagaagaaa cttccaggtg acggggttgt taccggttac    240
ggaacagtta atggcagaaa ggtctttgtt tcatcacagg actttactgt tataggcggt    300
tcattgggag agatgcacgc aaagaaaatt acaaaggtta tggatatggc tctgaaaatg    360
ggagcaccgt tcatagccat taatgattcc ggcggagctc gtattgagga aggtctggat    420
gctcttttcag gttacggaga tattttttac aggaatactc ttgcatcagg cgttattccg    480
cagatatcag taataatggg gccatgtgca ggtggtgcgg tatattcccc ggccataact    540
gattttatat tcatggtgga aaaaacaagt cagatgttta ttacaggccc acaggtaata    600
aagtctgtta cgggtgaaga tgtatcagtt gaaaatctgg gaggtgcaga tgttcatact    660
gctacaagcg tgtagcaca tttcaaatct tcaagcgaag aagagtgtat agaagatata    720
aagaggcttt taagttttat tcccgataat aatgtatcag atactatgta ctacggagtg    780
tctgatgctg ccgacagatt agccgaaagc ctcaacagca ttattccaga agagtcaaac    840
aagccatatg acatgtttga cgtaatagca gaagtagtag atgatggaga tttctttgaa    900
gttcagagtt atttctctca gaatataata atcggatttg caagaatgaa tggcagaagt    960
gttggtattg ttgcaaaacca gcctaagata atggcagggt cactagatat gaacgcggct   1020
gataaggcgg cacgtttcgt tcgtttctgt gatgcattta atattcctgt cgtttcatta   1080
accgatgtac ctgcattcct gcccggggta gcccaggagc ataacggcat aatacgtcac   1140
ggtgcaaaac tcctatatgc tttctctgaa gcaacagtac aaagataaa tgttattctt   1200
agaaaggcat atggaggagc atatattgct atgaacagta aaacaatagg tgccgatatg   1260
gttttggcat ggccatcagc tgaaattgca gttatgggac ctgacggagc agcaaatatt   1320
atatttaaaa aggatattgc tgcgtcggaa gatccagcag aaaccagaaa ggaaaagatt   1380
gcggaatata gagataaatt ctcaaatcct tatgtagcag catcaagagg gtatattgat   1440
gatgttatcg agccttctga aaccagagta aaaattataa ctgctctgga aatgctggat   1500
acaaagaggg aaaacaggcc ttcaaaaaaa catggaaaca ttccgcta              1548
```

<210> SEQ ID NO 45
<211> LENGTH: 516
<212> TYPE: PRT
<213> ORGANISM: C. cellulolyticum

<400> SEQUENCE: 45

```
Met Ser Gln Ile Glu Lys Ile Gln Asn Leu Lys Asn Met Lys Lys Thr
1               5                   10                  15

Ile Ala Lys Gly Gly Gly Glu Glu Lys Ile Ala Lys Arg His Ala Asp
            20                  25                  30

Gly Lys Leu Ser Ala Arg Glu Arg Ile His Leu Leu Phe Asp Glu Asn
        35                  40                  45

Ser Phe Val Glu Val Asp Ala Phe Ile Glu Ser Arg Cys Phe Asp Phe
    50                  55                  60

Gly Met Gln Lys Lys Lys Leu Pro Gly Asp Gly Val Val Thr Gly Tyr
65                  70                  75                  80

Gly Thr Val Asn Gly Arg Lys Val Phe Val Ser Ser Gln Asp Phe Thr
                85                  90                  95

Val Ile Gly Gly Ser Leu Gly Glu Met His Ala Lys Lys Ile Thr Lys
            100                 105                 110

Val Met Asp Met Ala Leu Lys Met Gly Ala Pro Phe Ile Ala Ile Asn
        115                 120                 125
```

-continued

```
Asp Ser Gly Gly Ala Arg Ile Glu Glu Gly Leu Asp Ala Leu Ser Gly
    130                 135                 140
Tyr Gly Asp Ile Phe Tyr Arg Asn Thr Leu Ala Ser Gly Val Ile Pro
145                 150                 155                 160
Gln Ile Ser Val Ile Met Gly Pro Cys Ala Gly Gly Ala Val Tyr Ser
                165                 170                 175
Pro Ala Ile Thr Asp Phe Ile Phe Met Val Glu Lys Thr Ser Gln Met
            180                 185                 190
Phe Ile Thr Gly Pro Gln Val Ile Lys Ser Val Thr Gly Glu Asp Val
        195                 200                 205
Ser Val Glu Asn Leu Gly Gly Ala Asp Val His Thr Ala Thr Ser Gly
    210                 215                 220
Val Ala His Phe Lys Ser Ser Glu Glu Cys Ile Glu Asp Ile
225                 230                 235                 240
Lys Arg Leu Leu Ser Phe Ile Pro Asp Asn Asn Val Ser Asp Thr Met
                245                 250                 255
Tyr Tyr Gly Val Ser Asp Ala Ala Asp Arg Leu Ala Glu Ser Leu Asn
            260                 265                 270
Ser Ile Ile Pro Glu Glu Ser Asn Lys Pro Tyr Asp Met Phe Asp Val
        275                 280                 285
Ile Ala Glu Val Val Asp Asp Gly Asp Phe Phe Glu Val Gln Ser Tyr
    290                 295                 300
Phe Ser Gln Asn Ile Ile Ile Gly Phe Ala Arg Met Asn Gly Arg Ser
305                 310                 315                 320
Val Gly Ile Val Ala Asn Gln Pro Lys Ile Met Ala Gly Ser Leu Asp
                325                 330                 335
Met Asn Ala Ala Asp Lys Ala Ala Arg Phe Val Arg Phe Cys Asp Ala
            340                 345                 350
Phe Asn Ile Pro Val Val Ser Leu Thr Asp Val Pro Ala Phe Leu Pro
        355                 360                 365
Gly Val Ala Gln Glu His Asn Gly Ile Ile Arg His Gly Ala Lys Leu
    370                 375                 380
Leu Tyr Ala Phe Ser Glu Ala Thr Val Pro Lys Ile Asn Val Ile Leu
385                 390                 395                 400
Arg Lys Ala Tyr Gly Gly Ala Tyr Ile Ala Met Asn Ser Lys Thr Ile
                405                 410                 415
Gly Ala Asp Met Val Leu Ala Trp Pro Ser Ala Glu Ile Ala Val Met
            420                 425                 430
Gly Pro Asp Gly Ala Ala Asn Ile Ile Phe Lys Lys Asp Ile Ala Ala
        435                 440                 445
Ser Glu Asp Pro Ala Glu Thr Arg Lys Glu Lys Ile Ala Glu Tyr Arg
    450                 455                 460
Asp Lys Phe Ser Asn Pro Tyr Val Ala Ala Ser Arg Gly Tyr Ile Asp
465                 470                 475                 480
Asp Val Ile Glu Pro Ser Glu Thr Arg Val Lys Ile Ile Thr Ala Leu
                485                 490                 495
Glu Met Leu Asp Thr Lys Arg Glu Asn Arg Pro Ser Lys Lys His Gly
            500                 505                 510
Asn Ile Pro Leu
            515

<210> SEQ ID NO 46
<211> LENGTH: 366
```

```
<212> TYPE: DNA
<213> ORGANISM: C. cellulolyticum

<400> SEQUENCE: 46
atgagtaaat atataataaa ggtaaacgga actccttatg aagtagaggt tgaagaagtg      60
ggcgggggaa ggcccatttc agctgctcca aagctaagag ctaccaagcc gggacatacc     120
tctgctgcaa aagcagcaca gccgcaggca ggtaaagcag gtgatgttgc tgctccaatg     180
ccgggaactg ttttaaaggt aaaggttgct atcggtgatg aagtaaagaa ggggcaggta     240
cttttaatac ttgaagctat gaaaatggag aatgaaatag ttgctccggc tgacggtaaa     300
gttacggcgt taaacgtcga ggccggaaag tctgttactg ctggagaact aatggtgtct     360
atagcc                                                                366

<210> SEQ ID NO 47
<211> LENGTH: 122
<212> TYPE: PRT
<213> ORGANISM: C. cellulolyticum

<400> SEQUENCE: 47

Met Ser Lys Tyr Ile Ile Lys Val Asn Gly Thr Pro Tyr Glu Val Glu
1               5                   10                  15

Val Glu Glu Val Gly Gly Gly Arg Pro Ile Ser Ala Ala Pro Lys Leu
            20                  25                  30

Arg Ala Thr Lys Pro Gly His Thr Ser Ala Ala Lys Ala Ala Gln Pro
        35                  40                  45

Gln Ala Gly Lys Ala Gly Asp Val Ala Ala Pro Met Pro Gly Thr Val
    50                  55                  60

Leu Lys Val Lys Val Ala Ile Gly Asp Glu Val Lys Lys Gly Gln Val
65                  70                  75                  80

Leu Leu Ile Leu Glu Ala Met Lys Met Glu Asn Glu Ile Val Ala Pro
                85                  90                  95

Ala Asp Gly Lys Val Thr Ala Leu Asn Val Glu Ala Gly Lys Ser Val
            100                 105                 110

Thr Ala Gly Glu Leu Met Val Ser Ile Ala
        115                 120

<210> SEQ ID NO 48
<211> LENGTH: 1530
<212> TYPE: DNA
<213> ORGANISM: C. cellulolyticum

<400> SEQUENCE: 48
atgccaggcg taagaattac ggaaacagtt ttaagagatg ctcaccagtc ccttatagca      60
accagaatga agaccgaaga aatgcttcca attgttgaga gcttgacaa tattggttac     120 cattcactgg aagcttgggg cggagctact tttgactcat gtatgagatt tttgaatgaa     180
gatccatgga tgagacttag aaaaataaaa gatgttgcaa agaaacacc tctgcaaatg     240 cttcttaggg gccagaacct tttaggatac aaacactatg ccgatgatat agttgagtac     300
tttgttcaga aggctgttgc aaacggcatg gacattatga aatattcga tgcactaaat     360 gatgccagga atatcgagac ggcaattaag gcatgtaaaa aggaaggcgg ccatgctcag     420
ggctgtattt gctatactat aagtcctgtt cacaatcttg agcttttgt aaaagatgca     480 aagcagttgg agagcatggg agcagattct atctgtataa aagacatggc cggacttctg     540
gtgccgtatc aggcttatga actggtaaag gctttgaaag aaagtgtaaa gataccgata     600
```

```
caattgcaca ctcactatac tagcggtgta gcatctatga cgtatttgaa ggctatagaa    660
gcaggtatag atattgttga ctgtgcaatt tcacctatgt caatgggaac gtcacagccg    720
cctacagagc ctttggtggc aactttaaag ggaactgatt tcgatactgg actggatttg    780
gaaaaactca gtgaaattgc agactatttc agacccctta agaaaaata tattgagagc    840 ggactattag acgttaaggt aatgggtgtt gacgttaaca ctcttattta tcaggtacct    900
ggtggaatgc tttcaaatct tgtttcacaa ttgaagcagt caaatgcttt ggataaaatat   960 gaagaggttc tcaaggaagt tcccagagta agagccgatt tcggctatcc tccgcttgta   1020
acaccatcaa gtcagatagt tggtacccaa gcggtactta atgtattgac tggtgagaga   1080
tacaagatgg taccaaagga atcaaaaggc gttgtaaagg gggaatacgg taaaacccct   1140
gcacctatta gtgatgaaat aaaagctaag attctgggcg atgaaaagcc tataacatgc   1200
agacctgctg accttattga acctgagctt gaaaagatta gagaagctgt taaggattat   1260
atagagcagg atgaagatgt actttcatac gcaatgcttc ctcaggttgc cgagaagttc   1320
tttaaacagc gtattgagga tagaaataag gctactgcac ccgcatcaga cgaaataaaa   1380
cccgaagttg tagcggcaat atcagccgta gtaaacgaaa tgggcgaaag agacggcaca   1440
cagtacagaa tcgaaatat ctctaagttg aaccagaatc agaacagatg gagtctgtat    1500
ggtatgcttg atagattcag aacaaaaatt                                    1530
```

<210> SEQ ID NO 49  
<211> LENGTH: 510  
<212> TYPE: PRT  
<213> ORGANISM: C. cellulolyticum

<400> SEQUENCE: 49

Met Pro Gly Val Arg Ile Thr Glu Thr Val Leu Arg Asp Ala His Gln
1               5                   10                  15

Ser Leu Ile Ala Thr Arg Met Lys Thr Glu Met Leu Pro Ile Val
            20                  25                  30

Glu Lys Leu Asp Asn Ile Gly Tyr His Ser Leu Glu Ala Trp Gly Gly
        35                  40                  45

Ala Thr Phe Asp Ser Cys Met Arg Phe Leu Asn Glu Asp Pro Trp Met
    50                  55                  60

Arg Leu Arg Lys Ile Lys Asp Val Ala Lys Lys Thr Pro Leu Gln Met
65                  70                  75                  80

Leu Leu Arg Gly Gln Asn Leu Leu Gly Tyr Lys His Tyr Ala Asp Asp
                85                  90                  95

Ile Val Glu Tyr Phe Val Gln Lys Val Ala Asn Gly Met Asp Ile
            100                 105                 110

Met Arg Ile Phe Asp Ala Leu Asn Asp Ala Arg Asn Ile Glu Thr Ala
        115                 120                 125

Ile Lys Ala Cys Lys Lys Glu Gly Gly His Ala Gln Gly Cys Ile Cys
    130                 135                 140

Tyr Thr Ile Ser Pro Val His Asn Leu Glu Leu Phe Val Lys Asp Ala
145                 150                 155                 160

Lys Gln Leu Glu Ser Met Gly Ala Asp Ser Ile Cys Ile Lys Asp Met
                165                 170                 175

Ala Gly Leu Leu Val Pro Tyr Gln Ala Tyr Glu Leu Val Lys Ala Leu
            180                 185                 190

Lys Glu Ser Val Lys Ile Pro Ile Gln Leu His Thr His Tyr Thr Ser
        195                 200                 205

```
Gly Val Ala Ser Met Thr Tyr Leu Lys Ala Ile Glu Ala Gly Ile Asp
    210                 215                 220
Ile Val Asp Cys Ala Ile Ser Pro Met Ser Met Gly Thr Ser Gln Pro
225                 230                 235                 240
Pro Thr Glu Pro Leu Val Ala Thr Leu Lys Gly Thr Asp Phe Asp Thr
                245                 250                 255
Gly Leu Asp Leu Glu Lys Leu Ser Glu Ile Ala Asp Tyr Phe Arg Pro
            260                 265                 270

Leu Lys Glu Lys Tyr Ile Glu Ser Gly Leu Leu Asp Val Lys Val Met
        275                 280                 285

Gly Val Asp Val Asn Thr Leu Ile Tyr Gln Val Pro Gly Gly Met Leu
    290                 295                 300
Ser Asn Leu Val Ser Gln Leu Lys Gln Ser Asn Ala Leu Asp Lys Tyr
305                 310                 315                 320
Glu Glu Val Leu Lys Glu Val Pro Arg Val Arg Ala Asp Phe Gly Tyr
                325                 330                 335
Pro Pro Leu Val Thr Pro Ser Ser Gln Ile Val Gly Thr Gln Ala Val
            340                 345                 350

Leu Asn Val Leu Thr Gly Glu Arg Tyr Lys Met Val Pro Lys Glu Ser
        355                 360                 365

Lys Gly Val Val Lys Gly Glu Tyr Gly Lys Thr Pro Ala Pro Ile Ser
    370                 375                 380
Asp Glu Ile Lys Ala Lys Ile Leu Gly Asp Glu Lys Pro Ile Thr Cys
385                 390                 395                 400

Arg Pro Ala Asp Leu Ile Glu Pro Glu Leu Glu Lys Ile Arg Glu Ala
                405                 410                 415
Val Lys Asp Tyr Ile Glu Gln Asp Glu Asp Val Leu Ser Tyr Ala Met
            420                 425                 430

Leu Pro Gln Val Ala Glu Lys Phe Phe Lys Gln Arg Ile Glu Asp Arg
        435                 440                 445

Asn Lys Ala Thr Ala Pro Ala Ser Asp Glu Ile Lys Pro Glu Val Val
    450                 455                 460
Ala Ala Ile Ser Ala Val Val Asn Glu Met Gly Glu Arg Asp Gly Thr
465                 470                 475                 480
Gln Tyr Arg Ile Gly Asn Ile Ser Lys Leu Asn Gln Asn Gln Asn Arg
                485                 490                 495
Trp Ser Leu Tyr Gly Met Leu Asp Arg Phe Arg Thr Lys Ile
            500                 505                 510
```

<210> SEQ ID NO 50
<211> LENGTH: 1581
<212> TYPE: DNA
<213> ORGANISM: C. kroppenstedtii

<400> SEQUENCE: 50

```
atgagtgagc aacctcacga tcccagcatg cctgagcgcc tcggacagct ggaagaagaa      60
agaaaccgca tccgactcgg cggcgggcag gcacgcctgg acaagcagca cgaccgcggc     120
aagatgaccg cccgcgagcg catcaccaag cttgtcgacg aagacacgtt ccaggaaacc     180
ggaatgttcg ccaagcaccg gacaacgcac ttcggcatgg acaaggccga cgcccccgcc     240
gacggcgtcg tcaccggatc cggcgcggtc tacggacggc cagtgcacat cgcgtcccag     300
gacttcagcg tcatgggcgg atctgctggc gaaatgcagt ccaacaaagt ggtcgccatg     360
atgaaggcgt ccgcgaccac cggcaccccc ttcgtcttta tcaacgactc cggcggagct     420
```

-continued

```
cgtgtccaag agggcatcga ctccctctcc ggatacggcc gcgtgttcta caacaacgtg    480
ctgctctccg gactcgtacc gcaggtctcc atcatcgccg gcccgtgcgc tggtggtgcg    540
gcctactcgc cggcactgac ggacttcatc atccagaccc gcaaggccaa catgttcatc    600
accggcccca aggtcatcga gtccgtgacc ggcgaaaaag tcacggccga cgaactcggt    660
ggtgccgatg cccacatgag cacagctggc aacattcact tcgtcgccga cgatgacgag    720
caagccatcc tgatcgcgca gaagctcctg agcttcctgc cgcaaaacaa caccgaagag    780
ccgcccatcg tcgatccgga cgaggttgtc gagcccgacg attccctccg cgacatcgtc    840
cccgtcgatg gccgcaaggg ctacgacgtc cgcgatatca tccgcaagat cgtcgactac    900
ggcgacttcc tcgaggtcca ggccggatac gcccaaaacc tcgtggtcgg atttgcccgc    960
gtcgttggcc ggacagtcgg tatcgtcgct aaccagtcgc aagtgatgtc cggcgttctg   1020
gacatcaact cgtcggacaa aggcgcaagc ttcgttcgct tctgcgactc cttcaatatt   1080
ccgctcctca ccctcgtcga cgtccccggc ttcatgccag gtgtcgcaca agagcatggc   1140
ggaatcattc gccacggcgc gaagatgctg ttcgcctact cggcggccac cgtgccgaag   1200
ctgaccgtgg tcctccgcaa atcctatggc ggatcgtacc tggccatgtg ctccaaggac   1260
cttggcgcgg accgcgtctg ggcgtggccc accgctgaaa ttgcggtcat gggtgccgac   1320
ggagccgtga acgtcgtctt ccgtaaggaa atcaagaaag cccaggaaga gggtggcgac   1380
gaagccgctg cagcaaagaa gagcgaactc gtccagctct acaaagacac cttctcgacg   1440
ccatacatgg cggcgtcccg aggcctcgtc gatgacatca tcgaccccgc ggacacacgt   1500
cgcgaaattg ctctggccct ggagttgctg accaacaagc gtgagaaccg gccgtccaag   1560
aagcacggcc tggcacccaa c                                             1581
```

<210> SEQ ID NO 51
<211> LENGTH: 527
<212> TYPE: PRT
<213> ORGANISM: C. kroppenstedtii

<400> SEQUENCE: 51

```
Met Ser Glu Gln Pro His Asp Pro Ser Met Pro Glu Arg Leu Gly Gln
1               5                   10                  15

Leu Glu Glu Glu Arg Asn Arg Ile Arg Leu Gly Gly Gly Gln Ala Arg
            20                  25                  30

Leu Asp Lys Gln His Asp Arg Gly Lys Met Thr Ala Arg Glu Arg Ile
        35                  40                  45

Thr Lys Leu Val Asp Glu Asp Thr Phe Gln Glu Thr Gly Met Phe Ala
    50                  55                  60

Lys His Arg Thr Thr His Phe Gly Met Asp Lys Ala Asp Ala Pro Ala
65                  70                  75                  80

Asp Gly Val Val Thr Gly Ser Gly Ala Val Tyr Gly Arg Pro Val His
                85                  90                  95

Ile Ala Ser Gln Asp Phe Ser Val Met Gly Gly Ser Ala Gly Glu Met
            100                 105                 110

Gln Ser Asn Lys Val Val Ala Met Met Lys Ala Ser Ala Thr Thr Gly
        115                 120                 125

Thr Pro Phe Val Phe Ile Asn Asp Ser Gly Gly Ala Arg Val Gln Glu
    130                 135                 140

Gly Ile Asp Ser Leu Ser Gly Tyr Gly Arg Val Phe Tyr Asn Asn Val
145                 150                 155                 160

Leu Leu Ser Gly Leu Val Pro Gln Val Ser Ile Ile Ala Gly Pro Cys
```

-continued

```
                165                 170                 175

Ala Gly Gly Ala Ala Tyr Ser Pro Ala Leu Thr Asp Phe Ile Ile Gln
            180                 185                 190

Thr Arg Lys Ala Asn Met Phe Ile Thr Gly Pro Lys Val Ile Glu Ser
        195                 200                 205

Val Thr Gly Glu Lys Val Thr Ala Asp Glu Leu Gly Gly Ala Asp Ala
    210                 215                 220

His Met Ser Thr Ala Gly Asn Ile His Phe Val Ala Asp Asp Asp Glu
225                 230                 235                 240

Gln Ala Ile Leu Ile Ala Gln Lys Leu Leu Ser Phe Leu Pro Gln Asn
                245                 250                 255

Asn Thr Glu Glu Pro Pro Ile Val Asp Pro Asp Glu Val Val Glu Pro
            260                 265                 270

Asp Asp Ser Leu Arg Asp Ile Val Pro Val Asp Gly Arg Lys Gly Tyr
        275                 280                 285

Asp Val Arg Asp Ile Ile Arg Lys Ile Val Asp Tyr Gly Asp Phe Leu
    290                 295                 300

Glu Val Gln Ala Gly Tyr Ala Gln Asn Leu Val Val Gly Phe Ala Arg
305                 310                 315                 320

Val Val Gly Arg Thr Val Gly Ile Val Ala Asn Gln Ser Gln Val Met
                325                 330                 335

Ser Gly Val Leu Asp Ile Asn Ser Ser Asp Lys Gly Ala Ser Phe Val
            340                 345                 350

Arg Phe Cys Asp Ser Phe Asn Ile Pro Leu Leu Thr Leu Val Asp Val
        355                 360                 365

Pro Gly Phe Met Pro Gly Val Ala Gln Glu His Gly Gly Ile Ile Arg
    370                 375                 380

His Gly Ala Lys Met Leu Phe Ala Tyr Ser Ala Ala Thr Val Pro Lys
385                 390                 395                 400

Leu Thr Val Val Leu Arg Lys Ser Tyr Gly Gly Ser Tyr Leu Ala Met
                405                 410                 415

Cys Ser Lys Asp Leu Gly Ala Asp Arg Val Trp Ala Trp Pro Thr Ala
            420                 425                 430

Glu Ile Ala Val Met Gly Ala Asp Gly Ala Val Asn Val Val Phe Arg
        435                 440                 445

Lys Glu Ile Lys Lys Ala Gln Glu Glu Gly Gly Asp Glu Ala Ala Ala
    450                 455                 460

Ala Lys Lys Ser Glu Leu Val Gln Leu Tyr Lys Asp Thr Phe Ser Thr
465                 470                 475                 480

Pro Tyr Met Ala Ala Ser Arg Gly Leu Val Asp Asp Ile Ile Asp Pro
                485                 490                 495

Ala Asp Thr Arg Arg Glu Ile Ala Leu Ala Leu Glu Leu Leu Thr Asn
            500                 505                 510

Lys Arg Glu Asn Arg Pro Ser Lys Lys His Gly Leu Ala Pro Asn
        515                 520                 525
```

<210> SEQ ID NO 52
<211> LENGTH: 369
<212> TYPE: DNA
<213> ORGANISM: C. kroppenstedtii

<400> SEQUENCE: 52

```
atgaaactga cagttaccgt caacggcgtc ccctattccg tggacgtaga agttgaacac     60
gaagaacgcc ccacactcgg caccatcatc actggtggca acagcaacgg gccaacaccc    120
```

| | |
|---|---|
| accgcgccga ccacctcatc tgtccagggt gtcagcgcca attcggtcac ggcacccctg | 180 |
| gctggttccg tcagcaaggt gcttgtggag gaaggccaag ccatcacggc cggcgaagtg | 240 |
| atcgttgtcc ttgaagccat gaagatggaa accgaaatta cggcccccaa cgacggcacc | 300 |
| gtcaccgcgc ttcacgtgca acccggcgac gccgttcagg gtggacagtc tctgctggag | 360 |
| atcggggac | 369 |

<210> SEQ ID NO 53
<211> LENGTH: 123
<212> TYPE: PRT
<213> ORGANISM: C. kroppenstedtii

<400> SEQUENCE: 53

Met Lys Leu Thr Val Thr Val Asn Gly Val Pro Tyr Ser Val Asp Val
1               5                   10                  15

Glu Val Glu His Glu Glu Arg Pro Thr Leu Gly Thr Ile Ile Thr Gly
            20                  25                  30

Gly Asn Ser Asn Gly Pro Thr Pro Thr Ala Pro Thr Thr Ser Ser Val
35 40 45

Gln Gly Val Ser Ala Asn Ser Val Thr Ala Pro Leu Ala Gly Ser Val
50 55 60

Ser Lys Val Leu Val Glu Glu Gly Gln Ala Ile Thr Ala Gly Glu Val
65 70 75 80

Ile Val Val Leu Glu Ala Met Lys Met Glu Thr Glu Ile Thr Ala Pro
85 90 95

Asn Asp Gly Thr Val Thr Ala Leu His Val Gln Pro Gly Asp Ala Val
100 105 110

Gln Gly Gly Gln Ser Leu Leu Glu Ile Gly Asp
115 120

<210> SEQ ID NO 54
<211> LENGTH: 1494
<212> TYPE: DNA
<213> ORGANISM: C. kroppenstedtii

<400> SEQUENCE: 54
atgaccacgc gaaaaattgg agtgaccgaa ctggctctgc gtgatgctca ccagagcctc 60
atggcaacac gcatggccct cgaagacatg gtcgatgcct gtgaggatat agacaaagcc 120
gggtactgga gcgtggaatg ctggggcggg gcaaccttcg acgcctgcat tcgcttcctg 180
aacgaagacc cgtgggagag actgcgcaca ttccgcaagc tcatgcccaa ctcacgcctt 240
cagatgctgc ttcgtggcca gaatcttctg ggataccgtc actacgagga cggcgtcgtc 300
gataagtttg ttgaaaaatc cgctgaaaac ggcatggacg tcttcagggt tttcgacgcg 360
ctcaacgacc cccgcaacct cgagcacgcc atgcaagctg tgaaaaaagt gggcaagcac 420
gcgcagggca ccatctgcta caccgtgtcc ccgctacacg acgtgcaggg ctacattgat 480
ctagcagggc gtttgctgga catgggcgcg gattcgatcg cgctcaaaga catggcagcg 540
ctgctcaaac cacagcccgc ctacgacatt atccgtggca ttaaggacac ctacggcgag 600
gatacgcaga tcaacgtcca ctgccactcc accaccggcg tcacgatggt caccctcatg 660
aaggccattg aagccggtgc ggatgtcgtc gacaccgcca tttcctccat gtccctcggc 720
ccagggcata accccaccga gtctctcgtc gaaatgctcg aaggaaccga ctacgagacc 780
gggcttgaca tggatcggct cattaacatc cgcgaccact tcaagacagt gcgcccgaag 840

```
tacgcggagt ttgagtcgaa aacactggtc aacaccaata ttttccaatc gcagattccg    900
ggcggaatgc tctccaacat ggaatcgcag ctcaaagccc agggcgcggg cgaccgtatc    960
gacgaggtca tgaaagaagt ccccgtcgtt cggaaagctg ccggataccc gccgttggtg   1020
acgccatcgt cccagatcgt cggcacccag gccgtgttca acgtgctgat gggccgctac   1080
aaagtactca cggctgaatt cgccgacctc ctcctcgggt actacggcga agcaccaggt   1140
gagagggata aagacctcat cgagcaagcc aagaagcaga ccggcaaaga gcccatcacc   1200
gagcgtcctg ctgacctcct tgagcccgaa tgggacaacc tggttgagga agctgacgaa   1260
ctcgacggca ccgacgggtc cgacgaagac gtcctcacaa acgccctgtt cccgcaggtc   1320
gcgccgggat tcttcaagac tcgccccgac ggcccgaaga acgtcggcaa gactaaggaa   1380
cagctcgagc gcgaagaggc gaaggcctcc ggcgacgcca ctgccatccg cgaaccgatt   1440
atgtacaaag tcaccacagg cggccgcagc cacactgtct ccgtggaacc cgca         1494

<210> SEQ ID NO 55
<211> LENGTH: 498
<212> TYPE: PRT
<213> ORGANISM: C. kroppenstedtii
<400> SEQUENCE: 55

Met Thr Thr Arg Lys Ile Gly Val Thr Glu Leu Ala Leu Arg Asp Ala
1               5                   10                  15

His Gln Ser Leu Met Ala Thr Arg Met Ala Leu Glu Asp Met Val Asp
            20                  25                  30

Ala Cys Glu Asp Ile Asp Lys Ala Gly Tyr Trp Ser Val Glu Cys Trp
        35                  40                  45

Gly Gly Ala Thr Phe Asp Ala Cys Ile Arg Phe Leu Asn Glu Asp Pro
    50                  55                  60

Trp Glu Arg Leu Arg Thr Phe Arg Lys Leu Met Pro Asn Ser Arg Leu
65                  70                  75                  80

Gln Met Leu Leu Arg Gly Gln Asn Leu Leu Gly Tyr Arg His Tyr Glu
                85                  90                  95

Asp Gly Val Val Asp Lys Phe Val Glu Lys Ser Ala Glu Asn Gly Met
            100                 105                 110

Asp Val Phe Arg Val Phe Asp Ala Leu Asn Asp Pro Arg Asn Leu Glu
        115                 120                 125

His Ala Met Gln Ala Val Lys Lys Val Gly Lys His Ala Gln Gly Thr
    130                 135                 140

Ile Cys Tyr Thr Val Ser Pro Leu His Asp Val Gln Gly Tyr Ile Asp
145                 150                 155                 160

Leu Ala Gly Arg Leu Leu Asp Met Gly Ala Asp Ser Ile Ala Leu Lys
                165                 170                 175

Asp Met Ala Ala Leu Leu Lys Pro Gln Pro Ala Tyr Asp Ile Ile Arg
            180                 185                 190

Gly Ile Lys Asp Thr Tyr Gly Glu Asp Thr Gln Ile Asn Val His Cys
        195                 200                 205

His Ser Thr Thr Gly Val Thr Met Val Thr Leu Met Lys Ala Ile Glu
    210                 215                 220

Ala Gly Ala Asp Val Val Asp Thr Ala Ile Ser Ser Met Ser Leu Gly
225                 230                 235                 240

Pro Gly His Asn Pro Thr Glu Ser Leu Val Glu Met Leu Glu Gly Thr
                245                 250                 255

Asp Tyr Glu Thr Gly Leu Asp Met Asp Arg Leu Ile Asn Ile Arg Asp
```

```
            260                 265                 270

His Phe Lys Thr Val Arg Pro Lys Tyr Ala Glu Phe Glu Ser Lys Thr
        275                 280                 285

Leu Val Asn Thr Asn Ile Phe Gln Ser Gln Ile Pro Gly Gly Met Leu
    290                 295                 300

Ser Asn Met Glu Ser Gln Leu Lys Ala Gln Gly Ala Gly Asp Arg Ile
305                 310                 315                 320

Asp Glu Val Met Lys Glu Val Pro Val Val Arg Lys Ala Ala Gly Tyr
                325                 330                 335

Pro Pro Leu Val Thr Pro Ser Ser Gln Ile Val Gly Thr Gln Ala Val
            340                 345                 350

Phe Asn Val Leu Met Gly Arg Tyr Lys Val Leu Thr Ala Glu Phe Ala
        355                 360                 365

Asp Leu Leu Leu Gly Tyr Tyr Gly Glu Ala Pro Gly Glu Arg Asp Lys
    370                 375                 380

Asp Leu Ile Glu Gln Ala Lys Lys Gln Thr Gly Lys Glu Pro Ile Thr
385                 390                 395                 400

Glu Arg Pro Ala Asp Leu Leu Glu Pro Glu Trp Asp Asn Leu Val Glu
                405                 410                 415

Glu Ala Asp Glu Leu Asp Gly Thr Asp Gly Ser Asp Glu Asp Val Leu
            420                 425                 430

Thr Asn Ala Leu Phe Pro Gln Val Ala Pro Gly Phe Phe Lys Thr Arg
        435                 440                 445

Pro Asp Gly Pro Lys Asn Val Gly Lys Thr Lys Glu Gln Leu Glu Arg
    450                 455                 460

Glu Glu Ala Lys Ala Ser Gly Asp Ala Thr Ala Ile Arg Glu Pro Ile
465                 470                 475                 480

Met Tyr Lys Val Thr Thr Gly Gly Arg Ser His Thr Val Ser Val Glu
                485                 490                 495

Pro Ala
```

<210> SEQ ID NO 56
<211> LENGTH: 285
<212> TYPE: DNA
<213> ORGANISM: C. kroppenstedtii

<400> SEQUENCE: 56

```
atgaatacag acaatgcatc ctctgctgaa ctcagtcagt tgttggcccg cctgtccaac      60
caggtagaaa agctctcccg caacgtcacc aagctcgaaa atgaagttgc ggcactgaag     120
cagcgctctg acgaggaaat tcctgaagat gtcttgattg cgatcagtgc ggccgtatcc     180
gcctacatgg gtaaccgcgg aaccgtgcgc gcagttcact tcttgcgcca tcgcagctgg     240
tcacagcaag gtcggcaggc agttcagcac aaggcgaaat ggcaa                     285
```

<210> SEQ ID NO 57
<211> LENGTH: 95
<212> TYPE: PRT
<213> ORGANISM: C. kroppenstedtii

<400> SEQUENCE: 57

```
Met Asn Thr Asp Asn Ala Ser Ser Ala Glu Leu Ser Gln Leu Leu Ala
1               5                   10                  15

Arg Leu Ser Asn Gln Val Glu Lys Leu Ser Arg Asn Val Thr Lys Leu
            20                  25                  30

Glu Asn Glu Val Ala Ala Leu Lys Gln Arg Ser Asp Glu Glu Ile Pro
```

```
                35                  40                  45
Glu Asp Val Leu Ile Ala Ile Ser Ala Ala Val Ser Ala Tyr Met Gly
            50                  55                  60

Asn Arg Gly Thr Val Arg Ala Val His Phe Leu Arg His Arg Ser Trp
65                  70                  75                  80

Ser Gln Gln Gly Arg Gln Ala Val Gln His Lys Ala Lys Trp Gln
                85                  90                  95

<210> SEQ ID NO 58
<211> LENGTH: 1542
<212> TYPE: DNA
<213> ORGANISM: G. bemidjiensis

<400> SEQUENCE: 58
atgtccatag aagagaagat aaaagcgctg aacgacaaga gagcaagct gaagctgggc      60
ggcgggcgct cgaagatcga ccagcagcac gcccagggaa gcctgaccgc ccgggagcgg    120
atagaggcgc tggtggacaa ggacagcttc aggaaatcg gcatcttcgc caggcaccgc    180
tgcaccaatt tcggcatggc cgggaaggaa ctgccggccg aaggggtggt caccggcgca    240
gggagcgtgg gcgggaggat ggtgcacctg gcgagccagg atttcaccgt cgccggggga    300
tcggcgggcg aggtgcacag cgacaagatc gtgcaggcga tgctggggtc gctgaagacc    360
ggaacccct tcgtcttcat gaacgattcc ggcggcgcca ggatccagga agggatcgac    420
tcgttagccg gctacggcaa ggtcttctac cacaacgtga tgctcagcgg ggtggtgccg    480
cagatctcgc tcatctgcgg ccctgtgcc ggggcgcgg cctacagccc ggcgctcacc    540
gatttcatca tccagaccgc caaggcgcgc atgttcatca ccggcccttc cgtgatcaag    600
gaggcgaccg cgaagagat cagcgccgag gagctgggag gccactgtc gcagatgaac    660
catagcggcg tagcccattt cgtggcggag aacgacctgg tggcgcttcg catctgcaag    720
aagctccttt cctacctccc ctccaacaac atcgaggacc cgccgcagtt ggaaagcgac    780
gacgtcatcg tcccggacaa gacgttgaac agcatcgtgc cgtcggagca aagaaggcc    840
tacgacgtga ggaacgtgat cacgcgcctg atcgacggcg cgacttcct ggaggtgcag    900
cctctgttcg ctgccaacat cgtggtcggg ttcgcagga tactcgggcg agcgtcggc    960
atcgtcgcca atcagccgtc ggtcttggcg ggggcgctgg acatcaacgc ttcggacaag   1020
ggagccaggt tcgtccggtt ctgcaacgcc ttcaacatcc cgctggtgac cctggtggac   1080
gttccgggtt ttctccccgg ggtacagcag gagaagggg ggatcatccg ccacggcgcc   1140
aagatgctct cgcctacgc cgcggccacc gtcccgaaga taaccgtcat catgcgcaag   1200
gcgtacggcg gcgccttcct cgccatgtgc ggcaaggagt tggagaccga tcgggttttc   1260
gcctggccca gcgccgagat cgcggtcatg gaccgcagg gagcggtcaa cgtcatcttc   1320
cggaacgaga tcgcccaggc ggaagatccc aagaaaaagc gcgacgagct gatcgcttct   1380
taccagggaa ccttcgccac tcctatgcg ccgcggcac gccgcgatgt ggacgacatc   1440
atcgagcccg ccgatacgag gcgccacctc gccatgacgc tggacatcct gagcaccaag   1500
cgcgaattca ggcccatgaa gaagcatggc ctcattccgc tg                      1542

<210> SEQ ID NO 59
<211> LENGTH: 514
<212> TYPE: PRT
<213> ORGANISM: G. bemidjiensis

<400> SEQUENCE: 59
```

```
Met Ser Ile Glu Glu Lys Ile Lys Ala Leu Asn Asp Lys Lys Ser Lys
1               5                   10                  15

Leu Lys Leu Gly Gly Arg Ser Lys Ile Asp Gln Gln His Ala Gln
        20                  25                  30

Gly Ser Leu Thr Ala Arg Glu Arg Ile Glu Ala Leu Val Asp Lys Asp
        35                  40                  45

Ser Phe Gln Glu Ile Gly Ile Phe Ala Arg His Arg Cys Thr Asn Phe
    50                  55                  60

Gly Met Ala Gly Lys Glu Leu Pro Ala Glu Gly Val Val Thr Gly Ala
65                  70                  75                  80

Gly Ser Val Gly Gly Arg Met Val His Leu Ala Ser Gln Asp Phe Thr
                85                  90                  95

Val Ala Gly Gly Ser Ala Gly Glu Val His Ser Asp Lys Ile Val Gln
            100                 105                 110

Ala Met Leu Gly Ser Leu Lys Thr Gly Thr Pro Phe Val Phe Met Asn
        115                 120                 125

Asp Ser Gly Gly Ala Arg Ile Gln Glu Gly Ile Asp Ser Leu Ala Gly
        130                 135                 140

Tyr Gly Lys Val Phe Tyr His Asn Val Met Leu Ser Gly Val Val Pro
145                 150                 155                 160

Gln Ile Ser Leu Ile Cys Gly Pro Cys Ala Gly Gly Ala Ala Tyr Ser
                165                 170                 175

Pro Ala Leu Thr Asp Phe Ile Ile Gln Thr Ala Lys Ala Arg Met Phe
        180                 185                 190

Ile Thr Gly Pro Ser Val Ile Lys Glu Ala Thr Gly Glu Glu Ile Ser
        195                 200                 205

Ala Glu Glu Leu Gly Gly Pro Leu Ser Gln Met Asn His Ser Gly Val
    210                 215                 220

Ala His Phe Val Ala Glu Asn Asp Leu Val Ala Leu Arg Ile Cys Lys
225                 230                 235                 240

Lys Leu Leu Ser Tyr Leu Pro Ser Asn Asn Ile Glu Asp Pro Pro Gln
                245                 250                 255

Leu Glu Ser Asp Asp Val Ile Val Pro Asp Lys Thr Leu Asn Ser Ile
        260                 265                 270

Val Pro Ser Glu Gln Lys Lys Ala Tyr Asp Val Arg Asn Val Ile Thr
    275                 280                 285

Arg Leu Ile Asp Gly Gly Asp Phe Leu Glu Val Gln Pro Leu Phe Ala
        290                 295                 300

Ala Asn Ile Val Val Gly Phe Gly Arg Ile Leu Gly Arg Ser Val Gly
305                 310                 315                 320

Ile Val Ala Asn Gln Pro Ser Val Leu Ala Gly Ala Leu Asp Ile Asn
            325                 330                 335

Ala Ser Asp Lys Gly Ala Arg Phe Val Arg Phe Cys Asn Ala Phe Asn
        340                 345                 350

Ile Pro Leu Val Thr Leu Val Asp Val Pro Gly Phe Leu Pro Gly Val
        355                 360                 365

Gln Gln Glu Lys Gly Gly Ile Ile Arg His Gly Ala Lys Met Leu Phe
    370                 375                 380

Ala Tyr Ala Ala Ala Thr Val Pro Lys Ile Thr Val Ile Met Arg Lys
385                 390                 395                 400

Ala Tyr Gly Gly Ala Phe Leu Ala Met Cys Gly Lys Glu Leu Glu Thr
                405                 410                 415

Asp Arg Val Phe Ala Trp Pro Ser Ala Glu Ile Ala Val Met Gly Pro
```

```
                420             425             430
Gln Gly Ala Val Asn Val Ile Phe Arg Asn Glu Ile Ala Gln Ala Glu
        435                 440                 445

Asp Pro Lys Lys Arg Asp Glu Leu Ile Ala Ser Tyr Gln Gly Thr
    450                 455                 460

Phe Ala Thr Pro Tyr Ala Ala Ala Arg Arg Asp Val Asp Ile
465             470                 475                 480

Ile Glu Pro Ala Asp Thr Arg Arg His Leu Ala Met Thr Leu Asp Ile
                485                 490                 495

Leu Ser Thr Lys Arg Glu Phe Arg Pro Met Lys Lys His Gly Leu Ile
            500                 505                 510

Pro Leu

<210> SEQ ID NO 60
<211> LENGTH: 393
<212> TYPE: DNA
<213> ORGANISM: G. bemidjiensis

<400> SEQUENCE: 60
gtgcaactga ccatgaccat tgacggaaag aaataccggg tggacgtaga agtcgaggaa       60
ggggaagagg tgcgtacgga aggggccttc cctcccaccg cgactatgca ggcgtacccg      120
gtgtattcgg cgcatccaac cgcgaccccg ccgctggccg cgccgacccc ggcctccagt      180
tcggaaaaga tctgccgcag tcccatcgcg ggggtggttt tcaagatcgt ggcgcaggtg      240
ggtcaacacc tggagatgaa cgacctgctg gtcgtcctcg aggcgatgaa gatggagacc      300
aacatcaccg cgcacatgtc cgggaaggtg aaaaagattc tggtttccgt gggcgaagcg      360
gtgcagcctg gacaggcaat tgccgaattt gcc                                   393

<210> SEQ ID NO 61
<211> LENGTH: 131
<212> TYPE: PRT
<213> ORGANISM: G. bemidjiensis

<400> SEQUENCE: 61

Val Gln Leu Thr Met Thr Ile Asp Gly Lys Lys Tyr Arg Val Asp Val
1               5                   10                  15

Glu Val Glu Glu Gly Glu Val Arg Thr Glu Gly Ala Phe Pro Pro
            20                  25                  30

Thr Ala Thr Met Gln Ala Tyr Pro Val Tyr Ser Ala His Pro Thr Ala
        35                  40                  45

Thr Pro Pro Leu Ala Ala Pro Thr Pro Ala Ser Ser Glu Lys Ile
    50                  55                  60

Cys Arg Ser Pro Ile Ala Gly Val Val Phe Lys Ile Val Ala Gln Val
65                  70                  75                  80

Gly Gln His Leu Glu Met Asn Asp Leu Leu Val Val Leu Glu Ala Met
                85                  90                  95

Lys Met Glu Thr Asn Ile Thr Ala His Met Ser Gly Lys Val Glu Lys
            100                 105                 110

Ile Leu Val Ser Val Gly Glu Ala Val Gln Pro Gly Gln Ala Ile Ala
        115                 120                 125

Glu Phe Ala
    130

<210> SEQ ID NO 62
<211> LENGTH: 1504
```

```
<212> TYPE: DNA
<213> ORGANISM: G. bemidjiensis

<400> SEQUENCE: 62
atggaccgca ttatcgacat aaccgaactg gctctgcgcg acgcgcacca gagccttatc    60
gctacgaggc tcgggataga cgacatggtt ccggtgtgcg aggacctgga ccaggcgggc   120
tactggtcca tcgagtgctg gggcggggcc acctatgacg cctgcatccg ctttctcaac   180
gaagatccgt gggtgaggct taggaccttc aaggagctga tgccgaaaac cccgctgcag   240
atgcttttgc gggggcagaa ccttttggga taccggcatt accaggacga ggtggtggac   300
cggttcgtcc agaagagcgc cgagaacggc atcgacgtgt ccggatcttc gatgcgctg    360
aacgatctga ggaacctgga gcggtcggtc caggcggtga agcagtgcgg aaagcacgcg   420
caggtcgcca tctcctatac catcagcccc attcacacca cggcgaaatt cgtggagcag   480
gcgaagcgcc tggtcgacat ggggtgcgac tccatctgca tcaaggacat ggcggcgctg   540
atcaagccgc acgcgacata cgacctggtg agagggatca agaggcctg cggcgaccgg   600
atccggatac agctgcatgc gcacgccacc agcggcgtga ccatggtgag ttacatgaag   660
gcggtggagg cgggcgtgga cggcgtggac acggcggtga gttccatgag cctcgggccc   720
ggacacaacc cgacggagag cttttgcggag atgctggaaa atacgggcta caccacgcgc   780
atcgacctcg gccgggtgaa caaggtgaag gagcatttcg ccaaggtgct ccccaggtac   840
tcagaattcc tctccaccat caccggcgcg gagacggaga tcttcaggag ccagattcca   900
ggcgggatgc tttccaacat ggagagccag ttgaagcagc aggggctgg ggaccggatg    960
cgcgacgtgc tggaagagat accgctggtg agaaaggaca cgggatacgt cccgctggta  1020
accccgacca gccagatcgt cgggacccag gcggtgctga acgtattgat ggggcgctac  1080
aaggtgctga ccggcgagtt cgccgacctg atgctcggct actacggcct cacgccggga  1140
gaacggaacc cggaggtggt ggagcaggcg cgccgccacg cgaataagga gccgatagag  1200
tgccgccccg cagatctatt ggagccggaa tggggcaagc tgcgggcggc ggcgctcccc  1260
ttggagggtt cgacggcag cgacgaggac gtgctcacct acgccctctt tccgcaggtg  1320
gcgccgaagt tcttcgccac gaggagtgaa ggaccccgaa acctggggcg cgatcccgtc  1380
accggagctt cggaaaccag cattcccgaa gggcaccccg ggaagatcac cggccccgtc  1440
acctacacgg tcaccttgag cgggcagccg cacaaggtga cggttgcacc ctacggccag  1500
gaat                                                                1504

<210> SEQ ID NO 63
<211> LENGTH: 501
<212> TYPE: PRT
<213> ORGANISM: G. bemidjiensis

<400> SEQUENCE: 63

Met Asp Arg Ile Ile Asp Ile Thr Glu Leu Ala Leu Arg Asp Ala His
1               5                   10                  15

Gln Ser Leu Ile Ala Thr Arg Leu Gly Ile Asp Asp Met Val Pro Val
            20                  25                  30

Cys Glu Asp Leu Asp Gln Ala Gly Tyr Trp Ser Ile Glu Cys Trp Gly
        35                  40                  45

Gly Ala Thr Tyr Asp Ala Cys Ile Arg Phe Leu Asn Glu Asp Pro Trp
    50                  55                  60

Val Arg Leu Arg Thr Phe Lys Glu Leu Met Pro Lys Thr Pro Leu Gln
65                  70                  75                  80
```

```
Met Leu Leu Arg Gly Gln Asn Leu Leu Gly Tyr Arg His Tyr Gln Asp
             85                  90                  95

Glu Val Val Asp Arg Phe Val Gln Lys Ser Ala Glu Asn Gly Ile Asp
                100                 105                 110

Val Phe Arg Ile Phe Asp Ala Leu Asn Asp Leu Arg Asn Leu Glu Arg
            115                 120                 125

Ser Val Gln Ala Val Lys Gln Cys Gly Lys His Ala Gln Val Ala Ile
130                 135                 140

Ser Tyr Thr Ile Ser Pro Ile His Thr Thr Ala Lys Phe Val Glu Gln
145                 150                 155                 160

Ala Lys Arg Leu Val Asp Met Gly Cys Asp Ser Ile Cys Ile Lys Asp
                165                 170                 175

Met Ala Ala Leu Ile Lys Pro His Ala Thr Tyr Asp Leu Val Arg Gly
                180                 185                 190

Ile Lys Glu Ala Cys Gly Asp Arg Ile Arg Ile Gln Leu His Ala His
            195                 200                 205

Ala Thr Ser Gly Val Thr Met Val Ser Tyr Met Lys Ala Val Glu Ala
210                 215                 220

Gly Val Asp Gly Val Asp Thr Ala Val Ser Ser Met Ser Leu Gly Pro
225                 230                 235                 240

Gly His Asn Pro Thr Glu Ser Phe Ala Glu Met Leu Glu Asn Thr Gly
                245                 250                 255

Tyr Thr Thr Arg Ile Asp Leu Gly Arg Val Asn Lys Val Lys Glu His
                260                 265                 270

Phe Ala Lys Val Leu Pro Arg Tyr Ser Glu Phe Leu Ser Thr Ile Thr
            275                 280                 285

Gly Ala Glu Thr Glu Ile Phe Arg Ser Gln Ile Pro Gly Gly Met Leu
290                 295                 300

Ser Asn Met Glu Ser Gln Leu Lys Gln Gln Gly Ala Gly Asp Arg Met
305                 310                 315                 320

Arg Asp Val Leu Glu Glu Ile Pro Leu Val Arg Lys Asp Thr Gly Tyr
                325                 330                 335

Val Pro Leu Val Thr Pro Thr Ser Gln Ile Val Gly Thr Gln Ala Val
                340                 345                 350

Leu Asn Val Leu Met Gly Arg Tyr Lys Val Leu Thr Gly Glu Phe Ala
            355                 360                 365

Asp Leu Met Leu Gly Tyr Tyr Gly Leu Thr Pro Gly Glu Arg Asn Pro
370                 375                 380

Glu Val Val Glu Gln Ala Arg Arg His Ala Asn Lys Glu Pro Ile Glu
385                 390                 395                 400

Cys Arg Pro Ala Asp Leu Leu Glu Pro Glu Trp Gly Lys Leu Arg Ala
                405                 410                 415

Ala Ala Leu Pro Leu Glu Gly Cys Asp Gly Ser Asp Glu Asp Val Leu
                420                 425                 430

Thr Tyr Ala Leu Phe Pro Gln Val Ala Pro Lys Phe Phe Ala Thr Arg
            435                 440                 445

Ser Glu Gly Pro Arg Asn Leu Gly Arg Asp Pro Val Thr Gly Ala Ser
450                 455                 460

Glu Thr Ser Ile Pro Glu Gly His Pro Gly Lys Ile Thr Gly Pro Val
465                 470                 475                 480

Thr Tyr Thr Val Thr Leu Ser Gly Gln Pro His Lys Val Thr Val Ala
                485                 490                 495
```

Pro Tyr Gly Gln Glu
        500

<210> SEQ ID NO 64
<211> LENGTH: 195
<212> TYPE: DNA
<213> ORGANISM: G. bemidjiensis

<400> SEQUENCE: 64

```
gtggacgaag agatggagca ggaacacgat ccggaaatca cgcccgaact gctgatggtg    60
atgtccgccg cgatagccgc gtatctgggc aagaccgtga ggataaggcg ggccaggttc   120
gtcgacccga atctgatcaa cgcctgggga cagtcgagcc gcgtggtgct gcaggcgtcg   180
cacaacttga ggaga                                                    195
```

<210> SEQ ID NO 65
<211> LENGTH: 65
<212> TYPE: PRT
<213> ORGANISM: G. bemidjiensis

<400> SEQUENCE: 65

Val Asp Glu Glu Met Glu Gln Glu His Asp Pro Glu Ile Thr Pro Glu
1               5                   10                  15

Leu Leu Met Val Met Ser Ala Ala Ile Ala Ala Tyr Leu Gly Lys Thr
            20                  25                  30

Val Arg Ile Arg Arg Ala Arg Phe Val Asp Pro Asn Leu Ile Asn Ala
        35                  40                  45

Trp Gly Gln Ser Ser Arg Val Val Leu Gln Ala Ser His Asn Leu Arg
    50                  55                  60

Arg
65

<210> SEQ ID NO 66
<211> LENGTH: 1548
<212> TYPE: DNA
<213> ORGANISM: D. propionicus

<400> SEQUENCE: 66

```
atgagcacaa aggaaaaatt agagcagcta agcaaaaaa gggccaaagc cttgctgggc     60
ggcggtcagg ataaaatcga caagatccac tcccagggca atataccgc cgtgagcgt    120
attcaactcc tcctcgaccc aggcaccttc gaggaatacg atgctttcaa gctccatcgc   180
tgctacaact tcggcatgga aaaaatcaag ttttcggcg acggtatcgt caccggatat   240
ggcaagctgg ccggccggcc ggtttatatt tacgcgcagg actttcggt cctcgccggt   300
tctctttccg gaaccttggc tgaaaaaata tgcaaaatca tggatctggg catgaaaaac   360
ggcattccgg tcatcggatt gaacgactcc ggtggcgccc gtatccagga aggtatcgag   420
gccctggcag atataccga atcttcacc cgtaatgttc tcgcttcggg tgttgttccc   480
cagatttccg gtgttttcgg accctgcgcc ggtggcgccc tttactctcc tgccctgacc   540
gacttcatca tccaggtcaa gatccagtcc tacatgttcc tgacaggtcc caaggtcgtt   600
aagactgtgt taaacgagga cgtcaccacc gagcagttgg tggtgcggc catgcatacc   660
accaagtccg gcgtcaccga ctatgctgcc gagaacgagg acgacgccat tcagtacatc   720
aaggatctga tgagctattt gccgcagaac aatctggaga tcctccgga tgcccctgc   780
gacgatccga tcaccgccg ctccgaactg ctcaacgaca tcattccgga caacccgaat   840
gccgcctacg acatgaaaaa ggtcatcacc gagacggcag acaacggtat cttctttgaa   900
```

-continued

```
atcaagaaga atttcgctcc gaacatcgtc atcggttttg cccgttatgg tggcaaggct    960
attggcatcg ttgccaacca gccgtcctac tacgccggtg ttctcgacat cgattcctcg   1020
atcaaaggtg cccgcttcat ccgcttctgc gactgcttca acattccgat ccttaccttc   1080
gtcgacgtcc ctggcttcct gcccggcact gcacaggaat cggcggcgt tatccgcaac    1140
ggcgccaaga tgctgtatgc ctacgccgaa tcgacagtgc caaaggtaac gattattacc   1200
cgtaaatcct atggcggcgc ctactgcgct atgtcgtcca agcacctgcg aaccgatatc   1260
aactactcct ggccgaccgg tgaaatcgcc gttatgggct ccaaaggcgc ggtcgaagtc   1320
ctgcacgcca agggcgctaa agcagcagaa gatcccagag cgttcctggc cgaaaaagaa   1380
aacgagtaca acgagcagtt ctccaatcca tattgtgcgg ccgagcgtgg ctatatcgac   1440
gatgtcattg aaccggccga aaccaggtac cgtatcatca acgcgtttga gtcgatctct   1500
ggaaagcgtg acacgatccc gatgaagaaa cacggcaata tcccgctg              1548
```

<210> SEQ ID NO 67
<211> LENGTH: 516
<212> TYPE: PRT
<213> ORGANISM: D. propionicus

<400> SEQUENCE: 67

```
Met Ser Thr Lys Glu Lys Leu Glu Gln Leu Lys Gln Lys Arg Ala Lys
1               5                   10                  15

Ala Leu Leu Gly Gly Gly Gln Asp Lys Ile Asp Lys Ile His Ser Gln
            20                  25                  30

Gly Lys Tyr Thr Ala Arg Glu Arg Ile Gln Leu Leu Asp Pro Gly
        35                  40                  45

Thr Phe Glu Glu Tyr Asp Ala Phe Lys Leu His Arg Cys Tyr Asn Phe
    50                  55                  60

Gly Met Glu Lys Ile Lys Phe Phe Gly Asp Gly Ile Val Thr Gly Tyr
65                  70                  75                  80

Gly Lys Leu Ala Gly Arg Pro Val Tyr Ile Tyr Ala Gln Asp Phe Ser
                85                  90                  95

Val Leu Ala Gly Ser Leu Ser Gly Thr Leu Ala Glu Lys Ile Cys Lys
            100                 105                 110

Ile Met Asp Leu Gly Met Lys Asn Gly Ile Pro Val Ile Gly Leu Asn
        115                 120                 125

Asp Ser Gly Gly Ala Arg Ile Gln Glu Gly Ile Glu Ala Leu Ala Gly
    130                 135                 140

Tyr Thr Glu Ile Phe Thr Arg Asn Val Leu Ala Ser Gly Val Val Pro
145                 150                 155                 160

Gln Ile Ser Gly Val Phe Gly Pro Cys Ala Gly Gly Ala Val Tyr Ser
                165                 170                 175

Pro Ala Leu Thr Asp Phe Ile Ile Gln Val Lys Ile Gln Ser Tyr Met
            180                 185                 190

Phe Leu Thr Gly Pro Lys Val Val Lys Thr Val Leu Asn Glu Asp Val
        195                 200                 205

Thr Thr Glu Gln Leu Gly Gly Ala Ala Met His Thr Thr Lys Ser Gly
    210                 215                 220

Val Thr Asp Tyr Ala Ala Glu Asn Glu Asp Ala Ile Gln Tyr Ile
225                 230                 235                 240

Lys Asp Leu Met Ser Tyr Leu Pro Gln Asn Asn Leu Glu Asn Pro Pro
                245                 250                 255
```

```
Asp Ala Pro Cys Asp Asp Pro Ile Thr Arg Arg Ser Glu Leu Leu Asn
                260                 265                 270

Asp Ile Ile Pro Asp Asn Pro Asn Ala Ala Tyr Asp Met Lys Lys Val
            275                 280                 285

Ile Thr Glu Thr Ala Asp Asn Gly Ile Phe Phe Glu Ile Lys Lys Asn
        290                 295                 300

Phe Ala Pro Asn Ile Val Ile Gly Phe Ala Arg Tyr Gly Gly Lys Ala
305                 310                 315                 320

Ile Gly Ile Val Ala Asn Gln Pro Ser Tyr Tyr Ala Gly Val Leu Asp
                325                 330                 335

Ile Asp Ser Ser Ile Lys Gly Ala Arg Phe Ile Arg Phe Cys Asp Cys
            340                 345                 350

Phe Asn Ile Pro Ile Leu Thr Phe Val Asp Val Pro Gly Phe Leu Pro
        355                 360                 365

Gly Thr Ala Gln Glu Phe Gly Gly Val Ile Arg Asn Gly Ala Lys Met
370                 375                 380

Leu Tyr Ala Tyr Ala Glu Ser Thr Val Pro Lys Val Thr Ile Ile Thr
385                 390                 395                 400

Arg Lys Ser Tyr Gly Gly Ala Tyr Cys Ala Met Ser Ser Lys His Leu
                405                 410                 415

Arg Thr Asp Ile Asn Tyr Ser Trp Pro Thr Gly Glu Ile Ala Val Met
            420                 425                 430

Gly Ser Lys Gly Ala Val Glu Val Leu His Ala Lys Gly Ala Lys Ala
        435                 440                 445

Ala Glu Asp Pro Arg Ala Phe Leu Ala Glu Lys Glu Asn Glu Tyr Asn
450                 455                 460

Glu Gln Phe Ser Asn Pro Tyr Cys Ala Ala Glu Arg Gly Tyr Ile Asp
465                 470                 475                 480

Asp Val Ile Glu Pro Ala Glu Thr Arg Tyr Arg Ile Ile Asn Ala Phe
                485                 490                 495

Glu Ser Ile Ser Gly Lys Arg Asp Thr Ile Pro Met Lys Lys His Gly
            500                 505                 510

Asn Ile Pro Leu
        515

<210> SEQ ID NO 68
<211> LENGTH: 195
<212> TYPE: DNA
<213> ORGANISM: D. propionicus

<400> SEQUENCE: 68
atggcaaaaa tgaacaaaaa aatggctgcg gcccttgcag ccgttaatgc ctacctgatg      60
caggaagagg aggcggcata ccaggcccag ttgctggctg ccaaatctgt tgcaccagcc     120
gggccaagct tatgggcaat tgccggccgt caggatatca tgaatttccg caggctgatt     180
caaatgaaag ccttc                                                      195

<210> SEQ ID NO 69
<211> LENGTH: 65
<212> TYPE: PRT
<213> ORGANISM: D. propionicus

<400> SEQUENCE: 69

Met Ala Lys Met Asn Lys Lys Met Ala Ala Ala Leu Ala Ala Val Asn
1               5                   10                  15

Ala Tyr Leu Met Gln Glu Glu Glu Ala Ala Tyr Gln Ala Gln Leu Leu
```

```
                    20                  25                  30
Ala Ala Lys Ser Val Ala Pro Ala Gly Pro Ser Leu Trp Ala Ile Ala
         35                  40                  45

Gly Arg Gln Asp Ile Met Asn Phe Arg Arg Leu Ile Gln Met Lys Ala
     50                  55                  60

Phe
65

<210> SEQ ID NO 70
<211> LENGTH: 1989
<212> TYPE: DNA
<213> ORGANISM: D. propionicus

<400> SEQUENCE: 70
```

| | | | | | |
|---|---|---|---|---|---|
| atgagcgacc | aagtgaaaat | gaccgccatg | aattatgcaa | ctgaccggcc | tgctgcagaa | 60 |
| aatccggtca | aagttatgga | cttgagcctt | cgtgacggcc | accagtctct | gttcgccacc | 120 |
| cgcgggcgca | ccgaggacat | gattccgatc | gcggaaatga | tggacgagat | cggcttctgg | 180 |
| gcagttgaga | cctggggtgg | cgccaccttt | gacaccatgc | accgcttcct | caacgaggac | 240 |
| ccgtgggagc | gtctccgcac | cctgaaacgt | tacatcaaga | gaccccctt | ctccatgttg | 300 |
| ctgcgcgcgc | agaacctggt | tggataccgt | aactatgccg | atgacttggc | caccgccttt | 360 |
| gttgagcgcg | ctgccgagaa | cggtatggat | atcttccgga | cctttgacgc | cctcaacgat | 420 |
| taccgtaact | tcgagaccgt | tgttaaacag | atcaagaaga | gcggcaagca | cttccagggt | 480 |
| tgtatttgct | attcgctgac | cgaaccgcgt | ctgggcgggg | atgtttatga | cctgaagtac | 540 |
| tatgtcgacc | gcgccaaagc | gcttgacgac | atgggcgctg | actccatctg | catcaaggac | 600 |
| atggccggtc | tgatcgcccc | atacgacgcc | tacgccatcg | tcaaggctat | caaggaagtc | 660 |
| accaagaccc | cgatccacct | gcacagccac | ttcacctctg | gtatggcgtc | catgagtcat | 720 |
| ctgaaggcca | ttgaggctgg | cgtagatatc | gttgacacct | gcatgacccc | gtacgctttc | 780 |
| cgtaccgccc | atcggccat | cgagccgttg | gtcatggccc | tgctcggcac | caaccgcgac | 840 |
| accggtttcg | acatcaagaa | actggccgcc | atcaacgagg | tgctagagaa | agaggttatg | 900 |
| ccgaaataca | agcacctcat | ggatgactcc | aagtgctcaa | tcatcgatat | caacgttctt | 960 |
| ctccatcaga | ccccgggcgg | catgctctcc | aacctggtca | accagttgcg | tgagatggat | 1020 |
| gctctggaca | gatcgatca | ggtctacaaa | gagctgccga | agttcggaa | agacctcggc | 1080 |
| cagattccgc | tggttacccc | gaccagccag | atcgttggca | tccagaccgt | gaacaacgtg | 1140 |
| ctgtttgaca | ctcctgatga | gcgctacaag | atgatcaccg | cccaggtcaa | agacctgtgc | 1200 |
| tacggtctct | atggtaaaac | cgctgtgccg | atcaaccctg | aactgcagaa | gaaggctctg | 1260 |
| aaaggctatc | cgcgcggtga | agagccgatc | acctgccgtc | cggcagaggt | gcttgagccc | 1320 |
| gagttggaaa | aggccaagaa | agagattggc | gatctcgcca | aggatatcga | tgacttggta | 1380 |
| ctctacgcca | tctacccggt | caccgggaag | aagttccttg | agtggaagta | tggcattacc | 1440 |
| ccggcaccgc | ccgaagtcaa | gccgctcacc | cttgaggatg | tcaagaagcg | tgatgaactg | 1500 |
| gtggccaagg | ccaaggctgg | caagctcatc | gagcccaagc | ccgctgctcc | ggagaagacc | 1560 |
| gctaacgttc | ggaccttcaa | cgtcttcgtc | gacggtgagt | atttcaacgt | tgaggtcgac | 1620 |
| ccgaccggtg | acttccagcc | gatggtcgcc | gctgctccgc | ggcctgccgc | acctgccgct | 1680 |
| gcaccgaaag | ctgctgcacc | tgccgctgct | gcacctgctg | ccgcgccgaa | ggctgctgca | 1740 |
| cctgccgccg | ccgctccggc | tccagccgct | gttgagggag | gaacccgct | gttggccccc | 1800 |

```
atgcccggca tgatcgtcaa gaatctggtc aatgttggtg atgcggtcaa agctggcgac   1860
cccatcctcg ttcttgaggc catgaagatg gagaacaatc tcggttctcc gtgcgatggt   1920
actgtgaagg cgcttaattt tggcagcggt gactcggttg ccaaggatac cgtcctggca   1980
atcatcgga                                                            1989
```

<210> SEQ ID NO 71
<211> LENGTH: 663
<212> TYPE: PRT
<213> ORGANISM: D. propionicus

<400> SEQUENCE: 71

```
Met Ser Asp Gln Val Lys Met Thr Ala Met Asn Tyr Ala Thr Asp Arg
1               5                   10                  15

Pro Ala Ala Glu Asn Pro Val Lys Val Met Asp Leu Ser Leu Arg Asp
            20                  25                  30

Gly His Gln Ser Leu Phe Ala Thr Arg Gly Arg Thr Glu Asp Met Ile
        35                  40                  45

Pro Ile Ala Glu Met Met Asp Glu Ile Gly Phe Trp Ala Val Glu Thr
    50                  55                  60

Trp Gly Gly Ala Thr Phe Asp Thr Met His Arg Phe Leu Asn Glu Asp
65                  70                  75                  80

Pro Trp Glu Arg Leu Arg Thr Leu Lys Arg Tyr Ile Lys Lys Thr Pro
                85                  90                  95

Phe Ser Met Leu Leu Arg Ala Gln Asn Leu Val Gly Tyr Arg Asn Tyr
            100                 105                 110

Ala Asp Asp Leu Ala Thr Ala Phe Val Glu Arg Ala Ala Glu Asn Gly
        115                 120                 125

Met Asp Ile Phe Arg Thr Phe Asp Ala Leu Asn Asp Tyr Arg Asn Phe
    130                 135                 140

Glu Thr Val Val Lys Gln Ile Lys Lys Ser Gly Lys His Phe Gln Gly
145                 150                 155                 160

Cys Ile Cys Tyr Ser Leu Thr Glu Pro Arg Leu Gly Gly Asp Val Tyr
                165                 170                 175

Asp Leu Lys Tyr Tyr Val Asp Arg Ala Lys Ala Leu Asp Met Gly
            180                 185                 190

Ala Asp Ser Ile Cys Ile Lys Asp Met Ala Gly Leu Ile Ala Pro Tyr
        195                 200                 205

Asp Ala Tyr Ala Ile Val Lys Ala Ile Lys Glu Val Thr Lys Thr Pro
    210                 215                 220

Ile His Leu His Ser His Phe Thr Ser Gly Met Ala Ser Met Ser His
225                 230                 235                 240

Leu Lys Ala Ile Glu Ala Gly Val Asp Ile Val Asp Thr Cys Met Thr
                245                 250                 255

Pro Tyr Ala Phe Arg Thr Ala His Pro Ala Ile Glu Pro Leu Val Met
            260                 265                 270

Ala Leu Leu Gly Thr Asn Arg Asp Thr Gly Phe Asp Ile Lys Lys Leu
        275                 280                 285

Ala Ala Ile Asn Glu Val Leu Glu Lys Glu Val Met Pro Lys Tyr Lys
    290                 295                 300

His Leu Met Asp Asp Ser Lys Cys Ser Ile Ile Asp Ile Asn Val Leu
305                 310                 315                 320

Leu His Gln Thr Pro Gly Gly Met Leu Ser Asn Leu Val Asn Gln Leu
                325                 330                 335
```

```
Arg Glu Met Asp Ala Leu Asp Lys Ile Asp Gln Val Tyr Lys Glu Leu
                340                 345                 350
Pro Lys Val Arg Lys Asp Leu Gly Gln Ile Pro Leu Val Thr Pro Thr
            355                 360                 365
Ser Gln Ile Val Gly Ile Gln Thr Val Asn Asn Val Leu Phe Asp Thr
370                 375                 380
Pro Asp Glu Arg Tyr Lys Met Ile Thr Ala Gln Val Lys Asp Leu Cys
385                 390                 395                 400
Tyr Gly Leu Tyr Gly Lys Thr Ala Val Pro Ile Asn Pro Glu Leu Gln
                405                 410                 415
Lys Lys Ala Leu Lys Gly Tyr Pro Arg Gly Glu Pro Ile Thr Cys
            420                 425                 430
Arg Pro Ala Glu Val Leu Glu Pro Glu Leu Glu Lys Ala Lys Lys Glu
            435                 440                 445
Ile Gly Asp Leu Ala Lys Asp Ile Asp Asp Leu Val Leu Tyr Ala Ile
        450                 455                 460
Tyr Pro Val Thr Gly Lys Lys Phe Leu Glu Trp Lys Tyr Gly Ile Thr
465                 470                 475                 480
Pro Ala Pro Pro Glu Val Lys Pro Leu Thr Leu Glu Asp Val Lys Lys
                485                 490                 495
Arg Asp Glu Leu Val Ala Lys Ala Lys Ala Gly Lys Leu Ile Glu Pro
            500                 505                 510
Lys Pro Ala Ala Pro Glu Lys Thr Ala Asn Val Arg Thr Phe Asn Val
        515                 520                 525
Phe Val Asp Gly Glu Tyr Phe Asn Val Glu Val Asp Pro Thr Gly Asp
530                 535                 540
Phe Gln Pro Met Val Ala Ala Pro Arg Pro Ala Ala Pro Ala Ala
545                 550                 555                 560
Ala Pro Lys Ala Ala Pro Ala Ala Ala Pro Ala Ala Ala Pro
                565                 570                 575
Lys Ala Ala Ala Pro Ala Ala Ala Pro Ala Pro Ala Ala Val Glu
            580                 585                 590
Gly Gly Thr Pro Leu Leu Ala Pro Met Pro Gly Met Ile Val Lys Asn
        595                 600                 605
Leu Val Asn Val Gly Asp Ala Val Lys Ala Gly Asp Pro Ile Leu Val
610                 615                 620
Leu Glu Ala Met Lys Met Glu Asn Asn Leu Gly Ser Pro Cys Asp Gly
625                 630                 635                 640
Thr Val Lys Ala Leu Asn Phe Gly Ser Gly Asp Ser Val Ala Lys Asp
                645                 650                 655
Thr Val Leu Ala Ile Ile Gly
            660

<210> SEQ ID NO 72
<211> LENGTH: 933
<212> TYPE: DNA
<213> ORGANISM: T. saccharolyticum

<400> SEQUENCE: 72
atgagcaagg tagcaataat aggatctggt tttgtaggtg caacatcggc atttacgctg        60
gcattaagtg ggactgtgac agatatcgtg ctggtggatt taaacaagga caaggctata       120
ggcgatgcac tggacataag ccatggcata ccgctaatac agcctgtaaa tgtgtatgca       180
ggtgactaca aagatgtgaa aggcgcagat gtaatagttg tgacagcagg tgctgctcaa       240
```

| | |
|---|---|
| aagccgggag agacacggct tgaccttgta aagaaaaata cagccatatt taagtccatg | 300 |
| atacctgagc ttttaaagta caatgacaag gccatatatt tgattgtgac aaatcccgta | 360 |
| gatatactga cgtacgttac atacaagatt tctggacttc catggggcag agtttttggt | 420 |
| tctggcaccg ttcttgacag ctcaaggttt agatacctttt taagcaagca ctgcaatata | 480 |
| gatccgagaa atgtccacgg aaggataatc ggcgagcatg gtgacacaga gtttgcagca | 540 |
| tggagcataa caacatatc gggtatatca tttaatgagt actgcagcat atgcggacgc | 600 |
| gtctgcaaca caaatttcag aaaggaagta gaagaagaag tcgtaaatgc tgcttacaag | 660 |
| ataatagaca aaaaaggtgc tacatactat gctgtggcag ttgcagtaag aaggattgtg | 720 |
| gagtgcatct taagagatga aaattccatc ctcacagtat catctccatt aaatggacag | 780 |
| tacggcgtga agatgtttc attaagcttg ccatctatcg taggcaggaa tggcgttgcc | 840 |
| aggattttgg acttgccttt atctgacgaa gaagtggaga agtttaggca ttcagcaagt | 900 |
| gtcatggcag atgtcataaa acaattagat ata | 933 |

<210> SEQ ID NO 73
<211> LENGTH: 2577
<212> TYPE: DNA
<213> ORGANISM: T. saccharolyticum

<400> SEQUENCE: 73

| | |
|---|---|
| atggcaacga caaaaacgga attagacgtt cagaagcaga tagatctact tgtgtcaaga | 60 |
| gcacaagagg ctcagaaaaa attcatgtct tacacgcaag agcaaatcga cgcaatagtt | 120 |
| aaggcaatgg ctttagcagg cgttgacaaa cacgtagagc tggcaaagat ggcgtacgaa | 180 |
| gagacaaaaa tgggtgtata cgaagataag ataacaaaaa atctcttcgc aacagagtac | 240 |
| gtgtaccacg acataaaaaa tgaaaagact gtaggaatca taaacgagaa catagaagaa | 300 |
| aactacatgg aagtggcaga accgataggc gtaattgccg gtgtcacacc tgtcacaaac | 360 |
| ccaacatcta ccacgatgtt taaatgctta atatccataa agacgcgaaa tcctataata | 420 |
| ttcagcttcc atccaaaggc aataaagtgc agcatcgcag cagccaaagt gatgtatgaa | 480 |
| gctgcactaa aggcaggcgc acctgaagga tgcataggat ggatagaaac gccatcaatt | 540 |
| gaggccacac agcttctcat gacacatcca ggcgtatcgc tgatccttgc aacgggcggt | 600 |
| gcaggaatgg taaaagcggc atacagctca ggaaaaccgg cattaggcgt aggtcctggc | 660 |
| aatgtgccat gctacatcga aaaatcagca acataaaga gggctgtatc ggatctcata | 720 |
| ctaagcaaga catttgacaa tggagtaata tgcgcatcag gcaggccgt aataatagac | 780 |
| gaggaaatag cagatgaagt caaaaagctt atgaaagaat acggctgcta cttcttaaac | 840 |
| aaagatgaaa taagaagct tgagaaattt gcaattgatg agcaaagctg cgccatgagc | 900 |
| cctgcagtgg taggtcagcc agcggcgaag attgctgaaa tggcaggctt caaagtcccc | 960 |
| gaaggcacaa agatattagt ggcagagtac gaagggagtag gtccaaaata tcctctatca | 1020 |
| agggagaaac taagcccgat tcttgcttgc tacaccgtca aagactacaa tgaaggaatc | 1080 |
| aaaaagtgcg aggaaatgac tgaattcgga ggtttaggcc actctgctgt aatacactct | 1140 |
| gaaaatcaaa acgtcataaa tgaatttgca aggcgagtcc gcacaggaag acttatcgta | 1200 |
| aattcaccat catcacaggg agcaatagga gatatataca atacaaacac gccatcacttt | 1260 |
| acattaggct gtggttctat gggaagaaac tcaacgacag acaatgtaag cgtcaagaac | 1320 |
| cttttgaata ttaagcgtgt cgtgataagg aatgatagaa tgaaatggtt caagattcca | 1380 |
| ccgaagattt actttgaaag cgggtcactc cagtacctgt gcaaagtcaa aagaaaaaaa | 1440 |

```
gcgtttatcg tcacagatcc attcatggtt aagcttggct tcgtagacaa agtgacatat    1500
caattagaca aagcaaacat cgaatacgaa atattctcag aagtagagcc agatccatct    1560
gttgacacag tcatgaacgg cgtaaaaata atgaattcgt acaatcctga cttaataatc    1620
gctgtaggcg gtggctctgc aatagacgca gcaaagggaa tgtggctttt ctacgaatat    1680
cctgatacag agtttgaaac attgaggctt aaatttgcag acatcagaaa aagggcattt    1740
aagttcccag aacttggcaa aaaagcgcta ttcatcgcaa taccgacaac aagcggcaca    1800
ggctcagaag tgacagcatt tgccgtaata accgacaaaa agagaaacat caagtatcca    1860
ctggcagact acgaacttac acctgacata gccataatag atcctgacct tacaaagact    1920
gtaccgccat ctgtaacagc agacacaggc atggatgtgc tgacacacgc catagaagca    1980
tacgtatcag taatggcatc agactacaca gatgcactgg cggaaaaggc tataaagatc    2040
gtatttgaat acctgccaag ggcttataaa aacggcaatg atgaagaagc ccgcgaaaag    2100
atgcacaatg cttcctgcat ggctggtatg gcattcacaa atgcattctt aggaataaac    2160
cacagcatgg cacacatact gggcggaaag ttccacatac cacacggaag agcaaatgca    2220
atacttctgc cgtatgtaat aaggtacaat gcagaaaaac ctacaaagtt tgtggcattc    2280
ccacaatacg aatatccaaa agcagcagaa agatatgcgg aaatcgccaa attcttagga    2340
ctgcctgctt caactgttga agaaggcgta gaaagcttaa tagaagctat aaagaacctc    2400
atgaaagagc ttaacattcc gcttacactt aaagacgccg gcatcaacaa agaacagttt    2460
gaaaaagaaa tagaggaaat gtcagacatc gccttcaacg atcagtgcac agggacaaac    2520
ccgagaatgc ctctcacaaa agaaattgca gagatctaca gaaaagcata cggtgca      2577

<210> SEQ ID NO 74
<211> LENGTH: 1752
<212> TYPE: DNA
<213> ORGANISM: T. saccharolyticum

<400> SEQUENCE: 74
atgcgtagaa ctaagataat atgcacgatt ggtcctgcca gtgaaaaata tgagatattg      60
aaagagctta tagaaagcgg tcttaatatt tgcaggttga attttttcaca tggggatcat    120 gaagagcatg gaagcagaat agacaatatt ataaagatta gagaagaact taagctgcct    180
attgcaatta tgcttgatac aaaagggcct gaaataagga ctggcagatt taaaggcggt    240
gttgcagagc ttaaagaagg ccagacattt acgataacat caagggaaat tgaaggagat    300
aacactattt gttctgtttc atacaagggg cttcctcaag atgtggagag aggttctcgc    360
atattgattg atgacggatt agtatcattg aaagtcaatg acgtaaaagg tgaagatata    420
gtatgcactg tggagaattc tggtacaata ggtgatcaca aaggtgtaaa tgtacctggt    480
acaaagctta atttgcctgc cataacgcaa aaagacgtgg atgatataga gtttggaata    540
aaaaaaggaa tcgacatgat tgcagcgtct tttgtcagaa aagcagcaga tgtaattgcc    600
ataaggagat tgttagaaga caatgacgct ggccatatac ttatcatatc aaaaattgaa    660
aatcgcgaag gcgtagaaaa tattgacgaa ataatcaaag tctctgatgg cataatggta    720
gcccgcggcg atttgggtgt cgaaattcct atagaggaaa tacctatcgt tcagaaaagg    780
ataattgaaa atgcaacaa agcaggtaaa ccagtagtta ctgctacaca tgcttgac    840 tctatgataa gaaatccaag gccaacaagg gcagaagtaa cagatgtagc caatgctata    900
ttggatggca ctgatgcgat aatgttgtct ggtgaaacag cgcaaggcaa atatcctgta    960
```

| | |
|---|---|
| gaggctttta agacgatgtc aaagatagct gaaaagattg agacgtatat aaattacaaa | 1020 |
| gaaaatttag ataaaaatgt ggattacaat atttctatga caaatgccat aagccatgct | 1080 |
| acgtgcacta ccgcgagaga tataggcgca actgccatta ttacatctac aatatcaggt | 1140 |
| tatactgcga gaatggtgtc taagtataga ccgtcagcac ctataatagc agtgacgcca | 1200 |
| aacaaagatg ttgcaagaag gcttagcatc gtgtggggtg tacatccatt gatatcacag | 1260 |
| gaagtcaatt ctacagatga aatgataaa gtatcagtaa atacggcttt aaatgaagga | 1320 |
| ttaattcgaa atggcgatat tgtagtaata tcggcaggaa tacctgtcgc gactacaggc | 1380 |
| acaacaaata tgttgaaggt tcatattgtg ggagatgtaa tagtaaaagg cacaggcata | 1440 |
| ggcactaaat ccataagtgg tgttgtttcc atcataagag atccatacaa ggacaaagat | 1500 |
| aagttcagag aaggagatat catcgttgct caaaaaactg aaagggatta tatgcctata | 1560 |
| attgagaagg cttcagctat cataacagaa gaaggtggac taacgtccca tgctgcaata | 1620 |
| gttggattga actatggatt acctgtcatt gtaggctgtg aaggagtaac ttcaaagctt | 1680 |
| aaagatggaa tgacggtaac tctcgatact gccagaggat tggtctacaa aggtatagtg | 1740 |
| aatataaaat ag | 1752 |

<210> SEQ ID NO 75
<211> LENGTH: 2226
<212> TYPE: DNA
<213> ORGANISM: T. saccharolyticum

<400> SEQUENCE: 75

| | |
|---|---|
| atgatcaatg aatggcgcgg gtttcaggag ggcaaatggc aaaagactat tgacgttcaa | 60 |
| gattttatcc agaaaaatta cacattatac gaaggcgatg atagtttttt agaagggcct | 120 |
| acagaaaaga ctattaagct ttggaacaaa gttcttgagc taatgaagga agaactgaaa | 180 |
| aaaggtgtgt tagatattga tacaaaaact gtatcgtcta acatcccca tgatgcgggg | 240 |
| tatatagaca aagatcttga ggaaatagtt ggattgcaga cagacaaacc tcttaaaaga | 300 |
| gctataatgc cttacggtgg cataagaatg gtcaaaaaag cttgcgaagc ttatggatat | 360 |
| aaagtggacc caaaagtaga agagatattt acgaagtaca aaagaccca caatgatggt | 420 |
| gtatttgatg catatactcc agaaataaga gcagcaagac atgccggcat aataacaggt | 480 |
| cttccagatg catatggcag aggaagaatc ataggtgatt acagaagagt tgctcttat | 540 |
| ggaattgata gactcatcga agaaaggaa aaagaaaaac ttgagcttga ttacgatgaa | 600 |
| tttgatgaag caactattcg cttgagaaa gaattgacag aacagataaa agcattaaac | 660 |
| gaaatgaaag agatggcttt aaagtacggt tatgacatat caaagcctgc aaaaaatgca | 720 |
| aaagaagctg tgcagtggac ttactttgcc ttccttgctg ctataaagga acaaaatggt | 780 |
| gccgctatgt cgctgggcag agtatctact tttttagata tatacattga aagagatctt | 840 |
| aaagaaggaa cattgacaga gaacaagca caagagttaa tggatcactt tgtcatgaag | 900 |
| cttagaatgg tgaggttctt aaggactcct gattacaatg aactatttag tggcgatcct | 960 |
| gtttgggtga ctgaatcaat tggcggtgta ggcgtagacg aagacctct tgtcactaaa | 1020 |
| aattcattca ggatattaaa tactttatat aacttaggtc ctgcacctga gccaaacttg | 1080 |
| acggttttat ggtccaaaaa ccttcctgaa aactttaaaa gattctgtgc caaggtatca | 1140 |
| atagatacaa gttctattca atatgaaaat gacgacttaa tgaggccaat atacaatgac | 1200 |
| gactatagca tcgcctgctg tgtgtcagct atgaagacgg gagaacagat gcaattttt | 1260 |
| ggagcaaggg caaatctcgc gaaggcgcta ctgtatgcta taaacggcgg tatcgatgaa | 1320 |

-continued

```
aggtataaaa cgcaagtggc accaaaattt aatcctataa cgtctgagta tttagactac    1380
gatgaggtaa tggcagcata tgacaatatg ttagagtggc ttgcaaaagt gtatgttaaa    1440
gctatgaata taatacacta catgcacgat aaatacgctt atgaaagatc ccttatggct    1500
ttgcatgata gagacatcgt aaggacgatg gcttttggaa tcgcaggtct ttctgttgcg    1560
gcagattcgt taagcgccat aaagtatgct aaagtaaaag ccataagaga tgaaaatggc    1620
atagcaatag attatgaagt ggaaggagat ttccctaagt ttggcaatga tgatgacagg    1680
gttgactcaa tagcagttga cattgtagaa agattcatga ataagcttaa aaagcacaag    1740
acttacagaa actctatacc aacactgtct gttttgacaa taacgtcaaa tgtggtgtac    1800
ggcaaaaaga cgggtgctac acctgacgga agaaaagcgg agaacctttt gcgccaggc     1860 gcaaatccga tgcacggcag agatacaaaa ggtgccatag catcaatgaa ttcagtatca    1920
aaaatacctt atgacagttc attggatggt atatcataca catttacgat tgtaccaaat    1980
gcgcttggca aggatgacga agataaaatt aataatcttg taggactatt agatggatat    2040
gcatttaatg cggggcacca cataaacatc aatgttttaa acagagatat gttgcttgat    2100
gctatggagc atcctgaaaa atatccgcag cttactataa gggtttcagg gtatgctgtc    2160
aatttcaata aattaacgag agagcaacag ttggaggtta tatcccgcac ttttcacgaa    2220
tctatg                                                              2226
```

<210> SEQ ID NO 76
<211> LENGTH: 2285
<212> TYPE: DNA
<213> ORGANISM: T. saccharolyticum

<400> SEQUENCE: 76

```
gtgtatacaa tatatttctt cttagtaaga ggaatgtata aaaataaata ttttaaagga     60
agggacgatc ttatgagcat tattcaaaac atcattgaaa aagctaaaag cgataaaaag    120
aaaattgttc tgccagaagg tgcagaaccc aggacattaa aagctgctga atagttttta    180
aaagaaggga ttgcagattt agtgcttctt ggaaatgaag atgagataag aaatgctgca    240
aaagacttgg acatatccaa agctgaaatc attgaccctg taaagtctga atgtttgat     300 aggtatgcta atgatttcta tgagttaagg aagaacaaag gaatcacgtt ggaaaaagcc    360
agagaaacaa tcaaggataa tatctatttt ggatgtatga tggttaaaga aggttatgct    420
gatggattgg tatctggcgc tattcatgct actgcagatt tattaagacc tgcatttcag    480
ataattaaaa cggctccagg agcaaagata gtatcaagct tttttataat ggaagtgcct    540
aattgtgaat atggtgaaaa tggtgtattc ttgtttgctg attgtgcggt caacccatcg    600
cctaatgcag aagaacttgc ttctattgcc gtacaatctg ctaatactgc aaagaatttg    660
ttgggctttg aaccaaaagt tgccatgcta tcattttcta caaaaggtag tgcatcacat    720
gaattagtag ataaagtaag aaaagcgaca gagatagcaa agaattgat gccagatgtt     780 gctatcgacg gtgaattgca attggatgct gctcttgtta aagaagttgc agagctaaaa    840
gcgccgggaa gcaaagttgc gggatgtgca aatgtgctta tattccctga tttacaagct    900
ggtaatatag gatataagct tgtacagagg ttagctaagg caaatgcaat tggacсctata    960 acacaaggaa tgggtgcacc ggttaatgat ttatcaagag gatgcagcta tagagatatt    1020
gttgacgtaa tagcaacaac agctgtgcag gctcaataaa atgtaaagta tggaggatga    1080
aaattatgaa aatactggtt attaattgcg gaagttcttc gctaaaatat caactgattg    1140
```

| | |
|---|---|
| aatcaactga tggaaatgtg ttggcaaaag gccttgctga agaatcggc ataaatgatt | 1200 |
| ccatgttgac acataatgct aacggagaaa aaatcaagat aaaaaaagac atgaaagatc | 1260 |
| acaaagacgc aataaaattg gttttagatg ctttggtaaa cagtgactac ggcgttataa | 1320 |
| aagatatgtc tgagatagat gctgtaggac atagagttgt tcacggagga gaatctttta | 1380 |
| catcatcagt tctcataaat gatgaagtgt taaaagcgat aacagattgc atagaattag | 1440 |
| ctccactgca caatcctgct aatatagaag gaattaaagc ttgccagcaa atcatgccaa | 1500 |
| acgttccaat ggtggcggta tttgatacag cctttcatca gacaatgcct gattatgcat | 1560 |
| atctttatcc aataccttat gaatactaca caaagtacag gattagaaga tatggatttc | 1620 |
| atggcacatc gcataaatat gtttcaaata gggctgcaga gattttgaat aaacctattg | 1680 |
| aagatttgaa aatcataact tgtcatcttg gaaatggctc cagcattgct gctgtcaaat | 1740 |
| atggtaaatc aattgacaca agcatgggat ttacaccatt agaaggtttg gctatgggta | 1800 |
| cacgatctgg aagcatagac ccatccatca tttcgtatct tatggaaaaa gaaaatataa | 1860 |
| gcgctgaaga agtagtaaat atattaaata aaaaatctgg tgtttacggt atttcaggaa | 1920 |
| taagcagcga ttttagagac ttagaagatg ccgccttaa aaatggagat gaaagagctc | 1980 |
| agttggcttt aaatgtgttt gcatatcgag taaagaagac gattggcgct tatgcagcag | 2040 |
| ctatgggagg cgtcgatgtc attgtattta cagcaggtgt tggtgaaaat ggtcctgaga | 2100 |
| tacgagaatt tatacttgat ggattagagt ttttagggtt cagcttggat aaagaaaaaa | 2160 |
| ataaagtcag aggaaaagaa actattatat ctacgccgaa ttcaaaagtt agcgtgatgg | 2220 |
| ttgtgcctac taatgaagaa tacatgattg ctaaagatac tgaaaagatt gtaaagagta | 2280 |
| taaaa | 2285 |

<210> SEQ ID NO 77
<211> LENGTH: 38
<212> TYPE: DNA
<213> ORGANISM: Artificial
<220> FEATURE:
<223> OTHER INFORMATION: pMU433 construction; X01648

<400> SEQUENCE: 77

| | |
|---|---|
| gtctttcgac tgagcctttc gttttatttg atgcctgg | 38 |

<210> SEQ ID NO 78
<211> LENGTH: 35
<212> TYPE: DNA
<213> ORGANISM: Artificial
<220> FEATURE:
<223> OTHER INFORMATION: pMU433 construction; X01649

<400> SEQUENCE: 78

| | |
|---|---|
| aattgtagaa tacaatccac ttcacaatgg gcacg | 35 |

<210> SEQ ID NO 79
<211> LENGTH: 34
<212> TYPE: DNA
<213> ORGANISM: Artificial
<220> FEATURE:
<223> OTHER INFORMATION: pMU433 construction; X01654

<400> SEQUENCE: 79

| | |
|---|---|
| aggggtcccg agcgcctacg aggaatttgt atcg | 34 |

<210> SEQ ID NO 80
<211> LENGTH: 35

```
<212> TYPE: DNA
<213> ORGANISM: Artificial
<220> FEATURE:
<223> OTHER INFORMATION: pMU433 construction; X01655

<400> SEQUENCE: 80
ccgtcagtag ctgaacagga gggacagctg ataga                        35

<210> SEQ ID NO 81
<211> LENGTH: 169
<212> TYPE: DNA
<213> ORGANISM: Artificial
<220> FEATURE:
<223> OTHER INFORMATION: adhE promoter

<400> SEQUENCE: 81
tcatataagt gtaaggtgat tgttaaatga ataacaaaaa ttatttacat cacacagtcc    60
aaaattcaat tcattcaagc gaatttcctg ttgaaatgct tgaaaaactg atacaatcac   120
ctgaaatgta gagatttatt gttaataaat taacacggag gtgtttatt              169

<210> SEQ ID NO 82
<211> LENGTH: 621
<212> TYPE: DNA
<213> ORGANISM: Artificial
<220> FEATURE:
<223> OTHER INFORMATION: cbp promoter

<400> SEQUENCE: 82
gagtcgtgac taagaacgtc aaagtaatta acaatacagc tattttttctc atgcttttac   60 cccttttcata aaatttaatt ttatcgttat cataaaaaat tatagacgtt atattgcttg  120
ccgggatata gtgctgggca ttcgttggtg caaaatgttc ggagtaaggt ggatattgat   180
ttgcatgttg atctattgca ttgaaatgat tagttatccg taaatattaa ttaatcatat   240
cataaattaa ttatatcata attgtttttga cgaatgaagg tttttggata aattatcaag   300
taaaggaacg ctaaaaattt tggcgtaaaa tatcaaaatg accacttgaa ttaatatggt   360
aaagtagata taatattttg gtaaacatgc cttcagcaag gttagattag ctgttttccgt  420 ataaattaac cgtatggtaa aacggcagtc agaaaaataa gtcataagat tccgttatga   480
aaatatactt cggtagttaa taataagaga tatgaggtaa gagatacaag ataagagata   540
taaggtacga atgtataaga tggtgctttt aggcacacta ataaaaaac aaataaacga    600 aaattttaag gaggacgaaa g                                             621

<210> SEQ ID NO 83
<211> LENGTH: 172
<212> TYPE: DNA
<213> ORGANISM: Artificial
<220> FEATURE:
<223> OTHER INFORMATION: pta promoter

<400> SEQUENCE: 83
gtattctaca attaaaccta atacgctcat aatatgcgcc tttctaaaaa attattaatt    60
gtacttatta ttttataaaa aatatgttaa aatgtaaaat gtgtatacaa tatatttctt   120
cttagtaaga ggaatgtata aaaataaata ttttaaagga agggacgatc tt           172

<210> SEQ ID NO 84
<211> LENGTH: 214
<212> TYPE: DNA
<213> ORGANISM: Artificial
<220> FEATURE:
```

<223> OTHER INFORMATION: hyd promoter

<400> SEQUENCE: 84

| | | | | | |
|---|---|---|---|---|---|
| ataagcgaaa | gggtaaattg | ctttgattta | gatgatttga | atatggtagt | cgactggatg | 60 |
| tgcaagtaaa | gaaaacatat | caaattagtc | gggattatca | gaaaataaaa | aaattttat | 120 |
| ttttaactgt | taaaaaaata | attaacatat | ggtataataa | ttatgtccta | ttttgcaatt | 180 |
| ttaaagatta | atttttttaa | aaggagggta | ttag | | | 214 |

<210> SEQ ID NO 85
<211> LENGTH: 251
<212> TYPE: DNA
<213> ORGANISM: Artificial
<220> FEATURE:
<223> OTHER INFORMATION: hfs promoter

<400> SEQUENCE: 85

| | | | | | |
|---|---|---|---|---|---|
| gctgtaattg | tccttgatga | cgataggaag | ataaacattc | caacaaaata | tcttcccagc | 60 |
| aatattgctg | aagaagatgc | catagatatt | tcattggatg | tcaatgaaag | aggacgaaaa | 120 |
| ttaaaaaagt | tgattgaaga | atcaagggag | gaagactaat | ttttaatttt | ttttaacgtt | 180 |
| aattgttaat | aaattaacta | ttgtttacac | actttctttt | atgtaataaa | ataattgtat | 240 |
| acagtatacg | g | | | | | 251 |

<210> SEQ ID NO 86
<211> LENGTH: 237
<212> TYPE: DNA
<213> ORGANISM: Artificial
<220> FEATURE:
<223> OTHER INFORMATION: ech promoter

<400> SEQUENCE: 86

| | | | | | |
|---|---|---|---|---|---|
| tactgaatgg | agaaactgca | caaaaagctt | gttgacggca | gcagaggaga | ttattcctct | 60 |
| gctatttttg | tgggaaaaac | tgcaaaattc | attgaaatat | tgttaaataa | taaacaaaat | 120 |
| taattaatat | taaatacaat | tgacttatca | tttaattaga | tttataatca | aatgggtat | 180 |
| ttaaaaatgt | atacaatata | taatattcat | taaatgaaat | aaagaaggag | tgaaaaa | 237 |

<210> SEQ ID NO 87
<211> LENGTH: 1670
<212> TYPE: DNA
<213> ORGANISM: Acinetobacter sp.

<400> SEQUENCE: 87

| | | | | | |
|---|---|---|---|---|---|
| cagaagatat | ggttcggtta | tcggttggga | ttgaacatat | tgatgatttg | attgcagatc | 60 |
| tggaacaagc | attggccaca | gtttgagcgt | aaattttata | aaaaacctct | gcaatttcag | 120 |
| aggttttttt | atatttgctt | tattatcgta | tgatgttcat | aattgatcta | gcaaataata | 180 |
| aaaattagag | caattactct | aaaaacattt | gtaatttcag | atacttaaca | ctagattttt | 240 |
| taaccaaatc | actttagatt | aactttagtt | ctggaaattt | tatttcccttt | taaccgtctt | 300 |
| caatccaaat | acaataatga | cagcctttac | agtttgatat | caatcaggga | aaaacgcgtg | 360 |
| aacaaaaaac | ttgaagctct | cttccgagag | aatgtaaaag | gtaaagtggc | tttgatcact | 420 |
| ggtgcatcta | gtggaatcgg | tttgacgatt | gcaaaaagaa | ttgctgcggc | aggtgctcat | 480 |
| gtattattgg | ttgcccgaac | ccaagaaaca | ctggaagaag | tgaaagctgc | aattgaacag | 540 |
| caaggggac | aggcctctat | ttttccttgt | gacctgactg | acatgaatgc | gattgaccag | 600 |
| ttatcacaac | aaattatggc | cagtgtcgat | catgtcgatt | tcctgatcaa | taatgcaggg | 660 |

```
cgttcgattc gccgtgccgt acacgagtcg tttgatcgct tccatgattt tgaacgcacc      720
atgcagctga attactttgg tgcggtacgt ttagtgttaa atttactgcc acatatgatt      780
aagcgtaaaa atggccagat catcaatatc agctctattg gtgtattggc caatgcgacc      840 cgttttctg cttatgtcgc gtctaaagct gcgctggatg ccttcagtcg ctgtctttca       900
gccgaggtac tcaagcataa aatctcaatt acctcgattt atatgccatt ggtgcgtacc      960
ccaatgatcg cacccaccaa aatttataaa tacgtgccca cgctttcccc agaagaagcc      1020
gcagatctca ttgtctacgc cattgtgaaa cgtccaacac gtattgcgac gcacttgggt      1080
cgtctggcgt caattaccta tgccatcgca ccagacatca ataatattct gatgtcgatt      1140
ggatttaacc tattcccaag ctcaacggct gcactgggtg aacaggaaaa attgaatctg      1200
ctacaacgtg cctatgcccg cttgttccca ggcgaacact ggtaaaattt ataaagaag      1260 cctctcatac cgagaggctt ttttatggtt acgaccatca gccagattta gaggaaattg      1320
acttttcctg tttttacatc ataaatcgca ccaacaatat caatttcttt gcgatccagc      1380
atatctttaa gtacagaact atgctgaata atgtattgaa tattatagtg aacattcata      1440
gcagtcacct gatcaataaa tgctttgctt aattcacgcg gttgcataat atcaaataca      1500
ctgccaaccg aatgcatgag tggcccaagc acgtattgga tgtgtggcat ttcctgaata      1560
tcggaaatct gctatgttg caatcttaac tggcatgcgc tggtgaccgc accacagtcg       1620
gtatgtccca aaaccagaat cactttggaa cctttggctt gacaggcaaa                 1670

<210> SEQ ID NO 88
<211> LENGTH: 1188
<212> TYPE: DNA
<213> ORGANISM: Geobacillus thermodenitrificans

<400> SEQUENCE: 88
ttacgccttg tgcggctcta cgatcgtccc ggcaaacgcg gcttcgtaaa tcgcacggat      60
gtcggcttcc aacagcggca acggactgcg ggcaagcaaa cgtttctgtt ggacagcatc      120
tttcgtcaag cttttctagcg cgctttcggg gatgccaaat ccccccaatg ttttcggaat     180
gccgacatcg gcgacgaacc gttctagttc ctcgacgcac cgataagacg cttccacttc     240
ggacaaaaaa cttgagttgc cgccaagcgc gttgaaaata tcggccattc tcttcgtaca     300
gctttgacgg atgtagccca tcacatacgg caacagcaca gcattcgatt caccatgagc     360
gatatgaaac tgaccaccga gcggataagc gagcgcatgc acaccggcta ccccggcgtt     420
gaaaaatgcc aagccggcca ataactgccg ttcgccata tcaatgcgcg cctgtttgtc       480
cgaaccgttg ccaccgcctt tgcgcagtga gcgtgaaatc agccgaatag cggcaacggc     540
caatccatcc gatgttgggc tcgcattgac cgacacatac gcctcaactg catgggtgag     600
tgcatcaatt cccgttgcgg ccgttacccg cggtggaacg gaaacggtca gctgcggatc      660
aacgatcgcg acgtcggcca ataagtaatc gtgcgtcacg acatctttcg tcgtttccaa     720
agacaagaca gagatgtttg tcacttccga cccggtgccc gatgtcgtgg gaatcaaaat    780
tttcggcaac cctttttct caagtgttcg cgttcctgtc aaatttaaat agtcagcgac      840
cgagccatca tgcaccgcca aaacagccgc cagtttcgcc aaatccagcg cgctgccacc    900
accaacaccg atgacaaggt caaacttttcc gtcgcgggca aacgccactg ccttttcccc   960
tgtctcaagc ggcggctctg gcacaacatc cgtatacaca tgcacgctat accccttcttg    1020 acggagcggg gacgtcactt gatcgactag gccgatcttc acaagcatcg ggtcggtaat     1080
```

| caccaaaata tgttttgctc ccaaccgctt cacttcagga actaactggt caagcgctcc | 1140 |
| ccagccgaca tggctgagcg gcggaaagac aatgcgggct acactcat | 1188 |

<210> SEQ ID NO 89
<211> LENGTH: 1164
<212> TYPE: DNA
<213> ORGANISM: Geobacillus thermodenitrificans

<400> SEQUENCE: 89

| ttataaagac gcacgcaaaa tggcgagcac atcatcacga tttaacgttt tgaaacggcc | 60 |
| aaactcacca aacgccatcg ctttatccgc catcagctcg agattttcct cgccgatgcc | 120 |
| ataatcagcc aatcgagacg cgccccgag gctcgaccaa aacgcgcgca accgctcgat | 180 |
| gccctcaagc gccacgtcgc gctccgtttt gccgtcgga tcgacgtcaa agacgcgcac | 240 |
| cgccagttgg gcgaaacggc tgacattttc atcaagcaca tgtttcatcc aattcgggaa | 300 |
| caaaatggcc aatcccccgg cgtgcgggat atcgtataca gcagagaccg catgctcgat | 360 |
| atcatgcgtc gcccaatcac cgcgcacgcc catttgcaaa aagccgttta aggcgatcgt | 420 |
| gcccgagtac atgatcgtct cgcgcagctc gtagttctct aagtcgtcaa ccaattttgg | 480 |
| cgccgcctca atgaccgttt taacactgc ctcgcacatc cggtcttgca gcggcgtgtt | 540 |
| cggcgtatga tggaaatatt gctcaaacac atgggacatc atatcgacga tgccgtaaac | 600 |
| ggtatggtct ttcggcaccg tcatcgtgta cgtcggatcc aaaatcgaaa attgcgggaa | 660 |
| tgtcaccggg ctgccccagc cgtattttc tttcgtctcc caattggtga tcaccgatcc | 720 |
| ggcgttcatt tccgagccgg tcgctgccag cgtcaggacc gtcccaaacg caacgcctc | 780 |
| agtgacagtc gctttttcg taatgaactc ccacggatcg ccatcaaact cgcgccggc | 840 |
| tgcaatcgct ttcgtacagt cgatcacact gccgccgcca acggcaagca aaattcaat | 900 |
| tccttcccgt ctgcaaatgt ctacccctt tttgacggtc gaaaggcgcg ggttcggttc | 960 |
| gacgcctggc agttcaacga cttcggcgcc aatgtccgtc aataggctca tgacttcatc | 1020 |
| atatagtccg tttcgtttaa tgctgccgcc cccatagaca agcagcactt ttttgccata | 1080 |
| tttcggcact tcttctttga gctgctcaat ttgtcctctc ccaaaaatga gtttggtcgg | 1140 |
| attgcgaaac gtaaaatttt gcat | 1164 |

<210> SEQ ID NO 90
<211> LENGTH: 59
<212> TYPE: DNA
<213> ORGANISM: Artificial
<220> FEATURE:
<223> OTHER INFORMATION: X12312 primer

<400> SEQUENCE: 90

| ttttgtctgt cttaattttt ggtatcatta taggatctat gtaacccagg aagcggcaa | 59 |

<210> SEQ ID NO 91
<211> LENGTH: 48
<212> TYPE: DNA
<213> ORGANISM: Artificial
<220> FEATURE:
<223> OTHER INFORMATION: X12313 primer

<400> SEQUENCE: 91

| acgagattac tgctgctgtg cagactttgc gttccattgc acggatca | 48 |

<210> SEQ ID NO 92
<211> LENGTH: 48

```
<212> TYPE: DNA
<213> ORGANISM: Artificial
<220> FEATURE:
<223> OTHER INFORMATION: X12314 primer

<400> SEQUENCE: 92
tgatccgtgc aatggaacgc aaagtctgca cagcagcagt aatctcgt            48

<210> SEQ ID NO 93
<211> LENGTH: 59
<212> TYPE: DNA
<213> ORGANISM: Artificial
<220> FEATURE:
<223> OTHER INFORMATION: X12315 primer

<400> SEQUENCE: 93
gataacaatt tcacacagga aacagctatg accatacggc ctcttctccc ataccaaat    59

<210> SEQ ID NO 94
<211> LENGTH: 59
<212> TYPE: DNA
<213> ORGANISM: Artificial
<220> FEATURE:
<223> OTHER INFORMATION: X12316 primer

<400> SEQUENCE: 94
ttttgtctgt cttaattttt ggtatcatta taggaacgca gttgctggat atcagaggt    59

<210> SEQ ID NO 95
<211> LENGTH: 48
<212> TYPE: DNA
<213> ORGANISM: Artificial
<220> FEATURE:
<223> OTHER INFORMATION: X12317 primer

<400> SEQUENCE: 95
tactggtcag agcttctgct gtcaactcgt tcacctgttg caggtact            48

<210> SEQ ID NO 96
<211> LENGTH: 48
<212> TYPE: DNA
<213> ORGANISM: Artificial
<220> FEATURE:
<223> OTHER INFORMATION: X12318 primer

<400> SEQUENCE: 96
agtacctgca acaggtgaac gagttgacag cagaagctct gaccagta              48

<210> SEQ ID NO 97
<211> LENGTH: 59
<212> TYPE: DNA
<213> ORGANISM: Artificial
<220> FEATURE:
<223> OTHER INFORMATION: X12319 primer

<400> SEQUENCE: 97
gataacaatt tcacacagga aacagctatg accatttggg atgtgtgcat tacccaacg    59

<210> SEQ ID NO 98
<211> LENGTH: 59
<212> TYPE: DNA
<213> ORGANISM: Artificial
<220> FEATURE:
<223> OTHER INFORMATION: X12320 primer

<400> SEQUENCE: 98
```
ttttgtctgt cttaattttt ggtatcatta taggatactg gtaaacgtct gccgaccaa    59

<210> SEQ ID NO 99
<211> LENGTH: 48
<212> TYPE: DNA
<213> ORGANISM: Artificial
<220> FEATURE:
<223> OTHER INFORMATION: X12321 primer

<400> SEQUENCE: 99
acagcttagc gccttctaca gcttcgcgcg aacgttcaat gattcgat                48

<210> SEQ ID NO 100
<211> LENGTH: 48
<212> TYPE: DNA
<213> ORGANISM: Artificial
<220> FEATURE:
<223> OTHER INFORMATION: X12322 primer

<400> SEQUENCE: 100
atcgaatcat tgaacgttcg cgcgaagctg tagaaggcgc taagctgt                48

<210> SEQ ID NO 101
<211> LENGTH: 59
<212> TYPE: DNA
<213> ORGANISM: Artificial
<220> FEATURE:
<223> OTHER INFORMATION: X12323 primer

<400> SEQUENCE: 101
gataacaatt tcacacagga aacagctatg accatgctga cattggctat ccctgcatt    59

<210> SEQ ID NO 102
<211> LENGTH: 59
<212> TYPE: DNA
<213> ORGANISM: Artificial
<220> FEATURE:
<223> OTHER INFORMATION: X12324 primer

<400> SEQUENCE: 102
ttttgtctgt cttaattttt ggtatcatta taggagcggg tcaatttcca gataacgca    59

<210> SEQ ID NO 103
<211> LENGTH: 48
<212> TYPE: DNA
<213> ORGANISM: Artificial
<220> FEATURE:
<223> OTHER INFORMATION: X12325 primer

<400> SEQUENCE: 103
tcaggaacag gaatacgcga ccaagatcgg cttgaaaggt ttgcacga                48

<210> SEQ ID NO 104
<211> LENGTH: 48
<212> TYPE: DNA
<213> ORGANISM: Artificial
<220> FEATURE:
<223> OTHER INFORMATION: X12326 primer

<400> SEQUENCE: 104
tcgtgcaaac ctttcaagcc gatcttggtc gcgtattcct gttcctga                48

<210> SEQ ID NO 105
<211> LENGTH: 59
<212> TYPE: DNA
<213> ORGANISM: Artificial

```
<220> FEATURE:
<223> OTHER INFORMATION: X12327 primer

<400> SEQUENCE: 105
gataacaatt tcacacagga aacagctatg accatgcgaa acatgcactg ccttacctt      59

<210> SEQ ID NO 106
<211> LENGTH: 59
<212> TYPE: DNA
<213> ORGANISM: Artificial
<220> FEATURE:
<223> OTHER INFORMATION: X12328 primer

<400> SEQUENCE: 106
ttttgtctgt cttaattttt ggtatcatta taggatggac cgaatggacg atggagttt      59

<210> SEQ ID NO 107
<211> LENGTH: 48
<212> TYPE: DNA
<213> ORGANISM: Artificial
<220> FEATURE:
<223> OTHER INFORMATION: X12329 primer

<400> SEQUENCE: 107
agaatgcctt tcacgcgttc catgtcgttg ctttatagac acccgcct                  48

<210> SEQ ID NO 108
<211> LENGTH: 48
<212> TYPE: DNA
<213> ORGANISM: Artificial
<220> FEATURE:
<223> OTHER INFORMATION: X12330 primer

<400> SEQUENCE: 108
aggcgggtgt ctataaagca acgacatgga acgcgtgaaa ggcattct                  48

<210> SEQ ID NO 109
<211> LENGTH: 59
<212> TYPE: DNA
<213> ORGANISM: Artificial
<220> FEATURE:
<223> OTHER INFORMATION: X12331 primer

<400> SEQUENCE: 109
gataacaatt tcacacagga aacagctatg accatttccg ttaacgatac gcttcgggt      59

<210> SEQ ID NO 110
<211> LENGTH: 59
<212> TYPE: DNA
<213> ORGANISM: Artificial
<220> FEATURE:
<223> OTHER INFORMATION: X12332 primer

<400> SEQUENCE: 110
ttttgtctgt cttaattttt ggtatcatta taggaattca aacgttatgc ccgacgctg      59

<210> SEQ ID NO 111
<211> LENGTH: 48
<212> TYPE: DNA
<213> ORGANISM: Artificial
<220> FEATURE:
<223> OTHER INFORMATION: X12333 primer

<400> SEQUENCE: 111
agcgggtcgg tgtaaatatt ccgttccttg atggtttctc ccagcact                  48
```

<210> SEQ ID NO 112
<211> LENGTH: 48
<212> TYPE: DNA
<213> ORGANISM: Artificial
<220> FEATURE:
<223> OTHER INFORMATION: X12334 primer

<400> SEQUENCE: 112
agtgctggga gaaaccatca aggaacggaa tatttacacc gacccgct                 48

<210> SEQ ID NO 113
<211> LENGTH: 59
<212> TYPE: DNA
<213> ORGANISM: Artificial
<220> FEATURE:
<223> OTHER INFORMATION: X12335 primer

<400> SEQUENCE: 113
gataacaatt tcacacagga aacagctatg accatttgaa attagccagt ggcggcaag     59

<210> SEQ ID NO 114
<211> LENGTH: 59
<212> TYPE: DNA
<213> ORGANISM: Artificial
<220> FEATURE:
<223> OTHER INFORMATION: X12336 primer

<400> SEQUENCE: 114
ttttgtctgt cttaattttt ggtatcatta taggacagcc gctacattaa aggcaccaa     59

<210> SEQ ID NO 115
<211> LENGTH: 48
<212> TYPE: DNA
<213> ORGANISM: Artificial
<220> FEATURE:
<223> OTHER INFORMATION: X12337 primer

<400> SEQUENCE: 115
ccagcagcgg cagatcaaat tcaatggcgg ttcgacttta gcctgtat                 48

<210> SEQ ID NO 116
<211> LENGTH: 48
<212> TYPE: DNA
<213> ORGANISM: Artificial
<220> FEATURE:
<223> OTHER INFORMATION: X12338 primer

<400> SEQUENCE: 116
atacaggcta aagtcgaacc gccattgaat ttgatctgcc gctgctgg                 48

<210> SEQ ID NO 117
<211> LENGTH: 59
<212> TYPE: DNA
<213> ORGANISM: Artificial
<220> FEATURE:
<223> OTHER INFORMATION: X12339 primer

<400> SEQUENCE: 117
gataacaatt tcacacagga aacagctatg accatatggt ttagcggcta tttgcgtgc     59

<210> SEQ ID NO 118
<211> LENGTH: 59
<212> TYPE: DNA
<213> ORGANISM: Artificial
<220> FEATURE:
<223> OTHER INFORMATION: X12340 primer

```
<400> SEQUENCE: 118
ttttgtctgt cttaattttt ggtatcatta taggatggcg aatggcactc cctatgtta        59

<210> SEQ ID NO 119
<211> LENGTH: 48
<212> TYPE: DNA
<213> ORGANISM: Artificial
<220> FEATURE:
<223> OTHER INFORMATION: X12341 primer

<400> SEQUENCE: 119
tgacaatcac caggtcacca gacatccgaa tgaaataacg ccgcgatg                   48

<210> SEQ ID NO 120
<211> LENGTH: 48
<212> TYPE: DNA
<213> ORGANISM: Artificial
<220> FEATURE:
<223> OTHER INFORMATION: X12342 primer

<400> SEQUENCE: 120
catcgcggcg ttatttcatt cggatgtctg gtgacctggt gattgtca                   48

<210> SEQ ID NO 121
<211> LENGTH: 59
<212> TYPE: DNA
<213> ORGANISM: Artificial
<220> FEATURE:
<223> OTHER INFORMATION: X12343 primer

<400> SEQUENCE: 121
gataacaatt tcacacagga aacagctatg accattgttg atgagatgtt tgccaccgc        59

<210> SEQ ID NO 122
<211> LENGTH: 59
<212> TYPE: DNA
<213> ORGANISM: Artificial
<220> FEATURE:
<223> OTHER INFORMATION: X12344 primer

<400> SEQUENCE: 122
ttttgtctgt cttaattttt ggtatcatta taggaatgct gtacgtaata cgcctgcga       59

<210> SEQ ID NO 123
<211> LENGTH: 48
<212> TYPE: DNA
<213> ORGANISM: Artificial
<220> FEATURE:
<223> OTHER INFORMATION: X12345 primer

<400> SEQUENCE: 123
tctttaacaa gctgcggcac aacgatggga gaaacttgct ttctgggc                   48

<210> SEQ ID NO 124
<211> LENGTH: 48
<212> TYPE: DNA
<213> ORGANISM: Artificial
<220> FEATURE:
<223> OTHER INFORMATION: X12346 primer

<400> SEQUENCE: 124
gcccagaaag caagtttctc ccatcgttgt gccgcagctt gttaaaga                   48

<210> SEQ ID NO 125
```

```
<210> SEQ ID NO 126
<211> LENGTH: 59
<212> TYPE: DNA
<213> ORGANISM: Artificial
<220> FEATURE:
<223> OTHER INFORMATION: X12347 primer

<400> SEQUENCE: 125
gataacaatt tcacacagga aacagctatg accatatctt tagcagcctg aacgtcgga      59

<210> SEQ ID NO 126
<211> LENGTH: 58
<212> TYPE: DNA
<213> ORGANISM: Artificial
<220> FEATURE:
<223> OTHER INFORMATION: X13802 primer

<400> SEQUENCE: 126
ttataggtta atgtcatgat aataatggtt tcttccgtca aagggcaaat caccgaaa       58

<210> SEQ ID NO 127
<211> LENGTH: 58
<212> TYPE: DNA
<213> ORGANISM: Artificial
<220> FEATURE:
<223> OTHER INFORMATION: X13803 primer

<400> SEQUENCE: 127
gggttccgcg cacatttccc cgaaaagtgc caccactcgg aataaccggt tcgggaaa       58

<210> SEQ ID NO 128
<211> LENGTH: 58
<212> TYPE: DNA
<213> ORGANISM: Artificial
<220> FEATURE:
<223> OTHER INFORMATION: X13804 primer

<400> SEQUENCE: 128
cgccttctat cgccttcttg acgagttctt ctgatacgac aaagcgttcg tcgcttca       58

<210> SEQ ID NO 129
<211> LENGTH: 58
<212> TYPE: DNA
<213> ORGANISM: Artificial
<220> FEATURE:
<223> OTHER INFORMATION: X13805 primer

<400> SEQUENCE: 129
actgttggga agggcgatcg gtgcgggcct cttcgaatga agcccagttc gcccattt       58

<210> SEQ ID NO 130
<211> LENGTH: 58
<212> TYPE: DNA
<213> ORGANISM: Artificial
<220> FEATURE:
<223> OTHER INFORMATION: X14576 primer

<400> SEQUENCE: 130
ttataggtta atgtcatgat aataatggtt tcttgcggat gcgaaggctt tgttgtat       58

<210> SEQ ID NO 131
<211> LENGTH: 48
<212> TYPE: DNA
<213> ORGANISM: Artificial
<220> FEATURE:
<223> OTHER INFORMATION: X14577 primer

<400> SEQUENCE: 131
```
tgggtagaaa aaataaacgg ctcagattcc tgtcacgaaa cggttgct    48

<210> SEQ ID NO 132
<211> LENGTH: 48
<212> TYPE: DNA
<213> ORGANISM: Artificial
<220> FEATURE:
<223> OTHER INFORMATION: X14578 primer

<400> SEQUENCE: 132
agcaaccgtt tcgtgacagg aatctgagcc gtttattttt tctaccca    48

<210> SEQ ID NO 133
<211> LENGTH: 48
<212> TYPE: DNA
<213> ORGANISM: Artificial
<220> FEATURE:
<223> OTHER INFORMATION: X14579 primer

<400> SEQUENCE: 133
ggtcaaacca ttgttaacgc gcattttagt gctccgctaa tgtcaact    48

<210> SEQ ID NO 134
<211> LENGTH: 48
<212> TYPE: DNA
<213> ORGANISM: Artificial
<220> FEATURE:
<223> OTHER INFORMATION: X14580 primer

<400> SEQUENCE: 134
agttgacatt agcggagcac taaaatgcgc gttaacaatg gtttgacc    48

<210> SEQ ID NO 135
<211> LENGTH: 58
<212> TYPE: DNA
<213> ORGANISM: Artificial
<220> FEATURE:
<223> OTHER INFORMATION: X14581 primer

<400> SEQUENCE: 135
gggttccgcg cacatttccc cgaaaagtgc cacctagaag cgatacctt cagcggca    58

<210> SEQ ID NO 136
<211> LENGTH: 58
<212> TYPE: DNA
<213> ORGANISM: Artificial
<220> FEATURE:
<223> OTHER INFORMATION: X14588 primer

<400> SEQUENCE: 136
ttataggtta atgtcatgat aataatggtt tctttctatg taacccagga agcggcaa    58

<210> SEQ ID NO 137
<211> LENGTH: 48
<212> TYPE: DNA
<213> ORGANISM: Artificial
<220> FEATURE:
<223> OTHER INFORMATION: X14589 primer

<400> SEQUENCE: 137
tgggtagaaa aaataaacgg ctcactttgc gttccattgc acggatca    48

<210> SEQ ID NO 138
<211> LENGTH: 48
<212> TYPE: DNA

<213> ORGANISM: Artificial
<220> FEATURE:
<223> OTHER INFORMATION: X14590 primer

<400> SEQUENCE: 138
tgatccgtgc aatggaacgc aaagtgagcc gtttattttt tctaccca                48

<210> SEQ ID NO 139
<211> LENGTH: 48
<212> TYPE: DNA
<213> ORGANISM: Artificial
<220> FEATURE:
<223> OTHER INFORMATION: X14591 primer

<400> SEQUENCE: 139
ataaagaact aagacaatct tcattttagt gctccgctaa tgtcaact                48

<210> SEQ ID NO 140
<211> LENGTH: 48
<212> TYPE: DNA
<213> ORGANISM: Artificial
<220> FEATURE:
<223> OTHER INFORMATION: X14592 primer

<400> SEQUENCE: 140
agttgacatt agcggagcac taaaatgaag attgtcttag ttctttat                48

<210> SEQ ID NO 141
<211> LENGTH: 48
<212> TYPE: DNA
<213> ORGANISM: Artificial
<220> FEATURE:
<223> OTHER INFORMATION: X14593 primer

<400> SEQUENCE: 141
acgagattac tgctgctgtg cagactattt cttatcgtgt ttaccgta                48

<210> SEQ ID NO 142
<211> LENGTH: 48
<212> TYPE: DNA
<213> ORGANISM: Artificial
<220> FEATURE:
<223> OTHER INFORMATION: X14594 primer

<400> SEQUENCE: 142
tacggtaaac acgataagaa atagtctgca cagcagcagt aatctcgt                48

<210> SEQ ID NO 143
<211> LENGTH: 58
<212> TYPE: DNA
<213> ORGANISM: Artificial
<220> FEATURE:
<223> OTHER INFORMATION: X14595 primer

<400> SEQUENCE: 143
gggttccgcg cacatttccc cgaaaagtgc caccacggcc tcttctccca taccaaat     58

<210> SEQ ID NO 144
<211> LENGTH: 58
<212> TYPE: DNA
<213> ORGANISM: Artificial
<220> FEATURE:
<223> OTHER INFORMATION: X15570 primer

<400> SEQUENCE: 144
ttataggtta atgtcatgat aataatggtt tctttgcgat ccgtagcaga caccataa     58

<210> SEQ ID NO 145
<211> LENGTH: 48
<212> TYPE: DNA
<213> ORGANISM: Artificial
<220> FEATURE:
<223> OTHER INFORMATION: X15571 primer

<400> SEQUENCE: 145
gaatactgcg ccagcgtttc acttcgttcc gcttgttctt cgatggtt                48

<210> SEQ ID NO 146
<211> LENGTH: 48
<212> TYPE: DNA
<213> ORGANISM: Artificial
<220> FEATURE:
<223> OTHER INFORMATION: X15572 primer

<400> SEQUENCE: 146
aaccatcgaa gaacaagcgg aacgaagtga aacgctggcg cagtattc                48

<210> SEQ ID NO 147
<211> LENGTH: 58
<212> TYPE: DNA
<213> ORGANISM: Artificial
<220> FEATURE:
<223> OTHER INFORMATION: X15573 primer

<400> SEQUENCE: 147
gggttccgcg cacatttccc cgaaaagtgc cacccatcaa tggcgatcac tttggcgt     58

<210> SEQ ID NO 148
<211> LENGTH: 58
<212> TYPE: DNA
<213> ORGANISM: Artificial
<220> FEATURE:
<223> OTHER INFORMATION: X15574 primer

<400> SEQUENCE: 148
ttataggtta atgtcatgat aataatggtt tcttaattga ccgccagttt gtcacacg     58

<210> SEQ ID NO 149
<211> LENGTH: 48
<212> TYPE: DNA
<213> ORGANISM: Artificial
<220> FEATURE:
<223> OTHER INFORMATION: X15575 primer

<400> SEQUENCE: 149
tcgccgtgca tttcaccatc aatcgagcgc ggcgacaact tcaataaa                48

<210> SEQ ID NO 150
<211> LENGTH: 48
<212> TYPE: DNA
<213> ORGANISM: Artificial
<220> FEATURE:
<223> OTHER INFORMATION: X15576 primer

<400> SEQUENCE: 150
tttattgaag ttgtcgccgc gctcgattga tggtgaaatg cacggcga                48

<210> SEQ ID NO 151
<211> LENGTH: 58
<212> TYPE: DNA
<213> ORGANISM: Artificial
<220> FEATURE:

<223> OTHER INFORMATION: X15577 primer

<400> SEQUENCE: 151
gggttccgcg cacatttccc cgaaaagtgc caccgccata aatcaccaat gcaccgct    58

<210> SEQ ID NO 152
<211> LENGTH: 58
<212> TYPE: DNA
<213> ORGANISM: Artificial
<220> FEATURE:
<223> OTHER INFORMATION: X15578 primer

<400> SEQUENCE: 152
ttataggtta atgtcatgat aataatggtt tcttcagctg gcaggcagta aaccattt    58

<210> SEQ ID NO 153
<211> LENGTH: 48
<212> TYPE: DNA
<213> ORGANISM: Artificial
<220> FEATURE:
<223> OTHER INFORMATION: X15579 primer

<400> SEQUENCE: 153
tcaaatgcgc tcagggtacc gatattctga acctgaaggc agttgggt    48

<210> SEQ ID NO 154
<211> LENGTH: 48
<212> TYPE: DNA
<213> ORGANISM: Artificial
<220> FEATURE:
<223> OTHER INFORMATION: X15580 primer

<400> SEQUENCE: 154
acccaactgc cttcaggttc agaatatcgg taccctgagc gcatttga    48

<210> SEQ ID NO 155
<211> LENGTH: 58
<212> TYPE: DNA
<213> ORGANISM: Artificial
<220> FEATURE:
<223> OTHER INFORMATION: X15581 primer

<400> SEQUENCE: 155
gggttccgcg cacatttccc cgaaaagtgc caccactggc ggtttaccta ccattcca    58

<210> SEQ ID NO 156
<211> LENGTH: 58
<212> TYPE: DNA
<213> ORGANISM: Artificial
<220> FEATURE:
<223> OTHER INFORMATION: X15586 primer

<400> SEQUENCE: 156
ttataggtta atgtcatgat aataatggtt tctttcgaca tcgctattgt caccacca    58

<210> SEQ ID NO 157
<211> LENGTH: 48
<212> TYPE: DNA
<213> ORGANISM: Artificial
<220> FEATURE:
<223> OTHER INFORMATION: X15587 primer

<400> SEQUENCE: 157
tttcggaagt tgtgccaca acataatgct ctcctgataa tgttaaac    48

```
<210> SEQ ID NO 158
<211> LENGTH: 48
<212> TYPE: DNA
<213> ORGANISM: Artificial
<220> FEATURE:
<223> OTHER INFORMATION: X15588 primer

<400> SEQUENCE: 158
gtttaacatt atcaggagag cattatgttg tggcacaaac ttccgaaa                48

<210> SEQ ID NO 159
<211> LENGTH: 58
<212> TYPE: DNA
<213> ORGANISM: Artificial
<220> FEATURE:
<223> OTHER INFORMATION: X15589 primer

<400> SEQUENCE: 159
gggttccgcg cacatttccc cgaaaagtgc caccccaagt ggtcggcaat ttcagcat     58

<210> SEQ ID NO 160
<211> LENGTH: 24
<212> TYPE: DNA
<213> ORGANISM: Artificial
<220> FEATURE:
<223> OTHER INFORMATION: X12354 primer

<400> SEQUENCE: 160
ttgctgtatt tgacaccgcg ttcc                                          24

<210> SEQ ID NO 161
<211> LENGTH: 24
<212> TYPE: DNA
<213> ORGANISM: Artificial
<220> FEATURE:
<223> OTHER INFORMATION: X12355 primer

<400> SEQUENCE: 161
tttcacgaaa gaagcggtcg gact                                          24

<210> SEQ ID NO 162
<211> LENGTH: 24
<212> TYPE: DNA
<213> ORGANISM: Artificial
<220> FEATURE:
<223> OTHER INFORMATION: X12356 primer

<400> SEQUENCE: 162
ggcaagttta acgtcgcagt agca                                          24

<210> SEQ ID NO 163
<211> LENGTH: 24
<212> TYPE: DNA
<213> ORGANISM: Artificial
<220> FEATURE:
<223> OTHER INFORMATION: X12357 primer

<400> SEQUENCE: 163
tttatggcgg tgtcgtttgg cttg                                          24

<210> SEQ ID NO 164
<211> LENGTH: 24
<212> TYPE: DNA
<213> ORGANISM: Artificial
<220> FEATURE:
<223> OTHER INFORMATION: X12358 primer
```

-continued

<400> SEQUENCE: 164
atatctggaa gaagagggcg cgaa                                      24

<210> SEQ ID NO 165
<211> LENGTH: 24
<212> TYPE: DNA
<213> ORGANISM: Artificial
<220> FEATURE:
<223> OTHER INFORMATION: X12359 primer

<400> SEQUENCE: 165
gatgcattac gccgtgtggt tgaa                                      24

<210> SEQ ID NO 166
<211> LENGTH: 24
<212> TYPE: DNA
<213> ORGANISM: Artificial
<220> FEATURE:
<223> OTHER INFORMATION: X12360 primer

<400> SEQUENCE: 166
aacagcaatt gtagcagcgt gtcg                                      24

<210> SEQ ID NO 167
<211> LENGTH: 24
<212> TYPE: DNA
<213> ORGANISM: Artificial
<220> FEATURE:
<223> OTHER INFORMATION: X12361 primer

<400> SEQUENCE: 167
ttgtttgcca gcatcacgat accc                                      24

<210> SEQ ID NO 168
<211> LENGTH: 24
<212> TYPE: DNA
<213> ORGANISM: Artificial
<220> FEATURE:
<223> OTHER INFORMATION: X12362 primer

<400> SEQUENCE: 168
ctgggcgttt atgcttgccg tatt                                      24

<210> SEQ ID NO 169
<211> LENGTH: 24
<212> TYPE: DNA
<213> ORGANISM: Artificial
<220> FEATURE:
<223> OTHER INFORMATION: X12363 primer

<400> SEQUENCE: 169
agtcgtcagt tgtgagctcg actt                                      24

<210> SEQ ID NO 170
<211> LENGTH: 24
<212> TYPE: DNA
<213> ORGANISM: Artificial
<220> FEATURE:
<223> OTHER INFORMATION: X12364 project

<400> SEQUENCE: 170
tattcacggt ggcgacgctt ctaa                                      24

<210> SEQ ID NO 171
<211> LENGTH: 24

```
<212> TYPE: DNA
<213> ORGANISM: Artificial
<220> FEATURE:
<223> OTHER INFORMATION: X12365 primer

<400> SEQUENCE: 171
cgcctgttgc aggatttcaa tggt                                            24

<210> SEQ ID NO 172
<211> LENGTH: 24
<212> TYPE: DNA
<213> ORGANISM: Artificial
<220> FEATURE:
<223> OTHER INFORMATION: X12366 primer

<400> SEQUENCE: 172
aaagcgttag gtgcaaacct ggtg                                            24

<210> SEQ ID NO 173
<211> LENGTH: 24
<212> TYPE: DNA
<213> ORGANISM: Artificial
<220> FEATURE:
<223> OTHER INFORMATION: X12367 primer

<400> SEQUENCE: 173
attgccgtgc ctgctatcaa acag                                            24

<210> SEQ ID NO 174
<211> LENGTH: 24
<212> TYPE: DNA
<213> ORGANISM: Artificial
<220> FEATURE:
<223> OTHER INFORMATION: X12368

<400> SEQUENCE: 174
gctatggcac tggaagccaa tgtt                                            24

<210> SEQ ID NO 175
<211> LENGTH: 24
<212> TYPE: DNA
<213> ORGANISM: Artificial
<220> FEATURE:
<223> OTHER INFORMATION: X12369

<400> SEQUENCE: 175
agaacgtagt gaagctgaac gcga                                            24

<210> SEQ ID NO 176
<211> LENGTH: 24
<212> TYPE: DNA
<213> ORGANISM: Artificial
<220> FEATURE:
<223> OTHER INFORMATION: X12370

<400> SEQUENCE: 176
tgaagcttac cgcctcatcc tgaa                                            24

<210> SEQ ID NO 177
<211> LENGTH: 24
<212> TYPE: DNA
<213> ORGANISM: Artificial
<220> FEATURE:
<223> OTHER INFORMATION: X12371

<400> SEQUENCE: 177
```

-continued agaatggtga accagagcaa ggga                                              24

<210> SEQ ID NO 178
<211> LENGTH: 24
<212> TYPE: DNA
<213> ORGANISM: Artificial
<220> FEATURE:
<223> OTHER INFORMATION: X12801

<400> SEQUENCE: 178
gattgattac gcggtgaaag cgca                                              24

<210> SEQ ID NO 179
<211> LENGTH: 24
<212> TYPE: DNA
<213> ORGANISM: Artificial
<220> FEATURE:
<223> OTHER INFORMATION: X12802

<400> SEQUENCE: 179
acacccggta tcaaacccttt ccat                                             24

<210> SEQ ID NO 180
<211> LENGTH: 24
<212> TYPE: DNA
<213> ORGANISM: Artificial
<220> FEATURE:
<223> OTHER INFORMATION: X14574

<400> SEQUENCE: 180
ccgtggcgat taacgtgaac aact                                              24

<210> SEQ ID NO 181
<211> LENGTH: 24
<212> TYPE: DNA
<213> ORGANISM: Artificial
<220> FEATURE:
<223> OTHER INFORMATION: X14575

<400> SEQUENCE: 181
agtcgatagt gccatcttca cgca                                              24

<210> SEQ ID NO 182
<211> LENGTH: 24
<212> TYPE: DNA
<213> ORGANISM: Artificial
<220> FEATURE:
<223> OTHER INFORMATION: X15590

<400> SEQUENCE: 182
actgttccct tcccgcgttt gata                                              24

<210> SEQ ID NO 183
<211> LENGTH: 24
<212> TYPE: DNA
<213> ORGANISM: Artificial
<220> FEATURE:
<223> OTHER INFORMATION: X15591

<400> SEQUENCE: 183
gcatcaactg ccgagttaaa cgca                                              24

<210> SEQ ID NO 184
<211> LENGTH: 24
<212> TYPE: DNA
<213> ORGANISM: Artificial

```
<220> FEATURE:
<223> OTHER INFORMATION: X15592

<400> SEQUENCE: 184
aggtcgaagc cagcttgatc agaa                                              24

<210> SEQ ID NO 185
<211> LENGTH: 24
<212> TYPE: DNA
<213> ORGANISM: Artificial
<220> FEATURE:
<223> OTHER INFORMATION: X15593

<400> SEQUENCE: 185
cgctgacggt ttgtgataac gctt                                              24

<210> SEQ ID NO 186
<211> LENGTH: 24
<212> TYPE: DNA
<213> ORGANISM: Artificial
<220> FEATURE:
<223> OTHER INFORMATION: X15594

<400> SEQUENCE: 186
taccttctgc tttgcccagt gagt                                              24

<210> SEQ ID NO 187
<211> LENGTH: 24
<212> TYPE: DNA
<213> ORGANISM: Artificial
<220> FEATURE:
<223> OTHER INFORMATION: X15595

<400> SEQUENCE: 187
tgaagcattg ctggtgggat ctga                                              24

<210> SEQ ID NO 188
<211> LENGTH: 24
<212> TYPE: DNA
<213> ORGANISM: Artificial
<220> FEATURE:
<223> OTHER INFORMATION: X15596

<400> SEQUENCE: 188
agtggcacca caccaatgct ttca                                              24

<210> SEQ ID NO 189
<211> LENGTH: 24
<212> TYPE: DNA
<213> ORGANISM: Artificial
<220> FEATURE:
<223> OTHER INFORMATION: X15597

<400> SEQUENCE: 189
tgaacgccag cttcacggat agat                                              24

<210> SEQ ID NO 190
<211> LENGTH: 58
<212> TYPE: DNA
<213> ORGANISM: Artificial
<220> FEATURE:
<223> OTHER INFORMATION: X16072

<400> SEQUENCE: 190
tctcagtagt agttgacatt agcggagcac taaaatgaag attgtcttag ttctttat        58
```

```
<210> SEQ ID NO 191
<211> LENGTH: 58
<212> TYPE: DNA
<213> ORGANISM: Artificial
<220> FEATURE:
<223> OTHER INFORMATION: X16073

<400> SEQUENCE: 191
cagtctttcg actgagcctt tcgttttacg gccgctattt cttatcgtgt ttaccgta        58

<210> SEQ ID NO 192
<211> LENGTH: 58
<212> TYPE: DNA
<213> ORGANISM: Artificial
<220> FEATURE:
<223> OTHER INFORMATION: X16082

<400> SEQUENCE: 192
tctcagtagt agttgacatt agcggagcac taaaatggca accgttctgt gtgttctg        58

<210> SEQ ID NO 193
<211> LENGTH: 58
<212> TYPE: DNA
<213> ORGANISM: Artificial
<220> FEATURE:
<223> OTHER INFORMATION: X16083

<400> SEQUENCE: 193
cagtctttcg actgagcctt tcgttttacg gccgttaggt cagacgatag ctctgtgc        58

<210> SEQ ID NO 194
<211> LENGTH: 59
<212> TYPE: DNA
<213> ORGANISM: Artificial
<220> FEATURE:
<223> OTHER INFORMATION: X16829

<400> SEQUENCE: 194
tgtgagcgga taacaatttc acacaggaaa cagctatgtc gaaggttatg aaaaccatg       59

<210> SEQ ID NO 195
<211> LENGTH: 48
<212> TYPE: DNA
<213> ORGANISM: Artificial
<220> FEATURE:
<223> OTHER INFORMATION: X16064

<400> SEQUENCE: 195
gctttcacac ctccaagatt tcgtctaatt ttgttcagca agcttctt                   48

<210> SEQ ID NO 196
<211> LENGTH: 48
<212> TYPE: DNA
<213> ORGANISM: Artificial
<220> FEATURE:
<223> OTHER INFORMATION: X16065

<400> SEQUENCE: 196
aagaagcttg ctgaacaaaa ttagacgaaa tcttggaggt gtgaaagc                   48

<210> SEQ ID NO 197
<211> LENGTH: 59
<212> TYPE: DNA
<213> ORGANISM: Artificial
<220> FEATURE:
<223> OTHER INFORMATION: X16830
```

-continued

<400> SEQUENCE: 197
cctcgaggtc gacggtatcg ataagcttga tatcttattc agccttaata gctcctgtt    59

<210> SEQ ID NO 198
<211> LENGTH: 59
<212> TYPE: DNA
<213> ORGANISM: Artificial
<220> FEATURE:
<223> OTHER INFORMATION: X16831

<400> SEQUENCE: 198
tgtgagcgga taacaatttc acacaggaaa cagctatggg aaagaaaatg atgacgact    59

<210> SEQ ID NO 199
<211> LENGTH: 50
<212> TYPE: DNA
<213> ORGANISM: Artificial
<220> FEATURE:
<223> OTHER INFORMATION: X16075

<400> SEQUENCE: 199
tacacctcct tatcttaata ggcgttctac ttcttcgtcc gcttgctgag    50

<210> SEQ ID NO 200
<211> LENGTH: 50
<212> TYPE: DNA
<213> ORGANISM: Artificial
<220> FEATURE:
<223> OTHER INFORMATION: X16076

<400> SEQUENCE: 200
ctcagcaagc ggacgaagaa gtagaacgcc tattaagata aggaggtgta    50

<210> SEQ ID NO 201
<211> LENGTH: 51
<212> TYPE: DNA
<213> ORGANISM: Artificial
<220> FEATURE:
<223> OTHER INFORMATION: X16077

<400> SEQUENCE: 201
cccgtctgat atttatggtt ctacgactta ctcttgaact ggagctccta c    51

<210> SEQ ID NO 202
<211> LENGTH: 51
<212> TYPE: DNA
<213> ORGANISM: Artificial
<220> FEATURE:
<223> OTHER INFORMATION: X16078

<400> SEQUENCE: 202
gtaggagctc cagttcaaga gtaagtcgta gaaccataaa tatcagacgg g    51

<210> SEQ ID NO 203
<211> LENGTH: 59
<212> TYPE: DNA
<213> ORGANISM: Artificial
<220> FEATURE:
<223> OTHER INFORMATION: X16832

<400> SEQUENCE: 203
ccctcgaggt cgacggtatc gataagcttg atatcctatt ggttctgccg gatatatat    59

<210> SEQ ID NO 204

```
<211> LENGTH: 59
<212> TYPE: DNA
<213> ORGANISM: Artificial
<220> FEATURE:
<223> OTHER INFORMATION: X16981

<400> SEQUENCE: 204
tgtgagcgga taacaatttc acacaggaaa cagctatgcc cgatatgaca aacgaatct    59

<210> SEQ ID NO 205
<211> LENGTH: 59
<212> TYPE: DNA
<213> ORGANISM: Artificial
<220> FEATURE:
<223> OTHER INFORMATION: X16982

<400> SEQUENCE: 205
ccctcgaggt cgacggtatc gataagcttg atatcttaaa caccagcttc gaagtcctt    59

<210> SEQ ID NO 206
<211> LENGTH: 5568
<212> TYPE: DNA
<213> ORGANISM: Artificial
<220> FEATURE:
<223> OTHER INFORMATION: Sequence of the PNO gene and flanking regions
      used to create FP66

<400> SEQUENCE: 206
tgagccgttt attttttcta cccatatcct tgaagcggtg ttataatgcc gcgccctcga      60 tatgggatt tttaacgacc tgattttcgg gtctcagtag tagttgacat tagcggagca     120
ctaaaatgaa acagagcgtt cgtccgatta ttagcaatgt tctgcgtaaa gaagttgccc    180
tgtatagcac cattattggt caggataaag gtaaagaacc gacaggtcgt acctatacca    240
gcggtccgaa accggcaagc catattgaag ttccgcatca tgttaccgtt ccggcaaccg    300
atcgtacccc gaatccggat gcacagtttt ttcagagcgt tgatggtagc aggcaaccca    360
gccatgttgc atatgccctg agcgataccg catttatcta tccgattacc ccgagcagcg    420
ttatgggtga actggcagat gtttggatgg cacagggtcg taaaaatgcc tttggtcagg    480
ttgttgatgt tcgtgaaatg cagagcgaag ccggtgcagc gggtgcactg catggtgcac    540
tggcagccgg tgcgattgca accacctta ccgcaagcca gggtctgctg ctgatgattc     600
cgaatatgta taaaatcgca ggcgaactga tgccgagcgt tattcatgtt gcagcacgtg    660
agctggcagg tcatgcactg agcatttttg gtggtcatgc agatgttatg gcagttcgtc    720
agaccggttg ggcaatgctg tgtagccata ccgttcagca gagccatgat atggcactga    780
ttagccatgt ggcaaccctg aaaagcagca ttccgtttgt tcatttttt gatggttttc     840 gcaccagcca cgaagtgaac aaaatcaaaa tgctgccgta tgccgaactg aaaaaactgg    900
ttccgcctgg caccatggaa cagcattggg cacgtagcct gaatccgatg catccgacca    960
ttcgtggcac caatcagagc gcagatatct attttcagaa tatggaaagc gccaaccagt   1020
attataccga tctggcagaa gttgttcaag aaaccatgga tgaagttgca ccgtatattg   1080
gtcgtcatta caaatctttt gagtatgttg gtgcaccgga tgcagaagag gtgaccgttc   1140
tgatgggtag cggtgccacc accgttaatg aagcagttga tctgctggtt aaacgcggta   1200 aaaagttgg tgcagttctg gttcatctgt atcgtccgtg gtcaaccaaa gcatttgaaa    1260
aagttctgcc gaaaaccgtg aaacgtattg cagcactgga tcgttgcaaa gaagttaccg   1320
cactgggcga accgctgtat ctggatgtta gcgccaccct gaacctgttt ccggaacgtc   1380
```

```
agaatgttaa agttattggt ggtcgttatg gtctgggtag caaagatttc attccggaac    1440
atgcactggc catttatgca aatctggcaa gcgaaaatcc gattcagcgt tttaccgttg    1500
gtattaccga tgatgttacc ggcaccagcg tgccgtttgt taatgaacgt gttgataccc    1560
tgccggaagg cacccgtcag tgtgtttttt ggggtattgg tagtgatggc accgttggtg    1620
caaatcgtag cgcagttcgt attattggtg ataatagcga tctgatggtg caggcgtatt    1680
ttcagtttga tgcatttaaa agcggtggtg ttaccagcag ccatctgcgt tttggtccta    1740
aaccgattac cgcacagtat ctggttacca atgcagatta tattgcctgc cactttcaag    1800
agtatgtgaa acgttttgat atgctggatg caattcgtga aggtggcacc tttgttctga    1860
atagccgttg gaccaccgaa gatatggaaa agaaattcc ggcagatttt cgtcgtaatg    1920
tggcacagaa aaaagtgcgc ttttataacg ttgatgcccg taaaatttgc gatagctttg    1980
gtctgggcaa acgcattaac atgctgatgc aggcatgttt tttcaaactg agcggtgttc    2040
tgccgctggc cgaagcacag cgtctgctga atgaaagcat tgttcatgag tatggcaaaa    2100
aaggtggtaa agtggtggaa atgaatcagg cagttgttaa tgcagtgttt gccggtgatc    2160
tgcctcaaga agttcaggtt ccggcagcat gggcaaatgc agttgatacc agcacccgca    2220
ccccgaccgg tattgaattt gttgataaaa tcatgcgtcc gctgatggat ttcaaaggtg    2280
atcagctgcc ggttagcgtt atgacaccgg tggtacatt tccggttggc accacccagt    2340
atgcaaaacg tgcaattgcg gcatttattc cgcagtggat tccggcaaat tgtacccagt    2400
gtaattattg cagctatgtt tgtccgcatg caaccattcg tccgtttgtg ctgaccgatc    2460
aagaagtgca gctggcaccg aaagctttg ttacccgtaa agcaaaaggt gattatcagg    2520
gtatgaactt tcgtattcag gttgcaccgg aagattgtac cggttgtcag gtttgtgttg    2580
aaacctgtcc ggatgatgca ctggaaatga ccgatgcgtt taccgccaca ccggttcagc    2640
gtaccaattg ggaatttgca attaaagttc cgaatcgtgg tacgatgacc gatcgctata    2700
gcctgaaagg tagccagttt cagcaaccgc tgctggaatt tagcggtgca tgtgaaggtt    2760
gtggtgaaac cccgtatgtt aaactgctga cccagctgtt tggtgaacgt accgttattg    2820
caaatgccac cggttgtagc agcatttggg gtggtacggc aggtctggct ccgtatacca    2880
ccaatgcaaa aggtcagggt ccggcatggg gtaatagcct gtttgaagat aatgccgaat    2940
ttggttttgg tattgcagtt gccaatgcac agaaacgtag ccgtgttcgt gattgtattc    3000
tgcaggccgt tgaaaaaaaa gtggccgatg aaggtctgac caccctgctg gcacagtggc    3060
tgcaggattg gaataccggt gataaaacac tgaaatatca ggaccagatt attgccggtc    3120
tggcacagca gcgtagtaaa gatcctctgc tggaacaaat ttatggcatg aaagatatgc    3180
tgccgaatat cagccagtgg attattggcg gtgatggttg gccaatgat attggctttg    3240 gtggcctgga tcatgttctg cgcagcggtc agaatctgaa tgttctggtg ctggataccg    3300
aaatgtatag caatacaggt ggtcaggcaa gcaaaagcac ccatatggca agcgttgcaa    3360
aatttgccct gggtggtaaa cgtaccaaca aaaaaaacct gaccgaaatg gccatgagct    3420
atggtaatgt ttatgttgca accgttagcc atggtaatat ggcccagtgt gttaaagcct    3480 tgttgaagc agaaagctat gatggtccga gcctgattgt tggttatgca ccgtgcattg    3540
aacatggtct gcgtgcaggt atggcacgta tggttcaaga atcagaagca gcaattgcaa    3600
ccggttattg gccactgtat cgtttttgatc gcgtctggc aaccgaaggt aaaaacccgt    3660
ttcagctgga tagcaaacgt attaaaggta acctgcaaga atatctggat cgccagaatc    3720
gttatgtgaa cctgaaaaaa aacaatccga aggtgccga tctgctgaaa gccagatgg    3780
```

```
cagataacat tacagcacgc tttaatcgtt atcgtcgtat gctggaaggt ccgaatacca   3840
aagcagcagc accgagcggt aatcatgtga ccattctgta tggtagtgaa accggtaata   3900
gcgaaggtct ggcaaaagaa ctggccaccg attttgaacg tcgtgaatat agcgttgcag   3960
ttcaggccct ggatgatatt gatgttgcgg atctggaaaa tatgggcttt gttgttattg   4020
ccgtttcaac ctgtggtcag ggccagtttc cgcgtaatag tcagctgttt tggcgtgaac   4080
tgcagcgtga taaccggaa ggttggctga aaaatctgaa atacaccgtt tttgcctgg    4140 gtgatagcac ctattacttt tattgtcata ccgccaaaca aatcgatgca cgtctggcag   4200
cgctgggtgc acagcgtgtt gttccgattg gtttcggtga tgatggtgat gaagatatgt   4260
ttcataccgg cttcaataat tggattccga gcgtttggaa tgagctgaaa accaaaactc   4320
cggaagaagc actgtttacc ccgtcaattg ccgttcagct gaccccgaat gcaacaccgc   4380
aggattttca ttttgccaaa agcacaccgg tgctgagcat taccggtgca gaacgtatta   4440
caccggcaga tcatacccgc aattttgtta ccattcgttg gaaaaccgat ctgagctatc   4500
aggttggtga tagcctgggt gttttccag aaaataccg tagcgttgtt gaagaattcc    4560
tgcagtatta tggcctgaac ccgaaagatg ttattaccat tgaaaataaa ggctcacgcg   4620
aactgccgca ttgtatggcc gttggtgacc tgtttaccaa agttctggat attctgggta   4680
aaccgaataa ccgcttctat aaaaccctga gctatttcgc cgttgataaa gcagaaaaag   4740
aacgcctgct gaaaattgca gaaatgggtc cggaatatag caacattctg tcagagatgt   4800
atcattatgc cgacatcttt catatgtttc gagcgcacg tccgacactg cagtatctga    4860
ttgaaatgat cccgaacatt aaaccgcgtt attatagcat tagtagcgca ccgattcata   4920
ctccgggtga agtgcatagc ctggttctga ttgatacctg gattaccctg agcggtaaac   4980
atcgtacggg tctgacctgt accatgctgg aacatctgca ggcaggtcag gtggtggatg   5040
gttgtattca tccgaccgca atggaatttc cggatcatga aaaaccggtt gttatgtgtg   5100
caatgggttc aggtctggca ccttttgttg catttctgcg tgaacgtagc accctgcgta   5160
aacagggtaa aaaaacgggc aatatggcgc tgtattttgg caatcgttac gaaaaaaccg   5220
aatttctgat gaaagaggaa ctgaaaggcc atatcaatga tggtctgctg acactgcgtt   5280
gtgcatttag ccgtgatgat ccgaaaaaaa aagtctatgt gcaggatctg atcaaaatgg   5340
atgaaaaaat gatgtatgat tacctggtgg ttcagaaagg cagcatgtat tgttgtggta   5400
gccgtagttt tatcaaaccg gtgcaagaaa gcctgaaaca ttgttttatg aaagcgggtg   5460
gtctgaccgc agaacaggca gaaaatgaag ttattgatat gtttaccacg ggtcgctata   5520
acattgaagc gtggcggccg taaaacgaaa ggctcagtcg aaagactg               5568
```

<210> SEQ ID NO 207
<211> LENGTH: 14039
<212> TYPE: DNA
<213> ORGANISM: Artificial
<220> FEATURE:
<223> OTHER INFORMATION: pMU2924

<400> SEQUENCE: 207

```
ctgacgggct tgtctgctcc cggcatccgc ttacagacaa gctgtgaccg tctccgggag     60
ctgcatgtgt cagaggtttt caccgtcatc accgaaacgc gcgagacgaa agggcctcgt    120
gatacgccta ttttatagg ttaatgtcat gataataatg gtttcttacg cagttgctgg     180
atatcagagg ttaatgcgag agagagtttt ccctgccatt cctgccaggg agaaaaaatc    240
```

-continued

```
agtttatcga tattgatcca ggtgttaggc agcatggcct gccactgcgc gagtgttttt    300
ggagcggctg gcgattgctc cgtctgcggc aatttcgcca gacaagcaga atcaagttct    360
accgtgccga cgttcaataa ccagcggctg ggatgtgaaa ggctggcgtt ggtgatatgc    420
gcaagctgac aatctcccac cagataacgg agatcgggaa tgattaaacc tttacgcgta    480
atgcgtgggc tttcatctaa tgcaatacgt gtcccgagcg gtagccagat gcccgccagc    540
gtgggaaccc acagcccgag cgtcatcagc agcgtcaacg gcacaagaat aatcagtaat    600
aacagcgcga gaacggcttt atatttaccc agcatgggta gttaatatcc tgatttagcg    660
aaaaattaag cattcaatac gggtattgtg gcatgtttaa ccgttcagtt gaaggttgcg    720
cctacactaa gcatagttgt tgatgaattt ttcaatatcg ccatagcttt caattaaatt    780
tgaaattttg taaatatttt ttagtagctt aaatgtgatt caacatcact ggagaaagtc    840
ttatgaaact cgccgtttat agcacaaaac agtacgacaa gaagtacctg caacaggtga    900
acgagttgag ccgtttattt tttctaccca tatccttgaa gcggtgttat aatgccgcgc    960
cctcgatatg gggattttta acgacctgat tttcgggtct cagtagtagt tgacattagc    1020
ggagcactaa aatgtcaata gatgatagga ttgaagacct tcttagaaga agagagatgg    1080
ttttagaagg cggtggttta gataaagtag agaaacaaca ccaaaaggga aagcttaccg    1140
caagagagag gatatacaag cttttagatg aagatagctt tgtggaaata gatgcgtatg    1200
ttgagcacag gtgtattgac tttggcatgg aaaagcaaag gataccggc gaaggcgtag    1260 tgacagggta tgggacgata gatggaaggc ttgtctacgt ttatgcacag gattttacgg    1320
ttttaggagg atcattaggc gagtatcatg caaagaaaat cacaaaaatc atggatatgg    1380
ctttaaagat gggagcaccg ctcattggat taaatgattc cggaggtgcc agaatacagg    1440
aaggcgtcga tgctttatcg ggatatggca acatattttt cagaaacacg ctggcatcag    1500
gcgtaatacc gcaaatatcg gtgataatgg ggcccagcgc tggaggtgca gtttattcgc    1560
ctgctcttac tgactttata ttcatggtag acaagacaag tcagatgttt ataactggac    1620
cgcaggtcat aaaagccgtc acaggtgaag atgtttcggc agaggagctt ggtggatcga    1680
ttactcacag cacgaaaagc ggtgtggcgc attttagggc tgaaaacgac gaagagtgtt    1740
tgaagatggt gaggaagcta ttaagttacc ttccatcaaa caatttggaa gatccgccac    1800
agttggcgac agatgacgac ataaacagat tttccgatag gcttattgag ataatcccag    1860
atagtcctaa taagccatac gatatgaaag aagtaatttc ggaaatagtg gatgaaggcg    1920
tgtattttga atcacaggca atgtatgcgc aaaacataat aacggcattt gcaaggctta    1980
atggaaggac ggtagggata atagcaaatc agcctaaagt tttggctgga tgtctcgaca    2040
tcaatgcgtc tgataaggca tcgaggttta aaggttttg cgatgcattt aacatcccgc    2100
ttctcaatat agtagatgtt ccaggatttt tgcctggaac gaatcaagag tacggtggaa    2160
taatacgcca tggggcaaag atgttgtacg cttactctga ggctacagtg ccaaaagtga    2220
ctctcattgt gaggaaagct tatggcggtg cttaccttgc catgtgcagc aaaagacttag    2280 gagctgattt tgttttggca tggcctactg ctgaaatagc ggtcatggga cctgatgggg    2340
cagcaaacat cgtgtttaaa aatgaaataa atcgtctga tgatcctgtg gctgcaagaa    2400
atgaaaagat aaatgagtac agggagaatt tcgcaaatcc atacagggca gcagcgagag    2460
gatatgtaga tgatgtagtt ctgccgcaag agacgagacc tcgcctcatc tcggcgttcg    2520
atatgcttat gagcaaaagg gagtcaaggc ccagcaaaaa gcatggcaat tttcctgttt    2580
aaaatcgatt taaggggaag tgaaagaatg gaagagataa atgaagaaat agttgctgtc    2640
```

```
attgaagctg cgatttacgc ggcatttggt cagtacgaaa agaatttccg catcaaggta    2700
ataaagagag tggactcaaa tatgccggaa tggagaaaag ctggccttta caatcagatg    2760
agatagatga ggaggatgga aatgaaaaaa tttatagtaa ctgtcaatgg aaaaaaatac    2820
gatgtggaag tagaagaagt aaaagtcgac gtggcaagtg agaaaaaagc aaaagaagat    2880
actgctgcta aaaatgcgtc agatgcaagt gtaaaaagca aacaggttga agtaaaaaac    2940
gaagtcaaag acggtttctc aatcaatgca ccgatgccgg aactatatt ggatgtcaaa    3000 ataagccaag gccagactgt cagacgaggc gatgtgcttt taatactgga agccatgaag    3060
atggaaaatg aaatcacgtc accttacgat ggcacaataa tatccataaa tgtttcaaaa    3120
ggtgcctctg taaatacagg cgatgtgctt ttgtacttaa aatgagagta aaggaggagt    3180
tttaatgtct aagataaaaa taacggagac tgtttttaaga gatgcacatc aatcgttgct    3240
ggcaaccaga atgacaaccg atgaaatgct tcctatagca gaaaaattag atgaagttgg    3300
ttttttctcg ctggaagcat ggggcggtgc tacatttgat gcatgtatga gatttttgaa    3360
tgaagaccca tgggaaagat taagactttt aaagaaggcg attaagaaga cactcttca    3420 aatgctttta agaggtcaaa atttactcgg atataaacac tatcccgatg atgtcgtaaa    3480
tgaatttata ataaaatctg ttgaaaatgg tatagatata ataagaattt ttgatgcgtt    3540
aaatgatgtg agaaatttag aagtgccaat aaaatctgca aaaagtgcag gtgctcatgt    3600
acaggcagct attgtatata cagttagtcc tgtacataat acagatcatt atttgaaagt    3660
ggcaaagtct cttcaagata tgggtgcgga ttccatatgc attaaggata tgtctggaat    3720
attatcaccc tatgttgcat acgatttgat taaatctctg aaaagagcac tttacacgcc    3780
aattcaactg catagccatt atacagcagg actggcttca atgacttatt aaaagccat    3840 agaagctggt gtagacgggg ttgatacagc tatttcttcg cttgccttag aacatcaca    3900 accagctaca gaatcaatcg tggctgcatt gaaagataca gaatatgata cagggctaga    3960
tttaaaattg cttgctgaga tagctcagca ttttaatgta gtcaaacaga atcacaaaaa    4020
tgacagcgat atgtctttgc ttatgtctgt tgatgttaaa gcattagaaa gtcaaatacc    4080 aggggggaatg ttatcaaatt tggtttcaca gctaaagcag cagaatgcat taaacaaata    4140
tcaagacgtc ttgaaagaag ttccaagggt acgcgaagat ttgggatatc tcctcttgt    4200 tactccaatg agccagatgg ttggaaccca ggctgtttta aatgttatta caggggagag    4260
atataaaatc gttcctaaag aaattaaaga ttatgtcaaa ggtttatatg ggatgccacc    4320
agctccaatt tcagattcta tacgaaagaa aataatcggc gatgaagaag taatttcaaa    4380
gaggccagca gatttactaa gtcctcaatt ggatgaattt aaaaatgaga taaggaatt    4440 tatagagcaa gatgaagatg ttttatcata tgcattattt cctcaagtag caagaagatt    4500
tttcgagtat aggcaagcca aaaaatacag aattgattca acattattaa atatcgaaga    4560
aagggttcat ccgatataac ggccgtaaaa cgaaaggctc agtcgaaaga ctgggccttt    4620
cgttttatct gttgtttgtc ggtgaacgct ctcctgagta ggacaaatcc gccgggagcg    4680
gatttgaacg ttgcgaagca acggcccgga gggtggcggg caggacgccc gccataaact    4740
gccaggcatc aaattaagca gaaggccatc ctgacggatg ccttttttgc gtttctacaa    4800
actcttcctg tcgtcatatc tacaagccat ccccccacag atacggtaaa ctagcctcgt    4860
ttttgcatca ggaaagcagc tatgaaccac tcctccagcc aggacagaaa tgcctcgact    4920
tcgctgctgc ccaaggttgc cgggtgacgc acaccgtgga aacggatgaa ggcacgaacc    4980
```

```
cagtggacat aagcctgttc ggttcgtaag ctgtaatgca agtagcgtat gcgctcacgc    5040
aactggtcca gaaccttgac cgaacgcagc ggtggtaacg gcgcagtggc ggttttcatg    5100
gcttgttatg actgtttttt tggggtacag tctatgcctc gggcatccaa gcagcaagcg    5160
cgttacgccg tgggtcgatg tttgatgtta tggagcagca acgatgttac gcagcagggc    5220
agtcgcccta aaacaaagtt aaacatcatg agggaagcgg tgatcgccga agtatcgact    5280
caactatcag aggtagttgg cgtcatcgag cgccatctcg aaccgacgtt gctggccgta    5340
catttgtacg gctccgcagt ggatggcggc ctgaagccac acagtgatat tgatttgctg    5400
gttacggtga ccgtaaggct tgatgaaaca acgcggcgag ctttgatcaa cgacctttg     5460 gaaacttcgg cttcccctgg agagagcgag attctccgcg ctgtagaagt caccattgtt    5520
gtgcacgacg acatcattcc gtggcgttat ccagctaagc gcgaactgca atttggagaa    5580
tggcagcgca atgacattct tgcaggtatc ttcgagccag ccacgatcga cattgatctg    5640
gctatcttgc tgacaaaagc aagagaacat agcgttgcct tggtaggtcc agcggcggag    5700
gaactctttg atccggttcc tgaacaggat ctatttgagg cgctaaatga aaccttaacg    5760
ctatggaact cgccgcccga ctgggctggc gatgagcgaa atgtagtgct tacgttgtcc    5820
cgcatttggt acagcgcagt aaccggcaaa atcgcgccga aggatgtcgc tgccgactgg    5880
gcaatggagc gcctgccggc ccagtatcag cccgtcatac ttgaagctag acaggcttat    5940
cttggacaag aagaagatcg cttggcctcg cgcgcagatc agttggaaga atttgtccac    6000
tacgtgaaag gcgagatcac caaggtagtc ggcaaataac cctcgagcca cccatgacca    6060 aaatcccta acgtgagtta cgcgtcgttc cactgtgaca gcagaagctc tgaccagtat    6120
ttctcagact acgctgcaaa acttaagcaa tctggaaaaa ggcgaaacct gcccgaacga    6180
actggtttaa tcttgccgct cccctgcatt ccagggagc tgattcagat aatcccaat     6240 gacctttcat cctctattct taaaatagtc ctgagtcaga aactgtaatt gagaaccaca    6300
atgaagaaag tagccgcgtt tgttgcgcta agcctgctga tggcgggatg tgtaagtaat    6360
gacaaaattg ctgttacgcc agaacagcta cagcatcatc gctttgtgct ggaaagcgta    6420
aacggtaagc ccgtgaccag cgataaaaat ccgccagaaa tcagctttgg tgaaaaaatg    6480
atgatttccg gcagcatgtg taaccgcttt agcggtgaag gcaaactgtc taatggtgaa    6540
ctgacagcca aagggctggc aatgacccgt atgatgtgcg ctaacccgca gcttaatgaa    6600
ctcgataaca ccattagcga aatgctgaaa gaaggtgcac aagtggatct gaccgcgaac    6660
cagttaacgc tggcgaccgc aaaacagaca ttaacttata agctggcgga tttaatgaat    6720
taatagctgc cacagctccc ggcggcaagt gactgttcgc tacagcgttt gccgttgggt    6780
aatgcacaca tcccaaggtg gcacttttcg gggaaatgtg cgcggaaccc ctatttgttt    6840
atttttctaa atacattcaa atatgtatcc gctcatgaga caataaccct gataaatgct    6900
tcaataatat tgaaaaagga agagtatgag tattcaacat ttccgtgtcg cccttattcc    6960
cttttttgcg gcattttgcc ttcctgtttt tgctcaccca gaaacgctgg tgaaagtaaa    7020
agatgctgaa gatcagttgg gtgcacgagt gggttacatc gaactggatc tcaacagcgg    7080
taagatcctt gagagttttc gccccgaaga acgttttcca atgatgagca cttttaaagt    7140
tctgctatgt ggcgcggtat tatcccgtat tgacgccggg caagagcaac tcggtcgccg    7200
catacactat tctcagaatg acttggttga gtactcacca gtcacagaaa agcatcttac    7260
ggatggcatg acagtaagag aattatgcag tgctgccata accatgagtg ataacactgc    7320
ggccaactta cttctgacaa cgatcggagg accgaaggag ctaaccgctt ttttgcacaa    7380
```

```
catgggggat catgtaactc gccttgatcg ttgggaaccg gagctgaatg aagccatacc   7440
aaacgacgag cgtgacacca cgatgcctgt agcaatggca acaacgttgc gcaaactatt   7500
aactggcgaa ctacttactc tagcttcccg gcaacaatta atagactgga tggaggcgga   7560
taaagttgca ggaccacttc tgcgctcggc ccttccggct ggctggttta ttgctgataa   7620
atctggagcc ggtgagcgtg ggtctcgcgg tatcattgca gcactggggc cagatggtaa   7680
gccctcccgt atcgtagtta tctacacgac ggggagtcag gcaactatgg atgaacgaaa   7740
tagacagatc gctgagatag gtgcctcact gattaagcat tggtaagcga tgaaatgtga   7800
ggtgaatcag ggttttcacc cgattttgtg ctgatcagaa ttttttttct ttttcccccct  7860
tgaaggggcg aagcctcatc cccatttctc tggtcaccag ccgggaaacc acgtaagctc   7920
cggcgtcacc cataacagat acggactttc tcaaaggaga gttatcaatg aacatcaaaa   7980
agtttgcaaa acaagcaaca gtattaacct ttactaccgc actgctggca ggaggcgcaa   8040
ctcaagcgtt tgcgaaagaa acgaaccaaa agccatataa ggaaacatac ggcatttccc   8100
atattacacg ccatgatatg ctgcaaatcc ctgaacagca aaaaaatgaa aaatatcaag   8160
ttcctgagtt cgattcgtcc acaattaaaa atatctcttc tgcaaaaggc ctggacgttt   8220
gggacagctg gccattacaa aacgctgacg gcactgtcgc aaactatcac ggctaccaca   8280
tcgtctttgc attagccgga gatcctaaaa atgcggatga cacatcgatt tacatgttct   8340
atcaaaaagt cggcgaaact tctattgaca gctggaaaaa cgctggccgc gtctttaaag   8400
acagcgacaa attcgatgca aatgattcta tcctaaaaga ccaaacacaa gaatggtcag   8460
gttcagccac atttacatct gacggaaaaa tccgtttatt ctacactgat ttctccggta   8520
aacattacgg caaacaaaca ctgacaactg cacaagttaa cgtatcagca tcagacagct   8580
ctttgaacat caacggtgta gaggattata atcaatctt tgacggtgac ggaaaaacgt    8640
atcaaaatgt acagcagttc atcgatgaag gcaactacag ctcaggcgac aaccatacgc   8700
tgagagatcc tcactacgta gaagataaag gccacaaata cttagtattt gaagcaaaca   8760
ctggaactga agatggctac caaggcgaag aatctttatt taacaaagca tactatggca   8820
aaagcacatc attcttccgt caagaaagtc aaaaacttct gcaaagcgat aaaaaacgca   8880
cggctgagtt agcaaacggc gctctcggta tgattgagct aaacgatgat tacacactga   8940
aaaaagtgat gaaaccgctg attgcatcta acacagtaac agatgaaatt gaacgcgcga   9000
acgtctttaa aatgaacggc aaatggtatc tgttcactga ctcccgcgga tcaaaaatga   9060
cgattgacgg cattacgtct aacgatattt acatgcttgg ttatgtttct aattcttaa    9120
ctggcccata caagccgctg aacaaaactg gccttgtgtt aaaaatggat cttgatccta   9180
acgatgtaac ctttacttac tcacacttcg ctgtacctca agcgaaagga aacaatgtcg   9240
tgattacaag ctatatgaca aacagaggat tctacgcaga caaacaatca cgtttgcgc    9300
ctagcttcct gctgaacatc aaaggcaaga aaacatctgt tgtcaaagac agcatccttg   9360
aacaaggaca attaacagtt aacaaataac caggagctat ttaatggcaa cagttaacca   9420
gctggtacgc aaaccacgtg ctcgcaaagt tgcgaaaagc aacgtgcctg cgctggaagc   9480
atgcccgcaa aaacgtggcg tatgtactcg tgtatatact accactccta aaaaaccgaa   9540
ctccgcgctg cgtaaagtat gccgtgttcg tctgactaac ggtttcgaag tgacttccta   9600
catcggtggt gaaggtcaca acctgcagga gcactccgtg atcctgatcc gtggcggtcg   9660
tgttaaagac ctccccgggtg ttcgttacca caccgtacgt ggtgcgcttg actgctccgg   9720
```

```
cgttaaagac cgtaagcagg ctcgttccaa gtatggcgtg aagcgtccta aggcttaatg   9780
gttctccgtt aagtaaggcc aaatagagga tctgaagatc agcagttcaa cctgttgata   9840
gtacgtacta agctctcatg tttcacgtac taagctctca tgtttaacgt actaagctct   9900
catgttttaac gaactaaacc ctcatggcta acgtactaag ctctcatggc taacgtacta   9960
agctctcatg tttcacgtac taagctctca tgtttgaaca ataaaattaa tataaatcag  10020
caacttaaat agcctctaag gttttaagtt ttataagaaa aaaagaata tataaggctt  10080
ttaaagcttt taaggtttaa cggttgtgga caacaagcca gggatgtaac gcactgagaa  10140
gcccttagag cctctcaaag caattttcag tgacacagga acacttaacg gctgacagac  10200
gctgccgcaa gcactcaggg cgcaagggct gctaaaggaa gcggaacacg tagaaagcca  10260
gtccgcagaa acggtgctga ccccggatga atgtcagcta ctgggctatc tggacaaggg  10320
aaaacgcaag cgcaaagaga aagcaggtag cttgcagtgg gcttacatgg cgatagctag  10380
actgggcggt tttatggaca gcaagcgaac cggaattgcc agctggggcg ccctctggta  10440
aggttgggaa gccctgcaaa gtaaactgga tggcttttctt gccgccaagg atctgatggc  10500
gcagggatc aagatctgat caagagacag gatgaggatc gtttcgcatg attgaacaag  10560
atggattgca cgcaggttct ccggccgctt gggtggagag gctattcggc tatgactggg  10620
cacaacagac aatcggctgc tctgatgccg ccgtgttccg gctgtcagcg caggggcgcc  10680
cggttctttt tgtcaagacc gacctgtccg gtgccctgaa tgaactccaa gacgaggcag  10740
cgcggctatc gtggctggcc acgacgggcg ttccttgcgc agctgtgctc gacgttgtca  10800
ctgaagcggg aagggactgg ctgctattgg gcgaagtgcc ggggcaggat ctcctgtcat  10860
ctcaccttgc tcctgccgag aaagtatcca tcatggctga tgcaatgcgg cggctgcata  10920
cgcttgatcc ggctacctgc ccattcgacc accaagcgaa acatcgcatc gagcgagcac  10980
gtactcggat ggaagccggt cttgtcgatc aggatgatct ggacgaagag catcagggc  11040
tcgcgccagc cgaactgttc gccaggctca aggcgcggat gcccgacggc gaggatctcg  11100
tcgtgaccca tggcgatgcc tgcttgccga atatcatggt ggaaaatggc cgcttttctg  11160
gattcatcga ctgtggccgg ctgggtgtgg cggaccgcta tcaggacata gcgttggcta  11220
cccgtgatat tgctgaagag cttggcggcg aatgggctga ccgcttcctc gtgctttacg  11280
gtatcgccgc tcccgattcg cagcgcatcg ccttctatcg ccttcttgac gagttcttct  11340
gaattccgga tccgaagagg cccgcaccga tcgcccttcc caacagttgc gcagcctgaa  11400
tggcgaatgg cgcctgatgc ggtatttttct ccttacgcat ctgtgcggta tttcacaccg  11460
cataggtaa taactgatat aattaaattg aagctctaat ttgtgagttt agtatacatg  11520
catttactta taatacagtt ttttagtttt gctggccgca tcttctcaaa tatgcttccc  11580
agcctgcttt tctgtaacgt tcaccctcta ccttagcatc ccttcccttt gcaaatagtc  11640
ctcttccaac aataataatg tcagatcctg tagagaccac atcatccacg gttctatact  11700
gttgacccaa tgcgtctccc ttgtcatcta aacccacacc gggtgtcata atcaaccaat  11760
cgtaaccttc atctcttcca cccatgtctc tttgagcaat aaagccgata acaaaatctt  11820
tgtcgctctt cgcaatgtca acagtaccct tagtatattc tccagtagat agggagccct  11880
tgcatgacaa ttctgctaac atcaaaaggc ctctaggttc ctttgttact cttctgccg  11940
cctgcttcaa accgctaaca ataccctggg ccaccacacc gtgtgcattc gtaatgtctg  12000
cccattctgc tattctgtat acaccgcag agtactgcaa tttgactgta ttaccaatgt  12060
cagcaaattt tctgtcttcg aagagtaaaa aattgtactt ggcggataat gcctttagcg  12120
```

```
gcttaactgt gccctccatg gaaaaatcag tcaagatatc cacatgtgtt tttagtaaac    12180
aaattttggg acctaatgct tcaactaact ccagtaattc cttggtggta cgaacatcca    12240
atgaagcaca caagtttgtt tgcttttcgt gcatgatatt aaatagcttg gcagcaacag    12300
gactaggatg agtagcagca cgttcctrat atgtagcttt cgacatgatt tatcttcgtt    12360 tcggttttg ttctgtgcag ttgggttaag aatactgggc aatttcatgt ttcttcaaca     12420
ctacatatgc gtatatatac caatctaagt ctgtgctcct tccttcgttc ttccttctgt    12480
tcggagatta ccgaatcaaa aaatttcaa agaaaccgaa atcaaaaaaa agaataaaaa     12540
aaaaatgatg aattgaaaag ctcttgttac ccatcattga attttgaaca tccgaacctg    12600
ggagttttcc ctgaaacaga tagtatattt gaacctgtat aataatatat agtctagcgc    12660
tttacggaag acaatgtatg tatttcggtt cctggagaaa ctattgcatc tattgcatag    12720
gtaatcttgc acgtcgcatc cccggttcat tttctgcgtt tccatcttgc acttcaatag    12780
catatctttg ttaacgaagc atctgtgctt cattttgtag aacaaaaatg caacgcgaga    12840
gcgctaattt ttcaaacaaa gaatctgagc tgcattttta cagaacagaa atgcaacgcg    12900
aaagcgctat tttaccaacg aagaatctgt gcttcatttt tgtaaaacaa aaatgcaacg    12960
cgagagcgct aatttttcaa acaaagaatc tgagctgcat ttttacagaa cagaaatgca    13020
acgcgagagc gctattttac caacaaagaa tctatacttc tttttttgttc tacaaaaatg    13080 catcccgaga gcgctatttt tctaacaaag catcttagat tacttttttt ctcctttgtg    13140
cgctctataa tgcagtctct tgataacttt ttgcactgta ggtccgttaa ggttagaaga    13200
aggctacttt ggtgtctatt ttctcttcca taaaaaaagc ctgactccac ttcccgcgtt    13260
tactgattac tagcgaagct gcgggtgcat ttttttcaaga taaaggcatc cccgattata    13320
ttctataccg atgtggattg cgcatacttt gtgaacagaa agtgatagcg ttgatgattc    13380
ttcattggtc agaaaattat gaacggtttc ttctattttg tctctatata ctacgtatag    13440
gaaatgttta cattttcgta ttgttttcga ttcactctat gaatagttct tactacaatt    13500
tttttgtcta aagagtaata ctagagataa acataaaaaa tgtagaggtc gagtttagat    13560
gcaagttcaa ggagcgaaag gtggatgggt aggttatata gggatatagc acagagatat    13620
atagcaaaga gatactttg agcaatgttt gtggaagcgg tattcgcaat attttagtag     13680
ctcgttacag tccggtgcgt ttttggtttt ttgaaagtgc gtcttcagag cgcttttggt    13740
tttcaaaagc gctctgaagt tcctatactt tctagctaga gaataggaac ttcggaatag    13800
gaacttcaaa gcgtttccga aaacgagcgc ttccgaaaat gcaacgcgag ctgcgcacat    13860
acagctcact gttcacgtcg cacctatatc tgcgtgttgc ctgtatatat atatacatga    13920
gaagaacggc atagtgcgtg tttatgctta aatgcgttat ggtgcactct cagtacaatc    13980
tgctctgatg ccgcatagtt aagccagccc cgacacccgc caacacccgc tgacgcgcc    14039
```

<210> SEQ ID NO 208
<211> LENGTH: 14251
<212> TYPE: DNA
<213> ORGANISM: Artificial
<220> FEATURE:
<223> OTHER INFORMATION: pMU2969

<400> SEQUENCE: 208

```
agccccgaca cccgccaaca cccgctgacg cgccctgacg ggcttgtctg ctcccggcat       60
ccgcttacag acaagctgtg accgtctccg ggagctgcat gtgtcagagg ttttcaccgt      120
```

-continued

| | |
|---|---|
| catcaccgaa acgcgcgaga cgaaagggcc tcgtgatacg cctattttta taggttaatg | 180 |
| tcatgataat aatggtttct tacgcagttg ctggatatca gaggttaatg cgagagagag | 240 |
| ttttccctgc cattcctgcc agggagaaaa aatcagttta tcgatattga tccaggtgtt | 300 |
| aggcagcatg gcctgccact gcgcgagtgt ttttggagcg gctggcgatt gctccgtctg | 360 |
| cggcaatttc gccagacaag cagaatcaag ttctaccgtg ccgacgttca ataaccagcg | 420 |
| gctgggatgt gaaaggctgg cgttggtgat atgcgcaagc tgacaatctc ccaccagata | 480 |
| acggagatcg ggaatgatta aacctttacg cgtaatgcgt gggctttcat ctaatgcaat | 540 |
| acgtgtcccg agcggtagcc agatgcccgc cagcgtggga acccacagcc cgagcgtcat | 600 |
| cagcagcgtc aacggcacaa gaataatcag taataacagc gcgagaacgg ctttatattt | 660 |
| acccagcatg ggtagttaat atcctgattt agcgaaaaat taagcattca atacgggtat | 720 |
| tgtggcatgt ttaaccgttc agttgaaggt tgcgcctaca ctaagcatag ttgttgatga | 780 |
| atttttcaat atcgccatag ctttcaatta aatttgaaat tttgtaaaat atttttagta | 840 |
| gcttaaatgt gattcaacat cactggagaa agtcttatga aactcgccgt ttatagcaca | 900 |
| aaacagtacg acaagaagta cctgcaacag gtgaacgagt tgagccgttt atttttttcta | 960 |
| cccatatcct tgaagcggtg ttataatgcc gcgccctcga tatggggatt tttaacgacc | 1020 |
| tgattttcgg gtctcagtag tagttgacat tagcggagca ctaaaatgag tccgcgagaa | 1080 |
| attgaggttt ccgagccgcg cgaggttggt atcaccgagc tcgtgctgcg cgatgcccat | 1140 |
| cagagcctga tggccacacg aatggcaatg gaagacatgg tcggcgcctg tgcagacatt | 1200 |
| gatgctgccg ggtactggtc agtggagtgt tggggtggtg ccacgtatga ctcgtgtatc | 1260 |
| cgcttcctca acgaggatcc ttgggagcgt ctgcgcacgt tccgcaagct gatgcccaac | 1320 |
| agccgtctcc agatgctgct gcgtggccag aacctgctgg gttaccgcca ctacaacgac | 1380 |
| gaggtcgtcg atcgcttcgt cgacaagtcc gctgagaacg gcatggacgt gttccgtgtc | 1440 |
| ttcgacgcca tgaatgatcc ccgcaacatg gcgcacgcca tggctgccgt caagaaggcc | 1500 |
| ggcaagcacg cgcagggcac catttgctac acgatcagcc cggtccacac cgttgagggc | 1560 |
| tatgtcaagc ttgctggtca gctgctcgac atgggtgctg attccatcgc cctgaaggac | 1620 |
| atggccgccc tgctcaagcc gcagccggcc tacgacatca tcaaggccat caaggacacc | 1680 |
| tacggccaga gacgcagat caacctgcac tgccactcca ccacgggtgt caccgaggtc | 1740 |
| tccctcatga aggccatcga ggccggcgtc gacgtcgtcg acaccgccat ctcgtccatg | 1800 |
| tcgctcggcc cgggccacaa ccccaccgag tcggttgccg agatgctcga gggcaccggg | 1860 |
| tacaccacca accttgacta cgatcgcctg cacaagatcc gcgatcactt caaggccatc | 1920 |
| cgcccgaagt acaagaagtt cgagtcgaag acgcttgtcg cacctcgat cttcaagtcg | 1980 |
| cagatccccg gcggcatgct ctccaacatg gagtcgcagc tgcgcgccca gggcgccgag | 2040 |
| gacaagatgg acgaggtcat ggcagaggtg ccgcgcgtcc gcaaggccgc cggcttcccg | 2100 |
| cccctggtca ccccgtccag ccagatcgtc ggcacgcagg ccgtgttcaa cgtgatgatg | 2160 |
| ggcgagtaca agaggatgac cggcgagttc gccgacatca tgctcggcta ctacggcgcc | 2220 |
| agcccggccg atcgcgatcc gaaggtggtc aagttggccg aggagcagtc cggcaagaag | 2280 |
| ccgatcaccc agcgcccggc cgatctgctg ccccccgagt gggaggagca gtccaaggag | 2340 |
| gccgcggccc tcaagggctt caacggcacc gacgaggacg tgctcaccta tgcactgttc | 2400 |
| ccgcaggtcg ctccggtctt cttcgagcat cgcgccgagg cccgcacag cgtggctctc | 2460 |
| accgatgccc agctgaaggc cgaggccgag ggcgacgaga agtcgctcgc cgtggccggt | 2520 |

```
cccgtcacct acaacgtgaa cgtgggcgga accgtccgcg aagtcaccgt tcagcaggcg   2580
tgaggatgat tgccaatcat ggctgaaaac aacaatttga agctcgccag caccatggaa   2640
ggtcgcgtgg agcagctcgc agagcagcgc caggtgatcg aagccggtgg cggcgaacgt   2700
cgcgtcgaga agcaacattc ccagggtaag cagaccgctc gtgagcgcct gaacaacctg   2760
ctcgatcccc attcgttcga cgaggtcggc gctttccgca agcaccgcac cacgttgttc   2820
ggcatggaca aggccgtcgt cccggcagat ggcgtggtca ccggccgtgg caccatcctt   2880
ggtcgtcccg tgcacgccgc gtcccaggac ttcacggtca tgggtggttc ggctggcgag   2940
acgcagtcca cgaaggtcgt cgagacgatg gaacaggcgc tgctcaccgg cacgcccttc   3000
ctgttcttct acgattcggg cggcgcccgg atccaggagg catcgactc gctgagcggt   3060 tacggcaaga tgttcttcgc caacgtgaag ctgtcgggcg tcgtgccgca gatcgccatc   3120
attgccggcc cctgtgccgg tggcgcctcg tattcgccgg cactgactga cttcatcatc   3180
atgaccaaga aggcccatat gttcatcacg ggccccagg tcatcaagtc ggtcaccggc   3240
gaggatgtca ccgctgacga actcggtggc gctgaggccc atatggccat ctcgggcaat   3300
atccacttcg tggccgagga cgacgacgcc gcggagctca ttgccaagaa gctgctgagc   3360
ttccttccgc agaacaacac tgaggaagca tccttcgtca acccgaacaa tgacgtcagc   3420
cccaataccg agctgcgcga catcgttccg attgacggca agaagggcta tgacgtgcgc   3480
gatgtcattg ccaagatcgt cgactggggt gactacctcg aggtcaaggc cggctatgcc   3540
accaacctcg tgaccgcctt cgcccgggtc aatggtcgtt cggtgggcat cgtggccaat   3600
cagccgtcgg tgatgtcggg ttgcctcgac atcaacgcct ctgacaaggc cgccgaattc   3660
gtgaatttct gcgattcgtt caacatcccg ctggtgcagc tggtcgacgt gccgggcttc   3720
ctgcccggcg tgcagcagga gtacggcggc atcattcgcc atggcgcgaa gatgctgtac   3780
gcctactccg aggccaccgt gccgaagatc accgtggtgc tccgcaaggc ctacggcggc   3840
tcctacctgg ccatgtgcaa ccgtgacctt ggtgccgacg ccgtgtacgc ctggcccagc   3900
gccgagattg cggtgatggg cgccgagggt gcggcaaatg tgatcttccg caaggagatc   3960
aaggctgccg acgatcccga cgccatgcgc gccgagaaga tcgaggagta ccagaacgcg   4020
ttcaacacgc cgtacgtggc cgccgcccgc ggtcaggtcg acgacgtgat tgacccggct   4080
gatacccgtc gaaagattgc ttccgccctg agatgtacg ccaccaagcg tcagacccgc   4140
ccggcgaaga agcatggaaa cttcccctgc tgagcgagga gagaaattat ggctgatgag   4200
gaagagaagg acctgatgat cgccacgctc aacaagcgcg tcgcgtcatt ggagtctgag   4260
ttgggttcac tccagagcga tacccagggt gtcaccgagg acgtactgac ggccatttcg   4320
gccgccgttg cggcctatct cggcaacgat ggatcggctg aggtcgtcca tttcgccccg   4380
agcccgaact gggtccgcga gggtcgtcgg gctctgcaga accattccat tcgttgatcc   4440
gggagtaact cacatgaaac tgaaggtaac agtcaacggc actgcgtatg acgttgacgt   4500
tgacgtcgac aagtcacacg aaaacccgat gggcaccatc ctgttcggcg gcggcaccgg   4560
cggcgcgccg gcaccgcgcg cagcaggtgg cgcaggcgcc ggtaaggccg agagggcga   4620 gattcccgct ccgctggccg gcaccgtctc caagatcctc gtgaaggagg gtgacacggt   4680
caaggctggt cagaccgtgc tcgttctcga ggccatgaag atggagaccg agatcaacgc   4740
tcccaccgac ggcaaggtcg agaaggtcct tgtcaaggag cgtgacgccg tgcagggcg   4800 tcagggtctc atcaagatcg gctgacggcc gtaaaacgaa aggctcagtc gaaagactgg   4860
```

```
gcctttcgtt ttatctgttg tttgtcggtg aacgctctcc tgagtaggac aaatccgccg    4920
ggagcggatt tgaacgttgc gaagcaacgg cccggagggt ggcgggcagg acgcccgcca    4980
taaactgcca ggcatcaaat taagcagaag gccatcctga cggatggcct ttttgcgttt    5040
ctacaaactc ttcctgtcgt catatctaca agccatcccc ccacagatac ggtaaactag    5100
cctcgttttt gcatcaggaa agcagctatg aaccactcct ccagccagga cagaaatgcc    5160
tcgacttcgc tgctgcccaa ggttgccggg tgacgcacac cgtggaaacg gatgaaggca    5220
cgaacccagt ggacataagc ctgttcggtt cgtaagctgt aatgcaagta gcgtatgcgc    5280
tcacgcaact ggtccagaac cttgaccgaa cgcagcggtg gtaacggcgc agtggcggtt    5340
ttcatggctt gttatgactg ttttttttggg gtacagtcta tgcctcgggc atccaagcag    5400
caagcgcgtt acgccgtggg tcgatgtttg atgttatgga gcagcaacga tgttacgcag    5460
cagggcagtc gccctaaaac aaagttaaac atcatgaggg aagcggtgat cgccgaagta    5520
tcgactcaac tatcagaggt agttggcgtc atcgagcgcc atctcgaacc gacgttgctg    5580
gccgtacatt tgtacggctc cgcagtggat ggcggcctga agccacacag tgatattgat    5640
ttgctggtta cggtgaccgt aaggcttgat gaaacaacgc ggcgagcttt gatcaacgac    5700
cttttggaaa cttcggcttc ccctggagag agcgagattc tccgcgctgt agaagtcacc    5760
attgttgtgc acgacgacat cattccgtgg cgttatccag ctaagcgcga actgcaattt    5820
ggagaatggc agcgcaatga cattcttgca ggtatcttcg agccagccac gatcgacatt    5880
gatctggcta tcttgctgac aaaagcaaga gaacatagcg ttgccttggt aggtccagcg    5940
gcggaggaac tctttgatcc ggttcctgaa caggatctat ttgaggcgct aaatgaaacc    6000
ttaacgctat ggaactcgcc gcccgactgg gctggcgatg agcgaaatgt agtgcttacg    6060
ttgtcccgca tttggtacag cgcagtaacc ggcaaaatcg cgccgaagga tgtcgctgcc    6120
gactgggcaa tggagcgcct gccggcccag tatcagcccg tcatacttga agctagacag    6180
gcttatcttg acaagaaga agatcgcttg gcctcgcgcg cagatcagtt ggaagaattt    6240
gtccactacg tgaaaggcga gatcaccaag gtagtcggca ataaccctc gagccaccca    6300 tgaccaaaat cccttaacgt gagttacgcg tcgttccact gtgacagcag aagctctgac    6360
cagtatttct cagactacgc tgcaaaactt aagcaatctg aaaaaggcg aaacctgccc    6420 gaacgaactg gttaatctt gccgctcccc tgcattccag gggagctgat tcagataatc    6480
cccaatgacc tttcatcctc tattcttaaa atagtcctga gtcagaaact gtaattgaga    6540
accacaatga agaaagtagc cgcgtttgtt gcgctaagcc tgctgatggc gggatgtgta    6600
agtaatgaca aaattgctgt tacgccagaa cagctacagc atcatcgctt tgtgctggaa    6660
agcgtaaacg gtaagcccgt gaccagcgat aaaaatccgc cagaaatcag ctttggtgaa    6720
aaaatgatga tttccggcag catgtgtaac cgctttagcg gtgaaggcaa actgtctaat    6780
ggtgaactga cagccaaagg gctggcaatg acccgtatga tgtgcgctaa cccgcagctt    6840
aatgaactcg ataacaccat tagcgaaatg ctgaagaag gtgcacaagt ggatctgacc    6900
gcgaaccagt taacgctggc gaccgcaaaa cagacattaa cttataagct ggcggattta    6960
atgaattaat agctgccaca gctcccggcg gcaagtgact gttcgctaca gcgtttgccg    7020
ttgggtaatg cacacatccc aaggtggcac ttttcgggga aatgtgcgcg gaacccctat    7080
ttgtttattt ttctaaatac attcaaatat gtatccgctc atgagacaat aaccctgata    7140
aatgcttcaa taatattgaa aaaggaagag tatgagtatt caacatttcc gtgtcgccct    7200
tattcccttt tttgcggcat tttgccttcc tgttttttgct cacccagaaa cgctggtgaa    7260
```

```
agtaaaagat gctgaagatc agttgggtgc acgagtgggt tacatcgaac tggatctcaa   7320
cagcggtaag atccttgaga gttttcgccc cgaagaacgt tttccaatga tgagcacttt   7380
taaagttctg ctatgtggcg cggtattatc ccgtattgac gccgggcaag agcaactcgg   7440
tcgccgcata cactattctc agaatgactt ggttgagtac tcaccagtca cagaaaagca   7500
tcttacggat ggcatgacag taagagaatt atgcagtgct gccataacca tgagtgataa   7560
cactgcggcc aacttacttc tgacaacgat cggaggaccg aaggagctaa ccgcttttt   7620
gcacaacatg ggggatcatg taactcgcct tgatcgttgg gaaccggagc tgaatgaagc   7680
cataccaaac gacgagcgtg acaccacgat gcctgtagca atggcaacaa cgttgcgcaa   7740
actattaact ggcgaactac ttactctagc ttcccggcaa caattaatag actggatgga   7800
ggcggataaa gttgcaggac cacttctgcg ctcggccctt ccggctggct ggtttattgc   7860
tgataaatct ggagccggtg agcgtgggtc tcgcggtatc attgcagcac tggggccaga   7920
tggtaagccc tcccgtatcg tagttatcta cacgacgggg agtcaggcaa ctatggatga   7980
acgaaataga cagatcgctg agataggtgc ctcactgatt aagcattggt aagcgatgaa   8040
atgtgaggtg aatcagggtt ttcacccgat tttgtgctga tcagaatttt ttttcttttt   8100
cccccttgaa ggggcgaagc ctcatcccca tttctctggt caccagccgg gaaaccacgt   8160
aagctccggc gtcacccata acagatacgg actttctcaa aggagagtta tcaatgaaca   8220
tcaaaaagtt tgcaaaacaa gcaacagtat taaccttac taccgcactg ctggcaggag   8280
gcgcaactca agcgtttgcg aaagaaacga accaaaagcc atataaggaa acatacggca   8340
tttcccatat tacacgccat gatatgctgc aaatccctga acagcaaaaa aatgaaaaat   8400
atcaagttcc tgagttcgat tcgtccacaa ttaaaaatat ctcttctgca aaaggcctgg   8460
acgtttggga cagctggcca ttacaaaacg ctgacggcac tgtcgcaaac tatcacggct   8520
accacatcgt ctttgcatta gccggagatc ctaaaaatgc ggatgacaca tcgatttaca   8580
tgttctatca aaaagtcggc gaaacttcta ttgacagctg gaaaaacgct ggccgcgtct   8640
ttaaagacag cgacaaattc gatgcaaatg attctatcct aaaagaccaa acacaagaat   8700
ggtcaggttc agccacattt acatctgacg gaaaaatccg tttattctac actgatttct   8760
ccggtaaaca ttacggcaaa caaacactga caactgcaca agttaacgta tcagcatcag   8820
acagctcttt gaacatcaac ggtgtagagg attataaatc aatctttgac ggtgacggaa   8880
aaacgtatca aaatgtacag cagttcatcg atgaaggcaa ctacagctca ggcgacaacc   8940
atacgctgag agatcctcac tacgtagaag ataaaggcca caatactta gtatttgaag   9000
caaacactgg aactgaagat ggctaccaag gcgaagaatc tttatttaac aaagcatact   9060
atggcaaaag cacatcattc ttccgtcaag aaagtcaaaa acttctgcaa agcgataaaa   9120
aacgcacggc tgagttagca aacggcgctc tcggtatgat tgagctaaac gatgattaca   9180
cactgaaaaa agtgatgaaa ccgctgattg catctaacac agtaacagat gaaattgaac   9240
gcgcgaacgt cttaaaatg aacggcaaat ggtatctgtt cactgactcc cgcggatcaa   9300
aaatgacgat tgacggcatt acgtctaacg atatttacat gcttggttat gtttctaatt   9360
cttaactgg cccatacaag ccgctgaaca aaactggcct tgtgttaaaa atggatcttg   9420
atcctaacga tgtaacccttt acttactcac acttcgctgt acctcaagcg aaggaaaca   9480
atgtcgtgat tacaagctat atgacaaaca gaggattcta cgcagacaaa caatcaacgt   9540
ttgcgcctag cttcctgctg aacatcaaag gcaagaaaac atctgttgtc aaagacagca   9600
```

```
tccttgaaca aggacaatta acagttaaca aataaccagg agctatttaa tggcaacagt    9660
taaccagctg gtacgcaaac cacgtgctcg caaagttgcg aaaagcaacg tgcctgcgct    9720
ggaagcatgc ccgcaaaaac gtggcgtatg tactcgtgta tatactacca ctcctaaaaa    9780
accgaactcc gcgctgcgta aagtatgccg tgttcgtctg actaacggtt tcgaagtgac    9840
ttcctacatc ggtggtgaag gtcacaacct gcaggagcac tccgtgatcc tgatccgtgg    9900
cggtcgtgtt aaagacctcc cgggtgttcg ttaccacacc gtacgtggtg cgcttgactg    9960
ctccggcgtt aaagaccgta agcaggctcg ttccaagtat ggcgtgaagc gtcctaaggc   10020
ttaatggttc tccgttaagt aaggccaaat agaggatctg aagatcagca gttcaacctg   10080
ttgatagtac gtactaagct ctcatgtttc acgtactaag ctctcatgtt taacgtacta   10140
agctctcatg tttaacgaac taaaccctca tggctaacgt actaagctct catggctaac   10200
gtactaagct ctcatgtttc acgtactaag ctctcatgtt tgaacaataa aattaatata   10260
aatcagcaac ttaaatagcc tctaaggttt taagttttat aagaaaaaaa agaatatata   10320
aggcttttaa agcttttaag gtttaacggt tgtggacaac aagccaggga tgtaacgcac   10380
tgagaagccc ttagagcctc tcaaagcaat tttcagtgac acaggaacac ttaacggctg   10440
acagacgctg ccgcaagcac tcagggcgca agggctgcta aaggaagcgg aacacgtaga   10500
aagccagtcc gcagaaacgg tgctgacccc ggatgaatgt cagctactgg gctatctgga   10560
caagggaaaa cgcaagcgca aagagaaagc aggtagcttg cagtgggctt acatggcgat   10620
agctagactg ggcggtttta tggacagcaa gcgaaccgga attgccagct ggggcgccct   10680
ctggtaaggt tgggaagccc tgcaaagtaa actggatggc tttcttgccg ccaaggatct   10740
gatggcgcag gggatcaaga tctgatcaag agacaggatg aggatcgttt cgcatgattg   10800
aacaagatgg attgcacgca ggttctccgg ccgcttgggt ggagaggcta ttcggctatg   10860
actgggcaca acagacaatc ggctgctctg atgccgccgt gttccggctg tcagcgcagg   10920
ggcgcccggt tctttttgtc aagaccgacc tgtccggtgc cctgaatgaa ctccaagacg   10980
aggcagcgcg gctatcgtgg ctggccacga cgggcgttcc ttgcgcagct gtgctcgacg   11040
ttgtcactga gcgggaagg gactggctgc tattgggcga agtgccgggg caggatctcc   11100
tgtcatctca ccttgctcct gccgagaaag tatccatcat ggctgatgca atgcggcggc   11160
tgcatacgct tgatccggct acctgcccat tcgaccacca agcgaaacat cgcatcgagc   11220
gagcacgtac tcggatggaa gccggtcttg tcgatcagga tgatctggac gaagagcatc   11280
aggggctcgc gccagccgaa ctgttcgcca ggctcaaggc gcggatgccc gacggcgagg   11340
atctcgtcgt gacccatggc gatgcctgct tgccgaatat catggtggaa aatggccgct   11400
tttctggatt catcgactgt ggccggctgg gtgtggcgga ccgctatcag gacatagcgt   11460
tggctacccg tgatattgct gaagagcttg gcggcgaatg ggctgaccgc ttcctcgtgc   11520
tttacggtat cgccgctccc gattcgcagc gcatcgcctt ctatcgcctt cttgacgagt   11580
tcttctgaat tccggatccg aagaggcccg caccgatcgc ccttcccaac agttgcgcag   11640
cctgaatggc gaatggcgcc tgatgcggta ttttctcctt acgcatctgt gcggtatttc   11700
acaccgcata gggtaataac tgatataatt aaattgaagc tctaatttgt gagtttagta   11760
tacatgcatt tacttataat acagtttttt agttttgctg gccgcatctt ctcaaatatg   11820
cttcccagcc tgcttttctg taacgttcac cctctacctt agcatccctt cccttttgcaa   11880 atagtcctct tccaacaata ataatgtcag atcctgtaga gaccacatca tccacggttc   11940
tatactgttg acccaatgcg tctcccttgt catctaaacc cacaccgggt gtcataatca   12000
```

```
accaatcgta accttcatct cttccaccca tgtctctttg agcaataaag ccgataacaa    12060
aatctttgtc gctcttcgca atgtcaacag taccctttagt atattctcca gtagataggg    12120
agcccttgca tgacaattct gctaacatca aaaggcctct aggttccttt gttacttctt    12180
ctgccgcctg cttcaaaccg ctaacaatac ctgggcccac cacaccgtgt gcattcgtaa    12240
tgtctgccca ttctgctatt ctgtatacac ccgcagagta ctgcaatttg actgtattac    12300
caatgtcagc aaattttctg tcttcgaaga gtaaaaaatt gtacttggcg ataatgcct    12360 ttagcggctt aactgtgccc tccatggaaa aatcagtcaa gatatccaca tgtgttttta    12420
gtaaacaaat tttgggacct aatgcttcaa ctaactccag taattccttg gtggtacgaa    12480
catccaatga agcacacaag tttgtttgct tttcgtgcat gatattaaat agcttggcag    12540
caacaggact aggatgagta gcagcacgtt ccttatatgt agctttcgac atgatttatc    12600
ttcgtttcgg ttttttgttct gtgcagttgg gttaagaata ctgggcaatt tcatgtttct    12660
tcaacactac atatgcgtat atataccaat ctaagtctgt gctccttcct tcgttcttcc    12720
ttctgttcgg agattaccga atcaaaaaaa tttcaaagaa accgaaatca aaaaaaagaa    12780
taaaaaaaaa atgatgaatt gaaagctct tgttacccat cattgaattt tgaacatccg    12840
aacctgggag ttttccctga aacagatagt atatttgaac ctgtataata atatatagtc    12900
tagcgcttta cggaagacaa tgtatgtatt tcggttcctg gagaaactat tgcatctatt    12960
gcataggtaa tcttgcacgt cgcatcccgg gttcattttc tgcgtttcca tcttgcactt    13020
caatagcata tctttgttaa cgaagcatct gtgcttcatt ttgtagaaca aaaatgcaac    13080
gcgagagcgc taatttttca aacaaagaat ctgagctgca ttttacaga acagaaatgc    13140 aacgcgaaag cgctattta ccaacgaaga atctgtgctt cattttgta aaacaaaat    13200 gcaacgcgag agcgctaatt tttcaaacaa agaatctgag ctgcattttt acagaacaga    13260
aatgcaacgc gagagcgcta ttttaccaac aaagaatcta tacttctttt ttgttctaca    13320
aaaatgcatc ccgagagcgc tatttttcta acaaagcatc ttagattact tttttttctcc    13380 tttgtgcgct ctataatgca gtctcttgat aacttttttgc actgtaggtc cgttaaggtt    13440
agaagaaggc tactttggtg tctatttttct cttccataaa aaaagcctga ctccacttcc    13500
cgcgtttact gattactagc gaagctgcgg gtgcattttt tcaagataaa ggcatccccg    13560
attatattct ataccgatgt ggattgcgca tactttgtga acgaaagtg atagcgttga    13620 tgattcttca ttggtcagaa aattatgaac ggtttcttct atttttgtctc tatatactac    13680 gtataggaaa tgtttacatt ttcgtattgt tttcgattca ctctatgaat agttcttact    13740 acaattttt tgtctaaaga gtaatactag agataaacat aaaaaatgta gaggtcgagt    13800
ttagatgcaa gttcaaggag cgaaaggtgg atgggtaggt tatataggga tatagcacag    13860
agatatatag caaagagata cttttgagca atgtttgtgg aagcggtatt cgcaatattt    13920
tagtagctcg ttacagtccg gtgcgttttt ggttttttga agtgcgtct tcagagcgct    13980 tttggttttc aaaagcgctc tgaagttcct atactttcta gctagagaat aggaacttcg    14040
gaataggaac ttcaaagcgt ttccgaaaac gagcgcttcc gaaaatgcaa cgcgagctgc    14100
gcacatacag ctcactgttc acgtcgcacc tatatctgcg tgttgcctgt atatatatat    14160
acatgagaag aacggcatag tgcgtgttta tgcttaaatg cgttatggtg cactctcagt    14220
acaatctgct ctgatgccgc atagttaagc c                                    14251
```

<210> SEQ ID NO 209

```
<211> LENGTH: 910
<212> TYPE: PRT
<213> ORGANISM: B. adolescentis

<400> SEQUENCE: 209
```

| | | | | | | | | | | | | | | |
|---|---|---|---|---|---|---|---|---|---|---|---|---|---|---|
| Met | Ala | Asp | Ala | Lys | Lys | Glu | Glu | Pro | Thr | Lys | Pro | Thr | Pro | Glu |
| 1 | | | | 5 | | | | | 10 | | | | | 15 |
| Glu | Lys | Leu | Ala | Ala | Ala | Glu | Ala | Glu | Val | Asp | Ala | Leu | Val | Lys | Lys |
| | | | | 20 | | | | | 25 | | | | | 30 |
| Gly | Leu | Lys | Ala | Leu | Asp | Glu | Phe | Glu | Lys | Leu | Asp | Gln | Lys | Gln | Val |
| | | | 35 | | | | | 40 | | | | | 45 |
| Asp | His | Ile | Val | Ala | Lys | Ala | Ser | Val | Ala | Ala | Leu | Asn | Lys | His | Leu |
| | 50 | | | | | 55 | | | | | 60 |
| Val | Leu | Ala | Lys | Met | Ala | Val | Glu | Glu | Thr | His | Arg | Gly | Leu | Val | Glu |
| 65 | | | | | 70 | | | | | 75 | | | | | 80 |
| Asp | Lys | Ala | Thr | Lys | Asn | Ile | Phe | Ala | Cys | Glu | His | Val | Thr | Asn | Tyr |
| | | | | 85 | | | | | 90 | | | | | 95 |
| Leu | Ala | Gly | Gln | Lys | Thr | Val | Gly | Ile | Ile | Arg | Glu | Asp | Asp | Val | Leu |
| | | | 100 | | | | | 105 | | | | | 110 |
| Gly | Ile | Asp | Glu | Ile | Ala | Glu | Pro | Val | Gly | Val | Val | Ala | Gly | Val | Thr |
| | | 115 | | | | | 120 | | | | | 125 |
| Pro | Val | Thr | Asn | Pro | Thr | Ser | Thr | Ala | Ile | Phe | Lys | Ser | Leu | Ile | Ala |
| 130 | | | | | 135 | | | | | 140 |
| Leu | Lys | Thr | Arg | Cys | Pro | Ile | Ile | Phe | Gly | Phe | His | Pro | Gly | Ala | Gln |
| 145 | | | | | 150 | | | | | 155 | | | | | 160 |
| Asn | Cys | Ser | Val | Ala | Ala | Ala | Lys | Ile | Val | Arg | Asp | Ala | Ala | Ile | Ala |
| | | | | 165 | | | | | 170 | | | | | 175 |
| Ala | Gly | Ala | Pro | Glu | Asn | Cys | Ile | Gln | Trp | Ile | Glu | His | Pro | Ser | Ile |
| | | | 180 | | | | | 185 | | | | | 190 |
| Glu | Ala | Thr | Gly | Ala | Leu | Met | Lys | His | Asp | Gly | Val | Ala | Thr | Ile | Leu |
| | | 195 | | | | | 200 | | | | | 205 |
| Ala | Thr | Gly | Gly | Pro | Gly | Met | Val | Lys | Ala | Ala | Tyr | Ser | Ser | Gly | Lys |
| 210 | | | | | 215 | | | | | 220 |
| Pro | Ala | Leu | Gly | Val | Gly | Ala | Gly | Asn | Ala | Pro | Ala | Tyr | Val | Asp | Lys |
| 225 | | | | | 230 | | | | | 235 | | | | | 240 |
| Asn | Val | Asp | Val | Val | Arg | Ala | Ala | Asn | Asp | Leu | Ile | Leu | Ser | Lys | His |
| | | | | 245 | | | | | 250 | | | | | 255 |
| Phe | Asp | Tyr | Gly | Met | Ile | Cys | Ala | Thr | Glu | Gln | Ala | Ile | Ile | Ala | Asp |
| | | | 260 | | | | | 265 | | | | | 270 |
| Lys | Asp | Ile | Tyr | Ala | Pro | Leu | Val | Lys | Glu | Leu | Lys | Arg | Arg | Lys | Ala |
| | | 275 | | | | | 280 | | | | | 285 |
| Tyr | Phe | Val | Asn | Ala | Asp | Glu | Lys | Ala | Lys | Leu | Glu | Gln | Tyr | Met | Phe |
| 290 | | | | | 295 | | | | | 300 |
| Gly | Cys | Thr | Ala | Tyr | Ser | Gly | Gln | Thr | Pro | Lys | Leu | Asn | Ser | Val | Val |
| 305 | | | | | 310 | | | | | 315 | | | | | 320 |
| Pro | Gly | Lys | Ser | Pro | Gln | Tyr | Ile | Ala | Lys | Ala | Gly | Phe | Glu | Ile |
| | | | | 325 | | | | | 330 | | | | | 335 |
| Pro | Glu | Asp | Ala | Thr | Ile | Leu | Ala | Ala | Glu | Cys | Lys | Glu | Val | Gly | Glu |
| | | | 340 | | | | | 345 | | | | | 350 |
| Asn | Glu | Pro | Leu | Thr | Met | Glu | Lys | Leu | Ala | Pro | Val | Gln | Ala | Val | Leu |
| | | | 355 | | | | | 360 | | | | | 365 |
| Lys | Ser | Asp | Asn | Lys | Glu | Gln | Ala | Phe | Glu | Met | Cys | Glu | Ala | Met | Leu |
| | 370 | | | | | 375 | | | | | 380 |
| Lys | His | Gly | Ala | Gly | His | Thr | Ala | Ala | Ile | His | Thr | Asn | Asp | Arg | Asp |

```
385                 390                 395                 400
Leu Val Arg Glu Tyr Gly Gln Arg Met His Ala Cys Arg Ile Ile Trp
                405                 410                 415
Asn Ser Pro Ser Ser Leu Gly Val Gly Asp Ile Tyr Asn Ala Ile
                420                 425                 430
Ala Pro Ser Leu Thr Leu Gly Cys Gly Ser Tyr Gly Asn Ser Val
                435                 440                 445
Ser Gly Asn Val Gln Ala Val Asn Leu Ile Asn Ile Lys Arg Ile Ala
            450                 455                 460
Arg Arg Asn Asn Asn Met Gln Trp Phe Lys Ile Pro Ala Lys Thr Tyr
465                 470                 475                 480
Phe Glu Pro Asn Ala Ile Lys Tyr Leu Arg Asp Met Tyr Gly Ile Glu
                485                 490                 495
Lys Ala Val Ile Val Cys Asp Lys Val Met Glu Gln Leu Gly Ile Val
                500                 505                 510
Asp Lys Ile Ile Asp Gln Leu Arg Ala Arg Ser Asn Arg Val Thr Phe
            515                 520                 525
Arg Ile Ile Asp Tyr Val Glu Pro Glu Pro Ser Val Glu Thr Val Glu
530                 535                 540
Arg Gly Ala Ala Met Met Arg Glu Glu Phe Glu Pro Asp Thr Ile Ile
545                 550                 555                 560
Ala Val Gly Gly Gly Ser Pro Met Asp Ala Ser Lys Ile Met Trp Leu
                565                 570                 575
Leu Tyr Glu His Pro Glu Ile Ser Phe Ser Asp Val Arg Glu Lys Phe
                580                 585                 590
Phe Asp Ile Arg Lys Arg Ala Phe Lys Ile Pro Pro Leu Gly Lys Lys
            595                 600                 605
Ala Lys Leu Val Cys Ile Pro Thr Ser Ser Gly Thr Gly Ser Glu Val
            610                 615                 620
Thr Pro Phe Ala Val Ile Thr Asp His Lys Thr Gly Tyr Lys Tyr Pro
625                 630                 635                 640
Ile Thr Asp Tyr Ala Leu Thr Pro Ser Val Ala Ile Val Asp Pro Val
                645                 650                 655
Leu Ala Arg Thr Gln Pro Arg Lys Leu Ala Ser Asp Ala Gly Phe Asp
                660                 665                 670
Ala Leu Thr His Ala Phe Glu Ala Tyr Val Ser Val Tyr Ala Asn Asp
                675                 680                 685
Phe Thr Asp Gly Met Ala Leu His Ala Ala Lys Leu Val Trp Asp Asn
                690                 695                 700
Leu Ala Glu Ser Val Asn Gly Glu Pro Gly Glu Lys Thr Arg Ala
705                 710                 715                 720
Gln Glu Lys Met His Asn Ala Ala Thr Met Ala Gly Met Ala Phe Gly
                725                 730                 735
Ser Ala Phe Leu Gly Met Cys His Gly Met Ala His Thr Ile Gly Ala
                740                 745                 750
Leu Cys His Val Ala His Gly Arg Thr Asn Ser Ile Leu Leu Pro Tyr
            755                 760                 765
Val Ile Arg Tyr Asn Gly Ser Val Pro Glu Pro Thr Ser Trp Pro
            770                 775                 780
Lys Tyr Asn Lys Tyr Ile Ala Pro Glu Arg Tyr Gln Glu Ile Ala Lys
785                 790                 795                 800
Asn Leu Gly Val Asn Pro Gly Lys Thr Pro Glu Glu Gly Val Glu Asn
                805                 810                 815
```

Leu Ala Lys Ala Val Glu Asp Tyr Arg Asp Asn Lys Leu Gly Met Asn
            820                 825                 830

Lys Ser Phe Gln Glu Cys Gly Val Asp Glu Asp Tyr Tyr Trp Ser Ile
        835                 840                 845

Ile Asp Gln Ile Gly Met Arg Ala Tyr Glu Asp Gln Cys Ala Pro Ala
    850                 855                 860

Asn Pro Arg Ile Pro Gln Ile Glu Asp Met Lys Asp Ile Ala Ile Ala
865                 870                 875                 880

Ala Tyr Tyr Gly Val Ser Gln Ala Glu Gly His Lys Leu Arg Val Gln
                885                 890                 895

Arg Gln Gly Glu Ala Ala Thr Glu Glu Ala Ser Glu Arg Ala
            900                 905                 910

<210> SEQ ID NO 210
<211> LENGTH: 292
<212> TYPE: PRT
<213> ORGANISM: B. adolescentis

<400> SEQUENCE: 210

Met Ser Glu His Ile Phe Arg Ser Thr Thr Arg His Met Leu Arg Asp
1               5                   10                  15

Ser Lys Asp Tyr Val Asn Gln Thr Leu Met Gly Gly Leu Ser Gly Phe
            20                  25                  30

Glu Ser Pro Ile Gly Leu Asp Arg Leu Asp Arg Ile Lys Ala Leu Lys
        35                  40                  45

Ser Gly Asp Ile Gly Phe Val His Ser Trp Asp Ile Asn Thr Ser Val
    50                  55                  60

Asp Gly Pro Gly Thr Arg Met Thr Val Phe Met Ser Gly Cys Pro Leu
65                  70                  75                  80

Arg Cys Gln Tyr Cys Gln Asn Pro Asp Thr Trp Lys Met Arg Asp Gly
                85                  90                  95

Lys Pro Val Tyr Tyr Glu Ala Met Val Lys Lys Ile Glu Arg Tyr Ala
            100                 105                 110

Asp Leu Phe Lys Ala Thr Gly Gly Ile Thr Phe Ser Gly Gly Glu
        115                 120                 125

Ser Met Met Gln Pro Ala Phe Val Ser Arg Val Phe His Ala Ala Lys
    130                 135                 140

Gln Met Gly Val His Thr Cys Leu Asp Thr Ser Gly Phe Leu Gly Ala
145                 150                 155                 160

Ser Tyr Thr Asp Asp Met Val Asp Ile Asp Leu Cys Leu Leu Asp
                165                 170                 175

Val Lys Ser Gly Asp Glu Glu Thr Tyr His Lys Val Thr Gly Gly Ile
            180                 185                 190

Leu Gln Pro Thr Ile Asp Phe Gly Gln Arg Leu Ala Lys Ala Gly Lys
        195                 200                 205

Lys Ile Trp Val Arg Phe Val Leu Val Pro Gly Leu Thr Ser Ser Glu
    210                 215                 220

Glu Asn Val Glu Asn Val Ala Lys Ile Cys Glu Thr Phe Gly Asp Ala
225                 230                 235                 240

Leu Glu His Ile Asp Val Leu Pro Phe His Leu Gly Arg Pro Lys
                245                 250                 255

Trp His Met Leu Asn Ile Pro Tyr Pro Leu Glu Asp Gln Lys Gly Pro
            260                 265                 270

Ser Ala Ala Met Lys Gln Arg Val Val Glu Gln Phe Gln Ser His Gly

-continued

```
                275                 280                 285

Phe Thr Val Tyr
    290

<210> SEQ ID NO 211
<211> LENGTH: 791
<212> TYPE: PRT
<213> ORGANISM: B. adolescentis

<400> SEQUENCE: 211

Met Ala Val Asp Ala Thr Ala Val Ser Gln Glu Leu Glu Ala
1               5                   10                  15

Lys Ala Trp Glu Gly Phe Thr Glu Gly Asn Trp Gln Lys Asp Ile Asp
            20                  25                  30

Val Arg Asp Phe Ile Gln Lys Asn Tyr Thr Pro Tyr Glu Gly Asp Glu
        35                  40                  45

Ser Phe Leu Ala Asp Ala Thr Asp Lys Thr Lys His Leu Trp Lys Tyr
    50                  55                  60

Leu Asp Asp Asn Tyr Leu Ser Val Glu Arg Lys Gln Arg Val Tyr Asp
65                  70                  75                  80

Val Asp Thr His Thr Pro Ala Gly Ile Asp Ala Phe Pro Ala Gly Tyr
                85                  90                  95

Ile Asp Ser Pro Glu Val Asp Asn Val Ile Val Gly Leu Gln Thr Asp
            100                 105                 110

Val Pro Cys Lys Arg Ala Met Met Pro Asn Gly Gly Trp Arg Met Val
        115                 120                 125

Glu Gln Ala Ile Lys Glu Ala Gly Lys Glu Pro Asp Pro Glu Ile Lys
    130                 135                 140

Lys Ile Phe Thr Lys Tyr Arg Lys Thr His Asn Asp Gly Val Phe Gly
145                 150                 155                 160

Val Tyr Thr Lys Gln Ile Lys Val Ala Arg His Asn Lys Ile Leu Thr
                165                 170                 175

Gly Leu Pro Asp Ala Tyr Gly Arg Gly Arg Ile Ile Gly Asp Tyr Arg
            180                 185                 190

Arg Val Ala Leu Tyr Gly Val Asn Ala Leu Ile Lys Phe Lys Gln Arg
        195                 200                 205

Asp Lys Asp Ser Ile Pro Tyr Arg Asn Asp Phe Thr Glu Pro Glu Ile
    210                 215                 220

Glu His Trp Ile Arg Phe Arg Glu Glu His Asp Glu Gln Ile Lys Ala
225                 230                 235                 240

Leu Lys Gln Leu Ile Asn Leu Gly Asn Glu Tyr Gly Leu Asp Leu Ser
                245                 250                 255

Arg Pro Ala Gln Thr Ala Gln Glu Ala Val Gln Trp Thr Tyr Met Gly
            260                 265                 270

Tyr Leu Ala Ser Val Lys Ser Gln Asp Gly Ala Ala Met Ser Phe Gly
        275                 280                 285

Arg Val Ser Thr Phe Phe Asp Val Tyr Phe Glu Arg Asp Leu Lys Ala
    290                 295                 300

Gly Lys Ile Thr Glu Thr Asp Ala Gln Glu Ile Ile Asp Asn Leu Val
305                 310                 315                 320

Met Lys Leu Arg Ile Val Arg Phe Leu Arg Thr Lys Asp Tyr Asp Ala
                325                 330                 335

Ile Phe Ser Gly Asp Pro Tyr Trp Ala Thr Trp Ser Asp Ala Gly Phe
            340                 345                 350
```

-continued

Gly Asp Asp Gly Arg Thr Met Val Thr Lys Thr Ser Phe Arg Leu Leu
        355                 360                 365

Asn Thr Leu Thr Leu Glu His Leu Gly Pro Gly Pro Glu Pro Asn Ile
    370                 375                 380

Thr Ile Phe Trp Asp Pro Lys Leu Pro Glu Ala Tyr Lys Arg Phe Cys
385                 390                 395                 400

Ala Arg Ile Ser Ile Asp Thr Ser Ala Ile Gln Tyr Glu Ser Asp Lys
            405                 410                 415

Glu Ile Arg Ser His Trp Gly Asp Ala Ala Ile Ala Cys Cys Val
        420                 425                 430

Ser Pro Met Arg Val Gly Lys Gln Met Gln Phe Phe Ala Ala Arg Val
        435                 440                 445

Asn Ser Ala Lys Ala Leu Leu Tyr Ala Ile Asn Gly Gly Arg Asp Glu
    450                 455                 460

Met Thr Gly Met Gln Val Ile Asp Lys Gly Val Ile Asp Pro Ile Lys
465                 470                 475                 480

Pro Glu Ala Asp Gly Thr Leu Asp Tyr Glu Lys Val Lys Ala Asn Tyr
            485                 490                 495

Glu Lys Ala Leu Glu Trp Leu Ser Glu Thr Tyr Val Met Ala Leu Asn
        500                 505                 510

Ile Ile His Tyr Met His Asp Lys Tyr Ala Tyr Glu Ser Ile Glu Met
        515                 520                 525

Ala Leu His Asp Lys Glu Val Tyr Arg Thr Leu Gly Cys Gly Met Ser
        530                 535                 540

Gly Leu Ser Ile Ala Ala Asp Ser Leu Ser Ala Cys Lys Tyr Ala Lys
545                 550                 555                 560

Val Tyr Pro Ile Tyr Asn Lys Asp Ala Lys Thr Thr Pro Gly His Glu
            565                 570                 575

Asn Glu Tyr Val Glu Gly Ala Asp Asp Leu Ile Val Gly Tyr Arg
        580                 585                 590

Thr Glu Gly Asp Phe Pro Leu Tyr Gly Asn Asp Asp Arg Ala Asp
        595                 600                 605

Asp Ile Ala Lys Trp Val Val Ser Thr Val Met Gly Gln Val Lys Arg
610                 615                 620

Leu Pro Val Tyr Arg Asp Ala Val Pro Thr Gln Ser Ile Leu Thr Ile
625                 630                 635                 640

Thr Ser Asn Val Glu Tyr Gly Lys Ala Thr Gly Ala Phe Pro Ser Gly
            645                 650                 655

His Lys Lys Gly Thr Pro Tyr Ala Pro Gly Ala Asn Pro Glu Asn Gly
            660                 665                 670

Met Asp Ser His Gly Met Leu Pro Ser Met Phe Ser Val Gly Lys Ile
        675                 680                 685

Asp Tyr Asn Asp Ala Leu Asp Gly Ile Ser Leu Thr Asn Thr Ile Thr
        690                 695                 700

Pro Asp Gly Leu Gly Arg Asp Glu Glu Arg Ile Gly Asn Leu Val
705                 710                 715                 720

Gly Ile Leu Asp Ala Gly Asn Gly His Gly Leu Tyr His Ala Asn Ile
            725                 730                 735

Asn Val Leu Arg Lys Glu Gln Leu Glu Asp Ala Val Glu His Pro Glu
        740                 745                 750

Lys Tyr Pro His Leu Thr Val Arg Val Ser Gly Tyr Ala Val Asn Phe
        755                 760                 765

Val Lys Leu Thr Lys Glu Gln Gln Leu Asp Val Ile Ser Arg Thr Phe

```
                770              775              780
His Gln Gly Ala Val Val Asp
785                 790
```

<210> SEQ ID NO 212
<211> LENGTH: 26
<212> TYPE: DNA
<213> ORGANISM: Artificial
<220> FEATURE:
<223> OTHER INFORMATION: X11316

<400> SEQUENCE: 212
gtaatacatc acctcgatga aagaga                                  26

<210> SEQ ID NO 213
<211> LENGTH: 29
<212> TYPE: DNA
<213> ORGANISM: Artificial
<220> FEATURE:
<223> OTHER INFORMATION: X11816

<400> SEQUENCE: 213
gcagtcatca ggatcgtagg agataagca                               29

<210> SEQ ID NO 214
<211> LENGTH: 30
<212> TYPE: DNA
<213> ORGANISM: Artificial
<220> FEATURE:
<223> OTHER INFORMATION: X11821

<400> SEQUENCE: 214
tcacaagagt gtgcagaaat aggaggtgga                              30

<210> SEQ ID NO 215
<211> LENGTH: 59
<212> TYPE: DNA
<213> ORGANISM: Artificial
<220> FEATURE:
<223> OTHER INFORMATION: X11822

<400> SEQUENCE: 215 gttggggaa aaagaggcaa caggaaagat cagagacagc aagcattgat aaggaaggg    59

<210> SEQ ID NO 216
<211> LENGTH: 59
<212> TYPE: DNA
<213> ORGANISM: Artificial
<220> FEATURE:
<223> OTHER INFORMATION: X11823

<400> SEQUENCE: 216
cccttcctta tcaatgcttg ctgtctctga tctttcctgt tgcctctttt tcccccaac    59

<210> SEQ ID NO 217
<211> LENGTH: 29
<212> TYPE: DNA
<213> ORGANISM: Artificial
<220> FEATURE:
<223> OTHER INFORMATION: X11824

<400> SEQUENCE: 217
aagcctacag gcgcaagata acacatcac                               29

<210> SEQ ID NO 218

```
<211> LENGTH: 35
<212> TYPE: DNA
<213> ORGANISM: Artificial
<220> FEATURE:
<223> OTHER INFORMATION: X11829

<400> SEQUENCE: 218
ctcagcattg atcttagcag attcaggatc taggt                              35

<210> SEQ ID NO 219
<211> LENGTH: 59
<212> TYPE: DNA
<213> ORGANISM: Artificial
<220> FEATURE:
<223> OTHER INFORMATION: X11830

<400> SEQUENCE: 219
tatgttatct ttctccaata aatctaatct tcatgtagac tatcagcagc agcagacat    59

<210> SEQ ID NO 220
<211> LENGTH: 59
<212> TYPE: DNA
<213> ORGANISM: Artificial
<220> FEATURE:
<223> OTHER INFORMATION: X11831

<400> SEQUENCE: 220
gataatataa agatgtctgc tgctgctgat agtctacatg aagattagat ttattggag    59

<210> SEQ ID NO 221
<211> LENGTH: 30
<212> TYPE: DNA
<213> ORGANISM: Artificial
<220> FEATURE:
<223> OTHER INFORMATION: X11845

<400> SEQUENCE: 221
ttacttgtga aactgtctcc gctatgtcag                                    30

<210> SEQ ID NO 222
<211> LENGTH: 59
<212> TYPE: DNA
<213> ORGANISM: Artificial
<220> FEATURE:
<223> OTHER INFORMATION: X14775

<400> SEQUENCE: 222 cccctccac aaacacaaat attgataata taaagatggc agacgcaaag aagaaggaa     59

<210> SEQ ID NO 223
<211> LENGTH: 34
<212> TYPE: DNA
<213> ORGANISM: Artificial
<220> FEATURE:
<223> OTHER INFORMATION: X14778

<400> SEQUENCE: 223
atttattgga gaaagataac atatcatact ttcc                               34

<210> SEQ ID NO 224
<211> LENGTH: 59
<212> TYPE: DNA
<213> ORGANISM: Artificial
<220> FEATURE:
<223> OTHER INFORMATION: X14829

<400> SEQUENCE: 224
```

```
gaaagtatga tatgttatct ttctccaata aatctagtct tctaggcggg ttatctact          59
```

<210> SEQ ID NO 225
<211> LENGTH: 59
<212> TYPE: DNA
<213> ORGANISM: Artificial
<220> FEATURE:
<223> OTHER INFORMATION: X14835

<400> SEQUENCE: 225

```
caaattctaa ccaacttcaa aatgacatag tacctcatct ataattttta ccctgatct          59
```

<210> SEQ ID NO 226
<211> LENGTH: 59
<212> TYPE: DNA
<213> ORGANISM: Artificial
<220> FEATURE:
<223> OTHER INFORMATION: X14836

<400> SEQUENCE: 226

```
agttagatca gggtaaaaat tatagatgag gtactatgtc attttgaagt tggttagaa          59
```

<210> SEQ ID NO 227
<211> LENGTH: 59
<212> TYPE: DNA
<213> ORGANISM: Artificial
<220> FEATURE:
<223> OTHER INFORMATION: X14837

<400> SEQUENCE: 227

```
ggtccatgta aaatgattgc tccaatgatt gaaattgatt caggtcaaaa tggattcag          59
```

<210> SEQ ID NO 228
<211> LENGTH: 59
<212> TYPE: DNA
<213> ORGANISM: Artificial
<220> FEATURE:
<223> OTHER INFORMATION: X14838

<400> SEQUENCE: 228

```
acgtccctga atccattttg acctgaatca atttcaatca ttggagcaat cattttaca          59
```

<210> SEQ ID NO 229
<211> LENGTH: 59
<212> TYPE: DNA
<213> ORGANISM: Artificial
<220> FEATURE:
<223> OTHER INFORMATION: X14843

<400> SEQUENCE: 229

```
ggtggaacca tttactgtat tttcaatgta acgctagaga ataaattcaa gttaaaaga          59
```

<210> SEQ ID NO 230
<211> LENGTH: 59
<212> TYPE: DNA
<213> ORGANISM: Artificial
<220> FEATURE:
<223> OTHER INFORMATION: X14844

<400> SEQUENCE: 230

```
catcatcttt taacttgaat ttattctcta gcgttacatt gaaaatacag taaatggtt          59
```

<210> SEQ ID NO 231
<211> LENGTH: 26
<212> TYPE: DNA

```
<213> ORGANISM: Artificial
<220> FEATURE:
<223> OTHER INFORMATION: X15380

<400> SEQUENCE: 231
taggtctaga gatctgttta gcttgc                                              26

<210> SEQ ID NO 232
<211> LENGTH: 23
<212> TYPE: DNA
<213> ORGANISM: Artificial
<220> FEATURE:
<223> OTHER INFORMATION: X15382

<400> SEQUENCE: 232
gagactacat gatagtccaa aga                                                 23

<210> SEQ ID NO 233
<211> LENGTH: 59
<212> TYPE: DNA
<213> ORGANISM: Artificial
<220> FEATURE:
<223> OTHER INFORMATION: X15546

<400> SEQUENCE: 233
ggacgaggca agctaaacag atctctagac ctactttata ttatcaatat ttgtgtttg          59

<210> SEQ ID NO 234
<211> LENGTH: 59
<212> TYPE: DNA
<213> ORGANISM: Artificial
<220> FEATURE:
<223> OTHER INFORMATION: X15547

<400> SEQUENCE: 234
ccgtttcttt tctttggact atcatgtagt ctcatttatt ggagaaagat aacatatca          59

<210> SEQ ID NO 235
<211> LENGTH: 59
<212> TYPE: DNA
<213> ORGANISM: Artificial
<220> FEATURE:
<223> OTHER INFORMATION: X15548

<400> SEQUENCE: 235
ggacgaggca agctaaacag atctctagac ctatgataag gaaggggagc gaaggaaaa         59

<210> SEQ ID NO 236
<211> LENGTH: 59
<212> TYPE: DNA
<213> ORGANISM: Artificial
<220> FEATURE:
<223> OTHER INFORMATION: X15549

<400> SEQUENCE: 236
ccgtttcttt tctttggact atcatgtagt ctcctctgat ctttcctgtt gcctcttt          59

<210> SEQ ID NO 237
<211> LENGTH: 59
<212> TYPE: DNA
<213> ORGANISM: Artificial
<220> FEATURE:
<223> OTHER INFORMATION: X15552

<400> SEQUENCE: 237
ccgtttcttt tctttggact atcatgtagt ctcgagtgat tatgagtatt tgtgagcag         59
```

-continued

<210> SEQ ID NO 238
<211> LENGTH: 31
<212> TYPE: DNA
<213> ORGANISM: Artificial
<220> FEATURE:
<223> OTHER INFORMATION: X15553

<400> SEQUENCE: 238
accagcgtct ggtggacaaa cggccttcaa c                              31

<210> SEQ ID NO 239
<211> LENGTH: 59
<212> TYPE: DNA
<213> ORGANISM: Artificial
<220> FEATURE:
<223> OTHER INFORMATION: X15554

<400> SEQUENCE: 239
ggacgaggca agctaaacag atctctagac ctaattaatt ttcagctgtt atttcgatt    59

<210> SEQ ID NO 240
<211> LENGTH: 59
<212> TYPE: DNA
<213> ORGANISM: Artificial
<220> FEATURE:
<223> OTHER INFORMATION: X15555

<400> SEQUENCE: 240
ccgtttcttt tctttggact atcatgtagt ctcgagtgat tatgagtatt tgtgagcag    59

<210> SEQ ID NO 241
<211> LENGTH: 25
<212> TYPE: DNA
<213> ORGANISM: Artificial
<220> FEATURE:
<223> OTHER INFORMATION: X15559

<400> SEQUENCE: 241
ggaaggcacc gatactagaa ctccg                                        25

<210> SEQ ID NO 242
<211> LENGTH: 59
<212> TYPE: DNA
<213> ORGANISM: Artificial
<220> FEATURE:
<223> OTHER INFORMATION: X15564

<400> SEQUENCE: 242
ctaatcaaat caaataaca gctgaaaatt aatctactta ttccttcga gattatatc     59

<210> SEQ ID NO 243
<211> LENGTH: 59
<212> TYPE: DNA
<213> ORGANISM: Artificial
<220> FEATURE:
<223> OTHER INFORMATION: X15565

<400> SEQUENCE: 243
gttcctagat ataatctcga agggaataag tagattaatt ttcagctgtt attttgatt    59

<210> SEQ ID NO 244
<211> LENGTH: 59
<212> TYPE: DNA
<213> ORGANISM: Artificial
<220> FEATURE:

<223> OTHER INFORMATION: X15566

<400> SEQUENCE: 244
tcggatcagt agataacccg cctagaagac taggagtgat tatgagtatt tgtgagcag        59

<210> SEQ ID NO 245
<211> LENGTH: 59
<212> TYPE: DNA
<213> ORGANISM: Artificial
<220> FEATURE:
<223> OTHER INFORMATION: X15567

<400> SEQUENCE: 245
aaaacttctg ctcacaaata ctcataatca ctcctagtct tctaggcggg ttatctact        59

<210> SEQ ID NO 246
<211> LENGTH: 59
<212> TYPE: DNA
<213> ORGANISM: Artificial
<220> FEATURE:
<223> OTHER INFORMATION: X15870

<400> SEQUENCE: 246
ctaatcaaat caaaataaca gctgaaaatt aatgagtgat tatgagtatt tgtgagcag        59

<210> SEQ ID NO 247
<211> LENGTH: 59
<212> TYPE: DNA
<213> ORGANISM: Artificial
<220> FEATURE:
<223> OTHER INFORMATION: X15871

<400> SEQUENCE: 247
aaaacttctg ctcacaaata ctcataatca ctcattaatt ttcagctgtt attttgatt        59

<210> SEQ ID NO 248
<211> LENGTH: 30
<212> TYPE: DNA
<213> ORGANISM: Artificial
<220> FEATURE:
<223> OTHER INFORMATION: X16096

<400> SEQUENCE: 248
catggtgctt agcagcagat gaaagtgtca        30

<210> SEQ ID NO 249
<211> LENGTH: 59
<212> TYPE: DNA
<213> ORGANISM: Artificial
<220> FEATURE:
<223> OTHER INFORMATION: X16097

<400> SEQUENCE: 249
gttcctagat ataatctcga agggaataag tagattaatt ttcagctgtt atttcgatt        59

<210> SEQ ID NO 250
<211> LENGTH: 59
<212> TYPE: DNA
<213> ORGANISM: Artificial
<220> FEATURE:
<223> OTHER INFORMATION: X16098

<400> SEQUENCE: 250
ctaatcaaat cgaaataaca gctgaaaatt aatctactta ttcccttcga gattatatc        59

```
<210> SEQ ID NO 251
<211> LENGTH: 59
<212> TYPE: DNA
<213> ORGANISM: Artificial
<220> FEATURE:
<223> OTHER INFORMATION: X16099

<400> SEQUENCE: 251
aaaacttctg ctcacaaata ctcataatca ctcctagtct tctaggcggg ttatctact      59

<210> SEQ ID NO 252
<211> LENGTH: 59
<212> TYPE: DNA
<213> ORGANISM: Artificial
<220> FEATURE:
<223> OTHER INFORMATION: X16100

<400> SEQUENCE: 252
tcggatcagt agataacccg cctagaagac taggagtgat tatgagtatt tgtgagcag      59

<210> SEQ ID NO 253
<211> LENGTH: 25
<212> TYPE: DNA
<213> ORGANISM: Artificial
<220> FEATURE:
<223> OTHER INFORMATION: X16463

<400> SEQUENCE: 253
cagagtttga agatatccaa atggt                                           25

<210> SEQ ID NO 254
<211> LENGTH: 29
<212> TYPE: DNA
<213> ORGANISM: Artificial
<220> FEATURE:
<223> OTHER INFORMATION: X16464

<400> SEQUENCE: 254
tttgttcttc ttgttattgt attgtgttg                                       29

<210> SEQ ID NO 255
<211> LENGTH: 30
<212> TYPE: DNA
<213> ORGANISM: Artificial
<220> FEATURE:
<223> OTHER INFORMATION: X16465

<400> SEQUENCE: 255
gctaattaac ataaaactca tgattcaacg                                      30

<210> SEQ ID NO 256
<211> LENGTH: 27
<212> TYPE: DNA
<213> ORGANISM: Artificial
<220> FEATURE:
<223> OTHER INFORMATION: X16466

<400> SEQUENCE: 256
acataggttt gcaagcttta taatctg                                         27

<210> SEQ ID NO 257
<211> LENGTH: 59
<212> TYPE: DNA
<213> ORGANISM: Artificial
<220> FEATURE:
<223> OTHER INFORMATION: X16467
```

```
<400> SEQUENCE: 257
agaacaacac aatacaataa caagaagaac aaataggtct agagatctgt ttagcttgc          59

<210> SEQ ID NO 258
<211> LENGTH: 59
<212> TYPE: DNA
<213> ORGANISM: Artificial
<220> FEATURE:
<223> OTHER INFORMATION: X16468

<400> SEQUENCE: 258
aaacgttgaa tcatgagttt tatgttaatt agcgagacta catgatagtc caaagaaaa          59

<210> SEQ ID NO 259
<211> LENGTH: 59
<212> TYPE: DNA
<213> ORGANISM: Artificial
<220> FEATURE:
<223> OTHER INFORMATION: X16469

<400> SEQUENCE: 259
agaacaacac aatacaataa caagaagaac aaactactta ttcccttcga gattatatc          59

<210> SEQ ID NO 260
<211> LENGTH: 59
<212> TYPE: DNA
<213> ORGANISM: Artificial
<220> FEATURE:
<223> OTHER INFORMATION: X16470

<400> SEQUENCE: 260
aaacgttgaa tcatgagttt tatgttaatt agcctagtct tctaggcggg ttatctact          59

<210> SEQ ID NO 261
<211> LENGTH: 25
<212> TYPE: DNA
<213> ORGANISM: Artificial
<220> FEATURE:
<223> OTHER INFORMATION: X16471

<400> SEQUENCE: 261
aagaatctgt tagttcgaac tccag                                              25

<210> SEQ ID NO 262
<211> LENGTH: 30
<212> TYPE: DNA
<213> ORGANISM: Artificial
<220> FEATURE:
<223> OTHER INFORMATION: X16472

<400> SEQUENCE: 262
tttgttggca atatgttttt gctatattac                                         30

<210> SEQ ID NO 263
<211> LENGTH: 25
<212> TYPE: DNA
<213> ORGANISM: Artificial
<220> FEATURE:
<223> OTHER INFORMATION: X16473

<400> SEQUENCE: 263
gccattagta gtgtactcaa acgaa                                              25

<210> SEQ ID NO 264
<211> LENGTH: 24
```

-continued

<212> TYPE: DNA
<213> ORGANISM: Artificial
<220> FEATURE:
<223> OTHER INFORMATION: X16474

<400> SEQUENCE: 264
acgactcaac atatgtatgt tgct                                    24

<210> SEQ ID NO 265
<211> LENGTH: 59
<212> TYPE: DNA
<213> ORGANISM: Artificial
<220> FEATURE:
<223> OTHER INFORMATION: X16475

<400> SEQUENCE: 265
cacgtaatat agcaaaaaca tattgccaac aaataggtct agagatctgt ttagcttgc    59

<210> SEQ ID NO 266
<211> LENGTH: 59
<212> TYPE: DNA
<213> ORGANISM: Artificial
<220> FEATURE:
<223> OTHER INFORMATION: X16476

<400> SEQUENCE: 266
aacaataatt cgtttgagta cactactaat ggcgagacta catgatagtc caaagaaaa    59

<210> SEQ ID NO 267
<211> LENGTH: 59
<212> TYPE: DNA
<213> ORGANISM: Artificial
<220> FEATURE:
<223> OTHER INFORMATION: X16477

<400> SEQUENCE: 267
cacgtaatat agcaaaaaca tattgccaac aaactactta ttcccttcga gattatatc    59

<210> SEQ ID NO 268
<211> LENGTH: 59
<212> TYPE: DNA
<213> ORGANISM: Artificial
<220> FEATURE:
<223> OTHER INFORMATION: X16478

<400> SEQUENCE: 268
aacaataatt cgtttgagta cactactaat ggcctagtct tctaggcggg ttatctact    59

<210> SEQ ID NO 269
<211> LENGTH: 31
<212> TYPE: DNA
<213> ORGANISM: Artificial
<220> FEATURE:
<223> OTHER INFORMATION: X16951

<400> SEQUENCE: 269
atgttccgct gatgtgatgt gcaagataaa c                            31

<210> SEQ ID NO 270
<211> LENGTH: 59
<212> TYPE: DNA
<213> ORGANISM: Artificial
<220> FEATURE:
<223> OTHER INFORMATION: X16952

<400> SEQUENCE: 270
gaggcaagct aaacagatct ctagacctat tgattgatt tgactgtgtt attttgcgt    59

<210> SEQ ID NO 271
<211> LENGTH: 59
<212> TYPE: DNA
<213> ORGANISM: Artificial
<220> FEATURE:
<223> OTHER INFORMATION: X16953

<400> SEQUENCE: 271
ataacctcac gcaaaataac acagtcaaat caatcaaata ggtctagaga tctgtttag    59

<210> SEQ ID NO 272
<211> LENGTH: 59
<212> TYPE: DNA
<213> ORGANISM: Artificial
<220> FEATURE:
<223> OTHER INFORMATION: X16954

<400> SEQUENCE: 272
aaaactttaa ctaataatta gagattaaat cgcttagaga ctacatgata gtccaaaga    59

<210> SEQ ID NO 273
<211> LENGTH: 59
<212> TYPE: DNA
<213> ORGANISM: Artificial
<220> FEATURE:
<223> OTHER INFORMATION: X16955

<400> SEQUENCE: 273 gtcccccgt tcttttctt tggactatca tgtagtctct aagcgattta atctctaat    59

<210> SEQ ID NO 274
<211> LENGTH: 36
<212> TYPE: DNA
<213> ORGANISM: Artificial
<220> FEATURE:
<223> OTHER INFORMATION: X16956

<400> SEQUENCE: 274
tcggtcattg ggtgagttta agcattagca gcaatg    36

<210> SEQ ID NO 275
<211> LENGTH: 59
<212> TYPE: DNA
<213> ORGANISM: Artificial
<220> FEATURE:
<223> OTHER INFORMATION: X16957

<400> SEQUENCE: 275
taaaacttta actaataatt agagattaaa tcgcttattt gattgatttg actgtgtta    59

<210> SEQ ID NO 276
<211> LENGTH: 59
<212> TYPE: DNA
<213> ORGANISM: Artificial
<220> FEATURE:
<223> OTHER INFORMATION: X16958

<400> SEQUENCE: 276
cacgcaaaat aacacagtca atcaatcaa ataagcgatt taatctctaa ttattagtt    59

<210> SEQ ID NO 277
<211> LENGTH: 1128
<212> TYPE: DNA
<213> ORGANISM: S. cerevisiae

<400> SEQUENCE: 277

```
atgtcgaagg gaaaggtttt gctggttctt tacgaaggtg gtaagcatgc tgaagagcag        60
gaaaagttat tggggtgtat tgaaaatgaa cttggtatca gaatttcat tgaagaacag        120
ggatacgagt tggttactac cattgacaag gaccctgagc aacctcaac ggtagacagg        180
gagttgaaag acgctgaaat tgtcattact acgccctttt tccccgccta catctcgaga       240
aacaggattg cagaagctcc taacctgaag ctctgtgtaa ccgctggcgt cggttcagac       300
catgtcgatt tagaagctgc aaatgaacgg aaaatcacgg tcaccgaagt tactggttct       360
aacgtcgttt ctgtcgcaga gcacgttatg gccacaattt tggttttgat aagaaactat       420
aatggtggtc atcaacaagc aattaatggt gagtgggata ttgccggcgt ggctaaaaat       480
gagtatgatc tggaagacaa aataatttca acggtaggtg ccggtagaat tggatatagg       540
gttctggaaa gattggtcgc atttaatccg aagaagttac tgtactacga ctaccaggaa       600
ctacctgcgg aagcaatcaa tagattgaac gaggccagca agcttttcaa tggcagaggt       660
gatattgttc agagagtaga gaaattggag gatatggttg ctcagtcaga tgttgttacc       720
atcaactgtc cattgcacaa ggactcaagg ggtttattca ataaaaagct tatttcccac       780
atgaaagatg gtgcatactt ggtgaatacc gctagaggtg ctatttgtgt cgcagaagat       840
gttgccgagg cagtcaagtc tggtaaattg gctggctatg gtggtgatgt ctgggataag       900
caaccagcac caaaagacca tccctggagg actatggaca ataaggacca cgtgggaaac       960
gcaatgactg ttcatatcag tggcacatct ctggatgctc aaaagaggta cgctcaggga      1020
gtaaagaaca tcctaaatag ttacttttcc aaaaagtttg attaccgtcc acaggatatt      1080
attgtgcaga atggttctta tgccaccaga gcttatggac agaagaaa                    1128
```

<210> SEQ ID NO 278
<211> LENGTH: 376
<212> TYPE: PRT
<213> ORGANISM: S. cerevisiae

<400> SEQUENCE: 278

```
Met Ser Lys Gly Lys Val Leu Leu Val Leu Tyr Glu Gly Gly Lys His
  1               5                  10                  15

Ala Glu Glu Gln Glu Lys Leu Leu Gly Cys Ile Glu Asn Glu Leu Gly
             20                  25                  30

Ile Arg Asn Phe Ile Glu Glu Gln Gly Tyr Glu Leu Val Thr Thr Ile
         35                  40                  45

Asp Lys Asp Pro Glu Pro Thr Ser Thr Val Asp Arg Glu Leu Lys Asp
     50                  55                  60

Ala Glu Ile Val Ile Thr Thr Pro Phe Phe Pro Ala Tyr Ile Ser Arg
 65                  70                  75                  80

Asn Arg Ile Ala Glu Ala Pro Asn Leu Lys Leu Cys Val Thr Ala Gly
                 85                  90                  95

Val Gly Ser Asp His Val Asp Leu Glu Ala Ala Asn Glu Arg Lys Ile
            100                 105                 110

Thr Val Thr Glu Val Thr Gly Ser Asn Val Val Ser Val Ala Glu His
        115                 120                 125

Val Met Ala Thr Ile Leu Val Leu Ile Arg Asn Tyr Asn Gly Gly His
    130                 135                 140

Gln Gln Ala Ile Asn Gly Glu Trp Asp Ile Ala Gly Val Ala Lys Asn
145                 150                 155                 160
```

| | | | | | | | | | | | |
|---|---|---|---|---|---|---|---|---|---|---|---|
|Glu|Tyr|Asp|Leu|Glu|Asp|Lys|Ile|Ile|Ser|Thr|Val|Gly|Ala|Gly|Arg|
| | | |165| | | |170| | | |175|

Ile Gly Tyr Arg Val Leu Glu Arg Leu Val Ala Phe Asn Pro Lys Lys
            180                 185                 190

Leu Leu Tyr Tyr Asp Tyr Gln Glu Leu Pro Ala Glu Ala Ile Asn Arg
            195                 200                 205

Leu Asn Glu Ala Ser Lys Leu Phe Asn Gly Arg Gly Asp Ile Val Gln
        210                 215                 220

Arg Val Glu Lys Leu Glu Asp Met Val Ala Gln Ser Asp Val Val Thr
225                 230                 235                 240

Ile Asn Cys Pro Leu His Lys Asp Ser Arg Gly Leu Phe Asn Lys Lys
                245                 250                 255

Leu Ile Ser His Met Lys Asp Gly Ala Tyr Leu Val Asn Thr Ala Arg
            260                 265                 270

Gly Ala Ile Cys Val Ala Glu Asp Val Ala Glu Ala Val Lys Ser Gly
        275                 280                 285

Lys Leu Ala Gly Tyr Gly Gly Asp Val Trp Asp Lys Gln Pro Ala Pro
    290                 295                 300

Lys Asp His Pro Trp Arg Thr Met Asp Asn Lys Asp His Val Gly Asn
305                 310                 315                 320

Ala Met Thr Val His Ile Ser Gly Thr Ser Leu Asp Ala Gln Lys Arg
                325                 330                 335

Tyr Ala Gln Gly Val Lys Asn Ile Leu Asn Ser Tyr Phe Ser Lys Lys
            340                 345                 350

Phe Asp Tyr Arg Pro Gln Asp Ile Ile Val Gln Asn Gly Ser Tyr Ala
        355                 360                 365

Thr Arg Ala Tyr Gly Gln Lys Lys
    370                 375

<210> SEQ ID NO 279
<211> LENGTH: 1158
<212> TYPE: DNA
<213> ORGANISM: B. stabilis

<400> SEQUENCE: 279
atggctaccg ttttgtgtgt cttgtatcca gatccagttg atggttatcc accacattat      60
gttagagata ccattccagt tattaccaga tacgctgatg tcaaactgc tccaactcca     120
gctggtccac caggttttag accaggtgaa ttggttggtt ctgtttctgg tgctttgggt     180
ttgagaggtt atttggaagc tcatggtcat actttgatcg ttacctctga taaggatggt     240
ccagattctg aattcgaaag aagattgcca gacgccgatg ttgttatttc tcaaccattt     300
tggccagctt acttgaccgc tgaaagaatt gctagagcac aaaattgag attggctttg     360
actgctggta ttggttctga tcatgttgat ttggatgctg ctgctagagc ccatattact     420
gttgctgaag ttactggttc caactctatt tcagttgccg aacacgttgt tatgactact     480
ttggctttgg tcagaaacta cttgccatct catgctattg ctcaacaagg tggttggaat     540
attgctgatt gtgtctctag atcctacgat gttgaaggta tgcattttgg tactgttggt     600
gctggtagaa ttggtttggc tgttttgaga agattgaagc catttggttt acacttgcac     660
tacacccaaa gacatagatt ggatgcagct atcgaacaag aattgggttt aacttatcat     720
gctgatccag cttcattggc tgctgctgtt gatatagtta acttgcaaat cccattatac     780
ccatccaccg aacatttgtt tgatgctgct atgattgcta gaatgaagag aggtgcatac     840
ttgattaaca ccgctagagc taaattggtt gatagagatg ctgttgttag agctgttact     900

```
tctggtcatt tggctggtta tggtggtgat gtttggtttc cacaaccagc tccagctgat    960
catccttgga gagctatgcc ttttaatggt atgactccac atatctccgg tacatctttg   1020
tctgctcaag ctagatatgc tgctggtact ttggaaatat tgcaatgttg gtttgacggt   1080
agaccaatca gaaacgaata tttgattgtc gacggtggta ctttagctgg tactggtgct   1140
caatcttaca gattaact                                                  1158
```

<210> SEQ ID NO 280
<211> LENGTH: 386
<212> TYPE: PRT
<213> ORGANISM: B. stabilis

<400> SEQUENCE: 280

```
Met Ala Thr Val Leu Cys Val Leu Tyr Pro Asp Pro Val Asp Gly Tyr
1               5                   10                  15

Pro Pro His Tyr Val Arg Asp Thr Ile Pro Val Ile Thr Arg Tyr Ala
            20                  25                  30

Asp Gly Gln Thr Ala Pro Thr Pro Ala Gly Pro Pro Gly Phe Arg Pro
        35                  40                  45

Gly Glu Leu Val Gly Ser Val Ser Gly Ala Leu Gly Leu Arg Gly Tyr
    50                  55                  60

Leu Glu Ala His Gly His Thr Leu Ile Val Thr Ser Asp Lys Asp Gly
65                  70                  75                  80

Pro Asp Ser Glu Phe Glu Arg Arg Leu Pro Asp Ala Asp Val Val Ile
                85                  90                  95

Ser Gln Pro Phe Trp Pro Ala Tyr Leu Thr Ala Glu Arg Ile Ala Arg
            100                 105                 110

Ala Pro Lys Leu Arg Leu Ala Leu Thr Ala Gly Ile Gly Ser Asp His
        115                 120                 125

Val Asp Leu Asp Ala Ala Ala Arg Ala His Ile Thr Val Ala Glu Val
    130                 135                 140

Thr Gly Ser Asn Ser Ile Ser Val Ala Glu His Val Val Met Thr Thr
145                 150                 155                 160

Leu Ala Leu Val Arg Asn Tyr Leu Pro Ser His Ala Ile Ala Gln Gln
                165                 170                 175

Gly Gly Trp Asn Ile Ala Asp Cys Val Ser Arg Ser Tyr Asp Val Glu
            180                 185                 190

Gly Met His Phe Gly Thr Val Gly Ala Gly Arg Ile Gly Leu Ala Val
        195                 200                 205

Leu Arg Arg Leu Lys Pro Phe Gly Leu His Leu His Tyr Thr Gln Arg
    210                 215                 220

His Arg Leu Asp Ala Ala Ile Glu Gln Glu Leu Gly Leu Thr Tyr His
225                 230                 235                 240

Ala Asp Pro Ala Ser Leu Ala Ala Val Asp Ile Val Asn Leu Gln
                245                 250                 255

Ile Pro Leu Tyr Pro Ser Thr Glu His Leu Phe Asp Ala Ala Met Ile
            260                 265                 270

Ala Arg Met Lys Arg Gly Ala Tyr Leu Ile Asn Thr Ala Arg Ala Lys
        275                 280                 285

Leu Val Asp Arg Asp Ala Val Val Arg Ala Val Thr Ser Gly His Leu
    290                 295                 300

Ala Gly Tyr Gly Gly Asp Val Trp Phe Pro Gln Pro Ala Pro Ala Asp
305                 310                 315                 320
```

```
His Pro Trp Arg Ala Met Pro Phe Asn Gly Met Thr Pro His Ile Ser
            325                 330                 335

Gly Thr Ser Leu Ser Ala Gln Ala Arg Tyr Ala Ala Gly Thr Leu Glu
        340                 345                 350

Ile Leu Gln Cys Trp Phe Asp Gly Arg Pro Ile Arg Asn Glu Tyr Leu
            355                 360                 365

Ile Val Asp Gly Gly Thr Leu Ala Gly Thr Gly Ala Gln Ser Tyr Arg
    370                 375                 380

Leu Thr
385

<210> SEQ ID NO 281
<211> LENGTH: 1647
<212> TYPE: DNA
<213> ORGANISM: S. cerevisiae

<400> SEQUENCE: 281
```

| | | | | |
|---|---|---|---|---|
| atgtcccctt ctaaaatgaa tgctacagta ggatctactt ccgaagttga acaaaaaatc | | | | 60 |
| agacaagaat tggctcttag tgacgaagtc accaccatca gacgcaatgc tccagctgcc | | | | 120 |
| gttttgtatg aagatggtct aaaagaaaat aaaactgtca tttcatcaag cggtgcattg | | | | 180 |
| atcgcttatt ccggtgttaa aaccggaaga tctccaaagg acaaacgtat tgttgaagaa | | | | 240 |
| cctacctcga agacgaaat ttggtggggt ccggtcaata aaccatgttc tgaaagaaca | | | | 300 |
| tggtctatca accgtgaaag agctgcagat tacttgagaa caagagacca catttatatt | | | | 360 |
| gtcgatgcat ttgcaggatg ggatccaaaa tacagaatca aagtccgcgt tgtttgtgcc | | | | 420 |
| agggcttacc acgctttatt catgacaaat atgcttatta gacctacaga agaagaatta | | | | 480 |
| gcccattttg gagaacctga ttttactgtc tggaacgctg gtcagttccc agccaattta | | | | 540 |
| cacacccagg atatgtcttc aaagagtact atagaaatta acttcaaagc aatggaaatg | | | | 600 |
| atcattttag gtaccgaata cgccggtgaa atgaaaaaag gtattttcac agttatgttt | | | | 660 |
| tacttgatgc ctgtgcacca taacgtttta actttgcact cttccgccaa ccagggtatt | | | | 720 |
| caaaacggtg acgttacttt attctttggc ctaagtggta ccgggaaaac cactttatcc | | | | 780 |
| gcagacccac atagattgtt gatcggcgat gatgaacatt gttggtccga ccatggtgtc | | | | 840 |
| ttcaatatcg aaggtggttg ttacgccaag tgtattaatt tatctgccga aaaggagcct | | | | 900 |
| gaaattttcg acgctatcaa gtttggttct gtattagaaa acgttatcta tgacgagaag | | | | 960 |
| tcgcatgtag tcgactatga cgactcttct attactgaaa atactagatg tgcctaccca | | | | 1020 |
| attgactaca ttccaagtgc caagattcca tgtttggcgg actctcatcc aaagaacatt | | | | 1080 |
| atcctgctaa cttgtgatgc ttcgggtgtt ttaccaccag tatctaaatt gactcctgaa | | | | 1140 |
| caagtcatgt accatttcat ctctggttac acttctaaaa tggctggtac tgagcaaggt | | | | 1200 |
| gtcactgaac tgaaccaac attttcatct tgtttcggac aacccttcct agccttgcac | | | | 1260 |
| cctattagat acgcaaccat gttagctaca aagatgtctc aacataaagc taatgcgtac | | | | 1320 |
| ttaatcaaca ccggctggac tggttcttcc tacgtatctg gtggtaaacg ttgcccattg | | | | 1380 |
| aagtacacaa gggccattct ggattctatt catgatggtt cgttagccaa tgaaacgtac | | | | 1440 |
| gaaactttac cgattttcaa tcttcaagta cctaccaagg ttaacggtgt tccagctgag | | | | 1500 |
| cttttgaatc ctgctaaaaa ctggtctcaa ggtgaatcca atacagagg tgcagttacc | | | | 1560 |
| aacttggcca acttgtttgt tcaaaatttc aagatttatc aagacagagc cacaccagat | | | | 1620 |
| gtattagccg ctggtcctca attcgag | | | | 1647 |

```
<210> SEQ ID NO 282
<211> LENGTH: 549
<212> TYPE: PRT
<213> ORGANISM: S. cerevisiae

<400> SEQUENCE: 282
```

| | | | | | | | | | | | | | | | |
|---|---|---|---|---|---|---|---|---|---|---|---|---|---|---|---|
| Met | Ser | Pro | Ser | Lys | Met | Asn | Ala | Thr | Val | Gly | Ser | Thr | Ser | Glu | Val |
| 1 | | | | 5 | | | | | 10 | | | | | 15 | |
| Glu | Gln | Lys | Ile | Arg | Gln | Glu | Leu | Ala | Leu | Ser | Asp | Glu | Val | Thr | Thr |
| | | | 20 | | | | | 25 | | | | | 30 | | |
| Ile | Arg | Arg | Asn | Ala | Pro | Ala | Ala | Val | Leu | Tyr | Glu | Asp | Gly | Leu | Lys |
| | | 35 | | | | | 40 | | | | | 45 | | | |
| Glu | Asn | Lys | Thr | Val | Ile | Ser | Ser | Gly | Ala | Leu | Ile | Ala | Tyr | Ser | |
| 50 | | | | | 55 | | | | | 60 | | | | | |
| Gly | Val | Lys | Thr | Gly | Arg | Ser | Pro | Lys | Asp | Lys | Arg | Ile | Val | Glu | Glu |
| 65 | | | | | 70 | | | | | 75 | | | | | 80 |
| Pro | Thr | Ser | Lys | Asp | Glu | Ile | Trp | Trp | Gly | Pro | Val | Asn | Lys | Pro | Cys |
| | | | | 85 | | | | | 90 | | | | | 95 | |
| Ser | Glu | Arg | Thr | Trp | Ser | Ile | Asn | Arg | Glu | Arg | Ala | Ala | Asp | Tyr | Leu |
| | | | 100 | | | | | 105 | | | | | 110 | | |
| Arg | Thr | Arg | Asp | His | Ile | Tyr | Ile | Val | Asp | Ala | Phe | Ala | Gly | Trp | Asp |
| | | 115 | | | | | 120 | | | | | 125 | | | |
| Pro | Lys | Tyr | Arg | Ile | Lys | Val | Arg | Val | Cys | Ala | Arg | Ala | Tyr | His | |
| | 130 | | | | | 135 | | | | | 140 | | | | |
| Ala | Leu | Phe | Met | Thr | Asn | Met | Leu | Ile | Arg | Pro | Thr | Glu | Glu | Leu | |
| 145 | | | | | 150 | | | | | 155 | | | | | 160 |
| Ala | His | Phe | Gly | Glu | Pro | Asp | Phe | Thr | Val | Trp | Asn | Ala | Gly | Gln | Phe |
| | | | | 165 | | | | | 170 | | | | | 175 | |
| Pro | Ala | Asn | Leu | His | Thr | Gln | Asp | Met | Ser | Ser | Lys | Ser | Thr | Ile | Glu |
| | | | 180 | | | | | 185 | | | | | 190 | | |
| Ile | Asn | Phe | Lys | Ala | Met | Glu | Met | Ile | Ile | Leu | Gly | Thr | Glu | Tyr | Ala |
| | | 195 | | | | | 200 | | | | | 205 | | | |
| Gly | Glu | Met | Lys | Lys | Gly | Ile | Phe | Thr | Val | Met | Phe | Tyr | Leu | Met | Pro |
| | 210 | | | | | 215 | | | | | 220 | | | | |
| Val | His | His | Asn | Val | Leu | Thr | Leu | His | Ser | Ser | Ala | Asn | Gln | Gly | Ile |
| 225 | | | | | 230 | | | | | 235 | | | | | 240 |
| Gln | Asn | Gly | Asp | Val | Thr | Leu | Phe | Phe | Gly | Leu | Ser | Gly | Thr | Gly | Lys |
| | | | | 245 | | | | | 250 | | | | | 255 | |
| Thr | Thr | Leu | Ser | Ala | Asp | Pro | His | Arg | Leu | Leu | Ile | Gly | Asp | Asp | Glu |
| | | | 260 | | | | | 265 | | | | | 270 | | |
| His | Cys | Trp | Ser | Asp | His | Gly | Val | Phe | Asn | Ile | Glu | Gly | Gly | Cys | Tyr |
| | | 275 | | | | | 280 | | | | | 285 | | | |
| Ala | Lys | Cys | Ile | Asn | Leu | Ser | Ala | Glu | Lys | Glu | Pro | Glu | Ile | Phe | Asp |
| | 290 | | | | | 295 | | | | | 300 | | | | |
| Ala | Ile | Lys | Phe | Gly | Ser | Val | Leu | Glu | Asn | Val | Ile | Tyr | Asp | Glu | Lys |
| 305 | | | | | 310 | | | | | 315 | | | | | 320 |
| Ser | His | Val | Val | Asp | Tyr | Asp | Ser | Ser | Ile | Thr | Glu | Asn | Thr | Arg | |
| | | | | 325 | | | | | 330 | | | | | 335 | |
| Cys | Ala | Tyr | Pro | Ile | Asp | Tyr | Ile | Pro | Ser | Ala | Lys | Ile | Pro | Cys | Leu |
| | | | 340 | | | | | 345 | | | | | 350 | | |
| Ala | Asp | Ser | His | Pro | Lys | Asn | Ile | Ile | Leu | Leu | Thr | Cys | Asp | Ala | Ser |
| | | 355 | | | | | 360 | | | | | 365 | | | |
| Gly | Val | Leu | Pro | Pro | Val | Ser | Lys | Leu | Thr | Pro | Glu | Gln | Val | Met | Tyr |
| | 370 | | | | | 375 | | | | | 380 | | | | |

His Phe Ile Ser Gly Tyr Thr Ser Lys Met Ala Gly Thr Glu Gln Gly
385                 390                 395                 400

Val Thr Glu Pro Glu Pro Thr Phe Ser Ser Cys Phe Gly Gln Pro Phe
                405                 410                 415

Leu Ala Leu His Pro Ile Arg Tyr Ala Thr Met Leu Ala Thr Lys Met
            420                 425                 430

Ser Gln His Lys Ala Asn Ala Tyr Leu Ile Asn Thr Gly Trp Thr Gly
        435                 440                 445

Ser Ser Tyr Val Ser Gly Gly Lys Arg Cys Pro Leu Lys Tyr Thr Arg
    450                 455                 460

Ala Ile Leu Asp Ser Ile His Asp Gly Ser Leu Ala Asn Glu Thr Tyr
465                 470                 475                 480

Glu Thr Leu Pro Ile Phe Asn Leu Gln Val Pro Thr Lys Val Asn Gly
                485                 490                 495

Val Pro Ala Glu Leu Leu Asn Pro Ala Lys Asn Trp Ser Gln Gly Glu
            500                 505                 510

Ser Lys Tyr Arg Gly Ala Val Thr Asn Leu Ala Asn Leu Phe Val Gln
        515                 520                 525

Asn Phe Lys Ile Tyr Gln Asp Arg Ala Thr Pro Asp Val Leu Ala Ala
    530                 535                 540

Gly Pro Gln Phe Glu
545

<210> SEQ ID NO 283
<211> LENGTH: 903
<212> TYPE: DNA
<213> ORGANISM: A. thaliana

<400> SEQUENCE: 283
atgcttgatt ggaaacctag gcgttctgac atgctggtgg atccttttgg tatagggaga      60
attgttcagg atggccttgt gttccgtcag aattttttcta ttaggtcata tgaaataggt     120
gctgatcgct ctgcatctat agaaaccgtc atgaatcatc tgcaggaaac ggcgcttaat     180
catgttaaga ctgctggatt gcttggagat gggtttggct ctacacctga gatgttttaag    240 aagaacttga tatgggttgt cactcgtatg caggttgtgg ttgataaata tcctacttgg    300
ggagatgttg ttgaagtaga cacctgggtc agtcaatctg gaagaatgg tatgcgtcgt     360 gattggctag ttcgggattg taatactgga gaaaccttaa cacgagcatc aagtgtgtgg    420
gtgatgatga ataaactgac aaggagattg tcaaagattc ctgaagaggt tcgaggggaa    480
atagagcctt attttgtgaa ttctgatcct gtccttgccg aggacagcag aaagttaaca    540
aaaattgatg acaagactgc tgactatgtt cgatctggtc tcactcctcg atggagtgac    600
ctagatgtta ccagcatgt gaataatgta agtacattg ggtggatcct ggagagtgct     660
ccagtgggaa taatggagag gcagaagctg aaaagcatga ctctggagta tcggagggaa    720
tgcgggagag acagtgtgct tcagtccctc actgcagtta cgggttgcga atacggtaac    780
ctggcaacag cgggggatgt ggaatgtcag catttgctcc gactccagga tggagcggaa    840
gtggtgagag aagaacaga gtggagtagt aaaacaccaa caacaacttg gggaactgca    900
ccg                                                                  903

<210> SEQ ID NO 284
<211> LENGTH: 301
<212> TYPE: PRT
<213> ORGANISM: A. thaliana

<400> SEQUENCE: 284

Met Leu Asp Trp Lys Pro Arg Arg Ser Asp Met Leu Val Asp Pro Phe
1               5                   10                  15

Gly Ile Gly Arg Ile Val Gln Asp Gly Leu Val Phe Arg Gln Asn Phe
            20                  25                  30

Ser Ile Arg Ser Tyr Glu Ile Gly Ala Asp Arg Ser Ala Ser Ile Glu
        35                  40                  45

Thr Val Met Asn His Leu Gln Glu Thr Ala Leu Asn His Val Lys Thr
    50                  55                  60

Ala Gly Leu Leu Gly Asp Gly Phe Gly Ser Thr Pro Glu Met Phe Lys
65              70                  75                  80

Lys Asn Leu Ile Trp Val Val Thr Arg Met Gln Val Val Asp Lys
                85                  90                  95

Tyr Pro Thr Trp Gly Asp Val Val Glu Val Asp Thr Trp Val Ser Gln
            100                 105                 110

Ser Gly Lys Asn Gly Met Arg Arg Asp Trp Leu Val Arg Asp Cys Asn
        115                 120                 125

Thr Gly Glu Thr Leu Thr Arg Ala Ser Ser Val Trp Val Met Met Asn
130                 135                 140

Lys Leu Thr Arg Arg Leu Ser Lys Ile Pro Glu Glu Val Arg Gly Glu
145                 150                 155                 160

Ile Glu Pro Tyr Phe Val Asn Ser Asp Pro Val Leu Ala Glu Asp Ser
                165                 170                 175

Arg Lys Leu Thr Lys Ile Asp Asp Lys Thr Ala Asp Tyr Val Arg Ser
            180                 185                 190

Gly Leu Thr Pro Arg Trp Ser Asp Leu Asp Val Asn Gln His Val Asn
        195                 200                 205

Asn Val Lys Tyr Ile Gly Trp Ile Leu Glu Ser Ala Pro Val Gly Ile
    210                 215                 220

Met Glu Arg Gln Lys Leu Lys Ser Met Thr Leu Glu Tyr Arg Arg Glu
225                 230                 235                 240

Cys Gly Arg Asp Ser Val Leu Gln Ser Leu Thr Ala Val Thr Gly Cys
                245                 250                 255

Asp Ile Gly Asn Leu Ala Thr Ala Gly Asp Val Glu Cys Gln His Leu
            260                 265                 270

Leu Arg Leu Gln Asp Gly Ala Glu Val Val Arg Gly Arg Thr Glu Trp
        275                 280                 285

Ser Ser Lys Thr Pro Thr Thr Thr Trp Gly Thr Ala Pro
    290                 295                 300

<210> SEQ ID NO 285
<211> LENGTH: 12309
<212> TYPE: DNA
<213> ORGANISM: Artificial
<220> FEATURE:
<223> OTHER INFORMATION: pMU2737

<400> SEQUENCE: 285

```
tctccgggag ctgcatgtgt cagaggtttt caccgtcatc accgaaacgc gcgagacgaa      60
agggcctcgt gatacgccta tttttatagg ttaatgtcat gataataatg gtttcttgtg     120
acattggcgc aacgaaggta tattttgttt tttgccggag gatagcagca gatcgctgca     180
caatgtccgt caagtctaac attgacactc tggggcaaaa tagaccggcg tcccggcctg     240
ctggaattta tcgctatgca tacagctgtc gggcatacg ctttacagac ggcggtgaaa     300
```

```
cgcctgtcac aatcacacta aacaaagagt acggaaccca ctcatggata ttcgtaagat    360
taaaaaactg atcgagctgg ttgaagaatc aggcatctcc gaactggaaa tttctgaagg    420
cgaagagtca gtacgcatta gccgtgcagc tcctgccgca agtttccctg tgatgcaaca    480
agcttacgct gcaccaatga tgcagcagcc agctcaatct aacgcagccg ctccggcgac    540
cgttccttcc atggaagcgc cagcagcagc ggaaatcagt ggtcacatcg tacgttcccc    600
gatggttggt actttctacc gcaccccaag cccggacgca aaagcgttca tcgaagtggg    660
tcagaaagtc aacgtgggcg ataccctgtg catcgttgaa gccatgaaaa tgatgaacca    720
gatcgaagcg gacaaatccg gtaccgtgaa agcaattctg gtcgaaagtg acaaccggt    780
agaatttgac gagccgctgg tcgtcatcga gtaacgaggc gaacacggcc tgatggtcaa    840
ctatctctac aagctcgacg acatcgtggc caaccacgag gctctggcgc agcgcggcga    900
agtgattgcc tcgcctgctg tcaaaagcct gctcaaccag aacgacgaag ccgcagtgg    960
cggcaatggc cagcaaggct cccggccatt cgcacagata gtgaattcaa cgcttggagg   1020
agggcgaaag tgagcaacca tcttttcgac gccatgcggg ccgccgcgcc cggtaacgca   1080
ccattcatcc ggatcgataa cacgcgcaca tggacctatg acgacgcctt cgctctttcc   1140
ggccgcattg ccagcgcgat ggacgcgctc ggcattcgcc ccggcgaccg cgttgcggtg   1200
caggtcgaga aaagtgccga ggcattgatc ctctatctcg cctgtcttcg aagcggcgcc   1260
gtctacctgc cgctcaacac cgcctatacg ctggctgagc tcgattattt tatcggcgat   1320
gcggagccgc gtttggtggt tgtcgcatcg tcggctcgag cgggcgtgga gacaatcgcc   1380
aagccccgcg gtgcgatcgt cgaaactctc gacgctgctg gcagcggctc gttgctggat   1440
ctcgcccgcg acgagccggc cgactttgtc gatgcctcgc gctccgccga tgatctggcg   1500
gcgatcctct acacgtccgg aacgacggga cgctccaagg gggcgatgct cacgcatggg   1560
aacctgctct cgaacgccct gaccttgcga gattttttggc gcgtcaccgc cggcgatcga   1620
ctgatccatg ccttgccgat cttccacacg catggactgt tcgtcgccac gaacgtcaca   1680
ctgctcgccg gcgcctcgat gttcctgctg tcgaagttcg acccggagga gatcctgtcg   1740
ctgatgccgc aggcaacgat gctgatgggc gtgccgacct tctacgtgcg cctcctgcag   1800
agcccgcgcc tcgacaagca agcggtcgcc aacatccgcc tcttcatttc cggttcggct   1860
ccactgcttg cagaaacaca taccgagttc caggcacgta ccggtcacgc cattctcgag   1920
cgctacggca tgacggaaac caatatgaac acgtccaacc cttatgaggg gaaacggatt   1980
gccggaacgg tcggcttccc gctgcctgat gtgacggtgc gcgtcaccga tcccgccacc   2040
gggctcgcgc tgccgcccga acaaaccggc atgatcgaga tcaaggggcc gaacgttttc   2100
aagggctatt ggcgcatgcc cgaaaaaacc gcggccgaat tcaccgccga cggtttcttc   2160
atcagcggcg atctcggcaa gatcgaccgc gacggttatg tccacatcgt cggccgcggc   2220
aaggatctgg tgatttcggg tggatacaac atctatccga aagaggttga gggcgagatc   2280
gaccagatcg agggtgtggt tgagagcgct gtgatcggcg tgccgcatcc cgatttcgga   2340
gaaggcgtaa cggccgtcgt cgtgcgcaag cccggcgctg ccctcgatga aaaggccatc   2400
gtcagcgccc tccaggaccg gctcgcgcgc tacaaacaac ccaagcgcat catctttgca   2460
gaggacttgc cgcgcaacac gatgggtaag gttcagaaaa acatcctgcg gcagcaatac   2520
gccgatcttt ataccaggac gtaaggcgac cgcgctctct gggaggagag tgcgtcgaca   2580
tcccgcatca atcttgaaaa cagcaactgc gacgcggagg cgtcggaggg aggggaatca   2640
```

-continued

```
tgggtattga attactgtcc ataggcctgc tgatcgccat gttcatcatt gcgacgatcc    2700
agccaatcaa catgggtgcg ctcgcctttg ccggcgcctt cgtgctcggc tcgatgatca    2760
tcgggatgaa aaccaacgaa atatttgccg gctttccgag tgatctgttc ctgacgctcg    2820
tcgccgtcac ctacctcttc gccatagcgc agatcaacgg cacgatcgac tggctcgtcg    2880
aatgtgccgt ccgcctggta cgcgggcgga tcggcttgat tccctgggtg atgttccttg    2940
tcgccgccat cattactggc ttcggtgcac ttgggcctgc tgcggtcgcc attctcgcac    3000
ccgtcgcgtt gagctttgcc gtgcagtacc gcattcatcc ggtgatgatg ggtctgatgg    3060
tgatccacgg cgcgcaggca ggcggcttct cgccgatcag catctatggc ggaatcacca    3120
accagatcgt tgcgaaggcc ggcctgcctt cgctccgac ctcgctgttt ctttccagct    3180
tcttctttaa cctggcgatc gcggtgctgg tgttcttcgt gttcggcggc gcgagggtga    3240
tgaagcacga tcccgcatca cttggcccct tgcccgaact ccatcccgag ggcgtatcgg    3300
cgtcgatcag aggccacggc ggcacgccgg caaaaccgat cagagagcat gcctatggta    3360
cggcggccga taccgcgacg acgttgcgtc tgaacaatga gagaattacc accttgatcg    3420
gcctgacggc gctcggcatc ggcgccctgg ttttcaagtt caatgttggc ctcgtcgcca    3480
tgaccgtcgc cgtcgtcctc gcgctgctgt caccgaaagac ccagaaggcc gcaatcgaca    3540
aggtcagttg gtcgaccgtg ctgctgattg ccggcatcat cacctatgtc ggcgtcatgg    3600
agaaggccga tacggtcgac tacgtggcga atggcatatc cagtctcggc atgccgctac    3660
tggtagcgct cctgctttgc tttacgggcg ccatcgtctc ggcctttgct tcctcgaccg    3720
cgctgctcgg cgcgatcatc ccgcttgccg ttccattcct cctgcaaggg cacatcagcg    3780
ccatcggtgt ggtcgcggcg atcgccatct cgacgacgat cgtcgacacc agcccattct    3840
ccaccaacgg cgcccttgtc gtcgccaatg cgccggacga cagccgtgag caggtgttgc    3900
gacagctact gatctacagc gccttgatcg ctatcatcgg tccgatcgtt gcctggttgg    3960
tgttcgtcgt gcccgggctg gtttgacgac gggctgctcc cagcgaaaag tgtgccgagc    4020
cctgttcggc acacttggag accgtggatg tcccaattac ggaactcggt cttcaggaaa    4080
aataagactc taaagcgtc aaaaggccgg attttccggc ctttttatt actgggatc    4140 gacaaccccc ataaggtaca atccccgctt tcttcaccca tcagggacaa aaaatggaca    4200
ctcgttttgt tcaggcccat aaagaggcgc gctgggcgct ggggctgacc cttttgtatc    4260
tggcagtttg gttagtagcc gcttacttat ctggcgttgc ccccggtttt accggctttc    4320
cgcgctggtt tgagatggcc tgcatcctga cgccgctgct gtttattgga ctgtgctggg    4380
cgatggtgaa atttatctat cgcgatatcc cactggagga tgacgatgca gcttgaagta    4440
attctaccgc tggtcgccta tctggtggtg gtgttcggta tctcggttta tgcgatgcgt    4500
aaacggagca ccggcaccct ccttaatgag tatttcctcg gcagccgctc tatgggcggt    4560
attgtgctgg cgatgacgct caccgcgacc tatatcagtg ccagttcgtt tatcggcggg    4620
ccaggagctg cttataaata cgggctgggc tgggtattgc tggcgatgat tcagcttcct    4680
gcagtctggc tttcactcgg tattctcggc aagaagtttg cgattcttgc gcgccgctac    4740
aatgcagtga cgctgaacga tatgctgttt gcccgctacc agagtcgtct tctggtgtgg    4800
ctggcgagtt tgagtttgct ggttgcgttc gttggtgcga tgaccgtgca gtttatcggc    4860
ggtgcgcgcc tgctggaaac cgcggcgggt attccttatg aaaccgggct gctgattttt    4920
ggtatcagca ttgcgttata taccgccttt ggtggctttc gcgccagcgt gctgaacgac    4980
accatgcaag ggcttgtgat gctgattggc accgttggtg gcacttttcg gggaaatgtg    5040
```

```
cgcggaaccc ctatttgttt attttttctaa atacattcaa atatgtatcc gctcatgaga   5100
caataaccct gataaatgct tcaataatat tgaaaaagga agagtatgag tattcaacat   5160
ttccgtgtcg cccttattcc cttttttgcg gcattttgcc ttcctgtttt tgctcaccca   5220
gaaacgctgg tgaaagtaaa agatgctgaa gatcagttgg gtgcacgagt gggttacatc   5280
gaactggatc tcaacagcgg taagatcctt gagagttttc gccccgaaga acgttttcca   5340
atgatgagca cttttaaagt tctgctatgt ggcgcggtat tatcccgtat tgacgccggg   5400
caagagcaac tcggtcgccg catacactat tctcagaatg acttggttga gtactcacca   5460
gtcacagaaa agcatcttac ggatggcatg acagtaagag aattatgcag tgctgccata   5520
accatgagtg ataacactgc ggccaactta cttctgacaa cgatcggagg accgaaggag   5580
ctaaccgctt ttttgcacaa catgggggat catgtaactc gccttgatcg ttgggaaccg   5640
gagctgaatg aagccatacc aaacgacgag cgtgacacca cgatgcctgt agcaatggca   5700
acaacgttgc gcaaactatt aactggcgaa ctacttactc tagcttcccg gcaacaatta   5760
atagactgga tggaggcgga taaagttgca ggaccacttc tgcgctcggc ccttccggct   5820
ggctggttta ttgctgataa atctggagcc ggtgagcgtg ggtctcgcgg tatcattgca   5880
gcactggggc cagatggtaa gccctcccgt atcgtagtta tctacacgac ggggagtcag   5940
gcaactatgg atgaacgaaa tagacagatc gctgagatag gtgcctcact gattaagcat   6000
tggtaagcga tgaaatgtga ggtgaatcag ggttttcacc cgattttgtg ctgatcagaa   6060
tttttttttct ttttcccccct tgaaggggcg aagcctcatc cccatttctc tggtcaccag   6120
ccgggaaacc acgtaagctc cggcgtcacc cataacagat acggactttc tcaaaggaga   6180
gttatcaatg aacatcaaaa agtttgcaaa acaagcaaca gtattaacct ttactaccgc   6240
actgctggca ggaggcgcaa ctcaagcgtt tgcgaaagaa acgaaccaaa agccatataa   6300
ggaaacatac ggcatttccc atattacacg ccatgatatg ctgcaaatcc ctgaacagca   6360
aaaaaatgaa aaatatcaag ttcctgagtt cgattcgtcc acaattaaaa atatctcttc   6420
tgcaaaaggc ctggacgttt gggacagctg gccattacaa aacgctgacg gcactgtcgc   6480
aaactatcac ggctaccaca tcgtctttgc attagccgga gatcctaaaa atgcggatga   6540
cacatcgatt tacatgttct atcaaaaagt cggcgaaact tctattgaca gctggaaaaa   6600
cgctggccgc gtctttaaag acagcgacaa attcgatgca aatgattcta tcctaaaaga   6660
ccaaacacaa gaatggtcag gttcagccac atttacatct gacggaaaaa tccgtttatt   6720
ctacactgat ttctccggta acattacgg caaacaaaca ctgacaactg cacaagttaa   6780
cgtatcagca tcagacagct ctttgaacat caacggtgta gaggattata aatcaatctt   6840
tgacggtgac ggaaaaacgt atcaaaatgt acagcagttc atcgatgaag gcaactacag   6900
ctcaggcgac aaccatacgc tgagagatcc tcactacgta gaagataaag gccacaaata   6960
cttagtattt gaagcaaaca ctggaactga agatggctac caaggcgaag aatctttatt   7020
taacaaagca tactatggca aaagcacatc attcttccgt caagaaagtc aaaaacttct   7080
gcaaagcgat aaaaaacgca cggctgagtt agcaaacggc gctctcggta tgattgagct   7140
aaacgatgat tacacactga aaaagtgat gaaaccgctg attgcatcta acacagtaac   7200
agatgaaatt gaacgcgcga acgtctttaa aatgaacggc aaatggtatc tgttcactga   7260
ctcccgcgga tcaaaaatga cgattgacgg cattacgtct aacgatattt acatgcttgg   7320
ttatgtttct aattctttaa ctggcccata caagccgctg aacaaaactg gccttgtgtt   7380
```

```
aaaaatggat cttgatccta acgatgtaac ctttacttac tcacacttcg ctgtacctca   7440
agcgaaagga acaatgtcg tgattacaag ctatatgaca aacagaggat tctacgcaga    7500
caaacaatca acgtttgcgc ctagcttcct gctgaacatc aaaggcaaga aaacatctgt   7560
tgtcaaagac agcatccttg aacaaggaca attaacagtt aacaaataac caggagctat   7620
ttaatggcaa cagttaacca gctggtacgc aaaccacgtg ctcgcaaagt tgcgaaaagc   7680
aacgtgcctg cgctggaagc atgcccgcaa aaacgtggcg tatgtactcg tgtatatact   7740
accactccta aaaaccgaa ctccgcgctg cgtaaagtat gccgtgttcg tctgactaac    7800
ggtttcgaag tgacttccta catcggtggt gaaggtcaca acctgcagga gcactccgtg   7860
atcctgatcc gtggcggtcg tgttaaagac ctcccgggtg ttcgttacca caccgtacgt   7920
ggtgcgcttg actgctccgg cgttaaagac cgtaagcagg ctcgttccaa gtatggcgtg   7980
aagcgtccta aggcttaatg gttctccgtt aagtaaggcc aaatagagga tctgaagatc   8040
agcagttcaa cctgttgata gtacgtacta agctctcatg tttcacgtac taagctctca   8100
tgtttaacgt actaagctct catgtttaac gaactaaacc ctcatggcta acgtactaag   8160
ctctcatggc taacgtacta agctctcatg tttcacgtac taagctctca tgtttgaaca   8220
ataaaattaa tataaatcag caacttaaat agcctctaag gttttaagtt ttataagaaa   8280
aaaaagaata tataaggctt ttaaagcttt taaggtttaa cggttgtgga caacaagcca   8340
gggatgtaac gcactgagaa gcccttagag cctctcaaag caattttcag tgacacagga   8400
acacttaacg gctgacagac gctgccgcaa gcactcaggg cgcaagggct gctaaaggaa   8460
gcggaacacg tagaaagcca gtccgcagaa acggtgctga ccccggatga atgtcagcta   8520
ctgggctatc tggacaaggg aaaacgcaag cgcaaagaga aagcaggtag cttgcagtgg   8580
gcttacatgg cgatagctag actgggcggt tttatggaca gcaagcgaac cggaattgcc   8640
agctggggcg ccctctggta aggttgggaa gccctgcaaa gtaaactgga tggctttctt   8700
gccgccaaga atctgatggc gcaggggatc aagatctgat caagagacag gatgaggatc   8760
gtttcgcatg attgaacaag atggattgca cgcaggttct ccggccgctt gggtggagag   8820
gctattcggc tatgactggg cacaacagac aatcggctgc tctgatgccg ccgtgttccg   8880
gctgtcagcg caggggcgcc cggttctttt tgtcaagacc gacctgtccg gtgccctgaa   8940
tgaactccaa gacgaggcag cgcggctatc gtggctggcc acgacgggcg ttccttgcgc   9000
agctgtgctc gacgttgtca ctgaagcggg aagggactgg ctgctattgg gcgaagtgcc   9060
ggggcaggat ctcctgtcat ctcaccttgc tcctgccgag aaagtatcca tcatggctga   9120
tgcaatgcgg cggctgcata cgcttgatcc ggctacctgc ccattcgacc accaagcgaa   9180
acatcgcatc gagcgagcac gtactcggat ggaagccggt cttgtcgatc aggatgatct   9240
ggacgaagag catcagggc tcgcgccagc cgaactgttc gccaggctca aggcgcggat   9300
gcccgacggc gaggatctcg tcgtgaccca tggcgatgcc tgcttgccga atatcatggt   9360
ggaaaatggc cgcttttctg gattcatcga ctgtggccgg ctgggtgtgg cggaccgcta   9420
tcaggacata gcgttggcta cccgtgatat tgctgaagag cttggcggcg aatgggctga   9480
ccgcttcctc gtgctttacg gtatcgccgc tcccgattcg cagcgcatcg ccttctatcg   9540
ccttcttgac gagttcttct gaattccgga tccgaagagg cccgcaccga tcgcccttcc   9600
caacagttgc gcagcctgaa tggcgaatgg cgcctgatgc ggtatttctc cttacgcat   9660 ctgtgcggta tttcacaccg catagggtaa taactgatat aattaaattg aagctctaat   9720
ttgtgagttt agtatacatg catttactta taatacagtt ttttagtttt gctggccgca   9780
```

```
tcttctcaaa tatgcttccc agcctgcttt tctgtaacgt tcaccctcta ccttagcatc   9840
ccttcccttt gcaaatagtc ctcttccaac aataataatg tcagatcctg tagagaccac   9900
atcatccacg gttctatact gttgacccaa tgcgtctccc ttgtcatcta aacccacacc   9960
gggtgtcata atcaaccaat cgtaaccttc atctcttcca cccatgtctc tttgagcaat  10020
aaagccgata acaaaatctt tgtcgctctt cgcaatgtca acagtaccct tagtatattc  10080
tccagtagat agggagccct tgcatgacaa ttctgctaac atcaaaaggc ctctaggttc  10140
ctttgttact tcttctgccg cctgcttcaa accgctaaca atacctgggc ccaccacacc  10200
gtgtgcattc gtaatgtctg cccattctgc tattctgtat acacccgcag agtactgcaa  10260
tttgactgta ttaccaatgt cagcaaattt tctgtcttcg aagagtaaaa aattgtactt  10320
ggcggataat gcctttagcg gcttaactgt gccctccatg gaaaaatcag tcaagatatc  10380
cacatgtgtt tttagtaaac aaattttggg acctaatgct tcaactaact ccagtaattc  10440
cttggtggta cgaacatcca atgaagcaca caagtttgtt tgcttttcgt gcatgatatt  10500
aaatagcttg gcagcaacag gactaggatg agtagcagca cgttccttat atgtagcttt  10560
cgacatgatt tatcttcgtt tcggtttttg ttctgtgcag ttgggttaag aatactgggc  10620
aatttcatgt ttcttcaaca ctacatatgc gtatatatac caatctaagt ctgtgctcct  10680
tccttcgttc ttccttctgt tcggagatta ccgaatcaaa aaaatttcaa agaaaccgaa  10740
atcaaaaaaa agaataaaaa aaaaatgatg aattgaaaag ctcttgttac ccatcattga  10800
attttgaaca tccgaacctg ggagttttcc ctgaaacaga tagtatattt gaacctgtat  10860
aataatatat agtctagcgc tttacggaag acaatgtatg tatttcggtt cctggagaaa  10920
ctattgcatc tattgcatag gtaatcttgc acgtcgcatc cccggttcat tttctgcgtt  10980
tccatcttgc acttcaatag catatctttg ttaacgaagc atctgtgctt cattttgtag  11040
aacaaaaatg caacgcgaga gcgctaattt ttcaaacaaa gaatctgagc tgcattttta  11100
cagaacagaa atgcaacgcg aaagcgctat tttaccaacg aagaatctgt gcttcatttt  11160
tgtaaaacaa aaatgcaacg cgagagcgct aattttttcaa acaaagaatc tgagctgcat  11220
ttttacagaa cagaaatgca acgcgagagc gctattttac caacaaagaa tctatacttc  11280
ttttttgttc tacaaaaatg catcccgaga gcgctatttt tctaacaaag catcttagat  11340
tactttttt ctcctttgtg cgctctataa tgcagtctct tgataacttt ttgcactgta  11400
ggtccgttaa ggttagaaga aggctacttt ggtgtctatt ttctcttcca taaaaaagc  11460
ctgactccac ttcccgcgtt tactgattac tagcgaagct gcgggtgcat tttttcaaga  11520
taaaggcatc cccgattata ttctataccg atgtggattg cgcatacttt gtgaacagaa  11580
agtgatagcg ttgatgattc ttcattggtc agaaaattat gaacggtttc ttctattttg  11640
tctctatata ctacgtatag gaaatgttta cattttcgta ttgttttcga ttcactctat  11700
gaatagttct tactacaatt ttttttgtcta aagagtaata ctagagataa acataaaaaa  11760
tgtagaggtc gagtttagat gcaagttcaa ggagcgaaag gtggatgggt aggttatata  11820
gggatatagc acagagatat atagcaaaga gatactttg agcaatgttt gtggaagcgg  11880
tattcgcaat attttagtag ctcgttacag tccggtgcgt ttttggtttt ttgaaagtgc  11940
gtcttcagag cgcttttggt tttcaaaagc gctctgaagt tcctatactt tctagctaga  12000
gaataggaac ttcggaatag gaacttcaaa gcgtttccga aaacgagcgc ttccgaaaat  12060
gcaacgcgag ctgcgcacat acagctcact gttcacgtcg cacctatatc tgcgtgttgc  12120
```

```
ctgtatatat atatacatga aagaacggc atagtgcgtg tttatgctta aatgcgttat     12180
ggtgcactct cagtacaatc tgctctgatg ccgcatagtt aagccagccc cgacacccgc     12240
caacacccgc tgacgcgccc tgacgggctt gtctgctccc ggcatccgct tacagacaag     12300
ctgtgaccg                                                             12309

<210> SEQ ID NO 286
<211> LENGTH: 8500
<212> TYPE: DNA
<213> ORGANISM: Artificial
<220> FEATURE:
<223> OTHER INFORMATION: pMU2898

<400> SEQUENCE: 286
caggggggcg agcctatgg aaaaacgcca gcaacgcggc ctttttacgg ttcctggcct       60
tttgctggcc ttttgtgagc cgtttatttt ttctacccat atccttgaag cggtgttata     120
atgccgcgcc ctcgatatgg ggatttttaa cgacctgatt ttcgggtctc agtagtagtt     180
gacattagcg gagcactaaa atgtcacaaa ttgaaaagat acaaaattta aaaaacatga     240
aaaaaactat agctaaaggc ggcggagaag agaaaatagc aaaaagacac gcagatggaa     300
agctttctgc cagagaaaga atccattgt tgtttgatga aaacagtttt gttgaggtag      360
atgcattcat agaatccaga tgctttgact ttggtatgca aagaagaaa cttccaggtg      420 acggggttgt taccggttac ggaacagtta atggcagaaa ggtctttgtt tcatcacagg     480
actttactgt tataggcggt tcattgggag agatgcacgc aaagaaaatt acaaaggtta     540
tggatatggc tctgaaaatg ggagcaccgt tcatagccat taatgattcc ggcggagctc     600
gtattgagga aggtctggat gctctttcag gttacggaga tatttttac aggaatactc      660 ttgcatcagg cgttattccg cagatatcag taataatggg gccatgtgca ggtggtgcgg     720
tatattcccc ggccataact gattttatat tcatggtgga aaaaacaagt cagatgttta    780
ttacaggccc acaggtaata aagtctgtta cgggtgaaga tgtatcagtt gaaaatctgg    840
gaggtgcaga tgttcatact gctacaagcg gtgtagcaca tttcaaatct tcaagcgaag    900
aagagtgtat agaagatata aagaggcttt taagttttat tcccgataat aatgtatcag    960
atactatgta ctacggagtg tctgatgctg ccgacagatt agccgaaagc tcaacagca   1020 ttattccaga agagtcaaac aagccatatg acatgtttga cgtaatagca gaagtagtag   1080
atgatggaga tttctttgaa gttcagagtt atttctctca gaatataata tcggatttg    1140 caagaatgaa tggcagaagt gttggtattg ttgcaaacca gcctaagata atggcagggt   1200
cactagatat gaacgcggct gataaggcgg cacgtttcgt tcgtttctgt gatgcattta   1260
atattcctgt cgtttcatta accgatgtac ctgcattcct gccgggggta gcccaggagc   1320
ataacggcat aatacgtcac ggtgcaaaac tcctatatgc ttttctctga agcaacagtac   1380 caaagataaa tgttattctt agaaaggcat atggaggagc atatattgct atgaacagta   1440
aaacaatagg tgccgatatg gttttggcat ggccatcagc tgaaattgca gttatgggac   1500
ctgacggagc agcaaatatt atatttaaaa aggatattgc tgcgtcggaa gatccagcag   1560
aaaccagaaa ggaaaagatt gcggaatata gagataaatt ctcaaatcct tatgtagcag   1620
catcaagagg gtatattgat gatgttatcg agccttctga aaccagagta aaaattataa   1680
ctgctctgga aatgctggat acaaagaggg aaaacaggcc ttcaaaaaaa catggaaaca   1740
ttccgctata atatagtata ggaaacaaaa tatctgaggg atgagtgtaa tgagtaaata   1800
tataataaag gtaaacggaa ctccttatga agtagaggtt gaagaagtgg gcggggaag    1860
```

```
gcccatttca gctgctccaa agctaagagc taccaagccg ggacatacct ctgctgcaaa   1920
agcagcacag ccgcaggcag gtaaagcagg tgatgttgct gctccaatgc cgggaactgt   1980
tttaaaggta aaggttgcta tcggtgatga agtaaagaag gggcaggtac ttttaatact   2040
tgaagctatg aaaatggaga atgaaatagt tgctccggct gacggtaaag ttacggcgtt   2100
aaacgtcgag gccggaaagt ctgttactgc tggagaacta atggtgtcta tagcctaaaa   2160
ggctgactta ccgcaaagga gatggaaaaa tgccaggcgt aagaattacg gaaacagttt   2220
taagagatgc tcaccagtcc cttatagcaa ccagaatgaa gaccgaagaa atgcttccaa   2280
ttgttgagaa gcttgacaat attggttacc attcactgga agcttggggc ggagctactt   2340
ttgactcatg tatgagattt ttgaatgaag atccatggat gagacttaga aaaataaaag   2400
atgttgcaaa gaaacacctc tgcaaatgc ttcttagggg ccagaacctt ttaggataca   2460
aacactatgc cgatgatata gttgagtact ttgttcagaa ggctgttgca acggcatgg   2520 acattatgag aatattcgat gcactaaatg atgccaggaa tatcgagacg gcaattaagg   2580
catgtaaaaa ggaaggcggc catgctcagg gctgtatttg ctatactata agtcctgttc   2640
acaatcttga gcttttttgta aaagatgcaa agcagttgga gagcatggga gcagattcta   2700
tctgtataaa agacatggcc ggacttctgg tgccgtatca ggcttatgaa ctggtaaagg   2760
ctttgaaaga aagtgtaaag ataccgatac aattgcacac tcactatact agcggtgtag   2820
catctatgac gtatttgaag gctatagaag caggtataga tattgttgac tgtgcaattt   2880
cacctatgtc aatgggaacg tcacagccgc ctacagagcc tttggtggca acttttaaagg   2940 gaactgattt cgatactgga ctggatttgg aaaaactcag tgaaattgca gactatttca   3000
gaccccttaa agaaaaatat attgagagcg gactattaga cgttaaggta atgggtgttg   3060
acgttaacac tcttatttat caggtacctg gtggaatgct ttcaaatctt gtttcacaat   3120
tgaagcagtc aaatgctttg gataaatatg aagaggttct caaggaagtt cccagagtaa   3180
gagccgattt cggctatcct ccgcttgtaa caccatcaag tcagatagtt ggtacccaag   3240
cggtacttaa tgtattgact ggtgagagat acaagatggt accaaaggaa tcaaaaggcg   3300
ttgtaaaggg ggaatacggt aaaaccccctg cacctattag tgatgaaata aaagctaaga   3360
ttctgggcga tgaaaagcct ataacatgca gacctgctga ccttattgaa cctgagcttg   3420
aaaagattag agaagctgtt aaggattata tagagcagga tgaagatgta ctttcatacg   3480
caatgcttcc tcaggttgcc gagaagttct ttaaacagcg tattgaggat agaaataagg   3540
ctactgcacc cgcatcagac gaaataaaac ccgaagttgt agcggcaata tcagccgtag   3600
taaacgaaat gggcgaaaga gacggcacac agtacagaat cggaaatatc tctaagttga   3660
accagaatca gaacagatgg agtctgtatg gtatgcttga tagattcaga acaaaaattt   3720
aacggccgta aaacgaaagg ctcagtcgaa agactgggcc tttcgtttta tctgttgttt   3780
gtcggtgaac gctctcctga gtaggacaaa tccgccggga gcggatttga acgttgcgaa   3840
gcaacggccc ggagggtggc gggcaggacg cccgccataa actgccaggc atcaaattaa   3900
gcagaaggcc atcctgacgg atggccttt tgcgtttcta caaactcttc ctgtcgtcat   3960
atctacaagc catcccccca cagatacggt aaactagcct cgttttttgca tcaggaaagc   4020 agctatgaac cactccttat aattaaattg aagctctaat ttgtgagttt agtatacatg   4080
catttactta taatacagtt ttttagtttt gctggccgca tcttctcaaa tatgcttccc   4140
agcctgcttt tctgtaacgt tcaccctcta ccttagcatc ccttcccttt gcaaatagtc   4200
```

```
ctcttccaac aataataatg tcagatcctg tagagaccac atcatccacg gttctatact    4260
gttgacccaa tgcgtctccc ttgtcatcta aacccacacc gggtgtcata atcaaccaat    4320
cgtaaccttc atctcttcca cccatgtctc tttgagcaat aaagccgata acaaaatctt    4380
tgtcgctctt cgcaatgtca acagtaccct tagtatattc tccagtagat agggagccct    4440
tgcatgacaa ttctgctaac atcaaaaggc ctctaggttc ctttgttact tcttctgccg    4500
cctgcttcaa accgctaaca ataccctggg ccaccacacc gtgtgcattc gtaatgtctg    4560
cccattctgc tattctgtat acacccgcag agtactgcaa tttgactgta ttaccaatgt    4620
cagcaaattt tctgtcttcg aagagtaaaa aattgtactt ggcggataat gcctttagcg    4680
gcttaactgt gccctccatg gaaaaatcag tcaagatatc cacatgtgtt tttagtaaac    4740
aaattttggg acctaatgct tcaactaact ccagtaattc cttggtggta cgaacatcca    4800
atgaagcaca caagtttgtt tgcttttcgt gcatgatatt aaatagcttg gcagcaacag    4860
gactaggatg agtagcagca cgttccttat atgtagcttt cgacatgatt tatcttcgtt    4920
tcggtttttg ttctgtgcag ttgggttaag aatactgggc aatttcatgt ttcttcaaca    4980
ctacatatgc gtatatatac caatctaagt ctgtgctcct tccttcgttc ttccttctgt    5040
tcggagatta ccgaatcaaa aaatttcaa agaaaccgaa atcaaaaaaa agaataaaaa     5100
aaaaatgatg aattgaaaag ctcttgttac ccatcattga attttgaaca tccgaacctg    5160
ggagttttcc ctgaaacaga tagtatattt gaacctgtat aataatatat agtctagcgc    5220
tttacggaag acaatgtatg tatttcggtt cctggagaaa ctattgcatc tattgcatag    5280
gtaatcttgc acgtcgcatc cccggttcat tttctgcgtt tccatcttgc acttcaatag    5340
catatctttg ttaacgaagc atctgtgctt cattttgtag aacaaaaatg caacgcgaga    5400
gcgctaattt tcaaacaaa gaatctgagc tgcatttta cagaacagaa atgcaacgcg     5460
aaagcgctat tttaccaacg aagaatctgt gcttcatttt tgtaaaacaa aaatgcaacg    5520
cgagagcgct aattttttcaa acaaagaatc tgagctgcat ttttacgaa cagaaatgca     5580
acgcgagagc gctatttac caacaaagaa tctatacttc tttttttgttc tacaaaaatg    5640
catcccgaga gcgctatttt tctaacaaag catcttagat tactttttttt ctcctttgtg    5700
cgctctataa tgcagtctct tgataacttt ttgcactgta ggtccgttaa ggttagaaga    5760
aggctacttt ggtgtctatt ttctcttcca taaaaaagc ctgactccac ttcccgcgtt     5820
tactgattac tagcgaagct gcgggtgcat tttttcaaga taaaggcatc cccgattata    5880
ttctataccg atgtggattg cgcatacttt gtgaacagaa agtgatagcg ttgatgattc    5940
ttcattggtc agaaaattat gaacggtttc ttctattttg tctctatata ctacgtatag    6000
gaaatgttta cattttcgta ttgttttcga ttcactctat gaatagttct tactacaatt    6060
tttttgtcta aagagtaata ctagagataa acataaaaaa tgtagaggtc gagtttagat    6120
gcaagttcaa ggagcgaaag gtggatgggt aggttatata gggatatagc acagagatat    6180
atagcaaaga gatactttg agcaatgttt gtggaagcgg tattcgcaat attttagtag    6240
ctcgttacag tccggtgcgt ttttggtttt ttgaaagtgc gtcttcagag cgcttttggt    6300
tttcaaaagc gctctgaagt tcctatactt tctagctaga aataggaac ttcggaatag     6360
gaacttcaaa gcgtttccga aaacgagcgc ttccgaaaat gcaacgcgag ctgcgcacat    6420
acagctcact gttcacgtcg cacctatatc tgcgtgttgc ctgtatatat atatacatga    6480
gaagaacggc atagtgcgtg tttatgctta aatgcgttat ggtgcactct cagtacaatc    6540
tgctctgatg ccgcatagtt aagccagccc cgacacccgc caacacccgc tgacgcgccc    6600
```

```
tgacgggctt gtctgctccc ggcatccgct tacagacaag ctgtgaccgt ctccgggagc    6660
tgcatgtgtc agaggttttc accgtcatca ccgaaacgcg cgagacgaaa gggcctcgtg    6720
atacgcctat ttttataggt taatgtcatg ataataatgg tttcttagac gtcaggtggc    6780
acttttcggg gaaatgtgcg cggaacccct atttgtttat ttttctaaat acattcaaat    6840
atgtatccgc tcatgagaca ataaccctga taaatgcttc aataatattg aaaaaggaag    6900
agtatgagta ttcaacattt ccgtgtcgcc cttattccct ttttgcggc attttgcctt     6960 cctgtttttg ctcacccaga aacgctggtg aaagtaaaag atgctgaaga tcagttgggt    7020
gcacgagtgg gttacatcga actggatctc aacagcggta agatccttga gtttttcgc    7080 cccgaagaac gttttccaat gatgagcact tttaaagttc tgctatgtgg cgcggtatta    7140
tcccgtattg acgccgggca agagcaactc ggtcgccgca tacactattc tcagaatgac    7200
ttggttgagt actcaccagt cacagaaaag catcttacgg atggcatgac agtaagagaa    7260
ttatgcagtg ctgccataac catgagtgat aacactgcgg ccaacttact tctgacaacg    7320
atcggaggac cgaaggagct aaccgctttt ttgcacaaca tgggggatca tgtaactcgc    7380
cttgatcgtt gggaaccgga gctgaatgaa gccataccaa acgacgagcg tgacaccacg    7440
atgcctgtag caatggcaac aacgttgcgc aaactattaa ctggcgaact acttactcta    7500
gcttcccggc aacaattaat agactggatg gaggcggata agttgcagg accacttctg     7560 cgctcggccc ttccggctgg ctggtttatt gctgataaat ctggagccgg tgagcgtggg    7620
tctcgcggta tcattgcagc actggggcca gatggtaagc cctcccgtat cgtagttatc    7680
tacacgacgg ggagtcaggc aactatggat gaacgaaata gacagatcgc tgagataggt    7740
gcctcactga ttaagcattg gtaactgtca gaccaagttt actcatatat actttagatt    7800
gatttaaaac ttcatttta atttaaaagg atctaggtga agatccttttt tgataatctc    7860 atgaccaaaa tcccttaacg tgagttttcg ttccactgag cgtcagaccc cgtagaaaag    7920
atcaaaggat cttcttgaga tccttttttt ctgcgcgtaa tctgctgctt gcaaacaaaa    7980
aaaccaccgc taccagcggt ggtttgtttg ccggatcaag agctaccaac tcttttttccg   8040 aaggtaactg gcttcagcag agcgcagata ccaaatactg tccttctagt gtagccgtag    8100
ttaggccacc acttcaagaa ctctgtagca ccgcctacat acctcgctct gctaatcctg    8160
ttaccagtgg ctgctgccag tggcgataag tcgtgtctta ccgggttgga ctcaagacga    8220
tagttaccgg ataaggcgca gcggtcgggc tgaacggggg gttcgtgcac acagcccagc    8280
ttggagcgaa cgacctacac cgaactgaga tacctacagc gtgagcattg agaaagcgcc    8340
acgcttcccg aagggagaaa ggcggacagg tatccggtaa gcggcagggt cggaacagga    8400
gagcgcacga gggagcttcc agggggaaac gcctggtatc tttatagtcc tgtcgggttt    8460
cgccacctct gacttgagcg tcgatttttg tgatgctcgt                           8500
```

<210> SEQ ID NO 287
<211> LENGTH: 8563
<212> TYPE: DNA
<213> ORGANISM: Artificial
<220> FEATURE:
<223> OTHER INFORMATION: pMU2899

<400> SEQUENCE: 287

```
ttgagcgtcg attttttgtga tgctcgtcag gggggcggag cctatggaaa aacgccagca      60
acgcggcctt tttacggttc ctggcctttt gctggccttt tgtgagccgt ttattttttc      120
```

```
tacccatatc cttgaagcgg tgttataatg ccgcgccctc gatatgggga tttttaacga    180
cctgattttc gggtctcagt agtagttgac attagcggag cactaaaatg acaaacaagc    240
tcagagagct caagcaaaag agagaaagaa tactaaagct tggtggagaa gataaaataa    300
aaaaacagca tgatagcaaa aaacttactt gtagagagag aatagaatat ttacttgacc    360
ctggaagctt caatgaaata gatatgtttg ttgaacacag atgtcaagaa tttgatatga    420
aagatacatt tgtcccctgt gatggtgttg taacgggtta tggaacaatc aatggcagaa    480 aagttttgt ttatgctcaa gattttactt cgataggcgg ttctcttggc gagatgcatg     540
caaaaaagat ttgtaaagtt ttggacttag cattaaaata tggttgtcca gtgataggta    600
taaatgattc tggtggtgca agaattcaag aaggtgttga tgcattagca ggatatggtg    660
aaatcttcta tagaaatacc atggcatcag gtgtaattcc acaaattgca gctataatgg    720
gaccttgtgc aggtggagct gtatactctc ctgctattat ggattttatt tttatggtgg    780
acaaaaccag ccaaatgttt gttacaggac ctcaggttat aaaagctgtg actggagagg    840
agatatcctt tgaagagctt ggtggcgctt acactcacag ctcaaagagt ggagttgctc    900 atttattgc agaggatgag tatcacctac ttgatatgat aaagtattta ttgtcgttta     960
taccttcaaa taacatggaa gacccacctt ttataatgtc atctgattca gaaaaaagat    1020
ttgttcccga gctcgaaaat ataattccgc aagagccaaa caaagcttat gatgtaaaag    1080
aaataattta taagtagta gacaaccaag aattttaga agtacaacct tattttgctc      1140
aaaatgctgt tgtaggattt ggtagaatag ggggctttag cgtaggaatt gtagcaaatc    1200
agcccaaagt gaacgctgga gtgcttgatt atgattcgtc tgacaagata gcacgatttg    1260
taagattttg tgatgctttt aatattccca taataacatt tacagacgtg cctggatttt    1320
tgccaggtgt taaccaagag cacaatggaa taattcgtca tggggctaag gttttgtatg    1380
catactcaga ggcaacagtt ccaaagataa atgtaatttt gagaaaagca tatggtgggg    1440
cttacattgc aatgagcagc aaacacattg gtgcagactt tgtgtttgca tggccaactg    1500
ccgagatagc tgttatggga ccagatggcg cagcaaatat tatatttaga aaagagatac    1560
aaagcgctca aaatcccgaa gaggaaagaa aagaaggat agaagagtat actcaaaagt     1620
ttgcaaatcc atacattgca gctgcccgtg ggtatgttga cgatgtgatt gagccacagc    1680
ttacccgtaa caaaatcatt gaggcgctca aaattccat tacaaaaaga gagcaaaggc     1740
ccccaaaaaa gcatggcaat attccattat aaaatgtatt tttgtaaaaa aaggagagtg    1800
ttttaaaaat gtatgctcag gtcagtacta tttcaaccat tacaaaagaa gaacttgctt    1860
gtatttgtgc atgtctgcac attgtgatgg gtgaaggtca atataaaatt accaacataa    1920
ctaaacagca aaacaagtgg gtcaaaggtg caagagaaat gatgctcaat cagtcacaga    1980
tgttttatag atggaggtaa agcttgtgat gagaaagttc aaggtgaaga tcaatagcca    2040
agaatttgtt gtagaagtgg aagaaatagg agttgaaaat gctacttctg tcgtgccaag    2100
gcctaagatt ggccattttg agccaaaaca ggaaaaacat gaggataaaa caaaacaaag    2160
ccctgtactt tcttctgata aaaattcggt tgttgcccag cttccgggta ctattgtaag    2220
gctgctaaaa agtgaaggtg atgttgttga tgcaaatgaa cctgttttaa ttcttgaagc    2280
catgaaaatg gaaaatgaaa taactgcacc tgtcaaagga aaaattaaaa gaatacatgt    2340
aaaggaaggg cagaaggtag caaaaggaga tttgctattt gaaatagagt aagaaaaatt    2400
ttctggaggt tttaaaaata tgggggtaa aaataacaga acaatactc agagatgctc       2460 atcagtcact cattgcaacc cgcatgacaa ctgaacagat gcttgagatt gctcctgtgc    2520
```

```
ttgaccaagt tggttattat tcggttgagt gctgggcgg tgctacattt gatgcgtgtc   2580
tgaggttttt caatgaagac ccatgggaaa gattaaaaag actgagaact gcttttaaaa   2640
agacaaagct ccagatgctt cttcgaggac aaaatcttgt tgggtataga cattattctg   2700
atgatgttgt tgaagagttt gtaaaaaagg ccatatacta tggcattgat attataagaa   2760
tatttgatgc acttaatgac atccggaata ttgaaatggc tctaaaaata acaaaaaaag   2820
aaaaaggaca tgcccaggtt gccatatcat acactgtctc accttatcat actattgaaa   2880
actatgtaaa tttggcaaaa caaatagaag aacttggggc agactcaatt tgtataaaag   2940
acatggctgg gcttctctct ccatttgatg cttataaact tgtaaaagcg ttaaaagagc   3000
aggtaaaact tcctattcat cttcatacac actacaccac aggatttgga tcaatgacat   3060
atttgaaagc tgtcgaagca ggtgtggatg gtattgacac ggctttatct ccgcttgcac   3120
tgggcacatc ccagcctcca accgaaacaa ttgtatatgc acttgaaaat acagaatatg   3180
ctccaaaact tgatttagaa aagatcaacg aggcaagcga atattttaaa gtactcagag   3240
aagaatatat aagaaagggg cttcttgacc cgaaagtatt aagtgttgat ataaacgctc   3300
ttcattatca aatacctggt ggaatgctat caaatcttat ttctcagcta aaagaacaag   3360
ggcaggaaga caagttagat gaggttttaa agaggtacc tgaggttcga aaagattttg   3420
gatatccgcc acttgtaact cctacgagtc aaattgtggg aacacaagct gttttgaatg   3480
ttatagcagg tgagagatac aaacttgtca caaagaaac aaaagcatat tttaaaggtg   3540
agtatgggaa acctccagct cctgtgaatg aagaggtaaa aagaaaaatc ttgaaagacg   3600
aaaaagagat aacctgcaga cctgcagatt tgattttgcc agagcttgaa aatgcaaaag   3660
aaagattaa ggagtatatt gaaaatgata ctgatgtggt aacttactgt ttattccctc   3720
aacttgcaga aaatttttc aaattaaggt tcgcaaaaaa atacaaggtt gacgctgatc   3780
ttgttcaggg taacaaagtg tatcctgtgt aacggccgta aaacgaaagg ctcagtcgaa   3840
agactgggcc tttcgtttta tctgttgttt gtcggtgaac gctctcctga gtaggacaaa   3900
tccgccggga gcggatttga acgttgcgaa gcaacggccc ggagggtggc gggcaggacg   3960
cccgccataa actgccaggc atcaaattaa gcagaaggcc atcctgacgg atggcctttt   4020
tgcgtttcta caaactcttc ctgtcgtcat atctacaagc catcccccca cagatacggt   4080
aaactagcct cgttttttgca tcaggaaagc agctatgaac cactccttat aattaaattg   4140
aagctctaat ttgtgagttt agtatacatg catttactta taatacagtt ttttagtttt   4200
gctggccgca tcttctcaaa tatgcttccc agcctgcttt tctgtaacgt tcaccctcta   4260
ccttagcatc ccttcccttt gcaaatagtc ctcttccaac aataataatg tcagatcctg   4320
tagagaccac atcatccacg gttctatact gttgacccaa tgcgtctccc ttgtcatcta   4380
aacccacacc gggtgtcata atcaaccaat cgtaaccttc atctcttcca cccatgtctc   4440
tttgagcaat aaagccgata acaaaatctt tgtcgctctt cgcaatgtca acagtaccct   4500
tagtatattc tccagtagat agggagccct tgcatgacaa ttctgctaac atcaaaaggc   4560
ctctaggttc ctttgttact tcttctgccg cctgcttcaa accgctaaca ataccctggc   4620
ccaccacacc gtgtgcattc gtaatgtctg cccattctgc tattctgtat acacccgcag   4680
agtactgcaa tttgactgta ttaccaatgt cagcaaattt tctgtcttcg aagagtaaaa   4740
aattgtactt ggcggataat gccttagcg gcttaactgt gccctccatg gaaaatcag   4800
tcaagatatc cacatgtgtt tttagtaaac aaattttggg acctaatgct tcaactaact   4860
```

```
ccagtaattc cttggtggta cgaacatcca atgaagcaca caagtttgtt tgcttttcgt   4920
gcatgatatt aaatagcttg gcagcaacag gactaggatg agtagcagca cgttccttat   4980
atgtagcttt cgacatgatt tatcttcgtt tcggttttg ttctgtgcag ttgggttaag    5040
aatactgggc aatttcatgt ttcttcaaca ctacatatgc gtatatatac caatctaagt   5100
ctgtgctcct tccttcgttc ttccttctgt tcggagatta ccgaatcaaa aaaatttcaa   5160
agaaaccgaa atcaaaaaaa agaataaaaa aaaaatgatg aattgaaaag ctcttgttac   5220
ccatcattga attttgaaca tccgaacctg ggagttttcc ctgaaacaga tagtatattt   5280
gaacctgtat aataatatat agtctagcgc tttacggaag acaatgtatg tatttcggtt   5340
cctggagaaa ctattgcatc tattgcatag gtaatcttgc acgtcgcatc cccggttcat   5400
tttctgcgtt tccatcttgc acttcaatag catatctttg ttaacgaagc atctgtgctt   5460
cattttgtag aacaaaaatg caacgcgaga gcgctaattt ttcaaacaaa gaatctgagc   5520
tgcatttta cagaacagaa atgcaacgcg aaagcgctat tttaccaacg aagaatctgt    5580
gcttcatttt tgtaaaacaa aaatgcaacg cgagagcgct aatttttcaa acaaagaatc   5640
tgagctgcat ttttacagaa cagaaatgca acgcgagagc gctattttac caacaaagaa   5700
tctatacttc ttttttgttc tacaaaaatg catcccgaga gcgctatttt ctaacaaag   5760
catcttagat tacttttttt ctcctttgtg cgctctataa tgcagtctct tgataacttt   5820
ttgcactgta ggtccgttaa ggttagaaga aggctacttt ggtgtctatt ttctcttcca   5880
taaaaaagc ctgactccac ttcccgcgtt tactgattac tagcgaagct gcgggtgcat    5940
tttttcaaga taaaggcatc cccgattata ttctataccg atgtggattg cgcatacttt   6000
gtgaacagaa agtgatagcg ttgatgattc ttcattggtc agaaaattat gaacggtttc   6060
ttctattttg tctctatata ctacgtatag gaaatgttta catttcgta ttgttttcga    6120
ttcactctat gaatagttct tactacaatt ttttgtcta aagagtaata ctagagataa    6180
acataaaaaa tgtagaggtc gagtttagat gcaagttcaa ggagcgaaag gtggatgggt   6240
aggttatata gggatatagc acagagatat atagcaaaga gatactttg agcaatgttt    6300
gtggaagcgg tattcgcaat attttagtag ctcgttacag tccggtgcgt ttttggtttt   6360
ttgaaagtgc gtcttcagag cgcttttggt tttcaaaagc gctctgaagt tcctatactt   6420
tctagctaga aataggaac ttcggaatag gaacttcaaa gcgtttccga aaacgagcgc    6480
ttccgaaaat gcaacgcgag ctgcgcacat acagctcact gttcacgtcg cacctatatc   6540
tgcgtgttgc ctgtatatat atatacatga gaagaacggc atagtgcgtg tttatgctta   6600
aatgcgttat ggtgcactct cagtacaatc tgctctgatg ccgcatagtt aagccagccc   6660
cgacacccgc caacacccgc tgacgcgccc tgacgggctt gtctgctccc ggcatccgct   6720
tacagacaag ctgtgaccgt ctccgggagc tgcatgtgtc agaggttttc accgtcatca   6780
ccgaaacgcg cgagacgaaa gggcctcgtg atacgcctat ttttataggt taatgtcatg   6840
ataataatgg tttcttagac gtcaggtggc acttttcggg gaaatgtgcg cggaacccct   6900
atttgtttat ttttctaaat acattcaaat atgtatccgc tcatgagaca ataaccctga   6960
taaatgcttc aataatattg aaaaggaag agtatgagta ttcaacattt ccgtgtcgcc    7020
cttattccct ttttttgcggc attttgcctt cctgtttttg ctcacccaga aacgctggtg   7080
aaagtaaaag atgctgaaga tcagttgggt gcacgagtgg gttacatcga actggatctc   7140
aacagcggta agatccttga gagttttcgc cccgaagaac gttttccaat gatgagcact   7200
tttaaagttc tgctatgtgg cgcggtatta tcccgtattg acgccgggca agagcaactc   7260
```

```
ggtcgccgca tacactattc tcagaatgac ttggttgagt actcaccagt cacagaaaag   7320
catcttacgg atggcatgac agtaagagaa ttatgcagtg ctgccataac catgagtgat   7380
aacactgcgg ccaacttact tctgacaacg atcggaggac cgaaggagct aaccgctttt   7440
ttgcacaaca tggggatca tgtaactcgc cttgatcgtt gggaaccgga gctgaatgaa   7500
gccataccaa acgacgagcg tgacaccacg atgcctgtag caatggcaac aacgttgcgc   7560
aaactattaa ctggcgaact acttactcta gcttcccggc aacaattaat agactggatg   7620
gaggcggata agttgcagg accacttctg cgctcggccc ttccggctgg ctggtttatt   7680
gctgataaat ctggagccgg tgagcgtggg tctcgcggta tcattgcagc actggggcca   7740
gatggtaagc cctcccgtat cgtagttatc tacacgacgg ggagtcaggc aactatggat   7800
gaacgaaata gacagatcgc tgagataggt gcctcactga ttaagcattg gtaactgtca   7860
gaccaagttt actcatatat actttagatt gatttaaaac ttcattttta atttaaaagg   7920
atctaggtga agatcctttt tgataatctc atgaccaaaa tcccttaacg tgagttttcg   7980
ttccactgag cgtcagaccc cgtagaaaag atcaaaggat cttcttgaga tcctttttt   8040 ctgcgcgtaa tctgctgctt gcaaacaaaa aaaccaccgc taccagcggt ggtttgtttg   8100
ccggatcaag agctaccaac tcttttccg aaggtaactg gcttcagcag agcgcagata   8160
ccaaatactg tccttctagt gtagccgtag ttaggccacc acttcaagaa ctctgtagca   8220
ccgcctacat acctcgctct gctaatcctg ttaccagtgg ctgctgccag tggcgataag   8280
tcgtgtctta ccgggttgga ctcaagacga tagttaccgg ataaggcgca gcggtcgggc   8340
tgaacggggg gttcgtgcac acagcccagc ttggagcgaa cgacctacac cgaactgaga   8400
tacctacagc gtgagcattg agaaagcgcc acgcttcccg aagggagaaa ggcggacagg   8460
tatccggtaa gcggcagggt cggaacagga gagcgcacga gggagcttcc agggggaaac   8520
gcctggtatc tttatagtcc tgtcgggttt cgccacctct gac                    8563

<210> SEQ ID NO 288
<211> LENGTH: 8652
<212> TYPE: DNA
<213> ORGANISM: Artificial
<220> FEATURE:
<223> OTHER INFORMATION: pMU2900

<400> SEQUENCE: 288
tttgtgatgc tcgtcagggg ggcggagcct atggaaaaac gccagcaacg cggcctttttt    60 acggttcctg gccttttgct ggccttttgt gagccgttta tttttctac ccatatcctt    120 gaagcggtgt tataatgccg cgccctcgat atgggggattt ttaacgacct gattttcggg   180
tctcagtagt agttgacatt agcggagcac taaaatgtca atagatgata ggattgaaga   240
ccttcttaga agaagagaga tggttttaga aggcggtggt ttagataaag tagagaaaca   300
acaccaaaag ggaaagctta ccgcaagaga gaggatatac aagcttttag atgaagatag   360
ctttgtggaa atagatgcgt atgttgagca caggtgtatt gactttggca tggaaaagca   420
aaggatacct ggcgaaggcg tagtgacagg gtatgggacg atagatggaa ggcttgtcta   480
cgtttatgca caggatttta cggttttagg aggatcatta ggcgagtatc atgcaaagaa   540
aatcacaaaa atcatggata tggctttaaa gatgggagca ccgctcattg gattaaatga   600
ttccggaggt gccagaatac aggaaggcgt cgatgcttta tcgggatatg caacatatt   660 tttcagaaac acgctggcat caggcgtaat accgcaaata tcggtgataa tggggcccag   720
```

```
cgctggaggt gcagtttatt cgcctgctct tactgacttt atattcatgg tagacaagac    780
aagtcagatg tttataactg gaccgcaggt cataaaagcc gtcacaggtg aagatgtttc    840
ggcagaggag cttggtggat cgattactca cagcacgaaa agcggtgtgg cgcattttag    900
ggctgaaaac gacgaagagt gtttgaagat ggtgaggaag ctattaagtt accttccatc    960
aaacaatttg gaagatccgc cacagttggc gacagatgac gacataaaca gattttccga   1020
taggcttatt gagataatcc cagatagtcc taataagcca tacgatatga agaagtaat   1080
ttcggaaata gtggatgaag gcgtgtattt tgaatcacag gcaatgtatg cgcaaaacat   1140
aataacggca tttgcaaggc ttaatggaag gacggtaggg ataatagcaa atcagcctaa   1200
agttttggct ggatgtctcg acatcaatgc gtctgataag gcatcgaggt ttataaggtt   1260
ttgcgatgca tttaacatcc cgcttctcaa tatagtagat gttccaggat ttttgcctgg   1320
aacgaatcaa gagtacggtg aataatacg ccatggggca aagatgttgt acgcttactc   1380
tgaggctaca gtgccaaaag tgactctcat tgtgaggaaa gcttatggcg gtgcttacct   1440
tgccatgtgc agcaaagact taggagctga ttttgttttg gcatggccta ctgctgaaat   1500
agcggtcatg ggacctgatg gggcagcaaa catcgtgttt aaaaatgaaa taaaatcgtc   1560
tgatgatcct gtggctgcaa gaaatgaaaa gataaatgag tacagggaga atttcgcaaa   1620
tccatacagg gcagcagcga gaggatatgt agatgatgta gttctgccgc aagagacgag   1680
acctcgcctc atctcggcgt tcgatatgct tatgagcaaa agggagtcaa ggcccagcaa   1740
aaagcatggc aatttttcctg ttttaaaatcg atttaagggg aagtgaaaga atggaagaga   1800
taaatgaaga aatagttgct gtcattgaag ctgcgattta cgcggcattt ggtcagtacg   1860
aaaagaattt ccgcatcaag gtaataaaga gagtggactc aaatatgccg aatggagaa   1920
aagctggcct ttacaatcag atgagataga tgaggaggat ggaaatgaaa aaatttatag   1980
taactgtcaa tggaaaaaaa tacgatgtgg aagtagaaga agtaaaagtc gacgtggcaa   2040
gtgagaaaaa agcaaagaaa gatactgctg ctaaaaatgc gtcagatgca agtgtaaaaa   2100
gcaaacaggt tgaagtaaaa aacgaagtca agacggtttt ctcaatcaat gcaccgatgc   2160
cgggaactat attggatgtc aaaataagcc aaggccagac tgtcagacga ggcgatgtgc   2220
ttttaatact ggaagccatg aagatggaaa atgaaatcac gtcaccttac gatggcacaa   2280
taatatccat aaatgtttca aaaggtgcct ctgtaaatac aggcgatgtg cttttgtact   2340
taaaatgaga gtaaaggagg agttttaatg tctaagataa aaataacgga gactgtttta   2400
agagatgcac atcaatcgtt gctggcaacc agaatgacaa ccgatgaaat gcttcctata   2460
gcagaaaaat tagatgaagt tggttttttc tcgctggaag catggggcgg tgctacattt   2520
gatgcatgta tgagattttt gaatgaagac ccatggaaa gattaagact tttaaagaag   2580
gcgattaaga agacacctct tcaaatgctt ttaagaggtc aaaatttact cggatataaa   2640
cactatcccg atgatgtcgt aaatgaattt ataataaaat ctgttgaaaa tggtatagat   2700
ataataagaa ttttttgatgc gttaaatgat gtgagaaatt tagaagtgcc aataaaatct   2760
gcaaaaagtg caggtgctca tgtacaggca gctattgtat atacagttag tcctgtacat   2820
aatacagatc attatttgaa agtggcaaag tctcttcaag atatgggtgc ggattccata   2880
tgcattaagg atatgtctgg aatattatca ccctatgttg catacgattt gattaaatct   2940
ctgaaaagag cactttacac gccaattcaa ctgcatagcc attatacagc aggactggct   3000
tcaatgactt atttaaaagc catagaagct ggtgtagacg gggttgatac agctatttct   3060
tcgcttgcct taggaacatc acaaccagct acagaatcaa tcgtggctgc attgaaagat   3120
```

| | |
|---|---|
| acagaatatg atacagggct agatttaaaa ttgcttgctg agatagctca gcattttaat | 3180 |
| gtagtcaaac agaatcacaa aaatgacagc gatatgtctt tgcttatgtc tgttgatgtt | 3240 |
| aaagcattag aaagtcaaat accaggggga atgttatcaa atttggtttc acagctaaag | 3300 |
| cagcagaatg cattaaacaa atatcaagac gtcttgaaag aagttccaag ggtacgcgaa | 3360 |
| gatttgggat atcctcctct tgttactcca atgagccaga tggttggaac ccaggctgtt | 3420 |
| ttaaatgtta ttacagggga gagatataaa atcgttccta aagaaattaa agattatgtc | 3480 |
| aaaggtttat atgggatgcc accagctcca atttcagatt ctatacgaaa gaaaataatc | 3540 |
| ggcgatgaag aagtaatttc aaagaggcca gcagatttac taagtcctca attggatgaa | 3600 |
| tttaaaaatg agataaagga atttatagag caagatgaag atgttttatc atatgcatta | 3660 |
| tttcctcaag tagcaagaag attttttcgag tataggcaag ccaaaaaata cagaattgat | 3720 |
| tcaacattat taaatatcga agaaagggtt catccgatat aacggccgta aaacgaaagg | 3780 |
| ctcagtcgaa agactgggcc tttcgtttta tctgttgttt gtcggtgaac gctctcctga | 3840 |
| gtaggacaaa tccgccggga gcggatttga acgttgcgaa gcaacggccc ggagggtggc | 3900 |
| gggcaggacg cccgccataa actgccaggc atcaaattaa gcagaaggcc atcctgacgg | 3960 |
| atggcctttt tgcgtttcta caaactcttc ctgtcgtcat atctacaagc catcccccca | 4020 |
| cagatacggt aaactagcct cgttttttgca tcaggaaagc agctatgaac cactcctgcg | 4080 |
| aagaggcccg caccgatcgc ccttcccaac agttgcgcag cctgaatggc gaatggcgcc | 4140 |
| tgatgcggta ttttctcctt acgcatctgt gcggtatttc acaccgcata gggtaataac | 4200 |
| tgatataatt aaattgaagc tctaatttgt gagtttagta tacatgcatt tacttataat | 4260 |
| acagtttttt agttttgctg gccgcatctt ctcaaatatg cttcccagcc tgcttttctg | 4320 |
| taacgttcac cctctacctt agcatccctt ccctttgcaa atagtcctct tccaacaata | 4380 |
| ataatgtcag atcctgtaga gaccacatca tccacggttc tatactgttg acccaatgcg | 4440 |
| tctcccttgt catctaaacc cacaccgggt gtcataatca accaatcgta accttcatct | 4500 |
| cttccaccca tgtctctttg agcaataaag ccgataacaa aatctttgtc gctcttcgca | 4560 |
| atgtcaacag taccccttagt atattctcca gtagatagggg agcccttgca tgacaattct | 4620 |
| gctaacatca aaaggcctct aggttccttt gttacttctt ctgccgcctg cttcaaaccg | 4680 |
| ctaacaatac ctgggcccac cacaccgtgt gcattcgtaa tgtctgccca ttctgctatt | 4740 |
| ctgtatacac ccgcagagta ctgcaatttg actgtattac caatgtcagc aaattttctg | 4800 |
| tcttcgaaga gtaaaaaatt gtacttggcg gataatgcct ttagcggctt aactgtgccc | 4860 |
| tccatggaaa aatcagtcaa gatatccaca tgtgttttta gtaaacaaat tttgggacct | 4920 |
| aatgcttcaa ctaactccag taattccttg gtggtacgaa catccaatga agcacacaag | 4980 |
| tttgtttgct tttcgtgcat gatattaaat agcttggcag caacaggact aggatgagta | 5040 |
| gcagcacgtt cctatatgt agctttcgac atgatttatc ttcgtttcgg ttttgttct | 5100 |
| gtgcagttgg gttaagaata ctgggcaatt tcatgtttct tcaacactac atatgcgtat | 5160 |
| atataccaat ctaagtctgt gctccttcct tcgttcttcc ttctgttcgg agattaccga | 5220 |
| atcaaaaaaa tttcaaagaa accgaaatca aaaaaagaa taaaaaaaaa atgatgaatt | 5280 |
| gaaaagctct tgttacccat cattgaattt tgaacatccg aacctgggag ttttccctga | 5340 |
| aacagatagt atatttgaac ctgtataata atatatagtc tagcgcttta cggaagacaa | 5400 |
| tgtatgtatt tcggttcctg gagaaactat tgcatctatt gcataggtaa tcttgcacgt | 5460 |

```
cgcatccccg gttcattttc tgcgtttcca tcttgcactt caatagcata tctttgttaa   5520
cgaagcatct gtgcttcatt ttgtagaaca aaaatgcaac gcgagagcgc taattttttca  5580 aacaaagaat ctgagctgca ttttttacaga acagaaatgc aacgcgaaag cgctatttta  5640
ccaacgaaga atctgtgctt cattttttgta aaacaaaaat gcaacgcgag agcgctaatt  5700
tttcaaacaa agaatctgag ctgcattttt acagaacaga aatgcaacgc gagagcgcta  5760
ttttaccaac aaagaatcta acttctttt tgttctaca aaaatgcatc ccgagagcgc    5820 tattttttcta acaaagcatc ttagattact ttttttctcc tttgtgcgct ctataatgca  5880
gtctcttgat aacttttttgc actgtaggtc cgttaaggtt agaagaaggc tactttggtg  5940
tctattttct cttccataaa aaaagcctga ctccacttcc cgcgtttact gattactagc  6000
gaagctgcgg gtgcatttttt tcaagataaa ggcatcccg attatattct ataccgatgt   6060
ggattgcgca tactttgtga acagaaagtg atagcgttga tgattcttca ttggtcagaa   6120
aattatgaac ggtttcttct attttgtctc tatatactac gtataggaaa tgtttacatt   6180
ttcgtattgt tttcgattca ctctatgaat agttcttact acaatttttt tgtctaaaga   6240
gtaatactag ataaaacat aaaaaatgta gaggtcgagt ttagatgcaa gttcaaggag    6300
cgaaaggtgg atgggtaggt tatatagggga tatagcacag agatatatag caaagagata  6360
cttttgagca atgtttgtgg aagcggtatt cgcaatatt tagtagctcg ttacagtccg   6420
gtgcgttttt ggtttttga aagtgcgtct tcagagcgct tttggttttc aaaagcgctc   6480
tgaagttcct atactttcta gctagagaat aggaacttcg gaataggaac ttcaaagcgt   6540
ttccgaaaac gagcgcttcc gaaaatgcaa cgcgagctgc gcacatacag ctcactgttc   6600
acgtcgcacc tatatctgcg tgttgcctgt atatatatat acatgagaag aacggcatag   6660
tgcgtgttta tgcttaaatg cgttatggtg cactctcagt acaatctgct ctgatgccgc   6720
atagttaagc cagccccgac acccgccaac accgctgac gcgccctgac gggcttgtct   6780
gctcccggca tccgcttaca gacaagctgt gaccgtctcc gggagctgca tgtgtcagag   6840
gttttcaccg tcatcaccga aacgcgcgag acgaaaggc ctcgtgatac gcctatttt   6900 ataggttaat gtcatgataa taatggtttc ttagacgtca ggtggcactt tcggggaaa   6960 tgtgcgcgga acccctattt gtttatttt ctaaatacat tcaaatatgt atccgctcat   7020
gagacaataa ccctgataaa tgcttcaata atattgaaaa aggaagagta tgagtattca   7080
acatttccgt gtcgccctta ttccctttt tgcggcattt gccttcctg ttttttgctca    7140 cccagaaacg ctggtgaaag taaaagatgc tgaagatcag ttgggtgcac gagtgggtta   7200
catcgaactg gatctcaaca gcggtaagat ccttgagagt tttcgccccg aagaacgttt   7260
tccaatgatg agcactttta aagttctgct atgtggcgcg gtattatccc gtattgacgc   7320
cgggcaagag caactcggtc gccgcataca ctattctcag aatgacttgg ttgagtactc   7380
accagtcaca gaaaagcatc ttacggatgg catgacagta agagaattat gcagtgctgc   7440
cataaccatg agtgataaca ctgcggccaa cttacttctg acaacgatcg gaggaccgaa   7500
ggagctaacc gctttttgc acaacatggg ggatcatgta actcgccttg atcgttggga   7560
accggagctg aatgaagcca taccaaacga cgagcgtgac accacgatgc ctgtagcaat   7620
ggcaacaacg ttgcgcaaac tattaactgg cgaactactt actctagctt cccggcaaca   7680
attaatagac tggatggagg cggataaagt tgcaggacca cttctgcgct cggcccttcc   7740
ggctggctgg tttattgctg ataaatctgg agccggtgag cgtgggtctc gcggtatcat   7800
tgcagcactg gggccagatg gtaagccctc ccgtatcgta gttatctaca cgacggggag   7860
```

```
tcaggcaact atggatgaac gaaatagaca gatcgctgag ataggtgcct cactgattaa    7920
gcattggtaa ctgtcagacc aagtttactc atatatactt tagattgatt taaaacttca    7980
tttttaattt aaaaggatct aggtgaagat ccttttttgat aatctcatga ccaaaatccc    8040
ttaacgtgag tttttcgttcc actgagcgtc agacccccgta gaaaagatca aaggatcttc    8100
ttgagatcct ttttttctgc gcgtaatctg ctgcttgcaa acaaaaaaac caccgctacc    8160
agcggtggtt tgtttgccgg atcaagagct accaactctt tttccgaagg taactggctt    8220
cagcagagcg cagataccaa atactgtcct tctagtgtag ccgtagttag gccaccactt    8280
caagaactct gtagcaccgc ctacatacct cgctctgcta atcctgttac cagtggctgc    8340
tgccagtggc gataagtcgt gtcttaccgg gttggactca agacgatagt taccggataa    8400
ggcgcagcgg tcgggctgaa cggggggttc gtgcacacag cccagcttgg agcgaacgac    8460
ctacaccgaa ctgagatacc tacagcgtga gcattgagaa agcgccacgc ttcccgaagg    8520
gagaaaggcg gacaggtatc cggtaagcgg cagggtcgga acaggagagc gcacgaggga    8580
gcttccaggg ggaaacgcct ggtatcttta tagtcctgtc gggtttcgcc acctctgact    8640
tgagcgtcga tt                                                         8652

<210> SEQ ID NO 289
<211> LENGTH: 8864
<212> TYPE: DNA
<213> ORGANISM: Artificial
<220> FEATURE:
<223> OTHER INFORMATION: pMU2901

<400> SEQUENCE: 289
ctcgtcaggg gggcggagcc tatggaaaaa cgccagcaac gcggcctttt tacggttcct      60
ggccttttgc tggccttttg tgagccgttt attttttcta cccatatcct tgaagcggtg     120
ttataatgcc gcgccctcga tatgggggatt tttaacgacc tgattttcgg gtctcagtag     180
tagttgacat tagcggagca ctaaaatgag tccgcgagaa attgaggttt ccgagccgcg     240
cgaggttggt atcaccgagc tcgtgctgcg cgatgcccat cagagcctga tggccacacg     300
aatggcaatg gaagacatgg tcggcgcctg tgcagacatt gatgctgccg ggtactggtc     360
agtggagtgt tggggtggtg ccacgtatga ctcgtgtatc cgcttcctca acgaggatcc     420
ttgggagcgt ctgcgcacgt tccgcaagct gatgcccaac agccgtctcc agatgctgct     480
gcgtggccag aacctgctgg gttaccgcca ctaacgac gaggtcgtcg atcgcttcgt     540
cgacaagtcc gctgagaacg gcatggacgt gttccgtgtc ttcgacgcca tgaatgatcc     600
ccgcaacatg gcgcacgcca tggctgccgt caagaaggcc ggcaagcacg cgcagggcac     660
catttgctac acgatcagcc cggtccacac cgttgagggc tatgtcaagc ttgctggtca     720
gctgctcgac atgggtgctg attccatcgc cctgaaggac atggccgccc tgctcaagcc     780
gcagccggcc tacgacatca tcaaggccat caaggacacc tacggccaga gacgcagat     840 caacctgcac tgccactcca ccacgggtgt caccgaggtc tccctcatga aggccatcga     900
ggccggcgtc gacgtcgtcg acaccgccat ctcgtccatg tcgctcggcc gggccacaa     960 ccccaccgag tcggttgccg agatgctcga gggcaccggg tacaccacca accttgacta    1020
cgatcgcctg cacaagatcc gcgatcactt caaggccatc cgcccgaagt acaagaagtt    1080
cgagtcgaag acgcttgtcg acacctcgat cttcaagtcg cagatccccg gcggcatgct    1140
ctccaacatg gagtcgcagc tgcgcgccca gggcgccgag gacaagatgg acgaggtcat    1200
```

```
ggcagaggtg ccgcgcgtcc gcaaggccgc cggcttcccg cccctggtca ccccgtccag   1260
ccagatcgtc ggcacgcagg ccgtgttcaa cgtgatgatg ggcgagtaca agaggatgac   1320
cggcgagttc gccgacatca tgctcggcta ctacggcgcc agcccggccg atcgcgatcc   1380
gaaggtggtc aagttggccg aggagcagtc cggcaagaag ccgatcaccc agcgcccggc   1440
cgatctgctg ccccccgagt gggaggagca gtccaaggag gccgcggccc tcaagggctt   1500
caacggcacc gacgaggacg tgctcaccta tgcactgttc ccgcaggtcg ctccggtctt   1560
cttcgagcat cgcgccgagg gcccgcacag cgtggctctc accgatgccc agctgaaggc   1620
cgaggccgag ggcgacgaga gtcgctcgc cgtggccggt cccgtcacct acaacgtgaa   1680
cgtgggcgga accgtccgcg aagtcaccgt tcagcaggcg tgaggatgat tgccaatcat   1740
ggctgaaaac aacaatttga agctcgccag caccatggaa ggtcgcgtgg agcagctcgc   1800
agagcagcgc caggtgatcg aagccggtgg cggcgaacgt cgcgtcgaga gcaacattc   1860
ccagggtaag cagaccgctc gtgagcgcct gaacaacctg ctcgatcccc attcgttcga   1920
cgaggtcggc gctttccgca agcaccgcac cacgttgttc ggcatggaca aggccgtcgt   1980
cccggcagat ggcgtggtca ccggccgtgg caccatcctt ggtcgtcccg tgcacgccgc   2040
gtcccaggac ttcacggtca tgggtggttc ggctggcgag acgcagtcca cgaaggtcgt   2100
cgagacgatg aacaggcgc tgctcaccgg cacgcccttc ctgttcttct acgattcggg   2160
cggcgcccga atcaggagg gcatcgactc gctgagcggt tacggcaaga tgttcttcgc   2220
caacgtgaag ctgtcgggcg tcgtgccgca gatcgccatc attgccggcc cctgtgccgg   2280
tggcgcctcg tattcgccgg cactgactga cttcatcatc atgaccaaga aggcccatat   2340
gttcatcacg ggcccccagg tcatcaagtc ggtcaccggc gaggatgtca ccgctgacga   2400
actcggtggc gctgaggccc atatggccat ctcgggcaat atccacttcg tggccgagga   2460
cgacgacgcc gcggagctca ttgccaagaa gctgctgagc ttccttccgc agaacaacac   2520
tgaggaagca tccttcgtca acccgaacaa tgacgtcagc cccaataccg agctgcgcga   2580
catcgttccg attgacggca agaagggcta tgacgtgcgc gatgtcattg ccaagatcgt   2640
cgactgggt gactacctcg aggtcaaggc cggctatgcc accaacctcg tgaccgcctt   2700
cgcccgggtc aatggtcgtt cggtgggcat cgtggccaat cagccgtcgg tgatgtcggg   2760
ttgcctcgac atcaacgcct ctgacaaggc cgccgaattc gtgaattct gcgattcgtt   2820
caacatcccg ctggtgcagc tggtcgacgt gccgggcttc ctgcccggcg tgcagcagga   2880
gtacggcggc atcattcgcc atggcgcgaa gatgctgtac gcctactccg aggccaccgt   2940
gccgaagatc accgtggtgc tccgcaaggc ctacggcggc tcctacctgg ccatgtgcaa   3000
ccgtgacctt ggtgccgacg ccgtgtacgc ctggcccagc gccgagattg cggtgatggg   3060
cgccgagggt gcggcaaatg tgatcttccg caaggagatc aaggctgccg acgatcccga   3120
cgccatgcgc gccgagaaga tcgaggagta ccagaacgcg ttcaacacgc gtacgtggc   3180
cgccgcccgc ggtcaggtcg acgacgtgat tgacccggct gataccccgtc gaaagattgc   3240
ttccgccctg gagatgtacg ccaccaagcg tcagacccgc ccggcgaaga agcatggaaa   3300
cttcccctgc tgagcgagga gagaaattat ggctgatgag gaagagaagg acctgatgat   3360
cgccacgctc aacaagcgcg tcgcgtcatt ggagtctgag ttgggttcac tccagagcga   3420
tacccagggt gtcaccgagg acgtactgac ggccatttcg gccgccgttg cggcctatct   3480
cggcaacgat ggatcggctg aggtcgtcca tttcgccccg agcccgaact gggtccgcga   3540
gggtcgtcgg gctctgcaga accattccat tcgttgatcc gggagtaact cacatgaaac   3600
```

```
tgaaggtaac agtcaacggc actgcgtatg acgttgacgt tgacgtcgac aagtcacacg    3660
aaaacccgat gggcaccatc ctgttcggcg gcggcaccgg cggcgcgccg gcaccgcgcg    3720
cagcaggtgg cgcaggcgcc ggtaaggccg gagagggcga gattcccgct ccgctggccg    3780
gcaccgtctc caagatcctc gtgaaggagg gtgacacggt caaggctggt cagaccgtgc    3840
tcgttctcga ggccatgaag atggagaccg agatcaacgc tcccaccgac ggcaaggtcg    3900
agaaggtcct tgtcaaggag cgtgacgccg tgcaggcgg tcagggtctc atcaagatcg    3960
gctgacggcc gtaaaacgaa aggctcagtc gaaagactgg gcctttcgtt ttatctgttg    4020
tttgtcggtg aacgctctcc tgagtaggac aaatccgccg ggagcggatt tgaacgttgc    4080
gaagcaacgg cccggagggt ggcgggcagg acgcccgcca taaactgcca ggcatcaaat    4140
taagcagaag gccatcctga cggatggcct ttttgcgttt ctacaaactc ttcctgtcgt    4200
catatctaca agccatcccc ccacagatac ggtaaactag cctcgttttt gcatcaggaa    4260
agcagctatg aaccactcct gcgaagaggc ccgcaccgat cgcccttccc aacagttgcg    4320
cagcctgaat ggcgaatggc gcctgatgcg gtattttctc cttacgcatc tgtgcggtat    4380
ttcacaccgc atagggtaat aactgatata attaaattga agctctaatt tgtgagttta    4440
gtatacatgc atttacttat aatacagttt tttagttttg ctggccgcat cttctcaaat    4500
atgcttccca gcctgctttt ctgtaacgtt caccctctac cttagcatcc cttccctttg    4560
caaatagtcc tcttccaaca ataataatgt cagatcctgt agagaccaca tcatccacgg    4620
ttctatactg ttgacccaat gcgtctccct tgtcatctaa acccacaccg ggtgtcataa    4680
tcaaccaatc gtaaccttca tctcttccac ccatgtctct ttgagcaata aagccgataa    4740
caaaatcttt gtcgctcttc gcaatgtcaa cagtaccctt agtatattct ccagtagata    4800
gggagcccct gcatgacaat tctgctaaca tcaaaaggcc tctaggttcc tttgttactt    4860
cttctgccgc ctgcttcaaa ccgctaacaa tacctgggcc caccacaccg tgtgcattcg    4920
taatgtctgc ccattctgct attctgtata cacccgcaga gtactgcaat ttgactgtat    4980
taccaatgtc agcaaatttt ctgtcttcga agagtaaaaa attgtacttg gcggataatg    5040
cctttagcgg cttaactgtg ccctccatgg aaaaatcagt caagatatcc acatgtgttt    5100
ttagtaaaca aattttggga cctaatgctt caactaactc cagtaattcc ttggtggtac    5160
gaacatccaa tgaagcacac aagtttgttt gcttttcgtg catgatatta aatagcttgg    5220
cagcaacagg actaggatga gtagcagcac gttccttata tgtagctttc gacatgattt    5280
atcttcgttt cggttttttgt tctgtgcagt tgggttaaga atactgggca atttcatgtt    5340
tcttcaacac tacatatgcg tatatatacc aatctaagtc tgtgctcctt ccttcgttct    5400
tccttctgtt cggagattac cgaatcaaaa aaatttcaaa gaaaccgaaa tcaaaaaaaa    5460
gaataaaaaa aaaatgatga attgaaaagc tcttgttacc catcattgaa ttttgaacat    5520
ccgaacctgg gagttttccc tgaaacagat agtatatttg aacctgtata ataatatata    5580
gtctagcgct ttacggaaga caatgtatgt atttcggttc ctggagaaac tattgcatct    5640
attgcatagg taatcttgca cgtcgcatcc ccggttcatt ttctgcgttt ccatcttgca    5700
cttcaatagc atatctttgt taacgaagca tctgtgcttc attttgtaga acaaaaatgc    5760
aacgcgagag cgctaatttt tcaaacaaag aatctgagct gcattttac agaacagaaa    5820
tgcaacgcga agcgctatt ttaccaacga agaatctgtg cttcattttt gtaaaacaaa    5880
aatgcaacgc gagagcgcta attttcaaa caaagaatct gagctgcatt tttacagaac    5940
```

| | | | | | |
|---|---|---|---|---|---|
| agaaatgcaa | cgcgagagcg | ctattttacc | aacaaagaat | ctatacttct | tttttgttct | 6000 |
| acaaaaatgc | atcccgagag | cgctattttt | ctaacaaagc | atcttagatt | actttttttc | 6060 |
| tcctttgtgc | gctctataat | gcagtctctt | gataactttt | tgcactgtag | gtccgttaag | 6120 |
| gttagaagaa | ggctactttg | tgtgtctattt | tctcttccat | aaaaaaagcc | tgactccact | 6180 |
| tcccgcgttt | actgattact | agcgaagctg | cgggtgcatt | ttttcaagat | aaaggcatcc | 6240 |
| ccgattatat | tctataccga | tgtggattgc | gcatactttg | tgaacagaaa | gtgatagcgt | 6300 |
| tgatgattct | tcattggtca | gaaaattatg | aacggtttct | tctattttgt | ctctatatac | 6360 |
| tacgtatagg | aaatgtttac | attttcgtat | tgttttcgat | tcactctatg | aatagttctt | 6420 |
| actacaattt | ttttgtctaa | agagtaatac | tagagataaa | cataaaaaat | gtagaggtcg | 6480 |
| agtttagatg | caagttcaag | gagcgaaagg | tggatgggta | ggttatatag | ggatatagca | 6540 |
| cagagatata | tagcaaagag | atacttttga | gcaatgtttg | tggaagcggt | attcgcaata | 6600 |
| ttttagtagc | tcgttacagt | ccggtgcgtt | tttggttttt | tgaaagtgcg | tcttcagagc | 6660 |
| gcttttggtt | ttcaaaagcg | ctctgaagtt | cctatacttt | ctagctagag | aataggaact | 6720 |
| tcggaatagg | aacttcaaag | cgtttccgaa | aacgagcgct | tccgaaaatg | caacgcgagc | 6780 |
| tgcgcacata | cagctcactg | ttcacgtcgc | acctatatct | gcgtgttgcc | tgtatatata | 6840 |
| tatacatgag | aagaacggca | tagtgcgtgt | ttatgcttaa | atgcgttatg | gtgcactctc | 6900 |
| agtacaatct | gctctgatgc | cgcatagtta | agccagcccc | gacacccgcc | aacacccgct | 6960 |
| gacgcgccct | gacgggcttg | tctgctcccg | gcatccgctt | acagacaagc | tgtgaccgtc | 7020 |
| tccgggagct | gcatgtgtca | gaggttttca | ccgtcatcac | cgaaacgcgc | gagacgaaag | 7080 |
| ggcctcgtga | tacgcctatt | tttataggtt | aatgtcatga | taataatggt | ttcttagacg | 7140 |
| tcaggtggca | cttttcgggg | aaatgtgcgc | ggaaccccta | tttgtttatt | tttctaaata | 7200 |
| cattcaaata | tgtatccgct | catgagacaa | taaccctgat | aaatgcttca | ataatattga | 7260 |
| aaaaggaaga | gtatgagtat | tcaacatttc | cgtgtcgccc | ttattccctt | ttttgcggca | 7320 |
| ttttgccttc | ctgtttttgc | tcacccagaa | acgctggtga | aagtaaaaga | tgctgaagat | 7380 |
| cagttgggtg | cacgagtggg | ttacatcgaa | ctggatctca | acagcggtaa | gatccttgag | 7440 |
| agttttcgcc | ccgaagaacg | ttttccaatg | atgagcactt | ttaaagttct | gctatgtggc | 7500 |
| gcggtattat | cccgtattga | cgccgggcaa | gagcaactcg | gtcgccgcat | acactattct | 7560 |
| cagaatgact | tggttgagta | ctcaccagtc | acagaaaagc | atcttacgga | tggcatgaca | 7620 |
| gtaagagaat | tatgcagtgc | tgccataacc | atgagtgata | acactgcggc | caacttactt | 7680 |
| ctgacaacga | tcggaggacc | gaaggagcta | accgcttttt | tgcacaacat | ggggatcat | 7740 |
| gtaactcgcc | ttgatcgttg | ggaaccggag | ctgaatgaag | ccataccaaa | cgacgagcgt | 7800 |
| gacaccacga | tgcctgtagc | aatggcaaca | acgttgcgca | aactattaac | tggcgaacta | 7860 |
| cttactctag | cttcccggca | acaattaata | gactggatgg | aggcggataa | agttgcagga | 7920 |
| ccacttctgc | gctcggccct | tccggctggc | tggtttattg | ctgataaatc | tggagccggt | 7980 |
| gagcgtgggt | ctcgcggtat | cattgcagca | ctggggccag | atggtaagcc | ctcccgtatc | 8040 |
| gtagttatct | acacgacggg | gagtcaggca | actatggatg | aacgaaatag | acagatcgct | 8100 |
| gagataggtg | cctcactgat | taagcattgg | taactgtcag | accaagttta | ctcatatata | 8160 |
| ctttagattg | atttaaaact | tcattttaa | tttaaaagga | tctaggtgaa | gatcctttt | 8220 |
| gataatctca | tgaccaaaat | cccttaacgt | gagttttcgt | tccactgagc | gtcagacccc | 8280 |
| gtagaaaaga | tcaaaggatc | ttcttgagat | cctttttttc | tgcgcgtaat | ctgctgcttg | 8340 |

-continued

```
caaacaaaaa aaccaccgct accagcggtg gtttgtttgc cggatcaaga gctaccaact      8400 cttttccga aggtaactgg cttcagcaga gcgcagatac caaatactgt ccttctagtg      8460
tagccgtagt taggccacca cttcaagaac tctgtagcac cgcctacata cctcgctctg      8520
ctaatcctgt taccagtggc tgctgccagt ggcgataagt cgtgtcttac cggggttggac     8580 tcaagacgat agttaccgga taaggcgcag cggtcgggct gaacgggggg ttcgtgcaca      8640
cagcccagct tggagcgaac gacctacacc gaactgagat acctacagcg tgagcattga      8700
gaaagcgcca cgcttcccga agggagaaag gcggacaggt atccggtaag cggcagggtc      8760
ggaacaggag agcgcacgag ggagcttcca gggggaaacg cctggtatct ttatagtcct      8820
gtcgggtttc gccacctctg acttgagcgt cgattttttgt gatg                     8864
```

<210> SEQ ID NO 290
<211> LENGTH: 1220
<212> TYPE: PRT
<213> ORGANISM: C. aurantiacus

<400> SEQUENCE: 290

```
Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
                20                  25                  30

Gly Ala Thr Val Ile Ile Ser Gly Arg Asn Arg Ala Lys Leu Thr Ala
            35                  40                  45

Leu Ala Glu Arg Met Gln Ala Glu Ala Gly Val Pro Ala Lys Arg Ile
50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
```

```
            275                 280                 285
Glu Thr Ser Leu Leu Ala Arg Thr Asp Leu Arg Thr Ile Asp Ala Ser
            290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                    325                 330                 335

Phe Arg Ser Ala Ala Ala Leu Ala Gln Phe Glu Gln Ala Val Asn Glu
                340                 345                 350

Ser Arg Arg Leu Ala Gly Ala Asp Phe Thr Pro Pro Ile Ala Leu Pro
            355                 360                 365

Leu Asp Pro Arg Asp Pro Ala Thr Ile Asp Ala Val Phe Asp Trp Gly
        370                 375                 380

Ala Gly Glu Asn Thr Gly Gly Ile His Ala Ala Val Ile Leu Pro Ala
385                 390                 395                 400

Thr Ser His Glu Pro Ala Pro Cys Val Ile Glu Val Asp Asp Glu Arg
                    405                 410                 415

Val Leu Asn Phe Leu Ala Asp Glu Ile Thr Gly Thr Ile Val Ile Ala
                420                 425                 430

Ser Arg Leu Ala Arg Tyr Trp Gln Ser Gln Arg Leu Thr Pro Gly Ala
            435                 440                 445

Arg Ala Arg Gly Pro Arg Val Ile Phe Leu Ser Asn Gly Ala Asp Gln
450                 455                 460

Asn Gly Asn Val Tyr Gly Arg Ile Gln Ser Ala Ala Ile Gly Gln Leu
465                 470                 475                 480

Ile Arg Val Trp Arg His Glu Ala Glu Leu Asp Tyr Gln Arg Ala Ser
                    485                 490                 495

Ala Ala Gly Asp His Val Leu Pro Pro Val Trp Ala Asn Gln Ile Val
                500                 505                 510

Arg Phe Ala Asn Arg Ser Leu Glu Gly Leu Glu Phe Ala Cys Ala Trp
            515                 520                 525

Thr Ala Gln Leu Leu His Ser Gln Arg His Ile Asn Glu Ile Thr Leu
        530                 535                 540

Asn Ile Pro Ala Asn Ile Ser Ala Thr Thr Gly Ala Arg Ser Ala Ser
545                 550                 555                 560

Val Gly Trp Ala Glu Ser Leu Ile Gly Leu His Leu Gly Lys Val Ala
                    565                 570                 575

Leu Ile Thr Gly Gly Ser Ala Gly Ile Gly Gly Gln Ile Gly Arg Leu
                580                 585                 590

Leu Ala Leu Ser Gly Ala Arg Val Met Leu Ala Ala Arg Asp Arg His
            595                 600                 605

Lys Leu Glu Gln Met Gln Ala Met Ile Gln Ser Glu Leu Ala Glu Val
        610                 615                 620

Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                    645                 650                 655

Ala Phe Gly Thr Val Asp Tyr Leu Ile Asn Asn Ala Gly Ile Ala Gly
                660                 665                 670

Val Glu Glu Met Val Ile Asp Met Pro Val Glu Gly Trp Arg His Thr
            675                 680                 685

Leu Phe Ala Asn Leu Ile Ser Asn Tyr Ser Leu Met Arg Lys Leu Ala
        690                 695                 700
```

-continued

```
Pro Leu Met Lys Lys Gln Gly Ser Gly Tyr Ile Leu Asn Val Ser Ser
705                 710                 715                 720

Tyr Phe Gly Gly Glu Lys Asp Ala Ala Ile Pro Tyr Pro Asn Arg Ala
                725                 730                 735

Asp Tyr Ala Val Ser Lys Ala Gly Gln Arg Ala Met Glu Val Phe
            740                 745                 750

Ala Arg Phe Leu Gly Pro Glu Ile Gln Ile Asn Ala Ile Ala Pro Gly
            755                 760                 765

Pro Val Glu Gly Asp Arg Leu Arg Gly Thr Gly Glu Arg Pro Gly Leu
            770                 775                 780

Phe Ala Arg Arg Ala Arg Leu Ile Leu Glu Asn Lys Arg Leu Asn Glu
785                 790                 795                 800

Leu His Ala Ala Leu Ile Ala Ala Arg Thr Asp Glu Arg Ser Met
                805                 810                 815

His Glu Leu Val Glu Leu Leu Pro Asn Asp Val Ala Ala Leu Glu
            820                 825                 830

Gln Asn Pro Ala Ala Pro Thr Ala Leu Arg Glu Leu Ala Arg Arg Phe
            835                 840                 845

Arg Ser Glu Gly Asp Pro Ala Ala Ser Ser Ser Ala Leu Leu Asn
850                 855                 860

Arg Ser Ile Ala Ala Lys Leu Leu Ala Arg Leu His Asn Gly Gly Tyr
865                 870                 875                 880

Val Leu Pro Ala Asp Ile Phe Ala Asn Leu Pro Asn Pro Pro Asp Pro
            885                 890                 895

Phe Phe Thr Arg Ala Gln Ile Asp Arg Glu Ala Arg Lys Val Arg Asp
            900                 905                 910

Gly Ile Met Gly Met Leu Tyr Leu Gln Arg Met Pro Thr Glu Phe Asp
            915                 920                 925

Val Ala Met Ala Thr Val Tyr Tyr Leu Ala Asp Arg Asn Val Ser Gly
            930                 935                 940

Glu Thr Phe His Pro Ser Gly Gly Leu Arg Tyr Glu Arg Thr Pro Thr
945                 950                 955                 960

Gly Gly Glu Leu Phe Gly Leu Pro Ser Pro Gln Arg Leu Ala Glu Leu
                965                 970                 975

Val Gly Ser Thr Val Tyr Leu Ile Gly Glu His Leu Thr Glu His Leu
            980                 985                 990

Asn Leu Leu Ala Arg Ala Tyr Leu Glu Arg Tyr Gly Ala Arg Gln Val
            995                 1000                1005

Val Met Ile Val Glu Thr Glu Thr Gly Ala Glu Thr Met Arg Arg
            1010                1015                1020

Leu Leu His Asp His Val Glu Ala Gly Arg Leu Met Thr Ile Val
            1025                1030                1035

Ala Gly Asp Gln Ile Glu Ala Ile Asp Gln Ala Ile Thr Arg
            1040                1045                1050

Tyr Gly Arg Pro Gly Pro Val Val Cys Thr Pro Phe Arg Pro Leu
            1055                1060                1065

Pro Thr Val Pro Leu Val Gly Arg Lys Asp Ser Asp Trp Ser Thr
            1070                1075                1080

Val Leu Ser Glu Ala Glu Phe Ala Glu Leu Cys Glu His Gln Leu
            1085                1090                1095

Thr His His Phe Arg Val Ala Arg Lys Ile Ala Leu Ser Asp Gly
            1100                1105                1110
```

```
Ala Ser Leu Ala Leu Val Thr Pro Glu Thr Ala Thr Ser Thr
    1115                1120                1125

Thr Glu Gln Phe Ala Leu Ala Asn Phe Ile Lys Thr Thr Leu His
    1130                1135                1140

Ala Phe Thr Ala Thr Ile Gly Val Glu Ser Glu Arg Thr Ala Gln
    1145                1150                1155

Arg Ile Leu Ile Asn Gln Val Asp Leu Thr Arg Arg Ala Arg Ala
    1160                1165                1170

Glu Glu Pro Arg Asp Pro His Glu Arg Gln Gln Glu Leu Glu Arg
    1175                1180                1185

Phe Ile Glu Ala Val Leu Leu Val Thr Ala Pro Leu Pro Pro Glu
    1190                1195                1200

Ala Asp Thr Arg Tyr Ala Gly Arg Ile His Arg Gly Arg Ala Ile
    1205                1210                1215

Thr Val
    1220

<210> SEQ ID NO 291
<211> LENGTH: 1219
<212> TYPE: PRT
<213> ORGANISM: C. aurantiacus

<400> SEQUENCE: 291

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255
```

```
Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
        275                 280                 285

Glu Thr Ser Leu Leu Ala Arg Thr Asp Leu Arg Thr Ile Asp Ala Ser
    290                 295                 300

Gly Arg Thr Thr Leu Ile Cys Ala Gly Asp Gln Ile Glu Val Met
305                 310                 315                 320

Ala Leu Thr Gly Met Leu Arg Thr Cys Gly Ser Val Ile Ile Gly
                325                 330                 335

Phe Arg Ser Ala Ala Ala Leu Ala Gln Phe Glu Gln Ala Val Asn Glu
            340                 345                 350

Ser Arg Arg Leu Ala Gly Ala Asp Phe Thr Pro Pro Ile Ala Leu Pro
        355                 360                 365

Leu Asp Pro Arg Asp Pro Ala Thr Ile Asp Ala Val Phe Asp Trp Ala
    370                 375                 380

Gly Glu Asn Thr Gly Gly Ile His Ala Ala Val Ile Leu Pro Ala Thr
385                 390                 395                 400

Ser His Glu Pro Ala Pro Cys Val Ile Glu Val Asp Asp Glu Arg Val
                405                 410                 415

Leu Asn Phe Leu Ala Asp Glu Ile Thr Gly Thr Ile Val Ile Ala Ser
            420                 425                 430

Arg Leu Ala Arg Tyr Trp Gln Ser Gln Arg Leu Thr Pro Gly Ala Arg
        435                 440                 445

Ala Arg Gly Pro Arg Val Ile Phe Leu Ser Asn Gly Ala Asp Gln Asn
    450                 455                 460

Gly Asn Val Tyr Gly Arg Ile Gln Ser Ala Ala Ile Gly Gln Leu Ile
465                 470                 475                 480

Arg Val Trp Arg His Glu Ala Glu Leu Asp Tyr Gln Arg Ala Ser Ala
                485                 490                 495

Ala Gly Asp His Val Leu Pro Pro Val Trp Ala Asn Gln Ile Val Arg
            500                 505                 510

Phe Ala Asn Arg Ser Leu Glu Gly Leu Glu Phe Ala Cys Ala Trp Thr
        515                 520                 525

Ala Gln Leu Leu His Ser Gln Arg His Ile Asn Glu Ile Thr Leu Asn
    530                 535                 540

Ile Pro Ala Asn Ile Ser Ala Thr Thr Gly Ala Arg Ser Ala Ser Val
545                 550                 555                 560

Gly Trp Ala Glu Ser Leu Ile Gly Leu His Leu Gly Lys Val Ala Leu
                565                 570                 575

Ile Thr Gly Gly Ser Ala Gly Ile Gly Gly Gln Ile Gly Arg Leu Leu
            580                 585                 590

Ala Leu Ser Gly Ala Arg Val Met Leu Ala Ala Arg Asp Arg His Lys
        595                 600                 605

Leu Glu Gln Met Gln Ala Met Ile Gln Ser Glu Leu Ala Glu Val Gly
    610                 615                 620

Tyr Thr Asp Val Glu Asp Arg Val His Ile Ala Pro Gly Cys Asp Val
625                 630                 635                 640

Ser Ser Glu Ala Gln Leu Ala Asp Leu Val Glu Arg Thr Leu Ser Ala
                645                 650                 655

Phe Gly Thr Val Asp Tyr Leu Ile Asn Asn Ala Gly Ile Ala Gly Val
            660                 665                 670
```

```
Glu Glu Met Val Ile Asp Met Pro Val Gly Trp Arg His Thr Leu
            675                 680                 685
Phe Ala Asn Leu Ile Ser Asn Tyr Ser Leu Met Arg Lys Leu Ala Pro
705     690             695                 700
Leu Met Lys Lys Gln Gly Ser Gly Tyr Ile Leu Asn Val Ser Ser Tyr
705             710                 715                 720
Phe Gly Gly Glu Lys Asp Ala Ala Ile Pro Tyr Pro Asn Arg Ala Asp
                725                 730                 735
Tyr Ala Val Ser Lys Ala Gly Gln Arg Ala Met Ala Glu Val Phe Ala
            740                 745                 750
Arg Phe Leu Gly Pro Glu Ile Gln Ile Asn Ala Ile Ala Pro Gly Pro
        755                 760                 765
Val Glu Gly Asp Arg Leu Arg Gly Thr Gly Glu Arg Pro Gly Leu Phe
770                 775                 780
Ala Arg Arg Ala Arg Leu Ile Leu Glu Asn Lys Arg Leu Asn Glu Leu
785                 790                 795                 800
His Ala Ala Leu Ile Ala Ala Ala Arg Thr Asp Glu Arg Ser Met His
                805                 810                 815
Glu Leu Val Glu Leu Leu Leu Pro Asn Asp Val Ala Ala Leu Glu Gln
                820                 825                 830
Asn Pro Ala Ala Pro Thr Ala Leu Arg Glu Leu Ala Arg Arg Phe Arg
835                 840                 845
Ser Glu Gly Asp Pro Ala Ala Ser Ser Ser Ala Leu Leu Asn Arg
850                 855                 860
Ser Ile Ala Ala Lys Leu Leu Ala Arg Leu His Asn Gly Gly Tyr Val
865                 870                 875                 880
Leu Pro Ala Asp Ile Phe Ala Asn Leu Pro Asn Pro Asp Pro Phe
                885                 890                 895
Phe Thr Arg Ala Gln Ile Asp Arg Glu Ala Arg Lys Val Arg Asp Gly
                900                 905                 910
Ile Met Gly Met Leu Tyr Leu Gln Arg Met Pro Thr Glu Phe Asp Val
                915                 920                 925
Ala Met Ala Thr Val Tyr Tyr Leu Ala Asp Arg Asn Val Ser Gly Glu
930                 935                 940
Thr Phe His Pro Ser Gly Gly Leu Arg Tyr Glu Arg Thr Pro Thr Gly
945                 950                 955                 960
Gly Glu Leu Phe Gly Leu Pro Ser Pro Glu Arg Leu Ala Glu Leu Val
                965                 970                 975
Gly Ser Thr Val Tyr Leu Ile Gly Glu His Leu Thr Gly His Leu Asn
            980                 985                 990
Leu Leu Ala Arg Ala Tyr Leu Glu  Arg Tyr Gly Ala Arg  Gln Val Val
            995                 1000                1005
Met Ile  Val Glu Thr Glu Thr  Gly Ala Glu Thr Met  Arg Arg Leu
1010                1015                1020
Leu His  Asp His Val Glu Ala  Gly Arg Leu Met Thr  Ile Val Ala
1025                1030                1035
Gly Asp  Gln Ile Glu Ala Ala  Ile Asp Gln Ala Ile  Thr Arg Tyr
1040                1045                1050
Gly Arg  Pro Gly Pro Val Val  Cys Thr Pro Phe Arg  Pro Leu Pro
1055                1060                1065
Thr Val  Pro Leu Val Gly Arg  Lys Asp Ser Asp Trp  Ser Thr Val
1070                1075                1080
Leu Ser  Glu Ala Glu Phe Ala  Glu Leu Cys Glu His  Gln Leu Thr
```

-continued

```
            1085                1090                1095

His His Phe Arg Val Ala Arg Lys Ile Ala Leu Ser Asp Gly Ala
        1100                1105                1110

Ser Leu Ala Leu Val Thr Pro Glu Thr Ala Thr Ser Thr Thr
        1115                1120                1125

Glu Gln Phe Ala Leu Ala Asn Phe Ile Lys Thr Thr Leu His Ala
        1130                1135                1140

Phe Thr Ala Thr Ile Gly Val Glu Ser Glu Arg Thr Ala Gln Arg
        1145                1150                1155

Ile Leu Ile Asn Gln Val Asp Leu Thr Arg Arg Ala Arg Ala Glu
        1160                1165                1170

Glu Pro Arg Asp Pro His Glu Arg Gln Gln Glu Leu Glu Arg Phe
        1175                1180                1185

Ile Glu Ala Val Leu Leu Val Thr Ala Pro Leu Pro Pro Glu Ala
        1190                1195                1200

Asp Thr Arg Tyr Ala Gly Arg Ile His Arg Gly Arg Ala Ile Thr
        1205                1210                1215

Val

<210> SEQ ID NO 292
<211> LENGTH: 1219
<212> TYPE: PRT
<213> ORGANISM: Chloroflexus sp.

<400> SEQUENCE: 292

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
```

```
            225                 230                 235                 240
Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
                260                 265                 270

Gly Glu Thr Ile Glu Val Thr His Gly Met Glu Leu Pro Ala Cys Ser
                275                 280                 285

Glu Thr Ser Leu Leu Ala Arg Thr Asp Leu Arg Thr Ile Asp Ala Ser
                290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
                340                 345                 350

Ser Arg Arg Leu Ala Gly Ala Asp Phe Thr Pro Pro Ile Ala Leu Pro
                355                 360                 365

Leu Asp Pro Arg Asp Pro Ala Thr Ile Asp Ala Val Phe Asp Trp Ala
                370                 375                 380

Gly Glu Asn Thr Gly Gly Ile His Ala Ala Val Ile Leu Pro Ala Thr
385                 390                 395                 400

Ser His Glu Pro Ala Pro Cys Val Ile Glu Val Asp Asp Glu Arg Val
                405                 410                 415

Leu Asn Phe Leu Ala Asp Glu Ile Thr Gly Thr Ile Val Ile Ala Ser
                420                 425                 430

Arg Leu Ala Arg Tyr Trp Gln Ser Gln Arg Leu Thr Pro Gly Ala Arg
                435                 440                 445

Ala Arg Gly Pro Arg Val Ile Phe Leu Ser Asn Gly Ala Asp Gln Asn
                450                 455                 460

Gly Asn Val Tyr Gly Arg Ile Gln Ser Ala Ala Ile Gly Gln Leu Ile
465                 470                 475                 480

Arg Val Trp Arg His Glu Ala Glu Leu Asp Tyr Gln Arg Ala Ser Ala
                485                 490                 495

Ala Gly Asp His Val Leu Pro Pro Val Trp Ala Asn Gln Ile Val Arg
                500                 505                 510

Phe Ala Asn Arg Ser Leu Glu Gly Leu Glu Phe Ala Cys Ala Trp Thr
                515                 520                 525

Ala Gln Leu Leu His Ser Gln Arg His Ile Asn Glu Ile Thr Leu Asn
                530                 535                 540

Ile Pro Ala Asn Ile Ser Ala Thr Thr Gly Ala Arg Ser Ala Ser Val
545                 550                 555                 560

Gly Trp Ala Glu Ser Leu Ile Gly Leu His Leu Gly Lys Val Ala Leu
                565                 570                 575

Ile Thr Gly Gly Ser Ala Gly Ile Gly Gly Gln Ile Gly Arg Leu Leu
                580                 585                 590

Ala Leu Ser Gly Ala Arg Val Met Leu Ala Ala Arg Asp Arg His Lys
                595                 600                 605

Leu Glu Gln Met Gln Ala Met Ile Gln Ser Leu Ala Glu Val Gly
                610                 615                 620

Tyr Thr Asp Val Glu Asp Arg Val His Ile Ala Pro Gly Cys Asp Val
625                 630                 635                 640

Ser Ser Glu Ala Gln Leu Ala Asp Leu Val Glu Arg Thr Leu Ser Ala
                645                 650                 655
```

```
Phe Gly Thr Val Asp Tyr Leu Ile Asn Asn Ala Gly Ile Ala Gly Val
            660                 665                 670

Glu Glu Met Val Ile Asp Met Pro Val Glu Gly Trp Arg His Thr Leu
            675                 680                 685

Phe Ala Asn Leu Ile Ser Asn Tyr Ser Leu Met Arg Lys Leu Ala Pro
            690                 695                 700

Leu Met Lys Lys Gln Gly Ser Gly Tyr Ile Leu Asn Val Ser Ser Tyr
705                 710                 715                 720

Phe Gly Gly Glu Lys Asp Ala Ala Ile Pro Tyr Pro Asn Arg Ala Asp
            725                 730                 735

Tyr Ala Val Ser Lys Ala Gly Gln Arg Ala Met Ala Glu Val Phe Ala
            740                 745                 750

Arg Phe Leu Gly Pro Glu Ile Gln Ile Asn Ala Ile Ala Pro Gly Pro
            755                 760                 765

Val Glu Gly Asp Arg Leu Arg Gly Thr Gly Glu Arg Pro Gly Leu Phe
            770                 775                 780

Ala Arg Arg Ala Arg Leu Ile Leu Glu Asn Lys Arg Leu Asn Glu Leu
785                 790                 795                 800

His Ala Ala Leu Ile Ala Ala Arg Thr Asp Glu Arg Ser Met His
            805                 810                 815

Glu Leu Val Glu Leu Leu Leu Pro Asn Asp Val Ala Ala Leu Glu Gln
            820                 825                 830

Asn Pro Ala Ala Pro Thr Ala Leu Arg Glu Leu Ala Arg Arg Phe Arg
            835                 840                 845

Ser Glu Gly Asp Pro Ala Ala Ser Ser Ser Ala Leu Leu Asn Arg
850                 855                 860

Ser Ile Ala Ala Lys Leu Leu Ala Arg Leu His Asn Gly Gly Tyr Val
865                 870                 875                 880

Leu Pro Ala Asp Ile Phe Ala Asn Leu Pro Asn Pro Asp Pro Phe
            885                 890                 895

Phe Thr Arg Ala Gln Ile Asp Arg Glu Ala Arg Lys Val Arg Asp Gly
            900                 905                 910

Ile Met Gly Met Leu Tyr Leu Gln Arg Met Pro Thr Glu Phe Asp Val
            915                 920                 925

Ala Met Ala Thr Val Tyr Tyr Leu Ala Asp Arg Asn Val Ser Gly Glu
            930                 935                 940

Thr Phe His Pro Ser Gly Leu Arg Tyr Glu Arg Thr Pro Thr Gly
945                 950                 955                 960

Gly Glu Leu Phe Gly Leu Pro Ser Pro Glu Arg Leu Ala Glu Leu Val
            965                 970                 975

Gly Ser Thr Val Tyr Leu Ile Gly Glu His Leu Thr Gly His Leu Asn
            980                 985                 990

Leu Leu Ala Arg Ala Tyr Leu Glu Arg Tyr Gly Ala Arg Gln Val Val
            995                1000                1005

Met Ile Val Glu Thr Glu Thr Gly Ala Glu Thr Met Arg Arg Leu
           1010                1015                1020

Leu His Asp His Val Glu Ala Gly Arg Leu Met Thr Ile Val Ala
           1025                1030                1035

Gly Asp Gln Ile Glu Ala Ala Ile Asp Gln Ala Ile Thr Arg Tyr
           1040                1045                1050

Gly Arg Pro Gly Pro Val Val Cys Thr Pro Phe Arg Pro Leu Pro
           1055                1060                1065
```

```
Thr Val Pro Leu Val Gly Arg Lys Asp Ser Asp Trp Ser Thr Val
    1070                1075                1080

Leu Ser Glu Ala Glu Phe Ala Glu Leu Cys Glu His Gln Leu Thr
    1085                1090                1095

His His Phe Arg Val Ala Arg Lys Ile Ala Leu Ser Asp Gly Ala
    1100                1105                1110

Ser Leu Ala Leu Val Thr Pro Glu Thr Ala Thr Ser Thr Thr
    1115                1120                1125

Glu Gln Phe Ala Leu Ala Asn Phe Ile Lys Thr Thr Leu His Ala
    1130                1135                1140

Phe Thr Ala Thr Ile Gly Val Glu Ser Glu Arg Thr Ala Gln Arg
    1145                1150                1155

Ile Leu Ile Asn Gln Val Asp Leu Thr Arg Arg Ala Arg Ala Glu
    1160                1165                1170

Glu Pro Arg Asp Pro His Glu Arg Gln Gln Glu Leu Glu Arg Phe
    1175                1180                1185

Ile Glu Ala Val Leu Leu Val Thr Ala Pro Leu Pro Pro Glu Ala
    1190                1195                1200

Asp Thr Arg Tyr Ala Gly Arg Ile His Arg Gly Arg Ala Ile Thr
    1205                1210                1215

Val
```

<210> SEQ ID NO 293
<211> LENGTH: 1219
<212> TYPE: PRT
<213> ORGANISM: C. aggregans

<400> SEQUENCE: 293

```
Met Ser Val Thr Gly Arg Leu Ala Gly Lys Ile Ala Leu Ile Thr Gly
1               5                   10                  15

Gly Ala Gly Asn Ile Gly Ser Glu Met Thr Arg Arg Phe Leu Ala Glu
                20                  25                  30

Gly Ala Thr Val Ile Ile Ser Gly Arg Asn Ser Ala Lys Leu Ala Ala
            35                  40                  45

Leu Ala Glu Arg Leu Arg Ser Glu Ala Gly Val Pro Ala Lys Arg Ile
        50                  55                  60

Asp Leu Glu Val Met Asp Gly Ser Asp Pro Ala Ala Val Arg Ala Gly
    65                  70                  75                  80

Val Ala Ala Ile Ile Gly Arg His Gly His Ile Asp Ile Leu Val Asn
                85                  90                  95

Asn Ala Gly Ser Thr Gly Ala Gln Arg Arg Leu Ala Glu Ile Pro Leu
                100                 105                 110

Asn Glu Thr Asp Arg Asp Leu Asp Asp Glu Ala Leu Ser Thr Ser
            115                 120                 125

Val Ala Asn Leu Leu Gly Met Ala Trp His Leu Met Arg Ile Leu Ser
    130                 135                 140

Pro His Met Pro Pro Gly Ser Ala Ile Ile Asn Ile Ser Thr Ile Phe
145                 150                 155                 160

Ser Arg Ala Glu Tyr Tyr Gly Arg Ile Pro Tyr Val Val Pro Lys Ala
                165                 170                 175

Ala Leu Asn Thr Leu Thr Gln Ile Ala Ala Arg Glu Leu Gly Ile Arg
            180                 185                 190

Gly Ile Arg Val Asn Thr Ile Phe Pro Gly Pro Ile Glu Ser Glu Arg
        195                 200                 205
```

```
Ile Gln Thr Val Phe Gln Arg Met Asp Gln Leu Lys Gly Arg Pro Glu
210                 215                 220

Gly Asp Thr Ala Ser Gln Phe Leu Ala Thr Met Arg Leu Tyr Arg Ala
225                 230                 235                 240

Asn Asp Gln Gly Gln Leu Glu Arg Arg Phe Pro Thr Ile Cys Asp Val
            245                 250                 255

Ala Asp Ala Ala Val Phe Leu Ala Ser Asp Glu Ala Ala Ala Leu Thr
        260                 265                 270

Gly Glu Thr Ile Glu Val Thr His Gly Met Glu Leu Pro Thr Ser Ser
    275                 280                 285

Glu Thr Ser Leu Leu Ala Arg Thr Asp Leu Arg Thr Ile Asp Ala Asn
290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Glu Ala Ala Leu Ala Gln Phe Gln Ala Ile Gly Glu
            340                 345                 350

Ser Arg Arg Leu Ala Gly Glu Ser Phe Ile Pro Pro Ile Ala Leu Pro
    355                 360                 365

Ile Asp Leu Arg Asn Pro Ser Thr Ile Asp Ala Leu Phe Asp Trp Ala
370                 375                 380

Gly Glu Asn Thr Gly Gly Ile His Ala Ala Val Ile Leu Pro Ala Ser
385                 390                 395                 400

Gly Arg Glu Pro Ala Thr Gln Val Ile Asp Ile Asp Asp Ala His Val
            405                 410                 415

Gln Ala Phe Leu Asn Asp Glu Ile Val Gly Ser Ile Ile Ile Ala Ser
        420                 425                 430

Arg Leu Ala Arg Tyr Trp Gln Ala Gln Arg Ile Ala Pro Gly Ala Arg
    435                 440                 445

Ala Arg Glu Pro Arg Val Ile Phe Leu Ser Asn Gly Ala Ser Thr Ala
450                 455                 460

Gly Asn Pro Tyr Gly Arg Ile Gln Ser Ala Ala Ile Glu Gln Leu Ile
465                 470                 475                 480

Arg Val Trp Arg His Glu Ala Ala Leu Asp Tyr Glu Arg Ala Thr Ala
                485                 490                 495

Ala Gly Glu Arg Val Leu Pro Ala Val Trp Ala Ser Gln Ile Val Arg
            500                 505                 510

Phe Ala Asn Arg Ser Leu Glu Gly Leu Glu Phe Ala Cys Ala Trp Thr
        515                 520                 525

Ala Gln Leu Leu His Ser Gln Arg Arg Ile Asn Glu Ile Thr Leu Thr
    530                 535                 540

Ile Pro Ala Asp Ile Ser Ala Thr Thr Gly Ala Arg Ser Ala Ser Val
545                 550                 555                 560

Gly Trp Ala Glu Ser Leu Ile Gly Leu His Leu Gly Lys Val Ala Leu
            565                 570                 575

Ile Thr Gly Gly Ser Ala Gly Ile Gly Gly Gln Ile Gly Arg Leu Leu
        580                 585                 590

Ala Leu Ser Gly Ala Arg Val Met Leu Ala Ala Arg Asp Pro His Lys
    595                 600                 605

Leu Glu Gln Ile Gln Ala Thr Ile Arg Ala Glu Leu Ala Glu Val Gly
610                 615                 620

Tyr Thr Asp Val Glu Glu Arg Val Gln Ile Ala Pro Gly Cys Asp Val
```

```
           625                 630                 635                 640
      Ser Ser Glu Glu Gln Leu Val Asp Leu Val Glu Arg Thr Leu Ala Ala
                       645                 650                 655
      Phe Gly Thr Val Asp Tyr Leu Ile Asn Asn Ala Gly Ile Ala Gly Val
                       660                 665                 670
      Glu Glu Met Val Ile Asp Met Pro Val Glu Gly Trp Arg Asn Thr Leu
                       675                 680                 685
      Tyr Ala Asn Leu Ile Ser Asn Tyr Ser Leu Met Arg Lys Leu Ala Pro
                       690                 695                 700
      Leu Met Lys Lys Gln Gly Ser Gly Tyr Val Leu Asn Val Ser Ser Tyr
      705                 710                 715                 720
      Phe Gly Gly Glu Lys Asp Ala Ala Ile Pro Tyr Pro Asn Arg Ala Asp
                       725                 730                 735
      Tyr Ala Val Ser Lys Ala Gly Gln Arg Ala Met Ala Glu Val Phe Ala
                       740                 745                 750
      Arg Phe Leu Gly Pro Glu Ile Gln Ile Asn Ala Ile Ala Pro Gly Pro
                       755                 760                 765
      Val Glu Gly Asp Arg Leu Arg Gly Thr Gly Glu Arg Pro Gly Leu Phe
                       770                 775                 780
      Ala Arg Arg Ala Arg Leu Ile Leu Glu Asn Lys Arg Leu Asn Glu Leu
      785                 790                 795                 800
      His Ala Ala Leu Ile Thr Ala Ala Arg Thr Asp Asn Arg Pro Met Arg
                       805                 810                 815
      Glu Leu Val Glu Leu Leu Leu Pro Asn Asp Val Ala Ala Leu Ala Gln
                       820                 825                 830
      His Pro Ala Ala Pro Asp Val Leu Arg Thr Leu Ala Lys Arg Phe Gln
                       835                 840                 845
      Ser Glu Gly Asp Pro Ala Ala Ser Ser Ser Ser Phe Leu Leu Asn Arg
                       850                 855                 860
      Ser Ile Ala Ala Lys Leu Leu Ala Arg Leu Ile Asn Gly Gly Tyr Asp
      865                 870                 875                 880
      Leu Pro Ala Asp Ile Phe Ala Asn Leu Ala Val Pro Pro Asp Pro Phe
                       885                 890                 895
      Phe Thr Arg Ala Gln Ile Asp Arg Glu Ala Arg Lys Val Arg Asp Gly
                       900                 905                 910
      Ile Met Gly Met Leu Tyr Leu Gln Arg Met Pro Thr Glu Phe Asp Val
                       915                 920                 925
      Ala Met Ala Thr Val Tyr Tyr Leu Ala Asp Arg Asn Val Ser Gly Glu
                       930                 935                 940
      Thr Phe His Pro Ser Gly Gly Leu Arg Tyr Glu Arg Thr Pro Thr Gly
      945                 950                 955                 960
      Gly Glu Leu Phe Gly Leu Pro Ala Pro Glu Arg Leu Ala Glu Leu Val
                       965                 970                 975
      Gly Ser Thr Val Tyr Leu Ile Gly Glu His Leu Thr Glu His Leu Asn
                       980                 985                 990
      Leu Leu Ala Arg Ala Tyr Leu Glu  Arg Tyr Gly Ala Arg  Gln Val Val
                       995                 1000                1005
      Met Ile Val Glu Thr Glu Ala  Gly Ala Glu Lys Met  Arg His Leu
           1010                1015                1020
      Leu His Asp His Val Glu Ala  Gly Arg Leu Pro Ile  Ile Val Ala
           1025                1030                1035
      Gly Asp Gln Ile Glu Ala Ala  Ile Asp Gln Ala Ile  Ala Asn Tyr
           1040                1045                1050
```

Gly Arg Pro Gly Pro Val Val Cys Thr Pro Phe Arg Pro Leu Pro
            1055                1060                1065

Ser Ala Pro Leu Val Gly Arg Lys Asp Ser Asp Trp Ser Thr Val
            1070                1075                1080

Leu Ser Glu Ala Glu Phe Ala Glu Leu Cys Glu His Gln Leu Thr
            1085                1090                1095

His His Phe Arg Val Ala Arg Lys Ile Ala Leu Ser Asp Gly Ala
            1100                1105                1110

Ser Leu Ala Leu Val Thr Pro Glu Thr Ala Thr Ser Ser Thr
            1115                1120                1125

Glu Gln Phe Ala Leu Ala Asn Phe Val Lys Thr Thr Leu His Ala
            1130                1135                1140

Phe Thr Ala Thr Ile Gly Val Glu Ser Glu Arg Thr Ala Gln Arg
            1145                1150                1155

Ile Leu Ile Asn Gln Val Asp Leu Thr Arg Arg Ala Arg Ala Glu
            1160                1165                1170

Glu Pro Arg Asp Pro Arg Glu Arg Gln Gln Glu Leu Glu Arg Phe
            1175                1180                1185

Ile Glu Ala Val Leu Leu Val Thr Ala Pro Leu Pro Pro Glu Ala
            1190                1195                1200

Asp Thr Arg Tyr Ala Gly Arg Ile His Arg Gly Arg Ala Ile Thr
            1205                1210                1215

Val

<210> SEQ ID NO 294
<211> LENGTH: 1221
<212> TYPE: PRT
<213> ORGANISM: O. trichoides

<400> SEQUENCE: 294

Met Phe Met Thr Arg Leu Asn Asp Lys Ile Ala Leu Ile Thr Gly Gly
1               5                   10                  15

Ala Gly Thr Ile Gly Glu Val Ile Thr Arg Arg Tyr Leu Glu Glu Gly
                20                  25                  30

Ala Thr Val Val Met Ala Gly Arg Asn Arg Asp Lys Leu Asp Arg Tyr
            35                  40                  45

Arg Glu Arg Leu Ile Thr Glu Phe His Ala Leu Pro Glu Arg Val Met
        50                  55                  60

Val Val Arg Met Asp Gly Ser Ser Asn Ala Glu Val Arg Met Gly Ile
65                  70                  75                  80

Ala Ala Val Val Ala His Phe Gly Arg Ile Asp Ile Leu Val Asn Asn
                85                  90                  95

Ala Gly Ser Ala Gly Ala Arg Gln Arg Leu Pro Ala Ile Pro Leu Leu
                100                 105                 110

Arg Ser Glu Leu Gln Ala Asp Glu Thr Glu Thr Leu Ala Asp Ser Ile
            115                 120                 125

Gly Asn Leu Ile Gly Ile Thr Trp Asn Leu Ile Arg Ala Ala Ala Pro
        130                 135                 140

Phe Met Pro Ala Gly Ser Ser Val Ile Asn Ile Ser Thr Ile Phe Ala
145                 150                 155                 160

Arg Thr Asp Tyr Tyr Gly Arg Ile Pro Tyr Val Val Pro Lys Ala Ala
                165                 170                 175

Leu His Ala Leu Thr Leu Ala Ala Ala Thr Glu Leu Gly Glu Arg Gly
            180                 185                 190

```
Ile Arg Val Asn Gln Ile Asn Pro Gly Pro Ile Asp Ser Asp Arg Ile
            195                 200                 205

Arg Thr Val Phe Arg Arg Met Asp Glu Leu Lys Gly Val Pro Glu Gln
210                 215                 220

Ser Thr Ala Asp Gly Phe Phe Gln Met Met Arg Leu Arg Arg Pro Asn
225                 230                 235                 240

Ala Glu Gly Asp Leu Val Lys Gly Phe Pro Lys Thr Leu Asp Val Ala
            245                 250                 255

Asn Val Ala Val Phe Leu Gly Ser Ala Glu Ser Ala Ala Leu Ser Gly
            260                 265                 270

Glu Thr Leu Asp Val Thr His Gly Met Ala Val Pro Thr Glu Ser Arg
            275                 280                 285

Thr Thr Leu Thr Ser Arg Pro Gly Leu Arg Ala Val Asp Gly Ser Gly
290                 295                 300

His Thr Thr Leu Ile Cys Val Gly Asp Gln Ile Glu Glu Ala Ala Ala
305                 310                 315                 320

Leu Thr Gly Val Leu Arg Ala Cys Gly Ala Glu Val Val Ile Gly Phe
            325                 330                 335

Arg Ser Arg Ala Ala Ile Ala Arg Phe Asp His Leu Ile Glu Arg Gly
            340                 345                 350

Arg His Leu Pro Ser Gln Glu His Val Ala Pro Val Leu Leu Tyr Leu
            355                 360                 365

Asn Pro Thr Glu Pro Glu Ser Ile Asp Gln Ala Leu Arg Trp Met Ala
            370                 375                 380

Thr Asn Leu Asp Leu Pro Thr Ser Val Ile Ile Leu Pro Ala Gln Arg
385                 390                 395                 400

Gln Pro Leu Pro Pro Ser Val Val Arg Ala Ser Asp Glu Glu Val Ala
            405                 410                 415

Tyr Phe Leu Arg Asp Glu Leu Ser Gly Met Ile Val Leu Ala Ser Arg
            420                 425                 430

Leu Ala Arg Phe Trp Gln Gln Ala Thr Leu Ala Pro Gly Asn Ala Pro
            435                 440                 445

Ile Gln Pro Arg Val Leu Phe Met Thr Asn Pro Asp Asp Gly Gln Gly
            450                 455                 460

Asn Leu Tyr Ala Glu Ile Leu Arg Ala Gly Val Glu Gln Leu Cys Arg
465                 470                 475                 480

Val Trp Arg His Glu Ser Gln Leu Asp Tyr Thr Arg Leu Ala Gln Met
            485                 490                 495

Asp Ala His Pro Pro His Ile Arg Pro Val Trp Ala Asn Gln Leu Val
            500                 505                 510

Arg Phe Ala Asn Asn Glu Gln Glu Asn Leu Glu Tyr Cys Cys Ala Trp
            515                 520                 525

Val Ala Lys Ile Leu Leu Ser Glu Arg Thr Ile Glu Glu Leu Asn Leu
530                 535                 540

Tyr Leu Pro Arg Gln Ile Gly Ser Thr Thr Gly Ser Arg Gln Pro Ser
545                 550                 555                 560

Phe Gly Trp Ala Glu Asn Leu Ile Gly Leu His Leu Gly Lys Thr Ala
            565                 570                 575

Leu Ile Thr Gly Gly Ser Ala Gly Ile Gly Ser Gln Ile Ala Arg Leu
            580                 585                 590

Leu Ala Leu Ser Gly Ala Arg Val Met Leu Cys Ala Arg Asp Glu Arg
            595                 600                 605
```

```
Lys Leu Ile Gln Met Arg Asp Met Ile Ile Ala Glu Leu Thr Glu Val
            610                 615                 620

Gly Tyr Asn Gln Val Glu Ser Arg Val Gln Ile Cys Ala Gly Cys Asp
625                 630                 635                 640

Val Gly Glu Glu Gln Leu Glu Ile Ala Val Gln Arg Thr Leu Asp
                    645                 650                 655

Leu Phe Gly His Val Asp Tyr Leu Ile Asn Asn Ala Gly Ile Ala Gly
                660                 665                 670

Ala Glu Glu Met Val Leu Asp Leu Pro Leu Ala Trp Gln Arg Thr
            675                 680                 685

Leu Arg Thr Asn Leu Ile Ser Asn Tyr Ser Leu Ile Arg Lys Leu Ala
        690                 695                 700

Pro Gln Met Lys Ser Arg Gly Ser Gly Tyr Ile Leu Asn Val Ser Ser
705                 710                 715                 720

Tyr Phe Gly Gly Glu Lys Tyr Ala Ala Ile Pro Tyr Pro Asn Arg Ala
                725                 730                 735

Asp Tyr Ala Val Ser Lys Ala Gly Gln Arg Ala Leu Gly Glu Ala Leu
            740                 745                 750

Ala Arg Leu Leu Gly Pro Glu Val Gln Ile Asn Ala Met Ala Pro Gly
        755                 760                 765

Pro Val Glu Gly Glu Arg Leu Arg Gly Ser Gly Asp Arg Pro Gly Leu
770                 775                 780

Phe Leu Arg Arg Gly Arg Leu Ile Leu Glu Asn Lys Arg Leu Asn Asp
785                 790                 795                 800

Leu His Ala Thr Leu Ile Ala Ala Glu Arg Glu Thr Gln Val Gly Met
                805                 810                 815

Arg Asp Leu Leu Ala Arg Leu His Asn Asp Val Cys Ala Leu Ile
            820                 825                 830

Asp Asp Pro Ala Ala Pro Thr His Leu Arg Ala Leu Ala Glu Arg Ile
        835                 840                 845

Trp Glu Gln Ser Asp Pro Asn Ser Tyr Ala Arg Ala Phe Phe Met Asn
            850                 855                 860

Ala Asn Ile Ala Thr Lys Leu Leu Ala Arg Leu Phe Asn Ala Asp Gln
865                 870                 875                 880

Ile Asp Ala Gln Thr Phe His Thr Ser Gln Pro Asn Leu Pro Pro Glu
                885                 890                 895

Pro Phe Phe Ala Arg Thr Gln Ile Asp Arg Glu Ala Arg Arg Val Arg
            900                 905                 910

Asp Gly Val Met Ser Met Leu Tyr Leu Gln Arg Met Pro Thr Glu Phe
            915                 920                 925

Asp Val Ala Leu Ala Thr Val Tyr Tyr Leu Asn Asp Arg Ser Val Ser
930                 935                 940

Gly Glu Thr Phe His Pro Ser Gly Gly Leu Arg His Glu Arg Thr Pro
945                 950                 955                 960

Thr Gly Ala Glu Leu Tyr Gly Ser Pro Ala Pro Gln Arg Leu Ala Ser
                965                 970                 975

Leu Ala Gly Ser Thr Val Tyr Leu Ile Gly Glu Ser Met Ala Ala His
                980                 985                 990

Leu Glu Ala Leu Ala Arg Ala Tyr Ile Glu Arg Tyr Ala Ala Thr Arg
            995                 1000                1005

Val Val Leu Ile Cys Ala Thr Pro Ala Gly Val Glu Arg Phe Ser
        1010                1015                1020

His His Leu Ala Asp His Leu Ala Ser Gly Ala Leu Ala Ile Leu
```

```
             1025                1030                1035

Ser Ala Glu Glu Gly Ile Glu Ala Ala Leu Ser Glu Ala Leu Arg
    1040                1045                1050

Arg Phe Gly Pro Pro Gly Pro Val Val Ser Thr Pro Phe Gln Pro
    1055                1060                1065

Leu Pro Ser Gln Pro Leu Ile Gly Arg Asn Asp Ser Asp Trp Ser
    1070                1075                1080

Thr Val Leu Asp Val Ala Gly Phe Ser Ala Met Cys Glu Gln Gln
    1085                1090                1095

Leu Thr His His Phe Arg Val Thr Arg Lys Leu Ser Leu Val Ala
    1100                1105                1110

Gly Val Ser Leu Val Leu Val Thr Pro Glu Thr Asp Ser His Ser
    1115                1120                1125

Ser Thr Glu Gln Phe Ala Leu Ala Asn Phe Val Lys Thr Thr Leu
    1130                1135                1140

His Ala Phe Thr Ala Thr Val Gly Val Glu Cys Glu Arg Thr Ala
    1145                1150                1155

His Arg Ile Leu Val Asn Gln Val Asp Leu Gly Arg Gln Ala Arg
    1160                1165                1170

Ala Glu Glu Pro Arg Ser Pro Ala Glu Gln Ala Gln Glu Met Glu
    1175                1180                1185

Arg Phe Ile Asp Ala Ile Met Leu Thr Thr Ala Pro Ile Pro Ala
    1190                1195                1200

Glu Glu Asp Asn Arg Tyr Thr Gly Arg Ile Tyr Arg Gly Arg Ala
    1205                1210                1215

Ile Thr Val
    1220

<210> SEQ ID NO 295
<211> LENGTH: 1229
<212> TYPE: PRT
<213> ORGANISM: R. castenholzii

<400> SEQUENCE: 295

Met Ser Thr Val Arg Arg Leu Glu Gly Lys Val Ala Leu Ile Thr Gly
1               5                   10                  15

Gly Ala Gly Asn Ile Gly Glu Val Ile Thr Arg Arg Phe Leu Ala Glu
            20                  25                  30

Gly Ala Thr Val Val Ile Thr Gly Arg Asn Ala Glu Lys Leu Ala Val
        35                  40                  45

Tyr Arg Arg Arg Leu Ile Asp Glu Glu Arg Val Ala Pro Glu Arg Val
    50                  55                  60

Val Ala Leu Arg Met Asp Gly Ser Asp Ile Ala Gln Val Arg Ala Gly
65                  70                  75                  80

Val Ala Gln Ile Val His Gly Gly Thr Asp Val Pro Ile Pro Leu His
                85                  90                  95

Arg Ile Asp Ile Leu Val Asn Asn Ala Gly Ser Ala Gly Pro Arg Arg
            100                 105                 110

Arg Leu Val Asp Ile Pro Leu Glu Pro Ser Glu Val Gln Pro Pro Asp
        115                 120                 125

Ser Glu Thr Leu Ala Gln Ala Val Gly Asn Leu Val Gly Ile Thr Trp
    130                 135                 140

Asn Leu Thr Arg Ala Ala Ala Pro His Met Pro Ser Gly Ser Ser Val
145                 150                 155                 160
```

-continued

```
Ile Asn Ile Ser Thr Ile Phe Ser Arg Thr Asp Tyr Tyr Gly Arg Ile
            165                 170                 175
Ala Tyr Val Ala Pro Lys Ala Ala Leu Asn Ala Leu Ser Asp Gly Leu
        180                 185                 190
Ala Arg Glu Leu Gly Val Arg Gly Ile Arg Val Asn Thr Ile Tyr Pro
    195                 200                 205
Gly Pro Ile Glu Ser Glu Arg Ile Tyr Thr Met Phe Gln Ala Met Asp
210                 215                 220
Ala Leu Lys Gly Gln Pro Glu Gly Asp Thr Ala Ser Gly Phe Leu Arg
225                 230                 235                 240
Met Met Arg Leu Ser Arg Ile Asp Gln Asn Gly Glu Val Val Lys Arg
                245                 250                 255
Phe Pro Ser Pro Val Asp Val Ala Asn Thr Ala Val Phe Leu Ala Ser
            260                 265                 270
Asp Glu Ser Ala Ala Phe Thr Gly His Ala Phe Glu Val Thr His Gly
        275                 280                 285
Met Glu Val Pro Thr Glu Ser Arg Thr Thr Phe Val Ser Arg Pro Gly
    290                 295                 300
Leu Arg Ser Val Asp Ala Thr Gly Lys Val Ile Leu Ile Cys Ala Gly
305                 310                 315                 320
Asp Gln Val Asp Asp Ala Val Ala Leu Ala Asp Thr Leu Arg Ser Cys
                325                 330                 335
Arg Ala Thr Val Val Ile Gly Phe Arg Asp Pro Arg Ala Leu Glu Lys
            340                 345                 350
Ala Ser Val Leu Leu Arg Glu Pro Arg His Ala Leu Ala Asp Met
        355                 360                 365
Tyr Gly Arg Pro Thr Met Thr Ala Glu Ala Arg Leu Val Arg Leu Asp
    370                 375                 380
Pro Leu Asp Pro Arg Ala Ala Ala Gln Thr Leu Glu Gln Ile His Ala
385                 390                 395                 400
Glu Leu Gly Ala Ile His His Ala Val Val Leu Pro Gly Gln Ser Arg
                405                 410                 415
His Ala Pro Ser Ala Ser Leu Ile Glu Val Asp Asp Gln Val Val Glu
            420                 425                 430
Arg Phe Leu His Gln Glu Leu Val Gly Thr Ile Ala Leu Ala Arg Glu
        435                 440                 445
Leu Ala Arg Phe Trp Glu Glu Tyr Pro Ser Gly Ser Ser Met His Arg
    450                 455                 460
Val Leu Phe Val Ser Asn Pro Asp Asp Gln Gln Gly Asn Gln Tyr Ser
465                 470                 475                 480
His Ile Leu Arg Ala Ala Val Glu Gln Leu Val Arg Val Trp Arg His
                485                 490                 495
Glu Ser Glu Tyr Asp Ser Val Asn Pro Ala His Gln Gln Glu Gly Gln
            500                 505                 510
Ser Ser Ala Ala Val Trp Ala Asn Gln Leu Ile Arg Tyr Val Asn Asn
        515                 520                 525
Glu Met Ala Asn Leu Asp Phe Thr Cys Ala Trp Val Ala Lys Leu Leu
    530                 535                 540
Gly Ser Asp Arg Arg Ile Ala Glu Ile Asn Leu Tyr Leu Pro Glu Glu
545                 550                 555                 560
Ile Val Gly Thr Ile Gly Val His Asn Pro Gly Phe Gly Trp Ala Glu
                565                 570                 575
Ser Leu Phe Gly Leu His Met Gly Lys Val Ala Leu Ile Thr Gly Gly
```

```
             580                 585                 590
Ser Ala Gly Ile Gly Gly Gln Ile Gly Arg Leu Leu Ala Leu Ser Gly
             595                 600                 605

Ala His Val Met Leu Ala Ala Arg Asn Ala Asp Gln Leu Glu Gln Met
             610                 615                 620

Arg Ala Ser Ile Val Arg Glu Val Arg Asp Ala Ser Tyr Pro Asp Ala
625                 630                 635                 640

Glu Ser Arg Val Ala Ile Phe Pro Gly Ser Asp Val Ser Asp Ile Asp
                     645                 650                 655

Gly Leu Glu Arg Leu Val Asn His Thr Val Arg Val Phe Gly Lys Val
                 660                 665                 670

Asp Tyr Leu Ile Asn Asn Ala Gly Ile Ala Gly Ala Glu Glu Met Val
             675                 680                 685

Ile Asp Met Pro Val Asp Ala Trp Arg His Thr Leu Arg Ala Asn Leu
         690                 695                 700

Ile Ser Asn Tyr Ala Leu Leu Arg Arg Leu Ala Pro Gln Met Lys Ala
705                 710                 715                 720

Ala Gly Gly Ala Tyr Val Leu Asn Val Ser Ser Tyr Phe Gly Gly Glu
                     725                 730                 735

Lys Tyr Val Ala Ile Pro Tyr Pro Asn Arg Ser Asp Tyr Ala Val Ser
                 740                 745                 750

Lys Ala Gly Gln Arg Ala Met Val Glu Ser Leu Ala Arg Phe Leu Gly
             755                 760                 765

Pro Glu Ile Gln Ile Asn Ala Ile Ala Pro Gly Pro Val Glu Gly Glu
         770                 775                 780

Arg Leu Lys Gly Ala Gly Ser Arg Pro Gly Leu Phe Met Arg Arg Ala
785                 790                 795                 800

Arg Leu Ile Leu Glu Asn Lys Arg Leu Asn Glu Val Phe Ala Ala Leu
                     805                 810                 815

Leu Ala Ala Arg His Glu Gly Ala Thr Ile Ala Asp Leu Leu Pro Asp
                 820                 825                 830

Leu Phe Ala Asn Asp Ile Gln Ser Ile Ala Asn Ser Ala Ala Met Pro
             835                 840                 845

Ala Pro Leu Arg Arg Leu Ala Thr Met Leu Arg Glu Thr Ser Asp Ala
         850                 855                 860

Gly Gly Ser Ala Gln Ser Tyr Leu Met Asn Ala Thr Ile Ala Arg Lys
865                 870                 875                 880

Leu Leu Asn Arg Leu Glu Asn Gly Gly Tyr Ile Thr Leu His Asp Arg
                     885                 890                 895

Arg Ala Leu Thr Val Glu Pro Pro Glu Pro Phe Phe Thr Glu Ala Gln
                 900                 905                 910

Ile Glu Arg Glu Ala Ile Lys Val Arg Asp Gly Ile Leu Gly Met Leu
             915                 920                 925

His Leu Gln Arg Met Pro Thr Glu Phe Asp Val Ala Leu Ala Thr Val
         930                 935                 940

Phe Tyr Leu Ala Asp Arg Asn Val Thr Gly Glu Thr Phe His Pro Ser
945                 950                 955                 960

Gly Gly Leu Arg Phe Glu Arg Thr Val Thr Glu Gly Glu Leu Phe Gly
                     965                 970                 975

Lys Pro Gly Gln Gln Arg Leu Glu Arg Leu Lys Gly Ser Val Val Tyr
                 980                 985                 990

Leu Ile Gly Glu His Leu Arg Gln  His Leu Val Leu Leu  Ala Arg Thr
             995                 1000                1005
```

Phe Leu Asp Glu Ile His Val Ala Arg Val Val Leu Leu Thr Glu
     1010                1015                1020

Thr Thr Gln Ala Ala Thr Asp Leu Ala Ala Glu Leu Ser Asp Tyr
     1025                1030                1035

Glu Ala Ala Gly Arg Phe Val Val Ile Pro Thr Cys Gly Asp Ile
     1040                1045                1050

Glu Gly Gly Ile Asp Arg Ala Met Ala Glu Tyr Gly Arg Pro Gly
     1055                1060                1065

Pro Val Ile Ser Thr Pro Phe Arg Pro Leu Pro Asp Arg Ala Leu
     1070                1075                1080

Ser Ala Arg Asn Gly Asp Trp Ser Ser Val Leu Thr Thr Ala Glu
     1085                1090                1095

Phe Glu Glu Leu Val Glu Gln Gln Ile Thr His His Phe Arg Val
     1100                1105                1110

Ala Arg Lys Ala Gly Leu Ile Glu Gly Ala Asn Val Thr Leu Val
     1115                1120                1125

Thr Pro Pro Thr Ser Ala Arg Ser Thr Ser Glu Glu Phe Ala Leu
     1130                1135                1140

Ala Asn Phe Val Lys Thr Thr Leu His Ala Leu Thr Ala Thr Ala
     1145                1150                1155

Gly Ala Glu Ser Glu Arg Thr Val Pro His Val Pro Val Asn Gln
     1160                1165                1170

Val Asp Leu Thr Arg Arg Ala Arg Ser Glu Glu Pro Arg Thr Pro
     1175                1180                1185

Ser Glu Glu Glu Glu Leu Gln Arg Phe Val Asn Ala Val Leu
     1190                1195                1200

Leu Thr Ser Ala Pro Leu Pro Thr Pro Leu Glu Ser Arg Tyr Arg
     1205                1210                1215

Ala Arg Ile Tyr Arg Gly Asn Ala Ile Thr Val
     1220                1225

<210> SEQ ID NO 296
<211> LENGTH: 1232
<212> TYPE: PRT
<213> ORGANISM: Roseiflexus sp.

<400> SEQUENCE: 296

Met Ser Thr Thr Arg Arg His Asp Arg Leu Glu Gly Lys Val Ala Leu
1               5                   10                  15

Ile Thr Gly Gly Ala Gly Asn Ile Gly Glu Val Ile Thr Arg Arg Phe
            20                  25                  30

Leu Ala Glu Gly Ala Thr Val Val Ile Thr Gly Arg Asn Val Glu Lys
        35                  40                  45

Leu Ala Ala Tyr Arg Arg Arg Leu Ile Asp Glu Glu Arg Ile Ala Pro
    50                  55                  60

Asp Arg Val Val Ala Leu Arg Met Asp Gly Ser Asp Met Ala Gln Val
65                  70                  75                  80

Arg Ala Ala Ile Ala Gln Ile Val His Gly Gly Ala Asp Val Pro Thr
                85                  90                  95

Pro Leu Lys Arg Ile Asp Ile Leu Val Asn Asn Ala Gly Ser Ala Gly
            100                 105                 110

Pro Arg Arg Arg Leu Val Asp Ile Pro Leu Glu Pro Ser Glu Val His
        115                 120                 125

Pro Pro Asp Thr Glu Thr Leu Ala Gln Ala Val Gly Asn Leu Val Gly

```
            130                 135                 140
Val Ala Trp Asn Leu Thr Arg Ala Ala Pro Tyr Met Pro Gly
145                 150                 155                 160

Ser Ser Ile Ile Asn Val Ser Thr Ile Phe Ser Arg Thr Asp Tyr Tyr
                165                 170                 175

Gly Arg Ile Ala Tyr Val Pro Lys Ala Ala Leu Asn Ala Leu Ser
                180                 185                 190

Gln Gly Leu Ala Arg Glu Leu Gly Val Arg Gly Ile Arg Val Asn Thr
            195                 200                 205

Ile Tyr Pro Gly Pro Ile Glu Ser Glu Arg Ile His Thr Val Phe Gln
210                 215                 220

Ala Met Asp Ala Leu Lys Gly Gln Pro Glu Gly Glu Thr Ala Arg Ser
225                 230                 235                 240

Phe Leu Arg Leu Met Arg Leu Ser Arg Ala Asp Thr Gln Gly Glu Val
                245                 250                 255

Thr Lys Arg Phe Pro Leu Pro Val Asp Val Ala Asn Thr Ala Val Phe
                260                 265                 270

Leu Ala Ser Glu Glu Ser Ala Ala Phe Thr Gly His Ala Phe Glu Val
            275                 280                 285

Thr His Gly Met Glu Ala Pro Val Glu Ser Arg Thr Thr Phe Val Ser
290                 295                 300

Arg Pro Gly Leu Arg Ser Val Asp Ala Thr Gly Asn Val Ile Leu Ile
305                 310                 315                 320

Cys Ala Gly Asp Gln Val Asp Asp Ala Ile Ala Leu Ser Asp Thr Leu
                325                 330                 335

Arg Ser Cys Arg Ala Thr Val Val Gly Phe Arg Asp Val Gln Ala
                340                 345                 350

Leu Glu Lys Ala Ser Ala Leu Leu Arg Glu Pro Arg His Val Ala Pro
            355                 360                 365

Ala Asp Met Tyr Gly Arg Pro Thr Met Val Ala Glu Thr Arg Leu Val
370                 375                 380

His Leu Asp Pro Leu Asp Ser Arg Ala Ala Gln Thr Leu Glu Arg
385                 390                 395                 400

Ile Arg Ala Glu Leu Gly Thr Leu His His Ala Val Ile Leu Pro Ala
                405                 410                 415

Ser Leu Arg His Ala Pro Thr Glu Ser Leu Ile Asp Val Asp Asp Arg
                420                 425                 430

Ile Ile Asp Arg Phe Leu Glu Gln Glu Leu Val Gly Ala Ile Ala Leu
            435                 440                 445

Ala Arg Glu Leu Ala Arg Phe Trp Glu Glu His Pro Ala Gly Ser Arg
450                 455                 460

Ala His Arg Val Leu Phe Val Ser Asn Pro Asp Gln Gln Gly Asn
465                 470                 475                 480

Arg Tyr Ala Asp Ile Leu Arg Ala Ala Val Glu Gln Leu Ala Arg Val
                485                 490                 495

Trp Arg His Glu Ser Glu Tyr Asp Ala Ala Asn Pro Ala His Arg His
                500                 505                 510

Glu Asp Gln Pro Gly Ala Ala Val Trp Ala Asn Gln Leu Ile Arg Tyr
            515                 520                 525

Val Asn Ser Glu Ser Ala Asn Leu Asp Phe Thr Cys Ala Trp Val Ala
530                 535                 540

Lys Leu Leu Gly Ser Asp Arg Arg Ile Ala Glu Ile Asn Leu Tyr Leu
545                 550                 555                 560
```

-continued

```
Pro Glu Gln Ile Val Ser Thr Ile Gly Val His Asn Pro Gly Phe Gly
            565                 570                 575

Trp Ala Glu Ser Leu Phe Gly Leu His Met Gly Lys Val Ala Leu Ile
            580                 585                 590

Thr Gly Gly Ser Ala Gly Ile Gly Ala Gln Ile Gly Arg Leu Leu Ala
            595                 600                 605

Leu Ser Gly Ala His Val Met Leu Ala Ala Arg Asn Ala Glu Gln Leu
            610                 615                 620

Glu Gln Met Arg Ala Leu Ile Val Arg Glu Val Arg Asp Ala Ser Tyr
625                 630                 635                 640

Pro Asp Ala Glu Ser Arg Val Ala Ile Phe Pro Asn Ser Asp Val Ser
                645                 650                 655

Asp Ile Asp Gly Leu Glu Arg Leu Val Asn His Thr Leu Arg Val Phe
            660                 665                 670

Gly Lys Val Asp Tyr Leu Ile Asn Asn Ala Gly Ile Ala Gly Ala Glu
            675                 680                 685

Glu Met Val Ile Asp Met Pro Val Asp Ala Trp Arg His Thr Leu Arg
690                 695                 700

Ala Asn Leu Ile Ser Asn Tyr Ala Leu Leu Arg Arg Leu Ala Pro Gln
705                 710                 715                 720

Met Lys Ala Ala Gly Gly Ala Tyr Val Leu Asn Val Ser Ser Tyr Phe
                725                 730                 735

Gly Gly Glu Lys Tyr Val Ala Ile Pro Tyr Pro Asn Arg Ala Asp Tyr
            740                 745                 750

Ala Val Ser Lys Ala Gly Gln Arg Ala Met Val Glu Ser Leu Ala Arg
            755                 760                 765

Phe Leu Gly Pro Glu Ile Gln Ile Asn Ala Ile Ala Pro Gly Pro Val
            770                 775                 780

Glu Gly Glu Arg Leu Lys Gly Ala Ala Asn Arg Pro Gly Leu Phe Met
785                 790                 795                 800

Arg Arg Ala Arg Leu Ile Leu Glu Asn Lys Arg Leu Asn Glu Val Phe
                805                 810                 815

Ala Ala Leu Leu Ala Ala Arg His Glu Gly Ala Val Ile Ala Ala Leu
            820                 825                 830

Leu Pro Asp Leu Phe Val Asn Asp Leu Gln Thr Ile Ala Asp Asn Pro
            835                 840                 845

Ala Met Pro Ala Pro Val Arg Arg Leu Ala Thr Met Leu Arg Glu Thr
850                 855                 860

Thr Asp Ala Gly Gly Ser Ala Gln Ser Tyr Leu Met Asn Ala Thr Ile
865                 870                 875                 880

Ala Arg Lys Leu Leu Asn Arg Leu Glu Asn Gly Gly Tyr Ile Thr Ala
                885                 890                 895

Gly Asp Arg Arg Ala Leu Thr Asn Glu Pro Pro Asp Pro Phe Phe Thr
            900                 905                 910

Glu Ala Gln Ile Glu Arg Glu Ala Ile Lys Val Arg Asp Gly Ile Leu
            915                 920                 925

Gly Met Leu His Leu Gln Arg Met Pro Thr Glu Phe Asp Val Ala Leu
930                 935                 940

Ala Thr Val Phe Tyr Leu Ala Asp Arg Asn Val Thr Gly Glu Thr Phe
945                 950                 955                 960

His Pro Ser Gly Gly Leu Arg Phe Glu Arg Thr Val Thr Glu Gly Glu
                965                 970                 975
```

```
Leu Phe Gly Lys Pro Gly Arg Gln Arg Leu Glu Arg Met Ala Gly Ser
            980                 985                 990

Val Val Tyr Leu Ile Gly Glu His  Leu Arg Gln His Leu  Leu Leu Leu
        995                 1000                1005

Ala Arg Thr Phe Leu Asp Glu  Ile His Val Ala Arg  Val Val Leu
        1010                1015                1020

Leu Thr Glu Thr Glu Gln Ala  Ala Ala Glu Leu Ala  Thr Val Phe
        1025                1030                1035

Ala Asp Glu Glu Ala Ala Gly  Arg Phe Val Ile Ile  Pro Thr Gly
        1040                1045                1050

Gly Asp Ile Glu Gly Gly Ile  Asp Arg Ala Met Ala  Glu Tyr Gly
        1055                1060                1065

Arg Pro Gly Pro Val Ile Ser  Thr Pro Phe Arg Pro  Leu Pro Ser
        1070                1075                1080

Arg Ala Leu Ser Ala Gln Asn  Gly Asp Trp Ser Asn  Val Leu Thr
        1085                1090                1095

Thr Pro Glu Phe Glu Glu Leu  Val Glu Gln His Ile  Thr His His
        1100                1105                1110

Phe Arg Val Val Arg Lys Ala  Gly Leu Ile Glu Gly  Ala Asn Val
        1115                1120                1125

Thr Leu Val Thr Pro Pro Thr  Ser Ala Arg Ser Thr  Ala Glu Glu
        1130                1135                1140

Phe Ala Leu Ala Asn Phe Ile  Lys Thr Thr Leu His  Ala Leu Thr
        1145                1150                1155

Ala Thr Ala Gly Ala Glu Ser  Glu Arg Thr Met Pro  His Val Pro
        1160                1165                1170

Val Asn Gln Val Asp Leu Thr  Arg Arg Ala Arg Ser  Glu Glu Pro
        1175                1180                1185

Arg Thr Pro Ala Glu Glu Glu  Glu Leu Gln Arg  Phe Val Asn
        1190                1195                1200

Ala Val Leu Leu Thr Ser Ala  Pro Leu Pro Thr Pro  Leu Glu Ser
        1205                1210                1215

Arg Tyr Arg Ala Arg Ile Tyr  Arg Gly Asn Ala Ile  Thr Val
        1220                1225                1230

<210> SEQ ID NO 297
<211> LENGTH: 1217
<212> TYPE: PRT
<213> ORGANISM: Erythrobacter sp

<400> SEQUENCE: 297

Met Ser Lys Glu Gly Asn Ala Ala Lys Gly Arg Leu Glu Gly Lys Val
1               5                   10                  15

Ala Leu Ile Thr Gly Ala Ala Gly Asn Leu Gly Asn Glu Ile Ser Arg
            20                  25                  30

Ala Phe Ala Arg Glu Gly Ala Phe Val Val Met Thr Gly Arg Thr Glu
        35                  40                  45

Glu Arg Ile Ser Ala Ala Arg Glu Gln Leu Ile Ala Asp Thr Gly Val
    50                  55                  60

Ala Pro Glu Arg Ile Asp Thr Ala Val Leu Asp Gly Gly Asn Pro Asp
65                  70                  75                  80

Ser Ile Arg Ala Ala Met Ala Lys Leu Arg Lys Glu Tyr Gly Arg Ile
                85                  90                  95

Asp Ile Leu Ile Asn Asn Ala Gly Ser Ala Gly Pro Lys Gln Pro Leu
            100                 105                 110
```

```
His Asn Val Pro Leu Ser Pro Gln Glu Met Glu Ala Cys Gly Asp Thr
            115                 120                 125

Glu Thr Val Arg Asp Ala Met Leu Asn Ile Leu Gly Val Thr Trp Asn
130                 135                 140

Met Ala Arg Ile Val Ala Pro Met Met Pro Val Gly Gly Ala Met Val
145                 150                 155                 160

Asn Ile Ser Thr Ile Phe Ser His Thr Arg Tyr Tyr Gly Arg Thr Ala
            165                 170                 175

Tyr Val Val Pro Lys Ala Ala Leu Asn Ala Leu Ser Asn Gln Leu Ala
            180                 185                 190

Ser Glu Leu Gly Pro Arg Gly Ile Arg Val Asn Thr Val Phe Pro Gly
            195                 200                 205

Pro Ile Glu Ser Asp Arg Ile Arg Thr Val Phe Ala Ala Met Asp Glu
210                 215                 220

Val Gln Ser Gln Pro Lys Asp Thr Thr Ala Asn Tyr Phe Thr Gly Arg
225                 230                 235                 240

Met Ala Leu Thr Arg Ser Val Asn Gly Lys Val Asp Gly Lys Pro Leu
            245                 250                 255

Pro Asn Pro Lys Asp Ile Ala Gly Thr Cys Leu Phe Leu Ala Ser Glu
            260                 265                 270

Glu Ala Ala Gly Ile Ala Gly Glu Glu Val Asp Val Thr His Gly Leu
            275                 280                 285

Ser Ala Asn Arg Thr Ser Ala Ser Thr Tyr Met Thr Arg Pro Ser Met
            290                 295                 300

Arg Ser Leu Asp Gly Ala Gly Leu Asn Ile Phe Ile Val Ser Gly Glu
305                 310                 315                 320

Asn Trp Asp Asp Ala Leu Val Ala Ala His Thr Leu Ile Gly Ser Gly
                325                 330                 335

Ala Lys Val Arg Leu Gly Leu Ala Arg Asn Ala Asp Val Ala Gln Ala
            340                 345                 350

Asn Ala Arg Leu Lys Ala Gln Gly Ile Gly Glu Glu Leu Thr Val Thr
            355                 360                 365

Arg Phe Asn Arg Ala Glu Pro Asp Ala Met Glu Asp Ala Leu Ala Ala
370                 375                 380

Phe Ser Gly Asp Val Asp Gly Ala Ile Thr Gly Ala Ile Ile Leu Pro
385                 390                 395                 400

Val Lys Pro Ser Gly His Phe Thr Gly Ser Leu Leu Ala Ala Asp Asp
            405                 410                 415

Asp Thr Val Thr Lys Phe Met Asp Thr Glu Leu Val Gly Ala Ile Ala
            420                 425                 430

Val Ser Arg Ser Leu Ala Arg Tyr Trp His Gly Arg Glu Asp Leu Gln
            435                 440                 445

Ser Pro Pro Arg Cys Val Phe Met Thr Asn Pro Gly Asp Pro Leu Gly
450                 455                 460

Asn Ser Phe Ala Ser Val Leu Ser Ala Gly Ile Thr Gln Leu Ile Arg
465                 470                 475                 480

Ile Trp Arg Asp Glu Glu Arg Val Gln Ala Gly Asn Gly Ser Thr Glu
                485                 490                 495

His Ala Val Trp Ser Asn Gln Ile Val Arg His Thr Asn Thr Glu Asp
            500                 505                 510

Glu Asn Thr Arg Phe Ala Ser Gly His Ala Thr Arg Val Leu Phe Arg
            515                 520                 525
```

```
Glu Gln His Ile Ala Glu Ile Asp Leu Lys Leu Pro Ala Asn Ile Ser
530                 535                 540

Glu Glu Thr Gly Ser Arg Lys Ala Met Val Gly Phe Ala Glu Asn Ile
545                 550                 555                 560

Thr Gly Leu His Leu Gly Lys Val Ala Phe Ile Thr Gly Gly Ser Ala
                565                 570                 575

Gly Ile Gly Gly Gln Val Ala Arg Leu Leu Ala Leu Ala Gly Ala Lys
                580                 585                 590

Val Met Met Val Ala Arg Arg Glu Ser Glu Leu Val Ala Ala Arg Asp
        595                 600                 605

Arg Ile Val Gly Glu Leu Gln Asp Ile Gly Phe Ala Gly Val Glu Arg
610                 615                 620

Arg Val Lys Tyr Met Ala Asp Ile Asp Val Ser Asp Phe Ala Ser Leu
625                 630                 635                 640

Asp Lys Ala Val Asp Ala Thr Leu Glu Glu Phe Gly Arg Ile Asp Tyr
                645                 650                 655

Leu Ile Asn Asn Ala Gly Val Ala Gly Ala Glu Asp Met Val Ile Asp
                660                 665                 670

Met Glu Pro Glu Ala Trp Arg Phe Thr Leu Asp Ala Asn Leu Ile Ser
        675                 680                 685

Asn Tyr His Leu Met Gln Arg Val Pro Leu Met Lys Glu Gln Gly
690                 695                 700

Ser Gly Tyr Val Leu Asn Val Ser Ser Tyr Phe Gly Gly Glu Lys Phe
705                 710                 715                 720

Leu Ala Val Ala Tyr Pro Asn Arg Ala Asp Tyr Gly Leu Ser Lys Ala
                725                 730                 735

Gly Gln Arg Ala Met Val Glu Ala Phe Ser Pro Phe Leu Gly Pro Glu
                740                 745                 750

Val Gln Cys Asn Ala Ile Ala Pro Gly Pro Val Asp Gly Asp Arg Leu
        755                 760                 765

Ser Gly Thr Gly Gly Lys Pro Gly Leu Phe Gln Arg Arg Ala Lys Leu
        770                 775                 780

Ile Leu Glu Asn Lys Arg Leu Asn Ala Val Tyr Ser Ala Val Ile His
785                 790                 795                 800

Ala Ile Arg Glu Gly Gly Asp Ala Ala Lys Ile Leu Thr Arg Leu Ser
                805                 810                 815

Arg Asn Ser Thr Ser Thr Leu Ser His Asp Ala Glu Ala Pro Glu Glu
                820                 825                 830

Leu Arg Lys Leu Ala Leu Asp Phe Ala Ser Gln Gly Asp Gly Leu Cys
        835                 840                 845

Thr Trp Asp Gln Tyr Leu Leu Thr Asp Ala Met Ala Gln Arg Leu Leu
850                 855                 860

Val Arg Leu Gln Leu Gly Gly Phe Leu Leu Gly Ser Asn Glu Trp Ala
865                 870                 875                 880

Ser Leu Ser Ser Ser Glu Gln Thr Trp Leu Lys Leu Ser Pro Pro Asp
                885                 890                 895

Asp Lys Pro Phe Leu Pro Ala Ala Gln Val Asp Lys Val Ala Asn Gly
                900                 905                 910

Val Gly Lys Gly Val Ile Ser Gln Leu His Leu Gly Ala Met Pro Thr
        915                 920                 925

Glu Ala Glu Val Ala Gln Ala Thr Val Phe Phe Leu Ala Asp Arg Ala
930                 935                 940

Val Ser Gly Glu Thr Phe Met Pro Ser Gly Gly Leu Arg Val Glu Arg
```

```
                945                 950                 955                 960
Ser Asn Thr Glu Arg Glu Met Phe Gly Ser Pro Lys Gln Arg Ile
                    965                 970                 975
Asp Lys Met Lys Gly Lys Thr Val Trp Ile Ile Gly Glu His Leu Ser
                980                 985                 990
Asp Tyr Val Ala Ala Thr Ile Glu Glu Leu Val Ser Gly Cys Gly Val
            995                 1000                1005
Ala Lys Val Val Leu Ile Ala Lys Asp Lys Ser Gly Glu Lys Ala
    1010                1015                1020
Val Arg Asp Gln Leu Pro Asn Asp Leu Ser Lys Asp Ala Leu Glu
    1025                1030                1035
Val Leu Ile Ala Gly Asp Gly Leu Glu Glu Ala Met Asp Glu Ala
    1040                1045                1050
Leu Gly His Trp Gly Lys Pro Thr Thr Val Leu Ser Met Pro Gly
    1055                1060                1065
Glu Pro Leu Pro Asp His Leu Phe Glu Gly Gly Asn Pro Leu Ser
    1070                1075                1080
Thr Lys Asp Phe Ala His Met Val Glu Ala Asn Ile Thr Arg His
    1085                1090                1095
Tyr Arg Val Thr Arg Lys Ala Ser Leu Tyr Asp Gly Cys Gln Val
    1100                1105                1110
Val Leu Val Ser Pro Asp Val Pro Tyr Gly Ser Asp Gly Pro Gly
    1115                1120                1125
Val Ala Leu Ala Asn Phe Val Lys Thr Ser Leu His Ala Phe Thr
    1130                1135                1140
Ala Thr Val Ala Val Glu Asn Glu Arg Leu Val His Asp Val Pro
    1145                1150                1155
Val Asn Gln Ile Asn Leu Thr Arg Arg Val Ser Ser Glu Glu Pro
    1160                1165                1170
Arg Asp Ala Asp Glu His Ala Glu Glu Leu Arg Arg Phe Thr Arg
    1175                1180                1185
Ala Val Leu Leu Val Gly Ala Pro Leu Pro Asp Ala Gln Asp Ser
    1190                1195                1200
Arg Tyr Arg Ser Lys Ile Tyr Arg Gly Thr Ser Met Thr Val
    1205                1210                1215

<210> SEQ ID NO 298
<211> LENGTH: 1210
<212> TYPE: PRT
<213> ORGANISM: Artificial
<220> FEATURE:
<223> OTHER INFORMATION: gamma proteobacterium NOR51-B

<400> SEQUENCE: 298

Met Asn Thr Glu Thr Arg Thr Thr Ser Gly Gly Arg Leu His Asp Lys
1               5                   10                  15

Val Val Ile Leu Thr Gly Ala Ala Gly Asn Ile Gly Ser Tyr Ile Ser
            20                  25                  30

Arg Ser Leu Leu Arg Glu Gly Ala Asn Leu Val Met Thr Gly Arg Asn
        35                  40                  45

Glu Pro Lys Leu Gln Ala Phe Val Glu Gly Leu Val Glu Glu Gly Phe
    50                  55                  60

Asp Arg Asp Asn Ile Leu Ile Ala Ile Gly Asp Ser Ala Lys Ala Asp
65                  70                  75                  80

Ile Cys Arg Glu Ile Val Lys Ala Thr Val Asn His Phe Gly Asn Ile
```

-continued

```
                85                  90                  95
Asp Val Leu Val Asn Ala Gly Gly Ala Gly Pro Arg Arg Thr Leu
            100                 105                 110
Arg Asp Ile Pro Phe Ser Glu Ser Glu Arg Leu Ala Arg Gly Asp Asp
            115                 120                 125
Glu Thr Met Leu Asp Ala Ala Met Asn Leu Leu Ala Gly Ala Trp Asn
            130                 135                 140
Met Thr Arg Ala Ala Val Pro His Met Ser Glu Gly Gly Ser Ile Val
145                 150                 155                 160
Asn Val Ser Thr Ile Phe Ser Arg Thr His Tyr Tyr Gly Arg Ile Pro
                165                 170                 175
Tyr Val Val Pro Lys Ser Gly Leu Asn Ala Leu Ser Ile Gly Leu Ala
                180                 185                 190
Lys Glu Leu Gly Glu Glu His Gly Ile Arg Val Asn Thr Leu Phe Pro
                195                 200                 205
Gly Pro Ile Glu Ser Glu Arg Ile Asp Thr Val Phe Gly Asn Met Asp
            210                 215                 220
Ala Leu Gln Ser Ala Pro Ala Gly Ala Thr Ser Gln Glu Phe Arg Asp
225                 230                 235                 240
Leu Met Ile Thr Arg Arg Glu Asn Pro Asp Gly Glu Tyr Glu Tyr Arg
                245                 250                 255
Tyr Pro Thr Pro Asn Asp Val Ala Ser Thr Val Thr Trp Leu Ala Ser
            260                 265                 270
Glu Glu Ser Ala Ala Leu Ser Gly His His Ile Glu Val Thr Asn Gly
            275                 280                 285
Met Gln Val Pro Ala Gln Ser Arg Ser Lys Leu Val Ser Trp Pro Asp
290                 295                 300
Lys Arg Leu Glu Asp Leu Ser Gly Gln Val Val Phe Leu Leu Ala Gly
305                 310                 315                 320
Ser Asp Tyr Glu Asp Ala Leu Ala Phe Ala Glu Arg His Met Val Ser
                325                 330                 335
Gly Ala Lys Val Val Leu Ala Phe Arg Ser Leu Glu Ser Leu Gly Leu
                340                 345                 350
Ala Arg Ser Leu Cys Ala Ser Arg Asp Leu Glu Ser Ile His Leu Leu
                355                 360                 365
His Leu Glu Pro Leu Arg Arg Glu Ser Ala Asp Arg Cys Phe Asp Tyr
            370                 375                 380
Ile Arg Asp His Phe Gly Arg Leu Asp Gly Ile Val Val Leu Pro Arg
385                 390                 395                 400
Ser Gly Asn Gly Glu His Gly Tyr Ser Leu Ser Thr Ala Gly Asp Asp
                405                 410                 415
Asp Val Glu Ala Phe Val Arg Asp Glu Ile Ile Ser Pro Val Ala Phe
                420                 425                 430
Ala Ala Ala Leu Ala Ile Asn Leu Asp Arg Trp Gly Ile Leu Glu Glu
                435                 440                 445
Ala Pro Ala Leu Thr Tyr Val Thr Asn Pro Thr Asp Gly His Gly Asp
            450                 455                 460
Tyr Leu Asn Glu Val Lys Arg Ala Ala Ile Glu Ala Leu Ile Arg Ile
465                 470                 475                 480
Trp Arg His Glu Asp Arg Gln Met Arg Lys Lys Gly Glu Arg Glu Trp
                485                 490                 495
Ala Met Leu Pro Asn Gln Leu Val Arg Tyr Asp Asn Asn Glu Glu Asp
            500                 505                 510
```

```
Asn Leu Thr Phe Thr Ala Asp Trp Ala Ala Thr Leu Thr Asn Arg Val
    515                 520                 525

Arg Arg Met Asp Pro Ile Asn Leu Trp Val Pro Glu Ser Ile Met Arg
    530                 535                 540

Ala Thr Gly Lys Ser Gly Met Pro Gln Ser Ile Gln Arg Val Leu Pro
545                 550                 555                 560

Gly Leu His Lys Gly Arg Thr Ala Val Ile Thr Gly Gly Ser Leu Gly
                565                 570                 575

Ile Gly Leu Gln Leu Gly Arg Phe Leu Ala Ile Ala Gly Ala Arg Val
            580                 585                 590

Leu Leu Ser Ala Arg Ser Lys Glu Lys Leu Glu Glu Ala Arg His Glu
        595                 600                 605

Ile Val Glu Glu Leu Arg Gly Val Gly Tyr Pro Asn Ala His Gln Arg
    610                 615                 620

Val His Ile Leu Pro Asp Ile Asp Val Gly Asp Glu Glu Ala Leu Glu
625                 630                 635                 640

Arg Leu Tyr Asn His Ser Ile Glu Leu Phe Gly Asn Val Asp Phe Leu
                645                 650                 655

Ile Asn Asn Ala Gly Ile Ser Gly Ala Glu Glu Met Val Val Asp Met
            660                 665                 670

Ser Leu Glu Ala Trp Asn Arg Thr Met Tyr Ala Asn Leu Ile Ser Asn
        675                 680                 685

Tyr Ser Leu Ile Arg Lys Tyr Ala Pro Lys Met Lys Ala Asn Gly Tyr
    690                 695                 700

Gly Val Val Leu Asn Val Ser Ser Tyr Phe Gly Gly Glu Lys Tyr Val
705                 710                 715                 720

Ala Val Ala Tyr Pro Asn Arg Ala Asp Tyr Ala Val Ser Lys Ala Gly
                725                 730                 735

Gln Arg Val Leu Ala Glu Ile Leu Ser Arg His Leu Gly Pro Glu Ile
            740                 745                 750

Arg Ile Asn Ala Leu Ala Pro Gly Pro Val Asp Gly Ala Arg Leu Arg
        755                 760                 765

Gly Leu Gly Gly Ala Pro Gly Leu Phe Glu Arg Arg Gly Arg Leu Val
    770                 775                 780

Leu Glu Asn Lys Arg Leu Asn Ser Val His Lys Ala Val Leu Ala Ala
785                 790                 795                 800

Leu Arg Glu Gly Ala Thr Pro Glu Val Ile Met Ala Leu Ser Arg Asn
                805                 810                 815

Ala Leu Gly Asp Ala Lys Pro Thr Ala Gly Gln Ser Lys Ala Leu Asp
            820                 825                 830

Lys Leu Phe Ala Gln Val Glu Asp Ser Pro Glu Gly Gly Asn Ser Thr
        835                 840                 845

Ala Phe Leu Leu Asn Arg Asp Leu Ala Glu Lys Leu Met Asn Arg Leu
    850                 855                 860

Val Thr Gly Gly Leu Phe Thr Pro Glu Ser Ala Thr Gln Phe Met Glu
865                 870                 875                 880

Gly Phe Val Asp Ala Pro Ala Ile Phe Phe Asp Glu Lys Ser Val Asn
                885                 890                 895

Lys Ala Ala Ala Gly Ile Glu Ala Gly Ile Leu Asn Arg Leu His Leu
            900                 905                 910

His Lys Met Pro Thr Asp Glu Gln Ile Gly Leu Ser Thr Val Phe His
        915                 920                 925
```

```
Leu Ala Asp Asp Ile Ala Ser Gly Glu Thr Phe His Pro Ser Gly Gly
    930                 935                 940

Leu Lys Phe Asp Arg Ser Val Thr Glu Gly Glu Leu Leu Pro Pro
945                 950                 955                 960

Asp Arg Asp Ser Leu Ala Lys Leu Lys Gly Lys Arg Val Val Leu Ile
                965                 970                 975

Gly Asp Ser Met Arg Glu Glu Leu Ser Ala Ile Gly Asn Gly Phe Ile
                980                 985                 990

Asn Gln Gly Val Ala Ser Leu Thr Val Leu Thr Arg Ser Pro Glu Ala
            995                 1000                1005

Cys Glu Glu Val Gln His Ser Leu Gln Lys Ser Asn Ser Val Thr
    1010                1015                1020

Leu Asp Val Arg Cys Ile Glu Asp Asn Ile Glu Asp Ala Leu Asp
    1025                1030                1035

Asp Leu Leu Gln Asn Gln Gly Gly Phe Asp Val Val Ser Ala
    1040                1045                1050

Pro Phe Ser Arg Leu Pro Tyr Asn Pro Leu Ala Ala Glu Arg Glu
    1055                1060                1065

Gly Ser Trp Asn Arg Val Leu Ser His Thr Asp Phe Ala Arg Leu
    1070                1075                1080

Ile Asp Glu Gln Leu Thr His His Phe Arg Val Ala Arg Arg Ala
    1085                1090                1095

Ala Leu Val Pro Asn Cys Gln Ile Val Leu Leu Thr Pro Asp Thr
    1100                1105                1110

Ser Phe Val Ser Ser Arg Glu Glu Phe Ala Leu Ala Leu Phe Val
    1115                1120                1125

Lys Asn Ser Leu His Ala Phe Thr Val Thr Leu Gly Val Glu Thr
    1130                1135                1140

Glu Arg Leu Pro Thr Val Pro Ala Val Asn Gln Val Gln Leu Thr
    1145                1150                1155

Arg Arg Ala Arg Ala Glu Glu Pro Ala Thr Glu Ser Glu Leu Gln
    1160                1165                1170

Glu Glu Met Glu Arg Leu Val Ser Ala Val Leu Gln Cys Ala Val
    1175                1180                1185

Pro Ala Pro Ser Pro Ser Glu Ser Arg Tyr Leu Ala Arg Ile Phe
    1190                1195                1200

Arg Gly Asn Ala Val Thr Val
    1205                1210

<210> SEQ ID NO 299
<211> LENGTH: 10
<212> TYPE: PRT
<213> ORGANISM: T. saccharolyticum

<400> SEQUENCE: 299

Met Lys Lys Phe Ile Val Thr Val Asn Gly
1               5                   10

<210> SEQ ID NO 300
<211> LENGTH: 24
<212> TYPE: DNA
<213> ORGANISM: Artificial
<220> FEATURE:
<223> OTHER INFORMATION: X13673 primer

<400> SEQUENCE: 300
atacgggata ataccgcgcc acat                                      24
```

```
<210> SEQ ID NO 301
<211> LENGTH: 24
<212> TYPE: DNA
<213> ORGANISM: Artificial
<220> FEATURE:
<223> OTHER INFORMATION: X13674 primer

<400> SEQUENCE: 301
ccattcgacc accaagcgaa acat                                          24
```

UNITED STATES PATENT AND TRADEMARK OFFICE
CERTIFICATE OF CORRECTION

PATENT NO. : 11,162,125 B2  
APPLICATION NO. : 16/166274  
DATED : November 2, 2021  
INVENTOR(S) : William Ryan Sillers et al.

Page 1 of 1

It is certified that error appears in the above-identified patent and that said Letters Patent is hereby corrected as shown below:

In the Claims

At Column 437, Claim number 15, Line number 11, please delete "1" after "a"

Signed and Sealed this  
Fifteenth Day of March, 2022

Drew Hirshfeld  
*Performing the Functions and Duties of the*  
*Under Secretary of Commerce for Intellectual Property and*  
*Director of the United States Patent and Trademark Office*